(12) United States Patent
Alexander et al.

(10) Patent No.: US 10,087,179 B2
(45) Date of Patent: *Oct. 2, 2018

(54) FUSED TRICYCLIC IMIDAZOLE DERIVATIVES AS MODULATORS OF TNF ACTIVITY

(71) Applicant: UCB BIOPHARMA SPRL, Brussels (BE)

(72) Inventors: Rikki Peter Alexander, Slough (GB); Gareth Neil Brace, Abingdon (GB); Julien Alistair Brown, Slough (GB); Mark Daniel Calmiano, Slough (GB); Prafulkumar Tulshibhai Chovatia, Abingdon (GB); Michael Deligny, Brussels (BE); Ellen Olivia Gallimore, Slough (GB); Jag Paul Heer, Brussels (BE); Victoria Elizabeth Jackson, Slough (GB); Boris Kroeplien, Slough (GB); Malcolm MacCoss, Seabrook Island, SC (US); Joanna Rachel Quincey, Slough (GB); Yogesh Anil Sabnis, Brussels (BE); Dominique Louis Léon Swinnen, Brussels (BE); Zhaoning Zhu, Slough (GB); Uwe Heinelt, Frankfurt am Main (DE); Volkmar Wehner, Frankfurt am main (DE)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/101,767

(22) PCT Filed: Dec. 8, 2014

(86) PCT No.: PCT/EP2014/076884
§ 371 (c)(1),
(2) Date: Jun. 3, 2016

(87) PCT Pub. No.: WO2015/086526
PCT Pub. Date: Jun. 18, 2015

(65) Prior Publication Data
US 2016/0376268 A1 Dec. 29, 2016

(30) Foreign Application Priority Data

Dec. 9, 2013 (GB) .................... 1321729.4

(51) Int. Cl.
*C07D 471/04* (2006.01)
*C07D 519/00* (2006.01)
*A61K 31/437* (2006.01)

(52) U.S. Cl.
CPC .......... *C07D 471/04* (2013.01); *A61K 31/437* (2013.01); *C07D 519/00* (2013.01)

(58) Field of Classification Search
CPC ........................... C07D 471/04; C07D 519/00
USPC ....................................... 546/80; 514/210.18
See application file for complete search history.

(56) References Cited

U.S. PATENT DOCUMENTS

2016/0304530 A1* 10/2016 Alexander ......... C07D 491/147

FOREIGN PATENT DOCUMENTS

| WO | 04/014900 A1 | 2/2004 |
| WO | 13/186229 A1 | 12/2013 |
| WO | 14/009295 A1 | 1/2014 |
| WO | 14/009296 A1 | 1/2014 |

OTHER PUBLICATIONS

Tansey et al., "The TNF superfamily in 2009: new pathways, new indications, and new drugs", Drug Discovery Today, 2009, 14(23/24), 1082-1088.
Carneiro et al., "Emerging Role for TNF-α in Erectile Dysfunction", J. Sexual Medicine, 2010, vol. 7, 3823-3834.
Wu et al., "Do TNF Inhibitors Reduce the Risk of Myocardial Infarction in Psoriasis Patients?", JAMA, 2013, 309(19), 2043-2044.
Hauwermeiren et al., "Safe TNF-based antitumor therapy following p55TNFR reduction in intestinal epithelium", The Journal of Clinical Investigation, 2013, 123(6), 2590-2603.

* cited by examiner

*Primary Examiner* — Rita J Desai
(74) *Attorney, Agent, or Firm* — McDonnell Boehnen Hulbert & Berghoff LLP

(57) ABSTRACT

A series of fused tricyclic imidazole derivatives, in particular dihydro-1H-cyclopenta[4,5]imidazo[1,2-a]pyridine derivatives, and analogues thereof, being potent modulators of human TNFα activity, are accordingly of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders.

11 Claims, No Drawings

FUSED TRICYCLIC IMIDAZOLE DERIVATIVES AS MODULATORS OF TNF ACTIVITY

This application is the US national phase under 35 U.S.C. § 371 of international application PCT/EP2014/076884, filed Dec. 8, 2014, which claims priority to GB application 1321729.4, filed Dec. 9, 2013.

The present invention relates to a class of fused tricyclic imidazole derivatives, and to their use in therapy. More particularly, this invention is concerned with pharmacologically active substituted fused imidazopyridine derivatives. In particular the present invention relates to dihydro-1H-cyclopenta[4,5]imidazo[1,2-a]pyridine derivatives.

These compounds are modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and ontological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certolizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

Co-pending international patent applications WO 2013/186229 (published 19 Dec. 2013), WO 2014/009295 (published 16 Jan. 2014) and WO 2014/009296 (also published 16 Jan. 2014) describe fused imidazole derivatives which are modulators of human TNFα activity.

None of the prior art available to date, however, discloses or suggests the precise structural class of fused imidazopyridine derivatives as provided by the present invention.

The compounds in accordance with the present invention potently inhibit the binding of a fluorescence conjugate to TNFα when tested in the fluorescence polarisation assay described herein. Indeed, when tested in that assay, the compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound).

Certain compounds in accordance with the present invention potently neutralise the activity of TNFα in a commercially available HEK-293 derived reporter cell line known as HEK-Blue™ CD40L. This is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, also referred to herein as the reporter gene assay, certain compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 20 nM or less (as before, the skilled person will appreciate that a lower $IC_{50}$ figure denotes a more active compound).

The present invention provides a compound of formula (I) or an N-oxide thereof, or a pharmaceutically acceptable salt or solvate thereof, or a glucuronide derivative thereof, or a co-crystal thereof:

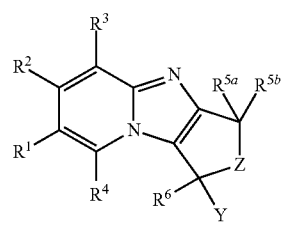

(I)

wherein

Y represents $C_{3-7}$ cycloalkyl, aryl, $C_{3-7}$ heterocycloalkyl or heteroaryl, any of which groups may be optionally substituted by one or more substituents;

Z represents a heteroatom, carbonyl; —S(O)—, —S(O)$_2$—, —S(O)(N—R$^d$), —NC(O)R$^d$, —N(CO)—OR$^d$, —NS(O)$_2$R$^d$, or —N(R$^d$); or an optionally substituted straight or branched $C_{1-4}$ alkylene chain;

$R^1$ and $R^2$ independently represent hydrogen, halogen, cyano, nitro, hydroxy, trifluoromethyl, trifluoromethoxy, —OR$^a$, —SR$^a$, —SOR$^a$, —SO$_2$R$^a$, —SF$_5$, —NR$^b$R$^c$, —NR$^c$COR$^d$, —NR$^c$CO$_2$R$^d$, —NHCONR$^b$R$^c$, —$NR^cSO_2R^e$, —$N(SO_2R^e)_2$, —$NHSO_2NR^bR^c$, —$COR^d$, —$CO_2R^d$, —$CONR^bR^c$, —$CON(OR^a)R^b$, —$SO_2NR^bR^c$, or —$S(O)(N-R^d)R^a$; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl($C_{1-6}$)alkyl-aryl-, heteroaryl($C_{3-7}$)heterocycloalkyl-, ($C_{3-7}$)cycloalkyl-heteroaryl-, ($C_{3-7}$)cycloalkyl($C_{1-6}$)alkyl-heteroaryl-, ($C_{4-7}$)cycloalkenyl-heteroaryl-, ($C_{4-9}$)bicycloalkyl-heteroaryl-, ($C_{4-9}$)bicycloalkenyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents;

$R^3$ and $R^4$ independently represents hydrogen, halogen, cyano, nitro, hydroxy, trifluoromethyl, trifluoromethoxy or —$OR^a$; or $C_{1-6}$ alkyl optionally substituted by one or more substituents; and $R^{5a}$ and $R^{5b}$ independently represent hydrogen, hydroxy, halogen, trifluoromethyl, cyano; or —$NR^bR^c$, —$NR^cC(O)R^d$, —(CO)$NR^cR^d$, —$NHS(O)_2R^e$, —S—$R^a$, —(SO)—$R^a$, —$S(O)_2R^a$, —$S(O)(N-R^d)$, —$S(O)_2(N-R^d)$, —$OR^a$, —$C(O)$—$OR^d$, —$O(CO)$—$R^d$—; $C_{1-6}$ alkyl, $C_{2-6}$ alkynyl, heteroaryl, any of which groups may be optionally substituted by one or more substituents; or $R^{5a}$ and $R^{5b}$ when taken together with the carbon to which they are attached represent a carbonyl, thiocarbonyl or —C=N—OH; and $R^6$ represents hydrogen, hydroxy, halogen, trifluoromethyl, cyano; or —$NR^bR^c$, —$NR^cC(O)R^d$, —(CO)$NR^cR^d$, —$NHS(O)_2R^e$, —S—$R^a$, —(SO)—$R^a$, —$S(O)_2R^a$, —$S(O)(N-R^d)$, —$S(O)_2(N-R^d)$, —$OR^a$, —$C(O)$—$OR^d$, or —$O(CO)$—$R^d$—; $C_{1-6}$ alkyl, $C_{2-6}$ alkynyl, heteroaryl, any of which groups may be optionally substituted by one or more substituents; or $R^6$ and Y together with the carbon to which they are attached form a $C_{3-7}$ cycloalkyl or $C_{3-7}$ heterocycloalkyl, optionally substituted with one or more substituents; and $R^a$ represents $C_{1-6}$ alkyl, aryl, aryl($C_{1-6}$)alkyl, $C_{3-7}$ cycloalkyl, $C_{3-7}$ heterocycloalkyl, heteroaryl or heteroaryl($C_{1-6}$)alkyl, any of which groups may be optionally substituted by one or more substituents;

$R^b$ and $R^c$ independently represent hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$heterocycloalkyl($C_{1-6}$)alkyl, heteroaryl or heteroaryl($C_{1-6}$)alkyl, any of which groups may be optionally substituted by one or more substituents; or $R^b$ and $R^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl, homopiperazin-1-yl, (imino)(oxo)thiazinan-4-yl, (oxo)thiazinan-4-yl or (dioxo)thiazinan-4-yl, any of which groups may be optionally substituted by one or more substituents;

$R^d$ represents hydrogen; or $C_{1-6}$ alkyl, $C_{3-7}$ cycloalkyl, aryl, $C_{3-7}$ heterocycloalkyl or heteroaryl, any of which groups may be optionally substituted by one or more substituents; and $R^e$ represents $C_{1-6}$ alkyl, aryl or heteroaryl, any of which groups may be optionally substituted by one or more substituents.

The present invention also provides a compound of formula (I) as defined above or an N-oxide thereof, or a pharmaceutically acceptable salt or solvate thereof, or a glucuronide derivative thereof, or a co-crystal thereof, for use in therapy.

The present invention also provides a compound of formula (I) as defined above or an N-oxide thereof, or a pharmaceutically acceptable salt or solvate thereof, or a glucuronide derivative thereof, or a co-crystal thereof, for use in the treatment and/or prevention of disorders for which the administration of a modulator of TNFα function is indicated.

In another aspect, the present invention provides for the use of a compound of formula (I) as defined above, or an N-oxide thereof, or a pharmaceutically acceptable salt thereof, for the manufacture of a medicament useful for the treatment of an inflammatory or autoimmune disorder, a neurological or neurodegenerative disorder, pain or a nociceptive disorder, a cardiovascular disorder, a metabolic disorder, an ocular disorder, or an oncological disorder.

In another aspect, the present invention provides a compound of formula (I) as defined above or an N-oxide thereof, or a pharmaceutically acceptable salt or solvate thereof, or a glucuronide derivative thereof, or a co-crystal thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (I) as defined above or an N-oxide thereof, or a pharmaceutically acceptable salt or solvate thereof, or a glucuronide derivative thereof, or a co-crystal thereof.

In another aspect, the present invention provides a method for the treatment and/or prevention of an inflammatory or autoimmune disorder, a neurological or neuro-degenerative disorder, pain or a nociceptive disorder, a cardiovascular disorder, a metabolic disorder, an ocular disorder, or an oncological disorder, which comprises administering to a patient in need of such treatment an effective amount of a compound of formula (I) as defined above or an N-oxide thereof, or a pharmaceutically acceptable salt or solvate thereof, or a glucuronide derivative thereof, or a co-crystal thereof.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of use in the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; ammonium salts; and salts formed with suitable organic ligands, e.g. quaternary ammonium salts, and meglumine salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

The present invention also includes co-crystals within its scope. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012). Typical examples of co-crystal formers, which may be present in the co-crystal alongside the active pharmaceutical ingredient, include L-ascorbic acid, citric acid, glutaric acid, urea and nicotinamide.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in *Design of Prodrugs*, ed. H. Bundgaard, Elsevier, 1985.

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The expression "$C_{1-4}$ alkylene chain" refers to a divalent straight or branched alkylene chain containing 1 to 4 carbon atoms. Typical examples include methylene, ethylene, methylmethylene, ethylmethylene and dimethylmethylene.

Suitable $C_{2-6}$ alkenyl groups include vinyl and allyl.

Suitable $C_{2-6}$ alkynyl groups include ethynyl, propargyl and butynyl.

The term "$C_{3-7}$ cycloalkyl" as used herein refers to monovalent groups of 3 to 7 carbon atoms derived from a saturated monocyclic hydrocarbon, and may comprise benzo-fused analogues thereof. Suitable $C_{3-7}$ cycloalkyl groups include cyclopropyl, cyclobutyl, benzocyclobutenyl, cyclopentyl, indanyl, cyclohexyl and cycloheptyl.

The term "$C_{4-7}$ cycloalkenyl" as used herein refers to monovalent groups of 4 to 7 carbon atoms derived from a partially unsaturated monocyclic hydrocarbon. Suitable $C_{4-7}$ cycloalkenyl groups include cyclobutenyl, cyclopentenyl, cyclohexenyl and cycloheptenyl.

The term "$C_{4-9}$ bicycloalkyl" as used herein refers to monovalent groups of 4 to 9 carbon atoms derived from a saturated bicyclic hydrocarbon. Typical $C_{4-9}$ bicycloalkyl groups include bicyclo[3.1.0]hexanyl, bicyclo[4.1.0]heptanyl, bicyclo[2.2.2]octanyl and bicyclo[3.3.1]-nonanyl.

Typical ($C_{4-9}$)bicycloalkenyl groups include bicyclo[3.1.0]hexenyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, dihydroisoindolinyl, isoindolinyl, oxazolidinyl, thiazolidinyl, isothiazolidinyl, imidazolidinyl, tetrahydropyranyl, chromanyl, tetrahydrothiopyranyl, piperidinyl, 1,2,3,4-tetrahydro quinolinyl, 1,2,3,4-tetrahydroisoquinolinyl, piperazinyl, 1,2,3,4-tetrahydro quinoxalinyl, hexahydro-[1,2,5]thiadiazolo[2,3-a]pyrazinyl, homopiperazinyl, morpholinyl, benzoxazinyl, thiomorpholinyl, azepanyl, oxazepanyl, diazepanyl, thiadiazepanyl, azocanyl, (imino)(oxo)thiazinanyl, (oxo)thiazinanyl and (dioxo)thiazinanyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable heterocycloalkenyl groups include thiazolinyl, imidazolinyl, dihydropyranyl, dihydrothiopyranyl and 1,2,3,6-tetrahydropyridinyl.

The term "$C_{4-9}$ heterobicycloalkyl" as used herein corresponds to $C_{4-9}$ bicycloalkyl wherein one or more of the carbon atoms have been replaced by one or more heteroatoms selected from oxygen, sulphur and nitrogen. Typical heterobicycloalkyl groups include 3-azabicyclo[3.1.0]hexanyl, 2-oxa-5-azabicyclo[2.2.1]heptanyl, 6-azabicyclo[3.2.0]heptanyl, 3-azabicyclo[3.1.1]heptanyl, 3-azabicyclo[4.1.0]heptanyl, 2-oxabicyclo[2.2.2]octanyl, quinuclidinyl, 2-oxa-5-azabicyclo-[2.2.2]octanyl, 3-azabicyclo[3.2.1]octanyl, 8-azabicyclo[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo[3.3.1]nonanyl 3,9-diazabicyclo[4.2.1]nonanyl, 3,7-dioxa-9-diazabicyclo-[3.3.1]nonanylanylheptanyl and 2,5-diazabicyclo-[2.2.1]heptanyl.

The term "$C_{4-9}$ spiroheterocycloalkyl" as used herein refers to saturated bicyclic ring systems containing 4 to 9 carbon atoms and at least one heteroatom selected from oxygen, sulphur and nitrogen, in which the two rings are linked by a common atom. Suitable spiroheterocycloalkyl groups include 5-azaspiro[2.3]hexanyl, 5-azaspiro-[2.4]heptanyl, 2-azaspiro[3.3]heptanyl, 2-oxa-6-azaspiro[3.3]heptanyl, 2-oxa-6-azaspiro-[3.4]octanyl, 2-oxa-6-azaspiro[3.5]nonanyl, 7-oxa-2-azaspiro[3.5]nonanyl, 2-oxa-7-azaspiro[3.5]nonanyl and 2,4,8-triazaspiro[4.5]decanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzofuryl, thienyl, benzothienyl, thieno[2,3-c]pyrazolyl, thieno[3,4-b][1,4]dioxinyl, dibenzothienyl, pyrrolyl, indolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-c]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of use in the invention possess two or more asymmetric centres, they may additionally exist as diastereomers. The invention is to be understood to extend to the use of all such enantiomers and diastereomers, and to mixtures thereof in any proportion, including racemates.

Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)↔enol ($CH=CHOH$) tautomers or amide ($NHC=O$)↔hydroxyimine ($N=COH$) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

Generally, Y represents $C_{3-7}$ cycloalkyl, aryl or heteroaryl, any of which groups may be optionally substituted by one or more substituents.

Typically, Y represents aryl or heteroaryl, either of which groups may be optionally substituted by one or more substituents.

In a first embodiment, Y represents optionally substituted $C_{3-7}$ cycloalkyl. In one aspect of that embodiment, Y represents unsubstituted $C_{3-7}$ cycloalkyl. In another aspect of that embodiment, Y represents monosubstituted $C_{3-7}$ cycloalkyl. In a further aspect of that embodiment, Y represents disubstituted $C_{3-7}$ cycloalkyl.

In a second embodiment, Y represents optionally substituted aryl. In one aspect of that embodiment, Y represents unsubstituted aryl. In another aspect of that embodiment, Y represents monosubstituted aryl. In a further aspect of that embodiment, Y represents disubstituted aryl.

In a third embodiment, Y represents optionally substituted $C_{3-7}$ heterocycloalkyl. In one aspect of that embodiment, Y represents unsubstituted $C_{3-7}$ heterocycloalkyl. In another aspect of that embodiment, Y represents monosubstituted $C_{3-7}$ heterocycloalkyl. In a further aspect of that embodiment, Y represents disubstituted $C_{3-7}$ heterocycloalkyl.

In a fourth embodiment, Y represents optionally substituted heteroaryl. In one aspect of that embodiment, Y represents unsubstituted heteroaryl. In another aspect of that embodiment, Y represents monosubstituted heteroaryl. In a further aspect of that embodiment, Y represents disubstituted heteroaryl.

Suitably, Y represents benzocyclobutenyl, phenyl, thienyl, thiazolyl, pyridinyl, pyrimidinyl or pyrazolyl any of which groups may be optionally substituted by one or more substituents.

Appropriately, Y represents phenyl, thienyl or thiazolyl, any of which groups may be optionally substituted by one or more substituents.

Appositely, Y represents phenyl, which may be optionally substituted by one or more substituents.

Examples of optional substituents which may be present on the moiety Y include one, two or three substituents independently selected from halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, $(C_{1-6})$alkylsulfonyloxy, amino, $C_{1-6}$ alkyl-amino, di($C_{1-6}$)alkylamino, arylamino, $C_{2-6}$ alkylcarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di($C_{1-6}$)alkyl-aminocarbonyl, aminosulfonyl, $C_{1-6}$ alkylaminosulfonyl and di($C_{1-6}$)alkylaminosulfonyl.

Examples of particular substituents on the moiety Y include fluoro, chloro, bromo, cyano, nitro, methyl, isopropyl, trifluoromethyl, hydroxy, methoxy, difluoromethoxy, trifluoromethoxy, methylthio, methylsulfinyl, methylsulfonyl, methylsulfonyloxy, amino, methylamino, tert-butylamino, dimethylamino, phenylamino, acetylamino, methylsulfonylamino, formyl, acetyl, cyclopropylcarbonyl, azetidinylcarbonyl, pyrrolidinyl-carbonyl, piperidinylcarbonyl, piperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl.

Typical examples of particular substituents on the moiety Y include chloro, fluoro, cyano, methoxy, methylsulphonyl, trifluoromethoxy and difluoromethoxy.

Typical values of Y include benzocyclobutenyl, phenyl, (methysulphonyl)phenyl (including 4-methylsulphonyl-phenyl), benzonitrile (including 2-benzonitrile, 3-benzonitrile and 4-benzonitrile), fluorophenyl (including 2-fluorophenyl, 3-fluorophenyl and 4-fluorophenyl), chlorophenyl (including 2-chloro-phenyl, 3-chlorophenyl and 4-chlorophenyl), difluorophenyl (including 2,6-difluoro-phenyl), (chloro)(fluoro)phenyl (including 5-chloro-2-fluorophenyl and 2-chloro-5-fluorophenyl), dichlorophenyl (including 2,5-dichlorophenyl and 2,6-dichlorophenyl), methylphenyl (including 4-methylphenyl), dimethylphenyl (including 2,5-dimethylphenyl and 2,6-dimethylphenyl), (trifluoromethyl)phenyl [including 2-(trifluoromethyl)phenyl], (chloro)(trifluoromethyl)phenyl [including 5-chloro-2-(trifluoromethyl)phenyl], (methyl)-(trifluoromethyl)phenyl [including 2-methyl-5-(trifluoromethyl)phenyl], bis(trifluoro-methyl)phenyl [including 2,5-bis(trifluoromethyl)phenyl], methoxyphenyl (including 2-methoxyphenyl), (difluoromethoxy)phenyl [including 2-(difluoromethoxy)phenyl, 3-(difluoromethoxy)phenyl and 4-(difluoromethoxy)phenyl], (bis-(difluoromethoxy))phenyl [including 2,5-(bis-(difluoromethoxy))-phenyl and including 2,6-(bis-(difluoromethoxy))-phenyl], (difluoromethoxy)(fluoro)phenyl [including 2-(difluoromethoxy)-5-fluorophenyl, 2-(difluoromethoxy)-3-fluorophenyl, 2-(difluoromethoxy)-6-fluorophenyl 5-(difluoromethoxy)-2-fluorophenyl, 2-(difluoromethoxy)-4-fluorophenyl, and 2-(difluoromethoxy)-5-fluorophenyl], (difluoromethoxy)(difluoro)phenyl [(including 2-difluoromethoxy-3,5-difluoro-phenyl and 2-difluoromethoxy-4,5-difluoro-phenyl)], (chloro)(difluoromethoxy)phenyl [including 2-chloro-5-(difluoromethoxy) phenyl, 5-chloro-2-(difluoromethoxy)phenyl, 5-chloro-3-(difluoromethoxy)phenyl, and 6-chloro-2-(difluoromethoxy)phenyl], (cyano) (difluoromethoxy) [including 6-cyano-2-(difluoromethoxy)-phenyl](trifluoromethoxy)phenyl [including 2-(trifluoromethoxy)-phenyl], methylsulfonyloxyphenyl], (chloro)(trifluoromethoxy)phenyl, [including 3-chloro-6-trifluoromethoxy-phenyl)], (amino)(chloro)phenyl [including 5-amino-2-chloro-phenyl)], methylthienyl [including 3-methylthien-2-yl], methylthiazolyl [including 2-methyl-1,3-thiazol-4-yl and 4-methyl-1,3-thiazol-4-yl], (chloro)thiazolyl (including 4-chloro-1,3-thiazolyl), (chloro)(methyl)thiazolyl [including 5-chloro-2-methyl-1,3-thiazol-4-yl], dimethylthiazolyl [including 2,4-dimethyl-1,3-thiazol-5-yl[, pyridinyl [including pyridin-3-yl and pyridin-4-yl], (methyl)(trifluoromethyphiazolyl [including 2-methyl-4-trifluoromethyl-1,3-thiazolyl], (dimethoxy)pyrimidinyl [including 4,6-dimethoxy-pyridin-5-yl] and (methoxy)pyrazinyl (including 5-methoxypyrazinyl).

Selected values of Y include phenyl, (methysulphonyl) phenyl, benzonitrile chlorophenyl, (chloro)(fluoro)phenyl, dichlorophenyl, dimethylphenyl, (trifluoromethyl)phenyl, (difluoromethoxy)phenyl, (bis-(difluoromethoxy))phenyl (difluoromethoxy)(fluoro)phenyl, (difluoromethoxy)(cyano) phenyl, (difluoromethoxy)(difluoro)phenyl, (chloro)(difluoromethoxy)phenyl, (chloro)(trifluoromethoxy)phenyl, (chloro)(methyl)thiazolyl, (chloro)thiazolyl, (methyl)(trifluoromethyl)thiazolyl, (dimethoxy)pyrimidinyl and (methoxy)pyrazinyl. Additional value of Y include (methoxy)phenyl.

Definitive values of Y include (difluoromethoxy)phenyl, (difluoromethoxy)(fluoro)phenyl, (chloro)(difluoromethoxy)phenyl and (difluoromethoxy)(cyano)phenyl, (methoxy)phenyl, (difluromethoxy)(difluoro)phenyl, and (chloro)phenyl.

Particular values of Y include (difluoromethoxy)phenyl, (difluoromethoxy)(fluoro)phenyl, (chloro)(difluoromethoxy)phenyl and (difluoromethoxy)(cyano)phenyl.

Illustrative values of Y include 2-difluoromethoxy-phenyl, 2-difluoromethoxy-5-chloro-phenyl, 2-difluoromethoxy-6-chloro-phenyl, 2-difluoromethoxy-6-fluoro-phenyl, and 2-difluoromethoxy-6-cyano-phenyl, 2-methoxy-phenyl, 3-chloro-phenyl, 2-difluoromethoxy-4,5-difluoro-phenyl, 2-difluoromethoxy-5-fluoro-phenyl and 2)difluoromethoxy-4-fluoro-phenyl.

Specific values of Y include 2-difluoromethoxy-phenyl, 2-difluoromethoxy-5-chloro-phenyl, 2-difluoromethoxy-6-chloro-phenyl, 2-difluoromethoxy-6-fluoro-phenyl, and 2-difluoromethoxy-6-cyano-phenyl.

In a particular embodiment, Y represents 2-(difluoromethoxy)phenyl.

In another particular embodiment, Y represents 2-difluoromethoxy-5-chloro-phenyl.

Generally, Z represents a heteroatom; —S(O), —S(O)$_2$, —S(O)(N—R$^d$), —NC(O)R$^d$, —N(CO)—OR$^d$, —NS(O)$_2$R$^d$, or —N(R$^d$); or an optionally substituted straight or branched $C_{1-4}$alkylene chain;

Particularly, Z represents an optionally substituted straight or branched $C_{1-4}$ alkylene chain.

In a first embodiment, Z represents an heteroatom. In one aspect of that embodiment Z represents an oxygen. In a second aspect of that embodiment, Z represents a sulphur. In a second embodiment, Z represents —S(O). In a third embodiment, Z represents —S(O)$_2$. In a fourth embodiment, Z represents S(O)(N—R$^d$). In a fifth embodiment, Z represents —NC(O)R$^d$. In a sixth embodiment, Z represents —N(CO)—OR$^d$.

In an seventh embodiment, Z represents —NS(O)$_2$R$^d$. In an eighth embodiment, Z represents —N(R$^d$).

In a ninth embodiment, Z represents an optionally substituted straight or branched $C_{1-4}$ alkylene chain. Typical values of Z according to this embodiment include methylene (—CH$_2$—), (methyl)methylene, ethylene (—CH$_2$CH$_2$—), (ethyl)methylene, (dimethyl)-methylene, (methyl)ethylene, propylene (—CH$_2$CH$_2$CH$_2$—), (propyl)methylene and (dimethyl)ethylene, any of which chains may be optionally substituted by one or more substituents. In one aspect of this embodiment Z represents an unsubstituted straight or branched $C_{1-4}$ alkylene chain. In a second aspect of this embodiment, Z represents a monosubstituted straight or branched $C_{1-4}$ alkylene chain. In a third aspect of this embodiment, Z represents a disubstituted straight or branched $C_{1-4}$ alkylene chain.

In a tenth embodiment, Z represents carbonyl.

Examples of typical substituents on the alkylene chain which may be present in a compound in accordance with the invention include halogen, hydroxy, oxo, $C_{1-6}$ alkoxy, aryl, —C(O)R$^d$, —CO$_2$R$^d$, —CONR$^b$R$^c$—S(O)(N—R$^d$)R$^a$, and —SO$_2$NR$^b$R$^c$.

A particular value of Z is methylene.

Suitably, R$^1$ and R$^2$ independently represent hydrogen, halogen, cyano, trifluoromethyl; —S(O)$_2$(N—R$^d$), or —CO$_2$R$^d$; or $C_{1-6}$ alkyl, $C_{2-6}$ alkynyl, aryl, $C_{3-7}$ heterocycloalkyl, $C_{3-7}$ heterocycloalkenyl, heteroaryl, ($C_{3-7}$)heterocycloalkyl($C_{1-6}$)alkyl-aryl-, heteroaryl-($C_{3-7}$)heterocycloalkyl-, ($C_{3-7}$)cycloalkyl-heteroaryl-, ($C_{3-7}$)cycloalkyl ($C_{1-6}$)alkyl-heteroaryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents.

Typically, R$^2$ represents hydrogen, halogen, cyano, nitro, hydroxy, trifluoromethyl, trifluoromethoxy or —OR$^a$; or $C_{1-6}$ alkyl optionally substituted by one or more substituents.

Generally, R$^3$ represents hydrogen, halogen, cyano, nitro, hydroxy, trifluoromethyl, trifluoromethoxy; —OR$^a$, —SR$^a$, —SOR$^a$, or —SO$_2$R$^a$; or $C_{1-6}$ alkyl optionally substituted by one or more substituents.

Typically, R$^3$ represents hydrogen, halogen, cyano, nitro, hydroxy, trifluoromethyl, trifluoromethoxy or —OR$^a$; or $C_{1-6}$ alkyl optionally substituted by one or more substituents.

Generally, R$^4$ represents hydrogen, halogen, cyano, nitro, hydroxy, trifluoromethyl, trifluoromethoxy; —OR$^a$, —SR$^a$, —SOR$^a$, or —SO$_2$R$^a$; or $C_{1-6}$ alkyl optionally substituted by one or more substituents Typically, R$^4$ represents hydrogen, halogen, cyano, nitro, hydroxy, trifluoromethyl, trifluoromethoxy or —OR$^a$; or $C_{1-6}$ alkyl optionally substituted by one or more substituents.

Generally, R$^{5a}$ represents hydrogen, hydroxy, halogen, cyano, trifluoromethyl; —NR$^b$R$^c$, —NR$^c$C(O)R$^d$, —(CO)NR$^c$R$^d$, —NHS(O)$_2$R$^e$, —S—R$^a$, —(SO)—R$^a$, —S(O)$_2$R$^a$, —S(O)(N—R$^d$), —S(O)$_2$(N—R$^d$), —OR$^a$, —C(O)2R$^d$, or —O(CO)—R$^d$—; or C$_{1-6}$ alkyl, C$_{2-6}$ alkenyl, C$_{2-6}$ alkynyl, aryl, or heteroaryl, any of which groups may be optionally substituted by one or more substituents.

Generally, R$^{5b}$ represents hydrogen, hydroxy, halogen, cyano, trifluoromethyl; —NR$^b$R$^c$, —NR$^c$C(O)R$^d$, —(CO)NR$^c$R$^d$, —NHS(O)$_2$R$^e$, —S—R$^a$, —(SO)—R$^a$, —S(O)$_2$R$^a$, —S(O)(N—R$^d$), —S(O)$_2$(N—R$^d$), —OR$^a$, —C(O)$_2$R$^d$, or —O(CO)—R$^d$—; or C$_{1-6}$ alkyl, C$_{2-6}$ alkenyl, C$_{2-6}$ alkynyl, aryl, or heteroaryl, any of which groups may be optionally substituted by one or more substituents.

Suitably, R$^{5a}$ represents hydrogen, hydroxy, halogen, cyano, trifluoromethyl; —NR$^b$R$^c$, —NR$^c$C(O)R$^d$, —(CO)NR$^c$R$^d$, —NHS(O)$_2$R$^e$, —S—R$^a$, —(SO)—R$^a$, —S(O)$_2$R$^a$, —S(O)(N—R$^d$), —S(O)$_2$(N—R$^d$), —OR$^a$, —C(O)2R$^d$, or —O(CO)—R$^d$—; or C$_{1-6}$ alkyl, C$_{2-6}$ alkenyl, C$_{2-6}$ alkynyl, aryl, heteroaryl, any of which groups may be optionally substituted by one or more substituents.

R$^{5b}$ represents hydrogen, hydroxy, halogen, cyano, or trifluoromethyl; or C$_{1-6}$ alkyl, any of which groups may be optionally substituted by one or more substituents.

Alternatively, R$^{5a}$ and R$^{5b}$ when taken together with the carbon to which they are attached represent a carbonyl, thiocarbonyl, or —C=N—OH.

Generally, R$^6$ represents hydrogen, hydroxy, halogen, cyano, trifluoromethyl; —NR$^b$R$^c$, —NR$^c$C(O)R$^d$, —(CO)NR$^c$R$^d$, —NHS(O)$_2$R$^e$, —S—R$^a$, —(SO)—R$^a$, —S(O)$_2$R$^a$, —S(O)(N—R$^d$), —S(O)$_2$(N—R$^d$), —OR$^a$, —C(O)2R$^d$, or —O(CO)—R$^d$—; or C$_{1-6}$ alkyl, C$_{2-6}$ alkenyl, C$_{2-6}$ alkynyl, aryl, heteroaryl, any of which groups may be optionally substituted by one or more substituents.

Examples of optional substituents which may be present on R$^1$, R$^2$, R$^3$, R$^4$ R$^{5a}$, R$^{5b}$ and R$^6$ include one, two or three substituents independently selected from halogen, halo-(C$_{1-6}$)alkyl, cyano, cyano(C$_{1-6}$)alkyl, nitro, nitro(C$_{1-6}$)alkyl, C$_{1-6}$ alkyl, (C$_{3-7}$)cycloalkyl, difluoromethyl, trifluoromethyl, difluoroethyl, trifluoroethyl, C$_{2-6}$ alkenyl, hydroxy, hydroxy(C$_{1-6}$)alkyl, C$_{1-6}$ alkoxy, difluoromethoxy, trifluoromethoxy, trifluoroethoxy, carboxy(C$_{3-7}$)cycloalkyl-oxy, C$_{1-3}$ alkylenedioxy, C$_{1-6}$ alkoxy(C$_{1-6}$)alkyl, C$_{1-6}$ alkylthio, C$_{1-6}$alkylsulphinyl, C$_{1-6}$ alkylsulphonyl, (C$_{1-6}$)alkylsulphonyl(C$_{1-6}$) alkyl, oxo, amino, amino(C$_{1-6}$)alkyl, C$_{1-6}$ alkyl-amino, di(C$_{1-6}$)alkylamino, hydroxy(C$_{1-6}$)alkylamino, C$_{1-6}$ alkoxyamino, (C$_{1-6}$)alkoxy-(C$_{1-6}$)alkylamino, [(C$_{1-6}$)alkoxy](hydroxy)(C$_{1-6}$)alkylamino, [(C$_{1-6}$)alkylthio](hydroxy)-(C$_{1-6}$)alkylamino, N—[(C$_{1-6}$)alkyl]-N-[hydroxy(C$_{1-6}$)alkyl]amino, di(C$_{1-6}$)alkylamino-(C$_{1-6}$)alkylamino, N-[di(C$_{1-6}$)alkylamino(C$_{1-6}$)alkyl]-N-[hydroxy(C$_{1-6}$)alkyl]amino, hydroxy(C$_{1-6}$)alkyl(C$_{3-7}$)cycloalkylamino, (hydroxy)[(C$_{3-7}$)cycloalkyl(C$_{1-6}$)alkyl]amino, (C$_{3-7}$)heterocycloalkyl(C$_{1-6}$)alkylamino, oxo(C$_{3-7}$)heterocycloalkyl(C$_{1-6}$) alkylamino, (C$_{1-6}$)alkylheteroarylamino, heteroaryl(C$_{1-6}$) alkylamino, (C$_{1-6}$)alkylheteroaryl(C$_{1-6}$)alkyl-amino, C$_{2-6}$ alkylcarbonylamino, N—[(C$_{1-6}$)alkyl]-N—[(C$_{2-6}$)alkylcarbonyl]amino, (C$_{2-6}$)alkyl-carbonylamino(C$_{1-6}$)alkyl, C$_{3-6}$ alkenylcarbonylamino, bis[(C$_{3-6}$)alkenylcarbonyl]amino, N—[(C$_{1-6}$)alkyl]-N—[(C$_{3-7}$)cycloalkylcarbonyl]amino, C$_{2-6}$ alkoxycarbonylamino, C$_{2-6}$ alkoxycarbonyl(C$_{1-6}$)alkylamino, C$_{1-6}$ alkylaminocarbonylamino, C$_{1-6}$ alkylsulphonyl-amino, N—[(C$_{1-6}$)alkyl]-N—[(C$_{1-6}$)alkylsulphonyl]amino, bis[(C$_{1-6}$)alkylsulphonyl]amino, N—[(C$_{1-6}$)alkyl]-N-[carboxy(C$_{1-6}$)alkyl]amino, carboxy(C$_{3-7}$)cycloalkylamino, carboxy-(C$_{3-7}$)cycloalkyl(C$_{1-6}$) alkylamino, formyl, C$_{2-6}$ alkylcarbonyl, (C$_{3-7}$) cycloalkylcarbonyl, phenylcarbonyl, (C$_{2-6}$) alkylcarbonyloxy(C$_{1-6}$)alkyl, carboxy, carboxy(C$_{1-6}$)alkyl, C$_{2-6}$ alkoxycarbonyl, C$_{2-6}$ alkoxycarbonyl(C$_{1-6}$)alkyl, morpholinyl(C$_{1-6}$)alkoxycarbonyl, C$_{2-6}$ alkoxycarbonylmethylidenyl, a carboxylic acid isostere or prodrug moiety Ω, —(C$_{1-6}$)alkyl-Ω, aminocarbonyl, C$_{1-6}$ alkylaminocarbonyl, hydroxy(C$_{1-6}$)alkylamino-carbonyl, di(C$_{1-6}$)alkylaminocarbonyl, aminocarbonyl(C$_{1-6}$)alkyl, aminosulphonyl, di(C$_{1-6}$) alkylaminosulphonyl, (C$_{1-6}$)alkylsulphoximinyl, [(C$_{1-6}$) alkyl][N—(C$_{1-6}$)alkyl]-sulphoximinyl and heteroaryl. An additional example of substituent include C$_{3-7}$cycloalkylsulphonyl.

By the expression "carboxylic acid isostere or prodrug moiety" is meant any functional group, structurally distinct from a carboxylic acid moiety, that will be recognised by a biological system as being similar to, and thus capable of mimicking, a carboxylic acid moiety, or will be readily convertible by a biological system in vivo into a carboxylic acid moiety. A synopsis of some common carboxylic acid isosteres is presented by N. A. Meanwell in *J. Med. Chem.,* 2011, 54, 2529-2591 (cf. in particular FIGS. 25 and 26). An alternative carboxylic acid isostere is described by N Pemberton et al. in *ACS Med. Chem. Lett.,* 2012, 3, 574-578. Typical examples of suitable carboxylic acid isostere or prodrug moieties represented by Ω include the functional groups of formula (i) to (xliii):

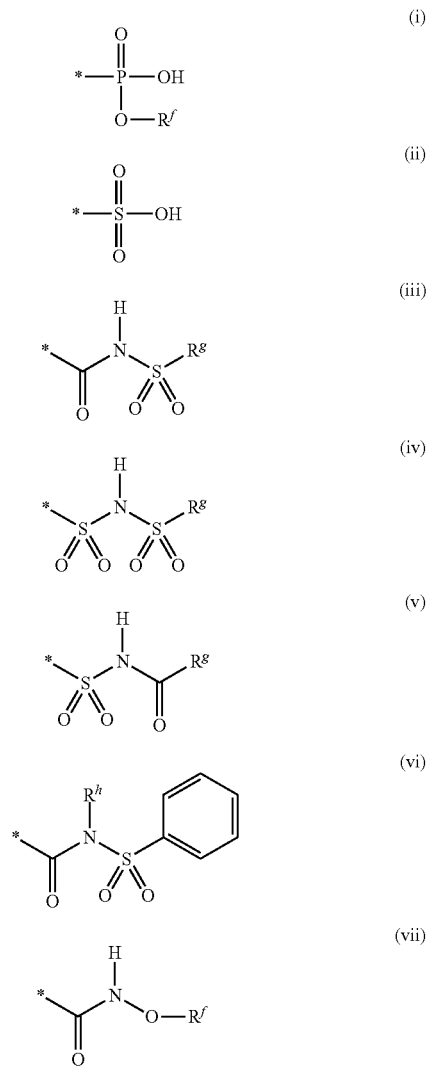

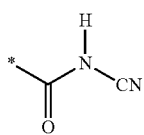 (viii)
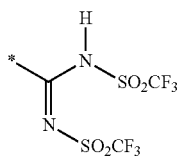 (ix)
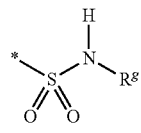 (x)
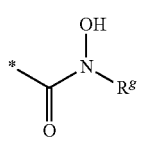 (xi)
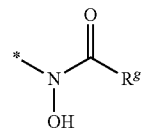 (xii)
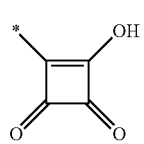 (xiii)
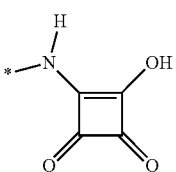 (xiv)
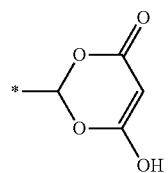 (xv)
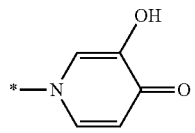 (xvi)
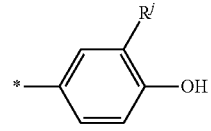 (xvii)
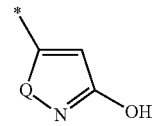 (xviii)
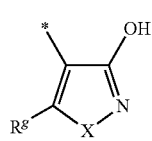 (xix)
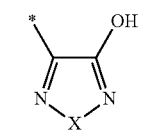 (xx)
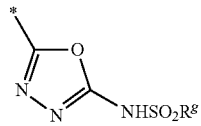 (xxi)
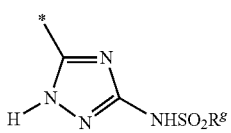 (xxii)
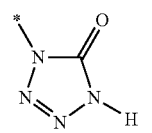 (xxiii)
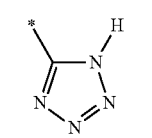 (xxiv)
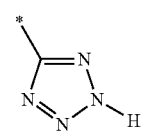 (xxv)
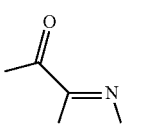 (xxvi)
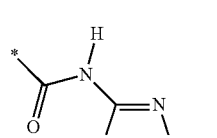 (xxvii)
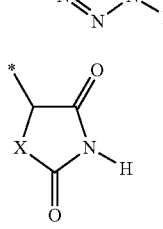 (xxviii)

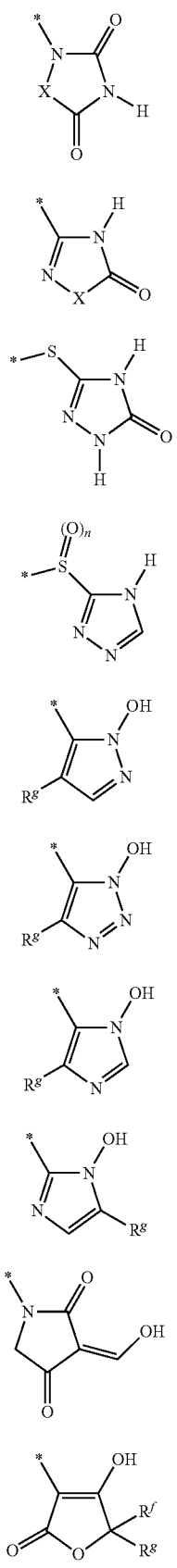
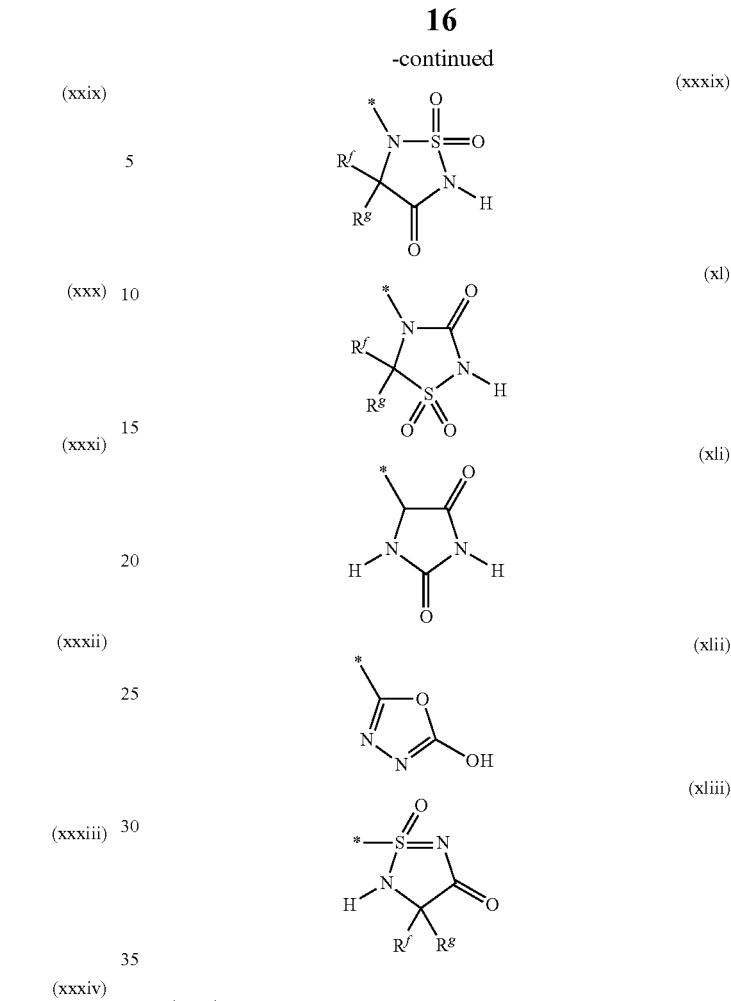

wherein
the asterisk (*) represents the site of attachment to the remainder of the molecule;
n is zero, 1 or 2;
X represents oxygen or sulphur;
$R^f$ represents hydrogen, $C_{1-6}$ alkyl or —CH$_2$CH(OH)CH$_2$OH;
$R^g$ represents $C_{1-6}$ alkyl, trifluoromethyl, —CH$_2$CH$_2$F, —CH$_2$CHF$_2$, —CH$_2$CF$_3$ or —CF$_2$CF$_3$;
$R^h$ represents hydrogen, cyano or —CO$_2$R$^d$, in which $R^d$ is as defined above; and
$R^j$ represents hydrogen or halogen.

In one embodiment, n is zero. In another embodiment, n is 1. In a further embodiment, n is 2.

In one embodiment, X represents oxygen. In another embodiment, X represents sulphur.

In one embodiment, $R^f$ represents hydrogen. In another embodiment, $R^f$ represents $C_{1-6}$ alkyl, especially methyl. In a further embodiment, $R^f$ is —CH$_2$CH(OH)CH$_2$OH.

In one embodiment, $R^g$ represents $C_{1-6}$ alkyl, especially methyl. In another embodiment, $R^g$ represents trifluoromethyl, —CH$_2$CH$_2$F, —CH$_2$CHF$_2$, —CH$_2$CF$_3$ or —CF$_2$CF$_3$. In a first aspect of that embodiment, $R^g$ represents trifluoromethyl. In a second aspect of that embodiment, $R^g$ represents —CH$_2$CH$_2$F. In a third aspect of that embodiment, $R^g$ represents —CH$_2$CHF$_2$. In a fourth aspect of that embodiment, $R^g$ represents —CH$_2$CF$_3$. In a fifth aspect of that embodiment, $R^g$ represents —CF$_2$CF$_3$.

In one embodiment, $R^h$ is hydrogen. In another embodiment, $R^h$ represents cyano. In a further embodiment, $R^h$ represents —CO$_2$R$^d$, especially methoxycarbonyl.

In one embodiment, $R^j$ represents hydrogen. In another embodiment, $R^j$ represents halogen, especially chloro.

In a selected embodiment, $\Omega$ represents tetrazolyl, especially a C-linked tetrazolyl moiety of formula (xxiv) or (xxv) as depicted above, in particular a group of formula (xxiv) as depicted above.

In another embodiment, $\Omega$ represents $C_{1-6}$ alkylsulphonylaminocarbonyl, i.e. a moiety of formula (iii) as depicted above wherein $R^g$ represents $C_{1-6}$ alkyl.

In another embodiment, $\Omega$ represents $C_{1-6}$ alkylaminosulphonyl, i.e. a moiety of formula (x) as depicted above wherein $R^g$ represents $C_{1-6}$ alkyl.

In a further embodiment, $\Omega$ represents $(C_{1-6})$alkylcarbonylaminosulphonyl, i.e. a moiety of formula (v) as depicted above wherein $R^g$ represents $C_{1-6}$ alkyl.

Examples of particular substituents on $R^1$, $R^2$, $R^3$, $R^4$ $R^{5a}$, $R^{5b}$ and $R^6$ include fluoro, chloro, bromo, fluoromethyl, fluoroisopropyl, cyano, cyanoethyl, nitro, nitromethyl, methyl, ethyl, isopropyl, isobutyl, tert-butyl, cyclopropyl, cyclobutyl, difluoromethyl, trifluoromethyl, difluoroethyl, trifluoro-ethyl, ethenyl, hydroxy, hydroxymethyl, hydroxyisopropyl, methoxy, isopropoxy, difluoromethoxy, trifluoromethoxy, trifluoroethoxy, carboxycyclobutyloxy, methylene-dioxy, ethylenedioxy, methoxymethyl, methoxyethyl, methylthio, methylsulphinyl, methylsulphonyl, methylsulphonylethyl, oxo, amino, aminomethyl, aminoisopropyl, methylamino, ethylamino, dimethylamino, hydroxyethylamino, hydroxypropylamino, (hydroxy)(methyl)propylamino, methoxyamino, methoxyethylamino, (hydroxy)-(methoxy)(methyl)propylamino, (hydroxy)(methylthio) butylamino, N-(hydroxyethyl)-N-(methyl)amino, dimethylaminoethylamino, (dimethylamino)(methyl)propylamino, N-(dimethylaminoethyl)-N-(hydroxyethyl)amino, hydroxymethylcyclopentylamino, hydroxycyclobutylmethylamino, (cyclopropyl)(hydroxy)propylamino, morpholinylethyl-amino, oxopyrrolidinylmethylamino, ethyloxadiazolylamino, methylthiadiazolylamino, thiazolylmethylamino, thiazolylethylamino, pyrimidinylmethylamino, methylpyrazolyl-methylamino, acetylamino, N-acetyl-N-methylamino, N-isopropylcarbonyl-N-methyl-amino, acetylaminomethyl, ethenylcarbonylamino, bis(ethenylcarbonyl)amino, N-cyclopropylcarbonyl-N-methylamino, methoxycarbonylamino, ethoxycarbonylamino, tert-butoxycarbonylamino, methoxycarbonylethylamino, ethylaminocarbonylamino, butylaminocarbonylamino, methylsulphonylamino, N-methyl-N-(methylsulphonyl) amino, bis(methylsulphonyl)amino, N-(carboxymethyl)-N-methylamino, N-(carboxyethyl)-N-methylamino, carboxycyclopentylamino, carboxycyclopropylmethylamino, formyl, acetyl, isopropylcarbonyl, cyclobutylcarbonyl, phenylcarbonyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, methylsulphonylamino-carbonyl, acetylaminosulphonyl, methoxyaminocarbonyl, tetrazolyl, tetrazolylmethyl, hydroxyoxadiazolyl, aminocarbonyl, methylamino carbonyl, hydroxyethylamino carbonyl, dimethylaminocarbonyl, aminocarbonylmethyl, aminosulphonyl, methylaminosulphonyl, dimethylaminosulphonyl, methylsulphoximinyl, (methyl)(N-methyl)sulphoximinyl and triazolyl. Additional examples of particular substituent include cyclopropylsulphonyl and tert-butoxy.

Suitable examples of particular substituents on $R^1$, $R^2$, $R^3$, $R^4$ $R^{5a}$, $R^{5b}$ and $R^6$ include fluoro, hydroxy, methyl-sulphonyl, methyl, trifluoromethyl, isopropyl, cyclopropyl, methoxy, ethoxycarbonyl, methylsulphoximinyl, oxo, carboxy, acetyl, chloro, hydroxyisopropyl, fluoroisopropyl, aminoisopropyl, methylsulphonyl, methylsulphinyl cyclopropylsulphonyl and tert-butoxy.

Typical examples of particular substituents on $R^1$, $R^2$, $R^3$, $R^4$, $R^{5a}$, $R^{5b}$ and $R^6$ include fluoro, hydroxy, methyl-sulphonyl, methyl, trifluoromethyl, isopropyl, cyclopropyl, methoxy, ethoxycarbonyl, methylsulphoximinyl, oxo, carboxy and acetyl.

Typically, $R^1$ represents hydrogen, halogen, cyano or —$CO_2R^d$; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl($C_{1-6}$)alkyl-aryl-, heteroaryl($C_{3-7}$)heterocycloalkyl-, $(C_{3-7})$cycloalkyl-heteroaryl-, $(C_{3-7})$cycloalkyl ($C_{1-6}$)alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl($C_{1-6}$)alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents.

Suitably, $R^1$ represents halogen, cyano or —$CO_2R^d$; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl-($C_{1-6}$)alkyl-aryl-, heteroaryl($C_{3-7}$)heterocycloalkyl-, $(C_{3-7})$ cycloalkyl-heteroaryl-, $(C_{3-7})$cycloalkyl($C_{1-6}$)alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$ heterocycloalkyl($C_{1-6}$)alkyl-heteroaryl-, $(C_{3-7})$ heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents.

Generally, $R^1$ represents halogen or cyano; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl($C_{1-6}$)alkyl-aryl-, heteroaryl($C_{3-7}$)heterocycloalkyl-, $(C_{3-7})$cycloalkyl-heteroaryl-, $(C_{3-7})$cycloalkyl-($C_{1-6}$)alkyl-heteroaryl-, $(C_{4-7})$ cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl ($C_{1-6}$)alkyl-heteroaryl-, $(C_{3-7})$heterocycloalkenyl-heteroaryl-, $(C_{4-9})$heterobicycloalkyl-heteroaryl- or $(C_{4-9})$ spiroheterocycloalkyl-heteroaryl-, any of which groups may be optionally substituted by one or more substituents.

More generally, $R^1$ represents aryl, $C_{3-7}$ heterocycloalkenyl, heteroaryl, $(C_{3-7})$heterocycloalkyl-heteroaryl-, $(C_{4-9})$ heterobicycloalkyl-heteroaryl-, $(C_{3-7})$cycloalkyl-heteroaryl-, or $(C_{4-9})$bicycloalkyl-heteroaryl-, any of which groups may be optionally substituted by one or more substituents.

Apositely, $R^1$ represents aryl, heteroaryl, or $(C_{3-7})$heterocycloalkyl-heteroaryl-, any of which groups may be optionally substituted by one or more substituents.

In a first embodiment, $R^1$ represents hydrogen.

In a second embodiment, $R^1$ represents halogen. In one aspect of that embodiment, $R^1$ represents bromo.

In a third embodiment, $R^1$ represents cyano.

In a fourth embodiment, $R^1$ represents —$CO_2R^d$.

In a fifth embodiment, $R^1$ represents optionally substituted $C_{1-6}$ alkyl. In one aspect of that embodiment, $R^1$ represents optionally substituted methyl. In another aspect of that embodiment, $R^1$ represents optionally substituted ethyl.

In a sixth embodiment, $R^1$ represents optionally substituted $C_{2-6}$ alkynyl. In one aspect of that embodiment, $R^1$ represents optionally substituted butynyl.

In a seventh embodiment, $R^1$ represents optionally substituted aryl. In one aspect of that embodiment, $R^1$ represents optionally substituted phenyl.

In an eighth embodiment, $R^1$ represents optionally substituted $C_{3-7}$ heterocycloalkyl.

In a ninth embodiment, $R^1$ represents optionally substituted $C_{3-7}$ heterocycloalkenyl. In one aspect of this embodiment, $R^1$ represents optionally substituted pyridine-2(1H)-one.

In a tenth embodiment, $R^1$ represents optionally substituted heteroaryl. In selected aspects of that embodiment, $R^1$ represents benzofuryl, thienyl, indolyl, pyrazolyl, indazolyl, isoxazolyl, thiazolyl, imidazolyl, pyridinyl, quinolinyl, pyridazinyl, pyrimidinyl or pyrazinyl, any of which groups may be optionally substituted by one or more substituents. In a first particular aspect of that embodiment, $R^1$ represents optionally substituted pyrimidinyl. In a second particular aspect of that embodiment, $R^1$ represents optionally substituted pyridinyl.

In an eleventh embodiment, $R^1$ represents optionally substituted $(C_{3-7})$-heterocycloalkyl($C_{1-6}$)alkyl-aryl-. In a first aspect of that embodiment, $R^1$ represents optionally substituted pyrrolidinylmethylphenyl-. In a second aspect of that embodiment, $R^1$ represents optionally substituted piperazinylmethylphenyl-.

In a twelfth embodiment, $R^1$ represents optionally substituted heteroaryl($C_{3-7}$)-heterocycloalkyl-. In one aspect of that embodiment, $R^1$ represents optionally substituted pyridinylpiperazinyl-.

In a thirteenth embodiment, $R^1$ represents optionally substituted $(C_{3-7})$cycloalkyl-heteroaryl-. In a first aspect of that embodiment, $R^1$ represents optionally substituted cyclohexylpyrazolyl-. In a second aspect of that embodiment, $R^1$ represents optionally substituted cyclohexylpyridinyl-. In a third aspect of that embodiment, $R^1$ represents optionally substituted cyclopropylpyrimidinyl-. In a fourth aspect of that embodiment, $R^1$ represents optionally substituted cyclobutylpyrimidinyl-. In a fifth aspect of that embodiment, $R^1$ represents optionally substituted cyclopentylpyrimidinyl-. In a sixth aspect of that embodiment, $R^1$ represents optionally substituted cyclohexylpyrimidinyl-. In a seventh aspect of that embodiment, $R^1$ represents optionally substituted cyclohexyl-pyrazinyl-. In an eighth aspect of that embodiment, $R^1$ represents optionally substituted cyclopropylpyridinyl In a fourteenth embodiment, $R^1$ represents optionally substituted $(C_{4-7})$-cyclo alkenyl-heteroaryl-.

In a fifteenth embodiment, $R^1$ represents optionally substituted $(C_{3-7})$-heterocycloalkyl-heteroaryl-. In a first aspect of that embodiment, $R^1$ represents optionally substituted pyrrolidinylpyridinyl-. In a second aspect of that embodiment, $R^1$ represents optionally substituted tetrahydropyranylpyridinyl-. In a third aspect of that embodiment, $R^1$ represents optionally substituted piperidinylpyridinyl-. In a fourth aspect of that embodiment, $R^1$ represents optionally substituted piperazinylpyridinyl-. In a fifth aspect of that embodiment, $R^1$ represents optionally substituted morpholinylpyridinyl-. In a sixth aspect of that embodiment, $R^1$ represents optionally substituted thiomorpholinyl-pyridinyl-. In a seventh aspect of that embodiment, $R^1$ represents optionally substituted diazepanylpyridinyl-. In an eighth aspect of that embodiment, $R^1$ represents optionally substituted oxetanylpyrimidinyl-. In a ninth aspect of that embodiment, $R^1$ represents optionally substituted azetidinylpyrimidinyl-. In a tenth aspect of that embodiment, $R^1$ represents optionally substituted tetrahydrofuranylpyrimidinyl-. In an eleventh aspect of that embodiment, $R^1$ represents optionally substituted pyrrolidinylpyrimidinyl-. In a twelfth aspect of that embodiment, $R^1$ represents optionally substituted tetrahydropyranyl-pyrimidinyl-. In a thirteenth aspect of that embodiment, $R^1$ represents optionally substituted piperidinylpyrimidinyl-. In a fourteenth aspect of that embodiment, $R^1$ represents optionally substituted piperazinylpyrimidinyl-. In a fifteenth aspect of that embodiment, $R^1$ represents optionally substituted morpholinylpyrimidinyl-. In a sixteenth aspect of that embodiment, $R^1$ represents optionally substituted thiomorpholinyl-pyrimidinyl-. In a seventeenth aspect of that embodiment, $R^1$ represents optionally substituted azepanylpyrimidinyl-. In an eighteenth aspect of that embodiment, $R^1$ represents optionally substituted oxazepanylpyrimidinyl-. In a nineteenth aspect of that embodiment, $R^1$ represents optionally substituted diazepanylpyrimidinyl-. In a twentieth aspect of that embodiment, $R^1$ represents optionally substituted thiadiazepanyl-pyrimidinyl-. In a twenty-first aspect of that embodiment, $R^1$ represents optionally substituted oxetanylpyrazinyl-. In a twenty-second aspect of that embodiment, $R^1$ represents optionally substituted piperidinylpyrazinyl-. In a twenty-third aspect of that embodiment, $R^1$ represents optionally substituted tetrahydropyranylpyridinyl. In a twenty-fourth aspect of this embodiment, $R^1$ represents tetrahydro-thiopyranylpyrimidinyl. In a twenty-fifth aspect of this embodiment, $R^1$ represents (imino)(oxo)thiazinanyl-pyrimidinyl. In a twenty-sixth aspect of this embodiment, $R^1$ represents (oxo)thiazinanyl-pyrimidinyl. In a twenty-seventh aspect of this embodiment, $R^1$ represents (dioxo)thiazinanyl-pyrimidinyl.

In a sixteenth embodiment, $R^1$ represents optionally substituted $(C_{3-7})$-heterocycloalkyl($C_{1-6}$)alkyl-heteroaryl-. In a first aspect of that embodiment, $R^1$ represents optionally substituted morpholinylmethylthienyl-. In a second aspect of that embodiment, $R^1$ represents optionally substituted morpholinylethylpyrazolyl-.

In a seventeenth embodiment, $R^1$ represents optionally substituted $(C_{3-7})$-heterocycloalkenyl-heteroaryl-.

In an eighteenth embodiment, $R^1$ represents optionally substituted $(C_{4-9})$-heterobicycloalkyl-heteroaryl-. In a first aspect of this embodiment, $R^1$ represents optionally substituted 3-azabicyclo[3.2.1]octanyl-pyrimidinyl. In a second aspect of this embodiment, $R^1$ represents optionally substituted 3-oxa-8-azabicyclo-[3.2.1]octanyl-pyrimidinyl. In a third aspect of this embodiment, $R^1$ represents optionally substituted 3,7-dioxa-9-azabicyclo[3.3.1]nonanyl-pyrimidnyl. In fourth aspect of this embodiment, R' represents optionally substituted 2,5-diazabicyclo[2.2.1]heptanyl-pyrimidnyl.

In a nineteenth embodiment, $R^1$ represents optionally substituted $(C_{4-9})$-spiroheterocycloalkyl-heteroaryl-.

In a twentieth embodiment, $R^1$ represents optionally substituted $(C_{3-7})$cycloalkyl-($C_{1-6}$)alkyl-heteroaryl-. In one aspect of that embodiment, $R^1$ represents optionally substituted cyclohexylmethylpyrimidinyl-.

In a twenty-first embodiment, $R^1$ represents optionally substituted $(C_{4-9})$-bicycloalkyl-heteroaryl-. In a particular aspect of this embodiment, $R^1$ represents optionally substituted bicyclo[3.1.0]hexanyl-pyrimidinyl.

In a twenty-second embodiment, $R^1$ represents optionally substituted $(C_{4-9})$-bicycloalkenyl-heteroaryl-.

Appositely, $R^1$ represents hydrogen, bromo, cyano or $-CO_2R^d$; or ethyl, butynyl, phenyl, pyrrolidinyl, piperidinyl, piperazinyl, morpholinyl, 1,2,3,6-tetrahydropyridinyl, 3,6-dihydropyridinyl, benzofuryl, thienyl, indolyl, pyrazolyl, indazolyl, isoxazolyl, thiazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, cyclohexylpyrazolyl, cyclohexylpyridinyl, cyclopropylpyrimidinyl, cyclobutylpyrimidinyl, cyclopentylpyrimidinyl, cyclohexyl-pyrimidinyl, cyclohexylpyrazinyl, cyclohexylmethylpyrimidinyl, cyclohexenylpyridinyl, cyclopropylpyridinyl, cyclohexenylpyrimidinyl, bicyclo[3.1.0]hexanylpyridinyl, bicyclo[3.1.0]hexanyl-pyrimidinyl, bicyclo[3.1.0]hexenyl-pyrimidinyl bicyclo[4.1.0]heptanylpyrimidinyl, bicyclo[2.2.2]octanylpyrimidinyl, pyrrolidinylpyridinyl, tetrahydropyranylpyridinyl, tetrahydro-thiopyranylpyrimidinyl, piperidinylpyridinyl, piperazinyl-pyridinyl, morpholinylpyridinyl, thiomorpholinylpyridinyl, diazepanylpyridinyl, oxetanylpyrimidinyl, azetidinylpyrimidinyl, tetrahydrofuranylpyrimidinyl, pyrrolidinyl-pyrimidinyl, tetrahydropyranylpyrimidinyl, piperidinylpyrimidinyl, piperazinyl-pyrimidinyl, hexahydro-[1,2,5]thiadiazolo[2,3-a]pyrazinylpyrimidinyl, morpholinyl-pyrimidinyl, thiomorpholinylpyrimidinyl, azepanylpyrimidinyl, oxazepanylpyrimidinyl, diazepanylpyrimidinyl, thiadiazepanylpyrimidinyl, oxetanylpyrazinyl, piperidinyl-pyrazinyl, morpholinylmethylthienyl, morpholinylethylpyrazolyl, 3-azabicyclo[3.1.0]-hexanylpyridinyl, 3-azabicyclo[3.1.0]hexanylpyridazinyl, 3-azabicyclo[3.1.0]hexanyl-pyrimidinyl, 2-oxa-5-azabicyclo[2.2.1]heptanylpyrimidinyl, 3-azabicyclo[3.1.1]heptanyl-pyrimidinyl, 3-azabicyclo[4.1.0]heptanylpyrimidinyl, 3-azabicyclo[4.1.0]heptanyl-pyrimidinyl, 2-oxabicyclo[2.2.2]octanylpyrimidinyl, 3-azabicyclo[3.2.1]octanyl-pyrimidinyl, 8-azabicyclo[3.2.1]octanylpyrimidinyl, 3-oxa-8-azabicyclo[3.2.1]octanyl-pyrimidinyl, 3,6-diazabicyclo[3.2.2]nonanylpyrimidinyl, 3-oxa-7-azabicyclo[3.3.1]-nonanylpyrimidinyl, 3,7-dioxa-9-azabicyclo[3.3.1]-nonanylpyrimidinyl, 5-azaspiro[2.3]hexanylpyrimidinyl, 5-azaspiro[2.4]heptanyl-pyrimidinyl, 2-azaspiro[3.3]heptanylpyrimidinyl, 2-oxa-6-azaspiro[3.3]heptanyl-pyrimidinyl, 2-oxa-6-azaspiro[3.4]octanylpyrimidinyl, 2-oxa-6-azaspiro[3.5]nonanyl-pyrimidinyl, 2-oxa-7-azaspiro[3.5]nonanylpyrimidinyl, 2,4,8-triazaspiro[4.5]decanyl-pyrimidinyl, 3,6-epiminofuro[3.2-b]furanyl-pyrimidinyl, (imino)(oxo)thiazinanyl-pyrimidinyl, (oxo)thiazinanyl-pyrimidinyl or (dioxo)thiazinanyl-pyrimidinyl, any of which groups may be optionally substituted by one or more substituents. Additionally, $R^1$ represents 2,5-diazabicyclo[2.2.1]heptanyl-pyrimidinyl or pyridine-2(1H)-one, either of which groups may be optionally substituted by one or more substituents.

Definitively, $R^1$ represents bromo, cyano, phenyl, pyridinyl, dihydropyridinyl, pyrimidinyl, cyclobutylpyrimidinyl, cyclopropylpyridinyl, bicyclo[3.1.0]hexanyl-pyrimidinyl, bicyclo[3.1.0]hexenyl-pyrimidinyl, pyrimidinyl, tetrahydropyranylpyridinyl, tetrahydro-thiopyranylpyrimidinyl, piperazinyl-pyridinyl, oxetanylpyrimidinyl, azetidinylpyrimidinyl, tetrahydrofuranylpyrimidinyl, piperidinylpyrimidinyl, piperazinyl-pyrimidinyl, morpholinyl-pyrimidinyl, thiomorpholinylpyrimidinyl, 2-oxa-5-azabicyclo[2.2.1]heptanylpyrimidinyl, 3-azabicyclo[3.2.1]octanyl-pyrimidinyl, 3-oxa-8-azabicyclo[3.2.1]octanyl-pyrimidinyl, 3,7-dioxa-9-azabicyclo[3.3.1]-nonanylpyrimidinyl, epiminofuro[3.2-b]furanyl-pyrimidinyl, (imino)(oxo)thiazinanyl-pyrimidinyl, (oxo)thiazinanyl-pyrimidinyl, (dioxo)thiazinanyl-pyrimidinyl, cyclopropylpyrimidinyl, 2,5-diazabicyclo[2.2.1]heptanyl-pyrimidinyl or pyridine-2(1H)-one, any of which groups may be optionally substituted by one or more substituents.

Appropriately, $R^1$ represents bromo, cyano, phenyl, pyridinyl, dihydropyridinyl, pyrimidinyl, cyclobutylpyrimidinyl, cyclopropylpyridinyl, bicyclo[3.1.0]hexanyl-pyrimidinyl, bicyclo[3.1.0]hexenyl-pyrimidinyl, pyrimidinyl, tetrahydropyranylpyridinyl, tetrahydro-thiopyranylpyrimidinyl, piperazinyl-pyridinyl, oxetanylpyrimidinyl, azetidinylpyrimidinyl, tetrahydrofuranylpyrimidinyl, piperidinylpyrimidinyl, piperazinyl-pyrimidinyl, morpholinyl-pyrimidinyl, thiomorpholinylpyrimidinyl, 2-oxa-5-azabicyclo[2.2.1]heptanylpyrimidinyl, 3-azabicyclo[3.2.1]octanyl-pyrimidinyl, 3-oxa-8-azabicyclo[3.2.1]octanyl-pyrimidinyl, 3,7-dioxa-9-azabicyclo[3.3.1]-nonanylpyrimidinyl, epiminofuro[3.2-b]furanyl-pyrimidinyl, (imino)(oxo)thiazinanyl-pyrimidinyl, (oxo)thiazinanyl-pyrimidinyl, (dioxo)thiazinanyl-pyrimidinyl, or cyclopropylpyrimidinyl, any of which groups may be optionally substituted by one or more substituents. Additionally, $R^1$ represents 2,5-diazabicyclo[2.2.1]heptanyl-pyrimidinyl or pyridine-2(1H)-one, either of which groups may be optionally substituted by one or more substituents.

Suitably, $R^1$ represents phenyl, pyridinyl, dihydropyridinyl, pyrimidinyl, cyclobutylpyrimidinyl, cyclopropylpyridinyl, bicyclo[3.1.0]hexanyl-pyrimidinyl, bicyclo[3.1.0]hexenyl-pyrimidinyl, pyrimidinyl, tetrahydropyranylpyridinyl, tetrahydro-thiopyranylpyrimidinyl, piperazinyl-pyridinyl, oxetanylpyrimidinyl, azetidinylpyrimidinyl, tetrahydrofuranylpyrimidinyl, piperidinylpyrimidinyl, piperazinyl-pyrimidinyl, morpholinyl-pyrimidinyl, thiomorpholinylpyrimidinyl, 2-oxa-5-azabicyclo[2.2.1]heptanylpyrimidinyl, 3-azabicyclo[3.2.1]octanyl-pyrimidinyl,3-oxa-8-azabicyclo[3.2.1]octanyl-pyrimidinyl,3,7-dioxa-9-azabicyclo[3.3.1]-nonanylpyrimidinyl, epiminofuro[3.2-b]furanyl-pyrimidinyl, 2,5-diazabicyclo[2.2.1]heptanyl-pyrimidinyl or pyridine-2(1H) one, any of which groups may be optionally substituted by one or more substituents.

Illustratively, $R^1$ represents phenyl, pyridinyl, dihydropyridinyl, pyrimidinyl, cyclobutylpyrimidinyl, cyclopropylpyridinyl, bicyclo[3.1.0]hexanyl-pyrimidinyl, bicyclo[3.1.0]hexenyl-pyrimidinyl, pyrimidinyl, tetrahydropyranylpyridinyl, tetrahydro-thiopyranylpyrimidinyl, piperazinyl-pyridinyl, oxetanylpyrimidinyl, azetidinylpyrimidinyl, tetrahydrofuranylpyrimidinyl, piperidinylpyrimidinyl, piperazinyl-pyrimidinyl, morpholinyl-pyrimidinyl, thiomorpholinylpyrimidinyl, 2-oxa-5-azabicyclo[2.2.1]heptanylpyrimidinyl, 3-azabicyclo[3.2.1]octanyl-pyrimidinyl, 3-oxa-8-azabicyclo[3.2.1]octanyl-pyrimidinyl, 3,7-dioxa-9-azabicyclo[3.3.1]-nonanylpyrimidinyl, or epiminofuro[3.2-b]furanyl-pyrimidinyl, any of which groups may be optionally substituted by one or more substituents.

Typical examples of optional substituents on $R^1$ include one, two or three substituents independently selected from halogen, halo$(C_{1-6})$alkyl, cyano, cyano$(C_{1-6})$alkyl, nitro$(C_{1-6})$alkyl, $C_{1-6}$ alkyl, trifluoromethyl, trifluoroethyl, $C_{2-6}$ alkenyl, hydroxy, hydroxy$(C_{1-6})$alkyl, $C_{1-6}$ alkoxy, trifluoroethoxy, carboxy$(C_{3-7})$cycloalkyloxy, $C_{1-6}$ alkylthio, $C_{1-6}$ alkylsulphonyl, $(C_{1-6})$alkylsulphonyl$(C_{1-6})$alkyl, oxo, amino, amino-$(C_{1-6})$alkyl, $C_{1-6}$ alkylamino, di$(C_{1-6})$alkylamino, $(C_{1-6})$alkoxy$(C_{1-6})$alkylamino, N—[$(C_{1-6})$alkyl]-N-[hydroxy$(C_{1-6})$alkyl]amino, $(C_{2-6})$alkylcarbonylamino $(C_{1-6})$alkyl, $C_{1-6}$ alkylsulphonylamino, N—[$(C_{1-6})$alkyl]-N—[$(C_{1-6})$alkylsulphonyl]amino, bis[$(C_{1-6})$alkyl-sulphonyl]amino, N—[$(C_{1-6})$alkyl]-N-[carboxy$(C_{1-6})$alkyl]amino, carboxy$(C_{3-7})$cycloalkyl-amino, carboxy$(C_{3-7})$cycloalkyl $(C_{1-6})$alkylamino, formyl, $C_{2-6}$ alkylcarbonyl, $(C_{2-6})$alkylcarbonyloxy$(C_{1-6})$alkyl, carboxy, carboxy$(C_{1-6})$alkyl, $C_{2-6}$ alkoxycarbonyl, $C_{2-6}$ alkoxycarbonyl$(C_{1-6})$alkyl, morpholinyl$(C_{1-6})$alkoxycarbonyl, $C_{2-6}$ alkoxycarbonyl-methylidenyl, aminocarbonyl, di$(C_{1-6})$alkylaminocarbonyl, aminosulphonyl, $(C_{1-6})$alkylsulphoximinyl, [$(C_{1-6})$alkyl][N—$(C_{1-6})$alkyl]sulphoximinyl and heteroaryl. Additional examples of optional substituents on $R^1$ include difluoromethyl, $C_{1-6}$ alkylsulphinyl, and $(C_{3-7})$cycloalkyl sulphonyl.

Appropriate examples of optional substitutents on $R^1$ include one, two or three substituents independently selected from selected from halogen, hydroxy, trifluoromethyl, $C_{1-6}$ alkyl, $C_{1-6}$ alkoxy, $C_{2-6}$ alkylcarbonyl, $C_{2-6}$ alkyloxycarbonyl, (hydroxy)$C_{1-6}$ alkyl, $(C_{3-7})$cycloalkyl, $C_{1-6}$ alkylsulphonyl, $(C_{1-6})$alkylsulphonyl$(C_{1-6})$alkyl, di$(C_{1-6})$alkylaminocarbonyl, $(C_{1-6})$alkylsulphoximinyl, oxo, carboxy, difluoromethyl, $C_{1-6}$ alkylsulphinyl, and $(C_{3-7})$cycloalkyl sulphonyl. Suitable examples of optional substituents on $R^1$ include one, two or three substituents independently selected from halogen, hydroxy, trifluoromethyl, $C_{1-6}$ alkyl, $C_{1-6}$ alkoxy, $C_{2-6}$ alkylcarbonyl, $C_{2-6}$ alkyloxycarbonyl, (hydroxy)$C_{1-6}$ alkyl, $(C_{3-7})$cycloalkyl, $C_{1-6}$ alkylsulphonyl, $(C_{1-6})$alkylsulphonyl$(C_{1-6})$alkyl, di$(C_{1-6})$alkylaminocarbonyl, $(C_{1-6})$alkylsulphoximinyl, oxo, and carboxy.

Typical examples of particular substituents on $R^1$ include one, two or three substituents independently selected from fluoro, chloro, fluoromethyl, fluoroisopropyl, cyano, cyanoethyl, nitromethyl, methyl, ethyl, isopropyl, cyclopropyl, cyclobutyl, isopropylmethyl, trifluoromethyl, trifluoroethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, methylsulphonylethyl, oxo, amino, aminomethyl, aminoisopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyamino-carbonyl, tetrazolyl, tetrazolylmethyl, hydroxyoxadiazolyl, aminocarbonyl, amino-sulphonyl, methylsulphoximinyl, (methyl)(N-methyl)sulphoximinyl and triazolyl.

Appropriate particular examples of substituents on $R^1$ include chloro, fluoro, methyl, trifluoromethyl, hydroxy, hydroxymethyl, hydroxyisopropyl, methoxy, methylsulphonyl, oxo, amino, acetyl, methoxycarbonyl, methylsulphoximinyl, ethoxycarbonyl, n-butoxycarbonyl, tert-butoxycarbonyl, fluoroisopropyl, aminoisopropyl difluoromethyl, methylsulphinyl, tert-butoxy and cyclopropylsulphonyl Particular examples of substituents on $R^1$ include chloro, fluoro, methyl, trifluoromethyl, hydroxy, hydroxymethyl, hydroxyisopropyl, methoxy, methylsulphonyl, oxo, amino, acetyl, methoxycarbonyl, methylsulphoximinyl, ethoxycarbonyl, n-butoxycarbonyl and tert-butoxycarbonyl.

In a particular embodiment, $R^1$ is substituted by hydroxy $(C_{1-6})$alkyl. In one aspect of that embodiment, $R^1$ is substituted by hydroxyisopropyl, especially 2-hydroxyprop-2-yl.

In second particular embodiment, $R^1$ is substituted by $C_{1-6}$ alkylsulphonyl. In one aspect of this embodiment, $R^1$ is substituted by methylsulphonyl.

In a third particular embodiment, $R^1$ is substituted by $(C_{1-6})$alkylsulphoximinyl. In one aspect of this embodiment, $R^1$ is substituted by a methylsulphoximinyl.

Selected values of $R^1$ include hydrogen, bromo, cyano, —$CO_2R^a$, methoxycarbonyl-ethyl, ethoxycarbonylethyl, hydroxybutynyl, chlorophenyl, hydroxyphenyl, methyl-sulphonylphenyl, (methylsulphonyl)methylphenyl, (methylsulphonyl)ethylphenyl, aminomethylphenyl, aminoisopropyl-phenyl, acetylaminomethylphenyl, acetylphenyl, methoxycarbonylphenyl, aminocarbonylphenyl, aminosulphonylphenyl, acetylaminosulphonylphenyl, (di-(trifluoromethyl))(hydroxy)phenyl, (methoxycarbonyl)(methyl) pyrrolidinyl, chloropyridinyl, oxopiperidinyl, ethoxycarbonylpiperidinyl, methylsulphonylpiperazinyl, morpholinyl, methylsulphonyl-1,2,3,6-tetrahydropyridinyl, acetyl-1,2,3,6-tetrahydropyridinyl, tert-butoxycarbonyl-1,2,3,6-tetrahydropyridinyl, methoxycarbonylmethyl-1,2,3,6-tetrahydropyridinyl, benzofuryl, thienyl, indolyl, pyrazolyl, methylpyrazolyl, dimethylpyrazolyl, (methyl)[N-methyl-N-(methylsulfonyl)amino]pyrazolyl, methylindazolyl, dimethylisoxazolyl, hydroxyisopropylthiazolyl, methylimidazolyl, dimethylimidazolyl, pyridinyl, tetrahydropyranylpyridinyl, fluoro-pyridinyl, cyanopyridinyl, methylpyridinyl, (cyano)(methyl)pyridinyl, dimethylpyridinyl, cyclopropylpyridinyl, trifluoromethylpyridinyl, ethenylpyridinyl, hydroxyisopropylpyridinyl, hydroxymethylpyridinyl, methoxypyridinyl, (methoxy)(methyl)pyridinyl, isopropoxypyridinyl, trifluoroethoxypyridinyl, (methyl)-(trifluoroethoxy)pyridinyl, methylsulphonylpyridinyl, methylsulphonylmethylpyridinyl, oxopyridinyl, (methyl)(oxo)-pyridinyl, (dimethyl)(oxo) pyridinyl, aminopyridinyl, methylaminopyridinyl, dimethyl-aminopyridinyl, methoxyethylaminopyridinyl, N-(hydroxyethyl)-N-(methyl)amino-pyridinyl, methylsulphonylaminopyridinyl, [bis(methylsulphonyl)amino]pyridinyl, carboxypyridinyl, quinolinyl, hydroxypyridazinyl, pyrimidinyl, isopropylpyrimidinyl, fluoroisopropyl-pyrimidinyl, hydroxyisopropylpyrimidinyl, methoxypyrimidinyl, carboxycyclobutyloxy-pyrimidinyl, methylthiopyrimidinyl, methylsulphonylpyrimidinyl, oxopyrimidinyl, aminopyrimidinyl, dimethylaminopyrimidinyl, methoxyethylaminopyrimidinyl, N-(carboxyethyl)-N-(methyl)aminopyrimidinyl, carboxycyclopentylaminopyrimidinyl, carboxycyclopropylmethylaminopyrimidinyl, acetoxyisopropylpyrimidinyl, ethoxycarbonylethylpyrimidinyl, hydroxypyrazinyl, hydroxyisopropylpyrazinyl, pyrrolidinylmethylphenyl, piperazinylmethylphenyl, pyridinylpiperazinyl, carboxy-cyclohexylpyrazolyl, carboxycyclohexylpyridinyl, fluoromethylcyclopropylpyrimidinyl, acetylaminomethylcyclopropylpyrimidinyl, hydroxymethylpyrimidinyl, hydroxycyclobutylpyrimidinyl, carboxy-cyclopentylpyrimidinyl, carboxycyclohexylpyrimidinyl, (carboxy)(methyl)cyclohexyl-pyrimidinyl, (carboxy)(hydroxy) cyclohexylpyrimidinyl, carboxymethylcyclohexylpyrimidinyl, ethoxycarbonylcyclohexylpyrimidinyl, (methoxycarbonyl)(methyl)-cyclohexylpyrimidinyl, (ethoxycarbonyl)(methyl)cyclohexylpyrimidinyl, carboxycyclo hexylpyrazinyl, carboxycyclohexylmethylpyrimidinyl, carboxycyclo hexenyl-pyridinyl, carboxycyclohexenylpyrimidinyl, ethoxycarbonylcyclohexenylpyrimidinyl, carboxybicyclo[3.1.0]hexanylpyridinyl, carboxybicyclo[3.1.0]hexenylpyridinyl carboxybicyclo[3.1.0]hexanylpyrimidinyl, ethoxycarbonylbicyclo[3.1.0]hexanylpyrimidinyl, carboxybicyclo[4.1.0]heptanyl-pyrimidinyl, carboxybicyclo[2.2.2]octanylpyrimidinyl, pyrrolidinylpyridinyl, hydroxypyrrolidinylpyridinyl, hydroxytetrahydropyranylpyridinyl, piperidinylpyridinyl, acetylpiperidinylpyridinyl, (carboxy)(methyl)piperidinylpyridinyl, [(carboxy)(methyl)-piperidinyl](fluoro)pyridinyl, [(carboxy)(methyl)piperidinyl](chloro)pyridinyl, piperazinylpyridinyl, (methyl)(piperazinyl)pyridinyl, cyanoethylpiperazinylpyridinyl, trifluoroethylpiperazinylpyridinyl, methylsulphonylpiperazinylpyridinyl, methyl-sulphonylethylpiperazinylpyridinyl, oxopiperazinylpyridinyl, acetylpiperazinylpyridinyl, (tert-butoxycarbonylpiperazinyl)(methyl) pyridinyl, methylpiperazinylpyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinyl-pyridinyl, (tert-butoxycarbonyl)-3,6-dihydropyridine, oxothiomorpholinylpyridinyl, dioxothiomorpholinylpyridinyl, oxodiazepanyl-pyridinyl, fluorooxetanylpyrimidinyl, hydroxyoxetanylpyrimidinyl, hydroxyazetidinyl-pyrimidinyl, (hydroxy)(methyl)azetidinylpyrimidinyl, (hydroxy)(trifluoromethyl)azetidinylpyrimidinyl, carboxyazetidinylpyrimidinyl, (tert-butoxycarbonyl)(hydroxy)azetidinylpyrimidinyl, tetrazolylazetidinylpyrimidinyl, hydroxytetrahydrofuranylpyrimidinyl, hydroxypyrrolidinylpyrimidinyl, carboxypyrrolidinylpyrimidinyl, (carboxy)(methyl)pyrrolidinylpyrimidinyl, carboxymethyl-pyrrolidinylpyrimidinyl, ethoxycarbonylpyrrolidinylpyrimidinyl, fluoro-tetrahydropyranylpyrimidinyl, hydroxytetrahydropyranylpyrimidinyl, (hydroxy)dioxidotetrahydrothiopyranyl)pyrimidinyl, piperidinylpyrimidinyl, difluoropiperidinyl-pyrimidinyl, (cyano)(methyl)piperidinylpyrimidinyl, (hydroxy)(nitromethyl)piperidinyl-pyrimidinyl, (hydroxy)(methyl)piperidinylpyrimidinyl, (hydroxy)(trifluoromethyl)-piperidinylpyrimidinyl, (hydroxymethyl)(methyl)piperidinylpyrimidinyl, methylsulphonylpiperidinylpyrimidinyl, oxopiperidinylpyrimidinyl, (formyl)(methyl)-piperidinylpyrimidinyl, carboxypiperidinylpyrimidinyl, (carboxy)(fluoro)piperidinyl-pyrimidinyl, (carboxy)(methyl)piperidinylpyrimidinyl, (carboxy)(ethyl)piperidinyl-pyrimidinyl, (carboxy)(trifluoromethyl)piperidinylpyrimidinyl, (carboxy)(hydroxy)-piperidinylpyrimidinyl, (carboxy)(hydroxymethyl)piperidinylpyrimidinyl, (carboxy)-(methoxy)piperidinylpyrimidinyl, (amino)(carboxy)piperidinylpyrimidinyl, carboxymethylpiperidinylpyrimidinyl, methoxycarbonylpiperidinylpyrimidinyl, ethoxycarbonylpiperidinylpyrimidinyl, (ethoxycarbonyl)(fluoro)piperidinylpyrimidinyl, (methoxy-carbonyl)(methyl)piperidinylpyrimidinyl, (ethyl)(methoxycarbonyl)piperidinyl-pyrimidinyl, (isopropyl)(methoxycarbonyl)piperidinylpyrimidinyl, (ethoxycarbonyl)-(methyl)piperidinylpyrimidinyl, (n-butoxycarbonyl)(methyl)piperidinylpyrimidinyl, (ethoxycarbonyl)(trifluoromethyl)piperidinylpyrimidinyl, (ethoxycarbonyl)-(hydroxymethyl)piperidinylpyrimidinyl, (methoxy)(methoxycarbonyl)piperidinyl-pyrimidinyl, (carboxy)(methoxycarbonyl)piperidinylpyrimidinyl, (methyl)-(morpholinylethoxycarbonyl)piperidinylpyrimidinyl, ethoxycarbonylmethylpiperidinyl-pyrimidinyl, methylsulphonylaminocarbonylpiperidinylpyrimidinyl, acetylpiperidinylpyrimidinyl, acetylamino-sulphonylpiperidinylpyrimidinyl, methoxyaminocarbonylpiperidinylpyrimidinyl, tetrazolylpiperidinylpyrimidinyl, hydroxyoxadiazolylpiperidinylpyrimidinyl, amino-sulphonylpiperidinylpyrimidinyl, piperazinylpyrimidinyl, methylsulphonylpiperazinyl-pyrimidinyl, oxopiperazinylpyrimidinyl, carboxypiperazinylpyrimidinyl, carboxyethyl-piperazinylpyrimidinyl, tert-butoxycarbonylpiperazinylpyrimidinyl, tetrazolylmethylpiperazinylpyrimidinyl, trioxohexahydro-[1,2,5]thiadiazolo[2,3-c]pyrazinylpyrimidinyl, morpholinylpyrimidinyl, dimethylmorpholinylpyrimidinyl, hydroxymethylmorpholinyl-pyrimidinyl, carboxymorpholinylpyrimidinyl, (carboxy)(methyl)morpholinylpyrimidinyl, carboxymethylmorpholinylpyrimidinyl, thiomorpholinylpyrimidinyl, oxothiomorpholinylpyrimidinyl, dioxothiomorpholinylpyrimidinyl, carboxyazepanylpyrimidinyl, carboxyoxazepanyl-pyrimidinyl, oxodiazepanylpyrimidinyl, (oxodiazepanyl)(trifluoromethyl)pyrimidinyl, (oxodiazepanyl)(methoxy)pyrimidinyl, (methyl)(oxo)diazepanylpyrimidinyl, dioxo-thiadiazepanylpyrimidinyl, hydroxyoxetanylpyrazinyl, (carboxy)(methyl)piperidinylpyrazinyl, (ethoxycarbonyl)(methyl)piperidinylpyrazinyl, morpholinylmethylthienyl, morpholinylethylpyrazolyl, isopropylmethylpyrazolyl, carboxy-3-azabicyclo[3.1.0]hexanylpyridinyl, carboxy-3-azabicyclo[3.1.0]hexanylpyridazinyl, carboxy-3-azabicyclo[3.1.0]hexanylpyrimidinyl, (carboxy)(methyl)-3-azabicyclo[3.1.0]hexanylpyrimidinyl, methoxycarbonyl-3-azabicyclo[3.1.0]hexanylpyrimidinyl, ethoxycarbonyl-3-azabicyclo[3.1.0]hexanyl-pyrimidinyl, 2-oxa-5-azabicyclo[2.2.1]heptanylpyrimidinyl, carboxy-2-oxa-5-azabicyclo-[2.2.1]heptanylpyrimidinyl, carboxy-3-azabicyclo[3.1.1]heptanylpyrimidinyl, carboxy-3-azabicyclo[4.1.0]heptanylpyridinyl, carboxy-3-azabicyclo[4.1.0]heptanylpyrimidinyl, methoxycarbonyl-3-azabicyclo[4.1.0]heptanylpyrimidinyl, ethoxycarbonyl-3-azabicyclo-[4.1.0]heptanylpyrimidinyl, (hydroxy)(methyl)(oxo)-2-oxabicyclo[2.2.2]octanyl-pyrimidinyl, carboxy-3-azabicyclo[3.2.1]octanylpyrimidinyl, methoxycarbonyl-3-azabicyclo[3.2.1]octanylpyrimidinyl, oxo-8-azabicyclo[3.2.1]octanylpyrimidinyl, ethoxycarbonylmethylidenyl-8-azabicyclo[3.2.1]octanylpyrimidinyl, 3-oxa-8-azabicyclo-[3.2.1]octanylpyrimidinyl, 3-carboxy-8-azabicyclo-[3.2.1]-octanylpyrimidinyl, 3-(dimethylamino carbonyl)-8-azabicyclo-[3.2.1]octanylpyrimidinyl, oxo-3,6-diazabicyclo[3.2.2]nonanylpyrimidinyl, 3,7-dioxa-9-azabicyclo[3.3.1]-nonanylpyrimidinyl, carboxy-3-oxa-7-azabicyclo[3.3.1]nonanylpyrimidinyl, carboxy-5-azaspiro[2.3]hexanylpyrimidinyl, (carboxy)(methyl)-5-azaspiro[2.3]hexanylpyrimidinyl, carboxy-5-azaspiro[2.4]heptanylpyrimidinyl, carboxy-2-azaspiro[3.3]heptanylpyrimidinyl, 2-oxa-6-azaspiro[3.3]heptanyl-pyrimidinyl, 2-oxa-6-azaspiro[3.4]octanylpyrimidinyl, 2-oxa-6-azaspiro[3.5]nonanyl-pyrimidinyl, 2-oxa-7-azaspiro[3.5]nonanylpyrimidinyl, (dioxo)(methyl)-2,4,8-triazaspiro[4.5]decanylpyrimidinyl, 3,6-epiminofuro[3.2-b]furanylpyrimidinyl methylsulphoximinylphenyl, (methyl)cyclobutyldiol-pyrimidinyl, (imino)(oxo)thiazinanylpyrimidinyl, (oxo)thiazinanyl-pyrimidinyl and (dioxo)thiazinanyl-pyrimidinyl. Additional values of $R^1$ include difluorocyclobutanyl-pyrimidinyl, difluoromethyl-pyrimidinyl, cyclopropyl-pyrimidinyl, aminoisopropyl-pyrimidinyl, (hydroxy)cyclopropyl-pyrimidinyl, (difluoro)(hydroxy)cyclobutyl-pyrimidinyl, (methyl)cyclobutane-diol, (hydroxy)(methyl)cyclohexyl-pyrimidinyl, (methyl)cyclohexane-diol, (chloro)(methoxy)pyridinyl, methylsulphinyl-phenyl, cyclopropylsulphonyl-phenyl, tert-butoxy-pyridinyl, methylsulphoximinylpyridinyl, piperazinyl-2-one-pyrimidinyl, (methyl)pyridine-2(1H)-one, (fluoro)pyridine-2(1H)-one, (chloro)pyridine-2(1H)-one, methylcarboxy-3-azabicyclo[3.2.1]octanylpyrimidinyl, 3-oxa-8-azabicyclo[3.2.1]octanylpyrimidinyl, and 2,5-diazabicyclo[2.2.1]hetanylpyrimidinyl.

Appropriate values of $R^1$ include bromo, cyano, (methylsulphonyl)methylphenyl, (methylsulphonyl)ethylphenyl, (di-(trifluoromethyl))(hydroxy)phenyl, chloropyridinyl, tetrahydropyranylpyridinyl, hydroxyisopropylpyridinyl, hydroxymethylpyridinyl, methoxypyridinyl, isopropoxypyridinyl, isopropylpyrimidinyl, hydroxyisopropylpyrimidinyl, hydroxymethylpyrimidinyl, hydroxycyclobutylpyrimidinyl, carboxybicyclo[3.1.0]hexanylpyridinyl, carboxybicyclo[3.1.0]hexenylpyridinyl piperazinylpyridinyl, (tert-butoxycarbonyl)-3,6-dihydropyridine, hydroxyoxetanylpyrimidinyl, hydroxyazetidinyl-pyrimidinyl, (hydroxy)(methyl)azetidinylpyrimidinyl, (hydroxy)(trifluoromethyl)azetidinylpyrimidinyl, (tert-butoxycarbonyl)(hydroxy)azetidinylpyrimidinyl, hydroxytetrahydrofuranylpyrimidinyl, -hydroxytetrahydropyranylpyrimidinyl, (hydroxy)dioxidotetrahydrothiopyranyl)pyrimidinyl, piperidinylpyrimidinyl, (cyano)(methyl)piperidinylpyrimidinyl, (hydroxy)(methyl)piperidinylpyrimidinyl, (carboxy)(methyl)piperidinylpyrimidinyl, acetylpiperidinylpyrimidinyl, piperazinylpyrimidinyl, carboxypiperazinylpyrimidinyl, tert-butoxycarbonylpiperazinylpyrimidinyl, morpholinylpyrimidinyl, thiomorpholinylpyrimidinyl, oxo-thiomorpholinylpyrimidinyl, dioxo-thiomorpholinylpyrimidinyl, oxodiazepanylpyrimidinyl, 2-oxa-5-azabicyclo[2.2.1]heptanylpyrimidinyl, carboxy-3-azabicyclo[3.2.1]octanylpyrimidinyl, oxo-8-azabicyclo[3.2.1]octanylpyrimidinyl, 3-carboxy-8-azabicyclo-[3.2.1]octanylpyrimidinyl, 3-(dimethylaminocarbonyl)-8-azabicyclo-[3.2.1]octanylpyrimidinyl, oxo-3,6-diazabicyclo[3.2.2]nonanylpyrimidinyl, 3,7-dioxa-9-azabicyclo[3.3.1]-nonanylpyrimidinyl, 3,6-epiminofuro[3.2-b]furanyl-pyrimidinyl, methylsulphoximinylphenyl, (methyl)cyclobutyldiol-pyrimidinyl, (imino)(oxo)thiazinanyl-pyrimidinyl, (oxo)thiazinanyl-pyrimidinyl, (dioxo)thiazinanyl-pyrimidinyl, difluorocyclobutanyl-pyrimidinyl, difluoromethyl-pyrimidinyl, cyclopropyl-pyrimidinyl, aminoisopropyl-pyrimidinyl, (hydroxy)cyclopropyl-pyrimidinyl, (difluoro)(hydroxy)cyclobutyl-pyrimidinyl, (methyl) cyclobutane-diol, (hydroxy)(methyl)cyclohexyl-pyrimidinyl, (methyl)cyclohexane-diol, (chloro)(methoxy)pyridinyl, methylsulphinyl-phenyl, cyclopropylsulphonyl-phenyl, tert-butoxy-pyridinyl, methylsulphoximinylpyridinyl, piperazinyl-2-one-pyrimidinyl, (methyl)pyridine-2(1H)-one, (fluoro)pyridine-2(1H)-one, (chloro)pyridine-2(1H)-one, methylcarboxy-3-azabicyclo[3.2.1]octanylpyrimidinyl, 3-oxa-8-azabicyclo[3.2.1]octanylpyrimidinyl, and 2,5-diazabicyclo[2.2.1]hetanylpyrimidinyl.

Illustrative values of $R^1$ include bromo, cyano, (methylsulphonyl)methylphenyl, (methylsulphonyl)ethylphenyl, (di-(trifluoromethyl))(hydroxy)phenyl, chloropyridinyl, tetrahydropyranylpyridinyl, hydroxyisopropylpyridinyl, hydroxymethylpyridinyl, methoxypyridinyl, isopropoxypyridinyl, isopropylpyrimidinyl, hydroxyisopropylpyrimidinyl, hydroxymethylpyrimidinyl, hydroxycyclobutylpyrimidinyl, carboxybicyclo[3.1.0]hexanylpyridinyl, carboxybicyclo[3.1.0]hexenylpyridinyl piperazinylpyridinyl, (tert-butoxycarbonyl)-3,6-dihydropyridine, hydroxyoxetanylpyrimidinyl, hydroxyazetidinyl-pyrimidinyl, (hydroxy)(methyl)azetidinylpyrimidinyl, (hydroxy)(trifluoromethyl)azetidinylpyrimidinyl, (tert-butoxycarbonyl)(hydroxy)azetidinylpyrimidinyl, hydroxytetrahydrofuranylpyrimidinyl, -hydroxytetrahydropyranylpyrimidinyl, (hydroxy)dioxidotetrahydrothiopyranyl)pyrimidinyl, piperidinylpyrimidinyl, (cyano)(methyl)piperidinylpyrimidinyl, (hydroxy)(methyl)piperidinylpyrimidinyl, (carboxy)(methyl)piperidinylpyrimidinyl, acetylpiperidinylpyrimidinyl, piperazinylpyrimidinyl, carboxypiperazinylpyrimidinyl, tert-butoxycarbonylpiperazinylpyrimidinyl, morpholinylpyrimidinyl, thiomorpholinylpyrimidinyl, oxo-thiomorpholinylpyrimidinyl, dioxo-thiomorpholinylpyrimidinyl, oxodiazepanylpyrimidinyl, 2-oxa-5-azabicyclo[2.2.1]heptanylpyrimidinyl, carboxy-3-azabicyclo[3.2.1]octanylpyrimidinyl, oxo-8-azabicyclo[3.2.1]octanylpyrimidinyl, 3-carboxy-8-azabicyclo-[3.2.1]octanylpyrimidinyl, 3-(dimethylaminocarbonyl)-8-azabicyclo-[3.2.1]octanylpyrimidinyl, oxo-3,6-diazabicyclo[3.2.2]nonanylpyrimidinyl, 3,7-dioxa-9-azabicyclo[3.3.1]-nonanylpyrimidinyl, 3,6-epiminofuro[3.2-b]furanyl-pyrimidinyl, methylsulphoximinylphenyl, (methyl)cyclobutyldiol-pyrimidinyl, (imino)(oxo)thiazinanyl-pyrimidinyl, (oxo)thiazinanyl-pyrimidinyl and (dioxo)thiazinanyl-pyrimidinyl.

Typically, $R^2$ represents hydrogen, halogen, cyano, nitro, hydroxy, trifluoromethyl, trifluoromethoxy; or —$OR^a$; or an optionally substituted $C_{1-6}$ alkyl.

Typical examples of optional substituents on $R^2$ include $C_{2-6}$ alkoxycarbonyl.

Typical examples of particular substituents on $R^2$ include ethoxycarbonyl.

In a first embodiment, $R^2$ represents hydrogen. In a second embodiment, $R^2$ represents halogen. In one aspect of that embodiment, $R^2$ represents fluoro. In another aspect of that embodiment, $R^2$ represents chloro. In a third embodiment, $R^2$ represents cyano. In a fourth embodiment, $R^2$ represents nitro. In a fifth embodiment, $R^2$ represents hydroxy. In a sixth embodiment, $R^2$ represents trifluoromethyl. In a seventh embodiment, $R^2$ represents trifluoromethoxy. In an eighth embodiment, $R^2$ represents —$OR^a$. In a ninth embodiment, $R^2$ represents optionally substituted $C_{1-6}$ alkyl. In one aspect of that embodiment, $R^2$ represents unsubstituted methyl. In another aspect of that embodiment, $R^2$ represents unsubstituted ethyl. In a further aspect of that embodiment, $R^2$ represents monosubstituted methyl or monosubstituted ethyl.

Typical values of $R^2$ include hydrogen, fluoro, chloro, trifluoromethyl, trifluoromethoxy, —$OR^a$, methyl and ethoxycarbonylethyl.

Particular values of $R^2$ include hydrogen and fluoro.

Typically, $R^3$ represents hydrogen, halogen or $C_{1-6}$ alkyl.

In a first embodiment, $R^3$ represents hydrogen. In a second embodiment, $R^3$ represents halogen. In one aspect of that embodiment, $R^3$ represents fluoro.

In a third embodiment, $R^3$ represents $C_{1-6}$ alkyl. In one aspect of that embodiment, $R^3$ represents unsubstituted $C_{1-6}$ alkyl. In a second aspect of that embodiment, $R^3$ represents substituted $C_{1-6}$ alkyl. In a particular aspect of this embodiment, $R^3$ represents methyl. In another particular aspect of that embodiment, $R^3$ represents ethyl.

In a particular embodiment, $R^3$ represents hydrogen.

Typically, $R^4$ represents hydrogen, halogen or $C_{1-6}$ alkyl.

In a first embodiment, $R^4$ represents hydrogen. In a second embodiment, $R^4$ represents halogen. In one aspect of that embodiment, $R^4$ represents fluoro. In a third embodiment, $R^4$ represents $C_{1-6}$ alkyl. In one aspect of that embodiment, $R^4$ represents unsubstituted $C_{1-6}$ alkyl. In a second aspect of that embodiment, $R^4$ represents substituted $C_{1-6}$ alkyl. In a particular aspect of this embodiment, $R^4$ represents methyl. In another particular aspect of that embodiment, $R^4$ represents ethyl.

In a particular embodiment, $R^4$ represents hydrogen.

Generally, $R^{5a}$ represents hydrogen, hydroxy, halogen, cyano, trifluoromethyl; —$NR^bR^c$, —$NR^cC(O)R^d$, —(CO)$NR^cR^d$, —$NHS(O)_2R^e$, —$S$—$R^a$, —(SO)—$R^a$, —$S(O)_2R^a$, —$S(O)(N$—$R^d)$, —$S(O)_2(N$—$R^d)$, —$OR^a$, —$C(O)2R^d$, or —$O(CO)$—$R^d$—; or $C_{1-6}$ alkyl, $C_{2-6}$ alkenyl, $C_{2-6}$ alkynyl, aryl, or heteroaryl, any of which groups may be optionally substituted by one or more substituents.

Suitably, $R^{5a}$ represents hydrogen, hydroxy, halogen, trifluoromethyl; —$NR^bR^c$, $S(O)_2R^a$, —$OR^a$, O—(CO)_$R^d$ or —$NR^cC(O)R^d$; or $C_{1-6}$ alkyl any of which groups may be optionally substituted. Typically, $R^{5a}$ represents hydrogen, hydroxy, halogen, trifluoromethyl; —$NR^bR^c$, $S(O)_2R^a$, —$OR^a$, or O—(CO)—$R^d$; or $C_{1-6}$ alkyl any of which groups may be optionally substituted.

Suitable examples of optional substituents on $R^{5a}$ include one, two or three substituents independently selected from halogen, hydroxy, trifluoromethyl, $C_{1-6}$ alkyl, $C_{1-6}$ alkoxy, $C_{2-6}$ alkylcarbonyl, $C_{2-6}$ alkyloxycarbonyl, (hydroxy)$C_{1-6}$ alkyl, $(C_{3-7})$cycloalkyl, $C_{1-6}$ alkylsulphonyl, $(C_{1-6})$alkylsulphonyl($C_{1-6}$)alkyl, di($C_{1-6}$)alkylaminocarbonyl, oxo, and carboxy.

Typical examples of particular substituents on $R^{5a}$ include one, two or three substituents independently selected from fluoro, chloro, fluoromethyl, fluoroisopropyl, cyano, cyanoethyl, nitromethyl, methyl, ethyl, isopropyl, isopropylmethyl, trifluoromethyl, trifluoroethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, methylsulphonylethyl, oxo, amino, aminomethyl, amino isopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyaminocarbonyl, tetrazolyl, tetrazolylmethyl, hydroxyoxadiazolyl, aminocarbonyl, amino-sulphonyl, methylsulphoximinyl and (methyl)(N-methyl)sulphoximinyl.

In a first embodiment, $R^{5a}$ represents hydrogen. In a second embodiment, $R^{5a}$ represents hydroxy. In a third embodiment, $R^{5a}$ represents halogen. In one aspect of this embodiment, $R^{5a}$ represents fluoro. In a fourth embodiment, $R^{5a}$ represents trifluoromethyl. In a fifth embodiment, $R^{5a}$ represents —$NR^bR^c$. In one aspect of that embodiment, $R^{5a}$ represents —$NH_2$. In a sixth embodiment, $R^{5a}$ represents —$NR^cC(O)R^d$. In a seventh embodiment, $R^{5a}$ represents —$C(O)$—$NR^cR^d$. In an eighth embodiment, $R^{5a}$ represents —$NHS(O)_2R^e$. In a ninth embodiment, $R^{5a}$ represents S—$R^a$. In a tenth embodiment, $R^{5a}$ represents —$S(O)$—$R^a$. In an eleventh embodiment, $R^{5a}$ represents —$S(O)_2R^a$. In a particular aspect of this embodiment, $R^{5a}$ represents —$S(O)_2$—CH3. In a twelfth embodiment, $R^{5a}$ represents —$S(O)(N$—$R^d)R^a$. In a thirteenth embodiment, $R^{5a}$ represents —$S(O)_2(N$—$R^d)$. In a fourteenth embodiment, $R^{5a}$ represents —$OR^a$. In one aspect of this embodiment, $R^a$ is a $C_{1-6}$ alkyl. In second aspect of this embodiment $R^a$ is an aryl. In a third aspect of this embodiment, $R^a$ is an heteroaryl. In a fifteenth embodiment, $R^{5a}$ represents O—(CO)—$R^d$. In a particular aspect of this embodiment, $R^{5a}$ represents —O—(CO)—$CH_3$. In a sixteenth embodiment, $R^{5a}$ represents —C(O)—$OR^d$. In a seventeenth embodiment, $R^{5a}$ represents optionally substituted $C_{1-6}$ alkyl. In one aspect of that embodiment, $R^{5a}$ represents substituted $C_{1-6}$ alkyl. In a second aspect of this embodiment, $R^{5a}$ represents unsubstituted $C_{1-6}$ alkyl. In a particular aspect of this embodiment, $R^{5a}$ represents methyl. In an eighteenth embodiment, $R^{5a}$ represents an optionally substituted $C_{2-6}$ alkynyl. In a nineteenth embodiment, $R^{5a}$ represents an optionally substituted heteroaryl.

In a twentieth embodiment $R^{5a}$ represents an optionally substituted aryl. In a twenty-first embodiment, $R^{5a}$ represents an optionally substituted $C_{2-6}$ alkenyl.

In a twenty-second embodiment, $R^{5a}$ represents cyano.

Generally, $R^{5b}$ represents hydrogen, hydroxy, halogen, cyano, trifluoromethyl —$NR^bR^c$, —$NR^cC(O)R^d$, —(CO) $NR^cR^d$, —$NHS(O)_2R^e$, —S—$R^a$, —(SO)—$R^a$, —$S(O)_2R^a$, —$S(O)(N$—$R^d)$, —$S(O)_2(N$—$R^d)$, —$OR^a$, —$C(O)_2R^d$, or —$O(CO)$—$R^d$—; or $C_{1-6}$ alkyl, $C_{2-6}$ alkenyl, $C_{2-6}$ alkynyl, aryl, or heteroaryl, any of which groups may be optionally substituted by one or more substituents.

Typically, $R^{5b}$ represents hydrogen, hydroxy, halogen, trifluoromethyl —$NR^bR^c$, $S(O)_2R^a$, —$OR^a$, or O—(CO)_$R^d$; or $C_{1-6}$ alkyl any of which groups may be optionally substituted.

Suitable examples of optional substituents on $R^{5b}$ include one, two or three substituents independently selected from halogen, hydroxy, trifluoromethyl, $C_{1-6}$ alkyl, $C_1$-6 alkoxy, $C_{2-6}$ alkylcarbonyl, $C_{2-6}$ alkyloxycarbonyl, (hydroxy)$C_{1-6}$ alkyl, $(C_{3-7})$cycloalkyl, $C_{1-6}$ alkylsulphonyl, $(C_{1-6})$alkylsulphonyl($C_{1-6}$)alkyl, di($C_{1-6}$)alkylaminocarbonyl, oxo, and carboxy.

Typical examples of particular substituents on $R^{5b}$ include one, two or three substituents independently selected from fluoro, chloro, fluoromethyl, fluoroisopropyl, cyano, cyanoethyl, nitromethyl, methyl, ethyl, isopropyl, isopropylmethyl, trifluoromethyl, trifluoroethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, methylsulphonylethyl, oxo, amino, aminomethyl, aminoisopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyaminocarbonyl, tetrazolyl, tetrazolylmethyl, hydroxyoxadiazolyl, aminocarbonyl, amino-sulphonyl, methylsulphoximinyl and (methyl)(N-methyl)sulphoximinyl.

In a first embodiment, $R^{5b}$ represents hydrogen. In a second embodiment, $R^{5b}$ represents hydroxy. In a third embodiment, $R^{5b}$ represents halogen. In one aspect of this embodiment, $R^{5b}$ represents fluoro. In a fourth embodiment, $R^{5b}$ represents trifluoromethyl. In a fifth embodiment, $R^{5b}$ represents —$NR^bR^c$. In one aspect of that embodiment, $R^{5b}$ represents —$NH_2$. In a sixth embodiment, $R^{5b}$ represents —$NR^cC(O)R^d$. In a seventh embodiment, $R^{5b}$ represents —$C(O)$—$NR^cR^d$. In an eighth embodiment, $R^{5b}$ represents —$NHS(O)_2R^e$. In a ninth embodiment, $R^{5a}$ represents S—$R^a$. In a tenth embodiment, $R^{5b}$ represents —$S(O)$—$R^a$. In an eleventh embodiment, $R^{5b}$ represents —$S(O)_2R^a$. In a particular aspect of this embodiment, $R^{5b}$ represents —$S(O)_2$—CH3. In a twelfth embodiment, $R^{5b}$ represents —$S(O)(N$—$R^d)R^a$. In a thirteenth embodiment, $R^{5b}$ represents —$S(O)_2(N$—$R^d)$. In a fourteenth embodiment, $R^{5b}$ represents —$OR^a$. In one aspect of this embodiment, $R^a$ is a $C_{1-6}$ alkyl. In second aspect of this embodiment $R^a$ is an aryl. In a third aspect of this embodiment, $R^a$ is an heteroaryl. In a fifteenth embodiment, $R^{5b}$ represents O—(CO)—$R^d$. In a particular aspect of this embodiment, $R^{5a}$ represents O—(CO)—$CH_3$. In a sixteenth embodiment, —C(O)—$OR^d$. In a seventeenth embodiment, $R^{5b}$ represents optionally substituted $C_{1-6}$ alkyl. In one aspect of that embodiment, $R^{5b}$ represents substituted $C_{1-6}$ alkyl. In a second aspect of this embodiment, $R^{5b}$ represents unsubstituted $C_{1-6}$ alkyl. In a particular aspect of this embodiment, $R^{5b}$ represents methyl. In an eighteenth embodiment, $R^{5b}$ represents an optionally substituted $C_{2-6}$ alkynyl. In a nineteenth embodiment, $R^{5b}$ represents an optionally substituted heteroaryl. In a twentieth embodiment $R^{5b}$ represents an optionally substituted aryl. In a twenty-first embodiment, $R^{5b}$ represents an optionally substituted $C_{2-6}$ alkenyl. In a twenty-second embodiment, $R^{5b}$ represents cyano.

Particularly, $R^{5b}$ represents hydrogen or methyl.

In an alternative embodiment, $R^{5a}$ and $R^{5b}$ when taken together with the carbon to which they are attached represent a carbonyl, thiocarbonyl or —C=N—OH.

In one aspect of that alternative embodiment, $R^{5a}$ and $R^{5b}$ when taken together with the carbon to which they are attached represent a carbonyl.

On a second aspect of that alternative embodiment, $R^{5a}$ and $R^{5b}$ when taken together with the carbon to which they are attached represent a thiocarbonyl.

In another aspect of that alternative embodiment, $R^{5a}$ and $R^{5b}$ when taken together with the carbon to which they are attached represent -C=N—OH.

Illustrative values of $R^{5a}$ include hydrogen, hydroxy, fluoro, trifluoromethyl, —N(CH$_3$)$_2$, —NH(CO)CH$_3$, —SO$_2$—CH$_3$, —O—(CO)—CH$_3$, methyl, methoxy, pyridinemethyloxy-, benzyloxy, (methoxycarbonyl)methyloxy-, (ethyloxycarbonyl)methyloxy-, (tert-butoxycarbonyl)methyloxy-, (hydroxycarbonyl)methyloxy and cyanomethyloxy.

Selected values of $R^{5a}$ include hydrogen, hydroxy, fluoro, trifluoromethyl, —N(CH$_3$)$_2$, —NH(CO)CH$_3$, —SO$_2$—CH$_3$, —O—(CO)—CH$_3$, methyl and methoxy.

Selected values of $R^{5b}$ include hydrogen, hydroxy, fluoro, trifluoromethyl, —N(CH$_3$)$_2$, —NH(CO)CH$_3$, —SO$_2$—CH$_3$, —O—(CO)—CH$_3$, methyl and methoxy.

In a particular embodiment, $R^{5a}$ is as defined above and $R^{5b}$ represents hydrogen. In a particular aspect of this embodiment, $R^{5a}$ is hydroxy.

In another particular embodiment $R^{5a}$ is as defined above and $R^{5b}$ represents $C_{1-4}$ alkyl, preferably methyl. In a particular aspect of this embodiment, $R^{5a}$ is hydroxy.

Generally, $R^6$ represents hydrogen, hydroxy, halogen, trifluoromethyl, —NR$^b$R$^c$, —NR$^c$C(O)R$^d$, —NHS(O)$_2$R$^e$, —S(O)$_2$R$^a$, —S(O)(N—R$^d$)R$^a$ or —O—(CO)—R$^d$; or $C_{1-6}$ alkoxy, $C_{1-6}$ alkyl, $C_{2-6}$ alkynyl, heteroaryl, any of which groups may be optionally substituted by one or more substituents.

Typically, $R^6$ represents hydrogen, hydroxy, halogen, or trifluoromethyl.

In a particular embodiment, $R^6$ represents hydrogen.

In an alternative embodiment, $R^6$ and Y together with the carbon to which they are attached form a $C_{3-7}$ cycloalkyl.

In another alternative embodiment, $R^6$ and Y together with the carbon to which they are attached form a $C_{3-7}$ heterocycloalkyl. In one particular aspect according to this embodiment, $R^6$ and Y together with the carbon to which they are attached form a dihydrobenzofuran. In a second particular aspect according to this embodiment, $R^6$ and Y together with the carbon to which they are attached form a 3H-benzofuranone. In a third particular aspect according to this embodiment, $R^6$ and Y together with the carbon to which they are attached form a dihydroisoindole. In a fourth particular aspect according to this embodiment, $R^6$ and Y together with the carbon to which they are attached form a dihydroisoindolone.

Typical examples of suitable substituents on $R^a$, $R^b$, $R^c$, $R^d$ or $R^e$, or on the heterocyclic moiety —NR$^b$R$^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$) alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylamino carbonyl.

Typical examples of specific substituents on $R^a$, $R^b$, $R^c$, $R^d$ or $R^e$, or on the heterocyclic moiety —NR$^b$R$^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Selected values of $R^a$ include methyl, ethyl, benzyl and isoindolylpropyl, any of which groups may be optionally substituted by one or more substituents.

Illustrative examples of suitable substituents on $R^a$ include $C_{1-6}$ alkoxy, oxo, cyano and $C_{2-6}$ alkoxycarbonyl.

Selected examples of suitable substituents on $R^a$ include $C_{1-6}$ alkoxy and oxo.

Selected examples of specific substituents on $R^a$ include methoxy and oxo.

In one embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl. In a first particular aspect of this embodiment $R^a$ represents methoxyethyl. In a second particular aspect of this embodiment, $R^a$ represents methoxycarbonyl. In a third aspect of this embodiment, $R^a$ represents ethoxycarbonyl. In a fourth aspect of this embodiment, $R^a$ represents tert-butoxy-carbonyl. In a fifth aspect of this embodiment, $R^a$ represents carboxy-methyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl.

In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl or pyridinyl-methyl. In a further embodiment, $R^a$ represents $C_{3-7}$ cycloalkyl. In another further embodiment, $R^a$ represents $C_{3-7}$ heterocycloalkyl.

Illustrative values of $R^a$ include methyl, methoxyethyl, benzyl, dioxoisoindolyl-propyl, pyridinylmethyl, methoxycarbonylmethyl, carboxymethyl, ethoxycarbonylmethyl, and tert-butoxy-carbonylmethyl Specific values of $R^a$ include methyl, methoxyethyl, benzyl and dioxoisoindolyl-propyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquino linylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$)alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylamino-ethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl, Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl, homopiperazin-1-yl, (imino)(oxo)thiazinan-4-yl, (oxo)thiazinan-4-yl or (dioxo)thiazinan-4-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonyl-amino, $C_{2-6}$ alkylcarbonylamino($C_{1-6}$)alkyl, $C_{2-6}$ alkoxycarbonylamino, $C_{1-6}$ alkyl-sulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxy-carbonylamino, methylsulphonylamino and aminocarbonyl.

Specific values of the heterocyclic moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, aminoazetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxoisothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl, oxohomopiperazin-1-yl, (imino)(oxo)thiazinan-4-yl, (oxo)thiazinan-4-yl and (dioxo)thiazinan-4-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl.

In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl.

In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl.

In a further embodiment, $R^d$ represents optionally substituted $C_{3-7}$ heterocycloalkyl, e.g. thiazolidinyl or oxo-thiazolidinyl.

Selected examples of specific values for $R^d$ include hydrogen, methyl, acetoxy-methyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Particular examples of selected values for $R^d$ include hydrogen and methyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

One sub-class of compounds according to the invention is represented by the compounds of formula (IIA) and N-oxides thereof, and pharmaceutically acceptable salts and solvates thereof, and glucuronide derivatives thereof, and co-crystals thereof:

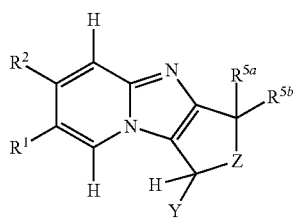

(IIA)

wherein $R^1$ represents halogen or cyano; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{3-7})$cycloalkyl-heteroaryl-, $(C_{3-7})$cycloalkyl-$(C_{1-6})$alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents.

$R^2$ represents hydrogen, halogen, trifluoromethyl or cyano; or an optionally substituted $C_{1-6}$ alkyl.

Z represents an oxygen atom or a sulphur atom; or —S(O), —N($R^d$); or an optionally substituted straight or branched $C_{1-4}$ alkylene chain.

$R^{5a}$ represents hydrogen, hydroxy, halogen, cyano, or trifluoromethyl; or —N$R^bR^c$, —N$R^cC(O)R^d$, —(CO)N$R^cR^d$, —NHS(O)$_2R^e$, —S—$R^a$, —(SO)—$R^a$, —S(O)$_2R^a$, —S(O)(N—$R^d$), —S(O)$_2$(N—$R^d$), —O$R^a$, —C(O)$_2R^d$, —O(CO)—$R^d$—; $C_{1-6}$ alkyl, $C_{2-6}$ alkenyl, $C_{2-6}$ alkynyl, aryl, or heteroaryl, any of which groups may be optionally substituted by one or more substituents; and $R^{5b}$ represents hydrogen, hydroxy, halogen, cyano, trifluoromethyl; or $C_{1-6}$ alkyl, any of which groups may be optionally substituted by one or more substituents;

or $R^{5a}$ and $R^{5b}$ when taken together with the carbon to which they are attached represent a carbonyl, thiocarbonyl, or —C=N—OH; and Y, $R^a$, $R^b$, $R^c$, $R^d$, $R^e$, are as defined above for compounds of formula (I).

Examples of optional substituents which may be present on $R^1$, $R^2$, $R^{5a}$ and $R^{5b}$ include one, two or three substituents independently selected from halogen, halo-$(C_{1-6})$alkyl, cyano, cyano$(C_{1-6})$alkyl, nitro, nitro$(C_{1-6})$alkyl, $C_{1-6}$ alkyl, $(C_{3-7})$cycloalkyl, difluoromethyl, trifluoromethyl, difluoroethyl, trifluoroethyl, $C_{2-6}$ alkenyl, hydroxy, hydroxy$(C_{1-6})$alkyl, $C_{1-6}$ alkoxy, difluoromethoxy, trifluoromethoxy, trifluoroethoxy, carboxy$(C_{3-7})$cycloalkyl-oxy, $C_{1-3}$ alkylenedioxy, $C_{1-6}$ alkoxy$(C_{1-6})$alkyl, $C_{1-6}$ alkylthio, $C_{1-6}$ alkylsulphinyl, $C_{1-6}$ alkylsulphonyl, $(C_{1-6})$alkylsulphonyl$(C_{1-6})$alkyl, oxo, amino, amino$(C_{1-6})$alkyl, $C_{1-6}$ alkyl-amino, di$(C_{1-6})$alkylamino, hydroxy$(C_{1-6})$alkylamino, $C_{1-6}$ alkoxyamino, $(C_{1-6})$alkoxy-$(C_{1-6})$alkylamino, [$(C_{1-6})$alkoxy](hydroxy)$(C_{1-6})$alkylamino, [$(C_{1-6})$alkylthio](hydroxy)-$(C_{1-6})$alkylamino, N—[$(C_{1-6})$alkyl]-N-[hydroxy$(C_{1-6})$alkyl]amino, di$(C_{1-6})$alkylamino-$(C_{1-6})$alkylamino, N-[di$(C_{1-6})$alkylamino$(C_{1-6})$alkyl]-N-[hydroxy$(C_{1-6})$alkyl] amino, hydroxy$(C_{1-6})$alkyl$(C_{3-7})$cycloalkylamino, (hydroxy)[$(C_{3-7})$cycloalkyl$(C_{1-6})$alkyl]amino, $(C_{3-7})$heterocycloalkyl$(C_{1-6})$alkylamino, oxo$(C_{3-7})$heterocycloalkyl$(C_{1-6})$alkylamino, $(C_{1-6})$alkylheteroarylamino, heteroaryl$(C_{1-6})$alkylamino, $(C_{1-6})$alkylheteroaryl$(C_{1-6})$alkyl-amino, $C_{2-6}$ alkylcarbonylamino, N—[$(C_{1-6})$alkyl]-N—[$(C_{2-6})$alkylcarbonyl]amino, $(C_{2-6})$alkyl-carbonylamino$(C_{1-6})$alkyl, $C_{3-6}$ alkenylcarbonylamino, bis[$(C_{3-6})$alkenylcarbonyl]amino, N—[$(C_{1-6})$alkyl]-N—[$(C_{3-7})$cycloalkylcarbonyl]amino, $C_{2-6}$ alkoxycarbonylamino, $C_{2-6}$ alkoxycarbonyl$(C_{1-6})$alkylamino, $C_{1-6}$ alkylaminocarbonylamino, $C_{1-6}$ alkylsulphonyl-amino, N—[$(C_{1-6})$alkyl]-N— [$(C_{1-6})$alkylsulphonyl] amino, bis[$(C_{1-6})$alkylsulphonyl]amino, N—[$(C_{1-6})$alkyl]-N-[carboxy$(C_{1-6})$alkyl]amino, carboxy$(C_{3-7})$cycloalkylamino, carboxy-$(C_{3-7})$cycloalkyl$(C_{1-6})$ alkylamino, formyl, $C_{2-6}$ alkylcarbonyl, $(C_{3-7})$ cycloalkylcarbonyl, phenylcarbonyl, $(C_{2-6})$ alkylcarbonyloxy$(C_{1-6})$alkyl, carboxy, carboxy$(C_{1-6})$alkyl, $C_{2-6}$ alkoxycarbonyl, $C_{2-6}$ alkoxycarbonyl$(C_{1-6})$alkyl, morpholinyl$(C_{1-6})$alkoxycarbonyl, $C_{2-6}$ alkoxycarbonylmethylidenyl, a carboxylic acid isostere or prodrug moiety Ω, —$(C_{1-6})$alkyl-Ω, aminocarbonyl, $C_{1-6}$ alkylaminocarbonyl, hydroxy$(C_{1-6})$alkylamino-carbonyl, di$(C_{1-6})$alkylaminocarbonyl, aminocarbonyl$(C_{1-6})$alkyl, aminosulphonyl, di$(C_{1-6})$alkylaminosulphonyl, $(C_{1-6})$alkylsulphoximinyl, [$(C_{1-6})$alkyl][N—$(C_{1-6})$alkyl]-sulphoximinyl and heteroaryl. An additional example of substituent include $C_{3-7}$cycloalkylsulphonyl.

Examples of particular substituents on $R^1$, $R^2$, $R^{5a}$ and $R^{5b}$ include fluoro, chloro, bromo, fluoromethyl, fluoroisopropyl, cyano, cyanoethyl, nitro, nitromethyl, methyl, ethyl, isopropyl, isobutyl, tert-butyl, cyclopropyl, cyclobutyl, difluoromethyl, trifluoromethyl, difluoroethyl, trifluoro-ethyl, ethenyl, hydroxy, hydroxymethyl, hydroxyisopropyl, methoxy, isopropoxy, difluoromethoxy, trifluoromethoxy, trifluoroethoxy, carboxycyclobutyloxy, methylene-dioxy, ethylenedioxy, methoxymethyl, methoxyethyl, methylthio, methylsulphinyl, methylsulphonyl, methylsulphonylethyl, oxo, amino, aminomethyl, aminoisopropyl, methylamino, ethylamino, dimethylamino, hydroxyethylamino, hydroxypropylamino, (hydroxy)(methyl)propylamino, methoxyamino, methoxyethylamino, (hydroxy)-(methoxy)(methyl)propylamino, (hydroxy)(methylthio)butylamino, N-(hydroxyethyl)-N-(methyl)amino, dimethylaminoethylamino, (dimethylamino)(methyl)propylamino, N-(dimethylaminoethyl)-N-(hydroxyethyl)amino, hydroxymethylcyclopentylamino, hydroxycyclobutylmethylamino, (cyclopropyl)(hydroxy)propylamino, morpholinylethylamino, oxopyrrolidinylmethylamino, ethyloxadiazolylamino, methylthiadiazolylamino, thiazolylmethylamino, thiazolylethylamino, pyrimidinylmethylamino, methylpyrazolyl-methylamino, acetylamino, N-acetyl-N-methylamino, N-isopropylcarbonyl-N-methyl-amino, acetylaminomethyl, ethenylcarbonylamino, bis(ethenylcarbonyl)amino, N-cyclopropylcarbonyl-N-methylamino, methoxycarbonylamino, ethoxycarbonylamino, tert-butoxycarbonylamino, methoxycarbonylethylamino, ethylaminocarbonylamino, butylaminocarbonylamino, methylsulphonylamino, N-methyl-N-(methylsulphonyl)amino, bis(methylsulphonyl)amino, N-(carboxymethyl)-N-methylamino, N-(carboxyethyl)-N-methylamino, carboxycyclopentylamino, carboxycyclopropylmethylamino, formyl, acetyl, isopropylcarbonyl, cyclobutylcarbonyl, phenylcarbonyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, methylsulphonylamino-carbonyl, acetylaminosulphonyl, methoxyaminocarbonyl, tetrazolyl, tetrazolylmethyl, hydroxyoxadiazolyl, aminocarbonyl, methylamino carbonyl, hydroxyethylamino carbonyl, dimethylaminocarbonyl, aminocarbonylmethyl, aminosulphonyl, methylaminosulphonyl, dimethylaminosulphonyl, methylsulphoximinyl and (methyl)(N-methyl)sulphoximinyl. Additional examples of particular substituent include cyclopropylsulphonyl and tert-butoxy.

Suitable examples of particular substituents on $R^1$, $R^2$, $R^{5b}$ and $R^6$ include fluoro, hydroxy, methyl-sulphonyl, methyl, trifluoromethyl, isopropyl, cyclopropyl, methoxy, ethoxycarbonyl, methylsulphoximinyl, oxo, carboxy, acetyl, chloro, hydroxyisopropyl, fluoroisopropyl, aminoisopropyl, methylsulphonyl, methylsulphinyl cyclopropylsulphonyl and tert-butoxy.

Generally, $R^1$ represents $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{3-7})$cycloalkyl-heteroaryl-, $(C_{3-7})$cycloalkyl-$(C_{1-6})$alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents.

Appropriately, $R^1$ represents aryl, $C_{3-7}$ heterocycloalkenyl, heteroaryl, $(C_{3-7})$heterocycloalkyl-heteroaryl-, $(C_{4-9})$heterobicycloalkyl-heteroaryl-, $(C_{3-7})$cycloalkyl-heteroaryl-, or $(C_{4-9})$bicycloalkyl-heteroaryl-, any of which groups may be optionally substituted by one or more substituents.

Typically, $R^1$ represents aryl, heteroaryl, $(C_{3-7})$cycloalkyl-heteroaryl or $(C_{3-7})$heterocycloalkyl-heteroaryl-, any of which groups may be optionally substituted by one or more substituents.

In a first embodiment, $R^1$ represents halogen. In one aspect of that embodiment, $R^1$ represents bromo. In a second embodiment, $R^1$ represents cyano. In a third embodiment, $R^1$ represents optionally substituted $C_{1-6}$ alkyl. In one aspect of that embodiment, $R^1$ represents optionally substituted methyl. In another aspect of that embodiment, $R^1$ represents optionally substituted ethyl. In a fourth embodiment, $R^1$ represents optionally substituted $C_{2-6}$ alkynyl. In one aspect of that embodiment, $R^1$ represents optionally substituted butynyl. In a fifth embodiment, $R^1$ represents optionally substituted aryl. In one aspect of that embodiment, $R^1$ represents optionally substituted phenyl. In sixth embodiment, $R^1$ represents optionally substituted $C_{3-7}$ heterocycloalkyl. In a seventh embodiment, $R^1$ represents optionally substituted $C_{3-7}$ heterocycloalkenyl. In one aspect of this embodiment, $R^1$ represents optionally substituted pyridine-2(1H)-one.

In an eighth embodiment, $R^1$ represents optionally substituted heteroaryl. In selected aspects of that embodiment, $R^1$ represents benzofuryl, thienyl, indolyl, pyrazolyl, indazolyl, isoxazolyl, thiazolyl, imidazolyl, pyridinyl, quinolinyl, pyridazinyl, pyrimidinyl or pyrazinyl, any of which groups may be optionally substituted by one or more substituents. In a first particular aspect of that embodiment, $R^1$ represents optionally substituted pyrimidinyl. In a second particular aspect of that embodiment, $R^1$ represents optionally substituted pyridinyl In ninth embodiment, $R^1$ represents optionally substituted $(C_{3-7})$-heterocycloalkyl$(C_{1-6})$alkyl-aryl-. In a first aspect of that embodiment, $R^1$ represents optionally substituted pyrrolidinylmethylphenyl-. In a second aspect of that embodiment, $R^1$ represents optionally substituted piperazinylmethylphenyl-.

In a tenth embodiment, $R^1$ represents optionally substituted heteroaryl$(C_{3-7})$-heterocycloalkyl-. In one aspect of that embodiment, $R^1$ represents optionally substituted pyridinylpiperazinyl-.

In an eleventh embodiment, $R^1$ represents optionally substituted $(C_{3-7})$cycloalkyl-heteroaryl-. In a first aspect of that embodiment, $R^1$ represents optionally substituted cyclohexylpyrazolyl-. In a second aspect of that embodiment, $R^1$ represents optionally substituted cyclohexylpyridinyl-. In a third aspect of that embodiment, $R^1$ represents optionally substituted cyclopropylpyrimidinyl-. In a fourth aspect of that embodiment, $R^1$ represents optionally substituted cyclobutylpyrimidinyl-. In a fifth aspect of that embodiment, $R^1$ represents optionally substituted cyclopentylpyrimidinyl-. In a sixth aspect of that embodiment, $R^1$ represents optionally substituted cyclohexylpyrimidinyl-. In a seventh aspect of that embodiment, $R^1$ represents optionally substituted cyclohexyl-pyrazinyl-. In an eighth aspect of that embodiment, $R^1$ represents optionally substituted cyclopropylpyridinyl.

In a twelfth embodiment, $R^1$ represents $(C_{3-7})$cycloalkyl-$(C_{1-6})$alkyl-heteroaryl-.

In a thirteenth embodiment, $R^1$ represents optionally substituted $(C_{4-7})$-cycloalkenyl-heteroaryl-.

In a fourteenth embodiment, $R^1$ represents optionally substituted $(C_{4-9})$-bicycloalkyl-heteroaryl-.

In a fifteenth embodiment, $R^1$ represents optionally substituted $(C_{3-7})$-heterocycloalkyl-heteroaryl-. In a first aspect of that embodiment, $R^1$ represents optionally substituted pyrrolidinylpyridinyl-. In a second aspect of that embodiment, $R^1$ represents optionally substituted tetrahydropyranylpyridinyl-. In a third aspect of that embodiment, $R^1$ represents optionally substituted piperidinylpyridinyl-. In a fourth aspect of that embodiment, $R^1$ represents optionally substituted piperazinylpyridinyl-. In a fifth aspect of that embodiment, $R^1$ represents optionally substituted morpholinylpyridinyl-. In a sixth aspect of that embodiment, $R^1$ represents optionally substituted thiomorpholinyl-pyridinyl-. In a seventh aspect of that embodiment, $R^1$ represents optionally substituted diazepanylpyridinyl-. In an eighth aspect of that embodiment, $R^1$ represents optionally substituted oxetanylpyrimidinyl-. In a ninth aspect of that embodiment, $R^1$ represents optionally substituted azetidinylpyrimidinyl-. In a tenth aspect of that embodiment, $R^1$ represents optionally substituted tetrahydrofuranylpyrimidinyl-. In an eleventh aspect of that embodiment, $R^1$ represents optionally substituted pyrrolidinylpyrimidinyl-. In a twelfth aspect of that embodiment, $R^1$ represents optionally substituted tetrahydropyranyl-pyrimidinyl-. In a thirteenth aspect of that embodiment, $R^1$ represents optionally substituted piperidinylpyrimidinyl-. In a fourteenth aspect of that embodiment, $R^1$ represents optionally substituted piperazinylpyrimidinyl-. In a fifteenth aspect of that embodiment, $R^1$ represents optionally substituted morpholinylpyrimidinyl-. In a sixteenth aspect of that embodiment, $R^1$ represents optionally substituted thiomorpholinyl-pyrimidinyl-. In a seventeenth aspect of that embodiment, $R^1$ represents optionally substituted azepanylpyrimidinyl-. In an eighteenth aspect of that embodiment, $R^1$ represents optionally substituted oxazepanylpyrimidinyl-. In a nineteenth aspect of that embodiment, $R^1$ represents optionally substituted diazepanylpyrimidinyl-. In a twentieth aspect of that embodiment, $R^1$ represents optionally substituted thiadiazepanyl-pyrimidinyl-. In a twenty-first aspect of that embodiment, $R^1$ represents optionally substituted oxetanylpyrazinyl-. In a twenty-second aspect of that embodiment, $R^1$ represents optionally substituted piperidinylpyrazinyl-. In a twenty-third aspect of that embodiment, $R^1$ represents optionally substituted tetrahydropyranylpyridinyl. In a twenty-fourth aspect of this embodiment, $R^1$ represents tetrahydro-thiopyranylpyrimidinyl. In a twenty-fifth aspect, $R^1$ represents (imino)(oxo)thiazinanyl-pyrimidinyl. In twenty-sixth aspect of that embodiment, $R^1$ represents (oxo)thiazinanyl-pyrimidinyl. In twenty-seventh aspect of that embodiment, $R^1$ represents and (dioxo)thiazinanyl-pyrimidinyl.

In a sixteenth embodiment, $R^1$ represents optionally substituted $(C_{3-7})$-heterocycloalkyl$(C_{1-6})$alkyl-heteroaryl-. In a first aspect of that embodiment, $R^1$ represents optionally substituted morpholinylmethylthienyl-. In a second aspect of that embodiment, $R^1$ represents optionally substituted morpholinylethylpyrazolyl-.

In a seventeenth embodiment, $R^1$ represents optionally substituted $(C_{3-7})$-heterocycloalkenyl-heteroaryl-.

In an eighteenth embodiment, $R^1$ represents optionally substituted $(C_{4-9})$-heterobicycloalkyl-heteroaryl-. In a first aspect of this embodiment, $R^1$ represents optionally substituted 3-azabicyclo[3.2.1]octanyl-pyrimidinyl. In a second aspect of this embodiment, $R^1$ represents optionally substituted 3-oxa-8-azabicyclo-[3.2.1]octanyl-pyrimidinyl. In a third aspect of this embodiment, $R^1$ represents optionally substituted 3,7-dioxa-9-azabicyclo[3.3.1]nonanyl-pyrimidnyl. In fourth aspect of this embodiment, $R^1$ represents optionally substituted 2,5-diazabicyclo[2.2.1]heptanyl-pyrimidnyl.

In a nineteenth embodiment, $R^1$ represents optionally substituted $(C_{4-9})$-spiroheterocycloalkyl-heteroaryl-.

In a twentieth embodiment, $R^1$ represents optionally substituted $(C_{4-9})$-bicycloalkyl-heteroaryl-. In a particular aspect of this embodiment, $R^1$ represents optionally substituted bicyclo[3.1.0]hexanyl-pyrimidinyl.

Appositely, $R^1$ represents bromo, cyano; or ethyl, butynyl, phenyl, pyrrolidinyl, piperidinyl, piperazinyl, morpholinyl, 1,2,3,6-tetrahydropyridinyl, 3,6-dihydropyridinyl, benzofuryl, thienyl, indolyl, pyrazolyl, indazolyl, isoxazolyl, thiazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, cyclohexylpyrazolyl, cyclohexylpyridinyl, cyclopropylpyrimidinyl, cyclobutylpyrimidinyl, cyclopentylpyrimidinyl, cyclohexylpyrimidinyl, cyclohexylpyrazinyl, cyclohexylmethylpyrimidinyl, cyclohexenylpyridinyl, cyclopropylpyridinyl, cyclohexenylpyrimidinyl, bicyclo[3.1.0]hexanylpyridinyl, bicyclo[3.1.0]hexanyl-pyrimidinyl, bicyclo[3.1.0]hexenyl-pyrimidinyl bicyclo[4.1.0]heptanylpyrimidinyl, bicyclo[2.2.2]octanylpyrimidinyl, pyrrolidinylpyridinyl, tetrahydropyranylpyridinyl, tetrahydro-thiopyranylpyrimidinyl, piperidinylpyridinyl, piperazinyl-pyridinyl, morpholinylpyridinyl, thiomorpholinylpyridinyl, diazepanylpyridinyl, oxetanylpyrimidinyl, azetidinylpyrimidinyl, tetrahydrofuranylpyrimidinyl, pyrrolidinyl-pyrimidinyl, tetrahydropyranylpyrimidinyl, piperidinylpyrimidinyl, piperazinyl-pyrimidinyl, hexahydro-[1,2,5]thiadiazolo[2,3-a]pyrazinylpyrimidinyl, morpholinyl-pyrimidinyl, thiomorpholinylpyrimidinyl, azepanylpyrimidinyl, oxazepanylpyrimidinyl, diazepanylpyrimidinyl, thiadiazepanylpyrimidinyl, oxetanylpyrazinyl, piperidinyl-pyrazinyl, morpholinylmethylthienyl, morpholinylethylpyrazolyl, 3-azabicyclo[3.1.0]-hexanylpyridinyl, 3-azabicyclo[3.1.0]hexanylpyridazinyl, 3-azabicyclo[3.1.0]hexanyl-pyrimidinyl, 2-oxa-5-azabicyclo[2.2.1]heptanylpyrimidinyl, 3-azabicyclo[3.1.1]heptanyl-pyrimidinyl, 3-azabicyclo[4.1.0]heptanylpyridinyl, 3-azabicyclo[4.1.0]heptanyl-pyrimidinyl, 2-oxabicyclo[2.2.2]octanylpyrimidinyl, 3-azabicyclo[3.2.1]octanyl-pyrimidinyl, 8-azabicyclo[3.2.1]octanylpyrimidinyl, 3-oxa-8-azabicyclo[3.2.1]octanyl-pyrimidinyl, 3,6-diazabicyclo[3.2.2]nonanylpyrimidinyl, 3-oxa-7-azabicyclo[3.3.1]-nonanylpyrimidinyl, 3,7-dioxa-9-azabicyclo[3.3.1]-nonanylpyrimidinyl, 5-azaspiro[2.3]hexanylpyrimidinyl, 5-azaspiro[2.4]heptanyl-pyrimidinyl, 2-azaspiro[3.3]heptanylpyrimidinyl, 2-oxa-6-azaspiro[3.3]heptanyl-pyrimidinyl, 2-oxa-6-azaspiro[3.4]octanylpyrimidinyl, 2-oxa-6-azaspiro[3.5]nonanyl-pyrimidinyl, 2-oxa-7-azaspiro[3.5]nonanylpyrimidinyl, 2,4,8-triazaspiro[4.5]decanyl-pyrimidinyl, 3,6-epiminofuro[3.2-b]furanyl-pyrimidinyl, (imino)(oxo)thiazinanyl-pyrimidinyl, (oxo)thiazinanyl-pyrimidinyl or (dioxo)thiazinanyl-pyrimidinyl, any of which groups may be optionally substituted by one or more substituents. Additionally, $R^1$ represents 2,5-diazabicyclo[2.2.1]heptanyl-pyrimidinyl or pyridine-2(1H)-one, which may be optionally substituted by one or more substituents.

Definitively, $R^1$ represents bromo, cyano, phenyl, pyridinyl, dihydropyridinyl, pyrimidinyl, cyclobutylpyrimidinyl, cyclopropylpyridinyl, bicyclo[3.1.0]hexanyl-pyrimidinyl, bicyclo[3.1.0]hexenyl-pyrimidinyl, pyrimidinyl, tetrahydropyranylpyridinyl, tetrahydro-thiopyranylpyrimidinyl, piperazinyl-pyridinyl, oxetanylpyrimidinyl, azetidinylpyrimidinyl, tetrahydrofuranylpyrimidinyl, piperidinylpyrimidinyl, piperazinyl-pyrimidinyl, morpholinyl-pyrimidinyl, thiomorpholinylpyrimidinyl, 2-oxa-5-azabicyclo[2.2.1]heptanylpyrimidinyl, 3-azabicyclo[3.2.1]octanyl-pyrimidinyl, 3-oxa-8-azabicyclo[3.2.1]octanyl-pyrimidinyl, 3,7-dioxa-9-azabicyclo[3.3.1]-nonanylpyrimidinyl, epiminofuro [3.2-b]furanyl-pyrimidinyl, (imino)(oxo)thiazinanyl-pyrimidinyl, (oxo)thiazinanyl-pyrimidinyl, (dioxo)thiazinanyl-pyrimidinyl, cyclopropylpyrimidinyl, 2,5-diazabicyclo[2.2.1]heptanyl-pyrimidinyl or pyridine-2(1H)-one, any of which groups may be optionally substituted by one or more substituents. Appropriately, $R^1$ represents bromo, cyano, phenyl, pyridinyl, dihydropyridinyl, pyrimidinyl, cyclobutylpyrimidinyl, cyclopropylpyridinyl, bicyclo[3.1.0]hexanyl-pyrimidinyl, bicyclo[3.1.0]hexenyl-pyrimidinyl, pyrimidinyl, tetrahydropyranylpyridinyl, tetrahydro-thiopyranylpyrimidinyl, piperazinyl-pyridinyl, oxetanylpyrimidinyl, azetidinylpyrimidinyl, tetrahydrofuranylpyrimidinyl, piperidinylpyrimidinyl, piperazinyl-pyrimidinyl, morpholinyl-pyrimidinyl, thiomorpholinylpyrimidinyl, 2-oxa-5-azabicyclo[2.2.1]heptanylpyrimidinyl, 3-azabicyclo[3.2.1]octanyl-pyrimidinyl, 3-oxa-8-azabicyclo[3.2.1]octanyl-pyrimidinyl, 3,7-dioxa-9-azabicyclo[3.3.1]-nonanylpyrimidinyl, epiminofuro [3.2-b]furanyl-pyrimidinyl, (imino)(oxo)thiazinanyl-pyrimidinyl, (oxo)thiazinanyl-pyrimidinyl, (dioxo)thiazinanyl-pyrimidinyl, or cyclopropylpyrimidinyl, any of which groups may be optionally substituted by one or more substituents. Additionally, $R^1$ represents 2,5-diazabicyclo[2.2.1]heptanyl-pyrimidinyl or pyridine-2(1H)-one, either of which groups may be optionally substituted by one or more substituents.

Suitably, $R^1$ represents phenyl, pyridinyl, dihydropyridinyl, pyrimidinyl, cyclobutylpyrimidinyl, cyclopropylpyridinyl, bicyclo[3.1.0]hexanyl-pyrimidinyl, bicyclo[3.1.0]hexenyl-pyrimidinyl, pyrimidinyl, tetrahydropyranylpyridinyl, tetrahydro-thiopyranylpyrimidinyl, piperazinyl-pyridinyl, oxetanylpyrimidinyl, azetidinylpyrimidinyl, tetrahydrofuranylpyrimidinyl, piperidinylpyrimidinyl, piperazinyl-pyrimidinyl, morpholinyl-pyrimidinyl, thiomorpholinylpyrimidinyl, 2-oxa-5-azabicyclo[2.2.1]heptanylpyrimidinyl, 3-azabicyclo[3.2.1]octanyl-pyrimidinyl, 3-oxa-8-azabicyclo[3.2.1]octanyl-pyrimidinyl,3,7-dioxa-9-azabicyclo[3.3.1]-nonanylpyrimidinyl, epiminofuro[3.2-b]furanyl-pyrimidinyl (imino)(oxo)thiazinanyl-pyrimidinyl, (oxo)thiazinanyl-pyrimidinyl, (dioxo)thiazinanyl-pyrimidinyl, 2,5-diazabicyclo[2.2.1]heptanyl-pyrimidinyl or pyridine-2(1H)-one, any of which groups may be optionally substituted by one or more substituents Illustratively, $R^1$ represents phenyl, pyridinyl, dihydropyridinyl, pyrimidinyl, cyclobutylpyrimidinyl, cyclopropylpyridinyl, bicyclo[3.1.0]hexanyl-pyrimidinyl, bicyclo[3.1.0]hexenyl-pyrimidinyl, pyrimidinyl, tetrahydropyranylpyridinyl, tetrahydro-thiopyranylpyrimidinyl, piperazinyl-pyridinyl, oxetanylpyrimidinyl, azetidinylpyrimidinyl, tetrahydrofuranylpyrimidinyl, piperidinylpyrimidinyl, piperazinyl-pyrimidinyl, morpholinyl-pyrimidinyl, thiomorpholinylpyrimidinyl, 2-oxa-5-azabicyclo[2.2.1]heptanylpyrimidinyl, 3-azabicyclo[3.2.1]octanyl-pyrimidinyl, 3-oxa-8-azabicyclo[3.2.1]octanyl-pyrimidinyl, 3,7-dioxa-9-azabicyclo[3.3.1]-nonanylpyrimidinyl, epiminofuro[3.2-b]furanyl-pyrimidinyl (imino)(oxo)thiazinanyl-pyrimidinyl, (oxo)thiazinanyl-pyrimidinyl or (dioxo)thiazinanyl-pyrimidinyl, any of which groups may be optionally substituted by one or more substituents.

Typical examples of optional substituents on $R^1$ include one, two or three substituents independently selected from halogen, halo($C_{1-6}$)alkyl, cyano, cyano($C_{1-6}$)alkyl, nitro($C_{1-6}$)alkyl, $C_{1-6}$ alkyl, $C_{3-7}$cycloalkyl, trifluoromethyl, trifluoroethyl, $C_{2-6}$ alkenyl, hydroxy, hydroxy($C_{1-6}$)alkyl, $C_{1-6}$ alkoxy, trifluoroethoxy, carboxy($C_{3-7}$)cyclo alkyloxy, $C_{1-6}$ alkylthio, $C_{1-6}$ alkylsulphonyl, ($C_{1-6}$)alkylsulphonyl($C_{1-6}$)alkyl, oxo, amino, amino-($C_{1-6}$)alkyl, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]amino, ($C_{2-6}$)alkylcarbonylamino($C_{1-6}$)alkyl, $C_{1-6}$ alkylsulphonylamino, N—[($C_{1-6}$)alkyl]-N— [($C_{1-6}$)alkylsulphonyl]amino, bis [($C_{1-6}$)alkyl-sulphonyl]amino, N—[($C_{1-6}$)alkyl]-N-[carboxy($C_{1-6}$)alkyl]amino, carboxy($C_{3-7}$)cycloalkyl-amino, carboxy($C_{3-7}$)cycloalkyl($C_{1-6}$)alkylamino, formyl, $C_{1-6}$ alkylcarbonyl, ($C_{2-6}$)alkyl-carbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonylmethylidenyl, ($C_{1-6}$)alkylsulphoximinyl and [($C_{1-6}$)alkyl][N—($C_{1-6}$)alkyl]sulphoximinyl. Additional examples of optional substituents on $R^1$ include one, two or three substituents independently selected difluoromethyl, $C_{1-6}$ alkylsulphinyl, and ($C_{3-7}$)cycloalkyl sulphonyl.

Appropriate examples of optional substituents on $R^1$ include one, two or three substituents independently selected from halogen, hydroxy, trifluoromethyl, $C_{1-6}$ alkyl, $C_{1-6}$ alkoxy, $C_{2-6}$ alkylcarbonyl, $C_{2-6}$ alkyloxycarbonyl, (hydroxy)$C_{1-6}$ alkyl, ($C_{3-7}$)cycloalkyl, $C_{1-6}$ alkylsulphonyl, ($C_{1-6}$)alkylsulphonyl($C_{1-6}$)alkyl, di($C_{1-6}$)alkylaminocarbonyl, ($C_{1-6}$)alkylsulphoximinyl, oxo, carboxy, difluoromethyl, $C_{1-6}$ alkylsulphinyl, and ($C_{3-7}$)cycloalkyl sulphonyl.

Suitable examples of optional substituents on $R^1$ include one, two or three substituents independently selected from halogen, hydroxy, $C_{1-6}$ alkyl, $C_{1-6}$ alkoxy, $C_{1-6}$ alkylcarbonyl, (hydroxy)$C_{1-6}$ alkyl, ($C_{3-7}$)cycloalkyl, $C_{1-6}$ alkylsulphonyl, ($C_{1-6}$)alkylsulphonyl($C_{1-6}$)alkyl, ($C_{1-6}$)alkylsulphoximinyl, oxo and carboxy.

Typical examples of particular substituents on $R^1$ include one, two or three substituents independently selected from fluoro, chloro, fluoromethyl, fluoroisopropyl, cyano, cyanoethyl, nitromethyl, methyl, ethyl, isopropyl, cyclopropyl, isopropylmethyl, trifluoromethyl, trifluoroethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, methylsulphonylethyl, oxo, amino, aminomethyl, aminoisopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis (methylsulphonyl)amino, N-(carboxyethyl)-N-(methyl) amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyamino-carbonyl, tetrazolyl, tetrazolylmethyl, hydroxyoxadiazolyl, aminocarbonyl, amino-sulphonyl, methylsulphoximinyl and (methyl)(N-methyl)sulphoximinyl.

Appropriate particular examples of substituents on $R^1$ include chloro, fluoro, methyl, trifluoromethyl, hydroxy, hydroxymethyl, hydroxyisopropyl, methoxy, methylsulphonyl, oxo, amino, acetyl, methoxycarbonyl, methylsulphoximinyl, ethoxycarbonyl, n-butoxycarbonyl, tert-butoxycarbonyl, fluoroisopropyl, aminoisopropyl, difluoromethyl, methylsulphinyl, tert-butoxy and cyclopropylsulphonyl. Particular examples of substituents on $R^1$ include chloro, fluoro, methyl, trifluoromethyl, hydroxy, hydroxymethyl, hydroxyisopropyl, methoxy, methylsulphonyl, methylsulphoximinyl, oxo, amino, acetyl, methoxycarbonyl, ethoxycarbonyl, n-butoxycarbonyl and tert-butoxycarbonyl.

In a particular embodiment, $R^1$ is substituted by hydroxy ($C_{1-6}$)alkyl. In one aspect of that embodiment, $R^1$ is substituted by hydroxyisopropyl, especially 2-hydroxyprop-2-yl.

In a particular embodiment, $R^1$ is substituted by hydroxy ($C_{1-6}$)alkyl. In one aspect of that embodiment, $R^1$ is substituted by hydroxyisopropyl, especially 2-hydroxyprop-2-yl.

In second particular embodiment, R¹ is substituted by C$_{1-6}$ alkylsulphonyl. In one aspect of this embodiment, R¹ is substituted by methylsulphonyl.

In a third particular embodiment R¹ is substituted by a halogen. In one aspect of this embodiment, R¹ is substituted by a fluoro.

In a fourth particular embodiment, R¹ is substituted by (C$_{1-6}$)alkylsulphoximinyl. In one aspect of this particular embodiment, R¹ is substituted by methylsulphoximinyl.

Selected values of R¹ include bromo, cyano, methoxycarbonyl-ethyl, ethoxycarbonylethyl, hydroxybutynyl, chlorophenyl, hydroxyphenyl, methyl-sulphonylphenyl, (methylsulphonyl)methylphenyl, (methylsulphonyl)ethylphenyl, aminomethylphenyl, aminoisopropylphenyl, acetylaminomethylphenyl, acetylphenyl, methoxycarbonylphenyl, aminocarbonylphenyl, aminosulphonylphenyl, acetylaminosulphonylphenyl, (di-(trifluoromethyl))(hydroxy)phenyl, (methoxycarbonyl)(methyl)pyrrolidinyl, chloropyridinyl, oxopiperidinyl, ethoxycarbonylpiperidinyl, methylsulphonylpiperazinyl, morpholinyl, methylsulphonyl-1,2,3,6-tetrahydropyridinyl, acetyl-1,2,3,6-tetrahydropyridinyl, tert-butoxycarbonyl-1,2,3,6-tetrahydropyridinyl, methoxycarbonylmethyl-1,2,3,6-tetrahydropyridinyl, benzofuryl, thienyl, indolyl, pyrazolyl, methylpyrazolyl, dimethylpyrazolyl, (methyl)[N-methyl-N-(methylsulfonyl)amino]pyrazolyl, methylindazolyl, dimethylisoxazolyl, hydroxyisopropylthiazolyl, methylimidazolyl, dimethylimidazolyl, pyridinyl, tetrahydropyranylpyridinyl, fluoropyridinyl, cyanopyridinyl, methylpyridinyl, (cyano)(methyl)pyridinyl, dimethylpyridinyl, cyclopropylpyridinyl, trifluoromethylpyridinyl, ethenylpyridinyl, hydroxyisopropylpyridinyl, hydroxymethylpyridinyl, methoxypyridinyl, (methoxy)(methyl)pyridinyl, isopropoxypyridinyl, trifluoroethoxypyridinyl, (methyl)-(trifluoroethoxy)pyridinyl, methylsulphonylpyridinyl, methylsulphonylmethylpyridinyl, oxopyridinyl, (methyl)(oxo)-pyridinyl, (dimethyl)(oxo)pyridinyl, aminopyridinyl, methylaminopyridinyl, dimethyl-aminopyridinyl, methoxyethylaminopyridinyl, N-(hydr oxyethyl)-N-(methyl)amino-pyridinyl, methylsulphonylaminopyridinyl, [bis(methylsulphonyl)amino]pyridinyl, carboxypyridinyl, quinolinyl, hydroxypyridazinyl, pyrimidinyl, isopropylpyrimidinyl, fluoroisopropyl-pyrimidinyl, hydroxyisopropylpyrimidinyl, methoxypyrimidinyl, carboxycyclobutyloxy-pyrimidinyl, methylthiopyrimidinyl, methylsulphonylpyrimidinyl, oxopyrimidinyl, aminopyrimidinyl, dimethylaminopyrimidinyl, methoxyethylaminopyrimidinyl, N-(carboxyethyl)-N-(methyl)aminopyrimidinyl, carboxycyclopentylaminopyrimidinyl, carboxycyclopropylmethylaminopyrimidinyl, acetoxyisopropylpyrimidinyl, ethoxycarbonylethylpyrimidinyl, hydroxypyrazinyl, hydroxyisopropylpyrazinyl, pyrrolidinylmethylphenyl, piperazinylmethylphenyl, pyridinylpiperazinyl, carboxy-cyclohexylpyrazolyl, carboxycyclohexylpyridinyl, fluoromethylcyclopropylpyrimidinyl, acetylaminomethylcyclopropylpyrimidinyl, hydroxymethylpyrimidinyl, hydroxycyclobutylpyrimidinyl, carboxy-cyclopentylpyrimidinyl, carboxycyclohexylpyrimidinyl, (carboxy)(methyl)cyclohexyl-pyrimidinyl, (carboxy)(hydroxy)cyclohexylpyrimidinyl, carboxymethylcyclohexylpyrimidinyl, ethoxycarbonylcyclohexylpyrimidinyl, (methoxycarbonyl)(methyl)-cyclohexylpyrimidinyl, (ethoxycarbonyl)(methyl)cyclohexylpyrimidinyl, carboxycyclohexylpyrazinyl, carboxycyclohexylmethylpyrimidinyl, carboxycyclohexenyl-pyridinyl, carboxycyclohexenylpyrimidinyl, ethoxycarbonylcyclohexenylpyrimidinyl, carboxybicyclo[3.1.0]hexanylpyridinyl, carboxybicyclo[3.1.0]hexenylpyridinyl carboxybicyclo[3.1.0]hexanylpyrimidinyl, ethoxycarbonylbicyclo[3.1.0]hexanylpyrimidinyl, carboxybicyclo[4.1.0]heptanyl-pyrimidinyl, carboxybicyclo[2.2.2]octanylpyrimidinyl, pyrrolidinylpyridinyl, hydroxypyrrolidinylpyridinyl, hydroxytetrahydropyranylpyridinyl, piperidinylpyridinyl, acetylpiperidinylpyridinyl, (carboxy)(methyl)piperidinylpyridinyl, [(carboxy)(methyl)-piperidinyl](fluoro)pyridinyl, [(carboxy)(methyl)piperidinyl](chloro)pyridinyl, piperazinylpyridinyl, (methyl)(piperazinyl)pyridinyl, cyanoethylpiperazinylpyridinyl, trifluoroethylpiperazinylpyridinyl, methylsulphonylpiperazinylpyridinyl, methyl-sulphonylethylpiperazinylpyridinyl, oxopiperazinylpyridinyl, acetylpiperazinylpyridinyl, (tert-butoxycarbonylpiperazinyl)(methyl)pyridinyl, methylpiperazinylpyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinylpyridinyl, (tert-butoxycarbonyl)-3,6-dihydropyridine, oxothiomorpholinylpyridinyl, dioxothiomorpholinylpyridinyl, oxodiazepanyl-pyridinyl, fluorooxetanylpyrimidinyl, hydroxyoxetanylpyrimidinyl, hydroxyazetidinyl-pyrimidinyl, (hydroxy)(methyl)azetidinylpyrimidinyl, (hydroxy)(trifluoromethyl)azetidinylpyrimidinyl, carboxyazetidinylpyrimidinyl, (tert-butoxycarbonyl)(hydroxy)azetidinylpyrimidinyl, tetrazolylazetidinylpyrimidinyl, hydroxytetrahydrofuranylpyrimidinyl, hydroxypyrrolidinylpyrimidinyl, carboxy-pyrrolidinylpyrimidinyl, (carboxy)(methyl)pyrrolidinylpyrimidinyl, carboxymethyl-pyrrolidinylpyrimidinyl, ethoxycarbonylpyrrolidinylpyrimidinyl, fluoro-tetrahydropyranylpyrimidinyl, hydroxytetrahydropyranylpyrimidinyl, (hydroxy)dioxidotetrahydrothiopyranyl)pyrimidinyl, piperidinylpyrimidinyl, difluoropiperidinylpyrimidinyl, (cyano)(methyl)piperidinylpyrimidinyl, (hydroxy)(nitromethyl)piperidinyl-pyrimidinyl, (hydroxy)(methyl)piperidinylpyrimidinyl, (hydroxy)(trifluoromethyl)-piperidinylpyrimidinyl, (hydroxymethyl)(methyl)piperidinylpyrimidinyl, methylsulphonylpiperidinylpyrimidinyl, oxopiperidinylpyrimidinyl, (formyl)(methyl)-piperidinylpyrimidinyl, carboxypiperidinylpyrimidinyl, (carboxy)(fluoro)piperidinyl-pyrimidinyl, (carboxy)(methyl)piperidinylpyrimidinyl, (carboxy)(ethyl)piperidinyl-pyrimidinyl, (carboxy)(trifluoromethyl)piperidinylpyrimidinyl, (carboxy)(hydroxy)-piperidinylpyrimidinyl, (carboxy)(hydroxymethyl)piperidinylpyrimidinyl, (carboxy)-(methoxy)piperidinylpyrimidinyl, (amino)(carboxy)piperidinylpyrimidinyl, carboxymethylpiperidinylpyrimidinyl, methoxycarbonylpiperidinylpyrimidinyl, ethoxycarbonylpiperidinylpyrimidinyl, (ethoxycarbonyl)(fluoro)piperidinylpyrimidinyl, (methoxy-carbonyl)(methyl)piperidinylpyrimidinyl, (ethyl)(methoxycarbonyl)piperidinylpyrimidinyl, (isopropyl)(methoxycarbonyl)piperidinylpyrimidinyl, (ethoxycarbonyl)-(methyl)piperidinylpyrimidinyl, (n-butoxycarbonyl)(methyl)piperidinylpyrimidinyl, (ethoxycarbonyl)(trifluoromethyl)piperidinylpyrimidinyl, (ethoxycarbonyl)-(hydroxymethyl)piperidinylpyrimidinyl, (methoxy)(methoxycarbonyl)piperidinyl-pyrimidinyl, (carboxy)(methoxycarbonyl)piperidinylpyrimidinyl, (methyl)-(morpholinylethoxycarbonyl)piperidinylpyrimidinyl, ethoxycarbonylmethylpiperidinyl-pyrimidinyl, methylsulphonylaminocarbonylpiperidinylpyrimidinyl, acetylpiperidinylpyrimidinyl, acetylamino-sulphonylpiperidinylpyrimidinyl, methoxyaminocarbonylpiperidinylpyrimidinyl, tetrazolylpiperidinylpyrimidinyl, hydroxyoxadiazolylpiperidinylpyrimidinyl, amino-sulphonylpiperidinylpyrimidinyl, piperazinylpyrimidinyl, methylsulphonylpiperazinyl-pyrimidinyl, oxopiperazinylpyrimidinyl, carboxypiperazinylpyrimidinyl, carboxyethyl-piperazinylpyrimidinyl, tert-butoxycarbonylpiperazinylpyrimidinyl, tetrazolylmethyl-piperazinylpyrimidinyl, trioxohexahydro-[1,2,5]thiadiazolo[2,3-c]pyrazinylpyrimidinyl, morpholinylpyrimidinyl, dimethylmorpholinylpyrimidinyl, hydroxymethylmorpholinyl-pyrimidinyl, carboxymorpholinylpyrimidinyl, (carboxy)(methyl)morpholinylpyrimidinyl, carboxymethylmorpholinylpyrimidinyl, thiomorpholinylpyrimidinyl, oxo-thiomorpholinylpyrimidinyl, dioxo-thiomorpholinylpyrimidinyl, carboxyazepanylpyrimidinyl, carboxyoxazepanyl-pyrimidinyl, oxodiazepanylpyrimidinyl, (oxodiazepanyl)(trifluoromethyl)pyrimidinyl, (oxodiazepanyl)(methoxy)pyrimidinyl, (methyl)(oxo)diazepanylpyrimidinyl, dioxo-thiadiazepanylpyrimidinyl, hydroxyoxetanylpyrazinyl, (carboxy)(methyl)piperidinyl-pyrazinyl, (ethoxycarbonyl)(methyl)piperidinylpyrazinyl, morpholinylmethylthienyl, morpholinylethylpyrazolyl, isopropylmethylpyrazolyl, carboxy-3-azabicyclo[3.1.0]hexanylpyridinyl, carboxy-3-azabicyclo[3.1.0]hexanylpyridazinyl, carboxy-3-azabicyclo[3.1.0]hexanylpyrimidinyl, (carboxy)(methyl)-3-azabicyclo[3.1.0]hexanylpyrimidinyl, methoxycarbonyl-3-azabicyclo[3.1.0]hexanylpyrimidinyl, ethoxycarbonyl-3-azabicyclo[3.1.0]hexanyl-pyrimidinyl, 2-oxa-5-azabicyclo[2.2.1]heptanylpyrimidinyl, carboxy-2-oxa-5-azabicyclo-[2.2.1]heptanylpyrimidinyl, carboxy-3-azabicyclo[3.1.1]heptanylpyrimidinyl, carboxy-3-azabicyclo[4.1.0]heptanylpyridinyl, carboxy-3-azabicyclo[4.1.0]heptanylpyrimidinyl, methoxycarbonyl-3-azabicyclo[4.1.0]heptanylpyrimidinyl, ethoxycarbonyl-3-azabicyclo-[4.1.0]heptanylpyrimidinyl, (hydroxy)(methyl)(oxo)-2-oxabicyclo[2.2.2]octanyl-pyrimidinyl, carboxy-3-azabicyclo[3.2.1]octanylpyrimidinyl, methoxycarbonyl-3-azabicyclo[3.2.1]octanylpyrimidinyl, oxo-8-azabicyclo[3.2.1]octanylpyrimidinyl, ethoxycarbonylmethylidenyl-8-azabicyclo[3.2.1]octanylpyrimidinyl, 3-oxa-8-azabicyclo-[3.2.1]octanylpyrimidinyl, 3-carboxy-8-azabicyclo-[3.2.1]octanylpyrimidinyl, 3-(dimethylaminocarbonyl)-8-azabicyclo-[3.2.1]octanylpyrimidinyl, oxo-3,6-diazabicyclo[3.2.2]nonanylpyrimidinyl, 3,7-dioxa-9-azabicyclo[3.3.1]-nonanylpyrimidinyl, carboxy-3-oxa-7-azabicyclo[3.3.1]nonanylpyrimidinyl, carboxy-5-azaspiro[2.3]hexanylpyrimidinyl, (carboxy)(methyl)-5-azaspiro[2.3]hexanylpyrimidinyl, carboxy-5-azaspiro[2.4]heptanyl-pyrimidinyl, carboxy-2-azaspiro[3.3]heptanylpyrimidinyl, 2-oxa-6-azaspiro[3.3]heptanyl-pyrimidinyl, 2-oxa-6-azaspiro[3.4]octanylpyrimidinyl, 2-oxa-6-azaspiro[3.5]nonanyl-pyrimidinyl, 2-oxa-7-azaspiro[3.5]nonanylpyrimidinyl, (dioxo)(methyl)-2,4,8-triazaspiro[4.5]decanylpyrimidinyl, 3,6-epiminofuro[3.2-b]furanyl-pyrimidinyl, (methyl)cylobutyldiol-pyrimidinyl, methylsulphoximinylphenyl, (imino)(oxo)thiazinanyl-pyrimidinyl, (oxo)thiazinanyl-pyrimidinyl and (dioxo)thiazinanyl-pyrimidinyl. Additional values of $R^1$ include difluorocyclobutanyl-pyrimidinyl, difluoromethyl-pyrimidinyl, cyclopropyl-pyrimidinyl, aminoisopropyl-pyrimidinyl, (hydroxy)cyclopropyl-pyrimidinyl, (difluoro)(hydroxy)cyclobutyl-pyrimidinyl, ((methyl)cyclobutane-diol)-pyrimidinyl, (hydroxy)(methyl)cyclohexyl-pyrimidinyl, ((methyl)cyclohexane-diol)-pyrimidinyl, (chloro)(methoxy)pyridinyl, methylsulphinyl-phenyl, cyclopropylsulphonyl-phenyl, tert-butoxy-pyridinyl, methylsulphoximinylpyridinyl, piperazinyl-2-one-pyrimidinyl, (methyl)pyridine-2(1H)-one, (fluoro)pyridine-2(1H)-one, (chloro)pyridine-2(1H)-one, methylcarboxy-3-azabicyclo[3.2.1]octanylpyrimidinyl, 3-oxa-8-azabicyclo[3.2.1]octanylpyrimidinyl, and 2,5-diazabicyclo[2.2.1]hetanylpyrimidinyl.

Appropriate values of $R^1$ include bromo, cyano, (methylsulphonyl)methylphenyl, (methylsulphonyl)ethylphenyl, (di-(trifluoromethyl))(hydroxy)phenyl, chloropyridinyl, tetrahydropyranylpyridinyl, hydroxyisopropylpyridinyl, hydroxymethylpyridinyl, methoxypyridinyl, isopropoxypyridinyl, isopropylpyrimidinyl, hydroxyisopropylpyrimidinyl, hydroxymethylpyrimidinyl, hydroxycyclobutylpyrimidinyl, carboxybicyclo[3.1.0]hexanylpyridinyl, carboxybicyclo[3.1.0]hexenylpyridinyl piperazinylpyridinyl, (tert-butoxycarbonyl)-3,6-dihydropyridine, hydroxyoxetanylpyrimidinyl, hydroxyazetidinyl-pyrimidinyl, (hydroxy)(methyl)azetidinylpyrimidinyl, (hydroxy)(trifluoromethyl)azetidinylpyrimidinyl, (tert-butoxycarbonyl)(hydroxy)azetidinylpyrimidinyl, hydroxytetrahydrofuranylpyrimidinyl, -hydroxytetrahydropyranylpyrimidinyl, (hydroxy)dioxidotetrahydrothiopyranyl)pyrimidinyl, piperidinylpyrimidinyl, (cyano)(methyl)piperidinylpyrimidinyl, (hydroxy)(methyl)piperidinylpyrimidinyl, (carboxy)(methyl)piperidinylpyrimidinyl, acetylpiperidinylpyrimidinyl, piperazinylpyrimidinyl, carboxypiperazinylpyrimidinyl, tert-butoxycarbonylpiperazinylpyrimidinyl, morpholinylpyrimidinyl, thiomorpholinylpyrimidinyl, oxo-thiomorpholinylpyrimidinyl, dioxo-thiomorpholinylpyrimidinyl, oxodiazepanylpyrimidinyl, 2-oxa-5-azabicyclo[2.2.1]heptanylpyrimidinyl, carboxy-3-azabicyclo[3.2.1]octanylpyrimidinyl, oxo-8-azabicyclo[3.2.1]octanylpyrimidinyl, 3-carboxy-8-azabicyclo-[3.2.1]octanylpyrimidinyl, 3-(dimethylaminocarbonyl)-8-azabicyclo-[3.2.1]octanylpyrimidinyl, oxo-3,6-diazabicyclo[3.2.2]nonanylpyrimidinyl, 3,7-dioxa-9-azabicyclo[3.3.1]-nonanylpyrimidinyl, 3,6-epiminofuro[3.2-b]furanyl-pyrimidinyl, methylsulphoximinylphenyl, (methyl)cyclobutyldiol-pyrimidinyl, (imino)(oxo)thiazinanyl-pyrimidinyl, (oxo)thiazinanyl-pyrimidinyl, (dioxo)thiazinanyl-pyrimidinyl, difluorocyclobutanyl-pyrimidinyl, difluoromethyl-pyrimidinyl, cyclopropyl-pyrimidinyl, aminoisopropyl-pyrimidinyl, (hydroxy)cyclopropyl-pyrimidinyl, (difluoro)(hydroxy)cyclobutyl-pyrimidinyl, ((methyl)cyclobutane-diol)-pyrimidinyl, (hydroxy)(methyl)cyclohexyl-pyrimidinyl, ((methyl)cyclohexane-diol)-pyrimidinyl, (chloro)(methoxy)pyridinyl, methylsulphinyl-phenyl, cyclopropylsulphonyl-phenyl, tert-butoxypyridinyl, methylsulphoximinylpyridinyl, piperazinyl-2-one-pyrimidinyl, (methyl)pyridine-2(1H)-one, (fluoro)pyridine-2(1H)-one, (chloro)pyridine-2(1H)-one, methylcarboxy-3-azabicyclo[3.2.1]octanylpyrimidinyl, 3-oxa-8-azabicyclo[3.2.1]octanylpyrimidinyl, and 2,5-diazabicyclo[2.2.1]hetanylpyrimidinyl.

Illustrative values of $R^1$ include bromo, cyano, (methylsulphonyl)methylphenyl, (methylsulphonyl)ethylphenyl, (di-(trifluoromethyl))(hydroxy)phenyl, chloropyridinyl, tetrahydropyranylpyridinyl, hydroxyisopropylpyridinyl, hydroxymethylpyridinyl, methoxypyridinyl, isopropoxypyridinyl, isopropylpyrimidinyl, hydroxyisopropylpyrimidinyl, hydroxymethylpyrimidinyl, hydroxycyclobutylpyrimidinyl, carboxybicyclo[3.1.0]hexanylpyridinyl, carboxybicyclo[3.1.0]hexenylpyridinyl piperazinylpyridinyl, (tert-butoxycarbonyl)-3,6-dihydropyridine, hydroxyoxetanylpyrimidinyl, hydroxyazetidinyl-pyrimidinyl, (hydroxy)(methyl)azetidinylpyrimidinyl, (hydroxy)(trifluoromethyl)azetidinylpyrimidinyl, (tert-butoxycarbonyl)(hydroxy)azetidinylpyrimidinyl, hydroxytetrahydrofuranylpyrimidinyl, -hydroxytetrahydropyranylpyrimidinyl, (hydroxy)dioxidotetrahydrothiopyranyl)pyrimidinyl, piperidinylpyrimidinyl, (cyano)(methyl)piperidinylpyrimidinyl, (hydroxy)(methyl)piperidinylpyrimidinyl, (carboxy)(methyl)piperidinylpyrimidinyl, acetylpiperidinylpyrimidinyl, piperazinylpyrimidinyl, carboxypiperazinylpyrimidinyl, tert-butoxycarbonylpiperazinylpyrimidinyl, morpholinylpyrimidinyl, thiomorpholinylpyrimidinyl, oxo-thiomorpholinylpyrimidinyl, dioxo-thiomorpholinylpyrimidinyl, oxodiazepanylpyrimidinyl, 2-oxa-5-azabicyclo[2.2.1]heptanylpyrimidinyl, carboxy-3-azabicyclo[3.2.1]octanylpyrimidinyl, oxo-8-azabicyclo[3.2.1]octanylpyrimidinyl, 3-carboxy-8-azabicyclo-[3.2.1]octanylpyrimidinyl, 3-(dimethylaminocarbonyl)-8-azabicyclo-[3.2.1]octanylpyrimidinyl, oxo-3,6-diazabicyclo[3.2.2]nonanylpyrimidinyl, 3,7-dioxa-9-azabicyclo[3.3.1]-nonanylpyrimidinyl, 3,6-epiminofuro[3.2-b]furanyl-pyrimidinyl, methylsulphoximinylphenyl, (imino)(oxo)thiazinanyl-pyrimidinyl, (oxo)thiazinanyl-pyrimidinyl and (dioxo)thiazinanyl-pyrimidinyl.

Typical examples of optional substituents on $R^2$ include $C_{2-6}$ alkoxycarbonyl.

Typical examples of particular substituents on $R^2$ include ethoxycarbonyl.

In a first embodiment, $R^2$ represents hydrogen. In a second embodiment, $R^2$ represents halogen. In one aspect of that embodiment, $R^2$ represents fluoro. In another aspect of that embodiment, $R^2$ represents chloro. In a third embodiment, $R^2$ represents trifluoromethyl. In a fourth embodiment, $R^2$ represents optionally substituted $C_{1-6}$ alkyl. In one aspect of that embodiment, $R^2$ represents unsubstituted methyl. In another aspect of that embodiment, $R^2$ represents unsubstituted ethyl. In a further aspect of that embodiment, $R^2$ represents monosubstituted methyl or monosubstituted ethyl. In a fifth embodiment $R^2$ represents cyano.

Typical values of $R^2$ include hydrogen, fluoro, chloro, trifluoromethyl, methyl and ethoxycarbonylethyl.

Particular values of $R^2$ include hydrogen and fluoro.

In a first embodiment, Z represents an oxygen atom. In a second embodiment, Z represents a sulphur atom. In a third embodiment, Z represents —S(O). In a fourth embodiment Z represents —N($R^d$). In one aspect of this embodiment X represents —NH.

In a fifth embodiment, Z represents an optionally substituted straight or branched $C_{1-4}$ alkylene chain. Typical values of Z according to this embodiment include methylene (—$CH_2$—), (methyl)methylene, ethylene (—$CH_2CH_2$—), (ethyl)methylene, (dimethyl)-methylene, (methyl)ethylene, propylene (—$CH_2CH_2CH_2$—), (propyl)methylene and (dimethyl)ethylene, any of which chains may be optionally substituted by one or more substituents. In one aspect of this embodiment Z represents an unsubstituted straight or branched $C_{1-4}$ alkylene chain. In a second aspect of this embodiment, Z represents a monosubstituted straight or branched $C_{1-4}$ alkylene chain. In a third aspect of this embodiment, Z represents a disubstituted straight or branched $C_{1-4}$ alkylene chain. In a particular aspect of this embodiment, Z represents an unsubstituted methylene.

Examples of typical substituents on the alkylene chain which may be present in a compound in accordance with the invention include halogen, hydroxy, oxo, $C_{1-6}$ alkoxy, aryl, —C(O)$R^d$, —$CO_2R^d$, —CONR$^b$R$^c$—S(O)(N—$R^d$)$R^a$, or —$SO_2NR^bR^c$.

Particular values of Z include methylene, —S(O), oxygen and sulphur.

In a specific embodiment, Z is methylene.

Suitably, $R^{5a}$ represents hydrogen, hydroxy, halogen, trifluoromethyl; —$NR^bR^c$, $S(O)_2R^a$, —$OR^a$, O—(CO)—$R^d$ or —$NR^cC(O)R^d$; or $C_{1-6}$ alkyl any of which groups may be optionally substituted.

Typically, $R^{5a}$ represents hydrogen, hydroxy, halogen, or trifluoromethyl; or —$NR^bR^c$, $S(O)_2R^a$, —$OR^a$, or O—(CO)—$R^d$; or $C_{1-6}$ alkyl any of which groups may be optionally substituted.

Suitable examples of optional substituents on $R^{5a}$ include one, two or three substituents independently selected from halogen, hydroxy, trifluoromethyl, $C_{1-6}$ alkyl, $C_{1-6}$ alkoxy, $C_{2-6}$ alkylcarbonyl, $C_{2-6}$ alkyloxycarbonyl, (hydroxy)$C_{1-6}$ alkyl, ($C_{3-7}$)cycloalkyl, $C_{1-6}$ alkylsulphonyl, ($C_{1-6}$)alkylsulphonyl($C_{1-6}$)alkyl, di($C_{1-6}$)alkylaminocarbonyl, oxo, and carboxy.

Typical examples of particular substituents on $R^{5a}$ include one, two or three substituents independently selected from fluoro, chloro, fluoromethyl, fluoroisopropyl, cyano, cyanoethyl, nitromethyl, methyl, ethyl, isopropyl, isopropylmethyl, trifluoromethyl, trifluoroethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, methylsulphonylethyl, oxo, amino, aminomethyl, amino isopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyaminocarbonyl, tetrazolyl, tetrazolylmethyl, hydroxyoxadiazolyl, aminocarbonyl, amino-sulphonyl, methylsulphoximinyl and (methyl)(N-methyl)sulphoximinyl.

In a first embodiment, $R^{5a}$ represents hydrogen. In a second embodiment, $R^{5a}$ represents hydroxy. In a third embodiment, $R^{5a}$ represents halogen. In one aspect of this embodiment, $R^{5a}$ represents fluoro. In a fourth embodiment, $R^{5a}$ represents trifluoromethyl. In a fifth embodiment, $R^{5a}$ represents —$NR^bR^c$. In one aspect of that embodiment, $R^{5a}$ represents —$NH_2$. In a sixth embodiment, $R^{5a}$ represents —$NR^cC(O)R^d$. In a seventh embodiment, $R^{5a}$ represents C(O)—$NR^cR^d$. In an eighth embodiment, $R^{5a}$ represents —$NHS(O)_2R^e$. In a ninth embodiment, $R^{5a}$ represents S—$R^a$. In a tenth embodiment, $R^{5a}$ represents —S(O)—$R^a$. In an eleventh embodiment, $R^{5a}$ represents —$S(O)_2R^a$. In a particular aspect of this embodiment, $R^{5a}$ represents —$S(O)_2$—$CH_3$. In a twelfth embodiment, $R^{5a}$ represents —S(O)(N—$R^d$)$R^a$. In a thirteenth embodiment, $R^{5a}$ represents —$S(O)_2(N—R^d)$. In a fourteenth embodiment, $R^{5a}$ represents —$OR^a$. In one aspect of this embodiment, $R^a$ is a $C_{1-6}$ alkyl. In second aspect of this embodiment $R^a$ is an aryl. In a third aspect of this embodiment, $R^a$ is an heteroaryl. In a fifteenth embodiment, $R^{5a}$ represents O—(CO)—$R^d$. In a particular aspect of this embodiment, $R^{5a}$ represents O—(CO)—$CH_3$. In a sixteenth embodiment, —C(O)—$OR^d$. In a seventeenth embodiment $R^{5a}$ represents optionally substituted $C_{1-6}$ alkyl. In one aspect of that embodiment, $R^{5a}$ represents substituted $C_{1-6}$ alkyl. In a second aspect of this embodiment, $R^{5a}$ represents unsubstituted $C_{1-6}$ alkyl. In a particular aspect of this embodiment, $R^{5a}$ represents methyl. In an eighteenth embodiment, $R^{5a}$ represents an optionally substituted $C_{2-6}$ alkynyl. In a nineteenth embodiment, $R^{5a}$ represents an optionally substituted heteroaryl.

In a twentieth embodiment $R^{5a}$ represents an optionally substituted aryl. In a twenty-first embodiment, $R^{5a}$ represents an optionally substituted $C_{2-6}$ alkenyl.

In a twenty-second embodiment, $R^{5a}$ represents cyano.

Typically, $R^{5b}$ represents hydrogen, hydroxy; or optionally substituted $C_{1-6}$ alkyl. $C_{1-6}$ alkoxy any of which groups may be optionally substituted.

In a first embodiment, $R^{5b}$ represents hydrogen. In a second embodiment, $R^{5b}$ represents hydroxy. In a third embodiment, $R^{5b}$ represents halogen. In one aspect of this embodiment, $R^{5a}$ represents fluoro. In a fourth embodiment, $R^{5b}$ represents trifluoromethyl. In fifth embodiment, $R^{5b}$ represents substituted or unsubstituted $C_{1-6}$ alkyl. In one aspect of that embodiment $R^{5b}$ is methyl. In a sixth embodiment, $R^{5b}$ represents cyano.

Particular values of $R^{5b}$ include hydrogen and methyl.

In a particular alternative embodiment, $R^{5a}$ and $R^{5b}$ when taken together with the carbon to which they are attached represent a carbonyl.

In second particular alternative embodiment, $R^{5a}$ and $R^{5b}$ when taken together with the carbon to which they are attached represent a thiocarbonyl.

In third particular alternative embodiment, $R^{5a}$ and $R^{5b}$ when taken together with the carbon to which they are attached represent-C=N—OH.

Illustrative values of $R^{5a}$ include hydrogen, hydroxy, fluoro, trifluoromethyl, —N(CH$_3$)$_2$, —NH(CO)CH$_3$, —SO$_2$—CH$_3$, —O—(CO)—CH$_3$, methyl, methoxy, pyridinemethyloxy-, benzyloxy, (methoxycarbonyl)methyloxy-, (ethyloxycarbonyl)methyloxy-, (tert-butoxycarbonyl)methyloxy-, (hydroxycarbonyl)methyloxy and cyanomethyloxy.

Selected values of $R^{5a}$ include hydrogen, hydroxy, fluoro, trifluoromethyl, —N(CH$_3$)$_2$, —NH(CO)CH$_3$, —SO$_2$—CH$_3$, —CO$_2$—CH$_3$, methyl and methoxy.

Selected values of $R^{5b}$ include hydrogen, hydroxy, fluoro, trifluoromethyl and methyl.

In a particular embodiment, $R^{5a}$ is as defined above and $R^{5b}$ represents hydrogen. In a particular aspect of this embodiment, $R^{5a}$ is hydroxy.

In another particular embodiment $R^{5a}$ is as defined above and $R^{5b}$ represents $C_{1-4}$ alkyl, preferably methyl. In a particular aspect of this embodiment, $R^{5a}$ is hydroxy.

A particular sub-group of the compounds of formula (HA) above is represented by the compounds of formula (JIB) and N-oxides thereof, and pharmaceutically acceptable salts and solvates thereof, and glucuronide derivatives thereof, and co-crystals thereof:

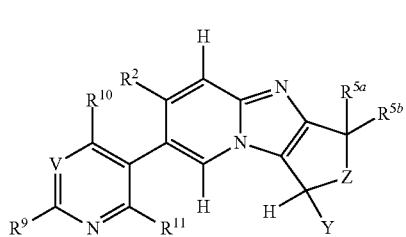

(IIB)

wherein

V represents C—$R^{12}$ or N;

$R^9$ represents hydrogen, halogen, halo($C_{1-6}$)alkyl, cyano, cyano($C_{1-6}$)alkyl, nitro($C_{1-6}$)alkyl, $C_{1-6}$ alkyl, trifluoromethyl, trifluoroethyl, $C_{2-6}$ alkenyl, hydroxy, hydroxy($C_{1-6}$)alkyl, $C_{1-6}$ alkoxy, trifluoroethoxy, carboxy($C_{3-7}$)cycloalkyloxy, $C_{1-6}$ alkylthio, $C_{1-6}$ alkylsulphonyl, ($C_{1-6}$)alkylsulphonyl($C_{1-6}$)alkyl, oxo, amino, amino-($C_{1-6}$)alkyl, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]amino, ($C_{2-6}$)alkylcarbonylamino($C_{1-6}$)alkyl, $C_{1-6}$ alkylsulphonylamino, N—[($C_{1-6}$)alkyl]-N—[($C_{1-6}$)alkylsulphonyl]amino, bis[($C_{1-6}$)alkyl-sulphonyl]amino, N—[($C_{1-6}$)alkyl]-N-[carboxy($C_{1-6}$)alkyl]amino, carboxy($C_{3-7}$)cycloalkylamino, carboxy($C_{3-7}$)cycloalkyl($C_{1-6}$)alkylamino, formyl, $C_{2-6}$ alkylcarbonyl, ($C_{2-6}$)alkyl-carbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonyl-methylidenyl, aminocarbonyl, di($C_{1-6}$)alkylaminocarbonyl, aminosulphonyl, ($C_{1-6}$)alkylsulphoximinyl or [($C_{1-6}$)alkyl][N—($C_{1-6}$)alkyl]sulphoximinyl; or $R^9$ represents ($C_{3-7}$)cycloalkyl, ($C_{3-7}$)cycloalkyl($C_{1-6}$)alkyl, ($C_{4-7}$)cycloalkenyl, ($C_{4-9}$)bicycloalkyl, ($C_{4-9}$)bicycloalkylene, ($C_{3-7}$)heterocycloalkyl, ($C_{3-7}$)heterocycloalkyl($C_{1-6}$)alkyl, ($C_{3-7}$)heterocycloalkenyl, ($C_{4-9}$)heterobicycloalkyl, ($C_{4-9}$)spiroheterocycloalkyl, or heteroaryl, any of which groups may be optionally substituted by one or more substituents; or $R^9$ represents $C_{1-6}$ alkylsulphinyl, ($C_{3-7}$)cycloalkylsulphonyl or difluoromethyl.

$R^{10}$ and $R^{11}$ independently represents hydrogen, halogen, cyano, trifluoromethyl, hydroxy; or —NR$^b$R$^c$, —OR$^a$; $C_{1-6}$ alkyl, or $C_{1-6}$ alkylsulphonyl.

$R^{12}$ represents hydrogen, halogen or $C_{1-6}$ alkyl; and

Z, Y, $R^2$, $R^{5a}$ and $R^{5b}$ are as defined above.

In one embodiment, V represents C—$R^{12}$. In another embodiment, V represents N.

Typically, $R^9$ represents hydrogen, halogen, halo($C_{1-6}$)alkyl, cyano, $C_{1-6}$ alkyl, trifluoromethyl, $C_{2-6}$ alkenyl, hydroxy, hydroxy($C_{1-6}$)alkyl, $C_{1-6}$ alkoxy, trifluoroethoxy, carboxy($C_{3-7}$)cycloalkyloxy, $C_{1-6}$ alkylthio, $C_{1-6}$ alkylsulphonyl, ($C_{1-6}$)alkylsulphonyl($C_{1-6}$)alkyl, amino, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]-amino, N—[($C_{1-6}$)alkyl]-N-[carboxy($C_{1-6}$)alkyl]amino, carboxy($C_{3-7}$)cycloalkylamino, carboxy($C_{3-7}$)cycloalkyl($C_{1-6}$)alkylamino, $C_{1-6}$ alkylsulphonylamino, ($C_{2-6}$)alkylcarbonyl-oxy($C_{1-6}$)alkyl, carboxy, morpholinyl($C_{1-6}$)alkoxycarbonyl, $C_{2-6}$ alkoxycarbonyl($C_{1-6}$)alkyl, $C_{2-6}$ alkoxycarbonylmethylidenyl, di($C_{1-6}$)alkylaminocarbonyl; or $R^9$ represents ($C_{3-7}$)cycloalkyl, ($C_{3-7}$)cycloalkyl-($C_{1-6}$)alkyl, ($C_{4-7}$)cycloalkenyl, ($C_{4-9}$)bicycloalkyl, ($C_{3-7}$)heterocycloalkyl, ($C_{4-9}$)heterobicycloalkyl ($C_{4-9}$)spiroheterocycloalkyl, ($C_{4-9}$)bicycloalkylene or heteroaryl, any of which groups may be optionally substituted by one or more substituents; or $R^9$ represents, amino sulphonyl, $C_{1-6}$ alkylsulphinyl, ($C_{3-7}$)cycloalkylsulphonyl or difluoromethyl.

Typically, $R^9$ represents halogen, hydroxy($C_{1-6}$)alkyl, $C_{1-6}$ alkylsulphonyl, ($C_{1-6}$)alkylsulphonyl($C_{1-6}$)alkyl, di($C_{1-6}$)alkylamino carbonyl; or $R^9$ represents ($C_{3-7}$)cycloalkyl, ($C_{4-7}$)cycloalkenyl, ($C_{4-9}$)bicycloalkyl, ($C_{3-7}$)heterocycloalkyl, ($C_{4-9}$)heterobicycloalkyl or ($C_{4-9}$)bicycloalkylene, any of which groups may be optionally substituted by one or more substituents; or $R^9$ represents $C_{1-6}$ alkoxy, aminosulphonyl, $C_{1-6}$ alkylsulphinyl, ($C_{3-7}$)cycloalkylsulphonyl or difluoromethyl. Suitably, $R^9$ represents halogen, hydroxy($C_{1-6}$)alkyl, $C_{1-6}$ alkylsulphonyl, ($C_{1-6}$)alkylsulphonyl($C_{1-6}$)alkyl, di($C_{1-6}$)alkylaminocarbonyl; or $R^9$ represents ($C_{3-7}$)cycloalkyl, ($C_{4-7}$)cycloalkenyl, ($C_{4-9}$)bicycloalkyl, ($C_{3-7}$)heterocycloalkyl, ($C_{4-9}$)heterobicycloalkyl or ($C_{4-9}$)bicycloalkylene, any of which groups may be optionally substituted by one or more substituents.

Where $R^9$ represents an optionally substituted $(C_{3-7})$cycloalkyl group, typical values include cyclopropyl, cyclobutyl, cyclopentyl, cyclohexyl and cycloheptyl, any of which groups may be optionally substituted by one or more substituents.

Where $R^9$ represents an optionally substituted $(C_{3-7})$cycloalkyl$(C_{1-6})$alkyl group, a typical value is cyclohexylmethyl, which group may be optionally substituted by one or more substituents.

Where $R^9$ represents an optionally substituted $(C_{4-7})$cycloalkenyl group, typical values include cyclobutenyl, cyclopentenyl, cyclohexenyl and cycloheptenyl, any of which groups may be optionally substituted by one or more substituents.

Where $R^9$ represents an optionally substituted $(C_{4-9})$bicycloalkyl group, typical values include bicyclo[3.1.0]hexanyl, bicyclo[4.1.0]heptanyl and bicyclo[2.2.2]octanyl, any of which groups may be optionally substituted by one or more substituents.

Where $R^9$ represents an optionally substituted $(C_{4-9})$bicycloalkenyl group, a typical value is bicyclo[3.1.0]hexenyl.

Where $R^9$ represents an optionally substituted $(C_{3-7})$heterocycloalkyl group, typical values include oxetanyl, azetidinyl, tetrahydrofuranyl, pyrrolidinyl, tetrahydro-pyranyl, piperidinyl, piperazinyl, hexahydro-[1,2,5]thiadiazolo[2,3-a]pyrazinyl, morpholinyl, thiomorpholinyl, azepanyl, oxazepanyl, diazepanyl, thiadiazepanyl, (imino)(oxo)thiazinanyl, (oxo)thiazinanyl or (dioxo)thiazinanyl, any of which groups may be optionally substituted by one or more substituents.

Where $R^9$ represents an optionally substituted $(C_{3-7})$heterocycloalkenyl group, a typical value is optionally substituted 1,2,3,6-tetrahydropyridinyl or 3,6-dihydropyridine.

Where $R^9$ represents an optionally substituted $(C_{4-9})$heterobicycloalkyl group, typical values include 3-azabicyclo[3.1.0]hexanyl, 2-oxa-5-azabicyclo[2.2.1]heptanyl, 3-azabicyclo[3.1.1]heptanyl, 3-azabicyclo[4.1.0]heptanyl, 2-oxabicyclo[2.2.2]octanyl, quinuclidinyl, 2-oxa-5-azabicyclo[2.2.2]octanyl, 3-azabicyclo[3.2.1]octanyl, 8-azabicyclo-[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo[3.3.1]nonanyl, 3,9-diazabicyclo-[4.2.1]nonanyl3,6-epimino[3,2b]-furanyl, 3,7-dioxa-9-diazabicyclo-[3.3.1]nonanylanylheptanyl and 2,5-diazabicyclo-[2.2.1]heptanyl, any of which groups may be optionally substituted by one or more substituents.

Where $R^9$ represents an optionally substituted $(C_{4-9})$spiroheterocycloalkyl group, typical values include 5-azaspiro[2.3]hexanyl, 5-azaspiro[2.4]heptanyl, 2-azaspiro[3.3]heptanyl, 2-oxa-6-azaspiro[3.3]heptanyl, 2-oxa-6-azaspiro[3.4]octanyl, 2-oxa-6-azaspiro-[3.5]nonanyl, 2-oxa-7-azaspiro[3.5]nonanyl and 2,4,8-triazaspiro[4.5]-decanyl, any of which groups may be optionally substituted by one or more substituents.

When $R^9$ represents an optionally substituted heteroaryl, typical values include triazolyl and (methyl)triazolyl.

Where $R^9$ represents a $C_{1-6}$ alkylsulphinyl, typical values include methylsulphinyl.

Where $R^9$ represents $(C_{3-7})$cycloalkylsulphonyl, typical values include cyclopropylsulphonyl. Illustratively, $R^9$ represents hydrogen, isopropyl, isopropylmethyl, hydroxy, hydroxymethyl, hydroxyisopropyl, methoxy, carboxy-cyclobutyloxy, methylthio, methylsulphonyl, methylsulphonylmethyl, methylamino, N-[carboxyethyl]-N-methylamino, carboxycyclopentylamino, carboxycyclopropylmethylamino or ethoxycarbonyl-ethyl; or $R^9$ represents cyclopropyl, cyclobutyl, cyclopentyl, cyclohexyl, cyclohexyl-methyl, cyclohexenyl, bicyclo[3.1.0]hexanyl, bicyclo[3.1.0]hexenyl bicyclo[4.1.0]heptanyl, bicyclo[2.2.2]-octanyl, oxetanyl, azetidinyl, tetrahydrofuranyl, pyrrolidinyl, tetrahydropyranyl, tetrahydrothiopyranylpyrimidinyl, piperidinyl, piperazinyl, hexahydro-[1,2,5]thiadiazolo[2,3-a]pyrazinyl, morpholinyl, thiomorpholinyl, azepanyl, oxazepanyl, diazepanyl, thiadiazepanyl, 3-azabicyclo[3.1.0]-hexanyl, 2-oxa-5-azabicyclo[2.2.1]heptanyl, 3-azabicyclo[3.1.1]heptanyl, 3-azabicyclo-[4.1.0]heptanyl, 2-oxabicyclo[2.2.2]octanyl, 3-azabicyclo[3.2.1]octanyl, 8-azabicyclo-[3.2.1]octanyl, 3-oxa-8-azabicyclo[3.2.1]octanyl, 3,6-diazabicyclo[3.2.2]nonanyl, 3-oxa-7-azabicyclo[3.3.1]nonanyl, 5-azaspiro[2.3]hexanyl, 5-azaspiro[2.4]heptanyl, 2-azaspiro-[3.3]heptanyl, 3,7-dioxa-9-azabicyclo[3.3.1]-nonanyl, epiminofuro [3.2-b]furanyl, (imino)(oxo)thiazinanyl, (oxo)thiazinanyl or (dioxo)thiazinanyl, any of which groups may be optionally substituted by one or more substituents. Additionally, $R^9$ represents difluoromethyl, fluoroisopropyl, aminoisopropyl, aminosulphonyl, tert-butoxy, cyclopropylsulphonyl, methylsulphinyl, or methylsulphoximinyl; or optionally substituted 2,5-diazabicyclo-[2.2.1]heptanyl, Appropriately, $R^9$ represents hydrogen, cyclopropyl, cyclobutyl, cyclohexyl, methoxy, bicyclo[3.1.0]hexanyl, bicyclo[3.1.0]hexenyl, tetrahydropyranyl, thiopyranyl, piperazinyl, oxetanyl, azetidinyl, tetrahydrofuranyl, piperidinyl, morpholinyl, thiomorpholinyl, 2-oxa-5-azabicyclo[2.2.1]heptanyl, 3-azabicyclo[3.2.1]octanyl, 3-oxa-8-azabicyclo[3.2.1]octanyl-pyrimidinyl, 3,7-dioxa-9-azabicyclo[3.3.1]-nonanyl, epiminofuro[3.2-b]furanyl; or $R^9$ represents difluoromethyl, hydroxyisopropyl, fluoroisopropyl, aminoisopropyl, aminosulphonyl, tert-butoxy, methylsulphonyl, cyclopropylmethylsulphonyl, methylsulphinyl, or methylsulphoximinyl; or optionally substituted 2,5-diazabicyclo-[2.2.1]heptanyl.

Apositely, $R^9$ represents hydrogen, cyclopropyl, cyclobutyl, bicyclo[3.1.0]hexanyl, bicyclo[3.1.0]hexenyl, tetrahydropyranyl, thiopyranyl, piperazinyl, oxetanyl, azetidinyl, tetrahydrofuranyl, piperidinyl, morpholinyl, thiomorpholinyl, 2-oxa-5-azabicyclo[2.2.1]heptanyl, 3-azabicyclo[3.2.1]octanyl, 3-oxa-8-azabicyclo[3.2.1]octanyl-pyrimidinyl, 3,7-dioxa-9-azabicyclo[3.3.1]-nonanyl, or epiminofuro[3.2-b]furanyl, any of which groups may be optionally substituted by one or more substituents.

Examples of optional substituents which may be present on $R^9$ include one, two or three substituents independently selected from halogen, halo$(C_{1-6})$alkyl, cyano, cyano-$(C_{1-6})$alkyl, nitro, nitro$(C_{1-6})$alkyl, $C_{1-6}$ alkyl, $C_{3-7}$ cycloalkyl, trifluoromethyl, trifluoroethyl, $C_{2-6}$ alkenyl, hydroxy, hydroxy$(C_{1-6})$alkyl, $C_{1-6}$ alkoxy, difluoromethoxy, trifluoromethoxy, trifluoro-ethoxy, $C_{1-6}$ alkylthio, $C_{1-6}$ alkylsulphonyl, $(C_{1-6})$alkylsulphonyl$(C_{1-6})$alkyl, oxo, amino, $C_{1-6}$ alkylamino, di$(C_{1-6})$alkylamino, $C_{2-6}$ alkylcarbonylamino, $(C_{2-6})$alkylcarbonylamino-$(C_{1-6})$alkyl, $C_{2-6}$ alkoxycarbonylamino, $C_{1-6}$ alkylsulphonylamino, formyl, $C_{1-6}$ alkylcarbonyl, carboxy, carboxy$(C_{1-6})$alkyl, $C_{2-6}$ alkoxycarbonyl, morpholinyl-$(C_{1-6})$alkoxycarbonyl, $C_{2-6}$ alkoxycarbonyl$(C_{1-6})$alkyl, $C_{2-6}$ alkoxycarbonylmethylidenyl, amino-carbonyl, $C_{1-6}$ alkylamino carbonyl, di$(C_{1-6})$alkylaminocarbonyl, amino sulphonyl, di$(C_{1-6})$alkylaminosulphonyl, $(C_{1-6})$alkylsulphoximinyl and [$(C_{1-6})$alkyl][N—$(C_{1-6})$alkyl]-sulphoximinyl.

Selected examples of optional substituents on $R^9$ include one, two or three substituents independently selected from halogen, cyano, trifluoromethyl, hydroxy, $C_{1-6}$ alkyl, $C_{3-7}$ cycloalkyl, $C_{1-6}$ alkoxy, $C_{1-6}$ alkylsulphonyl, $C_{1-6}$ alkylsulphoximinyl, $C_{1-6}$ alkylcarbonyl, $C_{1-6}$ alkoxycarbonyl oxo and carboxy.

Suitable examples of particular substituents on $R^9$ include one, two or three substituents independently selected from fluoro, fluoromethyl, chloro, bromo, cyano, cyanomethyl, cyanoethyl, nitro, nitromethyl, methyl, ethyl, isopropyl, cyclopropyl, trifluoromethyl, trifluoroethyl, ethenyl, hydroxy, hydroxymethyl, methoxy, ethoxy, difluoromethoxy, trifluoromethoxy, trifluoroethoxy, methylthio, methylsulphonyl, methylsulphonylmethyl, methylsulphonylethyl, oxo, amino, methylamino, dimethylamino, acetylamino, acetyl-aminomethyl, methoxycarbonylamino, ethoxycarbonylamino, tert-butoxycarbonylamino, methylsulphonylamino, formyl, acetyl, carboxy, carboxymethyl, carboxyethyl, methoxycarbonyl, ethoxycarbonyl, n-butoxycarbonyl, tert-butoxycarbonyl, morpholinyl-ethoxycarbonyl, methoxycarbonylmethyl, ethoxycarbonylmethyl, ethoxycarbonylethyl, ethoxycarbonylmethylidenyl, acetylaminosulphonyl, methoxyaminocarbonyl, tetrazolyl, tetrazolylmethyl, hydroxyoxadiazolyl, aminocarbonyl, methylaminocarbonyl, dimethyl-aminocarbonyl, methylsulphonylaminocarbonyl, aminosulphonyl, methylaminosulphonyl, dimethylaminosulphonyl, methylsulphoximinyl and (methyl)(N-methyl)sulphoximinyl.

Selected examples of particular substituents on $R^9$ include one, two or three substituents independently selected chloro, hydroxy, methyl, isopropyl, trifluoromethyl, tert-butoxycarbonyl, acetyl, oxo and carboxy. Additional example of particular substituent on $R^9$ include fluoro.

Typically, $R^9$ represents hydrogen, fluoro, fluoroisopropyl, cyano, methyl, isopropyl, trifluoromethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, amino, methylamino, dimethylamino, methoxyethylamino, N-(hydroxyethyl)-N-(methyl)amino, N-[carboxy-ethyl]-N-methylamino, carboxycyclopentylamino, carboxycyclopropylmethylamino, methylsulphonylamino, acetoxyisopropyl, carboxy, ethoxycarbonylethyl, cyclopropyl, fluoromethyl-cyclopropyl, acetylaminomethylcyclopropyl, hydroxycyclobutyl, carboxycyclopentyl, carboxycyclohexyl, (carboxy)(methyl)cyclohexyl, (carboxy)(hydroxy)cyclohexyl, carboxymethylcyclohexyl, ethoxycarbonylcyclohexyl, (methoxycarbonyl)(methyl)-cyclohexyl, (ethoxycarbonyl)(methyl)cyclohexyl, carboxycyclohexylmethyl, carboxy-cyclohexenyl, ethoxycarbonylcyclohexenyl, carboxybicyclo[3.1.0]hexanyl, ethoxycarbonylbicyclo[3.1.0]hexanyl, carboxybicyclo[4.1.0]heptanyl, carboxybicyclo-[2.2.2]octanyl, fluorooxetanyl, hydroxyoxetanyl, hydroxyazetidinyl, (hydroxy)(methyl)-azetidinyl, carboxyazetidinyl, (tert-butoxycarbonyl)(hydroxy)azetidinyl, tetrazolyl-azetidinyl, hydroxytetrahydrofuranyl, pyrrolidinyl, hydroxypyrrolidinyl, carboxy-pyrrolidinyl, (carboxy)(methyl)pyrrolidinyl, carboxymethylpyrrolidinyl, ethoxycarbonyl-pyrrolidinyl, fluorotetrahydropyranyl, hydroxytetrahydropyranyl, piperidinyl, difluoro-piperidinyl, (cyano)(methyl)piperidinyl, (hydroxy)(nitromethyl)piperidinyl, (hydroxy)-(methyl)piperidinyl, (hydroxy)(trifluoromethyl)piperidinyl, (hydroxymethyl)(methyl)-piperidinyl, methylsulphonylpiperidinyl, oxopiperidinyl, (formyl)(methyl)piperidinyl, acetylpiperidinyl, carboxypiperidinyl, (carboxy)(fluoro)piperidinyl, (carboxy)(methyl)-piperidinyl, (carboxy)(ethyl)piperidinyl, (carboxy)(trifluoromethyl)piperidinyl, (carboxy)-(hydroxy)piperidinyl, (carboxy)(hydroxymethyl)piperidinyl, (carboxy)(methoxy)-piperidinyl, (amino)(carboxy)piperidinyl, carboxymethylpiperidinyl, methoxycarbonyl-piperidinyl, (methoxycarbonyl)(methyl)piperidinyl, (ethyl)(methoxycarbonyl)piperidinyl, (isopropyl)(methoxycarbonyl)piperidinyl, (methoxy)(methoxycarbonyl)piperidinyl, (carboxy)(methoxycarbonyl)piperidinyl, ethoxycarbonylpiperidinyl, (ethoxycarbonyl)-(fluoro)piperidinyl, (ethoxycarbonyl)(methyl)piperidinyl, (ethoxycarbonyl)(trifluoro-methyl)piperidinyl, (ethoxycarbonyl)(hydroxymethyl)piperidinyl, (n-butoxycarbonyl)-(methyl)piperidinyl, (methyl)(morpholinylethoxycarbonyl)piperidinyl, ethoxycarbonyl-methylpiperidinyl, methylsulphonylaminocarbonylpiperidinyl, acetylaminosulphonyl-piperidinyl, methoxyaminocarbonylpiperidinyl, tetrazolylpiperidinyl, hydroxyoxadiazolyl-piperidinyl, amino sulphonylpiperidinyl, piperazinyl, methylpiperazinyl, cyanoethylpiperazinyl, trifluoroethylpiperazinyl, methylsulphonylpiperazinyl, methylsulphonylethylpiperazinyl, oxopiperazinyl, acetylpiperazinyl, carboxypiperazinyl, tert-butoxycarbonylpiperazinyl, carboxymethylpiperazinyl, carboxyethylpiperazinyl, ethoxycarbonylmethylpiperazinyl, ethoxycarbonylethylpiperazinyl, tetrazolylmethylpiperazinyl, trioxohexahydro-[1,2,5]thiadiazo[2,3-a]pyrazinyl, morpholinyl, dimethylmorpholinyl, hydroxymethyl-morpholinyl, carboxymorpholinyl, (carboxy)(methyl)morpholinyl, carboxymethyl-morpholinyl, thiomorpholinyl, oxothiomorpholinyl, dioxothiomorpholinyl, carboxy-azepanyl, carboxyoxazepanyl, oxodiazepanyl, (methyl)(oxo)diazepanyl, dioxo-thiadiazepanyl, carboxy-3-azabicyclo[3.1.0]hexanyl, (carboxy)(methyl)-3-azabicyclo-[3.1.0]hexanyl, methoxycarbonyl-3-azabicyclo[3.1.0]hexanyl, ethoxycarbonyl-3-azabicyclo[3.1.0]hexanyl, 2-oxa-5-azabicyclo[2.2.1]heptanyl, carboxy-2-oxa-5-azabicyclo[2.2.1]heptanyl, carboxy-3-azabicyclo[3.1.1]heptanyl, carboxy-3-azabicyclo-[4.1.0]heptanyl, methoxycarbonyl-3-azabicyclo[4.1.0]heptanyl, ethoxycarbonyl-3-azabicyclo[4.1.0]heptanyl, (hydroxy)(methyl)(oxo)-2-oxabicyclo[2.2.2]octanyl, carboxy-3-azabicyclo[3.2.1]octanyl, methoxycarbonyl-3-azabicyclo[3.2.1]octanyl, oxo-8-azabicyclo[3.2.1]octanyl, ethoxycarbonylmethylidenyl-8-azabicyclo[3.2.1]octanyl, 3-oxa-8-azabicyclo[3.2.1]octanyl, oxo-3,6-diazabicyclo[3.2.2]nonanyl, carboxy-3-oxa-7-azabicyclo[3.3.1]nonanyl, 3,7-dioxa-9-azabicyclo[3.3.1]nonanyl, carboxy-5-azaspiro[2.3]hexanyl, (carboxy)(methyl)-5-azaspiro-[2.3]hexanyl, carboxy-5-azaspiro[2.4]heptanyl, carboxy-2-azaspiro[3.3]heptanyl, 2-oxa-6-azaspiro[3.3]heptanyl, 2-oxa-6-azaspiro[3.4]octanyl, 2-oxa-6-azaspiro[3.5]nonanyl, 2-oxa-7-azaspiro[3.5]nonanyl, (dioxo)(methyl)-2,4,8-triazaspiro[4.5]decanyl, 3,6-epiminofuro[3.2-b]furanyl-pyrimidinyl, (methyl)cyclobutyldiol, (imino)(oxo)thiazinanyl, (oxo)thiazinanyl or (dioxo)thiazinanyl. Additionally, $R^9$ represents difluorocyclobutanyl, difluoromethyl, tert-butoxy, aminoisopropyl, hydroxycyclopropyl, (difluoro)(hydroxy)cyclobutyl, (methyl)cyclobutanediol, (hydroxyl)(methyl)cyclohexyl, (methyl)cyclohexanediol, tert-butoxy, aminosulphonyl, methylsulphinyl, methylsulphoximinyl, cyclopropylsulphonyl, 2,5-diazabicyclo[2.2.1]hetanyl and methylcarboxy-3-azabicyclo[3.2.1]octanyl.

Appropriate values of $R^9$ include chloro, tetrahydropyranyl, hydroxyisopropyl, hydroxymethyl, methoxy, isopropoxy, isopropyl, hydroxycyclobutyl, carboxybicyclo[3.1.0]hexanyl, carboxybicyclo[3.1.0]hexenyl, piperazinyl, hydroxyoxetanyl, hydroxyazetidinyl, (hydroxy)(methyl)azetidinyl, (hydroxy)(trifluoromethyl)azetidinyl, (tert-butoxycarbonyl)(hydroxy)azetidinyl, hydroxytetrahydrofuranyl, hydroxytetrahydropyranyl, (hydroxy)dioxidotetrahydrothiopyranyl), piperidinyl, (cyano)(methyl)piperidinyl, (hydroxy)(methyl)piperidinyl, (carboxy)(methyl)piperidinyl, acetylpiperidinyl, carboxypiperazinylpyrimidinyl, tert-butoxycarbonylpiperazinyl, morpholinyl, thiomorpholinyl, oxo-thiomorpholinyl, dioxo-thiomorpholinyl, oxodiazepanyl, 2-oxa-5-azabicyclo[2.2.1]heptanyl, carboxy-3-azabicyclo[3.2.1]octanyl, oxo-8-azabicyclo[3.2.1]octanyl, 3-carboxy-8-azabicyclo-[3.2.1]octanyl, 3-(dimethylamino carbonyl)-8-azabicyclo-[3.2.1]octanyl, oxo-3,6-diazabicyclo[3.2.2]nonanyl, 3,7-dioxa-9-azabicyclo[3.3.1]-nonanyl and 3,6-epiminofuro[3.2-b]furanyl; or difluorocyclobutanyl, difluoromethyl, tert-butoxy, aminoisopropyl, hydroxycyclopropyl, (difluoro)(hydroxy)cyclobutyl, (methyl)cyclobutanediol, (hydroxyl)(methyl)cyclohexyl, (methyl)cyclohexanediol, aminosulphonyl, methylsulphinyl, methylsulphoximinyl, cyclopropylsulphonyl, .2,5-diazabicyclo[2.2.1]hetanyl and methylcarboxy-3-azabicyclo[3.2.1]octanyl. Illustrative values of $R^9$ include chloro, tetrahydropyranyl, hydroxyisopropyl, hydroxymethyl, methoxy, isopropoxy, isopropyl, hydroxycyclobutyl, carboxybicyclo[3.1.0]hexanyl, carboxybicyclo[3.1.0]hexenyl, piperazinyl, hydroxyoxetanyl, hydroxyazetidinyl, (hydroxy)(methyl)azetidinyl, (hydroxy)(trifluoromethyl)azetidinyl, (tert-butoxycarbonyl)(hydroxy)azetidinyl, hydroxytetrahydrofuranyl, hydroxytetrahydropyranyl, (hydroxy)dioxidotetrahydrothiopyranyl), piperidinyl, (cyano)(methyl)piperidinyl, (hydroxy)(methyl)piperidinyl, (carboxy)(methyl)piperidinyl, acetylpiperidinyl, carboxypiperazinylpyrimidinyl, tert-butoxycarbonylpiperazinyl, morpholinyl, thiomorpholinyl, oxo-thiomorpholinyl, dioxo-thiomorpholinyl, oxodiazepanyl, 2-oxa-5-azabicyclo[2.2.1]heptanyl, carboxy-3-azabicyclo[3.2.1]octanyl, oxo-8-azabicyclo[3.2.1]octanyl, 3-carboxy-8-azabicyclo-[3.2.1]octanyl, 3-(dimethylamino carbonyl)-8-azabicyclo-[3.2.1]octanyl, oxo-3,6-diazabicyclo[3.2.2]nonanyl, 3,7-dioxa-9-azabicyclo[3.3.1]-nonanyl and 3,6-epiminofuro[3.2-b]furanyl.

In one embodiment $R^{10}$ represents hydrogen. In a second embodiment, $R^{10}$ represents halogen. In a third embodiment, $R^{10}$ represents cyano. In a fourth embodiment, $R^{10}$ represents trifluoromethyl. In a fifth embodiment, $R^{10}$ represents hydroxy. In a sixth embodiment, $R^{10}$ represents —$NR^bR^c$. In one aspect of this embodiment $R^{10}$ represents $NH_2$. In a seventh embodiment, $R^{11}$ represents —$OR^a$. In one aspect of that embodiment, $R^{10}$ represents methoxy. In an eighth embodiment, $R^{10}$ represents $C_{1-6}$ alkyl. In one aspect of that embodiment, $R^{10}$ represents methyl. In a ninth embodiment, $R^{10}$ represents $C_{1-6}$ alkylsulphonyl. In one aspect of that embodiment, $R^{10}$ represents methylsulphonyl.

In one embodiment $R^{11}$ represents hydrogen. In a second embodiment, $R^{11}$ represents halogen. In a third embodiment, $R^{11}$ represents cyano. In a fourth embodiment, $R^{11}$ represents trifluormethyl. In a fifth embodiment, $R^{11}$ represents hydroxy. In a sixth embodiment, $R^{11}$ represents —$NR^bR^c$. In one aspect of this embodiment $R^{11}$ represents $NH_2$. In a seventh embodiment, $R^{11}$ represents —$OR^a$. In one aspect of that embodiment, $R^{11}$ represents methoxy. In an eighth embodiment, $R^{11}$ represents $C_{1-6}$ alkyl. In one aspect of that embodiment, $R^{11}$ represents methyl. In a ninth embodiment, $R^{11}$ represents $C_{1-6}$ alkylsulphonyl. In one aspect of that embodiment, $R^{11}$ represents methylsulphonyl.

Particular values of $R^{10}$ and $R^{11}$ include hydrogen, methyl and methylsulphonyl.

Particular sub-groups of the compounds of formula (IIB) above are represented by the compounds of formula (IIC), (IID), (IIE), (IIF), (IIG), (IIH), (IIJ), (IIK), (IIL), (IIM) and N-oxides thereof, and pharmaceutically acceptable salts and solvates thereof, and glucuronide derivatives thereof, and co-crystals thereof:

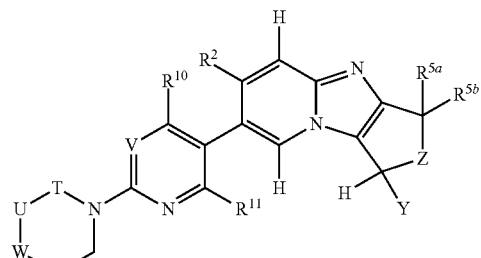

(IIC)

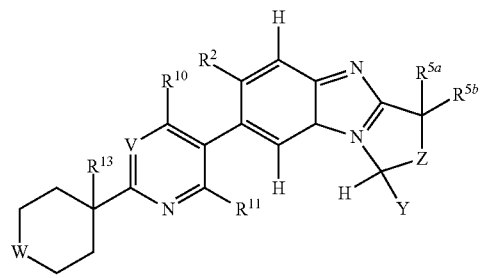

(IID)

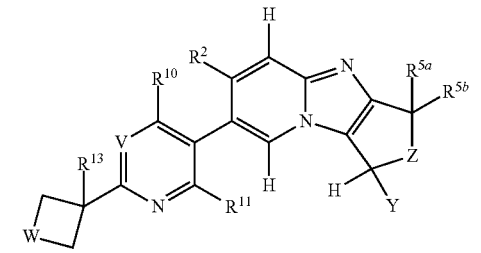

(IIE)

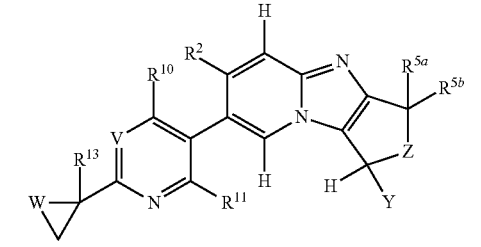

(IIF)

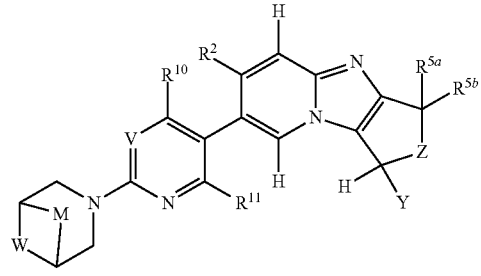

(IIG)

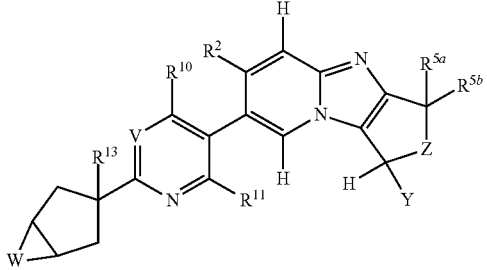

(IIH)

(IIJ)

(IIK)

(IIL)

(IIM)

wherein
T represents —CH$_2$— or —CH$_2$CH$_2$;
U represents C(O) or S(O)$_2$;
W represents O, S, S(O), S(O)$_2$, N(R$^{14}$), S(O)(N—R$^d$) or C(R$^{15}$)(R$^{16}$);
-M- represents —CH$_2$—, —CH$_2$CH$_2$— or CH$_2$—W—CH$_2$—;
Q represents C(R$^{15}$)(R$^{16}$);
R$^{13}$ represents hydrogen, halogen, cyano, halo(C$_{1-6}$)alkyl, hydroxy, C$_{1-6}$ alkoxy, C$_{1-6}$ alkylthio, C$_{1-6}$ alkylsulphinyl, C$_{1-6}$ alkylsulphonyl, amino, C$_{1-6}$ alkylamino, di(C$_{1-6}$)alkylamino, (C$_{2-6}$)alkylcarbonylamino, (C$_{2-6}$)alkylcarbonylamino(C$_{1-6}$)alkyl, (C$_{1-6}$)alkyl-sulphonylamino or (C$_{1-6}$)alkylsulphonylamino(C$_{1-6}$)alkyl;
R$^{14}$ represents hydrogen, cyano(C$_{1-6}$)alkyl, C$_{1-6}$ alkyl, trifluoromethyl, trifluoro-ethyl, C$_{1-6}$ alkylsulphonyl, (C$_{1-6}$) alkylsulphonyl(C$_{1-6}$)alkyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl(C$_{1-6}$)alkyl, a carboxylic acid isostere or prodrug moiety Ω as defined herein, —(C$_{1-6}$)alkyl-Ω, aminocarbonyl, C$_{1-6}$ alkylaminocarbonyl, di(C$_{1-6}$)alkylaminocarbonyl, aminosulphonyl or di(C$_{1-6}$)alkylamino-sulphonyl;

R$^{15}$ represents hydrogen, halogen, cyano, hydroxy, hydroxy(C$_{1-6}$)alkyl, C$_{1-6}$ alkylsulphonyl, formyl, C$_{2-6}$ alkylcarbonyl, di(C$_{1-6}$ alkyl)aminocarbonyl, carboxy, carboxy (C$_{1-6}$)alkyl, C$_{2-6}$ alkoxycarbonyl, C$_{2-6}$ alkoxycarbonyl(C$_{1-6}$) alkyl, aminosulphonyl, (C$_{1-6}$)alkyl-sulphoximinyl, [(C$_{1-6}$) alkyl][N—(C$_{1-6}$)alkyl]sulphoximinyl, a carboxylic acid isostere or prodrug moiety Ω as defined herein, or —(C$_{1-6}$) alkyl-Ω;
R$^{16}$ represents hydrogen, halogen, C$_{1-6}$ alkyl, C$_{3-7}$ cycloalkyl, trifluoromethyl, hydroxy, hydroxy-(C$_{1-6}$)alkyl, C$_{1-6}$ alkoxy, amino or carboxy; and
V, Y, Z, R$^2$, R$^{5a}$, R$^{5b}$, R$^{10}$ and R$^{11}$ are as defined above.
In one embodiment, T represents —CH$_2$—. In a second embodiment T represents —CH$_2$CH$_2$;
In one embodiment, U represents C(O). In another embodiment U represents S(O)$_2$.
Generally, W represents O, S(O)$_2$, S(O)(N—R$^d$), N(R$^{14}$) or C(R$^{15}$)(R$^{16}$).
Typically, W represents O, N(R$^{14}$) or C(R$^{15}$)(R$^{16}$).
In a first embodiment, W represents O. In a second embodiment, W represents S. In a third embodiment, W represents S(O). In a fourth embodiment, W represents S(O)$_2$. In a fifth embodiment, W represents N(R$^{14}$). In a particular aspect of this embodiment, W represents —NH. In a sixth embodiment, W represents C(R$^{15}$)(R$^{16}$). In a seventh embodiment W represents S(O)(N—R$^d$). In a particular aspect of that embodiment, W represents S(O)(NH).
In one embodiment, -M- represents —CH$_2$—. In a second embodiment, -M-represents —CH$_2$CH$_2$—. In a third embodiment M represents CH$_2$—W—CH$_2$. In one aspect of that embodiment, M represents CH$_2$—O—CH$_2$. In a second aspect of that embodiment, M represents CH$_2$—S(O)(N—R$^d$)—CH$_2$. In a third aspect of that embodiment, M represents CH$_2$—S—CH$_2$. In a fourth aspect of that embodiment, M represents CH$_2$—S(O)—CH$_2$. In a fifth aspect of that embodiment, M represents CH$_2$—S(O)$_2$—CH$_2$. In a sixth aspect of that embodiment, M represents CH$_2$—N(R$^{14}$)—CH$_2$. In a seventh aspect of that embodiment, M represents CH$_2$—C(R$^{15}$)(R$^{16}$)—CH$_2$.
In a first embodiment, R$^{13}$ represents hydrogen. In a second embodiment, R$^{13}$ represents halogen. In one aspect of that embodiment, R$^{13}$ represents fluoro. In a third embodiment, R$^{13}$ represents halo(C$_{1-6}$)alkyl. In one aspect of that embodiment, R$^{13}$ represents fluoromethyl. In another aspect of that embodiment R$^{13}$ represents trifluoromethyl. In a fourth embodiment, R$^{13}$ represents hydroxy. In a fifth embodiment, R$^{13}$ represents C$_{1-6}$ alkoxy. In a particular aspect of that embodiment, R$^{13}$ represents methoxy. In a sixth embodiment, R$^{13}$ represents C$_{1-6}$ alkylthio. In a particular aspect of that embodiment, R$^{13}$ represents methylthio. In a seventh embodiment, R$^{13}$ represents C$_{1-6}$ alkylsulphinyl. In a particular aspect of that embodiment, R$^{13}$ represents methylsulphinyl. In an eighth embodiment, R$^{13}$ represents C$_{1-6}$ alkylsulphonyl. In a particular aspect of that embodiment, R$^{13}$ represents methylsulphonyl. In a ninth embodiment, R$^{13}$ represents amino. In a tenth embodiment, R$^{13}$ represents C$_{1-6}$ alkylamino. In a particular aspect of that embodiment, R$^{13}$ represents methylamino. In an eleventh embodiment, R$^{13}$ represents di(C$_{1-6}$)alkylamino. In a particular aspect of that embodiment, R$^{13}$ represents dimethylamino. In a twelfth embodiment, R$^{13}$ represents (C$_{2-6}$) alkylcarbonylamino. In a particular aspect of that embodiment, R$^{13}$ represents acetylamino. In a thirteenth embodiment, R$^{13}$ represents (C$_{2-6}$)alkylcarbonylamino (C$_{1-6}$)alkyl. In a particular aspect of that embodiment, R$^{13}$ represents acetylaminomethyl. In a fourteenth embodiment, R$^{13}$ represents (C$_{1-6}$)alkylsulphonyl-amino. In a particular aspect of that embodiment, $R^{13}$ represents methylsulphonylamino. In a fifteenth embodiment, $R^{13}$ represents $(C_{1-6})$ alkylsulphonylamino$(C_{1-6})$alkyl. In a particular aspect of that embodiment, $R^{13}$ represents methylsulphonylaminomethyl. In a sixteenth embodiment, $R^{13}$ represents cyano.

Typically, $R^{13}$ represents hydrogen, halogen, halo$(C_{1-6})$ alkyl, hydroxy or $(C_{2-6})$alkylcarbonylamino$(C_{1-6})$alkyl.

Selected values of $R^{13}$ include hydrogen, fluoro, fluoromethyl, hydroxy, methoxy, methylthio, methylsulphinyl, methylsulphonyl, amino, methylamino, dimethylamino and acetylaminomethyl.

Particular values of $R^{13}$ include hydrogen, fluoro, fluoromethyl, hydroxy and acetylaminomethyl.

Suitably, $R^{13}$ represents hydrogen, hydroxy or fluoro.

Typically, $R^{14}$ represents hydrogen, cyano$(C_{1-6})$alkyl, $C_{1-6}$ alkyl, trifluoromethyl, trifluoroethyl, $C_{1-6}$ alkylsulphonyl, $(C_{1-6})$alkylsulphonyl$(C_{1-6})$alkyl, formyl, $C_{2-6}$ alkylcarbonyl, carboxy, carboxy$(C_{1-6})$alkyl, $C_{2-6}$ alkoxycarbonyl, $C_{2-6}$ alkoxycarbonyl-$(C_{1-6})$alkyl, tetrazolyl$(C_{1-6})$alkyl, aminocarbonyl, $C_{1-6}$ alkylaminocarbonyl, di$(C_{1-6})$alkylaminocarbonyl, aminosulphonyl, $C_{1-6}$ alkylamino sulphonyl or di$(C_{1-6})$alkylamino-sulphonyl.

Suitably, $R^{14}$ represents hydrogen, $C_{1-6}$ alkyl or $C_{2-6}$ alkylcarbonyl.

Typical values of $R^{14}$ include hydrogen, cyanoethyl, methyl, ethyl, isopropyl, trifluoromethyl, trifluoroethyl, methylsulphonyl, methylsulphonylethyl, formyl, acetyl, carboxy, carboxymethyl, carboxyethyl, methoxycarbonyl, ethoxycarbonyl, tert-butoxy-carbonyl, ethoxycarbonylmethyl, ethoxycarbonylethyl, tetrazolylmethyl, aminocarbonyl, methylamino-carbonyl, dimethylaminocarbonyl, aminosulphonyl, methylaminosulphonyl and dimethylaminosulphonyl.

Particular values of $R^{14}$ include hydrogen, methyl and acetyl.

In a particular embodiment $R^{14}$ represents hydrogen.

In a selected embodiment, $R^{14}$ represents $C_{1-6}$ alkyl.

In yet another particular embodiment, $R^{14}$ represents $C_{2-6}$ alkylcarbonyl.

Generally, $R^{15}$ represents halogen, carboxy, carboxy $(C_{1-6})$alkyl, $C_{2-6}$ alkoxycarbonyl, di$(C_{1-6}$ alkyl)aminocarbonyl, $C_{2-6}$ alkoxycarbonyl$(C_{1-6})$alkyl, a carboxylic acid isostere or prodrug moiety Ω as defined herein, or —$(C_{1-6})$alkyl-Ω.

Typically, $R^{15}$ represents hydrogen, halogen, cyano, hydroxy, hydroxy$(C_{1-6})$alkyl, $C_{1-6}$ alkylsulphonyl, formyl, carboxy, carboxy$(C_{1-6})$alkyl, $C_{2-6}$ alkoxycarbonyl, $C_{2-6}$ alkoxycarbonyl$(C_{1-6})$alkyl, aminosulphonyl, $(C_{1-6})$alkylsulphoximinyl, $[(C_{1-6})$alkyl][N—$(C_{1-6})$alkyl]sulphoximinyl, $(C_{1-6})$alkylsulphonylaminocarbonyl, $(C_{2-6})$alkylcarbonylamino-sulphonyl, $(C_{1-6})$alkoxyaminocarbonyl, tetrazolyl or hydroxyoxadiazolyl.

Typical values of $R^{15}$ include hydrogen, fluoro, cyano, hydroxy, hydroxymethyl, methylsulphonyl, formyl, carboxy, carboxymethyl, carboxyethyl, methoxycarbonyl, ethoxycarbonyl, tert-butoxycarbonyl, methoxycarbonylmethyl, methoxycarbonylethyl, ethoxycarbonylmethyl, ethoxycarbonylethyl, aminosulphonyl, methylsulphoximinyl, (methyl)(N-methyl)sulphoximinyl, methylsulphonylaminocarbonyl, dimethylaminocarbonyl, acetylaminosulphonyl, methoxyaminocarbonyl, tetrazolyl and hydroxyoxadiazolyl.

In a selected embodiment, $R^{15}$ represents carboxy.

Generally, $R^{16}$ represents hydrogen, halogen, $C_{3-7}$ cycloalkyl or $C_{1-6}$ alkyl.

Suitably, $R^{16}$ represents hydrogen or $C_{1-6}$ alkyl.

Selected values of $R^{16}$ include hydrogen, fluoro, methyl, ethyl, isopropyl, cyclopropyl, trifluoromethyl, hydroxy, hydroxymethyl, methoxy, amino and carboxy.

Particular values of $R^{16}$ include hydrogen and methyl.

In a first embodiment, $R^{16}$ represents hydrogen.

In a second embodiment, $R^{16}$ represents halogen. In one aspect of that embodiment, $R^{16}$ represents fluoro. In a third embodiment, $R^{16}$ represents $C_{1-6}$ alkyl. In a first aspect of that embodiment, $R^{16}$ represents methyl. In a second aspect of that embodiment, $R^{16}$ represents ethyl. In a third aspect of that embodiment, $R^{16}$ represents isopropyl. In a fourth embodiment, $R^{16}$ represents trifluoromethyl. In a fifth embodiment, $R^{16}$ represents hydroxy. In a sixth embodiment, $R^{16}$ represents hydroxy$(C_{1-6})$alkyl. In one aspect of that embodiment, $R^{16}$ represents hydroxymethyl. In a seventh embodiment, $R^{16}$ represents $C_{1-6}$ alkoxy. In one aspect of that embodiment, $R^{16}$ represents methoxy. In an eighth embodiment, $R^{16}$ represents amino. In a ninth embodiment, $R^{16}$ represents carboxy. In a tenth embodiment, $R^{16}$ represents a $C_{3-7}$ cycloalkyl. In one aspect of this embodiment, $R^{16}$ represents cyclopropyl.

An alternative sub-class of compounds according to the invention is represented by the compounds of formula (IIN) and N-oxides thereof, and pharmaceutically acceptable salts and solvates thereof, and glucuronide derivatives thereof, and co-crystals thereof:

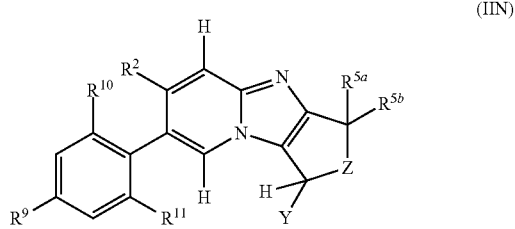

(IIN)

Z, $R^2$, $R^{5a}$, $R^{5b}$, $R^9$, $R^{10}$ and $R^{11}$ are as defined above.

In a particular embodiment of compounds of formula (IIN), Z represents methylene.

In a particular embodiment of compounds of formula (IIN), Y represents 2-difluromethoxy-phenyl. In another particular embodiment of compounds of formula (IIN), Y represents 2-difluromethoxy-5-chloro-phenyl.

In a particular embodiment of compounds of formula (IIN), $R^2$ represents hydrogen. In a particular embodiment of compounds of formula (IIN), $R^2$ represents fluorine.

In a particular embodiment of compounds of formula (IIN), $R^{5a}$ represents hydroxy.

In a particular embodiment of compounds of formula (IIN), $R^{5b}$ represents hydrogen.

In a particular embodiment of compounds of formula (IIN), $R^9$ represents $C_{1-4}$ alkylsulphonyl. In a particular aspect of that embodiment, $R^9$ represents methyl sulphonyl. In another particular embodiment of compounds of compounds of formula (IIN), $R^9$ represents $C_{3-7}$ cycloaklysulphonyl. In a particular aspect of this embodiment, $R^9$ represents cyclopropyl sulphonyl. In a further particular embodiment of compound of formula (IIN), $R^9$ represents aminosulphonyl. In another further particular embodiment of compound of formula (IIN), $R^9$ represents methylsulphoximinyl.

In a particular embodiment of compounds of formula (IIN), $R^{10}$ represents hydrogen.

In a particular embodiment of compounds of formula (IIN), $R^{11}$ represents hydrogen.

An alternative sub-class of compounds according to the invention is represented by the compounds of formula (IIP) and N-oxides thereof, and pharmaceutically acceptable salts and solvates thereof, and glucuronide derivatives thereof, and co-crystals thereof:

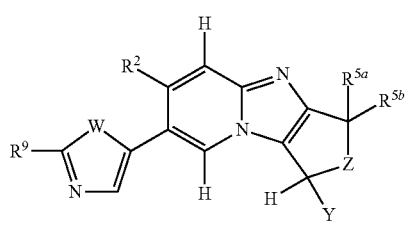

(IIP)

W, Z, $R^2$, $R^{5a}$, $R^{5b}$ and $R^9$ are as defined above.

Specific novel compounds in accordance with the present invention include each of the compounds whose preparation is described in the accompanying Examples, and pharmaceutically acceptable salts and solvates thereof, and co-crystals thereof.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, polymyositis, scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behçet's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy) and organ transplant rejection (including kidney allograft rejection).

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis and keratitis.

Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule such as methotrexate or prednisolone.

It will be apparent to the person skilled in the art that there are various synthetic pathways that can lead to the compounds according to the invention. The following processes are aimed at illustrating some of these synthetic pathways but should not be construed in any way as a limitation on how the compounds according to the invention should be made.

The compounds of formula (I) above may be prepared by a process which comprises reacting a compound of formula (III) with a compound of formula (IV), to afford a compound of formula (VI):

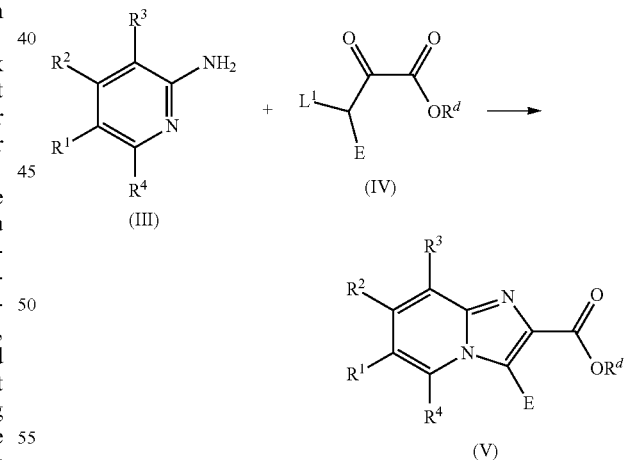

wherein Y, $R^d$, $R^1$, $R^2$, $R^3$ and $R^4$ are as defined above. $L^1$ represents a suitable leaving group. E represents —$CH_2$—Y or hydrogen.

The leaving group $L^1$ is typically a halogen atom, e.g. bromo.

The reaction is conveniently effected at an elevated temperature in a suitable solvent, e.g. a $C_{1-4}$ alkanol such as ethanol, or an ether such as 1,4-dioxane or dimethoxyethane, and in the presence of magnesium sulphate.

Alternatively, intermediates of formula (V), as defined here above, may be prepared according to a process which comprises reacting an intermediate of formula (VII) wherein; $R^d$, $R^1$, $R^2$, $R^3$ and $R^4$ are as defined above, with a compound of formula H—(CO)—Y, wherein Y as defined above, in the presence of Meldrum's acid.

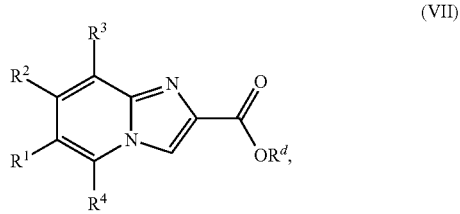

The reaction is conveniently effected in a suitable solvent e.g. acetonitrile, in the the presence of L-proline and magnesium sulphate, at elevated temperature, e.g. 80° C.

Intermediates of formula (VII), wherein $R^1$ is halogen, may be prepared from intermediates of formula (VIII) wherein $R^1$, $R^2$, $R^3$ and $R^4$ are as defined for intermediate of formula (VII) above, by reaction with intermediate of formula (IX) wherein, $L^1$ and $R^d$ are as defined for intermediate (IV) above.

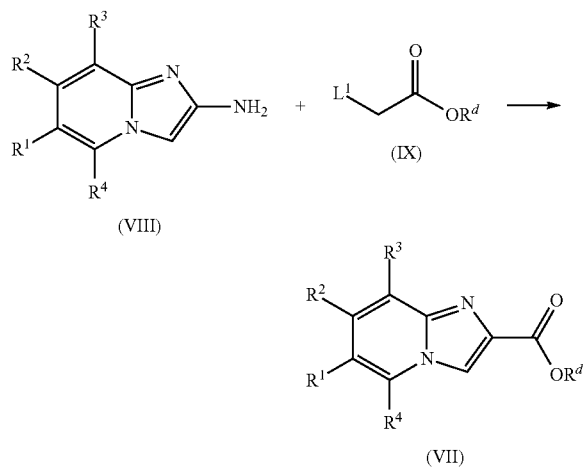

The reaction conditions are analogous to the ones used here above for the reaction between intermediate (III) and intermediate (IV). Compound of formula (V) wherein E is hydrogen, i.e. intermediate (VII), may be further transformed into compounds of formula (V) wherein E is —(CO)—H, for example by treatment with phosphoryl chloride in a suitable solvent, e.g. dimethylformamide.

This reaction is conveniently performed at elevated temperature in a suitable solvent, e.g. dimethylformamide.

Compound of formula (V) wherein E is —(CO)—H may be transformed into compound of formula (V) wherein E is —CH(OH)—Y, for example by treatment with Y—MgX in a suitable solvent, e.g. THF. Typically X is halogen, e.g. bromo or chloro.

Compound of formula (V) wherein E is —CH(OH)—Y may be transformed, for example into compound of formula (V) wherein E is —CH(Cl)—Y by reaction with sulfonylchloride in a suitable solvent e.g. dichloromethane.

Compound of formula (V) wherein E is —CH(Cl)—Y may be transformed into compound of formula (VI), wherein Y, $Q^1$, $R^d$, $R^1$, $R^2$, $R^3$ and $R^4$ are as defined above, for example in a three step reaction including (i) reaction with $Q^1$-$CH_2$-$L^2$ wherein $Q^1$ is, for example, an $C_{2-6}$ alkoxycarbonyl and $L^2$ is a suitable leaving group, e.g. $C_{2-6}$ alkoxycarbonyl, in the presence of a base, e.g. sodium hydride, in a suitable solvent e.g. THF, (ii) decarbalkoxylation by treatment with an acid, e.g. HCl, at elevated temperature and (iii) subsequent reaction with sulphonyl chloride, in suitable solvent, such as $C_{1-4}$ alkanol, suitably methanol.

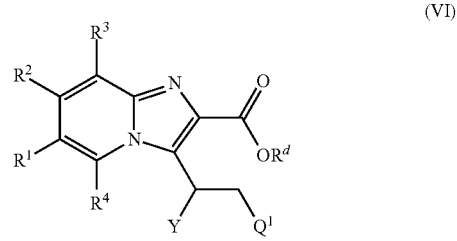

Alternatively, compound of formula (V) wherein E is hydrogen, i.e. intermediate (VII), may be transformed into compound of formula (V) wherein E is a halogen, e.g. iodo or bromo, for example, by treatment with the corresponding N-halo-succinimide, N-Bromo or N-iodo-succinimide in the presence of an acid, e.g. acetic acid.

Compound of formula (V) wherein E is halogen may be further transformed into compound of formula (V) wherein E is —CH(OH)—Y, by reaction for example with Y—(CO)H in the presence of an alkyl magnesium salt, e.g. isopropylmagnesiumchloride, in a suitable solvent, e.g. THF.

Compound of formula (V) above wherein E is —$CH_2$—Y, may be transformed into compound (VI) above by reaction with Q'-$CH_2$-$L^3$. Q' represents a $C_{2-6}$ alkoxycarbonyl and $L^3$ a suitable leaving group.

$L^3$ is typically a halogen, for example bromine.

$Q^1$ is typically methoxycarbonyl or ethylcarbonyl.

This reaction is conveniently performed in a suitable solvent, e.g. THF, in the presence of potassium bis(trimethylsilyl)amide.

Compound of formula (VI) may further be cyclized affording compound of formula (I) wherein $R^{5a}$ and $R^{5b}$ together with the carbon to which they are attached form a carbonyl and Z is CH-$Q^1$ and $Q^1$ is as defined above. Such reaction is typically performed in a suitable solvent, e.g. THF in the presence of a base, e.g. potassium tert-butoxide.

Compound of formula (I) wherein Z is CH-$Q^1$ may be transformed into compound of formula (I) wherein Z is —$CH_2$— for example by treatment with an acid, e.g. HCl, at elevated temperature.

Where they are not available commercially, compounds of formula (III) and (IV) and other starting materials mentioned hereabove can be prepared by methods analogous to those described in the Examples or other methods known to the skilled in the art.

It will be understood that any compound of formula (I) initially obtained from any of the above processes may, where appropriate, subsequently be elaborated into a further compound of formula(I) by techniques known in the art.

References to compound of formula (I) below will be understood as including all potential subclasses and subgroups mentioned here above.

A compound of formula (I) which contains a carbonyl group, in particular a compound of formula (I) wherein $R^{5a}$ and $R^{5b}$ with the carbon atom to which they are attached form a carbonyl, may be transformed into the corresponding compound wherein $R^{5a}$ is a hydroxy group and $R^{5b}$ is a hydrogen using for example lithium-tri-sec-butyl-borohydride or sodium borohydride in a suitable solvent e.g. THF.

A compound of formula (I) which contains a carbonyl group, in particular a compound of formula (I) wherein $R^{5a}$ and $R^{5b}$ with the carbon atom to which they are attached form a carbonyl, may be transformed into the corresponding compound wherein $R^{5a}$ is a trifluoromethyl and $R^{5b}$ is a hydroxy by treatment with trifluormethylsilane at room temperature in a suitable solvent e.g. dimethoxyethane.

A compound of formula (I) which contains a carbonyl group, in particular a compound of formula (I) wherein $R^{5a}$ and $R^{5b}$ with the carbon atom to which they are attached form a carbonyl, may be transformed into the corresponding compound wherein $R^{5a}$ is a ($C_{1-6}$ alkyl)sulphonylaryloxy trifluoromethyl and $R^{5b}$ is a hydrogen by treatment with ($C_{1-6}$ alkyl)sulphonylphenol, in the presence of Disiopropyl ε-1,2-diazenedicarboxylate, in a suitable solvent, e.g THF.

A compound of formula (I) which contains a carbonyl group, in particular a compound of formula (I) wherein $R^{5a}$ and $R^{5b}$ with the carbon atom to which they are attached form a carbonyl may transformed into the corresponding compound wherein $R^{5a}$ and $R^{5b}$ together with the carbon to which they are attached form a-C=N—OH, by treatment, for example with hydroxylamine chloride in the presence of pyridine in the presence of a suitable solvent such as ethanol.

A compound of formula (I) which contains a hydroxy group, in particular a compound of formula (I) wherein $R^{5a}$ is a hydroxy group and $R^{5b}$ is a hydrogen, may be transformed into corresponding compound wherein $R^{5a}$ and $R^{5b}$ are hydrogen for example by treatment with iodotrimethylsilane in a suitable solvent, e.g. acetonitrile.

A compound of formula (I) which contains a hydroxy group, in particular a compound of formula (I) wherein $R^{5a}$ is a hydroxy group and $R^{5b}$ is a hydrogen, may be transformed in a two step reaction into corresponding compound wherein $R^{5a}$ is —NH$_2$ and $R^{5b}$ is hydrogen for example by (i) treatment with diphenylphosphorylazide and 1,8-diazabicyclo[5.4.0]undec-7-ene. This reaction is conveniently performed at 0° C. in THF; (ii) subsequent aza-wittig reaction using PPh$_3$ in a suitable solvent, e.g. a mixture of water and toluene.

A compound of formula (I) which contains a hydroxy group, in particular a compound of formula (I) wherein $R^{5a}$ is a hydroxy group and $R^{5b}$ is a hydrogen, may be transformed into corresponding compound wherein $R^{5a}$ is —F and $R^{5b}$ is hydrogen by treatment with diethylaminosulfur trifluoride in a suitable solvent, e.g. THF.

A compound of formula (I) which contains a hydroxy group, in particular a compound of formula (I) wherein $R^{5a}$ is a hydroxy group and $R^{5b}$ is a hydrogen, may be transformed into the corresponding compound of formula (I) wherein $R^{5a}$ is a $C_{1-4}$ alkyl, e.g. methyl, and $R^{5b}$ is a hydrogen by treatment for example with an alkylmagnesium bromide in a suitable solvent, for example diethylether.

A compound of formula (I) which contains a hydroxy group, in particular a compound of formula (I) wherein $R^{5a}$ is a hydroxy group and $R^{5b}$ is a hydrogen may be transformed into the corresponding compound wherein $R^{5a}$ is a $C_{1-4}$ alkoxy, e.g. methoxy, and $R^{5b}$ is a hydrogen by treatment with a base e.g. sodium hydride, in a suitable solvent, e.g. THF, in the presence of a suitable alkylation agent, such as an alkylhalide, e.g. methyliodide.

A compound of formula (I), wherein $R^{5a}$ is a hydroxy group may be converted into the corresponding compound of formula (I) wherein $R^{5a}$ is $OR^a$ and $R^a$ is an alkyl substituted by an alkoxycarbonyl group, by treatment with a base, e.g. sodium hydride and addition of the corresponding alkoxycarbonylalkylhalide, in a suitable solvent e.g. tetrahydrofuran. It will be apparent that a similar reaction may be performed for the conversion of a compound of formula (I), wherein $R^{5a}$ is a hydroxy group into the corresponding compound of formula (I) wherein $R^{5a}$ is $OR^a$ and $R^a$ is a benzyl or an heteroarylalkyl group.

A compound of formula (I) which contains a hydroxy group may be alkylated by treatment with the appropriate alkyl halide in the presence of a base, e.g. sodium hydride, or silver oxide. A compound of formula (I) which contains hydroxy may be converted into the corresponding fluoro-substituted compound by treatment with diethylaminosulfur trifluoride (DAST) or bis(2-methoxyethyl)aminosulfur trifluoride (BAST). A compound of formula (I) which contains hydroxy may be converted into the corresponding difluoro-substituted compound via a two-step procedure which comprises: (i) treatment with an oxidising agent, e.g. manganese dioxide; and (ii) treatment of the carbonyl-containing compound thereby obtained with DAST.

A compound of formula (I) which contains an N—H moiety may be alkylated by treatment with the appropriate alkyl halide, typically at an elevated temperature in an organic solvent such as acetonitrile; or at ambient temperature in the presence of a base, e.g. an alkali metal carbonate such as potassium carbonate or cesium carbonate, in a suitable solvent, e.g. a dipolar aprotic solvent such as N,N-dimethylformamide. Alternatively, a compound of formula (I) which contains an N—H moiety may be alkylated by treatment with the appropriate alkyl tosylate in the presence of a base, e.g. an inorganic base such as sodium hydride, or an organic base such as 1,8-diazabicyclo[5.4.0]undec-7-ene (DBU).

A compound of formula (I) which contains an N—H moiety may be methylated by treatment with formaldehyde in the presence of a reducing agent, e.g. sodium triacetoxyborohydride.

A compound of formula (I) which contains an N—H moiety may be acylated by treatment with the appropriate acid chloride, e.g. acetyl chloride, or with the appropriate carboxylic acid anhydride, e.g. acetic anhydride, typically at ambient temperature in the presence of a base, e.g. an organic base such as triethylamine.

A compound of formula (I) which contains an N—H moiety may be converted into the corresponding compound wherein the nitrogen atom is substituted by $C_{1-6}$ alkylsulphonyl, e.g. methylsulphonyl, by treatment with the appropriate $C_{1-6}$ alkylsulphonyl chloride, e.g. methanesulphonyl chloride, or with the appropriate $C_{1-6}$ alkylsulphonic acid anhydride, e.g. methanesulphonic anhydride, typically at ambient temperature in the presence of a base, e.g. an organic base such as triethylamine or N,N-diisopropylethylamine.

A compound of formula (I) substituted by amino (—NH$_2$) may be converted into the corresponding compound substituted by $C_{1-6}$ alkylsulphonylamino, e.g. methylsulphonylamino, or bis[($C_{1-6}$)alkylsulphonyl]amino, e.g. bis(methylsulphonyl)amino, by treatment with the appropriate $C_{1-6}$ alkylsulphonyl halide, e.g. a $C_{1-6}$ alkylsulphonyl chloride such as methanesulphonyl chloride. Similarly, a compound of formula (I) substituted by hydroxy (—OH) may be converted into the corresponding compound substituted by $C_{1-6}$ alkyl-sulphonyloxy, e.g. methylsulphonyloxy, by treatment with the appropriate $C_{1-6}$ alkyl-sulphonyl halide, e.g. a $C_{1-6}$ alkylsulphonyl chloride such as methanesulphonyl chloride.

A compound of formula (I) containing the moiety —S— may be converted into the corresponding compound containing the moiety —S(O)— by treatment with 3-chloroperoxy-benzoic acid. Likewise, a compound of formula (I) containing the moiety —S(O)— may be converted into the corresponding compound containing the moiety —S(O)$_2$— by treatment with 3-chloroperoxybenzoic acid. Alternatively, a compound of formula (I) containing the moiety —S— may be converted into the corresponding compound containing the moiety —S(O)$_2$— by treatment with Oxone® (potassium peroxymonosulfate).

A compound of formula (I) containing an aromatic nitrogen atom may be converted into the corresponding N-oxide derivative by treatment with 3-chloroperoxy-benzoic acid.

A compound of formula (I) which contains a carbonyl may be converted into the corresponding alcohol by treatment with a suitable borohydride, e.g. lithium-tri-sec-butyl-borohydride or sodium borohydride, in a suitable solvent e.g. THF.

A bromophenyl derivative of formula (I) may be converted into the corresponding optionally substituted 2-oxopyrrolidin-1-ylphenyl or 2-oxooxazolidin-3-ylphenyl derivative by treatment with pyrrolidin-2-one or oxazolidin-2-one, or an appropriately substituted analogue thereof. The reaction is conveniently effected at an elevated temperature in the presence of copper(I) iodide, trans-N,N'-dimethylcyclohexane-1,2-diamine and an inorganic base such as potassium carbonate.

A compound of formula (I) wherein $R^1$ represents halogen, e.g. bromo, may be converted into the corresponding compound wherein $R^1$ represents an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected in the presence of a transition metal catalyst, e.g. [1,1'-bis(diphenylphosphino)ferrocene]dichloropalladium (II), tetrakis(triphenylphosphine)palladium(O), or bis[3-(diphenylphosphanyl)cyclopenta-2,4-dien-1-yl]iron-dichloropalladium-dichloromethane complex, and a base, e.g. an inorganic base such as sodium carbonate or potassium carbonate, or potassium phosphate. This reaction may conveniently be performed in a 1,4-dioxane with or without the use of micro wave technology.

A compound of formula (I) wherein $R^1$ represents halogen, e.g. bromo, may be converted into the corresponding compound wherein $R^1$ represents an optionally substituted aryl, heteroaryl or heterocycloalkenyl moiety via a two-step procedure which comprises: (i) reaction with bis(pinacolato) diboron or bis(neopentyl glycolato)diboron; and (ii) reaction of the compound thereby obtained with an appropriately functionalised halo- or tosyloxy-substituted aryl, heteroaryl or heterocycloalkenyl derivative. Step (i) is conveniently effected in the presence of a transition metal catalyst such as [1,1'-bis-(diphenylphosphino)ferrocene]dichloropalladium (II), or bis[3-(diphenylphosphanyl)-cyclopenta-2,4-dien-1-yl]iron-dichloropalladium-dichloromethane complex. Step (ii) is conveniently effected in the presence of a transition metal catalyst such as tetrakis-(triphenylphosphine)palladium(0), or bis[3-(diphenylphosphanyl)cyclopenta-2,4-dien-1-yl]iron-dichloropalladium-dichloromethane complex, and a base, e.g. an inorganic base such as sodium carbonate or potassium carbonate.

A compound of formula (I) wherein $R^1$ represents halogen, e.g. bromo, may be converted into the corresponding compound wherein $R^1$ represents an optionally an optionally substituted pyridine-2(1H)-one, via a two-step procedure which comprises: (i) reaction with the corresponding optionally substituted 4, 4, 5, 5-tetramethyl-1, 3, 2-dioxaborolan-2-yl)pyridine, in a suitable solvent, e.g. 1,4-dioxane, in the presence of an inorganic base e.g. sodium carbonate, and (ii) addition of (tris)(benzylideneacetone)dipalladum (0) and tri-tert-butylphoshonium tetrafluoroborate. The reaction is conveniently effected a high temperature in a microwave oven.

A compound of formula (I) wherein $R^1$ represents halogen, e.g. bromo, may be converted into the corresponding compound wherein $R^1$ represents an optionally substituted $C_{2-6}$ alkynyl moiety by treatment with an appropriately substituted alkyne derivative, e.g. 2-hydroxybut-3-yne. The reaction is conveniently accomplished with the assistance of a transition metal catalyst, e.g. tetrakis(triphenylphosphine) palladium(O), typically in the presence of copper(I) iodide and a base, e.g. an organic base such as triethylamine.

A compound of formula (I) wherein $R^1$ represents halogen, e.g. bromo, may be converted into the corresponding compound wherein $R^1$ represents an optionally substituted imidazol-1-yl moiety by treatment with the appropriately substituted imidazole derivative, typically in the presence of copper(II) acetate and an organic base such as N,N,N',N'-tetramethylethylenediamine (TMEDA).

A compound of formula (I) wherein $R^1$ represents halogen, e.g. bromo, may be converted into the corresponding compound wherein $R^1$ represents 2-(methoxycarbonyl)-ethyl via a two-step procedure which comprises: (i) reaction with methyl acrylate; and (ii) catalytic hydrogenation of the alkenyl derivative thereby obtained, typically by treatment with a hydrogenation catalyst, e.g. palladium on charcoal, under an atmosphere of hydrogen gas. Step (i) is typically effected in the presence of a transition metal catalyst, e.g. palladium(II) acetate or bis(dibenzylideneacetone)palladium(O), and a reagent such as tri(ortho-tolyl)phosphine.

In general, a compound of formula (I) containing a —C≡C— functionality may be converted into the corresponding compound containing a —CH—CH— functionality by catalytic hydrogenation, typically by treatment with a hydrogenation catalyst, e.g. palladium on charcoal, under an atmosphere of hydrogen gas, optionally in the presence of a base, e.g. an alkali metal hydroxide such as sodium hydroxide.

A compound of formula (I) wherein $R^1$ represents 6-methoxypyridin-3-yl may be converted into the corresponding compound wherein $R^1$ represents 2-oxo-1,2-dihydro-pyridin-5-yl by treatment with pyridine hydrochloride; or by heating with a mineral acid such as hydrochloric acid. By utilising similar methodology, a compound of formula (I) wherein $R^1$ represents 6-methoxy-4-methylpyridin-3-yl may be converted into the corresponding compound wherein $R^1$ represents 4-methyl-2-oxo-1,2-dihydropyridin-5-yl; and a compound of formula (I) wherein $R^1$ represents 6-methoxy-5-methylpyridin-3-yl may be converted into the corresponding compound wherein $R^1$ represents 3-methyl-2-oxo-1,2-dihydropyridin-5-yl.

A compound of formula (I) wherein $R^1$ represents 2-oxo-1,2-dihydropyridin-5-yl may be converted into the corresponding compound wherein $R^1$ represents 2-oxopiperidin-5-yl by catalytic hydrogenation, typically by treatment with gaseous hydrogen in the presence of a hydrogenation catalyst such as platinum(IV) oxide.

A compound of formula (I) wherein $R^1$ represents 2-methoxy-3-methyl-pyridin-yl may be converted into the corresponding compound wherein $R^1$ represents 3-methyl-pyridin-2(H)-one by treatment with sodium iodide and boron trifluoride ethyl etherate in acetonitrile.

A compound of formula (I) containing an ester moiety, e.g. a $C_{2-6}$ alkoxycarbonyl group such as methoxycarbonyl or ethoxycarbonyl, may be converted into the corresponding compound containing a carboxy (—$CO_2H$) moiety by treatment with an acid, e.g. a mineral acid such as hydrochloric acid.

A compound of formula (I) containing an N-(tert-butoxycarbonyl) moiety may be converted into the corresponding compound containing an N—H moiety by treatment with an acid, e.g. a mineral acid such as hydrochloric acid, or an organic acid such as trifluoroacetic acid. A compound of formula (I) containing an ester moiety, e.g. a $C_{2-6}$ alkoxycarbonyl group such as methoxycarbonyl or ethoxycarbonyl, may alternatively be converted into the corresponding compound containing a carboxy (—$CO_2H$) moiety by treatment with a base, e.g. an alkali metal hydroxide selected from lithium hydroxide, sodium hydroxide and potassium hydroxide; or an organic base such as sodium methoxide or sodium ethoxide.

A compound of formula (I) containing a carboxy (—$CO_2H$) moiety may be converted into the corresponding compound containing an amide moiety by treatment with the appropriate amine in the presence of a condensing agent such as 1-ethyl-3-(3-dimethyl-aminopropyl)carbodiimide.

A compound of formula (I) containing a carbonyl (C=O) moiety may be converted into the corresponding compound containing a —C(CH$_3$)(OH)— moiety by treatment with methylmagnesium bromide. Similarly, a compound of formula (I) containing a carbonyl (C=O) moiety may be converted into the corresponding compound containing a —C(CF$_3$)(OH)— moiety by treatment with (trifluoromethyl)trimethylsilane and cesium fluoride. A compound of formula (I) containing a carbonyl (C=O) moiety may be converted into the corresponding compound containing a —C(CH$_2$NO$_2$)(OH)— moiety by treatment with nitromethane.

A compound of formula (I) containing a hydroxymethyl moiety may be converted into the corresponding compound containing a formyl (—CHO) moiety by treatment with an oxidising agent such as Dess-Martin periodinane. A compound of formula (I) containing a hydroxymethyl moiety may be converted into the corresponding compound containing a carboxy moiety by treatment with an oxidising agent such as tetrapropylammonium perruthenate.

A compound of formula (I) wherein $R^1$ represents a substituent containing at least one nitrogen atom, which substituent is linked to the remainder of the molecule via a nitrogen atom, may be prepared by reacting a compound of formula (I) wherein $R^1$ represents halogen, e.g. bromo, with the appropriate compound of formula $R^1$—H [e.g. 1-(pyridin-3-yl)piperazine or morpholine]. The reaction is conveniently effected with the assistance of a transition metal catalyst, e.g. tris(dibenzylideneacetone)dipalladium(0), in the presence of an amination ligand such as 2-dicyclohexylphosphino-2',4',6'-triisopropyl-biphenyl (XPhos) or 2,2'-bis(diphenylphosphino)-1,1'-binaphthalene (BINAP) and a base, e.g. an inorganic base such as sodium tert-butoxide. Alternatively, the reaction may be effected using palladium diacetate, in the presence of a reagent such as [2',6'-bis(propan-2-yloxy)biphenyl-2-yl](dicyclohexyl)phosphane and a base, e.g. an inorganic base such as cesium carbonate.

A compound of formula (I) containing an oxo moiety can be converted into the corresponding compound containing an ethoxycarbonylmethylidene moiety by treatment with triethyl phosphonoacetate in the presence of a base such as sodium hydride.

A compounds of formula (IIB), (IIN), or (IIP) wherein $R^9$ represents ethenyl may be prepared by reacting a compound of (IIB), (IIN), or (IIP) wherein $R^9$ represents halogen, e.g. chloro, with potassium vinyl trifluoroborate. The reaction is typically effected in the presence of a transition metal catalyst, e.g. [1,1'-bis(diphenylphosphino)ferrocene]dichloropalladium(II), and a base, e.g. an organic base such as triethylamine.

A compound of formula (IIB), (IIN), or (IIP) wherein $R^9$ represents halogen, e.g. chloro, may be converted into the corresponding compound wherein $R^9$ represents an optionally substituted $C_{4-7}$ cycloalkenyl moiety by treatment with the appropriately substituted cycloalkenyl boronic acid or a cyclic ester thereof formed with an organic diol, e.g. pinacol, 1,3-propanediol or neopentyl glycol. The reaction is typically effected in the presence of a transition metal catalyst, e.g. bis[3-(diphenylphosphanyl)cyclopenta-2,4-dien-1-yl]iron-dichloropalladium-dichloromethane complex, and a base, e.g. an inorganic base such as potassium carbonate.

A compound of formula (IIB), (IIN), or (IIP) wherein $R^9$ represents a substituent containing at least one nitrogen atom, which substituent is linked to the remainder of the molecule via a nitrogen atom, may be prepared by reacting a compound of formula (IIB), (IIN), or (IIP) wherein $R^9$ represents halogen, e.g. chloro, with the appropriate compound of formula $R^9$—H [e.g. 2-methoxyethylamine, N-methyl-L-alanine, 2-aminocyclopentanecarboxylic acid, 3-aminocyclopentanecarboxylic acid, 1-(aminomethyl)cyclopropanecarboxylic acid, methyl azetidine-3-carboxylate, pyrrolidin-3-ol, pyrrolidine-3-carboxylic acid, piperidine-2-carboxylic acid, piperidine-3-carboxylic acid, 4-(1H-tetrazol-5-yl)piperidine, piperazine, 1-(methylsulfonyl)piperazine, piperazin-2-one, 2-(piperazin-1-yl)propanoic acid, morpholine, morpholine-2-carboxylic acid, thiomorpholine, thiomorpholine 1,1-dioxide, 1,4-diazepan-5-one, 2-oxa-5-azabicyclo[2.2.1]heptane or an appropriately substituted azaspiroalkane], optionally in the presence of a base, e.g. an organic base such as triethylamine or N,N-diisopropylethylamine and/or 1-methyl-2-pyrrolidinone, or pyridine, or an inorganic base such as potassium carbonate.

It will be apparent to the person skilled in the art that the synthesis of compounds of formula (I) with specific $R^1$ and $R^9$ groups or with specific substituents, which synthesis is not detailed here above, can be prepared according to the specific protocols described here after in the Examples.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt.

In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds in accordance with this invention potently inhibit the binding of a fluorescence conjugate to TNFα when tested in the fluorescence polarisation assay described below. Moreover, certain compounds in accordance with this invention potently inhibit TNFα-induced NF-κB activation in the reporter gene assay described below.

Fluorescence Polarisation Assay
Preparation of Compound (A)
1-(2,5-Dimethylbenzyl)-6-[4-(piperazin-1-ylmethyl)phenyl]-2-(pyridin-4-yl-methyl)-1H-benzimidazole hereinafter referred to as "Compound (A)" can be prepared by the procedure described in Example 499 of WO 2013/186229 (published 19 Dec. 2013); or by a procedure analogous thereto.

Preparation of Fluorescence Conjugate
Compound (A) (27.02 mg, 0.0538 mmol) was dissolved in DMSO (2 mL). 5 (−6) Carboxy-fluorescein succinimyl ester (24.16 mg, 0.0510 mmol) (Invitrogen catalogue number: C1311) was dissolved in DMSO (1 mL) to give a bright yellow solution. The two solutions were mixed at room temperature, the mixture turning red in colour. The mixture was stirred at room temperature. Shortly after mixing a 20 μL aliquot was removed and diluted in a 80:20 mixture of AcOH:H$_2$O for LC-MS analysis on the 1200RR-6140 LC-MS system. The chromatogram showed two closely eluting peaks at retention times of 1.42 and 1.50 minutes, both with mass (M+H)$^+$=860.8 amu, corresponding to the two products formed with the 5- and 6-substituted carboxyfluorescein group. A further peak at retention time 2.21 minutes had a mass of (M+H)$^+$=502.8 amu, corresponding to Compound (A). No peak was observed for unreacted 5(−6) carboxyfluorescein succinimyl ester. The peak areas were 20.0%, 39.6% and 31.4% for the three signals, indicating a 61.6% conversion to the two isomers of the desired fluorescence conjugate at that time-point. Further 20 μL aliquots were extracted after several hours and then after overnight stirring, diluted as before and subjected to LC-MS analysis. The percentage conversion was determined as 79.8% and 88.6% respectively at these time-points. The mixture was purified on a UV-directed preparative HPLC system. The pooled purified fractions were freeze-dried to remove excess solvent. After freeze-drying, an orange solid (23.3 mg) was recovered, equivalent to 0.027 mmol of fluorescence conjugate, corresponding to an overall yield of 53% for the reaction and preparative HPLC purification.

Inhibition of Binding of Fluorescence Conjugate to TNFα
Compounds were tested at 10 concentrations starting from 25 μM in a final assay concentration of 5% DMSO, by pre-incubation with TNFα for 60 minutes at ambient temperature in 20 mM Tris, 150 mM NaCl, 0.05% Tween 20, before addition of the fluorescence conjugate and a further incubation for 20 hours at ambient temperature. The final concentrations of TNFα and the fluorescence conjugate were 10 nM and 10 nM respectively in a total assay volume of 25 μL. Plates were read on a plate reader capable of detecting fluorescence polarisation (e.g. an Analyst HT plate reader; or an Envision plate reader). An IC$_{50}$ value was calculated using XLfit™ (4 parameter logistic model) in ActivityBase.

When tested in the fluorescence polarisation assay, the compounds of the accompanying Examples were all found to exhibit IC$_{50}$ values of 50 μM or better.

Reporter Gene Assay
Inhibition of TNFα-induced NF-κB Activation
Stimulation of HEK-293 cells by TNFα leads to activation of the NF-κB pathway. The reporter cell line used to determine TNFα activity was purchased from InvivoGen. HEK-Blue™ CD40L is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a dose-dependent manner by TNFα, with an EC50 of 0.5 ng/mL for human TNFα. Compounds were diluted from 10 mM DMSO stocks (final assay concentration 0.3% DMSO) to generate a 10-point 3-fold serial dilution curve (e.g., 30,000 nM to 2 nM final concentration). Diluted compound was preincubated with TNFα for 60 minutes prior to addition to a 384-well microtitre plate and incubated for 18 h. The final TNFα concentration in the assay plate was 0.5 ng/mL. SEAP activity was determined in the supernatant using a colorimetric substrate QUANTI-Blue™ or HEK-Blue™ Detection media (InvivoGen). Percentage inhibitions for compound dilutions were calculated between a DMSO control and maximum inhibition (by excess control compound) and an IC$_{50}$ value calculated using XLfit™ (4 parameter logistic model) in ActivityBase.

When tested in the reporter gene assay, certain compounds of the accompanying Examples were found to exhibit IC$_{50}$ values of 50 μM or better.

EXAMPLES

Nomenclature
Compounds were named with the aid of ACD/Name Batch (Network) ver. 12.0 or Accelyrs Draw 4.0
Abbreviations
DCM: Dichloromethane EtOAc: Ethyl acetate
DMF: N,N-Dimethylformamide MeOH: Methanol
DMSO: Dimethylsulfoxide SiO$_2$: Silica
Et$_2$O: Diethyl ether h: Hour
THF: Tetrahydrofuran AcOH: Acetic acid r.t.: Room temperature RT: retention time
br.: Broad M: Mass
Brine: Saturated aqueous sodium chloride solution
HPLC: High Performance Liquid Chromatography
LCMS: Liquid Chromatography Mass Spectrometry
ES+: Electrospray Positive Ionisation
TEA: Triethylamine
DEA: Diethylamine
DIPEA: N,N-di-iso-propylethylamine
DIAD: Diisopropyl (E)-1,2-diazenedicarboxylate
bs.: Broad singlet
$Boc_2O$: Di-tert butyl dicarbonate
DME dimethoxy ethane
TLC thin layer chromatography
sat. Saturated
aq. Aqueous
KHMDS: Potassium bis(trimethylsilyl)amide
TBAF: Tetra-n-butylammonium fluoride
MeCN: Acetonitrile
Dppf: 1,1'-Bis(diphenylphosphino)ferrocene
EtOH: Ethanol
SFC: Supercritical fluid chromatography
IPA isopropyl alcohol
BAST: bis(2-methoxyethyl)aminosulfur trifluoride (BAST).
DAST: diethylaminosulfur trifluoride
The methanolic ammonia solution is made by mixing 100 mL of an aqueous. solution of 37% w/w of $NH_4OH$ in 900 mL of MeOH.
All reactions involving air- or moisture-sensitive reagents were performed under a nitrogen atmosphere using dried solvents and glassware.
Analytical Conditions
All NMRs were obtained either at 300 MHz or 400 MHz.
Method 1:
Waters Acquity-SQD, Waters Acquity UPLC BEH C18, 2.1×50 mm, 1.7 μm column
Mobile phase A: 10 mM Ammonium Formate+0.1% Ammonia
Mobile phase B: 95% MeCN+5% $H_2O$+0.1% Ammonia
Gradient program (Flow Rate 1.0 mL/min, Column Temperature 40° C.):

| Time | A % | B % |
| --- | --- | --- |
| 0.00 | 95 | 5 |
| 0.50 | 95 | 5 |
| 1.75 | 5 | 95 |
| 2.00 | 5 | 95 |
| 2.25 | 95 | 5 |

Method 1b:
Waters Acquity-SDS, Waters Acquity BEH C18, 2.1×50 mm, 1.7 μm column
Mobile phase A: water+0.5% formic acid
Mobile phase B: MeCN+0.035% formic acid
Gradient program (Flow Rate 0.9 mL/min, column temperature 55° C.):

| Time | A % | B % |
| --- | --- | --- |
| 0.00 | 95 | 5 |
| 2.00 | 5 | 95 |
| 2.60 | 5 | 95 |
| 2.70 | 95 | 5 |
| 3.00 | 95 | 5 |

Method 2: Preparative HPLC for all compounds that required it was performed at pH 2.5 using a Luna C18, 21.2 mm, 5 mm column.
Mobile phase A: 99.92% water and 0.08% formic acid.
Mobile phase B: 99.92% MeCN and 0.08% formic acid.
Gradient program (flow rate 25 mL/min), column temperature: ambient, variable gradient.
Method 2b:
Column: Merck Purosphere® STAR-RP18; 25 mm×250 mm, 10μ at ambient temperature
Eluent: ACN:H2O+0.05% TFA (flow rate 25 ml/min)
Gradient: 5:95 (0 min)→95:5 (45 min),
Method 2c:
Column: Agilent Prep C-18, 21.2 mm×250 mm, 10μ at ambient temperature
Eluent: ACN:H2O (flow rate 40 ml/min)
Gradient: 3:97 (0 min)→90:10 (12.5 min)→90:10 (15 min)
Method 2d:
Column: Agilent Prep C-18, 30 mm×250 mm, 10μ at ambient temperature
Eluent: ACN:H2O (flow rate 75 ml/min)
Gradient: 10:90 (0 min)→90:10 (12.5 min)→90:10 (15 min)
Method 2e:
Column: Merck Purosphere® STAR-RP18; 25 mm×250 mm, 10μ at ambient temperature
Eluent: ACN:H2O+0.05% TFA (flow rate 25 ml/min)
Gradient: 10:90 (0 min)→90:10 (45 min),
Method 2f
Column: Agilent Prep C-18, 21.2 mm×250 mm, 10μ at ambient temperature
Eluent: ACN:H2O (flow rate 40 ml/min) Gradient: 10:90 (0 min)→90:10 (12.5 min)→90:10 (15 min)
It will be apparent to the one skilled in the art that different retention times (RT) may be obtained for LCMS if different analytical conditions are used Intermediate 1

(E)-Ethyl 4-[2-(difluoromethoxy)phenyl]-2-oxobut-3-enoate

A suspension of 2-(difluoromethoxy)benzaldehyde (295 g, 1714 mmol) and ethyl (triphenylphosphoranylidene)pyruvate (279.1 g, 742 mmol) was heated at 100° C. The dark red aldehyde immediately decolorized, and a yellow suspension was obtained, which slowly changed to a dark brown solution. 2-(Difluoromethoxy)benzaldehyde (52.5 g, 305 mmol) was added to the reaction mixture. Residual aldehyde was separated from the reaction mixture by distillation. The resulting mixture was stirred in heptane (500 mL) and $Et_2O$ (500 mL). The brown solid precipitate was filtered off, and washed with a 1:1 mixture of heptane and $Et_2O$ (3×250 mL). The filtrate was concentrated, yielding a brown oil (218.5 g). Purification by flash column chromatography ($SiO_2$, 2-20% EtOAc in heptane) gave the title compound (91 g) as a yellow oil. $^1H$ ($CDCl_3$, 300 MHz) δ 8.13 (d, J 16.3 Hz, 1H), 7.75 (dt, J 7.8, 1.6 Hz, 1H), 7.46 (dt, J 7.8, 1.7 Hz, 1H), 7.38 (d, J 16.3 Hz, 1H), 7.28 (br t, J 7.6 Hz, 1H), 7.20 (dd, J 7.3, 1.0 Hz, 1H), 6.59 (t, J 72.9 Hz, 1H), 4.40 (q, J 7.1 Hz, 2H), 1.42 (t, J 7.1 Hz, 3H). LCMS (ES+) 271 (M+H)+.

Intermediate 2

Ethyl 4-[2-(difluoromethoxy)phenyl]-2-[(triethylsilyl)oxy]but-2-enoate

To a nitrogen-flushed solution of Intermediate 1 (50 g, 185 mmol) in DCM (500 mL) was added rhodium(II)

acetate dimer (0.818 g, 1.85 mmol) and triethylsilane (35.5 mL, 25.8 g, 222 mmol). The resulting mixture was stirred at reflux. Additional triethylsilane (10 mL, 7.28 g, 62.6 mmol) and rhodium(II) acetate dimer (0.2 g, 0.453 mmol) were added after 4 h. Heating at reflux was continued for 15 h. The reaction mixture was cooled to r.t. and filtered over a tight pad of kieselguhr. The resulting material was rinsed with DCM and concentrated in vacuo to yield the title compound (61 g) as a clear yellow oil that was employed in subsequent steps with no further purification. 4:1 mixture of E/Z-isomers. Major isomer: $^1$H(CDCl3, 300 MHz) δ 7.33 7.02 (m, 4H), 6.51 (t, J 74.1 Hz, 1H), 6.11 (t, J 7.4 Hz, 1H), 4.21 (q, J 7.1 Hz, 2H), 3.57 (d, J 7.4 Hz, 2H), 1.30 (t, J 7.1 Hz, 3H), 1.07-0.91 (m, 9H), 0.83-0.64 (m, 6H). Minor isomer: $^1$H(CDCl$_3$, 300 MHz) δ 7.33-7.02 (m, 4H), 6.51 (t, J 74.1 Hz, 1H), 5.58 (t, J 8.0 Hz, 1H), 4.25 (q, J 7.1 Hz, 2H), 3.86 (d, J 8.0 Hz, 2H), 1.30 (t, J 7.1 Hz, 3H), 1.07-0.91 (m, 9H), 0.83-0.64 (m, 6H).

INTERMEDIATE 3

Ethyl 3-bromo-4-[2-(difluoromethoxy)phenyl]-2-oxobutanoate

To a stirred solution of Intermediate 2 (69 g, 179 mmol) in THF (700 mL) at r.t. was added N-bromosuccimide (35.0 g, 196 mmol). The resulting mixture was stirred at reflux for 2 h before being cooled to r.t. The reaction mixture was concentrated to approximately one-third of its original volume. DCM (500 mL) was added and the resulting mixture was washed with a sat. aq. sodium bicarbonate solution (700 mL), then extracted with DCM (250 mL), dried over sodium sulfate and concentrated in vacuo, to yield a crude yellow oil (97 g). After storage overnight at r.t. under nitrogen, the product had partly solidified. The resulting material was triturated in diisopropyl ether (300 mL) for 1 h at r.t. The precipitate was removed by filtration. The filtrate was concentrated in vacuo yielding clear yellow-brown oil (88 g). Purification by column chromatography (SiO$_2$, 2-20% EtOAc in heptane) afforded the title compound (58.3 g) as a light brown oil. $^1$H(CDCl$_3$, 300 MHz) δ 7.33-7.26 (m, 2H). 7.19-7.09 (m, 2H), 6.58 (t, J 73.5 Hz, 1H), 5.37 (dd, J 7.8, 7.1 Hz, 1H), 4.36 (q, J 7.1 Hz, 2H), 3.55 (dd, J 14.5, 7.1 Hz, 1H), 3.32 (dd, J 14.5, 7.8 Hz, 1H), 1.38 (t, J 7.1 Hz, 3H). LCMS (ES$^+$) 271 (M−Br)$^+$.

Intermediate 4

Ethyl 6-bromo-3-[[2-(difluoromethoxy)phenyl]methyl]imidazo[1,2-a]pyridine-2-carboxylate 5-Bromopyridin-2-amine (43.5 g, 251.0 mmol), Intermediate 3 (40.0 g, 140 mmol) and magnesium sulphate (50.0 g, 419.0 mmol) were suspended in 1,4-dioxane (1 L) and heated at 60° C. for 18 h. The reaction was cooled and the solids were filtered-off and washed with EtOAc. The filtrate was concentrated redissolved in EtOAc and washed with sat. sodium bicarbonate solution. The organic layer was washed with brine, dried over sodium sulfate and concentrated in vacuo to afford a brown oil. The oil was triturated with Et$_2$O for 1 h, filtered-off and dried in vacuo yielding the title compound (27.16 g, 44.9%). 61-1 (CDCl$_3$, 300 MHz) 8.07 (dd, J 1.8, 0.9 Hz, 1H), 7.58 (dd, J 9.6, 0.9 Hz, 1H), 7.32-7.21 (m, 2H), 7.19-7.12 (m, 1H), 7.07 (td, J 7.4, 1.3 Hz, 1H), 7.00 (dd, J 7.7, 1.6 Hz, 1H), 6.66 (t, J 73.6 Hz, 1H), 4.73 (s, 2H), 4.47 (q, J 7.1 Hz, 2H), 1.44 (t, J 7.1 Hz, 3H). LCMS (ES$^+$) RT 3.10 min, 271 (M−Br)$^+$.

Intermediate 5

Ethyl 6-bromo-3-[1-[2-(difluoromethoxy)phenyl]-3-ethoxy-3-oxo-propyl]imidazo[1,2-a]pyridine-2-carboxylate Intermediate 4 (13.0 g, 30.6 mmol) was dissolved in THF (600 ml) and the mixture was cooled to −100° C. 1M KHMDS in THF (34 mL, 34.0 mmol) was added drop wise and the resulting mixture was stirred at −95° C. for 15 minutes. Ethyl 2-bromoacetate (7.55 g, 45.2 mmol) was added and the resulting mixture was stirred at −95° C. for 30 minutes. EtOAc was added and the mixture was washed with water, the organics washed with brine, dried with sodium sulfate and concentrated in vacuo to afford a yellow oil. The residue was triturated with Et$_2$O and filtered yielding the title compound as a beige solid (10.8 g, 54%). δH (CDCl3, 300 MHz) 8.56 (s, 1H), 7.73 (dd, J 7.2, 2.2 Hz, 1H), 7.53 (dd, J 9.6, 0.8 Hz, 1H), 7.29 (dd, J 9.6, 1.8 Hz, 1H), 7.26-7.15 (m, 2H), 7.01-6.94 (m, 1H), 6.37 (t, J 73.5 Hz, 1H), 5.39 (dd, J 9.8, 5.8 Hz, 1H), 4.38 (qd, J 7.1, 0.8 Hz, 2H), 4.01 (qd, J 7.1, 3.4 Hz, 2H), 3.82 (dd, J 16.8, 9.8 Hz, 1H), 3.34 (dd, J 16.8, 5.8 Hz, 1H), 1.38 (t, J 7.1 Hz, 3H), 1.11 (t, J 7.1 Hz, 3H). LCMS (ES$^+$) RT 2.13 min, 511.0/513.0 (M−Br)$^+$.

Intermediate 6

7-Bromo-1-(2-difluoromethoxy-phenyl)-3-oxo-2,3-dihydro-1Hcyclopenta[4,5]imidazo[1,2-a]pyridine-2-carboxylic acid ethyl ester

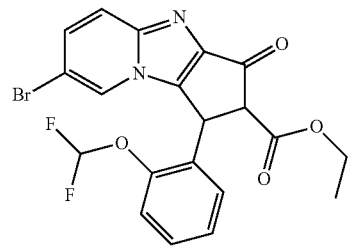 [SMILES: CCOC(=O)C1C(=O)c2nc3ccc(Br)cn3c2C1c1ccccc1OC(F)F]

Under an argon atmosphere, Intermediate 5 (4.0 g, 7.7 mmol) was dissolved in dry THF (150 mL). Potassium tert-butoxide (1.6 g, 14.26 mmol) was added and the mixture was stirred at r.t for 30 minutes. EtOAc was added and the reaction partitioned with water. The aq. layer was extracted with EtOAc (2×). The combined organic layers were washed with brine (×2), dried over sodium sulfate and concentrated in vacuo to yield a black oil. The residue was triturated with diisopropyl ether/DCM 7:3 and the solids were filtered off. The filtrate was concentrated in vacuo, and purified by preparative HPLC to afford the title compound as a yellow solid (792 mg, 22.7%). 15:1 mixture of diastereoisomers, major isomer: δH (CDCl3, 300 MHz) 7.76 (dd, J 1.8, 1.0 Hz, 1H), 7.63 (dd, J 9.8, 1.0 Hz, 1H), 7.43-7.33 (m, 2H), 7.30-7.22 (m, 1H), 7.16 (td, J 7.5, 1.2 Hz, 1H), 6.85-6.78 (m, 1H), 6.58 (t, J 70.0 Hz, 1H), 5.48 (d, J 2.6 Hz, 1H), 4.27 (q, J 7.1 Hz, 2H), 3.88 (d, J 2.6 Hz, 1H), 1.31 (t, J 7.1 Hz, 3H). LCMS (ES$^+$) RT 2.07 min, 465.0/467.0 (M+H)$^+$.

Intermediate 7

7-Bromo-6-fluoro-1-phenyl-1,2-dihydro-cyclopenta[4,5]imidazo[1,2-a]pyridin-3-one

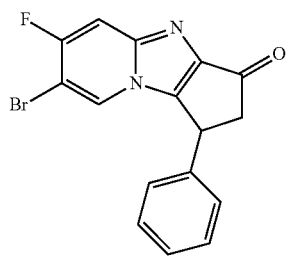 [SMILES: O=C1CC(c2ccccc2)c2c1nc1cc(F)c(Br)cn21]

Step 1: Preparation of 2-amino-4-fluoro-5-bromopyridine

To a solution of 2-amino-4-fluoropyridine (75.0 g, 0.67 mol) in dry MeCN (700 mL), N-bromosuccinimide (122.8 g, 0.69 mol) was added portionwise upon stirring and cooling in an ice-water bath. The reaction mixture was stirred at r.t. for 1 h. After evaporation under reduced pressure, the residue was thoroughly washed with water (3×300 mL), taken up by MeCN and concentrated in vacuo yielding the title compound as an off white solid (124 g, 97%). LCMS (ES$^+$) RT 0.79 min, 19.0/193.0 (M+H)$^+$.

Step 2: preparation of ethyl 6-bromo-7-fluoro-imidazo[1,2-a]pyridine-2-carboxylate To a solution of 2-amino-4-fluoro-5-bromopyridine (87.6 g, 0.459 mol) in DME (750 mL), ethyl bromopiruvate (116.3 g, 0.596 mol, 1.3 eq.) was added. The reaction mixture was stirred at r.t. overnight and the resulting white precipitate was filtered, washed with DME (150 mL), Et$_2$O (150 mL) and air dried at r.t. A suspension of the resulting white solid in i-PrOH (1000 mL) was stirred at 90° C. for 3 h. The solvent was distilled off under reduced pressure, the residue was stirred with a solution of KHCO$_3$ (75.0 g, 0.75 mol) in water (500 mL) at r.t. for 1 h. The precipitate was filtered, washed with water (3×500 mL), evaporated with MeCN and concentrated in vacuo yielding the title compound as an off white solid (108 g, 82%). $^1$H NMR (400 MHz, DMSO-d$_6$) δ 9.08 (d, J 7.1 Hz, 1 H), 8.45 (s, 1 H), 7.75 (d, J 9.8 Hz, 1 H), 4.31 (q, J 7.1 Hz, 2 H), 1.32 (t, J 7.1 Hz, 3 H). LCMS (ES$^+$) RT 1.44 min, 287.0/289.0 (M+H)$^+$.

Step 3: preparation of ethyl 6-bromo-7-fluoro-3-formyl-imidazo[1,2-a]pyridine-2-carboxylate To a suspension of ethyl 6-bromo-7-fluoro-imidazo[1,2-a]pyridine-2-carboxylate (50.0 g, 0.174 mol) in dry DMF (101.6 g, 1.39 mol, 8.0 eq.), Phosphoryl chloride (213.0 g, 1.39 mol, 8.0 eq.) was added dropwise over a period of 30-40 minutes. with vigorous stirring and heating to 75-85° C. The resulting dark-red solution was stirred at 85° C. for 4.5 h, cooled to r.t. and then carefully poured into an ice-water bath and left stirring for 20 minutes. The precipitate was filtered, thoroughly washed with water and suspended in water (500 mL). A 5 M aq. solution of sodium hydroxide was slowly added until pH~7-8, the precipitate was filtered, washed with water and concentrated in vacuo yielding the title compound as an off white solid (34.9 g, 63%). $^1$H NMR (400 MHz, DMSO-d$_6$) δ 10.42 (s, 1H), 9.71 (d, J 6.8 Hz, 1 H), 8.15 (d, J 9.0 Hz, 1 H), 4.43 (q, J 7.1 Hz, 2 H), 1.38 (t, J 7.1 Hz, 3 H), LCMS (ES$^+$) RT 1.71 min, 315.0/317.0 (M+H)$^+$.

Step 4: preparation of ethyl 6-bromo-7-fluoro-3-[hydroxy(phenyl)methyl]imidazo[1,2-a]pyridine-2-carboxylate To a suspension of ethyl 6-bromo-7-fluoro-3-formyl-imidazo[1,2-a]pyridine-2-carboxylate (46.4 g, 0.147 mol) in THF (3000 mL), at −45° C., phenylmagensium bromide (170 mL 1 M solution in THF, 0.17 mol, 1.15 eq.) was added dropwise, under an argon atmosphere. After this addition, the temperature was raised to −25° C. for 1 h and then to r.t. for 2 h. The reaction was quenched by addition of sat. solution of ammonium chloride (150 mL) and brine (150 mL). The mixture was concentrated under reduced pressure and diluted with EtOAc (1000 mL). The organic layer was separated and the aq. layer was extracted with EtOAc (500 mL). The combined organic layer was washed with brine (3×500 mL), dried over magnesium sulfate, filtered and concentrated under reduced pressure. The residue was purified by flash column chromatography (SiO$_2$,5-10% EtOAc in CHCl$_3$) yielding the title compound as an off white solid (42.1 g, 73%). $^1$H NMR (400 MHz, DMSO-d$_6$) δ 8.62 (d, J 6.9 Hz, 1 H), 7.82 (d, J 9.3 Hz, 1 H), 7.32-7.43 (m, 4 H), 7.27 (m, 1 H), 6.98 (d, J 4.4 Hz, 1 H), 6.75 (d, J 4.4 Hz, 1 H), 4.37 (q, J 7.1 Hz, 2 H), 1.33 (t, J 7.1 Hz, 3 H). LCMS (ES$^+$) RT 1.76 min, 393.0/395.0 (M+H)$^+$.

Step 5: preparation of ethyl 6-bromo-3-[chloro(phenyl)methyl]-7-fluoro-imidazo[1,2-a]pyridine-2-carboxylate To a solution of ethyl 6-bromo-7-fluoro-3-[hydroxy(phenyl)methyl]imidazo[1,2-a]pyridine-2-carboxylate (18.0 g, 41.2 mmol) in DCM (400 mL), a solution of SOCl$_2$ (31.3 g, 263 mmol, 6.4 eq.) in DCM (60 mL) was added with stirring. The reaction mixture was stirred at r.t. for 2 h. The solvent was evaporated before successive solubilisation and evaporation of benzene (2×200 mL). The residue was distributed between DCM (400 mL) and 10% aq. KHCO$_3$ (100 mL). After stirring at r.t. for 30 minutes., the organic layer was separated and the aq. layer was extracted with DCM (150 mL). The combined organic layer was dried over sodium sulfate, filtered and concentrated in vacuo yielding ethyl 6-bromo-3-[chloro(phenyl)methyl]-7-fluoro-imidazo[1,2-a]pyridine-2-carboxylate (15.8 g, 92%) used in the next step without any further purification.

Step 6: preparation of diethyl 2[(6-bromo-2-ethoxycarbonyl-7-fluoro-imidazo[1,2-a]pyridin-3-yl)-phenyl-methyl]propanedioate To a suspension of NaH (1.63 g of 60% suspension in mineral oil, 40.3 mmol) in THF (250 mL), under an argon atmosphere, diethyl malonate (6.46 g, 40.3 mmol) was added dropwise whilst cooling in an ice-water bath. The mixture was stirred at r.t. for 1 h. To the resulting clear solution, a solution of the crude ethyl 6-bromo-3-[chloro(phenyl)methyl]-7-fluoro-imidazo[1,2-a]pyridine-2-carboxylate in THF (400 mL) was added quickly with stirring. The reaction mixture was stirred at r.t. for 16 h before being concentrated under reduced pressure. The residue was distributed between EtOAc (500 mL) and 10% aq. KHCO$_3$ (100 mL); the organic layer was separated, washed with brine (2×150 mL), dried over magnesium sulfate, filtered and concentrated under reduced pressure. The residue was purified by flash column chromatography (SiO$_2$, 0-7% EtOAc in DCM) yielding the title compound as an off white solid (14.3 g, 69% for 2 steps from ethyl 6-bromo-3-[chloro (phenyl)methyl]-7-fluoro-imidazo[1,2-a]pyridine-2-carboxylate). $^1$H NMR (400 MHz, DMSO-d$_6$) δ 9.20 (br. s, 1 H), 7.78 (d, J 9.3 Hz, 1 H), 7.56 (m, 2 H), 7.30 (m, 2 H), 7.21 (m, 1 H), 5.90 (br s, 1 H), 5.47 (d, J 12.2 Hz, 1 H), 4.37 (q, J 7.1 Hz, 2 H), 4.07 (q, J 7.1 Hz, 2 H), 3.82 (q, J 7.1 Hz, 2 H), 1.34 (t, J 7.1 Hz, 3 H), 1.05 (t, J 7.1 Hz, 3 H), 0.78 (t, J 7.1 Hz, 3 H), LCMS (ES$^+$) RT 2.04 min, 535.0/537.0 (M+H)$^+$.

Step 7: preparation of methyl 6-bromo-7-fluoro-3-(2-methoxy-2-oxo-1-phenyl-ethyl)imidazo[1,2-a]pyridine-2-carboxylate A mixture of diethyl 2-[(6-bromo-2-ethoxycarbonyl-7-fluoro-imidazo[1,2-a]pyridin-3-yl)-phenyl-methyl]propanedioate (14.26 g, 26.6 mmol) and 6 M aq. HCl (330 mL) was stirred at 100° C. for 16 h. The mixture was evaporated under reduced pressure and the residue (a viscous oil) was successively taken up and solvents evaporated with MeCN (2×200 mL) and benzene (2×200 mL), concentrated in vacuo yielding 6-bromo-7-fluoro-3-(3-hydroxy-3-oxo-1-phenyl-propyl)imidazo[1,2-a]pyridine-2-carboxylic acid (13.4 g) used in the next step without any further purification
To MeOH (220 mL), upon stirring and cooling in an ice-water bath, SOCl$_2$ (88.2 g, 0.74 mol) was added dropwise. The resulting solution was stirred 30 minutes. at ~5° C. and poured onto the crude 6-bromo-7-fluoro-3-(3-hydroxy-3-oxo-1-phenyl-propyl)imidazo[1,2-a]pyridine-2-carboxylic acid. The reaction mixture was placed into a glass high-pressure-vessel and stirred at 50° C. for 16 h. After cooling to r.t., the solvent was evaporated, the residue was re-evaporated with benzene three times and concentrated in vacuo at 40-50° C. The residue was dissolved in CHCl$_3$ (250 mL); washed with 10% aq. KHCO$_3$ (85 mL), dried over sodium sulfate, filtered and concentrated under reduced pressure. The residue was purified by flash column chromatography (SiO$_2$, 0-20% EtOAc in DCM) yielding the title compound as an off white solid (9.9 g, 64%). $^1$H NMR (400 MHz, DMSO-d$_6$) δ 8.88 (d, J 6.4 Hz, 1 H), 7.73 (d, J 9.1 Hz, 1 H), 7.20-7.35 (m, 5 H), 5.70 (t, J 8.1 Hz, 1 H), 3.80 (s, 3 H), 3.52 (d, J 8.1 Hz, 2 H), 3.50 (s, 3 H). LCMS (ES$^+$) RT 1.84 min, 435.0/437.0 (M+H)$^+$.

Step 8: Preparation of 7-bromo-6-fluoro-3-oxo-1-phenyl-2,3-dihydro-1H-cyclopenta[4,5]imidazo[1,2-a]pyridine-2-carboxylic acid methyl ester

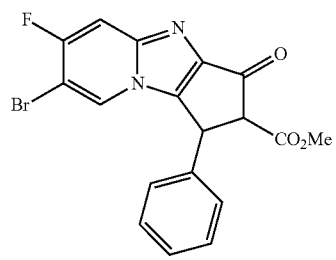 [SMILES: COC(=O)C1C(=O)c2nc3cc(F)c(Br)cn3c2C1c1ccccc1]

To a solution of methyl 6-bromo-7-fluoro-3-(2-methoxy-2-oxo-1-phenyl-ethyl)imidazo[1,2-a]pyridine-2-carboxylate (9.90 g, 22.7 mmol) in toluene (1000 mL), under an argon atmosphere, a solution of potassium tert-pentoxide (25% solution in toluene, 21 mL, 40.9 mmol, 1.8 eq.) was added whilst stirring and cooling to −10° C. during 10-15 minutes. The reaction mixture was stirred at −10° C. for 1 h and quenched by adding AcOH (2.5 mL). After warming up to r.t., 10% aq. KHCO$_3$ (95 mL) was added; the organic layer was separated and concentrated under reduced pressure. The residue was purified by flash column chromatography (SiO$_2$, 0-5% MeOH in DCM) yielding the title compound as an off white solid (5.1 g, 55%). $^1$H NMR (400 MHz, CDCl$_3$) 6.75 (d, J 6.4 Hz, 1 H), 7.43 (d, J 8.8 Hz, 1 H), 7.43-7.37 (m, 3 H), 7.12-7.18 (m, 2 H), 5.17 (d, J 2.7 Hz, 1 H), 3.98 (d, J 2.7 Hz, 1 H), 3.84 (s, 3 H), LCMS (ES$^+$) RT 1.68 min, 403.0/405.0 (M+H)$^+$.

Step 8: preparation of 7-bromo-6-fluoro-1-phenyl-1,2-dihydro-cyclopenta[4,5]imidazo[1,2-a]pyridin-3-one

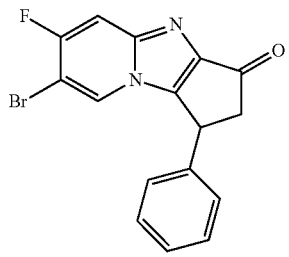

A mixture of 7-bromo-6-fluoro-3-oxo-1-phenyl-2,3-dihydro-1H-cyclopenta[4,5]imidazo[1,2-a]pyridine-2-carboxylic acid methyl ester (5.06 g, 12.5 mmol) and 6 M aq. HCl (100 mL) was stirred at 100° C. for 3 h. The resulting clear solution was evaporated under reduced pressure; the residue was distributed between CHCl$_3$ (200 mL) and 10% aq. KHCO$_3$ (50 mL). The aq. layer was extracted with CHCl$_3$ (100 mL). The combined organic layer was dried over sodium sulfate, filtered and concentrated under reduced pressure. The residue was suspended in CHCl$_3$ (40 mL); the suspension was stirred 15 minutes. at r.t. and filtered. The resulting precipitate was washed with CHCl$_3$ (5 mL), Et$_2$O (5 mL) and concentrated in vacuo (1-2 mm Hg) yielding 2.60 g of the title compound as an off white solid. The filtrate was concentrated under reduced pressure; the residue was purified by flash column chromatography (SiO$_2$, 0-5% MeOH in CHCl$_3$) yielding an additional 0.85 g as an off white solid. The two batches were pooled together yielding the title compound as an off white solid (3.45 g, 80%). $^1$H NMR (400 MHz, DMSO-d$_6$) δ 8.42 (d, J 6.4 Hz, 1 H), 7.87 (d, J 9.8 Hz, 1 H), 7.38-7.26 (m, 3 H), 7.18 (m, 2 H), 4.93 (dd, J 18.3 Hz, J 2.0 Hz, 1 H), 3.64 (dd, J 18.3 Hz, J 7.1 Hz, 1 H), 2.76 (dd, J$_1$ 18.3 Hz, J$_2$ 2.0 Hz, 1 H). LCMS (ES$^+$) RT 1.71 min, 345.0/347.0 (M+H)$^+$.

Intermediate 8 and 9

(R)-7-Bromo-6-fluoro-1-phenyl-1,2-dihydro-cyclopenta[4,5]imidazo[1,2-a]pyridin-3-one and (S)-7-Bromo-6-fluoro-1-phenyl-1,2-dihydro-cyclopenta[4,5]imidazo[1,2-a]pyridin-3-one

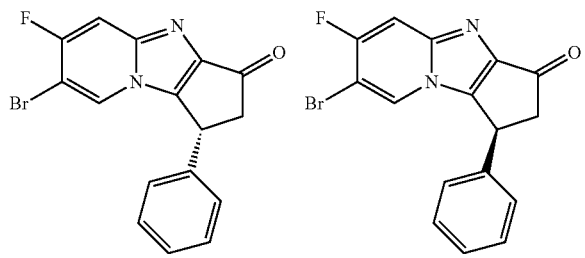

The title compounds were isolated by chiral separation of Intermediate 7 (1.1 g) under LC conditions on LUX cell-4 (76*265 mm*mm, flow 200 mL/min, 30° C., MeOH 100%, injection of 382 mL solution at a concentration of 1.1 g/L). The first eluting enantiomer (RT 6.09 min) was collected and the fractions were evaporated to yield 460 mg of (S)-7-bromo-6-fluoro-1-phenyl-1,2-dihydro-cyclopenta[4,5]imidazo[1,2-a]pyridin-3-one (Intermediate 9). The second eluting enantiomer (RT 8.35 min) was collected and the fractions were evaporated to yield 485 mg of (R)-7-bromo-6-fluoro-1-phenyl-1,2-dihydro-cyclopenta[4,5]imidazo[1,2-a]pyridin-3-one (Intermediate 8).

Intermediate 10

Ethyl 6-bromo-3-[[2-(difluoromethoxy)phenyl]methyl]-7-fluoro-imidazo[1,2-a]pyridine-2-carboxylate 5-bromo-4-fluoropyridin-2-amine (125 g, 654.0 mmol) Intermediate 3 (121.0 g, 344.0 mmol) and magnesium sulfate (124.0 g, 1033.0 mmol) were suspended in 1,4-dioxane (2.5 L) and heated at 80° C. for 72 h. The reaction was cooled and the solids were filtered off and washed with EtOAc. The reaction mixture was filtered and rinsed with EtOAc. The filtrate was diluted with 1 N sodium hydroxide and EtOAc and the layers were separated. The water layer was extracted with EtOAc (2×). The organic layers were combined and washed with 2 N HCl (2×). The acidic aq. layer was extracted with EtOAc (×2). All the organic layers were combined and washed with brine, dried with sodium sulfate and concentrated in vacuo. The residue was triturated with Et$_2$O, filtered off and rinsed with Et$_2$O to afford the title compound as a yellow solid (111 g, 71%). δH (CDCl$_3$, 300 MHz) 8.16 (d, J 6.3 Hz, 1H), 7.40 (d, J 8.4 Hz, 1H), 7.30-7.21 (m, 1H), 7.15 (br d, J 8.0 Hz, 1H), 7.11-7.02 (m, 2H), 6.66 (t, J 73.5 Hz, 1H), 4.71 (s, 2H), 4.47 (q, J 7.1 Hz, 2H), 1.43 (t, J 7.1 Hz, 3H). LCMS (ES$^+$) RT 2.13 min, 443.0/445.0 (M+H)$^+$.

Intermediate 11

Ethyl 6-bromo-3-[1-[2-(difluoromethoxy)phenyl]-3-ethoxy-3-oxo-propyl]-7-fluoro-imidazo[1,2-a]pyridine-2-carboxylate Intermediate 10 (30.0.0 g, 67.7 mmol) was dissolved in THF (400 ml) and the mixture cooled to −100° C. 1M KHMDS in THF (75.0 mL, 75.0 mmol) was added drop wise and the resulting mixture was stirred at −95° C. for 15 minutes. Ethyl 2-bromoacetate (11.3 mL, 102 mmol) was added and the resulting mixture was stirred at −95° C. for 30 minutes. EtOAc was added and the mixture was washed with water, and the organics washed with brine, dried with sodium sulfate and concentrated in vacuo to afford a black oil. The residue was triturated with Et$_2$O and filtered yielding the title compound as a light brown solid (26.5 g, 71%). δH (CDCl$_3$, 300 MHz) 8.67 (d, J 6.4 Hz, 1H), 7.74 (dd, J 7.3, 2.2 Hz, 1H), 7.33 (dd, J 8.3, 0.5 Hz, 1H), 7.29-7.16 (m, 2H), 6.99-6.93 (m, 1H), 6.37 (t, J 73.5 Hz, 1H), 5.32 (dd, J 10.1, 5.4 Hz, 1H), 4.37 (q, J 7.1 Hz, 2H), 4.09-3.95 (m, 2H), 3.89 (dd, J 16.9, 10.1 Hz, 1H), 3.31 (dd, J 16.9, 5.3 Hz, 1H), 1.37 (t, J 7.1 Hz, 3H), 1.14 (t, J 7.1 Hz, 3H). LCMS (ES$^+$) RT 2.16 min, 529.0/531.0 (M+H)$^+$.

Intermediate 12

7-Bromo-1-(2-difluoromethoxy-phenyl)-6-fluoro-3-oxo-2,3-dihydro-1H-cyclopenta[4,5]imidazo[1,2-a]pyridine-2-carboxylic acid ethyl ester

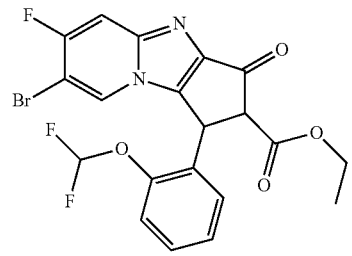 [SMILES: CCOC(=O)C1C(=O)c2nc3cc(F)c(Br)cn3c2C1c1ccccc1OC(F)F]

Under an argon atmosphere, Intermediate 11 (15.0 g, 28.3 mmol) was dissolved in dry THF (1 L). Potassium tert-butoxide (7.95 g, 70.8 mmol) was added and the mixture stirred at r.t for 30 minutes. The reaction was diluted with sat. ammonium chloride, stirred vigorously for a minute and then diluted with DCM. The layers were separated and the aq. layer was extracted with DCM. The combined organic layers were washed with brine, dried with sodium sulfate and concentrated in vacuo to afford a brown oil. The residue was crystallized from hot toluene (250 ml). The crystals were filtered off, washed with Et$_2$O yielding the title compound as light brown crystals (6.8 g, 50%). δH (CDCl$_3$, 300 MHz) 7.83 (d, J 6.3 Hz, 1H), 7.46-7.35 (m, 2H), 7.32-7.24 (m, 1H), 7.18 (td, J 7.5, 1.1 Hz, 1H), 6.83 (s, 1H), 6.58 (t, J 69.3 Hz, 1H), 5.47 (d, J 2.5 Hz, 1H), 4.28 (q, J 7.0 Hz, 2H), 3.89 (d, J 2.5 Hz, 1H), 1.32 (t, J 7.2 Hz, 3H). LCMS (ES$^+$) RT 2.09 min, 483.0/485.0 (M+H)$^+$.

Intermediate 13

[2-[(1R,5S)-8-methoxycarbonyl-3-azabicyclo[3.2.1]octan-3-yl]pyrimidin-5-yl]boronic acid (1R,5S)-3-tert-butoxycarbonyl-3-azabicyclo[3.2.1]octane-8-carboxylic acid (9.0 g, 35.3 mmol) was suspended in HCl solution (2.25 M in MeOH) and the reaction heated to reflux for 4 h. The reaction was allowed to cool to r.t. and then concentrated in vacuo to give a white solid. (2-chloro-pyrimidin-5-yl)boronic acid (5.58 g, 35.2 mmol) was added and the mixture suspended in EtOH (130 mL). TEA (9.90 mL, 70.5 mmol) was added and the reaction heated at 80° C.

for 5 h. The reaction was allowed to cool to r.t. and then water was added (30 mL). The reaction mixture was concentrated to around ⅓ volume and then more water added (100 mL). An off-white solid precipitated out, which was filtered and washed with water (2×30 mL) to afford the title compound (8.9 g, 86% yield) as an off-white powder. $^1$H NMR (300 MHz, DMSO-$d_6$) δ ppm 8.59 (s, 2H), 8.02 (s, 2H), 4.45 (dd, J 13.1, 3.4H, 2H), 3.62 (s, 3H), 2.98 (br d, J 12.4 Hz, 2H), 2.77 (s, 1H), 2.59 (br s, 2H), 1.66-1.63 (m, 2H), 1.38-1.33 (m, 2H). LCMS (ES$^+$) RT 0.97 min, 292.0 (M+H)$^+$.

Intermediates 14 and 15

(R)-7-Bromo-6-fluoro-1-(2-trifluoromethoxy-phenyl)-1,2-dihydro-cyclopenta[4,5]imidazo[1,2-a]pyridin-3-one and (S)-7-Bromo-6-fluoro-1-(2-trifluoromethoxy-phenyl)-1,2-dihydro-cyclopenta[4,5]imidazo[1,2-a]pyridin-3-one

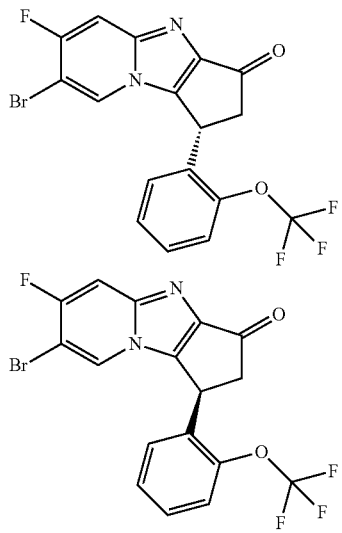

Step 1: Preparation of ethyl 6-bromo-7-fluoro-3-iodoimidazo[1,2-a]pyridine-2-carboxylate To a solution of ethyl 6-bromo-7-fluoroimidazo[1,2-a]pyridine-2-carboxylate (Intermediate 7, step 2, 10.3 g, 35.9 mmol, 1 eq) in AcOH (80 mL), N-iodosuccinimide (8.5 g, 37.6 mmol, 1.1 eq) was added. The reaction mixture was stirred at r.t. for 1 h to afford a white thick suspension. The solvent was evaporated under a reduced pressure, the residue was re-evaporated with CHCl$_3$ and dissolved in CHCl$_3$ (400 mL). The resulting yellow solution was washed with 10% aq. sodium thiosulfate (2×200 mL), brine (100 mL), dried over sodium sulfate, filtered, and concentrated in vacuo. The residue was washed with Et$_2$O (50 mL) and dried in vacuo, yielding the title compound as a white solid (14.0 g, 94%). $^1$H NMR (400 MHz, DMSO-$d_6$) δ 8.71 (d, J 6.6 Hz, 1H). 7.82 (d, J 9.1 Hz, 1H), 4.32 (q, J 7.1 Hz, 2H), 1.34 (t, J 7.1 Hz, 3H). LCMS (ES$^+$) RT 1.69 min, 413.0/415.0 (M+H)$^+$.

Step 2: Preparation of ethyl 6-bromo-7-fluoro-3-{hydroxy[2-(trifluoromethoxy)phenyl]methyl}imidazo[1,2-a]pyridine-2-carboxylate To a suspension of ethyl 6-bromo-7-fluoro-3-iodoimidazo[1,2-a]pyridine-2-carboxylate (29.57 g, 71.6 mmol, 1 eq) in THF (1 L), under an argon atmosphere, i-propylmagnesium chloride solution (36.0 mL, 2 M in THF, 72.0 mmol, 1 eq) was added drop wise over 3 minutes whilst stirring at −60° C. (internal thermometer). The reaction mixture was stirred at −60° C. for 15 min, then a solution of 2-(trifluoromethoxy)benzaldehyde (13.68 g, 72.0 mmol, 1 eq) in THF (50 mL) was added drop wise over 5 minutes. The stirring was continued upon spontaneous heating to −5° C. during 2 h. The mixture was quenched with sat. aq. ammonium chloride (250 mL), stirred at r.t. for 15 minutes, and extracted with EtOAc (2×300 mL). The organic layer was dried over sodium sulfate, filtered, and concentrated in vacuo. The residue was purified by column chromatography (SiO$_2$, 5-20% EtOAc in CHCl$_3$) yielding the title compound (17.38 g, 52%). $^1$H NMR (400 MHz, DMSO-$d_6$) δ 8.61 (d, J 6.6 Hz, 1H). 7.78-7.85 (m, 2H), 7.45-7.49 (m, 2H), 7.29-7.32 (m, 1H), 7.16 (d, J 4.2 Hz, 1H), 6.85 (d, J 4.4 Hz, 1H), 4.31 (q, J 7.1 Hz, 2H), 1.30 (t, J 7.1 Hz, 3H). LCMS (ES$^+$) RT 1.94 min, 477.0/479.0 (M+H)$^+$.

Step 3: Preparation of ethyl 6-bromo-7-fluoro-3-{chloro[2-(trifluoromethoxy)phenyl]methyl}imidazo[1,2-a]pyridine-2-carboxylate To a suspension of 6-bromo-7-fluoro-3-{hydroxy[2-(trifluoromethoxy)phenyl]methyl}imidazo[1,2-a]pyridine-2-carboxylate (18.27 g, 38.3 mmol, 1 eq) in DCM (440 mL), a solution of SOCl$_2$ (39.0 g, 328 mmol, 8.6 eq) in DCM (50 mL) was added. The reaction mixture was stirred at r.t. for 3 h and concentrated in vacuo. The residue was re-evaporated with absolute benzene (200 mL) and dissolved in DCM (300 mL). The resulted solution was washed with 10% aq. KHCO$_3$ (2×100 mL) at 5-10° C., dried over sodium sulfate, filtered, and concentrated in vacuo. The residue was re-evaporated with benzene (200 mL) and concentrated in vacuo at r.t to afford the title compound as a yellow solid (18.9 g).

Step 4: Preparation of diethyl {[6-bromo-2-(ethoxycarbonyl)-7-fluoroimidazo[1,2-a]pyridin-3-yl][2-(trifluoromethoxy)phenyl]methyl}propanedioate To a suspension of NaH (1.60 g of 60% in mineral oil, 40.0 mmol, 1 eq) in abs. THF (40 mL), upon stirring and cooling in an ice-water-bath, a solution of diethyl malonate (6.40 g, 40.0 mmol, 1 eq) in THF (40 mL) was added drop wise. The reaction mixture was stirred at r.t. for 30 minutes. To the clear solution, a solution of ethyl 6-bromo-7-fluoro-3-{chloro[2-(trifluoromethoxy)phenyl]methyl}imidazo[1,2-a]pyridine-2-carboxylate in THF (200 mL) was quickly added by stirring and cooling in a cold-water-bath. The mixture was stirred at r.t. for 6 h and concentrated in vacuo. The residue was distributed between EtOAc (500 mL) and water (250 mL); the organic layer was washed with 10% aq. KHCO$_3$ (200 mL), brine (200 mL), dried over magnesium sulfate, filtered, and concentrated in vacuo. The residue was purified by flash column chromatography (SiO$_2$, 0-5% EtOAc in DCM) yielding the title compound (16.4 g, 80% purity according 1H NMR). $^1$H NMR (400 MHz, DMSO-$d_6$) δ 8.93 (br. s, 1H,), 7.97 (br. s, 1H), 7.77 (d, J 7.0 Hz, 1H), 7.56-7.66 (m, 1H), 7.37-7.41 (m, 2H), 7.37-7.41 (m, 2H), 7.25-7.28 (m, 1H), 5.43-5.50 (m, 1H), 4.25-4.32 (m, 2H), 4.15-4.08 (m, 2H), 3.81-3.71 (m, 2H), 1.30-1.26 (m, 2H), 1.00 (t, J 6.7 Hz, 3H), 0.75 (t, J 6.6 Hz, 3H). LCMS (ES+) RT 2.21 min, 619.0/621.0 (M+H)+.

Step 5: Preparation of 6-bromo-3-{2-carboxy-1-[2-(trifluoromethoxy)phenyl]ethyl}-7-fluoroimidazo[1,2-a]pyridine-2-carboxylic acid A mixture of diethyl {[6-bromo-2-(ethoxycarbonyl)-7-fluoroimidazo[1,2-a]pyridin-3-yl][2-(trifluoromethoxy)phenyl]methyl}propanedioate (16.4 g) and 6M aq. HCl (200 mL) was stirred at 100° C. for 16 h. The mixture was concentrated in vacuo. The residue was re-evaporated with MeCN (2×150 mL), benzene (150 mL) and dried in vacuo yielding to the title compound as a brown vitreous solid (12.6 g).

Step 6: Preparation of methyl 6-bromo-7-fluoro-3-{3-methoxy-3-oxo-1-[2-(trifluoromethoxy)phenyl]propyl}imidazo[1,2-a]pyridine-2-carboxylate To MeOH (170 mL), whilst stirring and cooling in an ice-water-bath, SOCl$_2$ (64.3 g, 0.54 mol, 2.1 eq) was added drop wise and the mixture was stirred at 0° C. for 30 minutes. To the resulting solution of HCl in MeOH was added a solution of 6-bromo-3-{2-carboxy-1-[2-(trifluoromethoxy)phenyl]ethyl}-7-fluoroimidazo [1,2-a]pyridine-2-carboxylic acid (12.6 g, 25.7 mmol, 1 eq) in a small amount of MeOH. The solution was placed into a glass high-pressure-vessel and stirred at 50-60° C. for 16 h. After cooling to r.t., the reaction mixture was concentrated in vacuo and the residue re-evaporated with benzene (3×100 mL). The residue was dissolved in CHCl$_3$ (450 mL); washed with 10% aq. KHCO$_3$ (2×200 mL), dried over sodium sulfate, filtered, and concentrated in-vacuo. The residue was purified by column chromatography (SiO$_2$, 0-5% EtOAc in CHCl$_3$), yielding the title compound as a light-yellow solid (6.21 g, 31% over 4 steps). $^1$H NMR (400 MHz, DMSO-d$_6$) δ 9.01 (d, J 6.6 Hz, 1H), 7.76-7.78 (m, 1H), 7.72 (d, J 9.0 Hz, 1H), 7.36-7.43 (m, 2H), 7.20-7.23 (m, 1H), 5.69 (t, J 19.6 Hz, 1H), 3.71 (s, 3H), 3.51-3.57 (m, 2H), 3.51 (s, 3H). LCMS (ES+) RT 1.90 min, 519.0/521.0 (M+H)+.

Step 7: Preparation of 7-Bromo-6-fluoro-3-oxo-1-(2-trifluoromethoxy-phenyl)-2,3-dihydro-1H-cyclopenta[4,5]imidazo[1,2-a]pyridine-2-carboxylic acid methyl ester

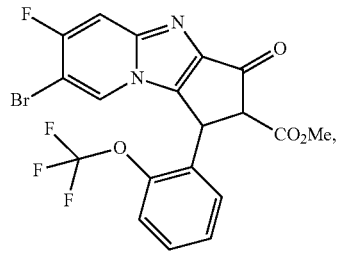 [SMILES: COC(=O)C1C(=O)c2nc3cc(F)c(Br)cn3c2C1c1ccccc1OC(F)(F)F]

At −10° C., a solution of potassium tert-pentoxide (11.0 mL of 25% in toluene, 18.8 mmol, 1.6 eq) was slowly added drop wise to a solution of methyl 6-bromo-7-fluoro-3-{3-methoxy-3-oxo-1-[2-(trifluoromethoxy)phenyl]propyl}imidazo[1,2-a]pyridine-2-carboxylate (6.20 g, 11.9 mmol, 1 eq) in toluene (700 mL). The reaction mixture was stirred at −10° C. for 30 minutes, quenched by addition of AcOH (1.5 mL), and warmed up to r.t. The organic layer was separated, washed with 10% aq. KHCO$_3$ (100 mL) and the solvents evaporated. The residue was purified by flash column chromatography (SiO$_2$, 0-15% EtOAc in CHCl$_3$), yielding the title compound as a light-yellow solid (3.30 g, 62%). $^1$H NMR (400 MHz, DMSO-d$_6$) δ 8.61 (d, J 6.9 Hz, 1H), 7.93 (d, J 9.8 Hz, 1H), 7.42-7.52 (m, 2H), 7.25-7.33 (m, 1H), 6.95-7.05 (m, 1H), 5.42 (br. s, 1H), 3.94 (d, J 2.4 Hz, 1H), 3.72 (s, 3H). LCMS (ES+) RT 1.91 min, 487.0/489.0 (M+H)+.

Step 8: Preparation of 7-Bromo-6-fluoro-1-(2-trifluoromethoxy-phenyl)-1,2-dihydro-cyclopenta[4,5]imidazo[1,2-a]pyridin-3-one

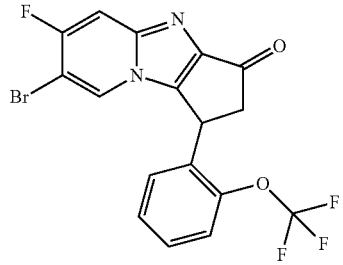 [SMILES: O=C1CC(c2ccccc2OC(F)(F)F)c2c1nc1cc(F)c(Br)cn21]

A solution of 7-bromo-6-fluoro-3-oxo-1-(2-trifluoromethoxy-phenyl)-2,3-dihydro-1H-cyclopenta[4,5]imidazo[1,2-a]pyridine-2-carboxylic acid methyl ester (3.30 g, 6.78 mmol, 1 eq) in aq. HCl (60 mL, 6 M) was stirred at 100° C. for 1 h. After cooling to r.t., the solvent was evaporated in vacuo. The residue was partitioned between EtOAc (300 mL) and 10% aq. KHCO$_3$ (100 mL). The organic layer was washed with brine (150 mL), dried over magnesium sulfate, filtered through a short pad of SiO$_2$, and concentrated in vacuo yielding to the title compound as a white solid (2.32 g, 80%). $^1$H NMR (400 MHz, DMSO-d$_6$) δ 8.53 (d, J 6.6 Hz, 1H) 7.88 (d, J 9.8 Hz, 1H), 7.40-7.50 (m, 2H), 7.25-7.35 (m, 1H), 6.95-7.05 (m, 1H), 5.15 (dd, J$_1$ 7.1 Hz, J$_2$ 1.9 Hz, 1H), 3.62 (dd, J$_1$ 18.0 Hz, J$_2$ 7.1 Hz, 1H), 2.70 (dd, J$_1$ 18.0, Hz, J$_2$ 1.9 Hz, 1H) LCMS (ES+) RT 1.91 min, 429.0/431.0 (M+H)+.

Step 9: Preparation of (R)-7-Bromo-6-fluoro-1-(2-trifluoromethoxy-phenyl)-1,2-dihydro-cyclopenta[4,5]imidazo[1,2-a]pyridin-3-one and (S)-7-Bromo-6-fluoro-1-(2-trifluoromethoxy-phenyl)-1,2-dihydro-cyclopenta[4,5]imidazo[1,2-a]pyridin-3-one

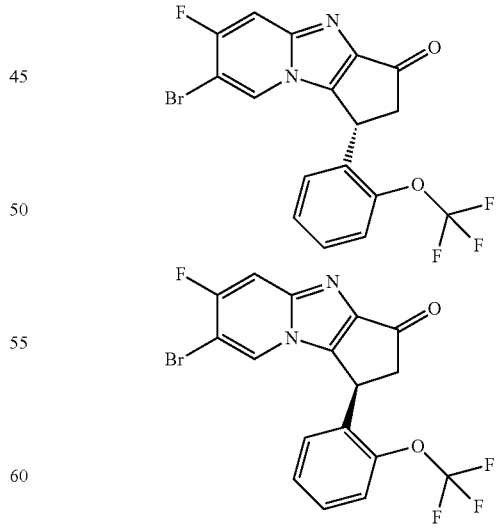

The title compounds were isolated by chiral purification of Intermediate 13 under SFC conditions on Lux-Cell-4 (50*291 mm*mm, flow 360 mL/min, 25° C., MeOH 30%->10 min MeOH 50%->14 min, injection of 10 mL solution at a concentration of 30 g/L). The first eluting enantiomer (RT 7.5 min) was collected and the fractions were evaporated to yield 335 mg of Intermediate 14. The second eluting enantiomer (RT 12.9 min) was collected and the fractions were evaporated to yield 357 mg of Intermediate 15.

Intermediate 16 and 17

(1R)-7-bromo-1-(2-chlorophenyl)-6-fluoro-1,2-dihydro-3H-cyclopenta[4,5]imidazo[1,2-a]pyridin-3-one or (1S)-7-bromo-1-(2-chlorophenyl)-6-fluoro-1,2-dihydro-3H-cyclopenta[4,5]imidazo[1,2-a]pyridin-3-one

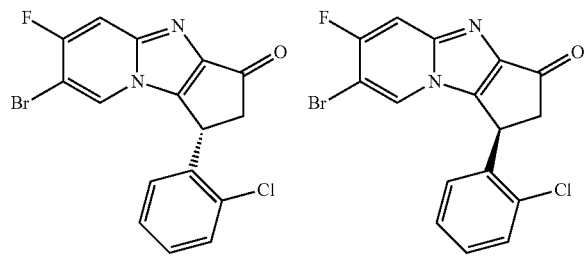

7-bromo-1-(2-chlorophenyl)-6-fluoro-1,2-dihydro-3H-cyclopenta[4,5]imidazo[1,2-a]pyridin-3-one was prepared from ethyl 6-bromo-7-fluoro-3-formyl-imidazo[1,2-a]pyridine-2-carboxylate (30.0 g, 95.0 mmol, 1 eq) and 2-chlorophenyl magnesium chloride (117 mmol, 1.2 eq) by the step wise procedure described for Intermediate 7 (3.70 g, 7.1% overall yield over 6 steps).

The title compounds were isolated by chiral purification of 7-bromo-1-(2-chlorophenyl)-6-fluoro-1,2-dihydro-3H-cyclopenta [4,5]imidazo[1,2-a]pyridin-3-one under SFC conditions on Whelko-O1 (R,R) (50*227 mm*mm, flow 360 mL/min, 25° C., CO₂+20% i-PrOH, injection of 18 mL solution at a concentration of 7.35 g/L). The first eluting enantiomer (RT 10.4 min) was collected and the fractions were evaporated to yield Intermediate 16. The second eluting enantiomer (RT 12.8 min) was collected and the fractions were evaporated to yield Intermediate 17. $^1$H NMR (400 MHz, DMSO-d$_6$) δ 8.67 (d, J 6.4 Hz, 1H), 7.90 (d, J 9.9 Hz, 1H), 7.56 (d, J 7.3 Hz, 1H), 7.34 (td, J 7.7 Hz, J 1.5 Hz, 1H), 7.22 (t, J 7.3 Hz, 1H), 6.71 (br. s, 1H), 5.21 (dd, J 7.1 Hz, J 2.0 Hz, 1H), 3.71 (dd, J 18.2 Hz, J 7.2 Hz, 1H), 2.65 (d, J 18.1 Hz, 1H). LCMS (ES+) RT 1.83 min, 379.0/381.0 (M+H)⁺.

Intermediate 18

(R)-7-Bromo-1-(2-chloro-phenyl)-6-fluoro-2,3-dihydro-1H-cyclopenta[4,5]imidazo[1,2-a]pyridin-3-ol

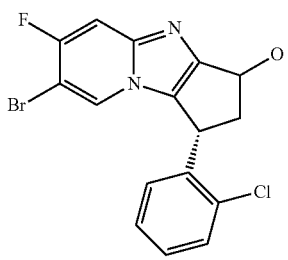

The title compound was prepared from Intermediate 16 (250 mg, 0.659 mmol, 1 eq.) and sodium borohydride (25.2 mg, 0.659 mmol 1 eq.) by the Method C (250 mg, 99%). The ratio of cis/trans isomers were 85/15 based on UV LCMS. LCMS (ES⁺) RT 4.56 and 4.64 min, 381.1/383.1 (M+H)⁺

Intermediate 19

(S)-7-Bromo-1-(2-chloro-phenyl)-6-fluoro-2,3-dihydro-1H-cyclopenta[4,5]imidazo[1,2-a]pyridin-3-ol

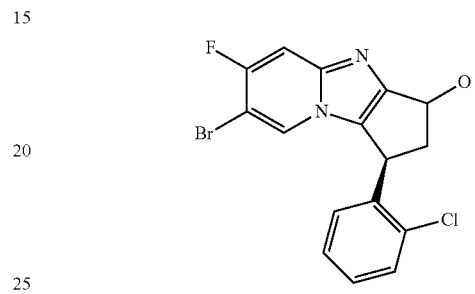

The title compound was prepared from Intermediate 17 (250 mg, 0.659 mmol, 1 eq.) and sodium borohydride (25.2 mg, 0.659 mmol 1 eq.) by the Method C (250 mg, 99%). The ratio of cis/trans isomers were 85/15 based on UV LCMS. LCMS (ES⁺) RT 4.56 and 4.64 min, 381.1/383.1 (M+H)⁺

Intermediate 20

Method D (R)-7-Bromo-1-(2-chloro-phenyl)-3,6-difluoro-2,3-dihydro-1H-cyclopenta[4,5]imidazo[1,2-a]pyridine

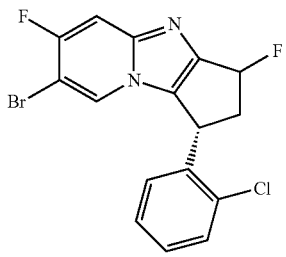 [SMILES: OC1C[C@H](c2ccccc2Cl)c2c1nc1cc(F)c(Br)cn21]

Intermediate 18 (250 mg, 655 mmol, 1 eq) was suspended in 5 ml of DCM, and at −30° C., diethylaminosulfur trifluoride (127 mg, 0.788 mmol, 1.2 eq) was added drop wise. The reaction mixture was stirred at −30° C. for 30 minutes before careful addition of a sat. solution of sodium bicarbonate (10 mL). At r.t. the crude mixture was extracted with DCM (2×30 mL). The organic layers were dried over magnesium sulfate and concentrated in vacuo. The residue was purified by flash column chromatography (SiO₂, 100% EtOAc), yielding the title compound as a colorless oil (147 mg, 67%). LCMS (ES⁺) RT 5.12 and 5.14 min, 383.1/385.1 (M+H)⁺

Intermediates 21 and 22

(1R,3R)-7-bromo-1-(2-chlorophenyl)-3,6-difluoro-2,3-dihydro-1H-cyclopenta[4,5]imidazo[1,2-a]pyridine and (1R,3S)-7-bromo-1-(2-chlorophenyl)-3,6-difluoro-2,3-dihydro-1H-cyclopenta[4,5]imidazo[1,2-a]pyridine

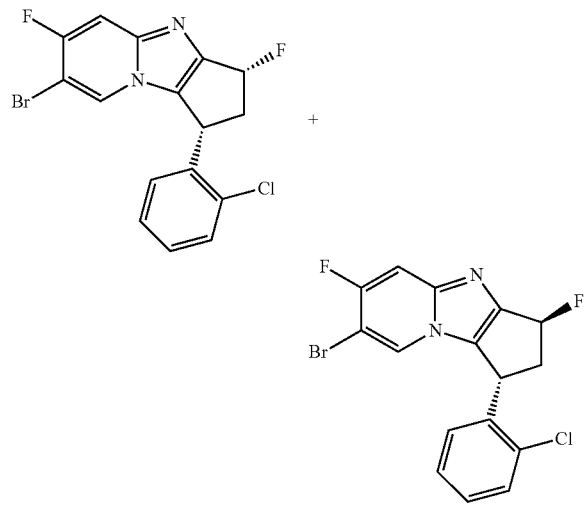

The title compounds were isolated by chiral purification of Intermediate 20 under SFC conditions on Whelko-O1 (R,R) (50*227 mm*mm, flow 360 mL/min, 25° C., CO$_2$+ 20% i-PrOH, injection of 18 mL solution at a concentration of 7.35 g/L). The first eluting enantiomer (RT 10.4 min) was collected and the fractions were evaporated to yield 50 mg of (1R,3R)-7-bromo-1-(2-chlorophenyl)-3,6-difluoro-2,3-dihydro-1H-cyclopenta[4,5]imidazo[1,2-a]pyridine. The second eluting enantiomer (RT 12.8 min) was collected and the fractions were evaporated to yield 48 mg of (1R,3S)-7-bromo-1-(2-chlorophenyl)-3,6-difluoro-2,3-dihydro-1H-cyclopenta[4,5]imidazo[1,2-a]pyridine.

Intermediate 23

(S)-7-Bromo-1-(2-chloro-phenyl)-3,6-difluoro-2,3-dihydro-1H-cyclopenta[4,5]imidazo[1,2-a]pyridine

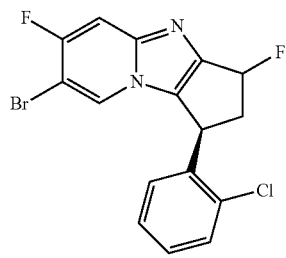 [SMILES: OC1C[C@@H](c2ccccc2Cl)c2c1nc1cc(F)c(Br)cn21]

The title compound was prepared from Intermediate 19 (250 mg, 655 mmol, 1 eq) and diethylaminosulfur trifluoride (127 mg, 0.788 mmol, 1.2 eq) by the Method D (255 mg, 99%). LCMS (ES$^+$) RT 5.10 and 5.12 min, 383.1/385.1 (M+H)'

Intermediate 24 and 25

(1S,3R)-7-bromo-1-(2-chlorophenyl)-3,6-difluoro-2,3-dihydro-1H-cyclopenta[4,5]imidazo[1,2-a]pyridine and (1S,3S)-7-bromo-1-(2-chlorophenyl)-3,6-difluoro-2,3-dihydro-1H-cyclopenta[4,5]imidazo[1,2-a]pyridine

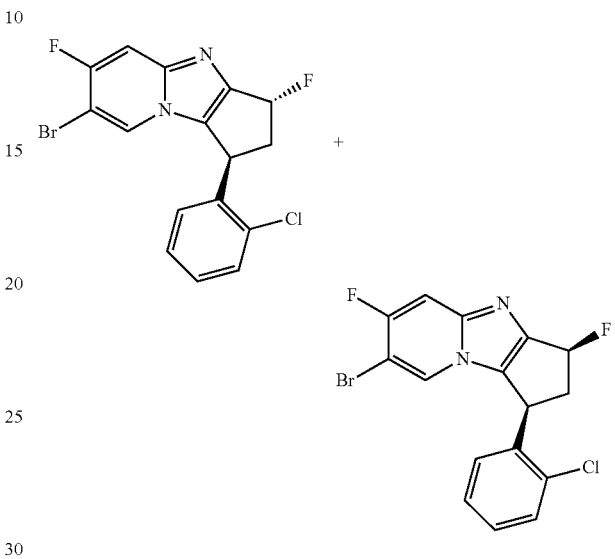

The title compounds were isolated by chiral purification of Intermediate 23 under SFC conditions on Whelko-O1 (R,R) (50*227 mm*mm, flow 360 mL/min, 25° C., CO$_2$+ 20% i$^-$PrOH, injection of 18 mL solution at a concentration of 6.4 g/L). The first eluting enantiomer (RT 9 min) was collected and the fractions were evaporated to yield 45 mg of (1S,3R)-7-bromo-1-(2-chlorophenyl)-3,6-difluoro-2,3-dihydro-1H-cyclopenta[4,5]imidazo[1,2-a]pyridine. The second eluting enantiomer (RT 17 min) was collected and the fractions were evaporated to yield 37 mg of (1S,3S)-7-bromo-1-(2-chlorophenyl)-3,6-difluoro-2,3-dihydro-1H-cyclopenta[4,5]imidazo [1,2-a]pyridine.

Intermediate 26

(1R,3S)-7-Bromo-1-(2-difluoromethoxy-phenyl)-6-fluoro-2,3-dihydro-1H-cyclopenta[4,5]imidazo[1,2-a]pyridin-3-ol

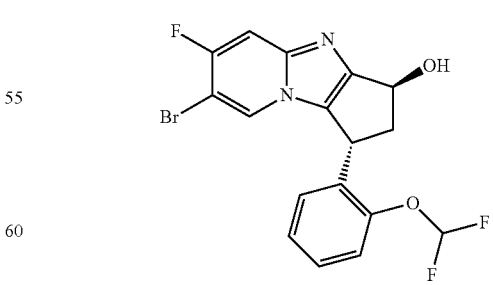

The title compound was prepared from Example 13 (4.64 g, 11.3 mmol, 1 eq.) and sodium borohydride (0.431 g, 1 eq.) by the Method C to yield 7-Bromo-1-(2-difluoromethoxy-phenyl)-6-fluoro-2,3-dihydro-1H-cyclopenta[4,5]imidazo

[1,2-a]pyridin-3-ol. The title compounds were isolated by chiral purification of 7-Bromo-1-(2-difluoromethoxy-phenyl)-6-fluoro-2,3-dihydro-1H-cyclopenta[4,5]imidazo[1,2-a]pyridin-3-ol under SFC conditions on Lux-Cell-4 (50*291 mm*mm, flow 360 mL/min, 25° C., $CO_2$+20% MeOH, injection of 6.8 mL solution at a concentration of 100 g/L). The first eluting diastereomer (RT 4.61 min) was collected and the fractions were evaporated to yield (1R,3R)-7-Bromo-1-(2-difluoromethoxy-phenyl)-6-fluoro-2,3-dihydro-1H-cyclopenta[4,5]imidazo[1,2-a]pyridin-3-ol (2.08 g, 44.6%). LCMS (ES$^+$) RT 4.02 min, 413.0/415.0 (M+H)$^+$. The second eluting diastereomer (RT 8.74 min) was collected and the fractions were evaporated to yield the title compound (0.425 g, 9.1%). LCMS (ES$^+$) RT 3.98 min, 413.0/415.0 (M+H)$^+$.

Intermediate 27

(1R,3R)-3-Azido-7-bromo-1-(2-difluoromethoxy-phenyl)-6-fluoro-2,3-dihydro-1H-cyclopenta[4,5]imidazo[1,2-a]pyridine

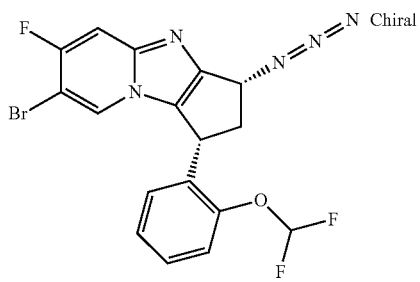

Intermediate 26 (0.100 g, 1.0 eq) was dissolved in 0.5 mL of toluene. At 0° C., diphenylphosphorylazide (1.3 eq.) was added drop wise followed by 1,8-diazabicyclo[5.4.0]undec-7-ene (1.4 eq.). The reaction mixture is stirred at 0° C. for 1 h and at r.t. for 16 h. The mixture was taken up in EtOAc and washed with water. The organic phase was dried over sodium sulfate and concentrated in vacuo to afford 110 mg (100%) of the title compound as a brown oil which was used in the next step without further purification. LCMS (ES$^+$) RT 5.12 min, 438.0/440.0 (M+H)$^+$.

Intermediate 28

(1R,3R)-7-Bromo-1-(2-difluoromethoxy-phenyl)-6-fluoro-2,3-dihydro-1H-cyclopenta[4,5]imidazo [1,2-a]pyridin-3-ylamine

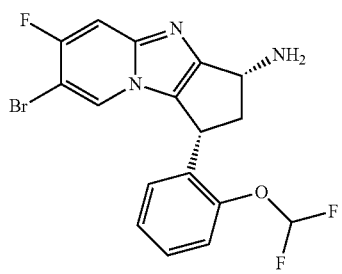 [SMILES: N[C@@H]1C[C@H](c2ccccc2OC(F)F)c2c1nc1cc(F)c(Br)cn21]

Intermediate 27 (110 mg, 1.0 eq.) was dissolved in 1.5 mL of a (2:1) mixture of toluene:water. Triphenylphosphine resin (1.5 eq., 3 mmol/g) was added and the reaction mixture was stirred for 48 h at r.t. The mixture was filtered, washed with EtOAc and extracted with 1N HCl. The aq. phase was neutralized with a sat. aq. sodium bicarbonate solution, extracted with EtOAc, dried over magnesium sulfate and concentrated in vacuo to afford 30 mg (29%) of the title compound which was used in the next step without further purification. LCMS (ES$^+$) RT 3.40 min, 412.0/414.0 (M+H)$^+$.

Intermediate 29

Method E (2-thiomorpholinopyrimidin-5-yl)boronic acid 2-chloropyrimidine-5-boronic acid (52.3 mmol, 8.53 g), thiomorpholine (52.3 mmol, 5.3 ml) and TEA (52.3 mmol, 7.3 ml) were dissolved in EtOH (100 ml) and heated at 80° C. for 4 h. The solvent was removed in vacuo and the resulting solid triturated with Et$_2$O yielding the title compound (8.64 g, 74%). $\delta_H$ (300 MHz, DMSO-d$_6$) 8.63 (s, 2H); 8.06 (s, 2H); 4.08 (m, 4H); 2.59 (m, 4H). LCMS (ES$^+$) RT 0.21 min 226.8 (M+H)$^+$.

Intermediate 30

[2-[(1R,5S)-7-oxo-3,6-diazabicyclo[3.2.2]nonan-3-yl]pyrimidin-5-yl]boronic acid; triethylammonium chloride The title compound was prepared from 2-chloropyrimidine-5-boronic acid (1.13 g, 7.14 mmol) and (1S,5R)-3,6-diazabicyclo[3.2.2]nonan-7-one (1.00 g, 7.13 mmol) by the Method E (2.70 g, 94.7%). This material was used crude in subsequent coupling reactions without the need for removal or separation of the associated TEA salt. $\delta_H$ (300 MHz, DMSO-d$_6$) 8.62 (s, 2H), 8.35 (d, 1H, J 4.7 Hz, NH), 8.08 (s, 2H), 4.88-4.75 (m, 2H). 3.63 (m, 1H), 3.43 (m, 1H), 3.25-3.10 (m, 1H), 3.05 (q, 6H, J 7.1 Hz, TEA), 2.57 (m, 1H), 1.75-1.55 (m, 4H), 1.18 (t, 9H, J 7.1 Hz, triethylamine).

Intermediate 31

4-[5-(4,4,5,5-tetramethyl-1,3,2-dioxaborolan-2-yl)pyrimidin-2-yl]piperazin-2-one The title compound was prepared from 2-chloro-5-(tetramethyl-1,3,2-dioxaborolan-2-yl)pyrimidine (3.5 g, 14.5 mmol) and piperazin-2-one (1.6 g, 16.0 mmol) by the Method E (2.0 g, 45%). $\delta_H$ (250 MHz, CDCl$_3$) 8.57 (s, 2H), 6.64 (s, 1H), 4.42 (s, 2H), 4.05 (s, 2H), 3.40 (s, 2H), 1.26 (s, 12H). LCMS (ES$^+$) RT 1.12 min, 305.0 (M+H)$^+$.

Intermediate 32

(1S,4S)-5-[5-(4,4,5,5-tetramethyl-1,3,2-dioxaborolan-2-yl)pyrimidin-2-yl]-2-oxa-5-azabicyclo[2.2.1]heptane The title compound was prepared from (1S,4S)-2-oxa-5-azabicyclo[2.2.1]heptane hydrochloride (1:1) (406 mg, 2.99 mmol) and 2-chloro-5-(tetramethyl-1,3,2-dioxaborolan-2-yl)pyrimidine (650 mg, 2.70 mmol) by the Method E (580 mg, 70%). $^1$H NMR (500 MHz, CDCl$_3$) δ ppm 8.59 (s, 2H), 5.11 (s, 1H), 4.71 (s, 1H), 3.92-3.83 (m, 2H), 3.66-3.53 (m, 2H), 2.02-1.89 (m, 2H), 1.32 (s, 12H).

Intermediate 33

Method F

4-(5-bromopyrimidin-2-yl)tetrahydropyran-4-ol

5-Bromo-2-iodopyrimidine (2 g, 7.02 mmol) was dissolved in dry toluene (30 mL) and cooled to −78° C. under nitrogen. A 2.5M solution of n-BuLi in hexane (2.95 mL) was added drop wise and the reaction stirred for 15 minutes prior to the drop wise addition of tetrahydro-4H-pyran-4-one (0.77 g, 7.72 mmol). The reaction was stirred at −78° C. for 30 min and then was allowed to warm to r.t. The reaction mixture was diluted with water (50 mL) and extracted with EtOAc (2×50 mL). The combined organic extracts were dried over magnesium sulfate and the solvent removed under reduced pressure to afford 1.91 g of crude product as an orange oil. The crude orange oil was purified by flash column chromatography ($SiO_2$, 10-100% EtOAc in heptane) to afford 762 mg (42%) of the title compound as a yellow oil. $^1H$ NMR (500 MHz, $CDCl_3$) δ ppm 8.79 (s, 2H), 4.24 (s, 1H), 3.99-3.89 (m, 4H), 2.37 (td, J 12.3, 11.6, 6.3 Hz, 2H), 1.54 (dd, J 13.6, 2.0 Hz, 2H).

Intermediate 34

Method G

[4-(5-bromopyrimidin-2-yl)tetrahydropyran-4-yl]oxy-trimethyl-silane

Trimethylsilyl chloride (277 mg, 2.55 mmol) was added to a stirred solution of Intermediate 33 (85%, 740 mg, 2.43 mmol) and imidazole (198 mg, 2.91 mmol) in DCM (15 mL) and the reaction was stirred for 1 h. Additional trimethylsilyl chloride (66 mg, 0.61 mmol) and imidazole (40 mg, 0.61 mmol) were added and the mixture was stirred for 1 h. The reaction was washed with water (2×15 mL) and the aq. phase re-extracted with DCM (20 mL). The combined organic extracts were dried over magnesium sulfate and concentrated under reduced pressure, the resulting yellow oil was purified by flash column chromatography ($SiO_2$, 0-15% EtOAc in heptane) to afford 623 mg (77%) of the title compound as a yellow oil, which crystallised upon standing. $^1H$ NMR (500 MHz, $CDCl_3$) δ ppm 8.80 (s, 2H), 3.90 (td, J 11.0, 2.5 Hz, 2H), 3.74 (dt, J 11.4, 4.1 Hz, 2H), 2.26 (ddd, J 14.1, 10.4, 4.4 Hz, 2H), 1.99 (dt, J 11.6, 2.1 Hz, 2H), 0.00 (s, 9H).

Intermediate 35

Method H

Trimethyl-[4-[5-(4,4,5,5-tetramethyl-1,3,2-dioxaborolan-2-yl)pyrimidin-2-yl]tetrahydropyran-4-yl]oxy-silane A solution of Intermediate 34 (623 mg, 1.88 mmol) in 1,4-dioxane (25 mL) was treated with bis-pinacolatodiboron (573 mg, 2.26 mmol) and potassium acetate (0.35 mL, 5.64 mmol). The mixture was degassed with nitrogen for 10 minutes prior to addition of Pd(dppf)$Cl_2$ DCM adduct (77 mg, 0.09 mmol) and then stirred at 80° C. for 1 h. The reaction was concentrated, redissolved in EtOAc (30 mL) and washed with a 10% w/v citric acid solution in water (30 mL). The organic phase was dried over magnesium sulfate and the solvent removed under reduced pressure. The resulting crude brown oil was purified by flash column chromatography ($SiO_2$, 10-40% EtOAc in heptane). The relevant fractions were combined to afford 228 mg (25%) of the title compound as a yellow oil that crystallised upon standing. $^1H$ NMR (500 MHz, $CDCl_3$) δ ppm 9.01 (s, 2H), 3.91 (t, J 9.9 Hz, 2H), 3.79-3.69 (m, 2H), 2.38-2.23 (m, 2H), 1.98 (d, J 13.2 Hz, 2H), 1.36 (s, 12H), 0.00 (s, 9H).

Intermediate 36 and 37

The following Intermediates were prepared by the Method E from 2-chloro-5-(tetramethyl-1,3,2-dioxaborolan-2-yl)pyrimidine using the appropriate amine

| Intermediate No. | Compound Name | $^1H$ NMR/LCMS |
|---|---|---|
| 36 | (1R,5S)-8-[5-(4,4,5,5-tetramethyl-1,3,2-dioxaborolan-2-yl)pyrimidin-2-yl]-3-oxa-8-azabicyclo[3.2.1]octane | $^1H$ NMR (500 MHz, $CDCl_3$) δ ppm 8.53 (s, 2H), 4.67 (s, 2H), 3.69 (d, J 10.8 Hz, 2H), 3.57 (d, J 10.7 Hz, 2H), 2.03 (d, J 7.0 Hz, 2H), 1.93 (d, J 4.7 Hz, 2H), 1.25 (s, 12H). LCMS (ES+) RT 1.37 min, 318.0 (M + H)+. |
| 37 | (1R,3R,6R,7R)-2-[5-(Tetramethyl-1,3,2-dioxaborolan-2-yl)pyrimidin-2-yl]-5,8-dioxa-2-azatricyclo[4.3.0.03,7}]nonane | LCMS (ES+) RT 1.17 min, 332.0 (M + H)+. |

Intermediate 38 to 43

The following Intermediates were prepared by the Method F from 5-Bromo-2-iodopyrimidine using the appropriate substituted ketone.

| Intermediate No. | Ketone | Compound Name | $^1H$ NMR/LCMS |
|---|---|---|---|
| 38 | cyclobutanone | 1-(5-bromopyrimidin-2-yl)cyclobutanol | $^1H$ NMR (500 MHz, MeOD-$d_4$) δ ppm 8.80 (s, 2H), 2.57 (dddd, J 11.2, 5.2, 4.4, 2.5 Hz, 2H), 2.32-2.23 (m, 2H), 1.93-1.76 (m, 2H). LCMS (ES+) RT 1.06 min, 229.0/231.0 (M + H)+. |
| 39 | oxetan-3-one | 3-(5-bromopyrimidin-2-yl)oxetan-3-ol | $^1H$ NMR (500 MHz, DMSO-$d_6$) δ ppm 9.07 (s, 2H), 6.43 (s, 1H), 4.94 (d, J 6.5 Hz, 2H), 4.67 (d, J 6.5 Hz, 2H). |
| 40 | tert-butyl 3-oxoazetidine-1-carboxylate | tert-butyl 3-(5-bromopyrimidin-2-yl)-3-hydroxy-azetidine-1-carboxylate | $^1H$ NMR (500 MHz, $CDCl_3$) δ ppm 8.84 (s, 2H), 4.91 (s, 1H), 4.35 (d, J 9.0 Hz, 2H), 4.22 (d, J 9.1 Hz, 2H), 1.48 (s, 9H) |

| Intermediate No. | Ketone | Compound Name | $^1$H NMR/LCMS |
|---|---|---|---|
| 41 | 1-methyl-piperidin-4-one | 4-(5-bromopyrimidin-2-yl)-1-methyl-piperidin-4-ol | LCMS (ES$^+$) RT 1.20 min, 272.0/274.0 (M + H)$^+$. |
| 42 | tetrahydro-thiopyran-4-one | 4-(5-bromopyrimidin-2-yl)tetrahydrothiopyran-4-ol | $^1$H NMR (500 MHz, CDCl$_3$) δ ppm 8.78 (s, 2H), 4.19 (s, 1H), 3.23 (td, J 13.6, 2.4 Hz, 2H), 2.56-2.47 (m, 2H), 2.35 (td, J 13.2, 3.7 Hz, 2H), 1.88 (d, J 13.5 Hz, 2H). |
| 43 | tetrahydro-furan-3-one | 3-(5-bromopyrimidin-2-yl)tetrahydrofuran-3-ol | $^1$H NMR (500 MHz, DMSO-d$_6$) δ 9.01 (s, 2H), 5.66 (s, 1H), 3.99-3.93 (m, 2H), 3.88-3.77 (m, 2H), 2.46 (dt, J 12.6, 8.9 Hz, 1H), 2.16 (ddd, J 12.6, 6.4, 3.5 Hz, 1H). |

Intermediates 44-48

The following Intermediates were prepared by the Method G. from the corresponding precursor Intermediate 38 to 43.

| Intermediate No. | Starting Material | Compound Name | $^1$H NMR/LCMS |
|---|---|---|---|
| 44 | Int 38 | [1-(5-bromopyrimidin-2-yl)cyclobutoxy]-trimethyl-silane | $^1$H NMR (500 MHz, MeOD-d$_4$) δ ppm 8.91 (s, 2H), 2.76 (tt, J 8.6, 3.1 Hz, 2H), 2.43 (qd, J 9.6, 2.7 Hz, 2H), 1.85 (tdd, J 13.1, 6.7, 3.3 Hz, 1H), 1.69-1.55 (m, 1H), −0.02 (s, 9H). |
| 45 | Int 39 | [3-(5-bromopyrimidin-2-yl)oxetan-3-yl]oxy-trimethyl-silane | $^1$H NMR (250 MHz, DMSO-d$_6$) δ ppm 9.11 (s, 2H), 4.97 (d, J 7.0 Hz, 2H), 4.75 (d, J 7.0 Hz, 2H), −0.05 (s, 9H). |
| 46 | Int 40 | tert-butyl 3-(5-bromo-pyrimidin-2-yl)-3-trimethylsilyloxy-azetidine-1-carboxylate | $^1$H NMR (500 MHz, CDCl$_3$) δ ppm 8.82 (s, 2H), 4.48 (d, J 9.5 Hz, 2H), 4.17 (d, J 9.5 Hz, 2H), 1.45 (s, 9H), 0.05 (s, 9H). |
| 47 | Int 41 | [4-(5-bromopyrimidin-2-yl)-1-methyl-4-piperidyl]oxy-trimethyl-silane | $^1$H NMR (250 MHz, CDCl$_3$) δ ppm 8.80 (s, 2H), 3.47 (d, J 13.4 Hz, 2H), 3.32-3.10 (m, 2H), 2.81 (d, J 4.9 Hz, 3H), 2.77-2.63 (m, 2H), 2.45 (d, J 13.7 Hz, 2H), −0.09 (d, J 1.7 Hz, 9H). |
| 48 | Int 43 | [3-(5-bromopyrimidin-2-yl)tetrahydrofuran-3-yl]oxy-trimethyl-silane | LCMS (ES+) RT 1.40 min, 317.0/319.0 (M + H)$^+$ |

Intermediates 49-53

The following Intermediates can be synthesised from the corresponding precursor Intermediates 44-48 by the Method H.

| Intermediate No. | Starting Material | Compound Name | $^1$H NMR/LCMS |
|---|---|---|---|
| 49 | Int 44 | trimethyl-[1-[5-(4,4,5,5-tetramethyl-1,3,2-dioxaborolan-2-yl)pyrimidin-2-yl]cyclobutoxy]silane | $^1$H NMR (500 MHz, CDCl$_3$) δ ppm 9.03 (s, 2H), 2.79 (tt, J 8.6, 3.2 Hz, 2H), 2.53-2.41 (m, 2H), 1.86 (dddd, J 13.2, 9.9, 6.7, 3.4 Hz, 1H), 1.70-1.60 (m, 1H), 1.36 (s, 12H), −0.03 (s, 9H). |
| 50 | Int 45 | trimethyl-[3-[5-(4,4,5,5-tetramethyl-1,3,2-dioxaborolan-2-yl)pyrimidin-2-yl]oxetan-3-yl]oxy-silane | $^1$H NMR (500 MHz, DMSO-d$_6$) δ ppm 9.00 (d, J 10.6 Hz, 2H), 5.00 (d, J 6.8 Hz, 2H), 4.75 (d, J 6.8 Hz, 2H), 1.33 (s, 12H), −0.06 (s, 9H) |
| 51 | Int 46 | tert-butyl 3-[5-(4,4,5,5-tetramethyl-1,3,2-dioxaborolan-2-yl)pyrimidin-2-yl]-3-trimethylsilyloxy-azetidine-1-carboxylate | $^1$H NMR (500 MHz, CDCl$_3$) δ ppm 9.04 (s, 2H), 4.52 (d, J 9.2 Hz, 2H), 4.17 (d, J 9.2 Hz, 2H), 1.45 (s, 9H), 1.36 (s, 12H), 0.02 (s, 9H). |
| 52 | Int 47 | trimethyl-[[1-methyl-4-[5-(4,4,5,5-tetramethyl-1,3,2-dioxaborolan-2-yl)pyrimidin-2-yl]-4-piperidyl]oxy]silane | $^1$H NMR (500 MHz, CDCl$_3$) δ ppm 9.00 (s, 2H), 2.60 (s, 4H), 2.35 (m, 5H), 2.13 (d, J 12.2 Hz, 2H), 1.36 (s, 12H), −0.07 (s, 9H). |

-continued

| Intermediate No. | Starting Material | Compound Name | $^1$H NMR/LCMS |
|---|---|---|---|
| 53 | Int 48 | trimethyl-[3-[5-(4,4,5,5-tetramethyl-1,3,2-dioxaborolan-2-yl)pyrimidin-2-yl]tetrahydrofuran-3-yl]oxy-silane | $^1$H NMR (500 MHz, CDCl$_3$) δ ppm 9.01 (s, 2H), 4.25 (d, J 9.1 Hz, 1H), 4.15 (td, J 8.4, 6.9 Hz, 1H), 4.12-4.05 (m, 2H), 2.72 (dt, J 12.7, 8.5 Hz, 1H), 2.37-2.30 (m, 1H), 1.36 (s, 12H), 0.01 (s, 9H). LCMS (ES$^+$) RT 1.58 min, 365.0 (M + H)$^+$. |

Intermediates 54

(R)-7-Bromo-1-(2-difluoromethoxy-phenyl)-6-fluoro-3-methylsulfanyl-2,3-dihydro-1H-cyclopenta[4,5]imidazo[1,2-a]pyridine

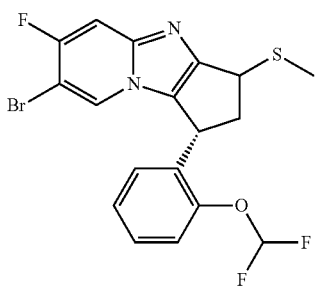 [SMILES: CSC1C[C@H](c2ccccc2OC(F)F)c2c1nc1cc(F)c(Br)cn21]

Example 19 (80 mg, 0.19 mmol) was dissolved in DCM (2 mL) under nitrogen. The mixture was then cooled to 0° C. and TEA (32 μL, 0.23 mmol) followed by methanesulfonyl chloride (18 μL, 0.32 mmol) was added. The reaction mixture was stirred at r.t. for 2 h. The mixture was cooled to 0° C., diluted with DCM (5 mL) and then water (5 mL) was added. The organic phase was washed with water (2×5 mL), dried over sodium sulfate and concentrated in vacuo to afford 95 mg of crude mesylate as a brown residue. The crude residue was dissolved in THF (1 mL) under nitrogen. The mixture was then cooled to 0° C. and sodium thiomethoxide (27 mg, 0.39 mmol) was added. The reaction mixture was allowed to warm to r.t. and stirred for 24 h. 15-Crown-5 (42 mg, 0.19 mmol) was added to the reaction mixture and stirred at r.t. for 24 h. Further sodium thiomethoxide (27 mg, 0.39 mmol) was added and the reaction mixture stirred at 50° C. for 5 h. The mixture was diluted with water (2 mL) and extracted with EtOAc (3×3 mL). The combined organic phase was washed with brine (5 mL), dried over sodium sulfate and concentrated in vacuo. The residue was purified by flash column chromatography (SiO$_2$, 0-100% EtOAc in heptane), to afford 46 mg (47%) of the title compound as a pale orange oil. LCMS (ES+) RT 1.99 min, 443.0/445.0 (M+H)$^+$.

Intermediate 55

2-{5-[(R)-1-(2-Difluoromethoxy-phenyl)-6-fluoro-3-methylsulfanyl-2,3-dihydro-1H-cyclopenta[4,5]imidazo[1,2-a]pyridin-7-yl]-pyrimidin-2-yl}-propan-2-ol

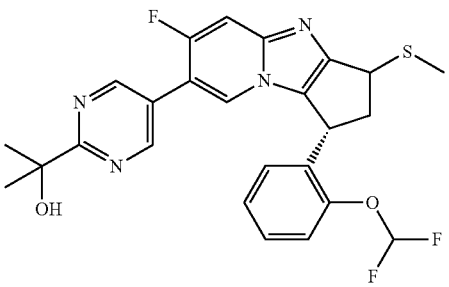 [SMILES: CSC1C[C@H](c2ccccc2OC(F)F)c2c1nc1cc(F)c(-c3cnc(C(C)(C)O)nc3)cn21]

The title compound was prepared from Intermediate 54 (45 mg, 0.10 mmol) and 2-pyrimidin-2-yl propan-2-ol boronate ester (40 mg, 0.15 mmol), by the Method A, (10 mg, 19%) of the title compound as a pale crystallising oil. LCMS (ES+) RT 1.81 min, 501.0 (M+H)$^+$.

Intermediate 56

4-(5-Bromopyridin-2-yl)oxan-4-ol

The title compound was prepared from 2,5dibromopyridine (5 g, 21.11 mmol) and tetrahydro-4H-pyran-4-one (2.92 mL, 0.03 mol) by the Method F (2.11 g, 39%). LCMS (ES+) RT 1.53 min, 258.0/260.0 (M+H)$^+$.

Intermediate 57

[4-(5-bromo-2-pyridyl)tetrahydropyran-4-yl]ox-trimethyl-silane

The title compound was prepared from Intermediate 56 (2.11 g, 8.17 mmol) and trimethylsilyl chloride (1.35 ml, 10.63 mmol) by the Method G (2.55 g, 91%). $^1$H NMR (500 MHz, CDCl$_3$) δ ppm 8.60 (d, J 2.0 Hz, 1H), 7.81 (dd, J 8.5, 2.4 Hz, 1H), 7.44-7.38 (m, 1H), 3.95-3.76 (m, 4H), 2.18 (ddd, J 14.7, 11.0, 4.8 Hz, 2H), 1.89 (dd, J 14.2, 2.5 Hz, 2H), 0.00 (s, 9H).

Intermediate 58

Trimethyl-[4-[5-(4,4,5,5-tetramethyl-1,3,2-dioxaborolan-2-yl)-2-pyridyl]tetrahydropyran-4-yl]oxy-silane The title compound was prepared from Intermediate 57 (1 g, 3.03 mmol) and 4,4,4',4',5,5,5',5'-octamethyl-2,2'-bi-1,3,2-dioxaborolane (923 mg, 3.63 mmol) by the Method H, (1.78 g, quantitative yield). $^1$H NMR (500 MHz, CDCl$_3$) δ 8.89 (s, 1H), 8.05 (dd, J 7.9, 1.5 Hz, 1H), 7.48 (d, J 7.9 Hz, 1H), 3.90 (td, J 11.1, 2.2 Hz, 2H), 3.82 (dt, J 11.3, 4.0 Hz, 2H), 2.22 (ddd, J 15.1, 11.3, 4.7 Hz, 2H), 1.91 (d, J 11.9 Hz, 2H), 1.35 (s, 12H), 0.00 (s, 9H).

Intermediate 59

4-(5-bromopyrimidin-2-yl)-1,1-dioxo-thian-4-ol

Sodium periodate (10.53 g, 49.23 mmol) was added to a solution of Intermediate 42 (3.46 g, 12.31 mmol) in a mixture of water (54 mL) and MeOH (40 mL) at 0° C. The reaction mixture was stirred and warmed progressively for 3 h before being heated at 70° C. for 18 h. The reaction mixture was allowed to cool to r.t., diluted with water (50 mL) and extracted using EtOAc (3×50 mL). The combined organic extracts were washed with water (20 mL), dried over sodium sulfate and concentrated in vacuo to give a bright yellow solid which was suspended in hot EtOAc (5 mL) and then diluted with heptane (15 mL). The mixture was left standing for 15 minutes and the resulting solid was filtered and concentrated in vacuo to afford 2.54 g (67%) of the title compound as an off-white solid. $^1$H NMR (500 MHz, CDCl$_3$) δ ppm 8.82 (s, 2H), 4.48 (s, 1H), 3.60 (td, J 13.9, 3.6 Hz, 2H), 3.10-2.97 (m, 2H), 2.89 (td, J 14.2, 3.5 Hz, 2H), 2.08-1.99 (m, 2H).

Intermediate 60

[4-(5-bromopyrimidin-2-yl)-1,1-dioxo-thian-4-yl]oxytrimethyl-silane

The title compound was prepared from Intermediate 59 (2.54 g, 8.27 mmol) trimethyl silyl chloride (1.18 ml, 9.21 mmol) by the Method G (2.7 g, 86%). $^1$H NMR (500 MHz, CDCl$_3$) δ ppm 8.81 (s, 2H), 3.44 (td, J 13.5, 3.6 Hz, 2H), 3.04-2.90 (m, 2H), 2.75-2.53 (m, 4H), 0.00 (s, 9H). LCMS (ES+) RT 2.03 min, 379.0/381.0 (M+H)+.

Intermediate 61

[1,1-dioxo-4-[5-(4,4,5,5-tetramethyl-1,3,2-dioxaborolan-2-yl)pyrimidin-2-yl]thian-4-yl]oxy-trimethyl-silane The title compound was prepared from Intermediate 60 (2.7 g, 7.12 mmol) and bis(pinacolato)diboron (2.16 g, 8.51 mmol) by the Method H (1.93 g, 59%). $^1$H NMR (500 MHz, DMSO-d$_6$) δ 8.99 (s, 2H), 3.28-3.20 (m, 2H), 3.14-3.05 (m, 2H), 2.62-2.52 (m, 2H), 2.43-2.33 (m, 2H), 1.32 (s, 12H), 0.00 (s, 9H).

Intermediate 62

4-[5-(4,4,5,5-tetramethyl-1,3,2-dioxaborolan-2-yl)pyrimidin-2-yl]-1,4-thiazinane 1,1-dioxide The title compound was prepared from thiomorpholine dioxide (562 mg, 4.16 mmol) and 2-chloro-5-(tetramethyl-1,3,2-dioxaborolan-2-yl)pyrimidine (1 g, 4.16 mmol) by the Method E (1.38 g, 85%). $^1$H NMR (500 MHz, DMSO-d$_6$) δ 8.55 (s, 2H), 4.33-4.16 (m, 4H), 3.25-3.12 (m, 4H), 1.28 (s, 12H).

Intermediate 63

Tert-Butyl-cyclopent-3-en-1-yloxy-dimethyl-silane

Cyclopent-3-en-1-ol (10 g, 118.9 mmol) was dissolved in DMF (100 mL) at 0° C., then 1H-imidazole (17.29 mL, 261.5 mmol) was added followed by tert-butyl(chloro)dimethylsilane (21.5 g, 142.7 mmol) and warmed up to r.t. The mixture was stirred at r.t. for 14 h, diluted with EtOAc (300 mL) and washed with 5% LiCl (2×100 mL), brine (50 mL), dried over sodium sulfate, filtered, and concentrated under reduced pressure. The crude residue was purified by flash column chromatography (SiO$_2$, 0-10% EtOAc in hexanes) to afford 17.2 g (73%) of the title product as a colourless clear liquid. $^1$H NMR (250 MHz, CDCl$_3$) δ ppm 5.66 (s, 2H), 4.53 (tt, J 7.0, 3.6 Hz, 1H), 2.57 (dd, J 15.2, 6.8 Hz, 2H), 2.27 (dd, J 15.3, 3.6 Hz, 2H), 0.89 (s, 9H), 0.06 (s, 6H).

Intermediate 64

Ethyl 3-[tert-butyl(dimethyl)silyl]oxybicyclo[3.1.0]hexane-6-carboxylate 1-(2-Ethoxy-2-oxoethylidene)diazenium (6.07 mL, 48.4 mmol) in DCM (4 mL) was added slowly via syringe pump over 6 h to the stirred solution of Intermediate 63 (8 g, 40.3 mmol) and rhodium (II) acetate (178.24 mg, 0.4 mmol) in DCM (150 mL) under nitrogen at r.t. The mixture was stirred for 14 h at r.t. then filtered through celite and concentrated under reduced pressure to provide a light brown oil. The crude material was purified by flash column chromatography (SiO$_2$, 5-30% EtOAc in heptane) to afford 7.15 g (59%) of the title compound as a mixture of isomers (exo:endo; 2.5:1) as a colourless clear oil. $^1$H NMR (500 MHz, CDCl$_3$) δ ppm 4.12-4.03 (m, 2H), 2.13 (dd, J 13.0, 7.2 Hz, 1H), 2.05 (ddd, J 13.2, 5.8, 3.4 Hz, 1H), 1.88-1.69 (m, 4H), 1.51 (d, J 14.7 Hz, 1H), 1.28-1.19 (m, 4H), 0.88-0.82 (m, 9H), 0.04-0.03 (m, 6H).

Intermediate 65

Ethyl 3-hydroxybicyclo[3.1.0]hexane-6-carboxylate

1M TBAF (68.13 mL) was added dropwise to the stirred solution of Intermediate 64 (95% pure, 10.2 g, 34.06 mmol) in THF (100 mL) at r.t. then the mixture was heated at 50° C. for 1 hour. The mixture was cooled to r.t. and concentrated under reduced pressure to provide light brownish oil. The residue was diluted with EtOAc (300 mL) and washed with water (2×100 mL), brine (50 mL), dried over magnesium sulfate and concentrated under reduced pressure to provide 9.4 g (crude) of the title compound as a light reddish oil. $^1$H NMR (500 MHz, CDCl$_3$) δ ppm 4.15-4.05 (m, 2H), 2.26 (dd, J 13.1, 7.1 Hz, 1H), 2.20-2.11 (m, 1H), 1.99-1.93 (m, 1H), 1.92-1.84 (m, 4H), 1.84-1.75 (m, 1H), 1.64-1.53 (m, 1H), 1.30-1.20 (m, 3H).

Intermediate 66

Ethyl (1S,5R)-3-oxobicyclo[3.1.0]hexane-6-carboxylate

Intermediate 65 (60% pure, 9.4 g, 33.14 mmol) was dissolved in DCM (100 mL). Dess-Martin periodinane (28.11 g, 0.07 mol) was added as a solid and the mixture was stirred at r.t for 15 h. The mixture was diluted with DCM (200 mL) and washed with sat. sodium bicarbonate (2×100 mL), water (100 mL), brine (50 mL) then dried over sodium sulfate and concentrated under reduced pressure to provide an off-white solid. The crude product was purified by flash column chromatography (SiO$_2$, 30-100% EtOAc in heptane) to afford 3.15 g (56%) of the title compound as a light brown oil. $^1$H NMR (500 MHz, CDCl$_3$) δ ppm 4.15 (q, J 7.1 Hz, 2H), 2.66 (ddt, J 18.5, 3.9, 1.6 Hz, 2H), 2.31 (d, J 1.8 Hz, 1H), 2.27 (d, J 1.7 Hz, 2H), 2.18 (td, J 3.4, 1.6 Hz, 2H), 1.31-1.23 (m, 3H).

Intermediate 67

Ethyl (1S,5S,6R)-3-(trifluoromethanesulfonyloxy) bicyclo[3.1.0]hex-2-ene-6-carboxylate Intermediate 66 (3 g, 17.84 mmol) was dissolved in dry toluene (60 mL), DIPEA (12.5 mL, 71.35 mmol) was added and the reaction mixture was heated to 45° C. Triflic anhydride (12 mL, 71.35 mmol) was added, temperature rose to 70° C. and reaction was cooled back down using an ice bath. The mixture was stirred for 1.5 h at 45° C. The reaction was diluted with EtOAc (200 mL) and washed with sat. sodium bicarbonate (2×100 mL). The aq. washes were extracted with EtOAc (200 mL), the organic extracts combined, washed with brine (50 mL), dried over sodium sulfate and concentrated. The crude product was purified by flash column chromatography (SiO$_2$, 0-20% EtOAc in heptane) to afford 2.73 g (51%) of the title product. $^1$H NMR (250 MHz, CDCl$_3$) δ ppm 5.87 (d, J 1.9 Hz, 1H), 4.14 (q, J 7.1 Hz, 2H), 3.00 (dd, J 17.2, 6.2 Hz, 1H), 2.75-2.60 (m, 1H), 2.46-2.31 (m, 1H), 2.23-2.11 (m, 1H), 1.39-1.32 (m, 1H), 1.32-1.16 (m, 3H).

Intermediate 68

Ethyl (1S,5S,6R)-3-(tetramethyl-1,3,2-dioxaborolan-2-yl)bicyclo[3.1.0]hex-2-ene-6-carboxylate Intermediate 67 (2.73 g, 9.09 mmol) was dissolved in 1,4-dioxane (60 mL) and degassed using nitrogen for 5 minutes. Bis(pinacolato)diborane (3.46 g, 13.64 mmol), potassium acetate (2.68 g, 27.28 mmol), 1,1'-bis(diphenylphosphanyl)ferrocene (0.15 g, 0.27 mmol) and Pd(dppf)Cl$_2$ DCM adduct (0.22 g, 0.27 mmol) were added and the reaction was heated under nitrogen at 90° C. for 18 h. The reaction was cooled to r.t. diluted with EtOAc (200 mL) and washed with a sat. aq. solution of sodium bicarbonate (2×100 mL). The aq. washes were re-extracted with EtOAc (50 mL). The organic extracts were combined, washed with brine, dried over sodium sulfate and concentrated. The crude residue was purified by flash column chromatography (SiO$_2$, 0-40% EtOAc in heptane) to afford 2.0 g (59%) of the title compound. $^1$H NMR (250 MHz, CDCl$_3$) δ ppm 6.66 (d, J 1.9 Hz, 1H), 4.11 (q, J 7.1 Hz, 2H), 2.88-2.73 (m, 1H), 2.66-2.44 (m, 2H), 2.33-2.22 (m, 1H), 1.34-1.18 (m, 16H).

Intermediate 69

2-[4-(5,5-dimethyl-1,3,2-dioxaborinan-2-yl)phenyl]-1,1,1,3,3,3-hexafluoro-propan-2-ol 2-(4-bromophenyl)-1,1,1,3,3,3-hexafluoro-2-propanol (0.93 mmol, 300 mg), bis(neopentyl glycolato)diboron (1.91 mmol, 450 mg) and potassium acetate (2.88 mmol, 285 mg) were dissolved in DMSO (5 mL). This was degassed with three cycles of vacuum and nitrogen prior to the addition of Pd(dppf)Cl$_2$ (5 mol %). The reaction was then heated for 1 h at 100° C. After being allowed to cool to r.t. the solution was filtered through celite and partitioned between EtOAc and water. The aq. layer was brought to pH 10 with 10% sodium hydroxide solution and washed with EtOAc. The resulting basic aq. layer was then reduced to pH5 using 2M HCl and extracted with EtOAc. The organic phase was dried over sodium sulfate, filtered and concentrated in vacuo yielding the title compound (255 mg, 77%). δ$_H$ (300 MHz, DMSO-d$_6$) 8.71 (s, 1H); 7.82 (d, J 8.5 Hz, 2H); 7.67 (d, J 8.0 Hz, 2H); 3.77 (s, 4H); 0.96 (s, 6H). LCMS (ES$^+$) RT 1.49 min 287.0 (M-[CH$_2$—C(CH$_3$)$_2$—CH$_2$]+3H)$^+$.

Intermediate 70

(1R,3R)-6-Fluoro-7-[4-(1-methanesulfonyl-ethyl)-phenyl]-1-phenyl-2,3-dihydro-1H-cyclopenta[4,5] imidazo[1,2-a]pyridin-3-ol

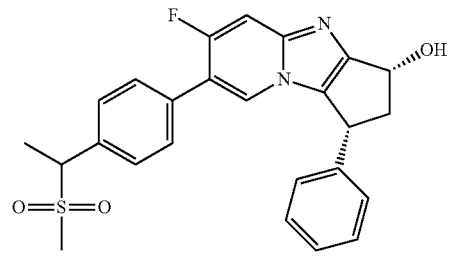 [SMILES: CC(c1ccc(-c2cn3c4c(nc3cc2F)[C@H](O)C[C@@H]4c2ccccc2)cc1)S(C)(=O)=O]

The title compound was prepared from Example 75 (0.2 g, 0.5794 mmol, 1.0 eq.) and lithium tri-sec-butylborohydride (0.8691 mL, 0.8691 mmol, 1.5 eq) by the Method B (0.2 g). LCMS (ES$^+$) RT 1.45 min, 451.0 (M+H)$^+$.

Intermediate 71

9-[5-(4,4,5,5-tetramethyl-1,3,2-dioxaborolan-2-yl) pyrimidin-2-yl]-3,7-dioxa-9-azabicyclo[3.3.1] nonane The title compound was prepared from 3,7-dioxa-9-azabicyclo[3.3.1]nonane (2.04 g, 15.8 mmol) and 2-chloro-5-(tetramethyl-1,3,2-dioxaborolan-2-yl)pyrimidine (3.8 g, 15.8 mmol) by the Method E (2.0 g, 76%). LCMS (ES+) RT 1.80 min, 334.0 (M+H)+.

Intermediate 72

(1R,3S)-7-bromo-1-[2-(difluoromethoxy)phenyl]-2,3-dihydro-1H-cyclopenta[4,5]imidazo[1,2-a]pyridin-3-ol

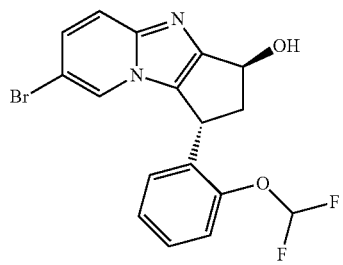 [SMILES: O[C@H]1C[C@H](c2ccccc2OC(F)F)c2c1nc1ccc(Br)cn21]

The title compound was prepared from Example 2 (0.50 g, 1.2 mmol) and sodium borohydride (0.05 g, 1.4 mmol) by the Method C to yield (R)-7-bromo-1-[2-(difluoromethoxy) phenyl]-2,3-dihydro-1H-cyclopenta[4,5]imidazo[1,2-a] pyridin-3-ol. The title compound was isolated by chiral purification of (R)-7-bromo-1-[2-(difluoromethoxy)phenyl]-2,3-dihydro-1H-cyclopenta[4,5]imidazo[1,2-a]pyridin-3-ol under SFC conditions on Lux-Cell-4 (50*291 mm*mm, flow 360 mL/min, 25° C., CO$_2$+20% MeOH, injection of 6.8 mL solution at a concentration of 100 g/L). The first eluting diastereomer (RT 4.61 min) was collected and the fractions were evaporated to yield (1R,3R)-7-bromo-1-[2-(difluoromethoxy)phenyl]-2,3-dihydro-1H-cyclopenta[4,5]imidazo[1,2-a]pyridin-3-ol. The second eluting diastereomer (RT 8.74 min) was collected and the fractions were evaporated to yield the title compound. LCMS (ES$^+$) RT 1.43 min, 395.0/397.0 (M+H)$^+$.

Intermediate 73

N-[(4-Bromophenyl)(methyl)oxo-$\lambda^6$-sulfanylidene]-2,2,2-trifluoroacetamide To a suspension of 1-bromo-4-methanesulfinylbenzene (5 g, 22.8 mmol), MgO (3.68 g, 91.3 mmol), tetrakis(acetato-KO)dirhodium(Rh-Rh) (0.25 g, 0.570 mmol) and 2,2,2-trifluoroacetamide (5.16 g, 45.6 mmol) in anhydrous DCM (150 mL) was added bis(acetyloxy)(phenyl)-lambda-3-iodane (11.03 g, 34.2 mmol) at room temperature. The reaction was left to stir at r.t. for 18 h. The reaction mixture was filtered over celite and the filter cake washed with DCM (30 mL). The filtrate was concentrated in vacuo and purified by column chromatography (SiO$_2$, 0-100% EtOAc in heptane) yielding the title compound as a light yellow oil (5.7 g, 97%). $^1$H NMR (250 MHz, CDCl$_3$) δ ppm 7.92-7.75 (m, 4H), 3.45 (s, 3H). LCMS (ES$^+$) RT 1.27 min, 330.0/332.0 (M+H)$^+$.

Intermediate 74

(4-bromophenyl)-imino-methyl-oxo-$\lambda^6$-sulfane

To a solution of Intermediate 73 (5.7 g, 17.1 mmol) in MeOH (100 mL) was added potassium carbonate (11.6 g, 83.7 mmol). The reaction was left to stir at r.t. for 2 h. The mixture was reduced in vacuo then diluted with water (50 mL). The product was extracted with EtOAc (3×100 mL). The combined organic fraction was dried (MgSO$_4$) and reduced in vacuo to yield the title compound as a yellow oil (4.00 g, 96%). $^1$H NMR (500 MHz, CDCl$_3$) δ ppm 7.89-7.83 (m, 2H), 7.70-7.65 (m, 2H), 3.09 (s, 3H), 2.65 (s, 1H). LCMS (ES$^+$) RT 0.81 min, 234.0/236.0 (M+H)$^+$.

Intermediate 75

Imino-methyl-oxo-[4-(4,4,5,5-tetramethyl-1,3,2-dioxaborolan-2-yl)phenyl]-$\lambda$-$^6$-sulfane The title compound was prepared from Intermediate 74 (4 g, 15.4 mmol) and 4,4,4',4',5,5,5',5'-octamethyl-2,2'-bi-1,3,2-dioxaborolane (4.69 g, 18.5 mmol) by the Method H (3.05 g, 60%). $^1$H NMR (500 MHz, CDCl$_3$) δ ppm 8.02-7.98 (m, 4H), 3.09 (s, 3H), 1.36 (s, 12H).

Intermediate 76

4-(5-bromopyrimidin-2-yl)-1,4-thiazinane 1-oxide

The title compound was prepared from 5-bromo-2-iodopyrimidine (1.98 g, 6.95 mmol) and thiomorpholine 1-oxide (1.3 g, 8.34 mmol) by the Method E (1.63 g, 85%). $^1$H NMR (250 MHz, CDCl$_3$) δ ppm 8.34 (s, 2H), 4.64-4.39 (m, 2H), 4.28-4.00 (m, 2H), 2.94-2.63 (m, 4H). LCMS (ES$^+$) RT 1.13 min, 276/278 (M+H)$^+$.

Intermediate 77

N-[4-(5-bromopyrimidin-2-yl)-1-oxo-1,4-thiazinan-1-ylidene]-2,2,2-trifluoro-acetamide To a suspension of Intermediate 76 (600 mg, 2.17 mmol), MgO (350 mg, 8.69 mmol), tetrakis(acetato-KO)dirhodium (Rh-Rh) (24 mg, 0.05 mmol) and 2,2,2-trifluoroacetamide (491 mg, 4.35 mmol) was added bis(acetyloxy)(phenyl)-lambda-3-iodane (1.05 g, 3.26 mmol). The reaction was stirred for 5 h at r.t. The reaction mixture was filtered over celite, concentrated and purified by column chromatography (SiO$_2$, 0-100% EtOAc in heptane) to yield the title compound as a white solid (706 mg, 83%). $^1$H NMR (250 MHz, CDCl$_3$) δ ppm 8.41 (s, 2H), 4.76-4.50 (m, 2H), 4.21-4.01 (m, 2H), 3.83-3.66 (m, 2H), 3.44-3.22 (m, 2H). LCMS (ES$^+$) RT 1.32 min 387/389 (M+H)$^+$.

Intermediate 78

4-(5-bromopyrimidin-2-yl)-1-imino-1,4-thiazinane-1-oxide

Intermediate 77 (706 mg, 1.81 mmol) was dissolved in MeOH (15 mL) and K$_2$CO$_3$ (1.25 g, 9.03 mmol) was added. The reaction was stirred at r.t. for 1 h. The reaction mixture was concentrated in vacuo and purified by column chromatography (SiO$_2$, 0-100% EtOAc in heptane, followed by 0-10% MeOH in DCM) to yield the title compound as a white solid (452 mg, 83%). $^1$H NMR (250 MHz, CDCl$_3$) δ ppm 8.36 (s, 2H), 4.47-4.36 (m, 2H), 4.29-4.18 (m, 2H), 3.08 (t, J 5.3 Hz, 4H). LCMS (ES$^+$) RT 0.91 min, 291.0/293.0 (M+H)$^+$.

Intermediate 79

1-imino-4-[5-(4,4,5,5-tetramethyl-1,3,2-dioxaborolan-2-yl)pyrimidin-2-yl]-1,4-thiazinane 1-oxide The title compound was prepared from Intermediate 78 (0.46 g, 1.57 mmol), and 4,4,4',4',5,5,5',5'-octamethyl-2,2'-bi-1,3,2-dioxaborolane (0.48 g, 1.88 mmol), by the Method H (0.327 g, 53%). $^1$H NMR (500 MHz, CDCl$_3$) δ ppm 8.64 (s, 2H), 4.62-4.50 (m, 2H), 4.33-4.21 (m, 2H), 3.23 (dd, J 12.4, 3.9 Hz, 2H), 3.11 (ddd, J 12.9, 8.2, 3.0 Hz, 2H), 1.33 (s, 12H). LCMS (ES$^+$) RT 1.13 min, 339.0 (M+H)$^+$.

Intermediate 80

[2-(Morpholin-4-yl)pyrimidin-5-yl]boronic acid

A solution of (2-chloropyrimidin-5-yl)boronic acid (1 g, 6.32 mmol), morpholine (2.19 mL, 25.26 mmol) and triethylamine (0.9 mL, 6.32 mmol) in ethanol (25 mL) was stirred at 20° C. for 1 h. Water (50 mL) was slowly added to the reaction mixture to form a precipitate that was collected by filtration, to afford the title compound as a cream solid (950 mg, 70%). 6H (250 MHz, DMSO-d$_6$) 8.63 (s, 2H), 8.05 (s, 2H), 3.68 (ddd, J 23.4, 5.7, 3.9 Hz, 8H). LCMS (ES$^+$) 210.0 (M+H)$^+$.

107

Intermediate 81

Ethyl 6-bromo-3-[(1E)-3-ethoxy-3-oxoprop-1-en-1-yl]-7-fluoroimidazo[1,2-a]pyridine-2-carboxylate

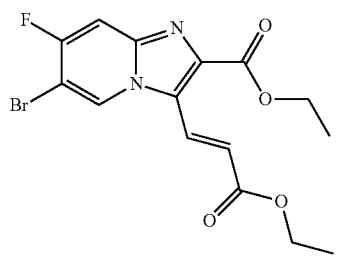 [SMILES: CCOC(=O)/C=C/c1c(C(=O)OCC)nc2cc(F)c(Br)cn12]

ethyl 6-bromo-7-fluoro-3-iodoimidazo[1,2-a]pyridine-2-carboxylate (5 g, 11.62 mmol) was dissolved in DMF (100 mL) under an atmosphere of nitrogen. Na$_2$CO$_3$ (1.36 g, 12.79 mmol) in water (6.4 ml) was added. Ethyl prop-2-enoate (1.36 ml, 12.79 mmol) and bis[3-(diphenylphosphanyl)cyclopenta-2,4-dien-1-yl]iron; dichloromethane; dichloropalladium (0.47 g, 0.58 mmol) were added and the mixture was warmed to 100° C. for 2 h. The reaction mixture was cooled and poured onto ice and the flask was washed with water (4×10 mL). The combined aqueous mixture was stirred for 45 mins, warming to r.t. The suspension was collected by filtration, washing with water (×3). The solid was dried under vacuo. The crude residue was purified by chromatography (SiO$_2$, 20-35% EtOAc in Heptane) and the title compound was isolated as a yellow solid (1.60 g, 36%). $^1$H NMR (500 MHz, CDCl$_3$) δ ppm 8.61 (d, J 6.2 Hz, 1H), 8.33 (d, J 16.6 Hz, 1H), 7.48 (d, J 8.0 Hz, 1H), 6.76 (d, J 16.6 Hz, 1H), 4.51 (q, J 7.1 Hz, 2H), 4.33 (q, J 7.1 Hz, 2H), 1.47 (t, J 7.1 Hz, 3H), 1.38 (t, J 7.1 Hz, 3H). LCMS (ES$^+$) RT 1.95 min, 385.0/387.0 (M+H)$^+$.

Intermediate 82

Ethyl 6-bromo-3-[3-ethoxy-1-(2-methoxyphenyl)-3-oxopropyl]-7-fluoroimidazon[1,2-a]pyridine-2-carboxylate A suspension of (1Z)-cycloocta-1,5-diene-chlororhodium (1:1) (128 mg, 0.26 mmol) in dry dioxane (15 mL) and water (3 mL) was sonicated at room temperature under a nitrogen atmosphere for 5 min. The resulting yellow solution was stirred at r.t. for 30 min before being added to a suspension of Intermediate 81 (1 g, 2.60 mmol) and (2-methoxyphenyl)boronic acid (986 mg, 6.49 mmol) in dry dioxane (15 mL) and K$_2$CO$_3$ (502 mg, 3.63 mmol) under a nitrogen atmosphere. The mixture was heated in the microwave reactor (200 W, 100° C.) for 30 min. The cooled reaction was filtered through a pad of celite, washed with EtOAc (3×50 mL) and the combined filtrates concentrated in-vacuo. The crude residue was purified by chromatography (SiO$_2$, 0-100% EtOAc in Heptane) and the title compound was isolated as a white solid (0.76 g, 53%). $^1$H NMR (500 MHz, CDCl$_3$) δ 8.75 (d, J 6.5 Hz, 1H), 7.62 (dd, J 7.7, 1.4 Hz, 1H), 7.32 (d, J 8.4 Hz, 1H), 7.24-7.16 (m, 1H), 6.96 (td, J 7.6, 0.9 Hz, 1H), 6.82-6.75 (m, 1H), 5.34 (dd, J 10.5, 5.1 Hz, 1H), 4.39 (qd, J 7.1, 1.2 Hz, 2H), 4.08-3.89 (m, 3H), 3.66 (s, 3H), 3.25 (dd, J 16.9, 5.1 Hz, 1H), 1.38 (td, J 7.1, 2.2 Hz, 3H), 1.13 (t, J 7.1 Hz, 3H). LCMS (ES$^+$) RT 3.76 min, 493.0/495.0 (M+H)$^+$.

108

Intermediate 83

Method L

Ethyl 7-bromo-6-fluoro-1-(2-methoxyphenyl)-3-oxo-2,3-dihydro-1H-cyclopenta[4,5]imidazo[1,2-a]pyridine-2-carboxylate

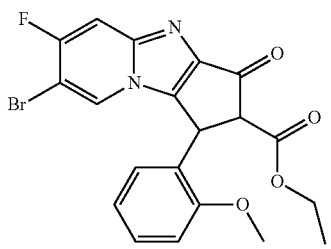 [SMILES: CCOC(=O)C1C(=O)c2nc3cc(F)c(Br)cn3c2C1c1ccccc1OC]

Intermediate 82 (372 mg, 0.75 mmol) was azeotroped with dry toluene (2×5 mL) and then dissolved in dry toluene (8 mL) under nitrogen. The reaction mixture was cooled to 0° C., potassium tert-pentoxide (0.59 mL, 2M solution in toluene, 1.2 mmol) was added drop wise to the stirred solution while maintain the temperature at 0° C. The reaction mixture was stirred at 0° C. for 30 min then additional potassium tert-pentoxide solution (0.2 mL) was added. The reaction mixture was stirred for a further 10 min at 0° C. then quenched with acetic acid (0.1 mL). The reaction was diluted with water (10 mL) and extracted with ethyl acetate (3×30 mL). The combined organic extracts were washed with brine (15 mL), dried over sodium sulfate and concentrated in vacuo. The crude residue was purified by chromatography (SiO$_2$, 0-70% EtOAc in Heptane) and the title compound was isolated as a yellow oil (0.18 g, 46%). LCMS (ES$^+$) RT 1.97 min, 447.0/449.0 (M+H)$^+$.

Intermediate 84

Method M 7-bromo-6-fluoro-1-(2-methoxyphenyl)-1,2-dihydro-3H-cyclopenta[4,5]imidazoa[1,2-a]pyridin-3-one

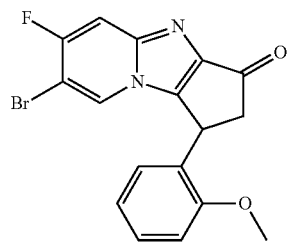 [SMILES: COc1ccccc1C1CC(=O)c2nc3cc(F)c(Br)cn3c21]

To a solution of intermediate 83 (180 mg, 0.4 mmol) in DMSO/de-ionised water 4:1(5 mL) nitrogen was bubbled through for 2 min. The reaction mixture was heated to 100° C. with stirring for 36 h under an atmosphere of nitrogen. De-ionised water (1 mL) was added and re-heated to 100° C. for 14 hours. The reaction mixture was diluted with ethyl acetate (50 mL), washed with water (3×20 mL), brine (1×20 mL), dried over sodium sulfate, filtered and concentrated in vacuo. The crude product was purified by chromatography (SiO$_2$, 0-80% EtOAc in Heptane) to yield the title compound as an orange solid (53 mg, 35%). $^1$H NMR (500 MHz, CDCl$_3$) δ 7.90 (d, J 6.5 Hz, 1H), 7.41 (d, J 8.8 Hz, 1H), 7.31 (td, J 8.3, 1.6 Hz, 1H), 6.98 (d, J 8.2 Hz, 1H), 6.94-6.88 (m, 1H), 6.83 (dd, J 7.5, 1.5 Hz, 1H), 5.08 (dd, J 6.9, 2.1 Hz, 1H), 3.89 (s, 3H), 3.60 (dd, J 18.4, 7.0 Hz, 1H), 2.98 (dd, J 18.4, 2.2 Hz, 1H). LCMS (ES$^+$) RT 3.03 min, 375.0/377.0 (M+H)$^+$.

Intermediate 85

7-bromo-6-fluoro-1-(2-methoxyphenyl)-2,3-dihydro-1H-cyclopenta[4,5]imidazo[1,2-a]pyridin-3-ol

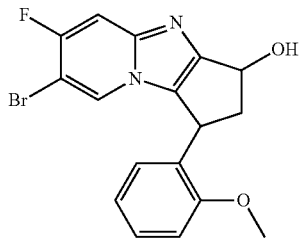 [SMILES: COc1ccccc1C1CC(O)c2nc3cc(F)c(Br)cn3c21]

The title compound was prepared from Intermediate 84 (53 mg, 0.14 mmol) and 1M lithium tri-sec-butylborohydride solution in THF (0.09 mL, 0.7 equiv,) by the Method B (42 mg, 60%). $^1$H NMR (500 MHz, CDCl$_3$) δ 7.87 (d, J 6.6 Hz, 1H), 7.33 (dd, J 9.1, 1.5 Hz, 1H), 7.28-7.23 (m, 1H), 7.15 (d, J 7.5 Hz, 1H), 6.96 (d, J 8.2 Hz, 1H), 6.91 (t, J 7.4 Hz, 1H), 5.38 (dd, J 7.3, 2.9 Hz, 1H), 4.82 (dd, J 8.5, 3.7 Hz, 1H), 3.95 (s, 3H), 3.53 (dt, J 14.2, 8.0 Hz, 1H), 2.44 (dt, J 14.1, 3.4 Hz, 1H). LCMS (ES$^+$) RT 1.08 min, 379.0/381.0 (M+H)$^+$.

Intermediate 86

2-(5-bromopyrimidin-2-yl)propan-2-ol

The title compound was prepared from 2.5M n-BuLi in hexane (14.7 mL, 36.9 mmol), 5-bromo-2-iodopyrimidine (10 g, 35.1 mmol), toluene (200 mL) and acetone (2.83 mL, 38.6 mmol) by the Method F (2.86 g, 37%). $^1$H NMR (500 MHz, CDCl3) δ 8.77 (s, 2H), 4.31 (s, 1H), 1.59 (s, 6H). LCMS (ES$^+$) RT 1.26 min, 219.0 (M+H)$^+$.

Intermediate 87

2-(5-bromopyrimidin-2-yl)propan-2-amine

Intermediate 86 (1.00 g, 4.61 mmol) was dissolved in acetonitrile (10 mL) and treated with concentrated sulfuric acid (1.28 mL, 8.53 mmol). The mixture was warmed to 60° C. for 3 h. Water was added (1 mL) and the reaction mixture was stirred at 60° C. for 15 h. The mixture was cooled down, poured in ice/water (60 mL), and pH was adjusted to 14 using a 6M solution of sodium hydroxide in water. The mixture was extracted with DCM (3×30 mL), the organic extracts were combined, dried over sodium sulfate, filtered and concentrated in vacuo. The resulting yellow residue (0.92 g) was dissolved in dioxane (6 mL), the solution was charged in a pressure tube, water (4 mL) and concentrated hydrogen chloride solution (12 M, 5 mL) was added. The reaction mixture was sealed and stirred at 100° C. for 15 h. The mixture was cooled down, poured in ice/water (60 mL), and pH was adjusted to 14 using a 6M solution of sodium hydroxide in water. The mixture was extracted with a 1:1 isopropanol:chloroform mixture (3×30 mL). The organic extracts were combined, dried over sodium sulfate, filtered and concentrated in vacuo yielding the title compound as a brown crystallising oil (621 mg, 46%).
$^1$H NMR (500 MHz, CDCl$_3$) δ 8.73 (s, 2H), 1.78 (bs, 2H), 1.53 (s, 6H).

Intermediate 88

Tert-butyl N-[2-(5-bromopyrimidin-2-yl)propan-2-yl]carbamate

Di-tert-butyl dicarbonate (627 mg, 2.87 mmol) and N-ethyl-N-(propan-2-yl)propan-2-amine (994 μl, 5.75 mmol) were added to a solution of Intermediate 87 (621 mg, 2.87 mmol) in THF. The reaction mixture was stirred at room temperature for 15 h. The reaction mixture was diluted with ethyl acetate (30 mL) and washed with water (2×15 mL). The aqueous washes were combined, re-extracted with ethyl acetate (2×15 mL). The organic extracts were combined, dried over sodium sulfate, filtered and concentrated in vacuo. The resulting orange oil was purified by chromatography (SiO$_2$, 0-50% EtOAc in Heptane) to yield the title compound as a colourless oil (300 mg, 33%). $^1$H NMR (500 MHz, CDCl$_3$) δ 8.73 (s, 2H), 1.69 (s, 6H), 1.40 (s, 9H). LCMS (ES$^+$) RT 1.35 min, 219.0 (M+H)$^+$.

Intermediate 89

Tert-butyl N-{2-[5-(tetramethyl-1,3,2-dioxaborolan-2-yl)pyrimidin-2-yl]propan-2-yl}carbamate The title compound was prepared from Intermediate 88 (300 mg, 0.95 mmol), diboron pinacol ester (361 mg, 1.42 mmol) and potassium acetate (279 mg, 2.85 mmol) in dioxane (5 mL) and dichloro[1,1'-bis(diphenylphospinoferrocene]-palladium dichloromethane adduct (39 mg, 0.05 mmol) by the Method H (149 mg, 36%). $^1$H NMR (500 MHz, CDCl$_3$) δ 8.97 (s, 2H), 6.17 (s, 1H), 1.72 (s, 6H), 1.42 (s, 9H), 1.35 (s, 12H). LCMS (ES$^+$) RT 1.38 min, 282.0 (M+H)$^+$.

Intermediate 90

(Z)-3,3-difluoro-N'-hydroxycyclobut-1-carboximidamide

A solution of 3,3-difluorocyclobutane-1-carbonitrile (1 g, 8.54 mmol) in ethanol (15 mL) was treated with hydroxylamine (50% in water) (5.25 mL, 86.0 mmol) and stirred at 80° C. for 3 h. The reaction mixture was allowed to cool and then concentrated in vacuo. The residue was partitioned between DCM (10 mL) and water (10 mL). The organic phase was separated, the aqueous phase was extracted with DCM (3×5 mL). The product re-extracted with 1:1 IPA/CHCl$_3$ (3×60 mL), organic separated and dried over sodium sulfate and concentrated in vacuo to afford the title compound as an orange gum (545 mg, 42%). $^1$H NMR (500 MHz, DMSO-d6) δ 9.07 (s, 1H), 5.44 (s, 2H), 2.84-2.59 (m, 5H). LCMS (ES$^+$) RT 0.25 min, 151.0 (M+H)$^+$.

Intermediate 91

3,3-difluorocyclobutane-1-carboximidamide

Intermediate 90 (1.1 g, 7.33 mmol) was dissolved in acetic acid (20 mL), acetic anhydride (1.04 mL, 11 mmol)

was added and reaction stirred for 30 minutes under nitrogen. Zinc dust (4.8 g, 73.27 mmol) added and reaction continued to stir at r.t. under nitrogen for 18 h. The reaction was filtered through Celite and washed with acetic acid, solvent concentrated in vacuo. The acetic acid was azeotroped with toluene (2×30 mL) to afford a gum/solid. This was sonicated in ether (30 mL) for 5 min and filtered. Solid was air-dried for 1.5 h yielding the title compound as an off-white solid (1.41 g, 64%). 1H NMR (500 MHz, DMSO-d6) δ 3.15 (s, 1H), 2.84 (s, 4H). LCMS (ES$^+$) RT 0.15 min, 135.0 (M+H)$^+$.

Intermediate 92

5-bromo-2-(3,3-difluorocyclobutyl)pyrimidine

Intermediate 91 (75%, 1 g, 3.86 mmol) and (2Z)-2-bromo-3-(dimethylamino)prop-2-enal (0.825 g, 4.63 mmol) were dissolved in EtOH (30 mL) and heated to 80° C. for 2.45 h. The reaction mixture was left standing at r.t. for 18 h and heated to 80° C. for 2 h and then at 90° C. for 2.5 h. The reaction was cooled to 80° C. and stirred for 18 h. The reaction was concentrated in vacuo and DCM (50 mL) and water (25 mL) added. The organics were filtered through Celite, and dried over sodium sulfate and concentrated in vacuo. The residue was purified by chromatography (SiO$_2$, 0-80% EtOAc in Heptane) yielding the title compound as a clear oil (130 mg, 13%). $^1$H NMR (500 MHz, CDCl$_3$) δ 8.74 (s, 2H), 3.59 (pd, J 8.6, 3.0 Hz, 1H), 2.99 (dt, J 16.6, 8.5 Hz, 4H). LCMS (ES$^+$) RT 1.24 min, 251.0 (M+H)$^+$.

Intermediate 93

2-(3,3-difluorocyclobutyl)-5-(tetramethyl-1,3,2-dioxaborolan-2-yl)pyrimidine

The title compound was prepared from Intermediate 92 (174 mg, 0.7 mmol), 4,4,4',4',5,5,5',5'-octamethyl-2,2'-bi-1,3,2-dioxaborolane (212.89 mg, 0.84 mmol), potassium acetate (205.7 mg, 2.1 mmol), dioxane (2 mL) and Pd(dppf)Cl$_2$.DCM (28.53 mg, 0.03 mmol) by the Method H (306 mg, 93%). $^1$H NMR (500 MHz, CDCl$_3$) δ 8.96 (s, 2H), 3.63 (pd, J 8.7, 3.0 Hz, 1H), 3.11-2.88 (m, 5H). LCMS (ES$^+$) RT 0.94 min, 215.0 (M+H)$^+$.

Intermediate 94

1-(5-bromopyrimidin-2-yl)ethan-1-one 5-bromo-2-iodopyrimidine (16 g, 56.16 mmol) and tributyl(1-ethoxyethenyl)stannane (25 g, 69.22 mmol) were dissolved in toluene (500 mL) and purged with N$_2$ for 10 mins. Palladium (2$^+$) chloride-triphenylphosphane (1:2:2) (3.5 g, 4.99 mmol) was added and the reaction mixture was heated at 130° C. for 18 h. The reaction was allowed to cool to r.t. Water (70 ml) and 6M HCl (280 ml) were added and the reaction mixture was allowed to stir vigorously for 4 h. The pH of the mixture was adjusted to pH 7 by the addition of saturated aqueous Na$_2$CO$_3$ (approximately 300 mL) and the mixture extracted with EtOAc (3×350 mL). The combined organic extracts were dried over magnesium sulfate, filtered and concentrated in vacuo. The residue was purified by chromatography (SiO$_2$, 20-100% EtOAc in Heptane) to afford the title compound as a golden-yellow solid (7.9 g, 70%). $^1$H NMR (500 MHz, CDCl$_3$) δ 8.97 (s, 2H), 2.77 (s, 3H).

Intermediate 95

5-bromo-2-(1,1-difluoroethyl)pyrimidine

BAST (50% in toluene) (28 ml, 75.94 mmol) was added drop wise to a stirred solution of Intermediate 94 (3.9 g, 19.4 mmol) in anhydrous DCM (100 mL) at 0° C. under an atmosphere of N$_2$. The mixture was allowed to stir at r.t. for 18 h. BAST (50% in toluene) (6 ml, 16.27 mmol) was added and the reaction mixture was allowed to stir at r.t. for 5 h. The reaction mixture was added drop wise to stirred ice/NaHCO$_3$ (sat, aq, 50 mL). The organic layer was separated and the crude product further extracted with DCM (2×75 mL). The combined organic phase was dried over sodium sulfate and concentrated in vacuo yielding the title compound as a brown solution in toluene (5.51 g, 95.5%). $^1$H NMR (500 MHz, CDCl$_3$) δ 8.90 (s, 2H), 2.05 (t, J 18.6 Hz, 3H).

Intermediate 96

2-(1,1-difluoroethyl)-5-(tetramethyl-1,3,2-dioxaborolan-2-yl)pyrimidine

The title compound was prepared from Intermediate 95 (75%, 5.5 g, 18.5 mmol), 4,4,4'%4'%5,5,5',5'-octamethyl-2,2'-bi-1,3,2-dioxaborolane (5.5 g, 21.66 mmol), potassium acetate (3.5 ml, 56.04 mmol), 1,4-dioxane (10 mL), and bis[3-(diphenylphosphanyl)cyclopenta-2,4-dien-1-yl]iron; dichloromethane; dichloropalladium (0.75 g, 0.92 mmol) by the Method H (3.3 g, 42.9%). 1H NMR (500 MHz, CDCl$_3$) δ 9.09 (d, J 2.9 Hz, 2H), 2.03 (td, J 18.6, 4.2 Hz, 3H), 1.35 (d, J 3.9 Hz, 12H).

Intermediate 97 ethyl (1S,5S,6R)-3-(5-{(1R)-1-[2-(difluoromethoxy)phenyl]-6-fluoro-2,3-dihydro-1H-cyclopenta[4,5]imidazo[1,2-a]pyridin-7-yl}pyrimidin-2-yl)bicyclo[3.1.0]hex-2-ene-6-carboxylate

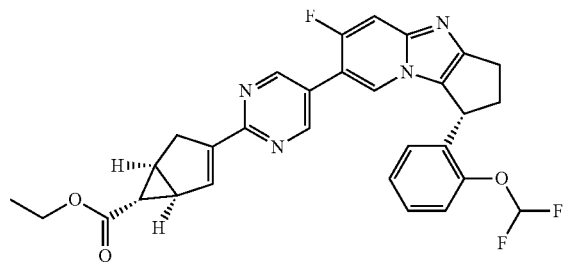 [SMILES: CCOC(=O)[C@H]1[C@@H]2C=C(c3ncc(-c4cn5c6c(nc5cc4F)CC[C@@H]6c4ccccc4OC(F)F)cn3)C[C@@H]21]

The title compound was prepared from Example 17 (150 mg, 0.38 mmol), Intermediate 68 (150 mg, 0.38 mmol), 2M sodium carbonate (0.65 mL), dioxane (3 mL), dichloro[1,1'-bis(diphenylphosphinoferrocene]-palladium dichloromethane adduct (31 mg, 0.04 mmol) by the Method A (150 mg, 72%). 1H NMR (500 MHz, CDCl$_3$) δ 8.67 (d, J 1.4 Hz, 2H), 7.53 (d, J 7.1 Hz, 1H), 7.39 (d, J 11.1 Hz, 1H), 7.29-7.26 (m, 1H), 7.22-7.15 (m, 2H), 7.11 (t, J 7.5 Hz, 1H), 6.89 (dd, J 7.7, 1.5 Hz, 1H), 6.62 (dd, J 74.3, 73.1 Hz, 1H), 4.95 (dd, J 8.4, 5.3 Hz, 1H), 4.17-4.12 (m, 2H), 3.29-3.13 (m, 2H), 3.13-2.91 (m, 3H), 2.62 (dq, J 4.8, 2.3 Hz, 1H), 2.43

Intermediate 98

Ethyl (1R,5S,6R)-3-(5-{(1R)-1-[2-(difluoromethoxy)phenyl]-6-fluoro-2,3-dihydro-1H-cyclopenta[4,5]imidazo[1,2-a]pyridin-7-yl}pyrimidin-2-yl)bicyclo[3.1.0]hexane-6-carboxylate

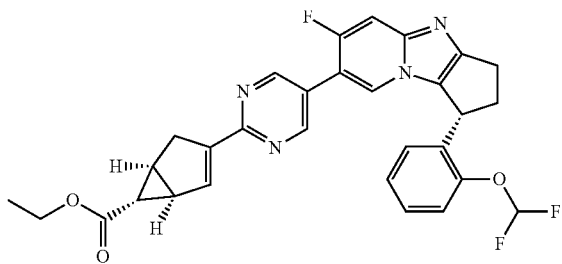 [SMILES: CCOC(=O)[C@H]1[C@@H]2C=C(c3ncc(-c4cn5c6c(nc5cc4F)CC[C@@H]6c4ccccc4OC(F)F)cn3)C[C@@H]21]

The title compound was prepared from Intermediate 97 (150 mg, 0.28 mmol), ethyl acetate (12 mL), triethylamine (38 μL, 0.28 mmol), palladium on carbon (10%, 30 mg, 0.024 mmol) by the procedure described for Example 96 yielding the title compound as a pale oil (105 mg, 70%). $^1$H NMR (500 MHz, CDCl$_3$) δ 8.69 (d, J 1.5 Hz, 2H), 7.55 (d, J 7.1 Hz, 1H), 7.39 (d, J 11.1 Hz, 1H), 7.30-7.26 (m, 1H), 7.19 (d, J 7.9 Hz, 1H), 7.13 (t, J 7.5 Hz, 1H), 6.89 (dd, J 7.7, 1.6 Hz, 1H), 6.63 (dd, J 74.2, 73.2 Hz, 1H), 4.96 (dd, J 8.5, 5.1 Hz, 1H), 4.07 (q, J 7.1 Hz, 2H), 3.77 (tt, J 9.0, 4.3 Hz, 1H), 3.23 (dtd, J 13.3, 8.9, 4.6 Hz, 1H), 3.16-3.03 (m, 1H), 2.98 (ddd, J 15.5, 8.7, 5.9 Hz, 1H), 2.54-2.49 (m, 3H), 2.47-2.37 (m, 1H), 1.98 (s, 2H), 1.55 (dd, J 6.7, 3.7 Hz, 2H), 1.21 (t, J 7.1 Hz, 3H). LCMS (ES$^+$) RT 2.97 min, 549.0 (M+H)$^+$.

Intermediate 99

5-bromo-2-(2-fluoropropan-2-yl)pyrimidine

The title compound was prepared from Intermediate 86 (6 g, 26.8 mmol) and DAST (5.3 mL, 40.3 mmol) by the Method D. $^1$H NMR (500 MHz, CDCl$_3$) δ 8.81 (s, 2H), 1.78 (d, J 21.7 Hz, 6H). LCMS (ES$^+$) RT 1.89 min, 293.0 (M+H)$^+$.

Intermediate 100

2-(2-fluoropropan-2-yl)-5-(tetramethyl-1,3,2-dioxaborolan-2-yl)pyrimidine

The title compound was prepared from Intermediate 99 (1.09 g, 4.98 mmol), diboron pinacol ester (1.9 g, 7.46 mmol), potassium acetate (1.46 g, 14.93 mmol), dioxane (10 mL), dichloro[1,1'-bis(diphenylphosphinoferrocene)-palladium dichloromethane adduct (203 mg, 0.25 mmol) by the Method H (945 mg, 22%). $^1$H NMR (500 MHz, CDCl$_3$) δ 9.03 (s, 2H), 1.79 (d, J 21.7 Hz, 6H), 1.36 (s, 12H). LCMS (ES$^+$) RT 1.02 min, 185.0 (M+H)$^+$.

Intermediate 101

5-bromo-2-{1-[(tert-butyldimethylsilyl)oxy]ethenyl}pyrimidine

Tert-Butyl(dimethyl)silyl trifluoromethanesulfonate (16.36 g, 61.88 mmol) was added drop wise to a stirred solution of Intermediate 94 (8.65 g, 43.03 mmol) and triethylamine (8.62 ml, 61.88 mmol) added drop wise in anhydrous DCM (300 mL) at 0° C. After 30 min the mixture was allowed to warm up to r.t. The reaction was quenched by the addition of water (300 mL), and the organic phase was washed with brine (200 mL), dried over magnesium sulfate, filtered and concentrated in vacuo. The residue was purified by chromatography (SiO$_2$, 1-8% EtOAc in Heptane) to afford the title compound as a yellow oil (9.09 g, 84%). LCMS (ES$^+$) RT 2.37 min, 317.0 (M+H)$^+$.

Intermediate 102

5-bromo-2-{1-[(tert-butyldimethylsilyl)oxy]cyclopropyl}pyrimidine

To a stirred solution of tBuOK (1.21 g, 0.01 mol) in anhydrous DMSO (25 mL) was added trimethylsulfoxonium iodide (2.51 g, 11.42 mmol) portion wise and the mixture heated to 50° C. for 45 min. A solution of Intermediate 101 (0.90 g, 2.86 mmol) in anhydrous DMSO (25 mL) was then added drop wise over 10 min to the reaction mixture. The reaction was stirred at 50° C. for 2 hr. The reaction was treated with a saturated aqueous solution of NH$_4$Cl (100 mL). EtOAc (125 mL) was then added and the two phases were separated. The aqueous phase was extracted with EtOAc (3×125 mL). The combined organic extracts were washed with water (2×125 mL) and brine (1×125 mL), dried over magnesium sulfate, filtered and concentrated in vacuo1. The residue was purified by chromatography (SiO$_2$, 5-40% DCM in Heptane) to afford the title compound as a light yellow oil (0.44 g, 47%). LCMS (ES$^+$) RT 2.38 min, 331.0 (M+H)$^+$.

Intermediate 103

2-{1-[(tert-butyldimethylsilyl)oxy]cyclopropyl}-5-(tetramethyl-1,3,2-dioxaborolan-2-yl)pyrimidine The title compound was prepared from Intermediate 102 (0.44 g, 1.32 mmol), bis(pinacolato)diboron (0.4 g, 1.59 mmol), potassium acetate (0.39 g, 3.97 mmol), dioxane (10 mL), dichloro[1,1'-bis(diphenylphospinoferrocene)-palladium dichloromethane adduct (54.06 mg, 0.07 mmol) by the Method H (720 mg, 96%). $^1$H NMR (500 MHz, CDCl$_3$) δ 8.88 (s, 2H), 1.53-1.48 (m, 2H), 1.35 (s, 12H), 1.34-1.31 (m, 2H), 0.91 (s, 9H), 0.14 (s, 6H). LCMS (ES$^+$) RT 1.95 min, 377.0 (M+H)$^+$.

Intermediate 104 Method N 2-(Difluoromethoxy)-4-fluorobenzaldehyde

Potassium hydroxide (40.04 g, 713.72 mmol) was dissolved in water (100 mL) and allowed to cool then acetonitrile (100 mL) was added and solution was cooled to −20° C. where it froze. 4-fluoro-2-hydroxybenzaldehyde (5 g, 35.69 mmol) was added followed by diethyl [bromo(difluoro)methyl]phosphonate (12.68 ml, 71.37 mmol) drop wise and reaction was stirred at −20° C. for 30 min. Reaction was extracted with ethyl acetate (2×100 mL), organic layer washed with brine (50 mL), dried over sodium sulfate and concentrated in vacuo. The residue was purified by chromatography, (SiO$_2$, 0-40% EtOAc in Heptane) to afford the title compound as a clear oil (3.5 g, 51%). $^1$H NMR (250 MHz, DMSO-d$_6$) δ 10.14 (s, 1H), 7.88 (dd, J 8.7, 6.7 Hz, 1H), 7.37 (t, J 73 Hz, 1H), 7.35-7.19 (m, 2H).

Intermediate 105

6-Bromo-3-{2-carboxy-1-[2-(difluoromethoxy)-4-fluorophenyl]ethyl}-7-fluoroimidazo[1,2-a]pyridine-2-carboxylic acid hydrochloride Ethyl 6-bromo-7-fluoro-3-iodoimidazo[1,2-a]pyridine-2-carboxylate (2 g, 6.97 mmol), intermediate 104 (2.65 g, 13.93 mmol) and L-proline (80.21 mg, 0.7 mmol) in acetonitrile (15 mL) were heated at 80° C. in sealed tube for 14 h, followed by 120° C. until complete conversion. The reaction mixture was concentrated in vacuo and triturated with 6M NaOH (50 mL) and extracted with ethyl acetate (50 mL×2). The aqueous layer was acidified with conc. HCl (pH ~3-4) and extracted with IPA: CHCl$_3$ (1:1) (2×50 mL). The organic layer concentrated in vacuo yielding the title compound as a beige solid (3.3 g, 55%). LCMS (ES$^+$) RT 1.70 min, 491.0/493.0 (M+H)$^+$.

Intermediate 106 Method O

Ethyl-6-bromo-3-{1-[2-(difluoromethoxy)-4-fluorophenyl]-3-ethoxy-3-oxopropyl}-7-fluoro imidazo[1,2-a]pyridine-2-carboxylate Oxalyl dichloride (1.78 ml, 18.76 mmol) was added drop wise to the stirred solution of Intermediate 105 (3.3 g, 3.75 mmol), N,N-dimethylformamide (58.05 μl, 0.75 mmol) in DCM (25 mL) stirred at r.t. for 2 h. The mixture was concentrated in vacuo and quenched with ethanol (10 mL) and stirred for 30 min. The mixture was concentrated in vacuo to provide brown oil. This was dissolved in ethyl acetate (200 mL) and washed with sat. aq. sodium bicarbonate (2×25 mL). The combined organic layer washed with water (25 mL), brine (25 mL), dried over sodium sulfate, filtered and concentrated in vacuo. The residue was purified by chromatography, (SiO$_2$, 0-50% EtOAc in Heptane) to afford the title compound as a light brown solid (950 mg, 46%). LCMS (ES$^+$) RT 1.49 min, 547.0/549.0 (M+H)1.

Intermediate 107

Ethyl 7-bromo-1-[2-(difluoromethoxy)-4-fluorophenyl]-6-fluoro-3-oxo-2,3-dihydro-1H-cyclopenta[4,5]imidazo[1,2-a]pyridine-2-carboxylate

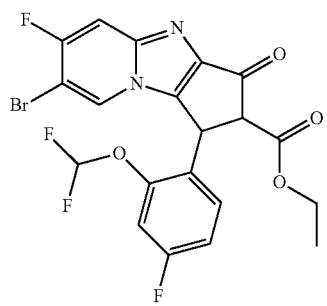 [SMILES: CCOC(=O)C1C(=O)c2nc3cc(F)c(Br)cn3c2C1c1ccc(F)cc1OC(F)F]

The title compound was prepared from Intermediate 106 (900 mg, 1.64 mmol) and potassium tert-pentoxide (1.48 ml, 2.63 mmol) by the Method L (490 mg, 55%). LCMS (ES$^+$) RT 2.00 min, 501.0/503.0 (M+H)$^+$.

Intermediate 108

7-bromo-1-[2-(difluoromethoxy)-4-fluorophenyl]-6-fluoro-1,2-dihydro-3H-cyclopenta[4,5]imidazo[1,2-a]pyridin-3-one

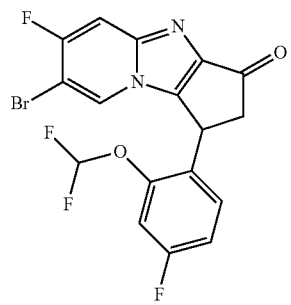 [SMILES: O=C1CC(c2ccc(F)cc2OC(F)F)c2c1nc1cc(F)c(Br)cn21]

The title compound was prepared from Intermediate 107 (490 mg, 0.68 mmol), DMSO (8 mL) and water (2 mL) by the Method M (285 mg, 77%). LCMS (ES$^+$) RT 1.96 min, 429.0/431.0 (M+H)$^+$.

Intermediate 109

7-bromo-1-[2-(difluoromethoxy)-4-fluorophenyl]-6-fluoro-2,3-dihydro-1H-cyclopenta[4,5]imidazo[1,2-a]pyridin-3-ol

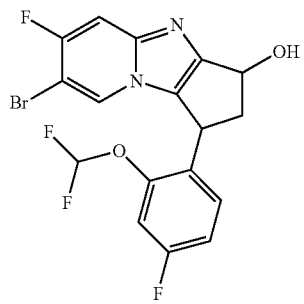 [SMILES: OC1CC(c2ccc(F)cc2OC(F)F)c2c1nc1cc(F)c(Br)cn21]

The title compound was prepared from Intermediate 108 (275 mg, 0.64 mmol), 1M lithium tri-sec-butylborohydride in THF (0.64 ml) and THF (10 mL) by the Method B (165 mg, 56%). LCMS (ES$^+$) RT 1.76 min, 431.0/433.0 (M+H)$^+$.

Intermediate 110

2-(Difluoromethoxy)-5-fluorobenzaldehyde

The title compound was prepared from 5-fluoro-2-hydroxybenzaldehyde (4.42 ml, 35.69 mmol, potassium hydroxide (40.04 g, 713.72 mmol), water (100 mL), acetonitrile (100 mL), diethyl [bromo(difluoro)methyl]phosphonate (12.68 ml, 71.37 mmol) by the Method N (2.4 g, 35%). $^1$H NMR (500 MHz, CDCl$_3$) δ 10.33 (d, J 3.0 Hz, 1H), 7.61 (dd, J 8.0, 3.1 Hz, 1H), 7.33 (ddd, J 9.0, 7.3, 3.2 Hz, 1H), 7.30-7.27 (m, 1H), 6.63 (t, J 72.4 Hz, 1H).

Intermediate 111

Method P

3-[6-Bromo-2-(ethoxycarbonyl)-7-fluoroimidazo[1,2-a]pyridin-3-yl]-3-[2-(difluoromethoxy)-5-fluorophenyl]propanoic acid Ethyl 6-bromo-7-fluoro-3-iodoimidazo[1,2-a]pyridine-2-carboxylate (2 g, 6.97 mmol), 2,2-dimethyl-1,3-dioxane-4,6-dione (2.01 g, 13.93 mmol), Intermediate 110 (2.65 g, 13.93 mmol) and L-proline (80.21 mg, 0.7 mmol) in acetonitrile (15 mL) were heated at 80° C. in sealed tube for 14 h, followed by 120° C. until complete conversion. The reaction mixture was concentrated in vacuo and the residue was washed with ethyl acetate (50 mL). The solid was filtered off and the filtrate was in vacuo to half of the volume and allow to stand for 30 min. The solid precipitate was filtered and washed with ethyl acetate (25 mL) to yield the title compound as a beige solid (1.6 g, 33%). LCMS (ES+) RT 1.85 min, 519.0/521.0 (M+H)1.

Intermediate 112

Ethyl-6-bromo-3-{1-[2-(difluoromethoxy)-5-fluorophenyl]-3-ethoxy-3-oxopropyl}-7-fluoro imidazo[1,2-a]pyridine-2-carboxylate The title compound was prepared from oxalyl choride (1.17 ml, 12.33 mmol), Intermediate 111 (1.6 g, 2.47 mmol), N,N-dimethylformamide (38.13 µl, 0.49 mmol) and DCM (25 mL) by the Method 0 (1.3 g, 96%). LCMS (ES+) RT 2.13 min, 547.0/549.0 (M+H)+.

Intermediate 113

Ethyl 7-bromo-1-[2-(difluoromethoxy)-5-fluorophenyl]-6-fluoro-3-oxo-2,3-dihydro-1H-cyclopenta[4,5]imidazo[1,2-a]pyridine-2-carboxylate

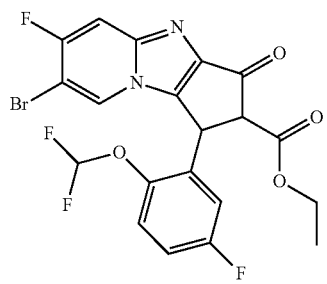 [SMILES: CCOC(=O)C1C(=O)c2nc3cc(F)c(Br)cn3c2C1c1cc(F)ccc1OC(F)F]

The title compound was prepared from Intermediate 112 (1.3 g, 2.38 mmol), toluene (80 mL) and potassium 2-methylbutan-2-olate (2.13 ml, 3.8 mmol) by the Method L (380 mg, 25%). LCMS (ES+) RT 1.98 min, 501.0/503.0 (M+H)+.

Intermediate 114

7-bromo-1-[2-(difluoromethoxy)-5-fluorophenyl]-6-fluoro-1,2-dihydro-3H-cyclopenta[4,5]imidazo[1,2-a]pyridin-3-one

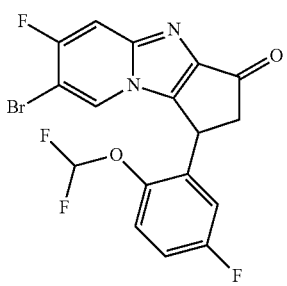 [SMILES: O=C1CC(c2cc(F)ccc2OC(F)F)c2c1nc1cc(F)c(Br)cn21]

The title compound was prepared from Intermediate 113 (380 mg, 0.61 mmol), DMSO (8 mL) and water (2 mL) by the Method M (265 mg, 97%). LCMS (ES+) RT 1.87 min, 429.0/431.0 (M+H)+.

Intermediate 115

7-bromo-1-[2-(difluoromethoxy)-5-fluorophenyl]-6-fluoro-2,3-dihydro-1H-cyclopenta[4,5]imidazo[1,2-a]pyridin-3-ol

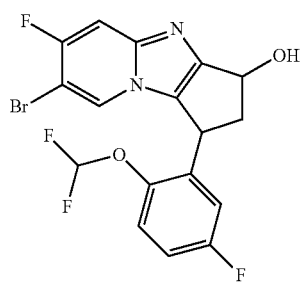 [SMILES: OC1CC(c2cc(F)ccc2OC(F)F)c2c1nc1cc(F)c(Br)cn21]

The title compound was prepared from Intermediate 114 (265 mg, 0.62 mmol), 1M lithium tri-sec-butylborohydride in THF (0.62 ml) and THF (10 mL) by the Method B (180 mg, 65%). LCMS (ES+) RT 1.73 min, 431.0/433.0 (M+H)+.

Intermediate 116

2-(Difluoromethoxy)-4,5-difluorobenzaldehyde

The title compound was prepared from potassium hydroxide (67.5 g, 1203 mmol), water (100 mL), MeCN (50 mL), 4,5-difluoro-2-hydroxybenzaldehyde (9.5 g, 60.09 mmol) and diethyl [bromo(difluoro)methyl]phosphonate (12.8 mL, 72.10 mmol), according to the Method N (3.95 g, 12%). $^1$H NMR (500 MHz, CDCl$_3$) δ 10.25 (d, J 3.0 Hz, 1H), 7.83-7.65 (m, 1H), 7.17 (dd, J 10.2, 6.1 Hz, 1H), 6.68 (t, J 71.8 Hz, 1H).

Intermediate 117

3-[6-Bromo-2-(ethoxycarbonyl)-7-fluoroimidazo[1,2-a]pyridin-3-yl]-3-[2-(difluoromethoxy)-4,5-difluorophenyl]propanoic acid The title compound was prepared from ethyl 6-bromo-7-fluoro-3-iodoimidazo[1,2-a]pyridine-2-carboxylate (2 g, 6.97 mmol), 2,2-dimethyl-1,3-dioxane-4,6-dione (2.74 g, 18.98 mmol), Intermediate 116 (3.95 g, 18.98 mmol) and L-proline (80.21 mg, 0.7 mmol) in acetonitrile (15 mL) by the Method P (3 g, 56%). LCMS (ES⁺) RT 1.98 min, 537.0/539.0 (M+H)⁺.

Intermediate 118

Ethyl-6-bromo-3-{1-[2-(difluoromethoxy)-4,5-difluorophenyl]-3-ethoxy-3-oxopropyl}-7-fluoroimidazo[1,2-a]pyridine-2-carboxylate The title compound was prepared from oxalyl chloride (1.86 ml, 19.54 mmol), Intermediate 117 (~70%, 3 g, 3.91 mmol), N,N-dimethylformamide (60.47 µl, 0.78 mmol) in DCM (25 mL) by the Method O (2.0 g, 89%). LCMS (ES⁺) RT 2.16 min, 565.0/567.0 (M+H)⁺.

Intermediate 119

Ethyl 7-bromo-1-[2-(difluoromethoxy)-4,5-difluorophenyl]-6-fluoro-3-oxo-2,3-dihydro-1H-cyclopenta[4,5]imidazo[1,2-a]pyridine-2-carboxylate

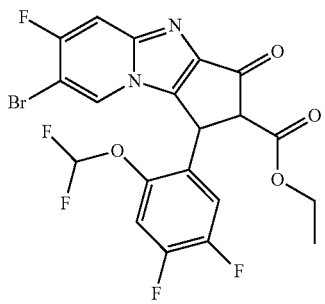 [SMILES: CCOC(=O)C1C(=O)c2nc3cc(F)c(Br)cn3c2C1c1cc(F)c(F)cc1OC(F)F]

The title compound was prepared from Intermediate 118 (1.96 g, 3.47 mmol), toluene (70 mL) and potassium 2-methylbutan-2-olate (3.11 ml, 5.55 mmol, 25% w/w in toluene) by the Method L (1.6 g, 58%). LCMS (ES⁺) RT 2.02 min, 519.0/521.0 (M+H)⁺.

Intermediate 120

7-bromo-1-[2-(difluoromethoxy)-4,5-difluorophenyl]-6-fluoro-1,2-dihydro-3H-cyclopenta[4,5]imidazo[1,2-a]pyridin-3-one

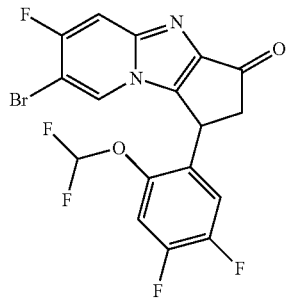 [SMILES: O=C1CC(c2cc(F)c(F)cc2OC(F)F)c2c1nc1cc(F)c(Br)cn21]

The title compound was prepared from Intermediate 119 (1.6 g, 2 mmol), DMSO (25 mL) and water (5 mL) by the Method M (512 mg, 51%). LCMS (ES⁺) RT 2.02 min, 447.0/449.0 (M+H)⁺.

Intermediate 121

7-bromo-1-[2-(difluoromethoxy)-4,5-difluorophenyl]-6-fluoro-2,3-dihydro-1H-cyclopenta[4,5]imidazo[1,2-a]pyridin-3-ol

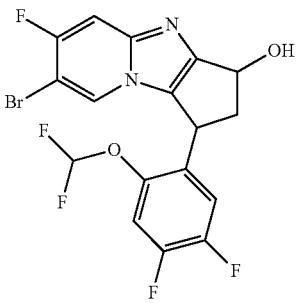 [SMILES: OC1CC(c2cc(F)c(F)cc2OC(F)F)c2c1nc1cc(F)c(Br)cn21]

The title compound was prepared from Intermediate 120 (512 mg, 1.03 mmol), 1M lithium tri-sec-butylborohydride in THF (1.03 ml) in THF (15 mL) by the Method B (354 mg, 76%). LCMS (ES⁺) RT 1.78 min, 449.0/451.0 (M+H)⁺.

Intermediate 122

3-[6-Bromo-2-(ethoxycarbonyl)-7-fluoroimidazo[1,2-a]pyridin-3-yl]-3-[2-(difluoromethoxy)-6-fluorophenyl]propanoic acid The title compound was prepared from ethyl 6-bromo-7-fluoro-3-iodoimidazo[1,2-a]pyridine-2-carboxylate (3.8 g, 13.24 mmol), 2,2-dimethyl-1,3-dioxane- 4,6-dione (3.82 g, 26.47 mmol), 2-(difluoromethoxy)-6-fluorobenzaldehyde (5.03 g, 26.47 mmol) and L-proline (152.39 mg, 1.32 mmol) in acetonitrile (30 mL) by the Method P (3.4 g, 33%). LCMS (ES⁺) RT 1.78 min, 519.0/521.0 (M+H)⁺.

Intermediate 123

Ethyl-6-bromo-3-{1-[2-(difluoromethoxy)-6-fluorophenyl]-3-ethoxy-3-oxopropyl}-7-fluoro imidazo[1,2-a]pyridine-2-carboxylate The title compound was prepared from oxalyl chloride (2.05 ml, 21.61 mmol), Intermediate 122 (3.4 g, 4.32 mmol), N,N-dimethylformamide (66.85 µl, 0.86 mmol) in DCM (25 mL) by the Method O (1.2 g, 44%). LCMS (ES⁺) RT 2.16 min, 547.0/549.0 (M+H)⁺.

Intermediate 124

Ethyl 7-bromo-1-[2-(difluoromethoxy)-6-fluorophenyl]-6-fluoro-3-oxo-2,3-dihydro-1H-cyclopenta[4,5]imidazo[1,2-a]pyridine-2-carboxylate

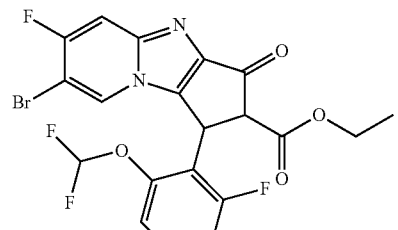

The title compound was prepared from Intermediate 123 (1.2 g, 2.13 mmol), toluene (50 mL) and potassium 2-methylbutan-2-olate in toluene (1.91 ml, 3.4 mmol) by the Method L (0.8 g, 56%). LCMS (ES⁺) RT 1.38 min, 501.0/503.0 (M+H)⁺.

Intermediate 125

7-bromo-1-[2-(difluoromethoxy)-6-fluorophenyl]-6-fluoro-1,2-dihydro-3H-cyclopenta[4,5]imidazo[1,2-a]pyridin-3-one

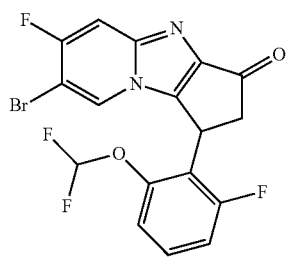 [SMILES: O=C1CC(c2c(F)cccc2OC(F)F)c2c1nc1cc(F)c(Br)cn21]

The title compound was prepared from Intermediate 124 (800 mg, 1.2 mmol), DMSO (8 mL) and water (2 mL) by the Method M (265 mg, 40%). LCMS (ES⁺) RT 1.24 min, 429.0/431.0 (M+H)⁺.

Intermediate 126

7-bromo-1-[2-(difluoromethoxy)-6-fluorophenyl]-6-fluoro-2,3-dihydro-1H-cyclopenta[4,5]imidazo[1,2-a]pyridin-3-ol

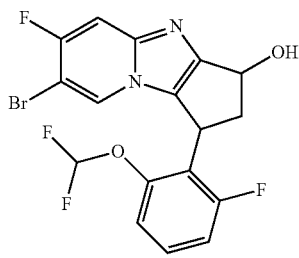 [SMILES: OC1CC(c2c(F)cccc2OC(F)F)c2c1nc1cc(F)c(Br)cn21]

The title compound was prepared from Intermediate 125 (265 mg, 0.48 mmol), 1M lithium tri-sec-butylborohydride in THF (0.48 ml) and THF (10 mL) by the Method B (170 mg, 79%). LCMS (ES⁺) RT 1.68 min, 431.0/433.0 (M+H)⁺.

Intermediate 127

3-[6-Bromo-2-(ethoxycarbonyl)-7-fluoroimidazo[1,2-a]pyridin-3-yl]-3-(3-chlorophenyl) propanoic acid The title compound was prepared from ethyl 6-bromo-7-fluoro-3-iodoimidazo[1,2-a]pyridine-2-carboxylate (3 g, 10.45 mmol), 2,2-dimethyl-1,3-dioxane-4,6-dione (3.01 g, 20.9 mmol), 3-chlorobenzaldehyde (2.94 g, 20.9 mmol) and L-proline (60.15 mg, 0.52 mmol) and MgSO₄ (2 g, 16.62 mmol) in acetonitrile (30 mL) by the Method P (4.6 g, 58%). LCMS (ES⁺) RT 1.96 min, 469.0/471.0 (M+H)⁺.

Intermediate 128

Ethyl 6-bromo-3-[1-(3-chlorophenyl)-3-ethoxy-3-oxopropyl]-7-fluoroimidazo[1,2-a]pyridine-2-carboxylate The title compound was prepared from oxalyl chloride (0.66 ml, 9.11 mmol), Intermediate 127 (4.6 g, 6.07 mmol) in EtOH (50 mL) by the Method O (2.9 g, 96%). LCMS (ES⁺) RT 2.23 min, 497.0/499.0 (M+H)⁺.

Intermediate 129

Ethyl 7-bromo-1-(3-chlorophenyl)-6-fluoro-3-oxo-2,3-dihydro-1H-cyclopenta[4,5]imidazo[1,2-a]pyridine-2-carboxylate

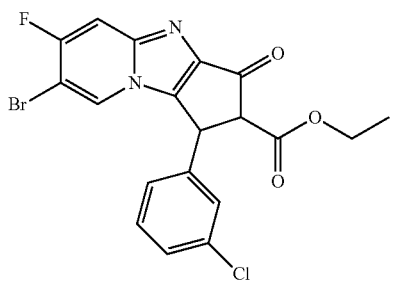 [SMILES: CCOC(=O)C1C(=O)c2nc3cc(F)c(Br)cn3c2C1c1cccc(Cl)c1]

The title compound was prepared from Intermediate 128 (2.9 g, 5.83 mmol), toluene (50 mL) and potassium 2-methylbutan-2-olate in toluene (5.23 ml, 9.32 mmol) by the Method L (540 mg, 15%). LCMS (ES⁺) RT 1.38 min, 451.0/453.0 (M+H)⁺.

Intermediate 130

7-bromo-1-(3-chlorophenyl)-6-fluoro-1,2-dihydro-3H-cyclopenta[4,5]imidazo[1,2-a]pyridin-3-one

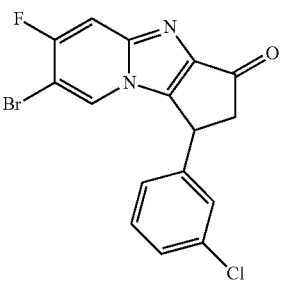 [SMILES: O=C1CC(c2cccc(Cl)c2)c2c1nc1cc(F)c(Br)cn21]

The title compound was prepared from Intermediate 129 (540 mg, 0.9 mmol), DMSO (8 mL) and water (2 mL) by the Method M (360 mg, 97%). LCMS (ES⁺) RT 1.29 min, 379.0/381.0 (M+H)⁺.

123

Intermediate 131

7-bromo-1-(3-chlorophenyl)-6-fluoro-2,3-dihydro-1H-cyclopenta[4,5]imidazo[1,2-a]pyridin-3-ol

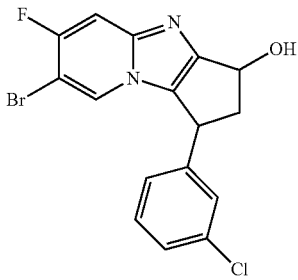 [SMILES: OC1CC(c2cccc(Cl)c2)c2c1nc1cc(F)c(Br)cn21]

The title compound was prepared from Intermediate 130 (360 mg, 0.87 mmol), 1M lithium tri-sec-butylborohydride in THF (0.87 ml) and THF (10 mL) by the Method B (260 mg, 62%). LCMS (ES+) RT 1.64 min, 381.0/383.0 (M+H)+.

Intermediate 132

3-[6-Bromo-2-(ethoxycarbonyl)-7-fluoroimidazo[1,2-a]pyridin-3-yl]-3-[5-chloro-2-(difluoromethoxy)phenyl]propanoic acid The title compound was prepared from ethyl 6-bromo-7-fluoro-3-iodoimidazo[1,2-a]pyridine-2-carboxylate (3 g, 10.45 mmol), 2,2-dimethyl-1,3-dioxane-4,6-dione (3.01 g, 20.9 mmol), 5-chloro-2-(difluoromethoxy)benzaldehyde (4.96 g, 24.03 mmol) and L-proline (60.15 mg, 0.52 mmol) and MgSO$_4$ (2 g, 16.62 mmol) in acetonitrile (30 mL) by the Method P (4.1 g, 53%). LCMS (ES+) RT 1.98 min, 535.0/537.0 (M+H)+.

Intermediate 133

Ethyl-6-bromo-3-{1-[5-chloro-2-(difluoromethoxy)phenyl]-3-ethoxy-3-oxopropyl}-7-fluoro imidazo[1,2-a]pyridine-2-carboxylate The title compound was prepared from oxalyl chloride (0.6 mL, 8.27 mmol), Intermediate 132 (4.1 g, 5.51 mmol) in EtOH (50 mL) by the Method O (2.0 g, 65%). LCMS (ES+) RT 2.19 min, 563.0/565.0 (M+H)+.

Intermediate 134

Ethyl 7-bromo-1-[5-chloro-2-(difluoromethoxy)phenyl]-6-fluoro-3-oxo-2,3-dihydro-1H-cyclopenta[4,5]imidazo[1,2-c]pyridine-2-carboxylate

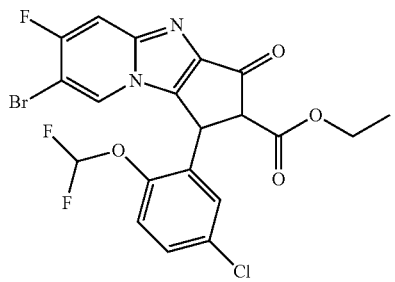 [SMILES: CCOC(=O)C1C(=O)c2nc3cc(F)c(Br)cn3c2C1c1cc(Cl)ccc1OC(F)F]

124

The title compound was prepared from Intermediate 133 (2.01 g, 3.57 mmol), toluene (50 mL) and potassium 2-methylbutan-2-olate in toluene (3.2 ml, 5.7 mmol) by the Method L (450 mg, 16%). LCMS (ES+) RT 1.38 min, 517.0/519.0 (M+H)+.

Intermediate 135

7-bromo-1-[5-chloro-2-(difluoromethoxy)phenyl]-6-fluoro-1,2-dihydro-3H-cyclopenta[4,5]imidazo[1,2-a]pyridin-3-one

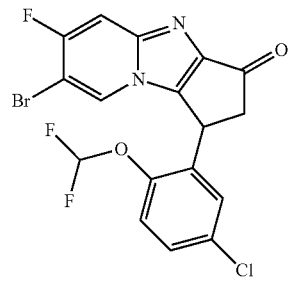 [SMILES: O=C1CC(c2cc(Cl)ccc2OC(F)F)c2c1nc1cc(F)c(Br)cn21]

The title compound was prepared from Intermediate 134 (450 mg, 0.56 mmol), DMSO (8 mL) and water (2 mL) by the Method M (275 mg, 99%). LCMS (ES+) RT 1.31 min, 445.0/447.0 (M+H)+.

Intermediate 136

7-bromo-1-[5-chloro-2-(difluoromethoxy)phenyl]-6-fluoro-2,3-dihydro-1H-cyclopenta[4,5]imidazo[1,2-a]pyridin-3-ol

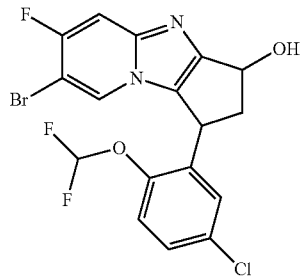

The title compound was prepared from Intermediate 135 (275 mg, 0.56 mmol), 1M lithium tri-sec-butylborohydride in THF (0.56 ml) and THF (10 mL) by the Method B (230 mg, 75%). LCMS (ES+) RT 1.77 min, 447.0/449.0 (M+H)+.

Intermediate 137

I-butyl [2-(5-{(1R,3R)-1-[2-(difluoromethoxy)phenyl]-6-fluoro-3-hydroxy-2,3-dihydro-1H-cyclopenta[4,5]imidazo[1,2-a]pyridin-7-yl}pyrimidin-2-yl)propan-2-yl]carbamate

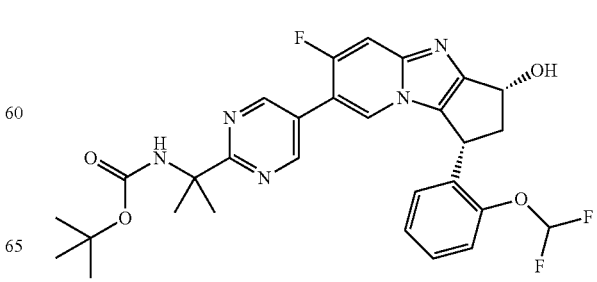

The title compound was prepared from Example 16 (150 mg, 0.31 mmol), Intermediate 89 (145 mg, 0.34 mmol), 2M sodium carbonate (0.46 mL), dioxane (3 mL) and dichloro[1,1'-bis(diphenylphosphinoferrocene]-palladium dichloromethane adduct (25 mg, 0.03 mmol) by the Method A (78 mg, 44%). $^1$H NMR (500 MHz, CDCl$_3$) δ 8.73 (d, J 1.4 Hz, 2H), 7.66 (d, J 7.1 Hz, 1H), 7.42 (d, J 10.9 Hz, 1H), 7.32-7.27 (m, 1H), 7.24-7.14 (m, 3H), 6.66 (dd, J 74.5, 72.9 Hz, 1H), 5.87 (s, 1H), 5.44 (dt, J 6.9, 3.4 Hz, 1H), 4.89 (dd, J 8.5, 4.0 Hz, 1H), 3.70 (d, J 3.8 Hz, 1H), 3.61 (dt, J 14.2, 8.2 Hz, 1H), 2.42 (dt, J 14.1, 3.6 Hz, 1H), 1.73 (s, 6H), 1.40 (s, 9H). LCMS (ES$^+$) RT 1.78 min, 570.0 (M+H)$^+$.

Intermediate 138

3-Methyl-1-[5-(4,4,5,5-tetramethyl-1,3,2-dioxaborolan-2-yl)pyrimidin-2-yl]azetidin-3-ol The title compound is prepared from 2-chloro-5-(4,4,5,5-tetramethyl-1,3,2-dioxaborolan-2-yl)pyrimidine and 3-methylazetidin-3-ol by the Method E. $^1$H (400 MHz, DMSO-d$_6$) 8.45 (s, 2H), 5.67 (s, 1H), 3.92 (m, 4H), 1.43 (s, 3H), 1.28 (s, 12H).

Intermediate 139

3-(trifluoromethyl)azetidin-3-ol

To a solution of 1-boc-3-azetidinone (11.3 g, 58.4 mmol) and (trifluoromethyl)trimethylsilane (9.22 g, 64.3 mmol) in THF (100 mL) cooled to ~−5° C. on an ice/brine bath was added portion wise caesium fluoride (9.77 g, 64.3 mmol). The resultant mixture was allowed to stir at r.t., TLC analysis after 4 hr indicated complete consumption of starting material and a less polar component. The reaction was quenched by the addition of saturated aqueous ammonium chloride solution (100 mL) and the aqueous phase extracted with EtOAc (3×100 mL). The organic phase was separated, dried over sodium sulphate, filtered and the volatiles were removed in vacuo to give a crude oil. The oil thus obtained was dissolved in DCM (100 mL) and trifluoroacetic acid (40 mL) added. The mixture was stirred at ambient temperature for four hours. The volatiles were removed in vacuo and the residue azeotroped with toluene (3×150 mL) to give the title compound trifluoroacetate salt as a brown solid (15 g). $^1$H NMR (400 MHz, d$_6$ DMSO): δ/ppm 9.48 (s, 2 H), 7.95 (d, J 0.3 Hz, 1 H), 4.28 (d, J 13.1 Hz, 2 H), 4.06 (m, 2 H).

The compound thus obtained was used in the subsequent reaction without further purification.

Intermediate 140

1-[5-(4,4,5,5-tetramethyl-1,3,2-dioxaborolan-2-yl)pyrimidin-2-yl]-3-(trifluoromethyl)azetidin-3-ol To a solution of Intermediate 2 (12 g) in MeCN (150 mL) was added triethylamine (30 mL) and 2-chloro-5-(4,4,5,5-tetramethyl-1,3,2-dioxaborolan-2-yl)pyrimidine (16 g) and the reaction stirred at 65° C. for 18 hr. The solvents were removed in vacuo and the solid residue triturated and washed with distilled water to give a beige solid and dried under high vacuum to give the title compound as a beige solid (18.5 g). $^1$H NMR (300 MHz, d$_6$DMSO): δ/ppm 8.53 (2H, s), 7.46 (1H, s), 4.33-4.31 (2H, m), 4.10-4.08 (2H, m), 1.29 (12H, s). LCMS (ES$^+$) RT 1.14 min, 346.0 (M+H)$^+$.

Intermediate 141

1-(5-bromopyrimidin-2-yl)-3,3-difluorocyclobutan-1-ol

The title compound was prepared from 2.5M n-BuLi in hexane (6.08 mL, 15.20 mmol), 5-bromo-2-iodopyrimidine (4.24 g, 14.88 mmol), toluene (45 mL) and 3,3-difluorocyclobutanone (1.74 g, 16.37 mmol) by the Method F (329 mg, 8.3%). $^1$H NMR (500 MHz, CDCl$_3$) δ 8.83 (s, 2H), 4.72 (s, 1H), 3.54-3.18 (m, 2H), 3.16-2.83 (m, 2H). LCMS (ES$^+$) RT 1.50 min, 267.0 (M+H)$^+$.

Intermediate 142

5-bromo-2-{3,3-difluoro-1-[(trimethylsilyl)oxy]cyclobutyl}pyrimidine

The title compound was prepared from Intermediate 141, (0.33 g, 1.24 mmol), trimethyl silyl chloride (0.175 ml, 1.36 mmol), imidazole (0.101 g, 1.49 mmol) in dichloromethane (5 mL) by the Method G (349 mg, 83%). 1H NMR (500 MHz, CDCl$_3$) δ 8.82 (s, 2H), 3.47 (ddd, J 14.7, 12.3, 9.3 Hz, 2H), 2.99 (ddd, J 14.6, 13.6, 12.1 Hz, 2H), 0.00 (s, 9H). LCMS (ES$^+$) RT 2.23 min, 233.0 (M+H)$^+$.

Intermediate 143

2-{3,3-difluoro-1-[(trimethylsilyl)oxy]cyclobutyl}-5-(tetramethyl-1,3,2-dioxaborolan-2-yl)pyrimidine The title compound was prepared from Intermediate 142 (329 mg, 0.98 mmol), diboron pinacol ester (372 mg, 1.46 mmol), potassium acetate (287 mg, 2.93 mmol) in dioxane (6 mL), dichloro[1,1'-bis(diphenylphospinoferrocene]-palladium dichloromethane adduct (40 mg, 0.05 mmol) by the Method H (200 mg, 53%). $^1$H NMR (500 MHz, CDCl$_3$) δ 9.04 (s, 2H), 3.58-3.47 (m, 2H), 2.98 (td, J 14.2, 11.7 Hz, 2H), 1.37 (s, 6H), 1.26 (s, 16H). LCMS (ES$^+$) RT 1.89 min, 302.0 (M+H)$^+$.

Intermediate 144

(1R)-7-[2-(1-{[tert-butyl(dimethyl)silyl]oxy}-3-hydroxy-3-methylcyclobutyl)pyrimidin-5-yl]-1-[2-(difluoromethoxy)phenyl]-6-fluoro-3-methyl-2,3-dihydro-1H-cyclopenta[4,5]imidazo[1,2-a]pyridin-3-ol

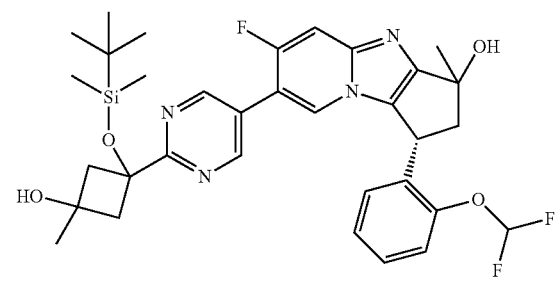 [SMILES: CC1(O)CC(O[Si](C)(C)C(C)(C)C)(c2ncc(-c3cn4c5c(nc4cc3F)C(C)(O)C[C@@H]5c3ccccc3OC(F)F)cn2)C1]

The title compound was prepared from Example 20 (0.6 g, 1.4 mmol), Intermediate 165 (0.65 g, 1.54 mmol), PdCl$_2$.dppf (0.11 g, 0.14 mmol), 2M K$_2$CO$_3$ in water (2.11 mL) in 1,4-dioxane (12 mL) by the Method A (0.484 g, 54%).

Intermediate 145

Ethyl 6-bromoimidazo[1,2-a]pyridine-2-carboxylate 5-bromopyridin-2-amine (60 g, 347 mmol) was dissolved in 1,4-Dioxane (1011 ml), and magnesium sulfate (125 g, 1040 mmol) was added followed by ethyl 3-bromo-2-oxo-propanoate (84 g, 386 mmol, 54 mL). The reaction mixture was heated to 80° C. for 18 h. The reaction mixture was cooled down to r.t. and triethyl amine (43.7 g, 432 mmol, 60 mL) was added, and the resulting slurry was diluted with a mixture of 10% EtOH in DCM (500 mL) and stirred vigorously for 10 minutes. The precipitate was filtered off, and washed with 10% EtOH in DCM (500 ml), until only MgSO$_4$ remained on the glass filter. The filtrate was concentrated in vacuo, and stirred in water (1.5 l), using a mechanical stirrer. The precipitate was filtered off, and washed thoroughly with water and dried in vacuo yielding the title compound as a beige solid (90.0 g, 93%). LCMS (ES$^+$) RT 1.71 min, 269.0/271.0 (M+H)$^+$.

Intermediate 146

3-(6-bromo-2-ethoxycarbonyl-imidazo [1,2-a]pyridin-3-yl)-3-[5-chloro-2-(difluoromethoxy)phenyl] propanoic acid The title compound was prepared from Intermediate 145 (76 g, 282 mmol), 2,2-dimethyl-1,3-dioxane- 4,6-dione (81 g, 564 mmol), 5-chloro-2-(difluoromethoxy)benzaldehyde (131 g, 564 mmol) and L-proline (1.62 g, 14.11 mmol) and MgSO$_4$ (102 g, 847 mmol) in acetonitrile (1.0 mL) by the Method P (115 g, 79%). LCMS (ES$^+$) RT 2.04 min, 517.0/519.0 (M+H)$^+$.

Intermediate 147

Ethyl 6-bromo-3-[1-[5-chloro-2-(difluoromethoxy) phenyl]-3-ethoxy-3-oxo-propyl]imidazo[1,2-a]pyridine-2-carboxylate The title compound was prepared from thionyl chloride (50.0 g, 420 mmol), Intermediate 146 (108.7 g, 210 mmol), in EtOH (1 L) by the Method O (94.5 g, 82%). LCMS (ES$^+$) RT 2.20 min, 545.0/547.0 (M+H)$^+$.

Intermediate 148

Ethyl 7-bromo-1-[5-chloro-2-(difluoromethoxy) phenyl]-3-oxo-2,3-dihydro-1H-cyclopenta[4,5]imidazo[1,2-a]pyridine-2-carboxylate

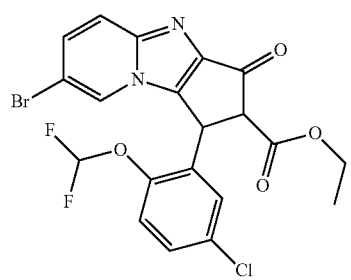 [SMILES: CCOC(=O)C1C(=O)c2nc3ccc(Br)cn3c2C1c1cc(Cl)ccc1OC(F)F]

The title compound was prepared from Intermediate 147 (72 g, 132 mmol), toluene (860 mL) and sodium tert-butoxide in toluene (31.7 g, 330 mmol) by the Method L (31.6 g, 48%). LCMS (ES$^+$) RT 2.12 min, 499.0/501.0 (M+H)$^+$.

Intermediate 149

5-bromo-2-cyclobutylpyrimidine-4-carboxylic acid

To a stirred suspension of cyclobutanecarboximidamide hydrochloride (1:1) (2 g, 14.9 mmol) in ethanol (16 mL) was added 2 M sodium ethoxide in ethanol (15 mL, 29.7 mmol) at r.t. The suspension was heated at 50° C. for 5 minutes before the drop wise addition of a solution of mucobromic acid (2.68 g, 10.4 mmol) in ethanol (8 mL) at 50° C. The reaction mixture was stirred at 50° C. for 30 minutes, further 2 M sodium ethoxide in ethanol (7.5 mL, 14.9 mmol) was added and the reaction stirred for a further 15 minutes at 50° C. The cooled reaction mixture was concentrated in vacuo, the resulting residue dissolved in 2 N hydrochloric acid (40 mL) and extracted with dichloromethane (3×100 mL). The combined organic extracts were washed with brine (100 mL), dried (Na$_2$SO$_4$) and reduced in vacuo. The residue was partitioned between EtOAc (100 mL) and 2 N sodium hydroxide solution (50 mL), the aqueous phase was separated and washed with EtOAc (100 mL). The combined aqueous extracts were acidified to pH 4 using 2 M hydrochloric acid, and re-extracted into dichloromethane (3×100 mL). The combined organic extracts were dried (Na$_2$SO$_4$) and reduced in vacuo to afford the title compound as a pale orange solid (830 mg, 19%). $^1$H NMR (250 MHz, MeOD) δ ppm 8.97 (s, 1H), 3.81 (p, J 8.1 Hz, 1H), 2.55-2.35 (m, 4H), 2.18-2.05 (m, 1H), 2.01-1.86 (m, 1H).

Intermediate 150

5-bromo-2-cyclobutylpyrimidine

Intermediate 149 (830 mg, 2.91 mmol) in p-xylene (10 mL) was heated at 140° C. for 5 h. The cooled reaction mixture was concentrated in vacuo. The residue was purified by chromatography, (SiO$_2$, 0-100% EtOAc in Heptane) to afford the title compound as a pale yellow oil (250 mg, 40%). $^1$H NMR (500 MHz, CDCl$_3$) δ ppm 8.71 (s, 2H), 3.78 (p, J 8.8 Hz, 1H), 2.49-2.34 (m, 4H), 2.17-2.02 (m, 1H), 2.00-1.86 (m, 1H).

Intermediate 151

2-cyclobutyl-5-(tetramethyl-1,3,2-dioxaborolan-2-yl) pyrimidine

The title compound was prepared from Intermediate 150 (250 mg, 1.17 mmol), diboron pinacol ester (447 mg, 1.76 mmol), potassium acetate (345 mg, 3.52 mmol) and dioxane (5 mL), dichloro[1,1'-bis(diphenylphospinoferrocene]-palladium dichloromethane adduct (48 mg, 0.06 mmol) by the Method H (310 mg, 90%). $^1$H NMR (500 MHz, CDCl$_3$) δ ppm 8.95 (s, 2H), 3.84 (p, J 8.6 Hz, 1H), 2.51-2.43 (m, 2H), 2.40 (q, J 9.8, 8.9 Hz, 2H), 2.09 (h, J 9.2 Hz, 1H), 1.94 (q, J 9.1 Hz, 1H), 1.35 (s, 12H).

Intermediate 152

8-(5-bromopyrimidin-2-yl)-1,4-dioxaspiro[4.5]decan-8-ol

The title compound was prepared from 5-bromo-2-iodopyrimidine (10 g, 34.4 mmol), toluene (200 mL), 2.5 M n-butyllithium in hexane (16 mL, 40 mmol) and 1,4-dioxaspiro[4.5]decan-8-one (6.14 g, 38.2 mmol) in dry toluene (40 mL) by the Method F (5.96 g, 38%). $^1$H NMR (500 MHz, CDCl$_3$) δ ppm 8.77 (s, 2H), 4.17 (s, 1H), 4.00 (t, J 3.3 Hz, 4H), 2.43-2.29 (m, 2H), 2.17-2.06 (m, 2H), 1.73 (t, J 15.4 Hz, 4H).

Intermediate 153

5-bromo-2-{1,4-dioxaspiro[4.5]dec-7-en-8-yl}pyrimidine

Intermediate 152 (2 g, 4.44 mmol), phosphorus oxychloride (0.58 mL, 6.23 mmol) and pyridine (10 mL) were stirred at room temperature for 4 h. The reaction mixture was concentrated in vacuo. And ice was added cautiously, followed by 10% aqueous sodium hydroxide solution (20 mL), and then extracted into dichloromethane (3×40 mL). The combined organic layer was washed with brine (40 mL), dried (Na$_2$SO$_4$) and concentrated in vacuo. The crude product was purified by chromatography, (SiO$_2$, 0-40% EtOAc in Heptane) yielding the title compound as a pale yellow oil (1.05 g). $^1$H NMR (500 MHz, CDCl$_3$) δ ppm 8.69 (s, 2H), 7.21 (dt, J 4.1, 2.4 Hz, 1H), 4.02 (s, 4H), 2.81 (ddt, J 6.5, 4.3, 1.9 Hz, 2H), 2.54 (d, J 3.6 Hz, 2H), 1.92 (t, J 6.6 Hz, 2H).

Intermediate 154

2-{1,4-dioxaspiro[4.5]dec-7-en-8-yl}-5-(tetramethyl-1,3,2-dioxaborolan-2-yl)pyrimidine The title compound was prepared from Intermediate 153 (1.05 g, 3.53 mmol), diboron pinacol ester (1.35 g, 5.30 mmol), potassium acetate (1.05 g, 10.06 mmol), dioxane (10 mL), dichloro[1,1'-bis(diphenylphospinoferrocene]-palladium dichloromethane adduct (145 mg, 0.17 mmol) by the Method H (1.36 g, 99%). $^1$H NMR (500 MHz, CDCl$_3$) δ ppm 8.92 (s, 2H), 7.27 (d, J 4.2 Hz, 1H), 4.02 (s, 4H), 2.86 (ddt, J 6.5, 4.3, 1.9 Hz, 2H), 2.57 (d, J 3.4 Hz, 2H), 1.93 (t, J 6.6 Hz, 2H), 1.35 (s, 12H).

Intermediate 155

(1R,3R)-1-[2-(difluoromethoxy)phenyl]-7-[2-(1,4-dioxaspiro[4.5]dec-7-en-8-yl)pyrimidin-5-yl]-6-fluoro-2,3-dihydro-1H-cyclopenta[4,5]imidazo[1,2-a]pyridin-3-ol

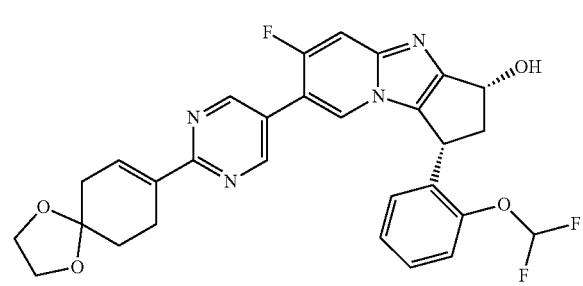 [SMILES: O[C@@H]1C[C@H](c2ccccc2OC(F)F)c2c1nc1cc(F)c(-c3cnc(C4=CCC5(CC4)OCCO5)nc3)cn21]

The title compound was prepared from Example 16 (300 mg, 0.62 mmol), intermediate 154 (286 mg, 0.74 mmol), 2 M solution of sodium carbonate in water (0.93 mL, 1.85 mmol), dioxane (3 mL) and dichloro[1,1'-bis(diphenylphospinoferrocene]-palladium dichloromethane adduct (50 mg, 0.06 mmol) by the Method A (146 mg, 40%). $^1$H NMR (500 MHz, CDCl$_3$) δ ppm 8.70 (d, J 1.1 Hz, 2H), 7.65 (d, J 7.1 Hz, 1H), 7.41 (d, J 10.9 Hz, 1H), 7.29 (d, J 8.1 Hz, 2H), 7.25-7.22 (m, 1H), 7.21-7.12 (m, 2H), 6.66 (dd, J 74.6, 72.9 Hz, 1H), 5.44 (d, J 4.6 Hz, 1H), 4.88 (dd, J 8.5, 3.9 Hz, 1H), 4.03 (s, 4H), 3.77 (s, 1H), 3.65-3.53 (m, 1H), 2.92-2.78 (m, 2H), 2.57 (s, 2H), 2.43 (dt, J 14.1, 3.5 Hz, 1H), 1.94 (t, J 6.5 Hz, 2H).

Intermediate 156

(1R,3R)-1-[2-(difluoromethoxy)phenyl]-7-[2-(1,4-dioxaspiro[4.5]dec-8-yl)pyrimidin-5-yl]-6-fluoro-2,3-dihydro-1H-cyclopenta[4,5]imidazo[1,2-a]pyridin-3-ol

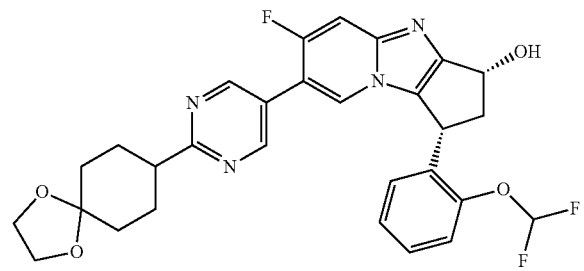 [SMILES: O[C@@H]1C[C@H](c2ccccc2OC(F)F)c2c1nc1cc(F)c(-c3cnc(C4CCC5(CC4)OCCO5)nc3)cn21]

A 0.05 M Solution of Intermediate 155 (120 mg, 0.22 mmol) in EtOH (4.32 mL) and triethylamine (30 μL, 0.22 mmol) was passed through the H-cube 10 times using 10% Pd/C Cat-cart at 1.0 mL/min, 50° C. and 100 bar pressure under controlled hydrogen. The crude product was purified by chromatography, (SiO$_2$, 20-100% EtOAc in Heptane followed by 1-50% MeOH in EtOAc) to afford the title compound as an off-white solid (38 mg, 23%). LCMS (ES$^+$) RT 1.11 min, 553.0 (M+H)$^+$.

INTERMEDIATE 157

4-(5-{(1R,3R)-1-[2-(difluoromethoxy)phenyl]-6-fluoro-3-hydroxy-2,3-dihydro-1H-cyclopenta[4,5]imidazo[1,2-a]pyridin-7-yl}pyrimidin-2-yl)cyclohexanone

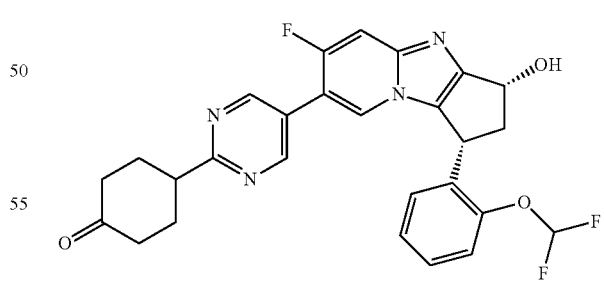

Intermediate 156 (70 mg, 0.09 mmol, 70% purity), 4 N hydrochloric acid (0.60 mL) and THF (2.0 mL) were charged in a sealed tube. The mixture was heated at 50° C. for 4 h. The reaction mixture was diluted with saturated aqueous sodium carbonate solution (5 mL) and extracted with EtOAc (3×10 mL). The combined organic phase was washed with water (10 mL) followed by brine (10 mL), dried (Na$_2$SO$_4$) and reduced in vacuo. The residue was purified by chromatography, (SiO$_2$, 20-100% EtOAc in heptane followed by 1-100% MeOH in EtOAc) yielding the title compound as a pale yellow solid (43 mg, 91%). $^1$H NMR (500 MHz, CDCl$_3$) δ ppm 8.72 (d, J 1.4 Hz, 2H), 7.68 (d, J 7.1 Hz, 1H), 7.44 (d, J 10.9 Hz, 1H), 7.31-7.27 (m, 1H), 7.25 (d, J 1.5 Hz, 1H), 7.21-7.08 (m, 2H), 6.67 (dd, J 74.8, 72.6 Hz, 1H), 5.46 (dd, J 7.3, 3.0 Hz, 1H), 4.89 (dd, J 8.5, 3.9 Hz, 1H), 4.45 (d, J 23.2 Hz, 1H), 3.67-3.55 (m, 1H), 3.41 (tt, J 10.7, 3.6 Hz, 1H), 2.60-2.47 (m, 4H), 2.47-2.35 (m, 3H), 2.21 (ddt, J 16.8, 11.9, 5.3 Hz, 2H). LCMS (ES$^1$) RT 1.05 min, 509.0 (M+H)$^+$.

Intermediate 158

2,2-dichloro-3-oxocyclobutyl 2,2-dimethylpropanoate

To a stirred mixture of vinyl pivalate (30 g, 234 mmol) and zinc (31 g, 474 mmol) in ether (250 mL) was added a solution of 2,2,2-trichloroacetyl chloride (34 mL, 304 mmol) in ether (250 mL) drop wise over 2.5 h in a water bath while maintaining the reaction temperature between 15-30° C. Reaction was filtered through Celite and washed through with ethyl acetate (200 mL). The filtrate was washed with water (200 mL), brine (200 mL), dried over sodium sulfate and concentrated under vacuum to afford the title compound as an orange liquid. (68 g, 97%). $^1$H NMR (500 MHz, CDCl$_3$) δ ppm 5.40 (dd, J 8.4, 6.2 Hz, 1H), 3.70 (dd, J 18.9, 8.4 Hz, 1H), 3.39 (dd, J 18.9, 6.2 Hz, 1H), 1.28 (s, 9H).

Intermediate 159

3-oxocyclobutyl 2,2-dimethylpropanoate

Zinc (74 g, 1.1 mol) was added to acetic acid (200 mL) with stirring and the suspension was cooled in an ice bath. Intermediate 158 (68 g, 228 mmol) in acetic acid (300 mL) was added drop wise over 2 h. Upon completion of addition, the reaction was warmed to r.t. and stirred for 1.5 h. The reaction was filtered washed with DCM (100 mL). The filtrate was diluted with EtOAc (800 mL) and washed sequentially with water (3×250 mL), saturated aqueous NaHCO$_3$ solution (3×250 mL) and brine (50 mL). The organic phase was dried over sodium sulfate and concentrated in vacuo. The residue was purified by chromatography (SiO$_2$, 0-10% EtOAc in heptane) yielding the title compound as a clear colourless oil (11 g, 28%). $^1$H NMR (500 MHz, CDCl$_3$) 5.26-5.19 (m, 1H), 3.51-3.40 (m, 2H), 3.19-3.07 (m, 2H), 1.22 (s, 9H).

Intermediate 160

3-(5-bromopyrimidin-2-yl)-3-hydroxycyclobutyl 2,2-dimethylpropanoate

The title compound was prepared from 5-bromo-2-iodopyrimidine (16.7 g, 58.8 mmol), DCM (200 mL), 2.5 M n-BuLi in hexane in hexane (23.5 mL), Intermediate 159 (10 g, 58.8 mmol) in DCM (50 mL) by the Method F yielding the title compound as a yellow solid (7.6 g, 35%). $^1$H NMR (500 MHz, CDCl$_3$) 8.78 (s, 2H), 5.22-5.14 (m, 1H), 3.03-2.93 (m, 2H), 2.67-2.58 (m, 2H), 1.22 (s, 9H).

Intermediate 161

1-(5-bromopyrimidin-2-yl)cyclobutane-1,3-diol

Intermediate 160 (6 g, 16.4 mmol) was dissolved in MeOH (120 mL) and K$_2$CO$_3$ (11.3 g, 82 mmol) was added and the reaction stirred for 18 h at r.t. The reaction was diluted with DCM (400 mL) and washed with water (150 mL). The aqueous phase was extracted with DCM (200 mL). The combined organic extracts were dried over sodium sulfate and concentrated in vacuo to afford the title compound as an off-white solid (2.94 g, 73%). $^1$H NMR (500 MHz, DMSO-d$_6$) 8.98 (s, 2H), 5.63 (s, 1H), 5.08 (d, J 6.2 Hz, 1H), 4.09-3.92 (m, 1H), 2.87-2.79 (m, 2H), 2.28-2.14 (m, 2H).

Intermediate 162

3-(5-bromopyrimidin-2-yl)-3-hydroxycyclobutan-1-one

To a stirred solution of Intermediate 161 (2 g, 8.1 mmol) in DCM (200 mL) was added Dess-Martin periodinane (4.1 g, 9.8 mmol). The reaction was stirred for 18 h and the resulting suspension diluted with DCM (100 mL) and washed with saturated aqueous NaHCO$_3$ solution (100 mL). The aqueous layer was re-extracted with DCM (100 mL) and the combined organic extracts dried over sodium sulfate and concentrated in vacuo. The crude residue was purified by chromatography (SiO$_2$, 0-30% EtOAc in heptane) to afford the title compound as an off white solid (1.37 g, 69%). $^1$H NMR (500 MHz, DMSO-d$_6$) 9.04 (s, 2H), 6.41 (s, 1H), 3.69-3.55 (m, 2H), 3.37-3.21 (m, 2H).

Intermediate 163

3-(5-bromopyrimidin-2-yl)-3-[(tert-butyldimethylsilyl)oxy]cyclobutan-1-one

The title compound was prepared from Intermediate 196 (1.37 g, 5.64 mmol), DMF (20 mL), 1H-imidazole (1.9 g, 28.18 mmol) and tert-butyl(chloro)dimethylsilane (2.0 g, 13.5 mmol) by the Method G (1.6 g 79%). $^1$H NMR (500 MHz, DMSO-d$_6$) 9.06 (s, 2H), 3.78-3.66 (m, 2H), 3.44-3.34 (m, 2H), 0.88 (s, 9H), 0.00 (s, 6H).

Intermediate 164

3-(5-bromopyrimidin-2-yl)-3-[(tert-butyldimethylsilyl)oxy]-1-methylcyclobutan-1-ol Intermediate 163 (1.35 g, 3.78 mmol) was dissolved in dry ether (40 mL) under N$_2$ with stirring and cooled to 0° C. using an ice bath. 3M MeMgBr in diethylether (2.52 mL) was added drop wise and reaction stirred for 30 minutes at 0° C. The reaction was quenched with saturated aqueous NH$_4$Cl solution (20 mL) and then water (20 mL). The mixture was extracted with EtOAc (2×50 mL), dried over sodium sulfate and concentrated in vacuo. The crude residue was purified by chromatography (SiO$_2$, 0-100% DCM in heptane) to afford the title compound as a clear oil (1.19 g, 84%). Major isomer ~70% abundance: $^1$H NMR (500 MHz, CDCl$_3$) 8.79 (s, 2H), 3.10-3.03 (m, 2H), 2.59-2.51 (m, 2H), 1.18 (s, 3H), 0.87 (s, 9H), ~0.14 (s, 6H). Minor isomer ~30% abundance: $^1$H NMR (500 MHz, CDCl$_3$) 8.79 (s, 2H), 2.78-2.63 (m, 4H), 1.49 (s, 3H), 0.95 (s, 9H), 0.04 (s, 6H).

Intermediate 165

3-[(tert-butyldimethylsilyl)oxy]-1-methyl-3-[5-tetramethyl-1,3,2-dioxaborolan-2-yl)pyrimidin-2-yl]-cyclobutan-1-ol Prepared from Intermediate 164 by the Method H. $^1$H NMR (500 MHz, CDCl$_3$) 9.02 (s, 2H), 3.15-3.08 (m, 2H), 2.58-2.50 (m, 2H), 1.37 (s, 12H), 1.27 (s, 3H), 0.87 (s, 9H), −0.16 (s, 6H).

Intermediate 166

(1R,3R)-7-bromo-1-[2-(difluoromethoxy)phenyl]-6-fluoro-3-methoxy-2,3-dihydro-1H-cyclopenta[4,5]imidazo[1,2-a]pyridine The title compound was prepared from Example 16 by a procedure analogous to Example 14.

Intermediate 167 and 168

(1R)-7-bromo-1-[5-chloro-2-(difluoromethoxy)phenyl]-6-fluoro-1,2-dihydro-3H-cyclopenta[4,5]imidazo[1,2-a]pyridin-3-ol and (1S)-7-bromo-1-[5-chloro-2-(difluoromethoxy)phenyl]-6-fluoro-1,2-dihydro-3H-cyclopenta[4,5]imidazo[1,2-a]pyridin-3-ol

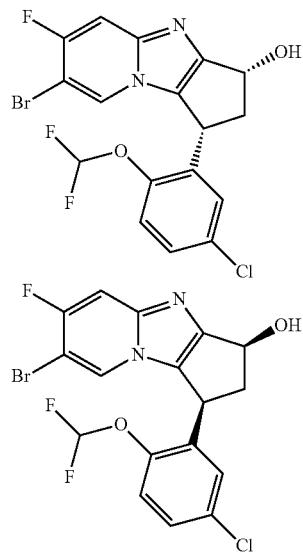

The title compounds were prepared from Examples 213 and 214 respectively, by Method B. LCMS (ES$^+$) RT 1.77 min, 447.0/449.0 (M+H)$^+$.

Intermediate 169

4-(5-bromopyrimidin-2-yl)-4-hydroxycyclohexan-1-one

To a stirred solution of Intermediate 152 (1.11 g, 2.96 mmol) in THF (4.5 mL) was added 4N HCl (1.5 mL). The mixture was heated to 50° C. in a pressure tube for 6.5 h. The cooled reaction mixture was added to a mixture of EtOAc (20 mL) and saturated NaHCO$_3$ (20 mL). The organic layer was separated and the aqueous layer was re-extracted with EtOAc (2×5 mL). The combined organic layers were washed with a 1:1 mixture of water and brine (4 mL), brine (4 mL), dried over magnesium sulfate, filtered and the solvent concentrated in vacuo. The crude product was purified by column chromatography (SiO$_2$, 0-50% EtOAc in heptane) yielding the title compound as a pale yellow solid (537 mg, 64%). LCMS (ES$^+$) RT 1.36 min, 271.0/273.0 (M+H)$^+$.

Intermediate 170

4-(5-bromopyrimidin-2-yl)-4-[(trimethylsilyl)oxy]cyclohexan-1-one

The title compound is prepared from Intermediate 169 (2.35 g, 8.06 mmol), 1H-imidazole (0.84 g, 12.37 mmol), dry DCM (60 mL) and chloro(trimethyl)silane (1.2 mL, 9.27 mmol) by the Method G (2.68 g, 94%). LCMS (ES$^+$) RT 2.28 min, 343.0/345.0 (M+H)$^+$.

Intermediate 171

4-(5-bromopyrimidin-2-yl)-1-methyl-4 [(trimethylsilyl)oxy]cyclohexan-1-ol

To a stirred solution of Intermediate 170 (482 mg, 1.33 mmol) in dry THF (20 mL) was added 1.4M bromo(methyl) magnesium in toluene/THF (1.5 mL) over 5 minutes at r.t. The reaction mixture was stirred for 21 h and then quenched with saturated NH$_4$Cl (1.0 mL). The volatiles were then concentrated in vacuo; EtOAc (10 mL) and water (10 mL) were then added, the organic layer was separated and the aqueous layer was re-extracted with EtOAc (2×5 mL). The combined organic layers were washed with a 1:1 mixture of water and brine (10 mL), brine (5 mL), dried over magnesium sulfate, filtered and the solvent concentrated in vacuo to give of the title compound (0.48 g, 100%). LCMS (ES$^+$) RT 2.20 min, 269.0/270.0 (M+H)$^+$.

Intermediate 172 AND 173

Isomer A: cis-1-(5-bromopyrimidin-2-yl)-4 methyl-cyclohexane-1,4-diol and Isomer B:trans-1-(5-bromopyrimidin-2-yl)-4 methylcyclohexane-1,4-diol To a solution of Intermediate 171 (27.78 g, 77.31 mmol) in dry THF (1 L) was added 1M N,N,N-tributylbutan-1-aminium fluoride in THF (90 mL) over 10 minutes under nitrogen gas at r.t. The reaction was stirred for 90 minutes and then the volatiles were concentrated in vacuo; EtOAc (200 mL), water (100 mL) and brine (100 mL) were then added. The organic layer was separated and the aqueous layer was re-extracted with EtOAc (4×100 mL). The organic layers were then combined and washed with a 1:1 mixture of water and brine (200 mL), brine (100 mL), dried over magnesium sulphate (150 mL), filtered and the solvent concentrated in vacuo. The oil was purified by column chromatography (SiO$_2$, 0-100% EtOAc in heptane): 5.7 g of the first eluted product was dissolved in DCM and adsorbed onto silica gel (20 g), then further purified by column chromatography (SiO$_2$, 0-60% EtOAc in heptane) to give (2.90 g, 13%) of the title compound, Isomer A:Intermediate 172 as a pink coloured solid; 4.5 g of the second eluted product was dissolved in DCM and adsorbed onto silica gel (21 g), then further purified by column chromatography (SiO$_2$, 17-100% EtOAc in heptane) to give (3.23 g, 12%) of the title compound Isomer B:Intermediate 173. Intermediate 172: LCMS (ES⁺) RT 0.95 min, 287.0/289.0 (M+H)⁺. Intermediate 173: LCMS (ES⁺) RT 3.11 min, 287.0/289.0 (M+H)⁺.

Intermediate 174

Isomer A: 1-methyl-4-[5-(tetramethyl-1,3,2-dioxaborolan-2-yl)pyrimidin-2-yl]cyclohexane-1,4-diol The title compound was prepared from Intermediate 172 (2.9 g, 10.1 mmol), 4,4,4%4%5,5,5',5'-octamethyl-2,2'-bi-1,3,2-dioxaborolane (3.12 g, 12.29 mmol), potassium acetate (3.20 g, 32.61 mmol), 1,4-dioxane (120 mL), bis[3-(diphenylphosphanyl)cyclopenta-2,4-dien-1-yl]iron; dichloromethane; dichloropalladium (0.41 g, 0.51 mmol) by the Method H (1.06 g, 24%). LCMS (ES⁺) RT 0.91 min, 253.0 (M+H)⁺.

Intermediate 175

Isomer B: 1-methyl-4-[5-(tetramethyl-1,3,2-dioxaborolan-2-yl)pyrimidin-2-yl]cyclohexane-1,4-diol The title compound was prepared from Intermediate 173 (3.23 g, 9 mmol), 4,4,4%4%5,5,5',5'-octamethyl-2,2'-bi-1,3,2-dioxaborolane (2.82 g, 11.11 mmol), potassium acetate (2.84 g, 28.94 mmol), 1,4-dioxane (130 mL), bis[3-(diphenylphosphanyl)cyclopenta-2,4-dien-1-yl]iron; dichloromethane; dichloropalladium (0.38 g, 0.47 mmol) by the Method H (1.12 g, 28%). LCMS (ES⁺) RT 0.80 min, 253.0 (M+H)⁺.

Intermediate 176

Tert-butyl-2-(41R,3R)-7-bromo-1-(5-chloro-2-(difluoromethoxy)phenyl)-2,3-dihydro-1H-cyclopenta[4,5]imidazo[1,2-a]pyridin-3-yl)oxy)acetate

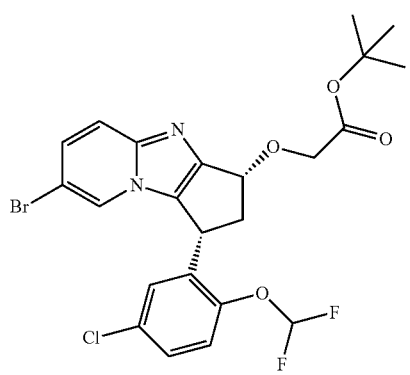 [SMILES: CC(C)(C)OC(=O)CO[C@@H]1C[C@H](c2cc(Cl)ccc2OC(F)F)c2c1nc1ccc(Br)cn21]

The title compound was prepared from Example 190 (50 mg, 0,116 mmol), THF (4 ml)., sodium hydride (10 mg, 0.256 mmol; 60% in oil) and tert.-butyl bromoacetate (93 mg, 0.466 mmol) in THF (0.25 ml) by the Method Q (42 mg, 66%). LCMS [M 1b](ES⁺) RT 1.94 min, 543.1 (M+H)⁺.

Intermediate 177

2-(difluoromethoxy)-3-fluorobenzaldehyde

The title compound was prepared from potassium hydroxide (80.09 g, 1427.43 mmol) in water (175 mL), MeCN (175 mL), 3-fluoro-2-hydroxybenzaldehyde (10 g, 71.37 mmol), diethyl [bromo(difluoro)methyl]phosphonate (13.95 ml, 78.51 mmol) by the Method N (4.55 g, 45%). 1H NMR (500 MHz, CDCl₃) δ ppm 10.35 (s, 1H), 7.73 (dt, J 7.8, 1.4 Hz, 1H), 7.45 (ddd, J 10.0, 8.2, 1.6 Hz, 1H), 7.37 (td, J 8.0, 4.7 Hz, 1H), 6.90-6.57 (m, 1H).

Intermediate 178

3-[6-bromo-2-(ethoxycarbonyl)-7-fluoroimidazo[1,2-a]pyridin-3-yl]-3-[2-(difluoromethoxy)-3-fluorophenyl]propanoic acid The title compound was prepared from ethyl 6-bromo-7-fluoro-3-iodoimidazo[1,2-a]pyridine-2-carboxylate (3.12 g, 10.88 mmol), 2,2-dimethyl-1,3-dioxane- 4,6-dione (3.14 g, 21.76 mmol), Intermediate 177 (4.55 g, 21.76 mmol) and L-proline (152.39 mg, 1.32 mmol) in acetonitrile (45 mL) by the Method P (6.5 g). The material was taken forward to the next step without purification.

Intermediate 179

Ethyl 6-bromo-3-[1-[2-(difluoromethoxy)-3-fluorophenyl]-3-ethoxy-3-oxo-propyl]-7-fluoro-imidazo[1,2-a]pyridine-2-carboxylate The title compound was prepared from Intermediate 178 (6.51 g, 7.53 mmol), EtOH (80 mL), and thionyl dichloride (1.09 ml, 15.0 mmol) by the Method O (2.13 g, 48.1%). 1H NMR (500 MHz, CDCl₃) δ ppm 8.69 (d, J 6.4 Hz, 1H), 7.56 (d, J 8.0 Hz, 1H), 7.36 (d, J 8.3 Hz, 1H), 7.22 (td, J 8.2, 5.3 Hz, 1H), 7.10 (ddd, J 10.0, 8.4, 1.4 Hz, 1H), 6.68 (dd, J 76.5, 73.7 Hz, 1H), 5.37 (dd, J 10.3, 5.1 Hz, 1H), 4.40 (qd, J 7.1, 4.6 Hz, 2H), 4.10-4.00 (m, 2H), 3.94 (dd, J 17.0, 10.3 Hz, 1H), 3.30 (dd, J 17.0, 5.1 Hz, 1H), 1.40 (t, J 7.1 Hz, 3H), 1.16 (t, J 7.1 Hz, 3H). LCMS (ES⁺) RT 1.42 min, 547.0/549.0 (M+H)⁺.

Intermediate 180

Ethyl 7-bromo-1-[2-(difluoromethoxy)-3-fluorophenyl]-6-fluoro-3-oxo-2,3-dihydro-1H-cyclopenta[4,5]imidazo[1,2-a]pyridine-2-carboxylate

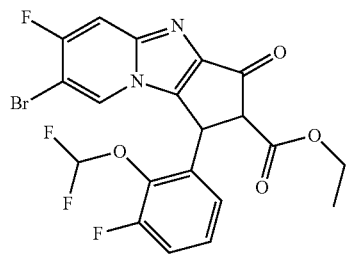 [SMILES: CCOC(=O)C1C(=O)c2nc3cc(F)c(Br)cn3c2C1c1cccc(F)c1OC(F)F]

The title compound was prepared from Intermediate 179 (2.13 g, 3.62 mmol), toluene (40 mL) and potassium 2-methylbutan-2-olate (2.74 g, 5.43 mmol) by the Method L (480 mg, 23%). LCMS (ES⁺) RT 1.98 min, 501.0/503.0 (M+H)⁺.

Intermediate 181

7-bromo-1-[2-(difluoromethoxy)-3-fluorophenyl]-6-fluoro-1,2-dihydro-3H-cyclopenta[4,5]imidazo[1,2-a]pyridin-3-one

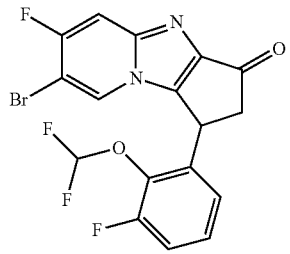 [SMILES: O=C1CC(c2cccc(F)c2OC(F)F)c2c1nc1cc(F)c(Br)cn21]

The title compound was prepared from Intermediate 180 (0.48 g, 0.83 mmol), DMSO (8 mL) and water (2 mL) by the Method M (267 mg, 75%). LCMS (ES$^+$) RT 1.99 min, 429.0/431.0 (M+H)$^+$.

Intermediate 182

7-bromo-1-[2-(difluoromethoxy)-3-fluorophenyl]-6-fluoro-2,3-dihydro-1H-cyclopenta[4,5]imidazo[1,2-a]pyridin-3-ol

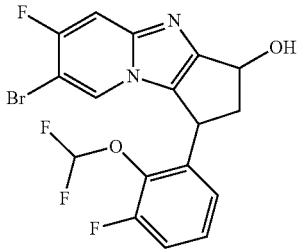 [SMILES: OC1CC(c2cccc(F)c2OC(F)F)c2c1nc1cc(F)c(Br)cn21]

The title compound was prepared from Intermediate 181 (0.61 g, 1.27 mmol), 1M lithium tri-sec-butylborohydride in THF (1.521 mL) and THF (10 mL) by the Method B (460 mg, 65%). LCMS (ES$^+$) RT 1.17 min, 431.0/433.0 (M+H)$^+$.

Intermediate 183

[2-[(1S,4S)-2-tert-butoxycarbonyl-2,5-diazabicyclo[2.2.1]heptan-5-yl]pyrimidin-5-yl]boronic acid The title compound was prepared from 2-chloropyrimidine-5-boronic acid (1.01 g, 6.38 mmol), (1S,4S)-2-boc-2,5-diazabicyclo[2.2.1]heptane (132 mg, 0.6325 mmol), ethanol (30 mL, 510 mmol) and triethylamine (0.9 mL, 6 mmol) by the Method E (1.22 g, 60%). δ$_H$ (300 MHz, DMSO-d$_6$) 8.67 (s, 2 H), 4.86-4.97 (m, 2 H), 4.39-4.51 (m, 2 H), 3.12-3.59 (m, 2 H), 1.86-1.97 (m, 2 H), 1.30-1.44 (m, 9 H).

Intermediate 184

(1R)-7-{2-[(1S,4S)-2-tert-butoxycarbonyl-2,5-diazabicyclo[2.2.1]hept-2-yl]pyrimidin-5-yl}-1-[2-(difluoromethoxy)phenyl]-3-methyl-2,3-dihydro-1H-cyclopenta[4,5]imidazo[1,2-a]pyridin-3-ol The title compound was prepared from Example 15 (501 mg, 1.22 mmol), Intermediate 183 (520 mg, 1.63 mmol), 1,4-dioxane (11 mL), 2 M aq sodium carbonate 2 mL) and 1,1'-bis(diphenylphosphino)ferrocene-palladium(II)dichloride (47 mg, 0.064 mmol) by the Method A (466 mg, 63%). δ$_{11}$ (300 MHz, DMSO-d$_6$) 8.54 (s, 2 H), 7.97 (d, 1 H, J 1.5 Hz), 7.65 (dd, 1 H, J 9.5, 0.8 Hz), 7.50 (dd, 1 H, J 9.4, 1.7 Hz), 7.36 (t, 1 H, J 74.1 Hz), 7.23-7.34 (m, 2 H), 7.10-7.17 (m, 1 H), 6.98 (dd, 1 H, J 7.7, 1.5 Hz), 5.26 (s, 1 H), 4.85-4.91 (m, 1 H), 4.79 (dd, 1 H, J 8.3, 4.3 Hz), 4.41-4.51 (m, 1 H), 3.49-3.58 (m, 1 H), 3.33-3.45 (m, 2 H), 3.09-3.20 (m, 2 H), 2.37 (dd, 1 H, J 13.4, 4.5 Hz), 1.88-1.96 (m, 2 H), 1.55 (s, 3 H), 1.39 (s, 9 H). NMR assignment for the major diastereoisomer. Material is a mixture (83:17) of the two diastereoisomers. LCMS (ES$^+$) 605 (M+H)$^+$, RT 2.34 minutes.

Intermediate 185

5-bromo-2-methanesulfinylpyridine

NaIO$_4$ (9.56 g, 44.69 mmol) was added as a slurry in water (10 mL) to a stirred solution of 5-bromo-2-(methylsulfanyl)pyridine (2.4 g, 11.76 mmol) in acetic acid (40 mL) at r.t. The mixture was stirred at r.t. for 2 h. After this time, a colourless precipitate had formed. The mixture was treated with water (50 mL) upon which the precipitate dissolved. The aqueous acidic mixture was basified through addition of saturated aqueous potassium carbonate solution and the product extracted with EtOAc (3×50 mL). The combined organic phase was washed with 10% aqueous sodium thiosulfate solution (50 mL), dried (Na$_2$SO$_4$) and reduced in vacuo to give the crude product as an amber glass (2.52 g) which solidified on standing. Purification by chromatography (SiO$_2$, 0-100% EtOAc in heptane) afforded the title compound as a pale yellow oil (2.04 g, 79%). δH (500 MHz, CDCl$_3$) 8.68 (d, J 2.0 Hz, 1H), 8.08 (dd, J 8.3, 2.2 Hz, 1H), 7.93 (d, J 8.3 Hz, 1H), 2.84 (s, 3H).

Intermediates 186-188

The following intermediates were prepared from the intermediates listed or from commercially available starting

| Number | Name | Intermediate used | Method |
|---|---|---|---|
| 186 | N-[(5-bromopyridin-2-yl)(methyl)oxo-$\lambda^6$-sulfanylidene]-2,2,2-trifluoro-acetamide $\delta_H$ (500 MHz, CDCl$_3$) 8.79 (d, J 1.4 Hz, 1H), 8.22-8.19 (m, 1H), 8.18 (dd, J 8.4, 2.0 Hz, 1H), 3.56 (s, 3H). | 185 | Int 73 |
| 187 | (5-bromopyridin-2-yl)(imino)methyl-$\lambda^6$-sulfanone $\delta_H$ (500 MHz, DMSO-d6) 8.88 (d, J 2.2 Hz, 1H), 8.37 (dd, J 8.4, 2.3 Hz, 1H), 8.01 (d, J 8.4 Hz, 1H), 4.54 (s, 1H), 3.17 (s, 3H). | 186 | Int 74 |
| 188 | imino(methyl)[5-(tetramethyl-1,3,2-dioxaborolan-2-yl)pyridin-2-yl]-$\lambda^6$-sulfanone $\delta$H (250 MHz, CDCl$_3$) 8.77 (s, 1H), 8.30 (d, J 6.5 Hz, 1H), 8.04 (d, J 5.3 Hz, 1H), 3.25 (s, 3H), 1.36 (s, 12H). | 187 | H |

Example 1

7-bromo-1-[2-(difluoromethoxy)phenyl]-1,2-dihydro-3H-cyclopenta[4,5]imidazo[1,2-a]pyridin-3-one

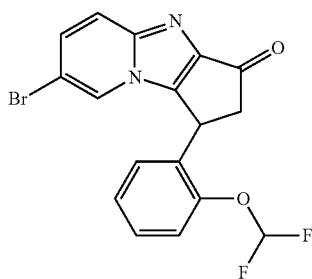 [SMILES: O=C1CC(c2ccccc2OC(F)F)c2c1nc1ccc(Br)cn21]

A solution of Intermediate 6 (10.0 g, 21.5 mmol) in DMSO (50 mL) and water (10 mL) was stirred at 100° C. for 48 h. The reaction mixture was cooled and poured onto iced water. The precipitate was then filtered off and dried in vacuo to yield the title compound as a cream solid (8.2 g, 97%). $\delta_H$ (DMSO-d$_6$, 400 MHz) 8.27 (d, J 0.7 Hz, 1 H), 7.73 (d, J 9.8 Hz, 1 H), 7.55 (dd, J 9.8 Hz, J 1.9 Hz, 1 H), 7.40 (m, 1 H), 7.26 (m, 2 H), 7.17 (t, J 7.6 Hz, 1 H), 6.92 (d, J 7.4 Hz, 1 H), 5.14 (dd, J 7.0 Hz, J 1.9 Hz, 1 H), 3.60 (dd, J 18.2 Hz, J 7.1 Hz, 1 H), 2.75 (dd, J 18.2 Hz, J 2.1 Hz, 1 H). LCMS (ES$^+$) RT 1.42 min, 393.0/395.0 (M+H)$^+$.

Examples 2 and 3

(R)-7-Bromo-1-(2-difluoromethoxy-phenyl)-1,2-dihydro-cyclopenta[4,5]imidazo[1,2-a]pyridin-3-one and (S)-7-Bromo-1-(2-difluoromethoxy-phenyl)-1,2-dihydro-cyclopenta[4,5]imidazo[1,2-a]pyridin-3-one

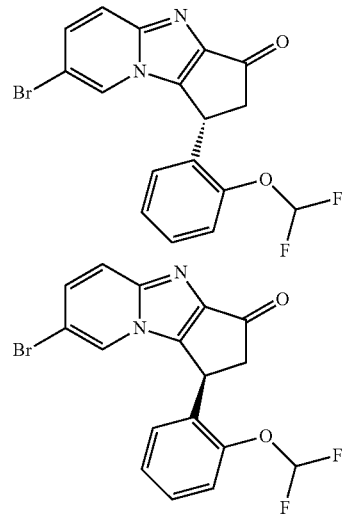

The title compounds were isolated by chiral separation of Example 1 under LC conditions on Chiralpak AD (100*500 mm*mm, flow 300 mL/min, 30° C., heptane-EtOH (1:1), injection of 84 mL solution at a concentration of 6.2 g/L). The first eluting enantiomer (RT 22 min) was collected and the fractions were evaporated to yield Example 2. The second eluting enantiomer (RT 32 min) was collected and the fractions were evaporated to yield the Example 3.

Example 4

Method A

1-[2-(difluoromethoxy)phenyl]-7-[2-(5-oxo-1,4-diazepan-1-yl)pyrimidin-5-yl]-1,2-dihydro-3H-cyclopenta[4,5]imidazo[1,2-a]pyridin-3-one

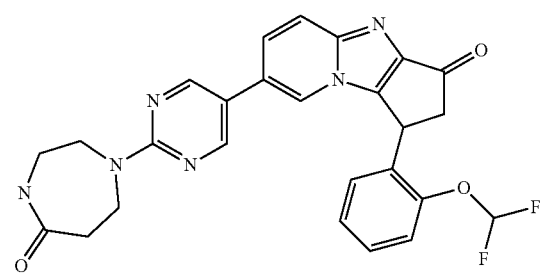 [SMILES: O=C1CCN(c2ncc(-c3ccc4nc5c(n4c3)C(c3ccccc3OC(F)F)CC5=O)cn2)CCN1]

A mixture of Example 1 (74 mg, 0.188 mmol), [2-(5-oxo-1,4-diazepan-1-yl)pyrimidin-5-yl]boronic acid (0.06218 g, 0.2635 mmol), Pd(dppf)Cl₂ DCM adduct (0.00392 g, 0.00470 mmol), and 2M sodium carbonate (1.5 mL) in 1,4-dioxane (4 mL) was de-gassed and stirred at 110° C. for 2.5 h. The reaction was cooled and diluted with EtOAc, washed with water, the aq. layer was extracted once more using EtOAc, organic extracts were dried over (magnesium sulfate) and concentrated in vacuo. The crystalline solid was triturated in EtOAc, filtered, washed with more EtOAc, then hexane and dried to give the title compound as pale yellow solid (66 mg, 70%). $\delta_H$ (DMSO-d₆, 400 MHz) 8.64 (s, 2 H), 8.22 (s, 1 H), 7.84 (m, 1 H), 7.78 (m, 1 H), 7.67 (m, 1 H), 7.38 (m, 1 H), 7.28 (t, J 72, 76 Hz, 1H), 7.15 (m, 1 H), 7.27 (m, 1H), 6.89 (m, 1 H), 5.17 (d, J 5.4 Hz, 1 H), 3.93 (m, 4H), 3.62 (m, 1 H), 3.29 (m, 2 H), 3.20 (m, 2 H), 2.77 (dd, J 18.2 Hz, J 1.6 Hz, 1 H). LCMS (ES⁺) RT 1.25 min, 505.0 (M+H)⁺.

Example 5

Method B (1R,3R)-7-bromo-1-[2-(difluoromethoxy)phenyl]-2,3-dihydro-1H-cyclopenta[4,5]imidazo[1,2-a]pyridin-3-ol

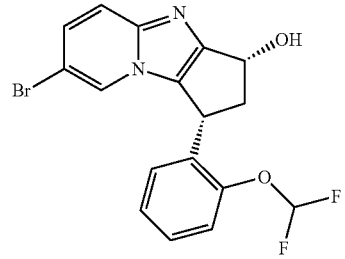

Lithium tri-sec-butylborohydride (0.041 mL, 1 M in THF) was added to a stirred solution of Example 2 (51 mg, 0.13 mmol) in dry THF (2 mL) at −78° C. under argon. After 30 minutes, the solution was diluted with MeOH and a 1 M aq. solution of sodium hydroxide was added. The solution was extracted with EtOAc, the organic layer was dried over magnesium sulfate, concentrated in vacuo and the resulting residue was purified by mass directed preparative HPLC, yielding the title compound as a white solid (16 mg, 31%). ¹H NMR (400 MHz, CDCl₃) δ 7.72 (d, J 0.5 Hz, 1 H), 7.51 (d, J 9.7 Hz, 1 H), 7.29 (ddd, J 8.6 Hz, J 6.7 Hz, J 2.4 Hz, 1 H), 7.12-7.23 (m, 4 H), 6.67 (dd, J 74.2 Hz, J 73.0 Hz, 1 H), 5.87 (s, 1 H), 5.47 (dd, J 7.2 Hz, J 2.4 Hz, 1 H), 4.84 (dd, J 8.6 Hz, J 4.0 Hz, 1H), 3.60 (dt, J 14.3 Hz, J 7.8 Hz, 1 H), 2.41 (dt, J 13.9 Hz, J 3.1 Hz, 1 H). LCMS (ES⁺) RT 3.6 min, 395.0/397.0 (M+H)⁺.

Example 6

(3Z)-7-bromo-1-[2-(difluoromethoxy)phenyl]-N-hydroxy-1,2-dihydro-3H-cyclopenta[4,5]imidazo[1,2-a]pyridin-3-imine

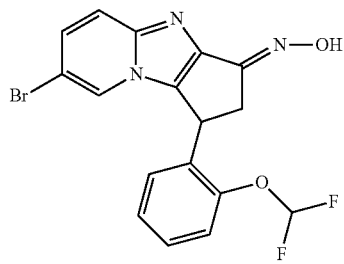 [SMILES: O/N=C1\CC(c2ccccc2OC(F)F)c2c1nc1ccc(Br)cn21]

To a solution of Example 1 (0.1 g, 0.25 mmol) in EtOH (2 mL), pyridine (0.2 mL) and hydroxylamine hydrochloride (0.026 g, 0.38 mmol) was added, and the reaction mixture was heated to 65° C. for 30 minutes. The reaction mixture was cooled to r.t., partitioned between EtOAc (50 mL) and water (50 mL). The organic phase was separated and washed with water (10 mL), brine (10 mL), dried over (sodium sulfate), filtered and concentrated in vacuo to give a solid. Washing with Et₂O gave the title compound as a beige solid (0.094 g, 91%). LCMS (ES⁺) RT 1.43 min, 408.0/410.0 (M+H)⁺.

Example 7

Method C 1-(5-{1-[2-(difluoromethoxy)phenyl]-3-hydroxy-2,3-dihydro-1H-cyclopenta[4,5]imidazo[1,2-a]pyridin-7-yl}pyrimidin-2-yl)-1,4-diazepan-5-one

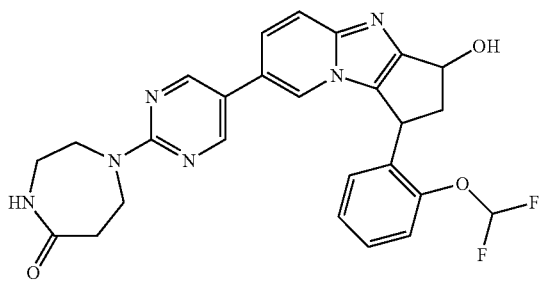 [SMILES: O=C1CCN(c2ncc(-c3ccc4nc5c(n4c3)C(c3ccccc3OC(F)F)CC5O)cn2)CCN1]

To a suspension of Example 4 (0.055 g, 0.11 mmol) in MeOH (0.5 mL) at r.t. was added THF to give a solution. To this was added sodium borohydride (0.004 g, 0.11 mmol) and the reaction mixture stirred at r.t. for 1 h. Ammonium chloride (2 mL) was added, the mixture was separated into EtOAc (3×5 mL) and organics washed with brine (5 mL), dried over (sodium sulfate), filtered and concentrated in vacuo to give a white solid, this was washed with DCM yielding the title compound (0.039 g, 71%). LCMS (ES⁺) RT 1.62 min, 507.0 (M+H)⁺.

Example 8

7-bromo-1-[2-(difluoromethoxy)phenyl]-3-methyl-2,3-dihydro-1H-cyclopenta[4,5]imidazo[1,2-a]pyridin-3-ol

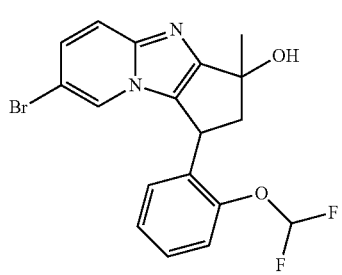 [SMILES: CC1(O)CC(c2ccccc2OC(F)F)c2c1nc1ccc(Br)cn21]

Methylmagnesium bromide (0.48 mL, 1.44 mmol) was added to a solution of Example 1 (0.24 g, 0.61 mmol) in Et$_2$O (5 mL) at −78° C. The reaction was stirred at r.t. for 18 h. The reaction mixture was treated with a sat. aq. solution of sodium bicarbonate and partitioned with EtOAc, the organics were extracted and dried over magnesium sulfate, and concentrated in vacuo. The residue was purified by preparative HPLC yielding the title compound as a white solid (9 mg, 3.6%). $^1$H NMR (DMSO-d$_6$) δ 8.00 (dd, J$_1$ 1.9 Hz, J$_2$ 0.7 Hz, 1 H), 7.57 (m, 1 H), 7.31 (m, 4 H), 7.15 (td, J$_1$ 7.6 Hz, J$_2$ 1.4 Hz, 1 H), 6.92 (dd, J$_1$ 7.7 Hz, J$_2$ 1.6 Hz, 1 H), 5.29 (s, 1 H), 4.76 (dd, J$_1$ 8.5 Hz, J$_2$ 4.4 Hz, 1 H), 3.11 (dd, J$_1$ 13.3 Hz, J$_2$ 8.5 Hz, 1 H), 2.33 (dd, J$_1$ 13.4 Hz, J$_2$ 4.5 Hz, 1 H), 1.53 (s, 3 H). LCMS (ES$^+$) RT 1.42 min, 409.0/411.0 (M+H)$^+$.

Example 9

7-Bromo-1-(2-difluoromethoxy-phenyl)-6-fluoro-1,2-dihydro-cyclopenta[4,5]imidazo[1,2-a]pyridin-3-one

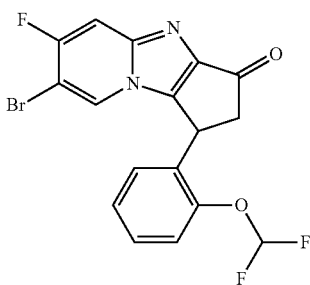 [SMILES: O=C1CC(c2ccccc2OC(F)F)c2c1nc1cc(F)c(Br)cn21]

A solution of Intermediate 12 (8.6 g, 17.7 mmol) in DMSO (200 mL) and water (20 mL) was stirred at 100° C. for 48 h. The reaction mixture was cooled and poured onto iced water. The precipitate was filtered off and dried in vacuo to yield the title compound as a cream solid (6.2 g, 76%). δ$_H$ (CDCl$_3$, 300 MHz) 7.83 (d, J 6.4 Hz, 1H), 7.44 (d, J 8.6 Hz, 1H), 7.41-7.31 (m, 1H), 7.29-7.23 (m, 1H), 7.18 (t, J 7.5 Hz, 1H), 6.86 (dd, J 7.7, 1.3 Hz, 1H), 6.65 (t, J 73.1 Hz, 1H), 5.12 (dd, J 7.0, 2.2 Hz, 1H), 3.64 (dd, J 18.4, 7.0 Hz, 1H), 2.92 (dd, J 18.4, 2.3 Hz, 1H). LCMS (ES$^+$) RT 2.89 min, 411.0/413.0 (M+H)$^+$.

Example 10

(1S,3S)-7-bromo-1-[2-(difluoromethoxy)phenyl]-2,3-dihydro-1H-cyclopenta[4,5]imidazo[1,2-a]pyridin-3-ol

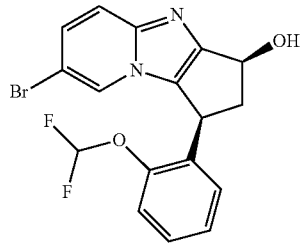 [SMILES: O[C@H]1C[C@@H](c2ccccc2OC(F)F)c2c1nc1ccc(Br)cn21]

The title compound was prepared from Example 3 (2 g, 5.086 mmol, 1 eq) and lithium tri-sec-butylborohydride by the Method B (1.68 g, 83%). $^1$H NMR (400 MHz, CDCl$_3$) δ 7.72 (s, 1 H), 7.53 (m, J 13.0 Hz, 1 H), 7.22 (m, 5 H), 6.67 (m, 1 H), 5.48 (dd, J 7.3 Hz, J 3.0 Hz, 1 H), 4.84 (dd, J 8.5 Hz, J 4.0 Hz, 1 H), 3.60 (m, 1 H), 2.42 (m, 1 H). LCMS (ES$^+$) RT 1.43 min, 395.0/397.0 (M+H)$^+$.

Example 11

7-bromo-1-[2-(difluoromethoxy)phenyl]-2,3-dihydro-1H-cyclopenta[4,5]imidazo[1,2-a]pyridin-3-ol

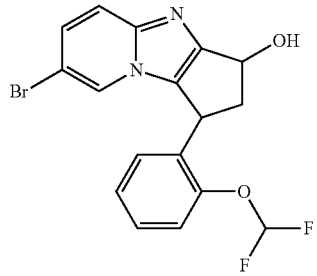 [SMILES: OC1CC(c2ccccc2OC(F)F)c2c1nc1ccc(Br)cn21]

The title compound was prepared from Example 1(0.05 g, 0.12 mmol) and sodium borohydride (0.005 g, 0.14 mmol) by the Method C (0.03 g, 64%). LCMS (ES$^1$) RT 1.43 min, 395.0/397.0 (M+H)$^+$.

Example 12 and 13

(S)-7-Bromo-1-(2-difluoromethoxy-phenyl)-6-fluoro-1,2-dihydro-cyclopenta[4,5]imidazo[1,2-a]pyridin-3-one; (R)-7-Bromo-1-(2-difluoromethoxy-phenyl)-6-fluoro-1,2-dihydro-cyclopenta[4,5]imidazo[1,2-a]pyridin-3-one

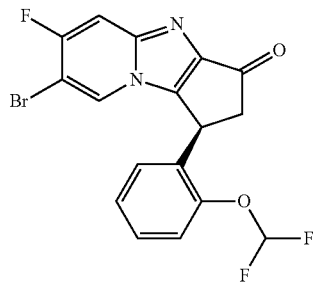

-continued

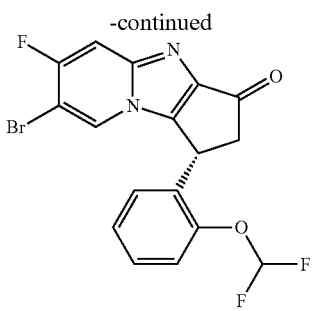

The title compounds were isolated by chiral separation of Example 9 under LC conditions on LUX cell-4 (76*265 mm*mm, flow 200 mL/min, 30° C., MeOH 100%, injection of 78 ml, solution at a concentration of 25 g/L). The first eluting enantiomer (RT 9 min) was collected and the fractions were evaporated to yield 880 mg of Example 12. The second eluting enantiomer (RT 14 min) was collected and the fractions were evaporated to yield 880 mg Example 13.

Example 14

(1R,3R)-7-Bromo-1-(2-difluoromethoxy-phenyl)-3-methoxy-2,3-dihydro-1H-cyclopenta[4,5]imidazo[1,2-a]pyridine

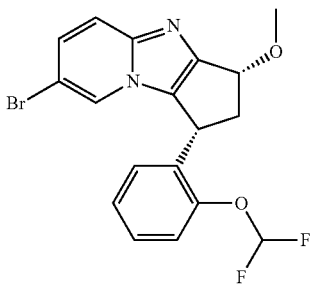 [SMILES: CO[C@@H]1C[C@H](c2ccccc2OC(F)F)c2c1nc1ccc(Br)cn21]

Example 5 (1.33 g, 3.36 mmol) was dissolved in THF (40 mL) under nitrogen. The mixture was then cooled to 0° C. and NaH (60% in mineral oil, 296 mg, 7.40 mmol) was added and the mixture was stirred for 20 minutes. Iodomethane (0.84 mL, 13.46 mmol) was then added at 0° C. and the mixture was stirred at r.t. for 30 minutes. Further iodomethane (0.42 mL, 6.73 mmol) was added at r.t. and the mixture was stirred for 30 minutes. The mixture was diluted with water (30 mL) and extracted with EtOAc (3×50 mL). The combined organic phases were washed with brine (50 mL), dried over sodium sulfate and concentrated in vacuo. The residue was purified by flash column chromatography (SiO$_2$, 20-100% EtOAc in heptane) to afford 1.25 g (90%) of the title compound as a white solid. $^1$H NMR (500 MHz, CDCl$_3$) δ ppm 7.79 (s, 1H), 7.63 (d, J 8.9 Hz, 1H), 7.31 (td, J 8.0, 7.2, 2.0 Hz, 2H), 7.24-7.11 (m, 3H), 6.69 (dd, J 74.2, 73.1 Hz, 1H), 4.94 (dd, J 7.3, 2.7 Hz, 1H), 4.85 (dd, J 8.7, 3.5 Hz, 1H), 3.67 (s, 3H), 3.57-3.46 (m, 1H), 2.41 (dt, J 14.3, 3.1 Hz, 1H). LCMS (ES$^+$) RT 1.90 min, 409.0/411.0 (M+H)$^+$.

Example 15

(R)-7-Bromo-1-(2-difluoromethoxy-phenyl)-3-methyl-2,3-dihydro-1H-cyclopenta[4,5]imidazo[1,2-a]pyridin-3-ol

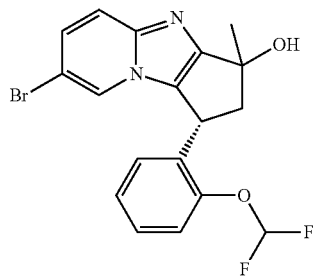 [SMILES: CC1(O)C[C@H](c2ccccc2OC(F)F)c2c1nc1ccc(Br)cn21]

To a solution of Example 2 (500 mg, 1.27 mmol) in toluene (25 mL) at −78° C. under an atmosphere of nitrogen was introduced methylmagnesium bromide (2.7 mL of a 1.4M solution in THF/toluene, 3.8 mmol) over 5 minutes. After 1 h at this temperature, the reaction mixture was re-treated with methylmagnesium bromide (0.7 mL of a 1.4M solution in THF/toluene, 1.0 mmol) and diluted with THF (10 mL). The reaction mixture was warmed to 0° C. over 1 h, whereupon MeOH (1 ml) was introduced drop wise. Once the reaction mixture had warmed to r.t., it was concentrated under reduced pressure and the residue was re-suspended in EtOAc (30 mL). The suspension was washed with 2M sodium carbonate (10 mL) and the organic phase dried over sodium sulfate. The filtrate was filtrated and concentrated to afford 493 mg (79%) of the title compound as a 78:22 mixture of epimers in favour of the 3R-stereoisomer. LCMS (ES+) RT 2.28 min, 409.0/411.0 (M+H)+.

Example 16

(1R,3R)-7-Bromo-1-(2-difluoromethoxy-phenyl)-6-fluoro-2,3-dihydro-1H-cyclopenta[4,5]imidazo[1,2-a]pyridin-3-ol

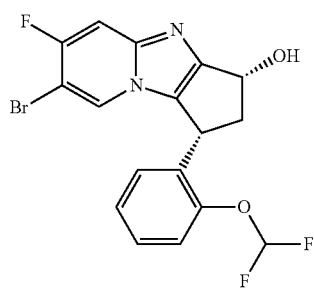 [SMILES: O[C@@H]1C[C@H](c2ccccc2OC(F)F)c2c1nc1cc(F)c(Br)cn21]

The title compound was prepared from Example 13 (400 mg, 0.97 mmol) and 1M lithium tri-sec-butylborohydride solution in THF (1.4 mL) by the Method B, (97 mg, 24%). LCMS (ES$^+$) RT 2.52 min, 413.0/415.0 (M+H)$^+$.

Example 17

(R)-7-Bromo-1-(2-difluoromethoxy-phenyl)-6-fluoro-2,3-dihydro-1H-cyclo penta[4,5]imidazo[1,2-a]pyridine

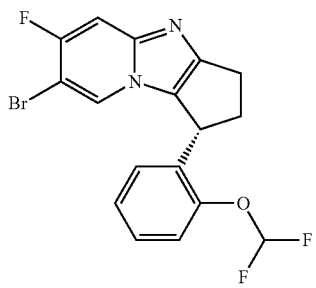 [SMILES: Fc1cc2nc3c(n2cc1Br)[C@@H](c1ccccc1OC(F)F)CC3]

Example 16 (165 mg, 0.32 mmol) was dissolved in MeCN (8 mL) under nitrogen. The mixture was then heated to 80° C., iodo(trimethyl)silane (0.45 mL, 3.20 mmol) was added drop wise and the mixture was stirred at 80° C. for 90 minutes. Further iodo(trimethyl)silane (0.45 mL, 3.20 mmol) was added drop wise at 80° C. and stirred for 90 minutes before drop wise addition of final portion of iodo (trimethyl)silane (0.45 mL, 3.20 mmol) and stirred for 90 minutes. The mixture was diluted with water (5 mL) and extracted with DCM (10 mL). The organic phase was washed with water (5 mL) followed by a sat. sodium bicarbonate solution in water (5 mL), sat. sodium thiosulfate solution in water (5 mL), brine (5 mL), then dried over sodium sulfate and concentrated in vacuo. The crude product was purified by flash column chromatography (SiO$_2$, 20-100% EtOAc in heptane then 1-100% MeOH in EtOAc) to afford 32 mg (24%) of the title compound as a pale yellow oil. LCMS (ES$^+$) RT 1.68 min, 397.0/399.0 (M+H)$^+$.

Example 18

(R)-7-Bromo-1-(2-difluoromethoxy-phenyl)-6-fluoro-3-trifluoromethyl-2,3-dihydro-1H-cyclopenta[4,5]imidazo[1,2-a]pyridin-3-ol

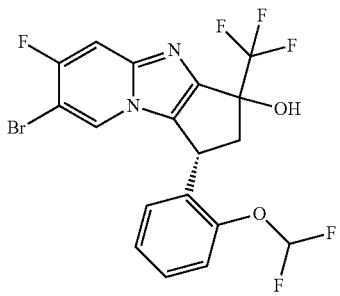 [SMILES: OC1(C(F)(F)F)C[C@H](c2ccccc2OC(F)F)c2c1nc1cc(F)c(Br)cn21]

Trimethyl(trifluoromethyl)silane (292 µL, 1.94 mmol) was added to a solution of Example 13 (200 mg, 0.49 mmol) in DME (2 mL). The mixture was stirred at r.t. for 10 minutes, then cesium fluoride (7.4 mg, 0.05 mmol) was added and the reaction mixture was stirred at r.t. for 36 h. The reaction mixture was quenched with a 4 M solution of aq. HCl (2 mL) and stirred in an ice bath for 10 minutes before warming to r.t. for 4 h. The mixture was diluted with water (15 mL) and extracted with EtOAc (3×20 mL), the combined organic extracts were washed with brine (10 mL), dried over sodium sulfate and concentrated in vacuo. The crude product was purified by flash column chromatography (SiO$_2$, 0-50% EtOAc in heptane) to afford 55 mg (22%) of the title compound as a brown gum. LCMS (ES$^+$) RT 1.95 min, 481.0/483.0 (M+H)$^+$.

Example 19

(R)-7-Bromo-1-(2-difluoromethoxy-phenyl)-6-fluoro-2,3-dihydro-1H-cyclopenta[4,5]imidazo[1,2-a]pyridin-3-ol

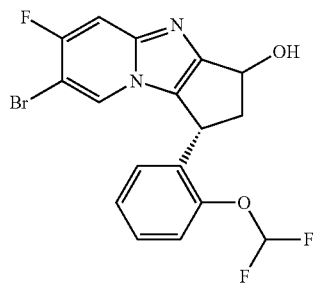

Example 13 (800 mg, 1.95 mmol) was dissolved in THF (20 mL) under nitrogen. The mixture was then cooled to −78° C. and 4 M solution of lithium borohydride in THF (0.73 mL) was added. The reaction mixture was stirred at −78° C. for 30 minutes before further addition of 4 M solution of lithium borohydride in THF (0.73 mL). The reaction mixture was stirred at −78° C. for 30 minutes and then quenched with sat. aq. solution of ammonium chloride (10 mL). The resulting mixture was extracted with EtOAc (3×15 mL). Combined organic layers were washed with brine (30 mL), dried over sodium sulfate and concentrated in vacuo. The residue was purified by flash column chromatography (SiO$_2$, 50-100% EtOAc in heptane then 1-100% MeOH in EtOAc to afford 700 mg (84%) of the title compound (approximately 2:1 ratio of diastereoisomers) as a pale orange crystallising oil. LCMS (ES$^+$) RT 2.49 min, 413.0/415.0 (M+H)$^+$.

Example 20

(R)-7-Bromo-1-(2-difluoromethoxy-phenyl)-6-fluoro-3-methyl-2,3-dihydro-1H-cyclopenta[4,5]imidazo[1,2-a]pyridin-3-ol

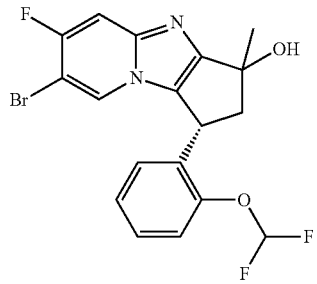 [SMILES: CC1(O)C[C@H](c2ccccc2OC(F)F)c2c1nc1cc(F)c(Br)cn21]

A solution of Example 13 (200 mg, 0.48 mmol) in toluene (5 mL) was added drop wise to a solution of methyl magnesium bromide in THF/toluene (1.4M, 1.04 mL, 1.46 mmol) in toluene (5 mL) at −78° C. The reaction mixture was stirred at −78° C. for 3 h. MeOH (1 mL) was added at −78° C. and the reaction mixture was warmed to r.t. before concentrated in vacuo. The brown residue was suspended in EtOAc (5 mL) and the mixture was washed with a 2M aq.

solution of sodium carbonate (3×3 mL). The aq. washes were combined and extracted with EtOAc (3×3 mL). The combined organic extracts dried over sodium sulfate and concentrated in vacuo. The crude brown residue was purified by flash column chromatography (SiO$_2$, 0-100% EtOAc in heptane) to afford 158 mg (51%) of the title compound as an orange glass. $^1$H NMR (500 MHz, CDCl$_3$) δ ppm 7.71 (dd, J 48.8, 6.5 Hz, 1H), 7.41-7.27 (m, 2H), 7.25-7.10 (m, 3H), 6.83-6.46 (m, 1H), 4.96 (ddd, J 129.3, 8.2, 4.8 Hz, 1H), 3.29 (ddd, J 29.0, 13.8, 8.3 Hz, 1H), 2.54 (ddd, J 73.0, 13.8, 4.8 Hz, 1H), 1.77 (d, J 4.9 Hz, 3H). LCMS (ES$^+$) RT 2.68 min, 427.0 (M+H)$^+$.

Examples 21 to 87

The following Examples were prepared by the Method A from the given precursor using the appropriate boronate ester or boronic acid.

| Example No. | Precursor | Compound Name | LCMS |
|---|---|---|---|
| 21 | Ex 19 | (R)-1-(2-Difluoromethoxy-phenyl)-6-fluoro-7-(6-methanesulfonyl-pyridin-3-yl)-2,3-dihydro-1H-cyclopenta[4,5]imidazo[1,2-a]pyridin-3-ol | LCMS (ES$^+$) RT 1.46 min 490.0 (M + H)$^+$. |
| 22 | Ex 16 | (1R,3R)-7-(6-Chloro-pyridin-3-yl)-1-(2-difluoromethoxy-phenyl)-6-fluoro-2,3-dihydro-1H-cyclopenta[4,5]imidazo[1,2-a]pyridin-3-ol | LCMS (ES$^+$) RT 1.62 min 446.0 (M + H)$^+$. |
| 23 | Ex 11 | 1-(5-{1-[2-(difluoromethoxy)phenyl]-3-hydroxy-2,3-dihydro-1H-cyclopenta[4,5]imidazo[1,2-a]pyridin-7-yl}pyrimidin-2-yl)-4-methylpiperidine-4-carboxylic acid ethyl ester | LCMS (ES$^+$) RT 1.34 min 564.0 (M + H)$^+$. |
| 24 | Ex 10 | (1S,5R,8R)-3-{5-[(1S,3S)-1-(2-Difluoromethoxy-phenyl)-3-hydroxy-2,3-dihydro-1H-cyclopenta[4,5]imidazo[1,2-a]pyridin-7-yl]-pyrimidin-2-yl}-3-aza-bicyclo[3.2.1]octane-8-carboxylic acid methyl ester | LCMS (ES$^+$) RT 1.37 min 562.0 (M + H)$^+$. |

-continued

| Example No. | Precursor | Compound Name | LCMS |
|---|---|---|---|
| 25 | Ex 5 | (1S,5R,8R)-3-{5-[(1R,3R)-1-(2-Difluoromethoxy-phenyl)-3-hydroxy-2,3-dihydro-1H-cyclopenta[4,5]imidazo[1,2-a]pyridin-7-yl]-pyrimidin-2-yl}-3-aza-bicyclo[3.2.1]octane-8-carboxylic acid methyl ester | LCMS (ES+) RT 1.37 min 562.0 (M + H)+. |
| 26 | Ex 15 | (1S,5R,8R)-3-{5-[(R)-1-(2-Difluoro-methoxy-phenyl)-3-hydroxy-3-methyl-2,3-dihydro-1H-cyclopenta[4,5]imidazo[1,2-a]pyridin-7-yl]-pyrimidin-2-yl}-3-aza-bicyclo[3.2.1]octane-8-carboxylic acid methyl ester | LCMS (ES+) RT 1.53 min 576.0 (M + H)+. |
| 27 | Ex 1 | 1-(2-Difluoromethoxy-phenyl)-7-(6-methanesulfonyl-pyridin-3-yl)-1,2-di-hydro-cyclopenta[4,5]imidazo[1,2-a]pyridin-3-one | LCMS (ES+) RT 1.15 min 470.0 (M + H)+. |

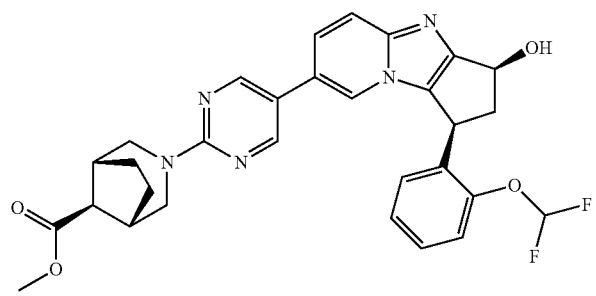 [SMILES: COC(=O)[C@@H]1[C@@H]2CC[C@H]1CN(c1ncc(-c3ccc4nc5c(n4c3)[C@H](c3ccccc3OC(F)F)C[C@@H]5O)cn1)C2]
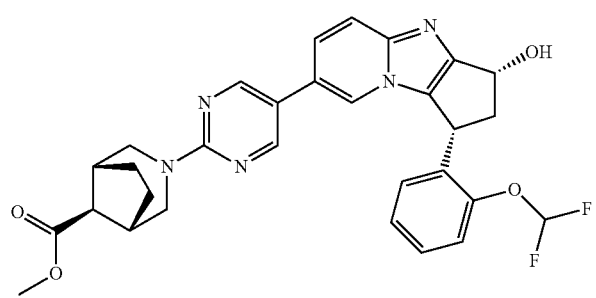 [SMILES: COC(=O)[C@@H]1[C@@H]2CC[C@H]1CN(c1ncc(-c3ccc4nc5c(n4c3)[C@@H](c3ccccc3OC(F)F)C[C@H]5O)cn1)C2]
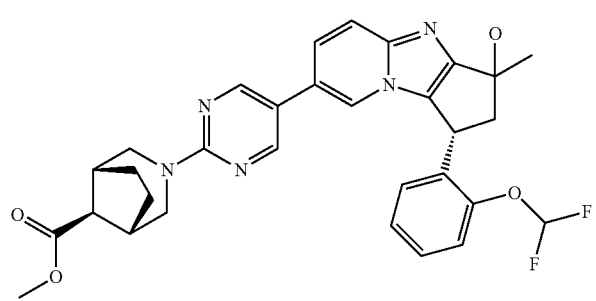 [SMILES: COC(=O)[C@@H]1[C@@H]2CC[C@H]1CN(c1ncc(-c3ccc4nc5c(n4c3)[C@@H](c3ccccc3OC(F)F)CC5(C)O)cn1)C2]

| Example No. | Precursor | Compound Name | LCMS |
|---|---|---|---|
| 28 | Ex 5 | (1R,3R)-7-(2-Chloro-pyrimidin-5-yl)-1-(2-difluoromethoxy-phenyl)-2,3-dihydro-1H-cyclopenta[4,5]imidazo[1,2-a]pyridin-3-ol | LCMS (ES+) RT 1.45 min 428.0 (M + H)+. |
| 29 | Ex 2 | (R)-1-(2-Difluoromethoxy-phenyl)-7-(2-thiomorpholin-4-yl-pyrimidin-5-yl)-1,2-dihydro-cyclopenta[4,5]imidazo[1,2-a]pyridin-3-one | LCMS (ES+) RT 1.63 min 494.0 (M + H)+. |
| 30 | Ex 9 | 4-{5-[1-(2-Difluoromethoxy-phenyl)-6-fluoro-3-oxo-2,3-dihydro-1H-cyclopenta[4,5]imidazo[1,2-a]pyridin-7-yl]-pyridin-2-yl}-piperazine-1-carboxylic acid tert-butyl ester | LCMS (ES+) RT 1.59 min 595.0 (M + H)+. |
| 31 | Ex 5 | (1S,5S,6R)-3-{5-[1-((R)-2-Difluoro-methoxy-phenyl)-3-hydroxy-2,3-dihydro-1H-cyclopenta[4,5]imidazo[1,2-a]pyridin-7-yl]-pyrimidin-2-yl}-bicyclo[3.1.0]hex-2-ene-6-carboxylic acid ethyl ester | LCMS (ES+) RT 1.68 min 545.0 (M + H)+. |

-continued

| Example No. | Precursor | Compound Name | LCMS |
|---|---|---|---|
| | | 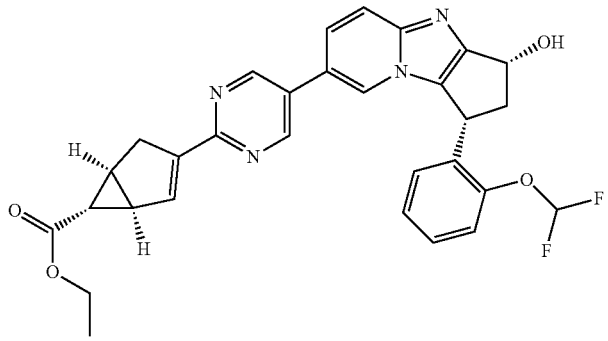 [SMILES: CCOC(=O)[C@H]1[C@@H]2C=C(c3ncc(-c4ccc5nc6c(n5c4)[C@@H](c4ccccc4OC(F)F)C[C@H]6O)cn3)C[C@@H]21] | |
| 32 | Ex 5 | 4-{5-[(1R,3R)-1-(2-Difluoromethoxy-phenyl)-3-hydroxy-2,3-dihydro-1H-cyclopenta[4,5]imidazo[1,2-a]pyridin-7-yl]-pyrimidin-2-yl}-3,6-dihydro-2H-pyridine-1-carboxylic acid tert-butyl ester | LCMS (ES+) RT 1.21 min 576.0 (M + H)+. |
| | | 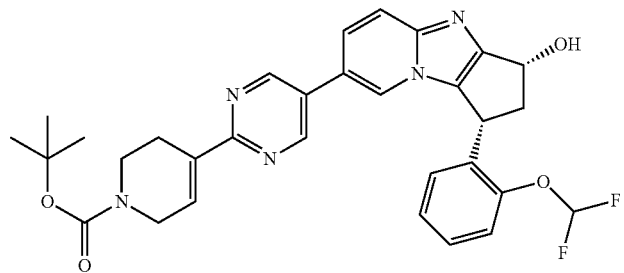 [SMILES: CC(C)(C)OC(=O)N1CC=C(c2ncc(-c3ccc4nc5c(n4c3)[C@@H](c3ccccc3OC(F)F)C[C@H]5O)cn2)CC1] | |
| 33 | Ex 14 | (1R,3R)-1-[2-(difluoromethoxy)phenyl]-3-methoxy-7-[4-(methylsulfonyl)phenyl]-2,3-dihydro-1H-cyclopenta[4,5]imidazo[1,2-a]pyridine | LCMS (ES+) RT 1.45 min 485.0 (M + H)+. |
| | | 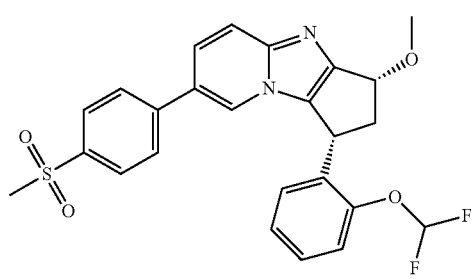 | |
| 34 | Ex 5 | (1R,3R)-1-[2-(difluoromethoxy)phenyl]-7-[4-(methylsulfonyl)phenyl]-2,3-dihydro-1H-cyclopenta[4,5]imidazo[1,2-a]pyridin-3-ol | LCMS (condition pH10) RT 1.30 min, 471.0 (M + H)+ |
| | | 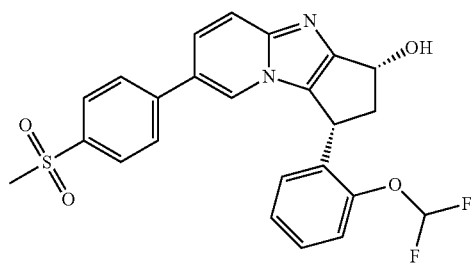 | |

-continued

| Example No. | Precursor | Compound Name | LCMS |
|---|---|---|---|
| 35 | Ex 10 | (1S,3S)-1-[2-(difluoromethoxy)phenyl]-7-[4-(methylsulfonyl)phenyl]-2,3-dihydro-1H-cyclopenta[4,5]imidazo[1,2-a]pyridin-3-ol | LCMS (ES+) RT 1.30 min, 471.0 (M + H)+ |
| 36 | Ex 5 | (1R,3R)-1-[2-(difluoromethoxy)phenyl]-7-[2-(morpholin-4-yl)pyrimidin-5-yl]-2,3-dihydro-1H-cyclopenta[4,5]imidazo[1,2-a]pyridin-3-ol | LCMS (ES+) RT 1.33 min, 480.0 (M + H)+. |
| 37 | Ex 10 | (1S,3S)-1-[2-(difluoromethoxy)phenyl]-7-[2-(morpholin-4-yl)pyrimidin-5-yl]-2,3-dihydro-1H-cyclopenta[4,5]imidazo[1,2-a]pyridin-3-ol | LCMS (ES+) RT 1.34 min, 480.0 (M + H)+. |
| 38 | Ex 12 | (S)-1-(2-Difluoromethoxy-phenyl)-6-fluoro-7-(4-methanesulfonyl-phenyl)-1,2-dihydro-cyclopenta[4,5]imidazo[1,2-a]pyridin-3-one | LCMS (ES+) RT 1.35 min, 487.0 (M + H)+. |

| Example No. | Precursor | Compound Name | LCMS |
|---|---|---|---|
| 39 | Ex 13 | (R)-1-(2-Difluoromethoxy-phenyl)-6-fluoro-7-(4-methanesulfonyl-phenyl)-1,2-dihydro-cyclopenta[4,5]imidazo[1,2-a]pyridin-3-one | LCMS (ES+) RT 1.35 min, 487.0 (M + H)+. |
| 40 | Ex 2 | (1S,5R,8R)-3-{5-[(R)-1-(2-Difluoromethoxy-phenyl)-3-oxo-2,3-dihydro-1H-cyclopenta[4,5]imidazo[1,2-a]pyridin-7-yl]-pyrimidin-2-yl}-3-aza-bicyclo[3.2.1]octane-8-carboxylic acid methyl ester | LCMS (ES+) RT 1.13 min, 560.0 (M + H)+. |
| 41 | Ex 2 | (1R)-1-[2-(difluoromethoxy)phenyl]-7-[4-(methylsulfonyl)phenyl]-1,2-dihydro-3H-cyclopenta[4,5]imidazo[1,2-a]pyridin-3-one | LCMS (ES+) RT 1.33 min, 469.0 (M + H)+. |
| 42 | Int 8 | (1R)-6-fluoro-7-{4-[(methylsulfonyl)methyl]phenyl}-1-phenyl-1,2-dihydro-3H-cyclopenta[4,5]imidazo[1,2-a]pyridin-3-one | LCMS (ES+) RT 1.29 min, 435.0 (M + H)+. |

-continued

| Example No. | Precursor | Compound Name | LCMS |
|---|---|---|---|
| 43 | Ex 14 | 2-(5-{(1R,3R)-1-[2-(difluoromethoxy)phenyl]-3-methoxy-2,3-dihydro-1H-cyclopenta[4,5]imidazo[1,2-a]pyridin-7-yl}pyridin-2-yl)propan-2-ol | LCMS (ES+) RT 1.42 min, 466.0 (M + H)+. |
| 44 | Ex 14 | (1R,3R)-1-[2-(difluoromethoxy)phenyl]-3-methoxy-7-(6-methoxypyridin-3-yl)-2,3-dihydro-1H-cyclopenta[4,5]imidazo[1,2-a]pyridine | LCMS (ES+) RT 1.53 min, 438.0 (M + H)+. |
| 45 | Ex 5 | (1R,3R)-1-[2-(difluoromethoxy)phenyl]-7-[6-(propan-2-yloxy)pyridin-3-yl]-2,3-dihydro-1H-cyclopenta[4,5]imidazo[1,2-a]pyridin-3-ol | LCMS (ES+) RT 1.58 min, 452.0 (M + H)+. |
| 46 | Ex 16 | (1R,3R)-1-(2-Difluoromethoxy-phenyl)-6-fluoro-7-(4-methanesulfonyl-phenyl)-2,3-dihydro-1H-cyclopenta[4,5]imidazo[1,2-a]pyridin-3-ol | LCMS (ES+) RT 1.53 min, 489.0 (M + H)+. |

-continued

| Example No. | Precursor | Compound Name | LCMS |
|---|---|---|---|
| 47 | Ex 5 | (1R,3R)-1-[2-(difluoromethoxy)phenyl]-7-[6-(tetrahydro-2H-pyran-4-yl)pyridin-3-yl]-2,3-dihydro-1H-cyclopenta[4,5]imidazo[1,2-a]pyridin-3-ol | LCMS (ES+) RT 1.36 min, 478.0 (M + H)+ |
| 48 | Ex 14 | (1R,3R)-1-[2-(difluoromethoxy)phenyl]-3-methoxy-7-[6-(tetrahydro-2H-pyran-4-yl)pyridin-3-yl]-2,3-dihydro-1H-cyclopenta[4,5]imidazo[1,2-a]pyridine | LCMS (ES+) RT 1.48 min, 492.0 (M + H)+ |
| 49 | Ex 5 | (1R,3R)-1-[2-(difluoromethoxy)phenyl]-7-[6-(hydroxymethyl)pyridin-3-yl]-2,3-dihydro-1H-cyclopenta[4,5]imidazo[1,2-a]pyridin-3-ol | LCMS (ES+) RT 1.44 min, 424.0 (M + H)+ |
| 50 | Ex5 | (1R,3R)-1-[2-(difluoromethoxy)phenyl]-7-(6-methoxypyridin-3-yl)-2,3-dihydro-1H-cyclopenta[4,5]imidazo[1,2-a]pyridin-3-ol | LCMS (ES+) RT 1.42 min, 424.0 (M + H)+ |

-continued

| Example No. | Precursor | Compound Name | LCMS |
|---|---|---|---|
| 51 | Ex 16 | (1R,3R)-1-[2-(difluoromethoxy)phenyl]-6-fluoro-7-[2-(propan-2-yl)pyrimidin-5-yl]-2,3-dihydro-1H-cyclopenta[4,5]imidazo[1,2-a]pyridin-3-ol | LCMS (ES+) RT 1.46 min, 454.0 (M + H)+ |
| 52 | Ex 16 | (1R,3R)-1-[2-(difluoromethoxy)phenyl]-6-fluoro-7-[6-(tetrahydro-2H-pyran-4-yl)pyridin-3-yl]-2,3-dihydro-1H-cyclopenta[4,5]imidazo[1,2-a]pyridin-3-ol | LCMS (ES+) RT 1.38 min, 496.0 (M + H)+ |
| 53 | Int 28 | (1R,3R)-1-[2-(difluoromethoxy)phenyl]-6-fluoro-7-[6-(tetrahydro-2H-pyran-4-yl)pyridin-3-yl]-2,3-dihydro-1H-cyclopenta[4,5]imidazo[1,2-a]pyridin-3-amine | LCMS (ES+) RT 1.36 min, 495.0 (M + H)+ |
| 54 | Ex 5 | (1R,3R)-1-[2-(difluoromethoxy)phenyl]-7-[4-(1,1,1,3,3,3-hexafluoro-2-hydroxypropan-2-yl)phenyl]-2,3-dihydro-1H-cyclopenta[4,5]imidazo[1,2-a]pyridin-3-ol | LCMS (ES+) RT 1.53 min, 559.0 (M + H)+ |

-continued

| Example No. | Precursor | Compound Name | LCMS |
|---|---|---|---|
| 55 | Ex 16 | (1R,5S)-3-(5-{(1R,3R)-1-[2-(difluoromethoxy)phenyl]-6-fluoro-3-hydroxy-2,3-dihydro-1H-cyclopenta[4,5]imidazo[1,2-a]pyridin-7-yl}pyrimidin-2-yl)-3,6-diazabicyclo[3.2.2]nonan-7-one | LCMS (ES+) RT 1.42 min, 551.0 (M + H)+ |
| 56 | Ex 16 | (1R,3R)-1-(2-Difluoromethoxy-phenyl)-6-fluoro-7-[2-(3-hydroxy-3-methyl-azetidin-1-yl)-pyrimidin-5-yl]-2,3-dihydro-1H-cyclopenta[4,5]imidazo[1,2-a]pyridin-3-ol | LCMS (ES+) RT 1.28 min, 498.0 (M + H)+ |
| 57 | Ex 16 | (1R,3R)-1-[2-(difluoromethoxy)phenyl]-6-fluoro-7-{2-[3-hydroxy-3-(trifluoromethyl)azetidin-1-yl]pyrimidin-5-yl}-2,3-dihydro-1H-cyclopenta[4,5]imidazo[1,2-a]pyridin-3-ol | LCMS (ES+) RT 1.37 min, 552.0 (M + H)+ |
| 58 | Ex 14 | 2-(5-{(1R,3R)-1-[2-(difluoromethoxy)phenyl]-3-methoxy-2,3-dihydro-1H-cyclopenta[4,5]imidazo[1,2-a]pyridin-7-yl}pyrimidin-2-yl)propan-2-ol | LCMS (ES+) RT 1.52 min, 467.0 (M + H)+ |

-continued

| Example No. | Precursor | Compound Name | LCMS |
|---|---|---|---|
| 59 | Ex 14 | 4-(5-{(1R,3R)-1-[2-(difluoromethoxy)phenyl]-3-methoxy-2,3-dihydro-1H-cyclopenta[4,5]imidazo[1,2-a]pyridin-7-yl}pyrimidin-2-yl)piperazin-2-one | LCMS (ES+) RT 1.32 min, 507.0 (M + H)+ |
| 60 | Ex 14 | (1R,3R)-1-[2-(difluoromethoxy)phenyl]-3-methoxy-7-{2-[(1S,4S)-2-oxa-5-azabicyclo[2.2.1]hept-5-yl]pyrimidin-5-yl}-2,3-dihydro-1H-cyclopenta[4,5]imidazo[1,2-a]pyridine | LCMS (ES+) RT 1.42 min, 506.0 (M + H)+ |
| 61 | Ex 16 | (1R,3R)-1-[2-(difluoromethoxy)phenyl]-7-{2-[(1s,5s)-3,7-dioxa-9-azabicyclo[3.3.1]non-9-yl]pyrimidin-5-yl}-6-fluoro-2,3-dihydro-1H-cyclopenta[4,5]imidazo[1,2-a]pyridin-3-ol | LCMS (ES+) RT 1.32 min, 540.0 (M + H)+ |
| 62 | Ex 16 | (1R,3R)-1-[2-(difluoromethoxy)phenyl]-6-fluoro-7-{2-[(3R,3aR,6R)-hexahydro-3,6-epiminofuro[3,2-b]furan-7-yl]pyrimidin-5-yl}-2,3-dihydro-1H-cyclopenta[4,5]imidazo[1,2-a]pyridin-3-ol | LCMS (ES+) RT 1.30 min, 538.0 (M + H)+ |

-continued

| Example No. | Precursor | Compound Name | LCMS |
|---|---|---|---|
| 63 | Ex 17 | 2-(5-{(1R)-1-[2-(difluoromethoxy)phenyl]-6-fluoro-2,3-dihydro-1H-cyclopenta[4,5]imidazo[1,2-a]pyridin-7-yl}pyrimidin-2-yl)propan-2-ol | LCMS (ES+) RT 1.47 min, 455.0 (M + H)+ |
| 64 | Ex 18 | (1R,3R)-1-[2-(difluoromethoxy)phenyl]-6-fluoro-7-[2-(2-hydroxypropan-2-yl)pyrimidin-5-yl]-3-(trifluoromethyl)-2,3-dihydro-1H-cyclopenta[4,5]imidazo[1,2-a]pyridin-3-ol | LCMS (ES+) RT 1.43 min, 539.0 (M + H)+ |
| 65 | Ex 15 | 1-[2-(difluoromethoxy)phenyl]-3-methyl-7-[6-(methylsulfonyl)pyridin-3-yl]-2,3-dihydro-1H-cyclopenta[4,5]imidazo[1,2-a]pyridin-3-ol | LCMS (ES+) RT 1.29 min, 486.0 (M + H)+ |
| 66 | Ex 13 | (1R)-1-[2-(difluoromethoxy)phenyl]-7-[6-(methylsulfonyl)pyridin-3-yl]-1,2-dihydro-3H-cyclopenta[4,5]imidazo[1,2-a]pyridin-3-one | LCMS (ES+) RT 1.29 min, 470.0 (M + H)+ |

-continued

| Example No. | Precursor | Compound Name | LCMS |
|---|---|---|---|
| 67 | Ex 15 | (1R,3R)-1-[2-(difluoromethoxy)phenyl]-3-methyl-7-[4-(methylsulfonyl)phenyl]-2,3-dihydro-1H-cyclopenta[4,5]imidazo[1,2-a]pyridin-3-ol | LCMS (ES+) RT 1.34 min, 485.0 (M + H)+ |
| 68 | Ex 8 | 1-(2-Difluoromethoxy-phenyl)-7-(6-methanesulfonyl-pyridin-3-yl)-3-methyl-2,3-dihydro-1H-cyclopenta[4,5]imidazo[1,2-a]pyridin-3-ol | LCMS (ES+) RT 1.45 min, 486.0 (M + H)+ |
| 69 | Ex 5 | 4-(5-{(1R,3R)-1-[2-(difluoromethoxy)phenyl]-3-hydroxy-2,3-dihydro-1H-cyclopenta[4,5]imidazo[1,2-a]pyridin-7-yl}pyrimidin-2-yl)piperazin-2-one | LCMS (ES+) RT 1.19 min, 493.0 (M + H)+ |
| 70 | Ex 5 | (1R,3R)-1-[2-(difluoromethoxy)phenyl]-7-[2-(2-hydroxypropan-2-yl)pyrimidin-5-yl]-2,3-dihydro-1H-cyclopenta[4,5]imidazo[1,2-a]pyridin-3-ol | LCMS (ES+) RT 1.29 min, 453.0 (M + H)+ |

-continued

| Example No. | Precursor | Compound Name | LCMS |
|---|---|---|---|
| 71 | Ex 5 | (1R,3R)-1-[2-(difluoromethoxy)phenyl]-7-{2-[(1R,5S)-3-oxa-8-azabicyclo[3.2.1]oct-8-yl]pyrimidin-5-yl}-2,3-dihydro-1H-cyclopenta[4,5]imidazo[1,2-a]pyridin-3-ol | LCMS (ES+) RT 1.40 min, 506.0 (M + H)+ |
| 72 | Ex 5 | (1R,3R)-1-[2-(difluoromethoxy)phenyl]-7-{2-[(1S,4S)-2-oxa-5-azabicyclo[2.2.1]hept-5-yl]pyrimidin-5-yl}-2,3-dihydro-1H-cyclopenta[4,5]imidazo[1,2-a]pyridin-3-ol | LCMS (ES+) RT 1.29 min, 492.0 (M + H)+ |
| 73 | Ex 16 | (1R,3R)-1-[2-(difluoromethoxy)phenyl]-6-fluoro-7-[2-(2-hydroxypropan-2-yl)pyrimidin-5-yl]-2,3-dihydro-1H-cyclopenta[4,5]imidazo[1,2-a]pyridin-3-ol | LCMS (ES+) RT 1.31 min, 471.0 (M + H)+ |
| 74 | Int 8 | ((R)-6-Fluoro-7-[4-(1-methanesulfonyl-ethyl)-phenyl]-1-phenyl-1,2-dihydro-cyclopenta[4,5]imidazo[1,2-a]pyridin-3-one | LCMS (ES+) RT 1.53 min, 449.0 (M + H)+ |

-continued

| Example No. | Precursor | Compound Name | LCMS |
|---|---|---|---|
| 75 | Int 17 | (S)-1-(2-Chloro-phenyl)-6-fluoro-7-[2-(1-hydroxy-1-methyl-ethyl)-pyrimidin-5-yl]-1,2-dihydro-cyclopenta[4,5]imidazo[1,2-a]pyridin-3-one | LCMS (ES+) RT 1.53 min, 437.0 (M + H)+ |
| 76 | Int 16 | (R)-1-(2-Chloro-phenyl)-6-fluoro-7-[2-(1-hydroxy-1-methyl-ethyl)-pyrimidin-5-yl]-1,2-dihydro-cyclopenta[4,5]imidazo[1,2-a]pyridin-3-one | LCMS (ES+) RT 1.53 min, 437.0 (M + H)+ |
| 77 | Int 22 | 2-{5-[(1R,3S)-1-(2-chlorophenyl)-3,6-difluoro-2,3-dihydro-1H-cyclopenta[4,5]imidazo[1,2-a]pyridin-7-yl]pyrimidin-2-yl}propan-2-ol | LCMS (ES+) RT 1.47 min, 441.0 (M + H)+ |
| 78 | Int 21 | 2-{5-[(1R,3R)-1-(2-chlorophenyl)-3,6-difluoro-2,3-dihydro-1H-cyclopenta[4,5]imidazo[1,2-a]pyridin-7-yl]pyrimidin-2-yl}propan-2-ol | LCMS (ES+) RT 1.47 min, 441.0 (M + H)+ |

-continued

| Example No. | Precursor | Compound Name | LCMS |
|---|---|---|---|
| 79 | Int 25 | 2-{5-[(1S,3S)-1-(2-chlorophenyl)-3,6-difluoro-2,3-dihydro-1H-cyclopenta[4,5]imidazo[1,2-a]pyridin-7-yl]pyrimidin-2-yl}propan-2-ol | LCMS (ES+) RT 1.47 min, 441.0 (M + H)+ |
| 80 | Int 24 | 2-{5-[(1S,3R)-1-(2-chlorophenyl)-3,6-difluoro-2,3-dihydro-1H-cyclopenta[4,5]imidazo[1,2-a]pyridin-7-yl]pyrimidin-2-yl}propan-2-ol | LCMS (ES+) RT 1.47 min, 441.0 (M + H)+ |
| 81 | Int 14 | (R)-6-Fluoro-7-[2-(1-hydroxy-1-methyl-ethyl)-pyrimidin-5-yl]-1-(2-trifluoromethoxy-phenyl)-1,2-dihydro-cyclopenta[4,5]imidazo[1,2-a]pyridin-3-one | LCMS (ES+) RT 1.53 min, 487.0 (M + H)+ |
| 82 | Int 9 | (S)-6-Fluoro-7-(2-morpholin-4-yl-pyrimidin-5-yl)-1-phenyl-1,2-dihydro-cyclopenta[4,5]imidazo[1,2-a]pyridin-3-one | LCMS (ES+) RT 1.42 min, 430.0 (M + H)+ |

| Example No. | Precursor | Compound Name | LCMS |
|---|---|---|---|
| 83 | Int 8 | (R)-6-Fluoro-7-(2-morpholin-4-yl-pyrimidin-5-yl)-1-phenyl-1,2-dihydro-cyclopenta[4,5]imidazo[1,2-a]pyridin-3-one | LCMS (ES+) RT 1.42 min, 430.0 (M + H)+ |
| 84 | Ex 5 | (1R,3R)-1-(2-Difluoromethoxy-phenyl)-7-[4-(2,2,2-trifluoro-1-hydroxy-1-trifluoromethyl-ethyl)-phenyl]-2,3-dihydro-1H-cyclopenta[4,5]imidazo[1,2-a]pyridin-3-ol | LCMS (ES+) RT 1.53 min, 559.0 (M + H)+ |
| 85 | Ex 13 | (R)-1-(2-Difluoromethoxy-phenyl)-6-fluoro-7-[2-(1-hydroxy-1-methyl-ethyl)-pyrimidin-5-yl]-1,2-dihydro-cyclopenta[4,5]imidazo[1,2-a]pyridin-3-one | LCMS (ES+) RT 1.45 min, 469.0 (M + H)+ |
| 86 | Ex 14 | (1S,5R,8R)-3-{5-[(1R,3R)-1-(2-Di-fluoromethoxy-phenyl)-3-methoxy-2,3-di-hydro-1H-cyclopenta[4,5]imidazo[1,2-a]pyridin-7-yl]-pyrimidin-2-yl}-3-aza-bicyclo[3.2.1]octane-8-carboxylic acid methyl ester | LCMS (ES+) RT 1.52 min, 576.0 (M + H)+ |

| Example No. | Precursor | Compound Name | LCMS |
|---|---|---|---|
| 87 | Ex 118 | 1-[2-(difluoromethoxy)phenyl]-2-(hydroxymethyl)-7-[2-(morpholin-4-yl)pyrimidin-5-yl]-2,3-dihydro-1H-cyclopenta[4,5]imidazo[1,2-a]pyridin-3-ol | LCMS (ES+) RT 1.31 min, 510.0 (M + H)+ |

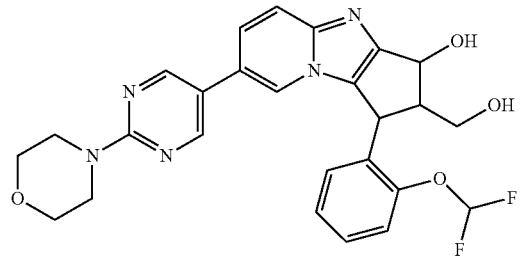

Example 88 Method I (1S,5R,8R)-3-{5-[(1S,3S)-1-(2-Difluoromethoxy-phenyl)-3-hydroxy-2,3-dihydro-1H-cyclopenta[4,5]imidazo[1,2-a]pyridin-7-yl]-pyrimidin-2-yl}-3-azabicyclo[3.2.1]octane-8-carboxylic acid

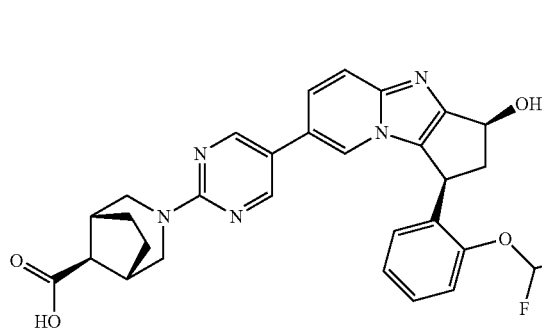

Example 24 140 mg, 0.249 mmol was dissolved in THF (2 mL). Water (2 mL and lithium hydroxide monohydrate (105 mg, 2.47 mmol) were added and the reaction permitted to stir for 5 h. Once complete, the reaction mixture was washed with EtOAc. The aq. layer was then acidified to pH 4 with AcOH and extracted with EtOAc. The combined organic phase was dried, filtered and reduced in vacuo. Trituration of the crude material with MeCN gave the title compound (90 mg, 66%). $\delta_H$ (300 MHz, DMSO-$d_6$) 12.07 (br.s, 1H), 8.53 (s, 2H), 8.00 (m, 1H), 7.66 (dd, J 9.5 Hz, J 0.8 Hz, 1H), 7.51 (dd, J 9.5 Hz, J 1.8 Hz, 1H), 7.37 (t, J 74.1 Hz, 1H), 7.28 (m, 2H), 7.13 (m, 1H), 6.95 (dd, J 7.8 Hz, J 1.5 Hz, 1H), 5.48 (d, J 5.2 Hz, 1H), 5.13 (m, 1H), 4.76 (dd, J 8.3 Hz, J 3.7 Hz, 1H), 4.39 (d, J 12.2 Hz, 2H), 3.45 (m, 1H), 3.00 (d, J 12.3 Hz, 2H), 2.66 (s, 1H), 2.58 (br.s, 2H), 2.08 (dt, J 13.8 Hz, J 3.7 Hz, 1H), 1.67 (m, 2H), 1.31 (d, J 8.0 Hz, 2H). LCMS (ES+) RT 1.09 min 548.8 (M+H)+.

Example 89

4-{5-[1-(2-Difluoromethoxy-phenyl)-6-fluoro-3-hydroxy-2,3-dihydro-1H-cyclopenta[4,5]imidazo[1,2-a]pyridin-7-yl]-pyridin-2-yl}-piperazine-1-carboxylic acid tert-butyl ester

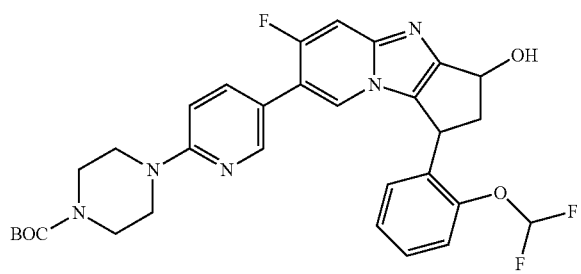 [SMILES: CC(C)(C)OC(=O)N1CCN(c2ccc(-c3cn4c5c(nc4cc3F)C(O)CC5c3ccccc3OC(F)F)cn2)CC1]

The title compound was prepared from Example 30 (0.084 g, 0.14 mmol) and sodium borohydride (0.0059 g, 0.16 mmol) by the Method C, (0.084 g). LCMS (ES+) RT 2.01 min, 596.0 (M+H)+.

Example 90 Method J

1-[2-(difluoromethoxy)phenyl]-6-fluoro-7-[6-(piperazin-1-yl)pyridin-3-yl]-2,3-dihydro-1H-cyclopenta[4,5]imidazo[1,2-a]pyridin-3-ol

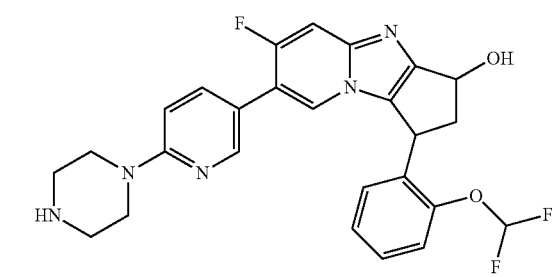 [SMILES: OC1CC(c2ccccc2OC(F)F)c2c1nc1cc(F)c(-c3ccc(N4CCNCC4)nc3)cn21]

Example 89 (0.084 g, 0.14 mmol) was dissolved in HCl (4 mol/L) in 1,4-dioxane (2.00 mL) and stirred at r.t for 1 h. The precipitate was filtered and dried in vacuo. The solid was purified by preparative HPLC yielding the title compound as an off white solid (0.009 g, 10%). $^1$H NMR (DMSO-d$_6$) δ: 8.13 (d, J 1.4 Hz, 1 H), 7.86 (d, J 7.6 Hz, 1 H), 7.58 (m, 2 H), 7.28 (m, 3 H), 7.14 (td, J 7.6 Hz, J 1.4 Hz, 1 H), 6.95 (dd, J 7.7 Hz, J 1.6 Hz, 1 H), 6.86 (d, J 9.0 Hz, 1 H), 5.48 (d, J 5.3 Hz, 1 H), 4.74 (dd, J 8.6 Hz, J 4.0 Hz, 1H), 3.69 (d, J 4.3 Hz, 1 H), 3.43 (m, 5 H), 2.75 (m, 5 H), 2.06 (m, 1 H). LCMS (ES$^+$) RT 1.54 min, 496.8 (M+H)$^+$.

Example 91

1-(5-{1-[2-(difluoromethoxy)phenyl]-3-hydroxy-2,3-dihydro-1H-cyclopenta[4,5]imidazo[1,2-a]pyridin-7-yl}pyrimidin-2-yl)-4-methylpiperidine-4-carboxylic acid

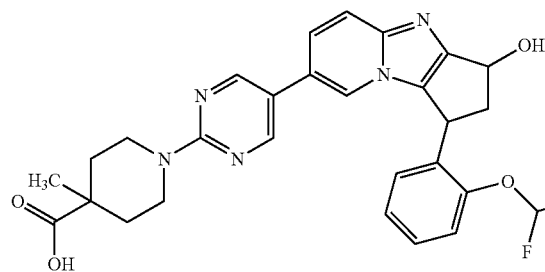

The title compound was prepared from Example 23 (0.111 g, 0.19 mmol) and lithium hydroxide monohydrate (0.029 g, 0.39 mmol) by the Method I (0.010 g, 9%). $^1$H NMR (DMSO-d$_6$, 400 MHz) δ: 8.53 (m, 2 H), 7.99 (s, 1 H), 7.65 (m, 1 H), 7.51 (m, 1 H), 7.31 (m, 3H), 7.13 (m, 1 H), 6.95 (dd, J 7.9 Hz, J 1.6 Hz, 1 H), 5.48 (m, 1 H), 5.12 (m, 1 H), 4.76 (dd, J 8.3 Hz, J 3.7 Hz, 1 H), 4.23 (m, 2 H), 3.43 (m, 1 H), 2.27 (m, 2 H), 2.08 (m, 1 H), 1.98 (m, 2 H), 1.28 (m, 2 H), 1.12 (s, 3 H). LCMS (ES$^+$) RT 1.24 min, 536.8 (M+H)$^+$.

Examples 92 and 93

(R)-1-(2-Difluoromethoxy-phenyl)-7-[2-(1,1-dioxo-thiomorpholin-4-yl)-pyrimidin-5-yl]-1,2-dihydro-cyclopenta[4,5]imidazo[1,2-a]pyridin-3-one and (R)-1-(2-Difluoromethoxy-phenyl)-7-[2-(1-oxo-thio morpholin-4-yl)-pyrimidin-5-yl]-1,2-dihydro-cyclopenta[4,5]imidazo[1,2-a]pyridin-3-one

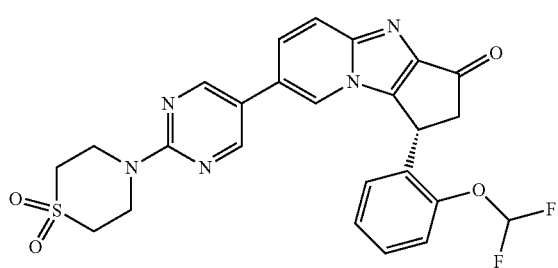

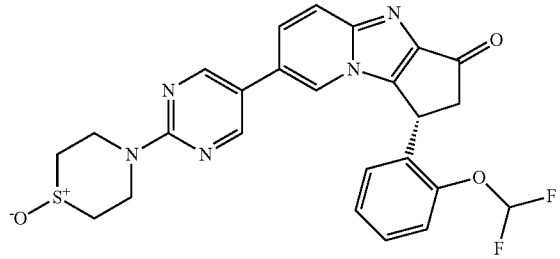

Example 29 (2.05 mmol, 1.01 g) was diluted with MeOH (20 mL) and cooled to 0° C. Oxone® (3.04 mmol, 1.87 g) in water (15 mL) was added and the reaction permitted to warm to r.t. over 12 h. At this point, the reaction mixture contained approximately 25% sulphoxide and 75% sulphone. The solvent was removed in vacuo and EtOAc added. The resulting solid was filtered off before purification by flash column chromatography (SiO$_2$, 0-20% EtOH in DCM) yielding both title compounds. Example 92 (560 mg, 52%): δ$_H$ (300 MHz, DMSO-d$_6$) 8.71 (s, 2H); 8.25 (m, 1H); 7.85 (dd, J 9.7 Hz, J 1.0 Hz, 1H); 7.79 (dd, J 9.7 Hz, J 1.8 Hz, 1H); 7.37 (m, 1H); 7.28 (t, J 73.9 Hz, 1H); 7.27 (m, 1H); 7.14 (td, J 7.5 Hz, J 1.1 Hz, 1H); 6.88 (d, J 7.4 Hz, 1H); 5.17 (dd, J 6.9 Hz, J 1.8 Hz, 1H); 4.24 (m, 4H); 3.63 (dd, J 18.2 Hz, J 7.1 Hz, 1H); 3.17 (m, 4H); 2.77 (dd, J 18.1 Hz, J 2.1 Hz, 1H). LCMS (ES$^+$) RT 1.84 min 526.6 (M+H)$^+$. Example 93 (150 mg, 15%): δ$_H$ (300 MHz, DMSO-d$_6$) 8.68 (s, 2H); 8.23 (m, 1H); 7.84 (dd, J 9.7 Hz, J 1.0 Hz, 1H); 7.78 (dd, J 9.7 Hz, J 1.8 Hz, 1H); 7.37 (m, 1H); 7.28 (t, J 73.9 Hz, 1H); 7.27 (m, 1H); 7.14 (td, J 7.5 Hz, J 1.1 Hz, 1H); 6.88 (m, 1H); 5.16 (dd, J 6.8 Hz, J 1.8 Hz, 1H); 4.49 (m, 2H); 3.95 (m, 2H); 3.63 (dd, J 18.2 Hz, J 7.2 Hz, 1H); 2.88 (m, 2H); 2.76 (m, 3H). LCMS (ES$^+$) RT 1.64 min 510.6 (M+H)$^+$.

Example 94

(1R,5S,8R)-3-{5-[(1R,3R)-1-(2-Difluoromethoxy-phenyl)-3-hydroxy-2,3-dihydro-1H-cyclopenta[4,5]imidazo[1,2-a]pyridin-7-yl]-pyrimidin-2-yl}-3-azabicyclo[3.2.1]octane-8-carboxylic acid

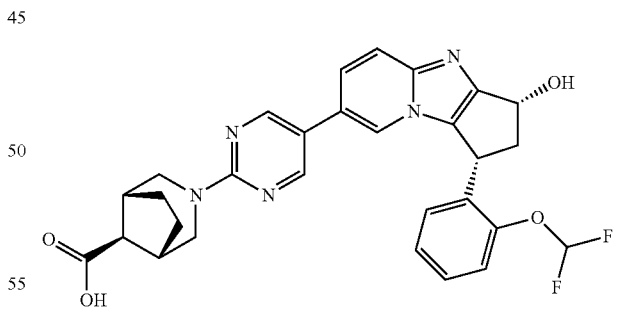

The title compound prepared from Example 25 (178 mg, 0.32 mmol) and lithium hydroxide monohydrate (53 mg, 1.26 mmol) by the Method I (87 mg, 50%). δ$_H$ (300 MHz, DMSO-d$_6$) 12.07-12.23 (m, 1 H), 8.47 (s, 2 H), 7.92-7.95 (m, 1 H), 7.59 (dd, J 9.5, 0.8 Hz, 1 H), 7.45 (dd, J 9.5, 1.8 Hz, 1 H), 7.30 (t, J 74.1 Hz, 1 H), 7.23 (dd, J 6.8, 1.6 Hz, 1 H), 7.17-7.21 (m, 1 H), 7.06 (td, J 7.8, 1.7 Hz, 1 H), 6.88 (dd, J 7.8, 1.5 Hz, 1 H), 5.41 (d, J 5.2 Hz, 1 H), 5.02-5.09 (m, 1 H), 4.69 (dd, J 8.4, 3.8 Hz, 1 H), 4.29-4.38 (m, 2H), 3.32-3.44 (m, 1 H), 2.88-2.97 (m, 2 H), 2.58 (s, 1 H), 2.48-2.54 (m, 2 H), 2.02 (dt, J 13.7, 3.7 Hz, 1 H), 1.55-1.67 (m, 2 H), 1.24-1.35 (m, 2 H). LCMS (ES⁺) RT 1.08 minutes, 548 (M+H)⁺.

Example 95

(1R,3S)-1-(2-Difluoromethoxy-phenyl)-7-(6-methanesulfonyl-pyridin-3-yl)-3-methyl-2,3-dihydro-1H-cyclopenta[4,5]imidazo[1,2-a]pyridin-3-ol

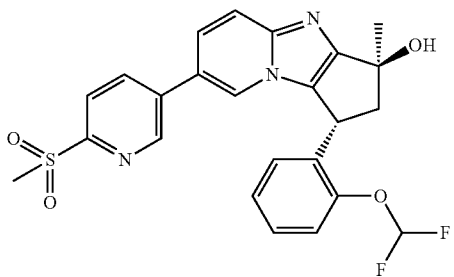 [SMILES: C[C@]1(O)C[C@H](c2ccccc2OC(F)F)c2c1nc1ccc(-c3ccc(S(C)(=O)=O)nc3)cn21]

The title compound was obtained by purification by column chromatography (50-100% EtOAc in heptane followed by 0-50% MeOH in DCM) and by preparative HPLC (acidic method) of the crude mixture obtained for Example 65 (combined fractions were neutralized to pH ~7 with a sat. aq. solution of sodium bicarbonate prior to concentration, dissolved into water (12 mL) and extracted with EtOAc (25 mL)) afforded 16.1 mg (4%) of the title compound as beige solid. ¹H NMR (500 MHz, CDCl₃) δ ppm 8.75 (d, J 1.7 Hz, 1H), 8.14 (d, J 8.1 Hz, 1H), 8.00 (dd, J 8.1, 2.2 Hz, 1H), 7.91 (d, J 9.4 Hz, 1H), 7.75 (s, 1H), 7.52 (dd, J 9.4, 1.7 Hz, 1H), 7.36-7.28 (m, 1H), 7.24 (d, J 8.4 Hz, 1H), 7.15 (td, J 7.6, 1.0 Hz, 1H), 6.92 (dd, J 7.7, 1.5 Hz, 1H), 6.81-6.46 (m, 1H), 5.24 (dd, J 7.9, 5.8 Hz, 1H), 3.37 (dd, J 13.8, 8.0 Hz, 1H), 3.25 (s, 3H), 2.56 (dd, J 13.8, 5.8 Hz, 1H), 1.87 (s, 3H), 1.25 (s, 1H). LCMS (ES⁺) RT 1.97 min 486.0 (M+H)⁺.

Example 96

Ethyl (1R,3R,5S,6r)-3-(5-{(1R,3R)-1-[2-(difluoromethoxy)phenyl]-3-hydroxy-2,3-dihydro-1H-cyclopenta[4,5]imidazo[1,2-a]pyridin-7-yl}pyrimidin-2-yl)-bicyclo[3.1.0]hexane-6-carboxylate

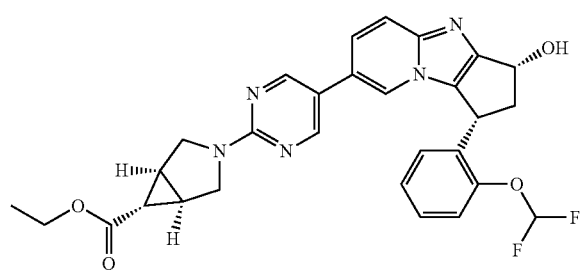 [SMILES: CCOC(=O)[C@H]1[C@@H]2CN(c3ncc(-c4ccc5nc6c(n5c4)[C@@H](c4ccccc4OC(F)F)C[C@H]6O)cn3)C[C@@H]21]

Example 31 (37 mg, 68 μmol) was dissolved in EtOAc (5 mL), and palladium on carbon (10%, 7.5 mg, 10 mol %) and TEA (10 μL, 68 μmol) were added. The suspension was de-gassed using vacuum/nitrogen/hydrogen and the reaction stirred under hydrogen at ambient temperature and pressure for 48 h with 4 retreatments (reaction mixture filtered, and/or addition of extra palladium catalyst and TEA). The reaction mixture was filtered through celite and concentrated in vacuo. The crude residue was purified by preparative HPLC (Method D) to afford 5.7 mg (13%) of the title compound as a brown oil. ¹H NMR (500 MHz, CDCl₃) δ ppm 8.75 (s, 2H), 7.99-7.78 (m, 2H), 7.59-7.47 (m, 1H), 7.36-7.29 (m, 1H), 7.22 (dt, J 21.9, 7.6 Hz, 2H), 7.09-6.87 (m, 1H), 6.71 (dd, J 74.6, 72.7 Hz, 1H), 5.53 (dd, J 7.3, 3.2 Hz, 1H), 4.96 (dd, J 8.5, 4.0 Hz, 1H), 4.09 (q, J 7.1 Hz, 2H), 3.80 (ddd, J 13.3, 9.5, 3.7 Hz, 1H), 3.66 (dt, J 14.2, 8.2 Hz, 1H), 3.53 (d, J 21.3 Hz, 1H), 2.94 (s, 1H), 2.61-2.47 (m, 4H), 2.02 (d, J 8.6 Hz, 2H), 1.55 (t, J 2.9 Hz, 1H), 1.24 (t, J 7.1 Hz, 3H). LCMS (ES+) RT 1.49 min, 547.0 (M+H)⁺.

Example 97

(1R,3R)-6-fluoro-7-{4-[(methylsulfonyl)methyl]phenyl}-1-phenyl-2,3-dihydro-1H-cyclopenta[4,5]imidazo[1,2-a]pyridin-3-ol

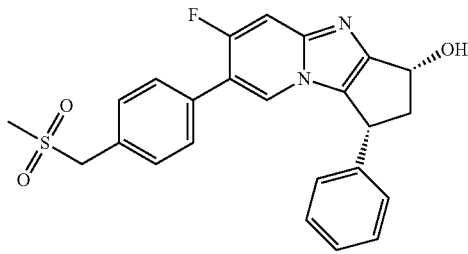 [SMILES: CS(=O)(=O)Cc1ccc(-c2cn3c4c(nc3cc2F)[C@H](O)C[C@@H]4c2ccccc2)cc1]

The title compound was prepared from Example 42 (1 eq, 0.800 mmol) and lithium tri-sec-butyl borohydride (1 M in THF, 1.2 mmol, 1.5 eq). By the Method B (30 mg, 9%). ¹H NMR (400 MHz, CDCl₃) δ 7.50 (d, J 7.3 Hz, 1H), 7.45 (d, J 7.8 Hz, 1H), 7.44 (s, 1H), 7.36-7.39 (m, 3 H), 7.28-7.34 (m, 5 H), 5.45 (m, 1 H), 4.42 (m, 1 H), 4.27 (s, 2 H), 3.59 (m, 1 H), 2.81 (s, 3 H), 2.47 (m, 1 H). LCMS (ES+) RT 1.25 min, 437.0 (M+H)⁺.

Example 98

(1S,3 S)-1-(2-Difluoromethoxy-phenyl)-6-fluoro-7-(4-methanesulfonyl-phenyl)-2,3-dihydro-1H-cyclopenta[4,5]imidazo[1,2-a]pyridin-3-ol

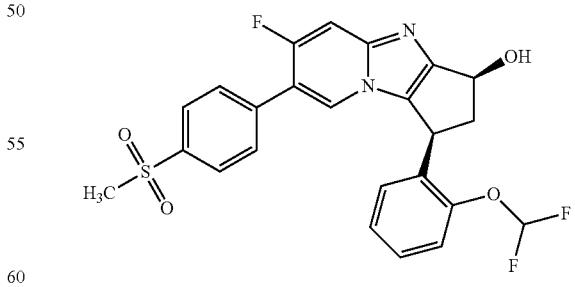

The title compound was prepared from Example 38 (67 mg, 0.14 mmol) and lithium tri-sec-butylborohydride (1.0M in THF, 0.2 mL, 0.2 mmol) by the Method B (36 mg, 54%). δ$_H$ (300 MHz, DMSO-d₆) 8.06 (d, J 7.5 Hz, 1H), 8.00 (m, 2H), 7.74 (dd, J 8.6 Hz, J 1.7 Hz, 2H), 7.67 (d, J 11.9 Hz, 1H), 7.33 (t, J 73.9 Hz, 1H), 7.30 (m, 1H), 7.23 (m, 1H), 7.12

(td, J 7.6, J 1.5 Hz, 1H), 6.92 (dd, J 7.7 Hz, J 1.6 Hz, 1H), 5.51 (br.s, 1H), 5.12 (m, 1H), 4.76 (dd, J 8.5 Hz, J 3.8 Hz, 1H), 3.45 (m, 1H), 3.24 (s, 3H), 2.06 (dt, J 13.6 Hz, J 3.5 Hz, 1H). LCMS (ES') RT 1.94 min 489.6 (M+H)+.

Example 99

(1S,5R,8R)-3-{5-[(R)-1-(2-Difluoromethoxy-phenyl)-3-oxo-2,3-dihydro-1H-cyclopenta[4,5]imidazo[1,2-a]pyridin-7-yl]-pyrimidin-2-yl}-3-aza-bicyclo[3.2.1]octane-8-carboxylic acid

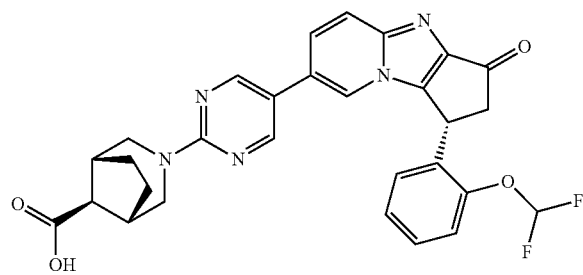 [SMILES: O=C1C[C@H](c2ccccc2OC(F)F)c2c1nc1ccc(-c3cnc(N4C[C@H]5CC[C@@H](C4)[C@@H]5C(=O)O)nc3)cn21]

The title compound was prepared from Example 40 (191 mg, 0.34 mmol) and lithium hydroxide monohydrate (74 mg, 1.81 mmol) by the Method I (92 mg, 49%). $\delta_H$ (300 MHz, DMSO-$d_6$) 12.13-12.32 (m, 1 H), 8.58 (s, 2 H), 8.20 (t, J 1.1 Hz, 1 H), 7.83 (dd, J 9.6, 0.9 Hz, 1 H), 7.76 (dd, J 9.7, 1.7 Hz, 1 H), 7.33-7.41 (m, 1 H), 7.24-7.30 (m, 1H), 7.28 (t, J 73.9 Hz, 1 H), 7.14 (td, J 7.6, 1.1 Hz, 1 H), 6.85-6.92 (m, 1 H), 5.13-5.19 (m, 1 H), 4.38-4.46 (m, 2 H), 3.57-3.67 (m, 1 H), 3.01 (d, 2 H, J 12.2 Hz), 2.72-2.81 (m, 1 H), 2.67 (s, 1 H), 2.56-2.62 (m, 2 H), 1.63-1.74 (m, 2 H), 1.31-1.41 (m, 2 H). LCMS (ES+) RT 1.31 min, 546 (M+H)+.

Example 100

(1S,5R,8R)-3-{5-[(R)-1-(2-Difluoromethoxy-phenyl)-3-oxo-2,3-dihydro-1H-cyclopenta[4,5]imidazo[1,2-a]pyridin-7-yl]-pyrimidin-2-yl}-3-aza-bicyclo[3.2.1]octane-8-carboxylic acid dimethylamide

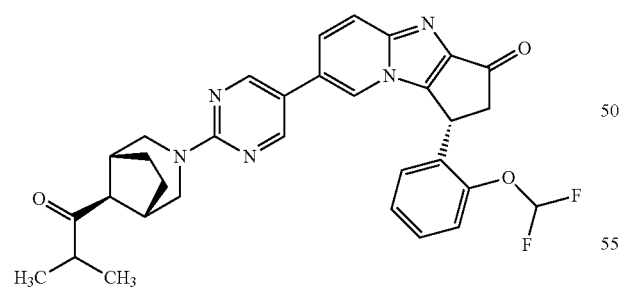

To a solution of Example 99 (33 mg, 0.06 mmol) in THF (5 mL) was added DIPEA (0.06 mL, 0.3 mmol), 1-hydroxybenzotriazole hydrate (21 mg, 0.14 mmol), 1-(3-dimethylaminopropyl)-3-ethylcarbodiimide hydrochloride (23 mg, 0.12 mmol) and dimethylamine (0.06 mL, 0.1 mmol) and reaction mixture stirred at r.t. for 18 h. The reaction mixture was concentrated in vacuo. Residue dissolved in water (25 mL) and extracted with EtOAc (3×25 mL). Combined organics were dried over (sodium sulfate), filtered and concentrated in vacuo. The residue was purified by flash column chromatography (SiO$_2$, 0-20% MeOH in EtOAc) and the material freeze dried from MeCN/water to give title compound (25 mg, 72%) as a beige solid. $\delta_H$ (300 MHz, DMSO-$d_6$) 8.59 (s, 2H), 8.20-8.22 (m, 1 H), 7.83 (dd, J 9.7, 1.1 Hz, 1 H), 7.76 (dd, J 9.7, 1.8 Hz, 1 H), 7.34-7.41 (m, 1 H), 7.24-7.30 (m, 1 H), 7.28 (t, J 73.9 Hz, 1 H), 7.14 (td, J 7.5, 1.1 Hz, 1 H), 6.85-6.92 (m, 1 H), 5.13-5.18 (m, 1 H), 4.36-4.44 (m, 2 H), 3.57-3.68 (m, 1 H), 3.11 (s, 1 H), 3.08 (s, 3 H), 2.94 (s, 1 H), 2.81 (s, 3 H), 2.71-2.81 (m, 2 H), 2.41-2.49 (m, 2 H), 1.76-1.84 (m, 2 H), 1.29-1.38 (m, 2 H). LCMS (ES+) RT 2.10 min, 573 (M+H)+.

Example 101

(1S,5R,8R)-3-{5-[(R)-1-(2-Difluoromethoxy-phenyl)-3-hydroxy-3-methyl-2,3-dihydro-1H-cyclopenta[4,5]imidazo[1,2-a]pyridin-7-yl]-pyrimidin-2-yl}-3-aza-bicyclo[3.2.1]octane-8-carboxylic acid

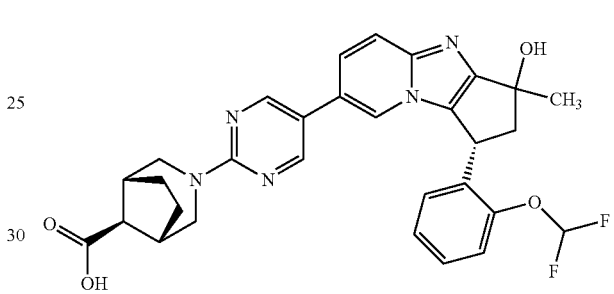

The title compound was prepared from of Example 26 (54 mg, 0.09 mmol) and lithium hydroxide monohydrate (19 mg, 0.45 mmol) by the Method I (28 mg, 53%). Material is a mixture 79:21 of the two diastereoisomers, assignment given for the major diastereoisomer; $\delta_H$ (300 MHz, DMSO-$d_6$) 12.04-12.24 (m, 1 H), 8.46 (s, 2 H), 7.88-7.92 (m, 1 H), 7.58 (dd, J 9.4, 0.9 Hz, 1 H), 7.44 (dd, J 9.4, 1.8 Hz, 1 H), 7.29 (t, J 74.1 Hz, 1 H), 7.21-7.25 (m, 1 H), 7.17-7.21 (m, 1 H), 7.03-7.10 (m, 1 H), 6.91 (dd, J 7.7, 1.5 Hz, 1 H), 5.19 (s, 1 H), 4.69-4.75 (m, 1 H), 4.29-4.38 (m, 2 H), 3.01-3.12 (m, 1 H), 2.89-2.96 m, 2 H), 2.58 (s, 1 H), 2.48-2.54 (m, 2 H), 2.30 (dd, J 13.5, 4.4 Hz, 1 H), 1.56-1.65 (m, 2 H), 1.48 (s, 3 H), 1.24-1.33 (m, 2 H). LCMS (ES+) RT 1.52 min, 562 (M+H)+.

Example 102

(1S,3S)-6-fluoro-3-methoxy-7-{4-[1-(methylsulfonyl)ethyl]phenyl}-1-phenyl-2,3-dihydro-1H-cyclopenta[4,5]imidazo[1,2-a]pyridine

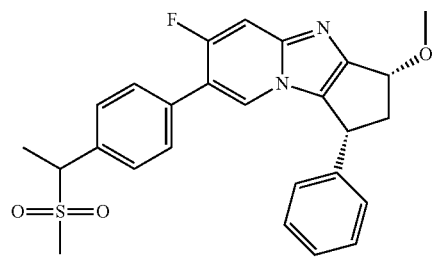 [SMILES: CO[C@@H]1C[C@H](c2ccccc2)c2c1nc1cc(F)c(-c3ccc(C(C)S(C)(=O)=O)cc3)cn21]

Example 74 (19.5 mg, 0.0447 mmol, 1.0 eq) was dissolved in THF (1 mL) and cooled down to 0° C. Sodium hydroxide (0.00214 g, 0.0536 mmol, 1.2 eq) was added in one portion. After 30 minutes, under stirring at 0° C., iodomethane (0.00641 g, 0.0447 mmol, 1 eq) was added. After 1 h, a second equivalent of iodomethane was added and the temperature raised to r.t. overnight. Solvents were evaporated and the residue was purified by prep HPLC, yielding the title compound as an off white solid (8 mg, 38%). LCMS (ES+) RT 1.42 min, 465.0 (M+H)$^+$.

Example 103

(1S,3S)-6-fluoro-7-[2-(morpholin-4-yl)pyrimidin-5-yl]-1-phenyl-2,3-dihydro-1H-cyclopenta[4,5]imidazo[1,2-a]pyridin-3-ol

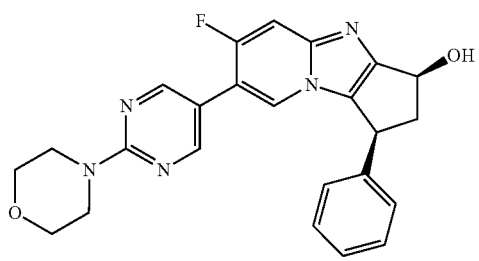 [SMILES: O[C@H]1C[C@@H](c2ccccc2)c2c1nc1cc(F)c(-c3cnc(N4CCOCC4)nc3)cn21]

The title compound was prepared from Example 82 (344 mg, 1.0 eq.) and lithium tri-sec-butylborohydride (1.5 eq.) by the Method B (130 mg, 38%). LCMS (ES$^+$) RT 3.32 min, 432 (M+H)$^+$.

Example 104

(1S,3S)-6-fluoro-3-methoxy-7-[2-(morpholin-4-yl)pyrimidin-5-yl]-1-phenyl-2,3-dihydro-1H-cyclopenta[4,5]imidazo[1,2-a]pyridine

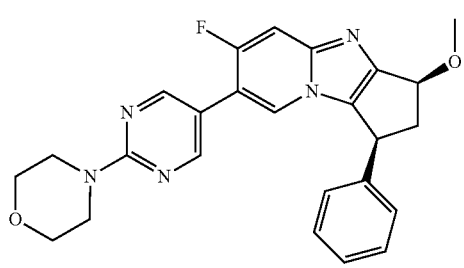 [SMILES: CO[C@H]1C[C@@H](c2ccccc2)c2c1nc1cc(F)c(-c3cnc(N4CCOCC4)nc3)cn21]

Example 103 (46.3 mg, 1.0 eq.) was dissolved in THF (9.3 mL/mmol). At 0° C., NaH (60% in mineral oil, 1.2 eq.) was added and the reaction mixture was stirred for 10 minutes at 0° C. Iodomethane (1.2 eq.) was added and the mixture heated at 60° C. for 16 h. The reaction was quenched with ammonium chloride (sat. solution), extracted with EtOAc, dried over magnesium sulfate and concentrated in vacuo. The residue was purified by flash column chromatography (SiO$_2$, 0-% MeOH in DCM), followed by MS directed preparative reverse chromatography, yielding the title compound as a white solid (3 mg, 6%). LCMS (ES$^+$) RT 1.45 min, 446.0 (M+H)$^+$.

Example 105

(1R,3R)-6-fluoro-7-[2-(morpholin-4-yl)pyrimidin-5-yl]-1-phenyl-2,3-dihydro-1H-cyclopenta[4,5]imidazo[1,2-a]pyridin-3-ol

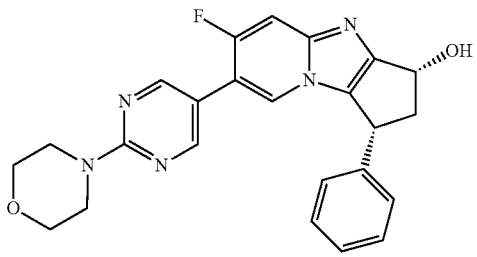 [SMILES: O[C@@H]1C[C@H](c2ccccc2)c2c1nc1cc(F)c(-c3cnc(N4CCOCC4)nc3)cn21]

The title compound was prepared from Example 83 (230 mg, 1.0 eq.) and lithium tri-sec-butylborohydride (1.5 eq.) by the Method B (105 mg, 46%). LCMS (ES$^+$) RT 3.33 min, 432 (M+H)$^+$.

Example 106

(1R,3R)-6-fluoro-3-methoxy-7-[2-(morpholin-4-yl)pyrimidin-5-yl]-1-phenyl-2,3-dihydro-1H-cyclopenta[4,5]imidazo[1,2-a]pyridine

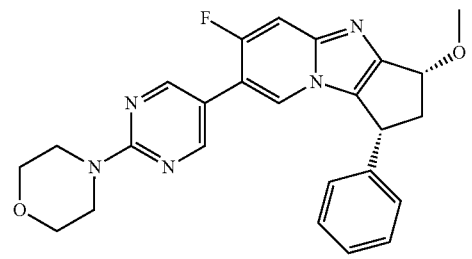 [SMILES: CO[C@@H]1C[C@H](c2ccccc2)c2c1nc1cc(F)c(-c3cnc(N4CCOCC4)nc3)cn21]

The title compound was prepared from Example 105 (95 mg, 1.2 eq.), NaH (60% in mineral oil, 1.3 eq.), iodomethane (1.3 eq.) in THF (9.1 mL/mmol) by the method described in Example 103. The residue was purified by flash column chromatography (SiO$_2$, 0-4% MeOH in DCM), yielding the title compound as a yellow solid (42 mg, 43%). LCMS (ES$^+$) RT 1.45 min, 446.0 (M+H)$^+$.

Example 107

(1R,3R)-7-bromo-1-[2-(difluoromethoxy)phenyl]-3-[3-(methylsulfonyl)phenoxy]-2,3-dihydro-1H-cyclopenta[4,5]imidazo[1,2-a]pyridine

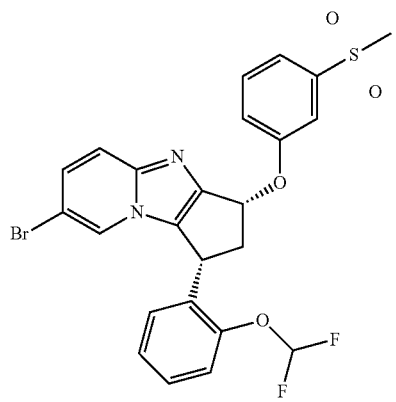

Intermediate 72 (100 mg, 1.0 eq.) and 3-methanesulfonylphenol (1.0 eq.) were dissolved in THF (4 mL/mmol). At 0° C., triphenylphosphine resin (1.1 eq., 1.88 mmol/g) followed by a solution of DIAD (1.4 eq.) in THF (0.5 mL). The reaction mixture was stirred at r.t. for 16 h, quenched with sodium bicarbonate (sat. solution, 1 mL) and concentrated in vacuo. The residue was taken up by EtOAc, dried over magnesium sulfate and evaporated. The residue was purified by flash column chromatography (SiO$_2$, 1-5% MeOH in DCM), followed by UV directed preparative reverse chromatography (basic Gradient 50-80), yielding the title compound as an off-white solid (33 mg, 24%). LCMS (ES+) RT 1.59 min, 550.0 (M+H)$^+$.

Example 108

(1R,3R)-1-[2-(difluoromethoxy)phenyl]-3-[3-(methylsulfonyl)phenoxy]-2,3-dihydro-1H-cyclopenta[4,5]imidazo[1,2-a]pyridine-7-carbonitrile

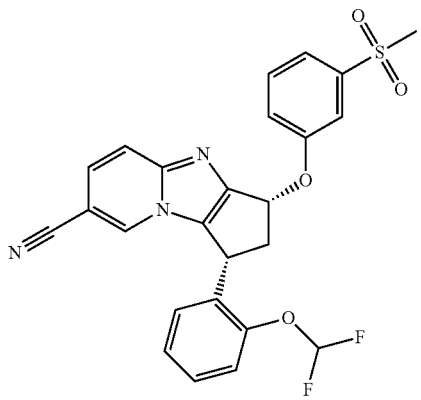 [SMILES: CS(=O)(=O)c1cccc(O[C@@H]2C[C@H](c3ccccc3OC(F)F)c3c2nc2ccc(C#N)cn32)c1]

Example 107 (56 mg, 1.0 eq.) was dissolved in DMF (19.6 mL/mmol) and the solution was degassed with argon. Zinc cyanide (1.1 eq.) and tetrakis(triphenylphosphine)palladium(O) (0.3 eq.) were added and the reaction mixture was heated at 120° C. for 3 h. The mixture was filtered on celite, taken up by Et$_2$O, washed with brine, dried over magnesium sulfate and concentrated in vacuo. The residue was purified by MS directed preparative reverse chromatography, yielding the title compound as a white solid glass (10 mg, 18%). LCMS (ES+) RT 1.51 min, 496.0 (M+H)$^+$.

Example 109

(S)-1-(2-chlorophenyl)-6-fluoro-7-[2-(2-hydroxypropan-2-yl)pyrimidin-5-yl]-2,3-dihydro-1H-cyclopenta[4,5]imidazo[1,2-a]pyridin-3-ol

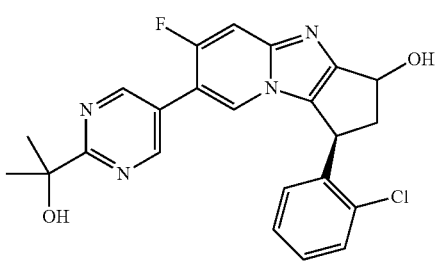 [SMILES: CC(C)(O)c1ncc(-c2cn3c4c(nc3cc2F)C(O)C[C@H]4c2ccccc2Cl)cn1]

The title compound was prepared from Example 75 (50 mg, 0.114 mmol, 1 eq.) and sodium borohydride (4.3 mg, 0.114 mmol 1 eq.) by the Method C (32 mg, 21%). LCMS (ES+) RT 1.32 min, 439.0 (M+H)$^+$.

Example 110

(R)-1-(2-chlorophenyl)-6-fluoro-7-[2-(2-hydroxypropan-2-yl)pyrimidin-5-yl]-2,3-dihydro-1H-cyclopenta[4,5]imidazo[1,2-a]pyridin-3-ol

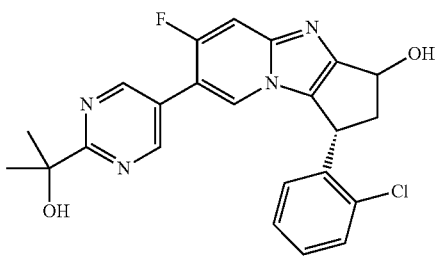 [SMILES: CC(C)(O)c1ncc(-c2cn3c4c(nc3cc2F)C(O)C[C@@H]4c2ccccc2Cl)cn1]

The title compound was prepared from Example 76 (50 mg, 0.114 mmol, 1 eq.) and sodium borohydride (4.3 mg, 0.114 mmol 1 eq.) by the Method C (11 mg, 10%). LCMS (ES+) RT 1.32 min, 439.0 (M+H)$^+$.

Example 111

(1R,3R)-6-fluoro-7-[2-(2-hydroxypropan-2-yl)pyrimidin-5-yl]-1-[2-(trifluoromethoxy)phenyl]-2,3-dihydro-1H-cyclopenta[4,5]imidazo[1,2-a]pyridin-3-ol

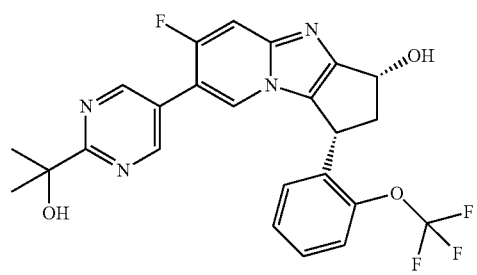 [SMILES: CC(C)(O)c1ncc(-c2cn3c4c(nc3cc2F)[C@H](O)C[C@@H]4c2ccccc2OC(F)(F)F)cn1]

The title compound was prepared from Example 81 (95.3 mg, 1.0 eq.), MeOH (10.2 mL/mmol) and sodium borohydride (1.0 eq.) by the Method C. The residue was precipitated in MeOH, filtered and dried under reduced pressure. The title compound was isolated by chiral purification under SFC conditions on Chiralpak IA (50*266 mm*mm, flow 360 mL/min, 25° C., CO$_2$+20% MeOH, injection of 5.33 mL solution at a concentration of 30 g/L). The first eluting enantiomer (RT 6.7 min) was collected and the fractions were evaporated to yield the title compound as a white solid (9.2 mg, 10%). LCMS (ES+) RT 1.38 min, 489.0 (M+H)$^+$.

Example 112

(1R,3S)-6-fluoro-7-[2-(2-hydroxypropan-2-yl)pyrimidin-5-yl]-1-[2-(trifluoromethoxy)phenyl]-2,3-dihydro-1H-cyclopenta[4,5]imidazo[1,2-a]pyridin-3-ol

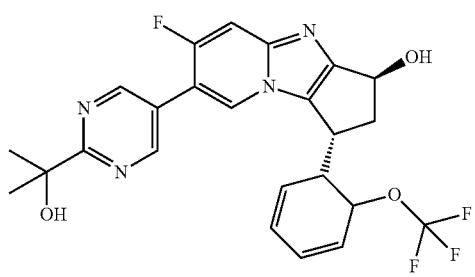 [SMILES: CC(C)(O)c1ncc(-c2cn3c4c(nc3cc2F)[C@@H](O)C[C@@H]4C2C=CC=CC2OC(F)(F)F)cn1]

The second eluting enantiomer (RT 9.5 min) from the purification described in Example 111 was collected and the fractions were evaporated to yield the title compound as a white solid (12 mg, 12%). LCMS (ES+) RT 1.38 min, 489.0 (M+H)$^+$.

Example 113

(1R,3R)-1-(2-Difluoromethoxy-phenyl)-7-[2-(1-oxo-thiomorpholin-4-yl)-pyrimidin-5-yl]-2,3-dihydro-1H-cyclopenta[4,5]imidazo[1,2-a]pyridin-3-ol

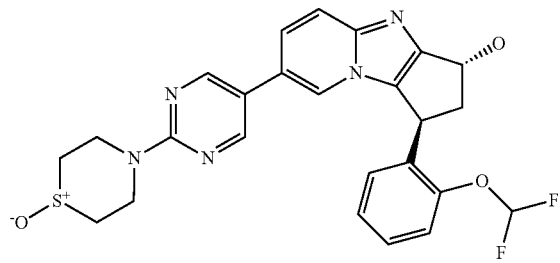

The title compound was prepared from Example 93 (0.24 mmol, 120 mg) and lithium tri-sec-butylborohydride (1.0M in THF, 0.4 mmol, 0.4 mL) by the Method B (76 mg, 62%). $\delta_H$ (300 MHz, DMSO-d$_6$) 8.63 (s, 2H); 8.03 (m, 1H); 7.68 (dd, J 9.5 Hz, J 0.9 Hz, 1H); 7.54 (dd, J 9.5 Hz, J 1.8 Hz, 1H); 7.37 (t, J 74.1 Hz, 1H); 7.29 (m, 2H); 7.13 (m, 1H); 6.94 (dd, J 8.0 Hz, J 1.5 Hz, 1H); 5.48 (d, J 5.2 Hz, 1H); 5.13 (m, 1H); 4.77 (m, 1H); 4.48 (m, 2H); 3.95 (m, 2H); 3.45 (m, 1H); 2.88 (m, 2H); 2.73 (m, 2H); 2.08 (m, 1H). LCMS (ES$^+$) RT 1.64 min 512.8 (M+H)$^+$.

Example 114

(1R,3R)-1-(2-Difluoromethoxy-phenyl)-7-[2-(1,1-dioxo-thio morpholin-4-yl)-pyrimidin-5-yl]-2,3-dihydro-1H-cyclopenta[4,5]imidazo[1,2-a]pyridin-3-ol

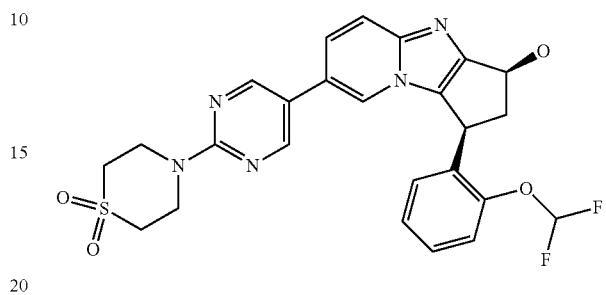

The title compound was prepared from Example 92 (0.95 mmol, 500 mg) and lithium tri-sec-butylborohydride (1.0M in THF, 1.0 mmol, 1.0 mL) by the Method B (365 mg, 73%). $\delta_H$ (300 MHz, DMSO-d$_6$) 8.66 (s, 2H); 8.04 (dd, J 1.4 Hz, J 0.9 Hz, 1H); 7.69 (dd, J 9.5 Hz, J 0.8 Hz, 1H); 7.55 (dd, J 9.5 Hz, J 1.8 Hz, 1H); 7.37 (t, J 74.1 Hz, 1H); 7.29 (m, 2H); 7.13 (m, 1H); 6.94 (m, 1H); 5.48 (d, J 5.2 Hz, 1H); 5.13 (m, 1H); 4.77 (dd, J 8.5 Hz, J 3.8 Hz, 1H); 4.23 (m, 4H); 3.45 (m, 1H); 3.16 (m, 4H); 2.08 (dt, J 13.4 Hz, J 3.5 Hz, 1H). LCMS (ES') RT 1.80 min 528.6 (M+H)$^+$.

Example 115

(R)-1-(2-Difluoromethoxy-phenyl)-6-fluoro-7-[2-(1-hydroxy-1-methyl-ethyl)-1,6-dihydro-pyrimidin-5-yl]-1,2-dihydro-cyclopenta[4,5]imidazo[1,2-a]pyridin-3-one

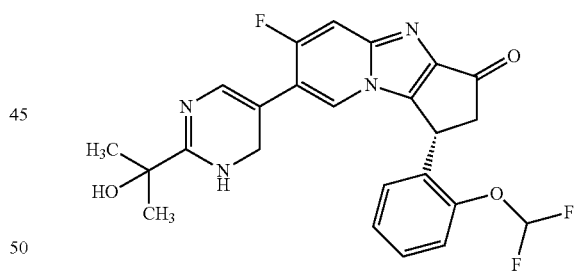

Example 85 (0.32 mmol, 150 mg) was dissolved in THF (10 ml). Ammonium acetate (0.38 mmol, 30 mg), AcOH (0.35 mmol, 20 µl) and sodium triacetoxyborohydride (0.45 mmol, 100 mg) were added and the reaction stirred at r.t. for 12 h. The reaction was quenched with sodium hydroxide and extracted with further EtOAc. The combined organic phase was dried over sodium sulfate, filtered and concentrated in vacuo before purification by preparative HPLC yielding the title compound (40 mg, 27%). $\delta_H$ (400 MHz, DMSO-d$_6$) 7.62 (d, J 13.2 Hz, 1H); 7.57 (d, J 7.7 Hz, 1H); 7.39 (d, J 8.4 Hz, J 1.6 Hz, 1H); 7.28 (m, 1H); 7.27 (t, J 73.9 Hz, 1H); 7.17 (td, J 7.6 Hz, J 1.1 Hz, 1H); 6.94 (m, 1H); 6.76 (s, 1H); 5.13 (dd, J 6.9 Hz, J 2.0 Hz, 1H); 4.16 (m, 1H); 3.99 (m, 1H); 3.58 (dd, J 18.2 Hz, J 7.0 Hz, 1H); 2.77 (dd, J 18.2 Hz, J 2.0 Hz, 1H); 1.26 (s, 6H). LCMS (ES$^+$) RT 1.54 min 471.6 (M+H)$^+$.

Example 116

(1R,3S)-1-(2-Difluoromethoxy-phenyl)-6-fluoro-7-(4-methanesulfonyl-phenyl)-2,3-dihydro-1H-cyclopenta[4,5]imidazo[1,2-a]pyridin-3-ylamine

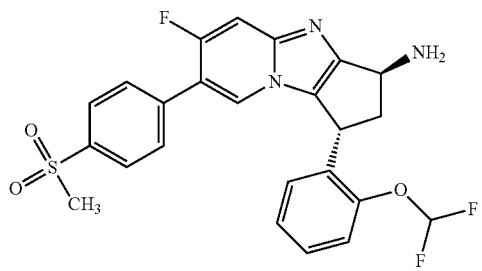 [SMILES: CS(=O)(=O)c1ccc(-c2cn3c4c(nc3cc2F)[C@@H](N)C[C@@H]4c2ccccc2OC(F)F)cc1]

Example 46 (0.20 mmol, 100 mg) was dissolved in THF (10 mL) and cooled to 0° C. Diphenylphosphoryl azide (0.27 mmol, 60 µL) and 1,8-diazabicyclo[5.4.0]undec-7-ene (0.27 mmol, 40 µL) were added and the reaction stirred for 12 h. The solvent was then removed in vacuo before purification by flash column chromatography (SiO$_2$, 40-80% EtOAc in hexanes) yielding the (1R,3S)-3-Azido-1-(2-difluoromethoxy-phenyl)-6-fluoro-7-(4-methanesulfonyl-phenyl)-2,3-dihydro-1H-cyclopenta[4,5]imidazo[1,2-a]pyridine (45 mg, 43%). This was dissolved in THF (5 ml) and triphenylphosphine resin (0.23 mmol, 150 mg) added. The reaction was heated to 60° C. for 12 h prior to filtration of the resin. Concentration of the solvent in vacuo gave the title compound (26 mg, 27% over two steps). δ$_H$ (300 MHz, DMSO-d$_6$) 8.12 (d, J 7.6 Hz, 1H); 8.00 (d, J 8.5 Hz, 2H); 7.74 (dd, J 8.5 Hz, J 1.7 Hz, 2H); 7.64 (d, J 12.0 Hz, 1H); 7.30 (t, J 74.1 Hz, 1H); 7.29 (m, 1H); 7.22 (m, 1H); 7.07 (td, J 7.5 Hz, J 1.3 Hz, 1H); 6.64 (dd, J 7.7 Hz, J 1.5 Hz, 1H); 4.98 (dd, J 8.1 Hz, J 3.5 Hz, 1H); 4.40 (m, 1H); 3.24 (s, 3H); 2.72 (m, 1H); 2.59 (m, 1H). LCMS (ES$^+$) RT 1.66 min 488.6 (M+H)$^+$.

Example 117

(8-anti)-3-(5-{(1R,3R)-1-[2-(difluoromethoxy)phenyl]-3-methoxy-2,3-dihydro-1H-cyclopenta[4,5]imidazo[1,2-a]pyridin-7-yl}pyrimidin-2-yl)-3-azabicyclo[3.2.1]octane-8-carboxylic acid

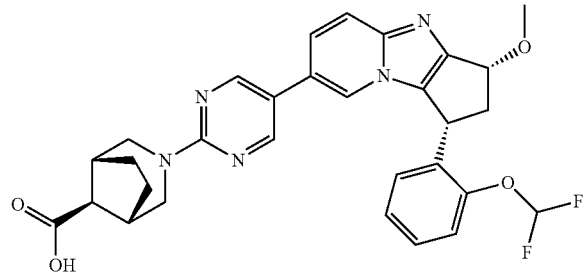 [SMILES: CO[C@@H]1C[C@H](c2ccccc2OC(F)F)c2c1nc1ccc(-c3cnc(N4C[C@H]5CC[C@@H](C4)[C@@H]5C(=O)O)nc3)cn21]

The title compound was prepared from Example 86 (106 mg, 0.18 mmol) and lithium hydroxide monohydrate (31 mg, 0.73 mmol) by the Method I (55 mg, 53%). δ$_H$ (400 MHz, DMSO-d$_6$) 12.00-12.26 (m, 1 H), 8.55 (s, 2 H), 8.08-8.10 (m, 1 H), 7.70 (dd, J 9.5, 0.8 Hz, 1 H), 7.56 (dd, J 9.5, 1.8 Hz, 1 H), 7.37 (t, J 74.1 Hz, 1 H), 7.30 (dd, J 6.8, 1.4 Hz, 1 H), 7.23-7.28 (m, 1 H), 7.11 (td, J 7.6, 1.7 Hz, 1 H), 6.81 (dd, J 7.7, 1.6 Hz, 1H), 4.77-4.85 (m, 2 H), 4.37-4.45 (m, 2 H), 3.42-3.47 (m, 4 H), 2.96-3.03 (m, 2 H), 2.66 (d, J 0.4 Hz, 1 H), 2.55-2.61 (m, 2 H), 2.14-2.22 (m, 1 H), 1.64-1.72 (m, 2 H), 1.31-1.41 (m, 2H). LCMS (ES+) RT 1.44 min, 562 (M+H)$^+$.

Example 118

7-bromo-1-[2-(difluoromethoxy)phenyl]-2-(hydroxymethyl)-2,3-dihydro-1H-cyclopenta[4,5]imidazo[1,2-a]pyridin-3-ol

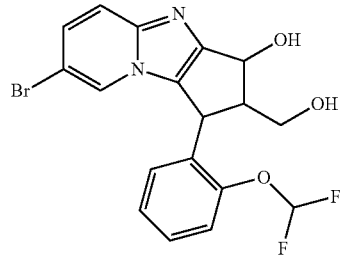 [SMILES: OCC1C(O)c2nc3ccc(Br)cn3c2C1c1ccccc1OC(F)F]

The title compound was prepared from Intermediate 6 (0.25 g, 0.53 mmol) and sodium borohydride (0.022 g, 0.59 mmol) by the Method C (0.036 g, 16% Yield). $^1$H NMR (DMSO-d$_6$) δ: 7.93 (m, 1H), 7.70 (m, 1H), 7.58 (m, 1H), 7.32 (m, 3H), 7.17 (m, 1H), 6.93 (dd, J 7.7 Hz, J 1.6 Hz, 1H), 5.51 (d, J 5.7 Hz, 1H), 5.21 (m, 1H), 4.98 (dd, J 5.7 Hz, J 3.0 Hz, 1H), 4.81 (t, J 5.0 Hz, 1H), 4.55 (d, J 3.8 Hz, 1H), 3.79 (m, 1H), 3.62 (m, 1H). LCMS (ES$^+$) RT 1.20 min 425.0/427.0 (M+H)$^+$.

Example 119

(1R,3S)-1-[2-(difluoromethoxy)phenyl]-3-methyl-7-{2-[(1S,4S)-2-oxa-5-azabicyclo[2.2.1]hept-5-yl]pyrimidin-5-yl}-2,3-dihydro-1H-cyclopenta[4,5]imidazo[1,2-a]pyridin-3-ol

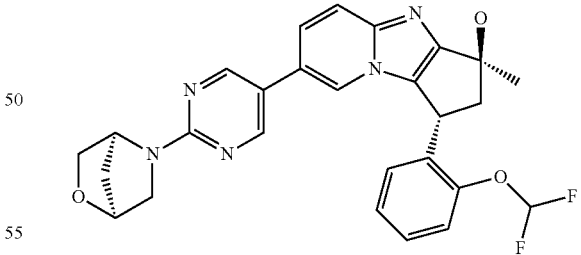

The title compound was prepared from Example 15 (245 mg, 0.60 mmol) and (1S,4S)-5-[5-(4,4,5,5-tetramethyl-1,3,2-dioxaborolan-2-yl)pyrimidin-2-yl]-2-oxa-5-azabicyclo[2.2.1]heptane (272 mg, 0.90 mmol) by the Method A, to afford the product as a 4:1 epimeric mixture. Separation of the epimers by chiral-LC chromatography (Chiralcel OD-H® column, 85:15 heptane/EtOH eluent) afforded 23 mg (8%) of the title compound as a green solid. $^1$H NMR (500 MHz, MeOD-d$_4$) δ ppm 8.43 (s, 2H), 7.79 (s, 1H), 7.68 (d, J 9.5 Hz, 1H), 7.54 (dd, J 9.5, 1.8 Hz, 1H), 7.37-7.31 (m, 1H), 7.26 (d, J 8.1 Hz, 1H), 7.18-7.12 (m, 1H), 6.95 (t, J 73.9 Hz, 1H), 6.83 (dd, J 7.7, 1.2 Hz, 1H), 5.17 (dd, J 7.9, 5.6 Hz, 1H), 5.02 (s, 1H), 4.70 (s, 1H), 3.87 (dd, J 7.4, 1.3 Hz, 1H), 3.79 (d, J 7.4 Hz, 1H), 3.55 (dd, J 10.8, 1.3 Hz, 1H), 3.50 (d, J 10.9 Hz, 1H), 3.24 (dd, J 13.6, 8.0 Hz, 1H), 2.51 (dd, J 13.6, 5.6 Hz, 1H), 1.98 (s, 2H), 1.71 (s, 3H). LCMS (ES⁺) RT 1.31 min 506.0 (M+H)⁺.

Example 120

(1R,3R)-1-[2-(difluoromethoxy)phenyl]-3-methyl-7-{2-[(1S,4S)-2-oxa-5-azabicyclo[2.2.1]hept-5-yl]pyrimidin-5-yl}-2,3-dihydro-1H-cyclopenta[4,5]imidazo[1,2-a]pyridin-3-ol

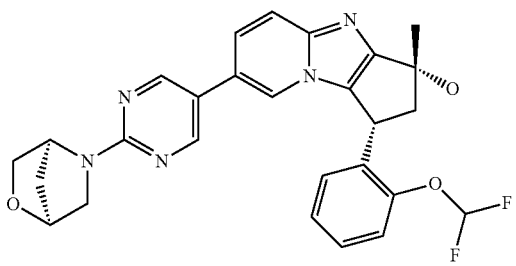 [SMILES: C[C@@]1(O)C[C@H](c2ccccc2OC(F)F)c2c1nc1ccc(-c3cnc(N4C[C@@H]5C[C@H]4CO5)nc3)cn21]

The title compound, 108 mg (36%), was isolated as a pale green solid by chiral-LC chromatography from the mixture of epimers separated in Example 119.

¹H NMR (500 MHz, MeOD-d₄) □ ppm 8.43 (s, 2H), 7.84 (s, 1H), 7.65 (d, J 9.4 Hz, 1H), 7.51 (d, J 11.2 Hz, 1H), 7.31 (td, J 7.8, 7.3, 1.6 Hz, 1H), 7.26 (d, J 8.0 Hz, 1H), 7.17-7.12 (m, 1H), 7.09 (dd, J 7.7, 1.6 Hz, 1H), 7.00 (t, J 73.9 Hz, 1H), 5.02 (s, 1H), 4.94 (dd, J 8.4, 4.9 Hz, 1H), 4.70 (s, 1H), 3.87 (dd, J 7.4, 1.2 Hz, 1H), 3.78 (d, J 7.4 Hz, 1H), 3.55 (dd, J 10.8, 1.1 Hz, 1H), 3.50 (d, J 10.9 Hz, 1H), 3.28 (d, J 8.4 Hz, 1H), 2.52 (dd, J 13.5, 4.9 Hz, 1H), 1.98 (s, 2H), 1.69 (s, 3H). LCMS (ES⁺) RT 1.31 min 506.0 (M+H)⁺.

Example 121 Method K (1R,3R)-1-[2-(difluoromethoxy)phenyl]-6-fluoro-7-[2-(4-hydroxytetrahydro-2H-pyran-4-yl)pyrimidin-5-yl]-2,3-dihydro-1H-cyclopenta[4,5]imidazo[1,2-a]pyridin-3-ol

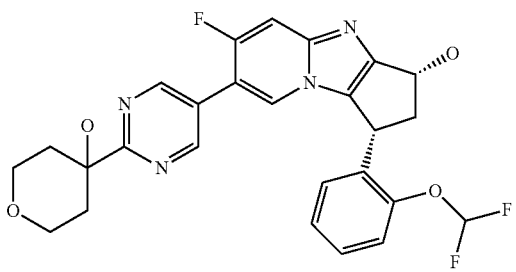 [SMILES: O[C@@H]1C[C@H](c2ccccc2OC(F)F)c2c1nc1cc(F)c(-c3cnc(C4(O)CCOCC4)nc3)cn21]

Example 16 (95 mg, 0.23 mmol), Intermediate 35 (89% purity, 98 mg, 0.23 mmol), a 2M solution of sodium carbonate in water (0.35 mL, 0.69 mmol) and 1,4-dioxane (2 mL) were placed in a microwave tube. The mixture was degassed with nitrogen before the addition of Pd(dppf)Cl₂DCM adduct (19 mg, 0.02 mmol). The reaction was sealed under nitrogen and stirred in the microwave at 120° C. for 1 h. A 1M solution of TBAF in THF (1.38 mL) was added to the cooled reaction and the mixture was stirred at r.t. for 3 days. The mixture was diluted with water (3 mL) and extracted with EtOAc (2×5 mL). The combined organic phase was washed with water (2×5 mL), brine (5 mL), dried over sodium sulfate and concentrated in vacuo. The crude product was purified by preparative HPLC (Method C) to afford 35 mg (29%) of the title compound as an off-white solid. ¹H NMR (500 MHz, CDCl₃) δ ppm 8.78 (d, J 1.4 Hz, 2H), 7.70 (d, J 7.1 Hz, 1H), 7.46 (d, J 10.9 Hz, 1H), 7.32-7.27 (m, 1H), 7.26-7.23 (m, 1H), 7.21-7.14 (m, 2H), 6.67 (dd, J 74.7, 72.6 Hz, 1H), 5.46 (dd, J 7.3, 3.1 Hz, 1H), 4.90 (dd, J 8.5, 3.8 Hz, 1H), 4.45 (s, 1H), 3.97 (m, 4H), 3.67-3.57 (m, 1H), 2.42 (ddd, J 14.8, 11.6, 6.9 Hz, 3H), 1.57 (d, J 11.8 Hz, 2H). LCMS (ES⁺) RT 1.25 min 513.0 (M+H)⁺.

Example 122

(1R,3S)-1-[2-(difluoromethoxy)phenyl]-7-[2-(2-hydroxypropan-2-yl)pyrimidin-5-yl]-3-methyl-2,3-dihydro-1H-cyclopenta[4,5]imidazo[1,2-a]pyridin-3-ol

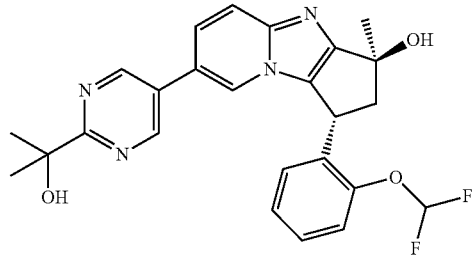 [SMILES: CC(C)(O)c1ncc(-c2ccc3nc4c(n3c2)[C@@H](c2ccccc2OC(F)F)C[C@]4(C)O)cn1]

A mixture of Example 15 (245 mg, 0.599 mmol), 2-[5-(tetramethyl-1,3,2-dioxaborolan-2-yl)pyrimidin-2-yl]propan-2-ol (237 mg, 0.897 mmol), sodium carbonate (190 mg, 1.795 mmol) in 1,4-dioxane (5 mL) was degassed with nitrogen for 10 minutes then Pd(dppf)Cl₂ DCM adduct (49 mg, 10 mol %) was added as well as water (1.5 mL) and the reaction mixture was heated at 120° C. for 1 h in the microwave reactor. The reaction mixture was passed through a hydrophobic frit and concentrated. The crude residue was purified by flash column chromatography (SiO₂, 0-100% EtOAc in heptane then 0-100% MeOH in EtOAc), and then by preparative HPLC to afford 8.2 mg (3%) of the title compound as an off-white solid. ¹H NMR (500 MHz, CDCl₃) δ ppm 8.68 (s, 2H), 7.71 (d, J 9.4 Hz, 1H), 7.60 (s, 1H), 7.29 (dd, J 9.4, 1.8 Hz, 1H), 7.27-7.22 (m, 1H), 7.17 (d, J 8.1 Hz, 1H), 7.09-7.04 (m, 1H), 6.81 (dd, J 7.7, 1.5 Hz, 1H), 6.75-6.40 (m, 1H), 5.11 (dd, J 7.8, 5.8 Hz, 1H), 4.45 (s, 1H), 3.30 (dd, J 13.7, 8.0 Hz, 1H), 2.45 (dd, J 13.7, 5.8 Hz, 1H), 1.80 (s, 3H), 1.54 (s, 6H). LCMS (ES+) RT 1.32 min 467.0 (M+H)⁺.

Example 123

(1R,3R)-1-[2-(difluoromethoxy)phenyl]-7-[2-(2-hydroxypropan-2-yl)pyrimidin-5-yl]-3-methyl-2,3-dihydro-1H-cyclopenta[4,5]imidazo[1,2-a]pyridin-3-ol

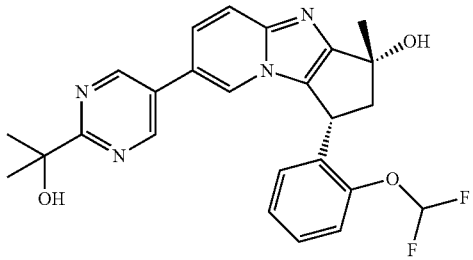 [SMILES: CC(C)(O)c1ncc(-c2ccc3nc4c(n3c2)[C@@H](c2ccccc2OC(F)F)C[C@@]4(C)O)cn1]

A mixture of Example 15 (245 mg, 0.599 mmol), 2-[5-(tetramethyl-1,3,2-dioxaborolan-2-yl)pyrimidin-2-yl]propan-2-ol (237 mg, 0.897 mmol), sodium carbonate (190 mg, 1.795 mmol) in 1,4-dioxane (5 mL) was purged out with nitrogen for 10 minutes then Pd(dppf)Cl$_2$ DCM adduct (49 mg, 10 mol %) and water (1.5 mL) were added. The reaction mixture was heated at 120° C. for 1 h in the microwave reactor. The reaction mixture was passed through a hydrophobic frit and concentrated. The resulting crude residue was purified by flash column chromatography (SiO$_2$, 0-100% EtOAc in heptane then 0-100% MeOH in EtOAc) and then by preparative HPLC to afford 35 mg (12%) of the title compound as an off-white solid. 1H NMR (500 MHz, CDCl$_3$) δ ppm 8.71 (s, 2H), 7.76 (d, J 9.3 Hz, 2H), 7.35 (d, J 10.8 Hz, 1H), 7.25-7.20 (m, 1H), 7.17 (dd, J 7.8, 1.6 Hz, 1H), 7.13 (d, J 8.1 Hz, 1H), 7.10-7.05 (m, 1H), 6.62 (dd, J 74.7, 72.7 Hz, 1H), 4.88 (dd, J 8.4, 4.1 Hz, 1H), 4.43 (d, J 26.7 Hz, 1H), 3.25 (dd, J 13.8, 8.5 Hz, 1H), 2.64 (dd, J 13.8, 4.2 Hz, 2H), 1.78 (s, 3H), 1.55 (s, 6H). LCMS (ES+) RT 1.32 min 467.0 (M+H)$^+$.

Example 124

(1R,3R)-1-[2-(difluoromethoxy)phenyl]-3-methyl-7-{2-[(1R,5S)-3-oxa-8-azabicyclo[3.2.1]oct-8-yl]pyrimidin-5-yl}-2,3-dihydro-1H-cyclopenta[4,5]imidazo[1,2-a]pyridin-3-ol

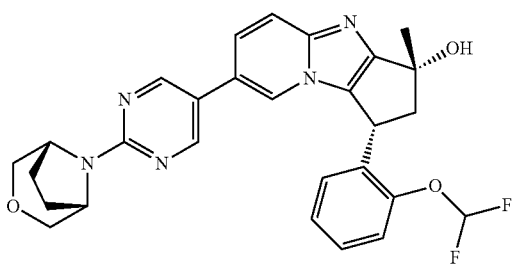 [SMILES: C[C@@]1(O)C[C@H](c2ccccc2OC(F)F)c2c1nc1ccc(-c3cnc(N4[C@@H]5CC[C@H]4COC5)nc3)cn21]

A mixture of Example 15 (245 mg, 0.587 mmol), Intermediate 36 (280 mg, 0.883 mmol), sodium carbonate (190 mg, 1.795 mmol) in 1,4-dioxane (5 mL) was degassed with nitrogen then Pd(dppf)Cl$_2$ DCM adduct (49 mg, 10 mol %) and water (1.5 mL) were added. The reaction mixture was heated at 120° C. for 1 h in a microwave reactor. The reaction mixture was passed through a hydrophobic frit and concentrated. The crude residue was purified by flash column chromatography (SiO$_2$, 0-100% EtOAc in heptane then 0-100% MeOH in EtOAc) and then by chiral preparative HPLC (85% heptane: 15% EtOH on chiralcel OD-H column) to afford 12 mg (4%) of the title compound as a pale green solid. $^1$H NMR (500 MHz, CDCl$_3$) δ ppm 8.38 (s, 2H), 7.93 (d, J 9.3 Hz, 1H), 7.62 (s, 1H), 7.54 (d, J 9.1 Hz, 1H), 7.39-7.32 (m, 1H), 7.26 (d, J 8.4 Hz, 1H), 7.18 (t, J 7.5 Hz, 1H), 6.95 (d, J 7.5 Hz, 1H), 6.65 (t, J 73.3 Hz, 1H), 5.31-5.19 (m, 1H), 4.70 (s, 2H), 3.78 (d, J 10.8 Hz, 2H), 3.68 (d, J 11.0 Hz, 2H), 3.41 (dd, J 13.8, 8.0 Hz, 1H), 2.56 (dd, J 13.8, 5.6 Hz, 1H), 2.14 (q, J 6.3, 5.7 Hz, 3H), 2.07-1.98 (m, 2H), 1.91 (s, 3H). LCMS (ES$^+$) RT 1.44 min 520.0 (M+H)+.

Example 125

4-(5-{(1R,3R)-1-[2-(difluoromethoxy)phenyl]-3-hydroxy-3-methyl-2,3-dihydro-1H-cyclopenta[4,5]imidazo[1,2-a]pyridin-7-yl}pyrimidin-2-yl)piperazin-2-one

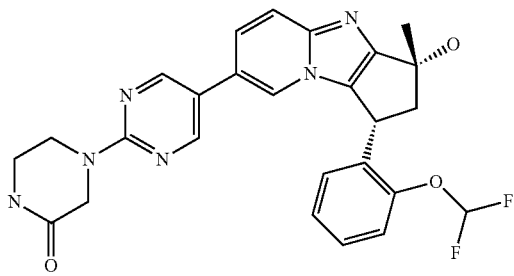 [SMILES: C[C@@]1(O)C[C@H](c2ccccc2OC(F)F)c2c1nc1ccc(-c3cnc(N4CCNC(=O)C4)nc3)cn21]

A mixture of Example 15 (245 mg, 0.587 mmol), Intermediate 31 (270 mg, 0.888 mmol), sodium carbonate (190 mg, 1.795 mmol) in 1,4-dioxane (5 mL) was degassed with nitrogen then Pd(dppf)Cl$_2$ DCM adduct (49 mg, 10 mol %) and water (1.5 mL) were added. The reaction mixture was heated at 120° C. for 1 h in a microwave reactor. The reaction mixture was passed through a hydrophobic frit and concentrated. The crude residue was purified by flash column chromatography (SiO$_2$, 0-100% EtOAc in heptane then 0-100% MeOH in EtOAc) and then by preparative HPLC to afford 59 mg (19%) of the title compound as a white solid. 1H NMR (500 MHz, CDCl$_3$) δ ppm 8.34 (s, 2H), 7.73 (d, J 9.4 Hz, 1H), 7.63 (s, 1H), 7.32 (dd, J 9.4, 1.7 Hz, 1H), 7.24-7.20 (m, 1H), 7.17 (dd, J 7.8, 1.6 Hz, 1H), 7.13 (d, J 8.2 Hz, 1H), 7.08 (t, J 7.5 Hz, 1H), 6.61 (dd, J 74.7, 72.7 Hz, 1H), 6.25 (s, 1H), 4.86 (dd, J 8.4, 4.2 Hz, 1H), 4.39 (s, 2H), 4.08-3.97 (m, 2H), 3.43 (td, J 5.3, 2.8 Hz, 2H), 3.23 (dd, J 13.8, 8.5 Hz, 1H), 2.63 (dd, J 13.8, 4.2 Hz, 1H), 1.94 (s, 1H), 1.77 (s, 3H). LCMS (ES+) RT 1.24 min 507.0 (M+H)$^+$.

Example 126

4-(5-{(1R,3S)-1-[2-(difluoromethoxy)phenyl]-3-hydroxy-3-methyl-2,3-dihydro-1H-cyclopenta[4,5]imidazo[1,2-a]pyridin-7-yl}pyrimidin-2-yl)piperazin-2-one

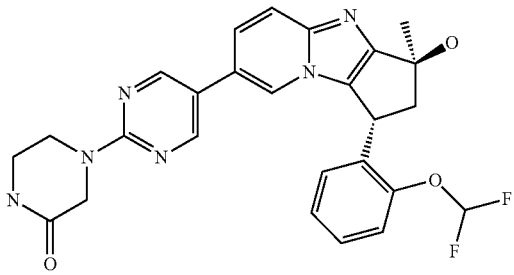 [SMILES: C[C@]1(O)C[C@H](c2ccccc2OC(F)F)c2c1nc1ccc(-c3cnc(N4CCNC(=O)C4)nc3)cn21]

A mixture of Example 15 (245 mg, 0.587 mmol), Intermediate 31 (270 mg, 0.888 mmol), sodium carbonate (190 mg, 1.795 mmol) in 1,4-dioxane (5 mL) was degassed with nitrogen then Pd(dppf)Cl$_2$ DCM adduct (49 mg, 10 mol %) and water (1.5 mL) were added. The reaction mixture was heated at 120° C. for 1 h in a microwave reactor. The reaction mixture was passed through a hydrophobic frit and concentrated. The crude residue was purified by flash column chromatography (SiO$_2$, 0-100% EtOAc in heptane then 0-100% MeOH in EtOAc) and then by preparative HPLC to afford 17 mg (5%) of the title compound as a white solid. $^1$H NMR (500 MHz, CDCl$_3$) δ ppm 8.33 (s, 2H), 7.89 (d, J 9.4 Hz, 1H), 7.54 (s, 1H), 7.48 (d, J 9.4 Hz, 1H), 7.31-7.23 (m, 1H), 7.19-7.16 (m, 1H), 7.09 (t, J 7.5 Hz, 1H), 6.85 (d, J 6.4 Hz, 1H), 6.56 (t, J 73.3 Hz, 1H), 6.12 (s, 1H), 5.16 (dd, J 7.9, 5.7 Hz, 1H), 4.39 (s, 2H), 4.02 (d, J 4.4, 4.0 Hz, 2H), 3.42 (dq, J 5.2, 2.8 Hz, 2H), 3.32 (dd, J 13.8, 8.1 Hz, 1H), 2.48 (dd, J 13.8, 5.7 Hz, 1H), 1.81 (s, 3H). LCMS (ES+) RT 1.24 min 507.0 (M+H)$^+$.

Example 12 to 132

The following title compounds were prepared from the assigned precursor by the Method K

| Example No. | Precursor | Compound Name | LCMS |
|---|---|---|---|
| 127 | Ex 16 | (1R,3R)-1-[2-(difluoromethoxy)phenyl]-6-fluoro-7-[2-(1-hydroxycyclobutyl)pyrimidin-5-yl]-2,3-dihydro-1H-cyclopenta[4,5]imidazo[1,2-a]pyridin-3-ol | LCMS (ES$^+$) RT 1.36 min 483.0 (M + H)$^+$. |
| 128 | Ex 16 | 3-{5-[(1R,3R)-1-(2-Difluoromethoxy-phenyl)-6-fluoro-3-hydroxy-2,3-dihydro-1H-cyclopenta[4,5]imidazo[1,2-a]pyridin-7-yl]-pyrimidin-2-yl}-3-hydroxy-azetidine-1-carboxylic acid tert-butyl ester | LCMS (ES+) RT 1.66 min 584.0 (M + H)+. |

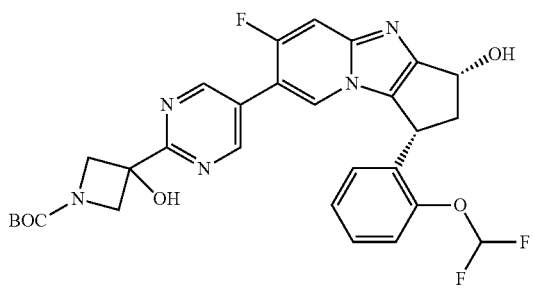 [SMILES: CC(C)(C)OC(=O)N1CC(O)(c2ncc(-c3cn4c5c(nc4cc3F)[C@H](O)C[C@@H]5c3ccccc3OC(F)F)cn2)C1]

-continued

| Example No. | Precursor | Compound Name | LCMS |
|---|---|---|---|
| 129 | Ex 16 | (1R,3R)-1-[2-(difluoromethoxy)phenyl]-6-fluoro-7-[2-(3-hydroxyoxetan-3-yl)pyrimidin-5-yl]-2,3-dihydro-1H-cyclopenta[4,5]imidazo[1,2-a]pyridin-3-ol | LCMS (ES+) RT 1.21 min 485.0 (M + H)+. |
| 130 | Ex 16 | (1R,3R)-1-[2-(difluoromethoxy)phenyl]-6-fluoro-7-[2-(4-hydroxy-1-methylpiperidin-4-yl)pyrimidin-5-yl]-2,3-dihydro-1H-cyclopenta[4,5]imidazo[1,2-a]pyridin-3-ol | LCMS (ES+) RT 1.24 min 526.0 (M + H)+. |
| 131 | Ex 16 | (1R,3R)-1-[2-(difluoromethoxy)phenyl]-6-fluoro-7-[6-(4-hydroxytetrahydro-2H-pyran-4-yl)pyridin-3-yl]-2,3-dihydro-1H-cyclopenta[4,5]imidazo[1,2a]pyridin-3-ol | LCMS (ES+) RT 1.29 min 512.0 (M + H)+. |
| 132 | Ex 16 | (1R,3R)-1-[2-(difluoromethoxy)phenyl]-6-fluoro-7-[2-(4-hydroxy-1,1-dioxidotetrahydro-2H-thiopyran-4-yl)pyrimidin-5-yl]-2,3-dihydro-1H-cyclopenta[4,5]imidazo[1,2-a]pyridin-3-ol | LCMS (ES+) RT 1.24 min 561.0 (M + H)+. |

Example 133

Tert-butyl 4-(5-{(1R,3R)-1-[2-(difluoromethoxy)phenyl]-3-hydroxy-2,3-dihydro-1H-cyclopenta[4,5]imidazo[1,2-a]pyridin-7-yl}pyrimidin-2-yl)piperidine-1-carboxylate

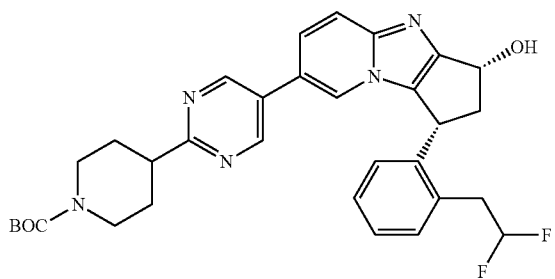 [SMILES: CC(C)(C)OC(=O)N1CCC(c2ncc(-c3ccc4nc5c(n4c3)[C@@H](c3ccccc3CC(F)F)C[C@H]5O)cn2)CC1]

A solution of Example 32 (89%, 442 mg, 0.68 mmol) in EtOAc (15 mL) and TEA (100 μl, 0.71 mmol) was passed 14 times over 10% palladium on carbon on a H-cube (50-100 bars, r.t. to 50° C.). The crude product was purified by flash column chromatography (SiO$_2$, 0-10% MeOH in EtOAc) Two batches of the title compound were obtained, one afforded a white solid, 163 mg (38%, 93% purity) and other afforded a white solid, 111 mg (27%, 98% purity). $^1$H NMR (500 MHz, CDCl$_3$) δ ppm 8.74 (s, 2H), 7.84-7.71 (m, 2H), 7.37 (dd, J 9.4, 1.8 Hz, 1H), 7.31-7.27 (m, 1H), 7.25-7.11 (m, 3H), 6.68 (dd, J 74.7, 72.7 Hz, 1H), 5.49 (dd, J 7.3, 3.2 Hz, 1H), 4.92 (dd, J 8.5, 4.0 Hz, 1H), 4.23 (s, 2H), 3.68-3.58 (m, 1H), 3.06 (tt, J 11.6, 3.7 Hz, 1H), 2.88 (s, 2H), 2.45 (dt, J 14.1, 3.7 Hz, 1H), 2.00 (d, J 9.6 Hz, 2H), 1.82 (qd, J 12.6, 4.3 Hz, 3H), 1.47 (s, 9H). LCMS (ES+) RT 1.78 min 578.0 (M+H)$^+$.

Example 134

(1R,3R)-1-[2-(difluoromethoxy)phenyl]-7-[2-(piperidin-4-yl)pyrimidin-5-yl]-2,3-dihydro-1H-cyclopenta[4,5]imidazo[1,2-a]pyridin-3-ol

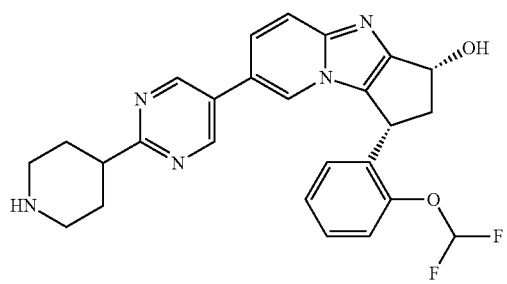 [SMILES: O[C@@H]1C[C@H](c2ccccc2OC(F)F)c2c1nc1ccc(-c3cnc(C4CCNCC4)nc3)cn21]

A 6 M solution of HCl in DCM (640 μl) was added to a solution of Example 133 (220 mg, 0.38 mmol) in DCM (1 mL). The mixture was stirred at r.t. for 1 h. The reaction mixture was basified to pH 10 using a sat. solution of sodium carbonate in water, a solid precipitated which was filtered and washed with water (6 mL) and Et$_2$O (6 mL), dried for 3 h to afford 150 mg (80%) of the title compound as a white solid. $^1$H NMR (500 MHz, DMSO-d$_6$) δ ppm 8.94 (s, 2H), 8.23 (s, 1H), 7.73 (d, J 9.5 Hz, 1H), 7.63 (dd, J 9.5, 1.8 Hz, 1H), 7.53-7.20 (m, 3H), 7.15-7.09 (m, 1H), 6.91 (dd, J 7.7, 1.4 Hz, 1H), 5.51 (s, 1H), 5.13 (dd, J 7.1, 3.0 Hz, 1H), 4.77 (dd, J 8.6, 3.8 Hz, 1H), 3.52-3.40 (m, 1H), 3.03 (d, J 12.2 Hz, 2H), 2.91 (tt, J 11.6, 3.5 Hz, 1H), 2.69-2.55 (m, 2H), 2.08 (dt, J 13.6, 3.5 Hz, 1H), 1.85 (d, J 11.4 Hz, 2H), 1.67 (tdd, J 12.3, 8.0, 3.7 Hz, 2H). LCMS (ES$^+$) RT 1.78 min 478.0 (M+H)$^+$.

Example 135

Acetic acid (1R,3R)-7-[2-(1-acetyl-piperidin-4-yl)-pyrimidin-5-yl]-1-(2-difluoromethoxy-phenyl)-2,3-dihydro-1H-cyclopenta[4,5]imidazo[1,2-a]pyridin-3-yl ester

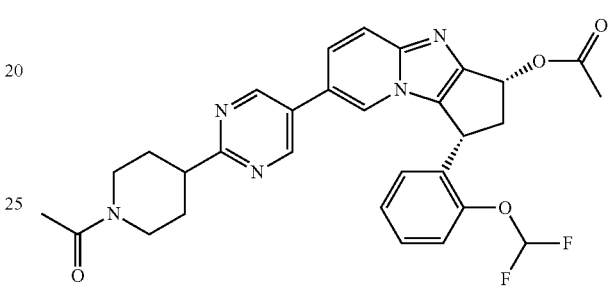

To a solution of Example 134 (100 mg, 0.21 mmol) in DCM (2 mL) was added TEA (58.22 μl, 0.42 mmol) and the mixture was stirred for 5 minutes, acetic anhydride (22 μl, 0.23 mmol) was added and the mixture was stirred at r.t. for 2 h. The reaction mixture was diluted with water (2 mL) and extracted with DCM (2 mL), the organic extract was washed with brine (2 mL), dried over sodium sulfate and concentrated in vacuo to afford 111 mg (95%) of the title compound as an orange gum. $^1$H NMR (500 MHz, CDCl$_3$) δ ppm 8.74 (s, 2H), 7.86-7.75 (m, 2H), 7.40 (dd, J 9.4, 1.7 Hz, 1H), 7.33-7.27 (m, 1H), 7.22 (d, J 8.1 Hz, 1H), 7.17-7.12 (m, 1H), 7.06 (dd, J 7.8, 1.6 Hz, 1H), 6.68 (dd, J 74.3, 72.7 Hz, 1H), 6.25 (dd, J 7.4, 3.2 Hz, 1H), 4.96 (dd, J 8.5, 3.9 Hz, 1H), 4.71 (d, J 13.4 Hz, 1H), 3.94 (d, J 13.8 Hz, 1H), 3.82-3.69 (m, 1H), 3.32-3.04 (m, 3H), 2.83-2.70 (m, 1H), 2.39 (dt, J 14.6, 3.6 Hz, 1H), 2.13 (s, 3H), 2.10 (s, 3H), 2.06 (d, J 15.9 Hz, 1H), 1.90 (qd, J 12.5, 4.1 Hz, 1H), 1.80 (qd, J 12.5, 4.3 Hz, 1H). LCMS (ES+) RT 1.80 min 562.0 (M+H)$^+$.

Example 136

(1R,3R)-1-[2-(difluoromethoxy)phenyl]-6-fluoro-7-[2-(3-hydroxyazetidin-3-yl)pyrimidin-5-yl]-2,3-dihydro-1H-cyclopenta[4,5]imidazo[1,2-a]pyridin-3-ol

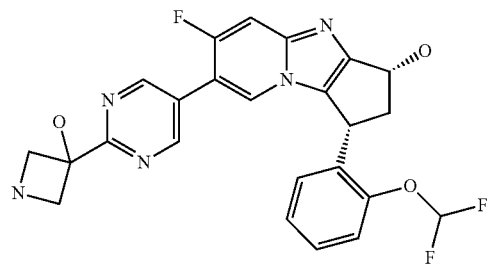 [SMILES: O[C@@H]1C[C@H](c2ccccc2OC(F)F)c2c1nc1cc(F)c(-c3cnc(C4(O)CNC4)nc3)cn21]

A 4M solution of HCl in 1,4-dioxane (51μL, 0.206 mmol) was added to a solution of Example 127 (60 mg, 0.103 mmol) in 1,4-dioxane (2 mL) at r.t. The reaction mixture was stirred at r.t. for 1 hour and concentrated under nitrogen flow. The residue was dissolved in 1,4-dioxane (2 mL) and a 4 M solution of HCl in 1,4-dioxane (51 μL, 0.206 mmol) was added at r.t. The reaction mixture was stirred at r.t. for 5 h and concentrated under nitrogen flow. The resulting residue was purified by preparative HPLC to afford 8.6 mg (16%) of the title compound as an off-white solid. $^1$H NMR (500 MHz, DMSO-$d_6$) δ ppm 8.97 (s, 2H), 8.37 (s, 2H), 8.22 (d, J 7.5 Hz, 1H), 7.71 (d, J 11.7 Hz, 1H), 7.48-7.17 (m, 3H), 7.12 (t, J 7.5 Hz, 1H), 6.93-6.90 (m, 1H), 5.54 (s, 1H), 5.12 (dd, J 7.2, 3.0 Hz, 1H), 4.75 (dd, J 8.5, 3.9 Hz, 1H), 4.14 (s, 2H), 3.80 (d, J 9.0 Hz, 3H), 2.12-1.98 (m, 2H). LCMS (ES+) 1.14 min, 484.0 (M+H)$^+$.

Example 137

(1R,3R)-1-[2-(difluoromethoxy)phenyl]-6-fluoro-7-[2-(3-hydroxy-1-methylazetidin-3-yl)pyrimidin-5-yl]-2,3-dihydro-1H-cyclopenta[4,5]imidazo[1,2-a]pyridin-3-ol

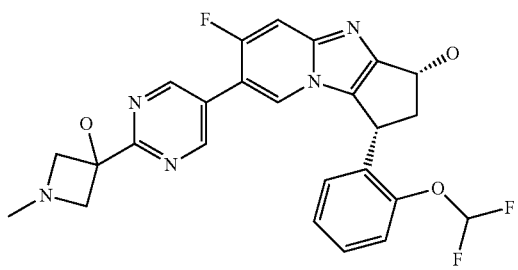 [SMILES: CN1CC(O)(c2ncc(-c3cn4c5c(nc4cc3F)[C@H](O)C[C@@H]5c3ccccc3OC(F)F)cn2)C1]

Trifluoroacetic acid (135 μl, 1.77 mmol) was added to a solution of Example 136 (127 mg, 0.16 mmol) in DCM (2 mL) at 0° C. The reaction mixture was stirred at 0° C. for 30 minutes and r.t. for 3 h. The reaction mixture was concentrated in vacuo to afford 130 mg (64% purity) of an oil which was dissolved in EtOH (5 mL) and a 37% aq. formaldehyde solution (0.047 ml, 0.62 mmol) was added at r.t. The mixture was stirred for 20 minutes and sodium triacetoxyborohydride (74 mg, 0.348 mmol) was added in one portion followed by AcOH (0.1 mL). The whole mixture was stirred at r.t. under nitrogen for 3.5 h. Additional 37% aq. formaldehyde solution (0.047 ml, 0.62 mmol) and sodium triacetoxyborohydride (74 mg, 0.348 mmol) were added at r.t. and the reaction mixture was stirred overnight. The reaction mixture was quenched with a sat. solution of sodium bicarbonate in water (~3 mL) and the mixture was extracted with DCM (3×5 mL). The organic extracts were combined, dried over sodium sulfate, filtered and concentrated in vacuo. The resulting residue was purified by preparative HPLC to afford 24 mg (35%) of the title compound as an off-white solid. $^1$H NMR (500 MHz, CDCl$_3$) δ ppm 8.84 (d, J 1.4 Hz, 2H), 7.69 (d, J 7.1 Hz, 1H), 7.44 (d, J 10.9 Hz, 1H), 7.32-7.27 (m, 1H), 7.26 (s, 1H), 7.22-7.14 (m, 2H), 6.67 (dd, J 74.7, 72.7 Hz, 1H), 5.45 (dd, J 7.3, 3.1 Hz, 1H), 4.90 (dd, J 8.5, 3.9 Hz, 1H), 3.98 (d, J 7.9 Hz, 2H), 3.65-3.57 (m, 1H), 3.51 (d, J 8.1 Hz, 2H), 2.56 (s, 3H), 2.44 (dt, J 14.1, 3.6 Hz, 1H), 1.71 (d, J 8.6 Hz, 2H). LCMS (ES+) 1.20 min, 498.0 (M+H)$^+$.

Example 138

(1R)-1-[2-(difluoromethoxy)phenyl]-3,6-difluoro-7-[6-(methylsulfonyl)pyridin-3-yl]-2,3-dihydro-1H-cyclopenta[4,5]imidazo[1,2-a]pyridine

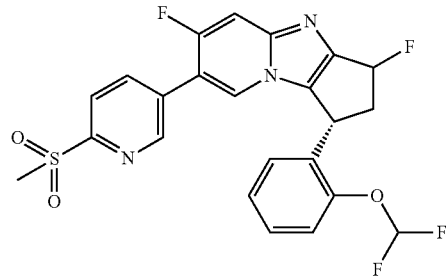 [SMILES: CS(=O)(=O)c1ccc(-c2cn3c4c(nc3cc2F)C(F)C[C@@H]4c2ccccc2OC(F)F)cn1]

To a stirred solution of Example 21 (110 mg, 0.225 mmol) in THF (3 mL) was added diethylaminosulfur trifluoride (55 μL, 0.341 mmol). The reaction mixture was stirred at r.t. under nitrogen for 1 h. The reaction mixture was diluted with water (15 mL) and adjusted to pH ~8 (using 11 mL of a sat. aq. solution of sodium bicarbonate) before being extracted with DCM (30 mL). The organic layer was passed through a hydrophobic frit and concentrated under reduced pressure. The resulting crude residue was purified by preparative HPLC (Method C) followed by flash column chromatography eluting with 0 to 100% EtOAc in heptane and then 0 to 100% MeOH in EtOAc to afford 14 mg (12%) of the title compound as a white solid. $^1$H NMR (500 MHz, CDCl$_3$) δ ppm 8.65 (d, J 24.8 Hz, 1H), 8.09 (d, J 8.1 Hz, 1H), 7.96 (tt, J 8.4, 1.8 Hz, 1H), 7.74 (d, J 7.1 Hz, 1H), 7.57-7.36 (m, 1H), 7.31-7.20 (m, 1H), 7.18-7.04 (m, 3H), 6.83-6.38 (m, 1H), 6.23-5.91 (m, 1H), 5.24-4.80 (m, 1H), 3.65-3.23 (m, 1H), 3.19 (d, J 5.5 Hz, 3H), 2.84-2.53 (m, 1H). LCMS (ES+) 1.46 min, 492.0 (M+H)$^+$.

Example 139

1-[4-(5-{(1R,3R)-1-[2-(difluoromethoxy)phenyl]-3-hydroxy-2,3-dihydro-1H-cyclopenta[4,5]imidazo[1,2-a]pyridin-7-yl}pyrimidin-2-yl)piperidin-1-yl]ethanone

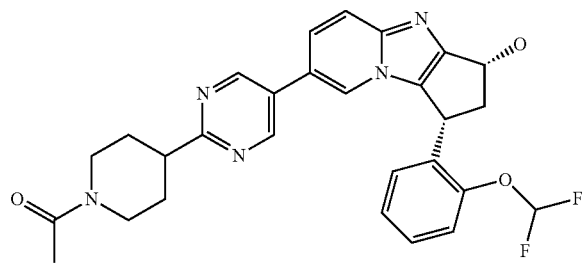 [SMILES: CC(=O)N1CCC(c2ncc(-c3ccc4nc5c(n4c3)[C@@H](c3ccccc3OC(F)F)C[C@H]5O)cn2)CC1]

To a solution of Example 135 (110 mg, 0.19 mmol) in THF (1 mL) and water (0.5 mL) was added a 2M aq. lithium hydroxide solution (98 μL). The reaction mixture was stirred at r.t. for 2.5 h. The mixture was diluted with water (3 mL) and extracted with EtOAc (6 mL) and 1:1 i-PrOH/CHCl$_3$ (3 mL), the combined organic extracts were washed with a 2 M aq. sodium carbonate solution (12 mL) and brine (6 mL), dried over sodium sulfate and concentrated in vacuo to afford 58 mg (55%) of the title compound as an off-white solid. $^1$H NMR (500 MHz, DMSO-$d_6$) δ ppm 8.96 (s, 2H), 8.24 (s, 1H), 7.73 (d, J 9.4 Hz, 1H), 7.64 (dd, J 9.5, 1.8 Hz, 1H), 7.53-7.18 (m, 3H), 7.11 (t, J 7.4 Hz, 1H), 6.90 (d, J 7.2 Hz, 1H), 5.51 (d, J 5.1 Hz, 1H), 5.13 (s, 1H), 4.77 (dd, J 8.6, 3.8 Hz, 1H), 4.42 (d, J 13.1 Hz, 1H), 3.88 (d, J 13.6 Hz, 1H), 3.51-3.41 (m, 1H), 3.23-3.14 (m, 1H), 3.11 (tt, J 11.3, 3.6 Hz, 1H), 2.70 (t, J 11.4 Hz, 1H), 2.12-2.05 (m, 1H), 2.02 (s, 3H), 2.00-1.90 (m, 2H), 1.79-1.66 (m, 1H), 1.63-1.52 (m, 1H). LCMS (ES+) 1.25 min, 520.0 (M+H)$^+$.

Example 140

2-{5-[(1R)-1-[2-(difluoromethoxy)phenyl]-6-fluoro-3-(methylsulfonyl)-2,3-dihydro-1H-cyclopenta[4,5]imidazo[1,2-a]pyridin-7-yl]pyrimidin-2-yl}propan-2-ol

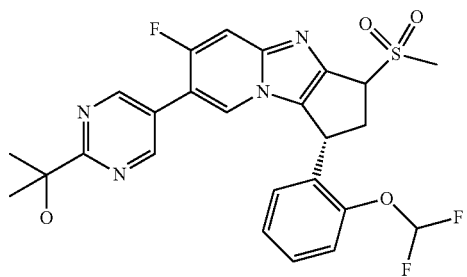 [SMILES: CC(C)(O)c1ncc(-c2cn3c4c(nc3cc2F)C(S(C)(=O)=O)C[C@@H]4c2ccccc2OC(F)F)cn1]

Intermediate 55 (10 mg, 0.02 mmol) was dissolved in DCM (1 mL) and 3-chlorobenzenecarboperoxoic acid (9 mg, 0.04 mmol) was added. The reaction mixture was stirred at r.t. for 24 h. The mixture was quenched with sat. aq. solution of sodium carbonate (3 mL) and extracted with DCM (3×3 mL). Combined organic layers were washed with brine (5 mL), dried over sodium sulfate and concentrated in vacuo. The residue was purified by flash column chromatography (SiO$_2$, 50-100% EtOAc in heptane) to afford 7.5 mg (70%) of the title compound (approximately 1:1 ratio of diastereoisomers) as a pale yellow solid. $^1$H NMR (500 MHz, CDCl$_3$) δ ppm 8.74 (s, 2H), 7.63-7.45 (m, 2H), 7.39-7.30 (m, 1H), 7.26-6.89 (m, 3H), 6.85-6.44 (m, 1H), 5.26-5.01 (m, 1H), 4.82-4.68 (m, 1H), 4.44 (s, 1H), 3.89-3.56 (m, 1H), 3.31 (d, J 42.9 Hz, 3H), 3.10-2.76 (m, 1H), 1.62 (s, 6H). LCMS (ES+) 1.35 min, 533.0 (M+H)$^+$.

Example 141

(1R,3S)-1-[2-(difluoromethoxy)phenyl]-6-fluoro-7-[2-(2-hydroxypropan-2-yl)pyrimidin-5-yl]-3-methyl-2,3-dihydro-1H-cyclopenta[4,5]imidazo[1,2-a]pyridin-3-ol

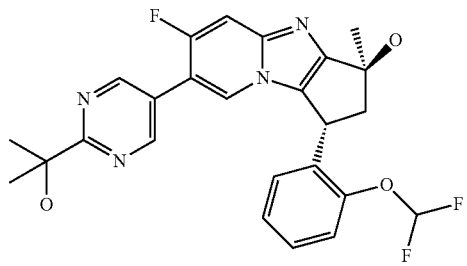 [SMILES: CC(C)(O)c1ncc(-c2cn3c4c(nc3cc2F)[C@@](C)(O)C[C@@H]4c2ccccc2OC(F)F)cn1]

Example 20 (158 mg, 0.37 mmol) and 2-[5-(tetramethyl-1,3,2-dioxaborolan-2-yl)pyrimidin-2-yl]propan-2-ol (146.53 mg, 0.55 mmol) were dissolved in 1,4-dioxane (5 mL) before a 2M aq. solution of sodium carbonate (0.55 ml) was added. The mixture was degassed with nitrogen before Pd(dppf)Cl$_2$ DCM adduct (30 mg, 0.04 mmol) was added and the reaction mixture stirred at 80° C. for 2 h. The reaction mixture was cooled to r.t., diluted with EtOAc (5 mL) and washed with water (3×3 mL). The aq. washes were combined and extracted with EtOAc (3×3 mL). The organic extracts were combined, dried over sodium sulfate, and concentrated in vacuo. The resulting brown residue was purified by flash column chromatography (SiO$_2$, 0-15% MeOH in DCM). Purification by chiral preparative HPLC (85% heptane: 15% EtOH on AD Chiral Pak Column) afforded 10 mg (5.5%) of the title compound as a white solid. $^1$H NMR (500 MHz, CDCl$_3$) δ ppm 8.74 (d, J 1.4 Hz, 2H), 7.54 (d, J 7.1 Hz, 1H), 7.46 (d, J 10.9 Hz, 1H), 7.35-7.29 (m, 1H), 7.23 (d, J 8.0 Hz, 1H), 7.15 (t, J 7.5 Hz, 1H), 6.87 (dd, J 7.7, 1.4 Hz, 1H), 6.81-6.45 (m, 1H), 5.14 (dd, J 7.7, 5.9 Hz, 1H), 4.48 (s, 1H), 3.34 (dd, J 13.8, 7.9 Hz, 1H), 2.51 (dd, J 13.8, 5.7 Hz, 1H), 2.31 (s, 1H), 1.83 (s, 3H), 1.62 (s, 6H). LCMS (ES+) RT 1.35 min 484.0 (M+H)$^+$.

Example 142

(1R,3R)-1-[2-(difluoromethoxy)phenyl]-6-fluoro-7-[2-(2-hydroxypropan-2-yl)pyrimidin-5-yl]-3-methyl-2,3-dihydro-1H-cyclopenta[4,5]imidazo[1,2-a]pyridin-3-ol

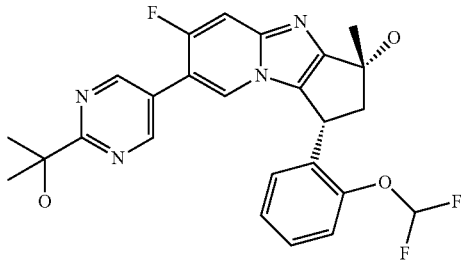 [SMILES: CC(C)(O)c1ncc(-c2cn3c4c(nc3cc2F)[C@](C)(O)C[C@@H]4c2ccccc2OC(F)F)cn1]

The title compound, 43 mg (24%), was isolated as a colourless glass by chiral preparative HPLC (85% Heptane: 15% EtOH on AD Chiral Pak Column) from the mixture of epimers separated in Example 141. $^1$H NMR (500 MHz, CDCl$_3$) δ ppm 8.75 (d, J 1.4 Hz, 2H), 7.67 (d, J 7.1 Hz, 1H), 7.43 (d, J 10.9 Hz, 1H), 7.29 (td, J 7.9, 7.3, 1.7 Hz, 1H), 7.22-7.12 (m, 3H), 6.66 (dd, J 74.6, 72.7 Hz, 1H), 4.90 (dd, J 8.4, 4.0 Hz, 1H), 4.50 (s, 1H), 3.30 (dd, J 13.8, 8.5 Hz, 1H), 2.88 (s, 1H), 2.66 (dd, J 13.8, 4.0 Hz, 1H), 1.81 (s, 3H), 1.62 (s, 6H). LCMS (ES+) RT 1.35 min 484.0 (M+H)$^+$.

Example 143

(1R,3S)-1-[2-(difluoromethoxy)phenyl]-7-[2-(3,7-dioxa-9-azabicyclo[3.3.1]non-9-yl)pyrimidin-5-yl]-6-fluoro-3-methyl-2,3-dihydro-1H-cyclopenta[4,5]imidazo[1,2-a]pyridin-3-ol

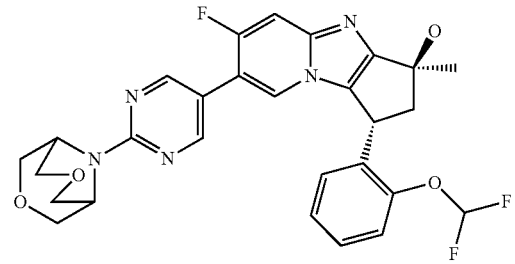 [SMILES: C[C@]1(O)C[C@H](c2ccccc2OC(F)F)c2c1nc1cc(F)c(-c3cnc(N4C5COCC4COC5)nc3)cn21]

Example 20 (130 mg, 0.29 mmol) was dissolved in 1,4-dioxane (2 mL) in a microwave tube and then Intermediate 71 (96 mg, 0.29 mmol) was added. Sodium carbonate (92 mg, 0.62 mmol) was added and the mixture was degassed with nitrogen before addition of Pd(dppf)Cl$_2$ DCM adduct (24 mg, 0.029 mmol) and water (0.6 mL). The reaction mixture was stirred for 1 h at 120° C. in a microwave reactor. The reaction mixture was passed through a hydrophobic frit and concentrated in vacuo. The resulting crude product was purified using preparative HPLC to afford a cream solid. The racemic compound was purified by chiral SFC (30% EtOH: 70% CO$_2$ on IC Chiral Pak 25 cm Column) to afford 10 mg (6%) of the title compound as a yellow oil. $^1$H NMR (500 MHz, CDCl$_3$) δ ppm 8.33 (d, J 1.3 Hz, 2H), 7.43 (d, J 7.1 Hz, 1H), 7.39 (d, J 10.8 Hz, 1H), 7.32-7.28 (m, 1H), 7.22 (d, J 8.1 Hz, 1H), 7.17-7.09 (m, 1H), 6.86 (dd, J 7.7, 1.4 Hz, 1H), 6.62 (t, J 73.1 Hz, 1H), 5.12 (dd, J 7.8, 5.8 Hz, 1H), 4.56 (s, 2H), 4.13 (d, J 11.2 Hz, 4H), 3.92 (dd, J 10.9, 2.1 Hz, 4H), 3.33 (dd, J 13.8, 7.9 Hz, 1H), 2.48 (dd, J 13.7, 5.7 Hz, 1H), 1.82 (s, 3H). LCMS (ES+) RT 1.36 min 554.0 (M+H)1.

Example 144

(1R,3R)-1-[2-(difluoromethoxy)phenyl]-7-[2-(3,7-dioxa-9-azabicyclo[3.3.1]non-9-yl)pyrimidin-5-yl]-6-fluoro-3-methyl-2,3-dihydro-1H-cyclopenta[4,5]imidazo[1,2-a]pyridin-3-ol

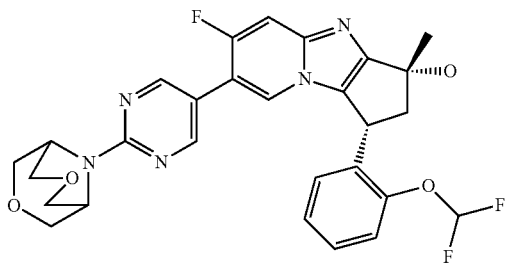 [SMILES: C[C@@]1(O)C[C@H](c2ccccc2OC(F)F)c2c1nc1cc(F)c(-c3cnc(N4C5COCC4COC5)nc3)cn21]

The title compound, 48 mg (30%), was isolated as a white solid by chiral SFC (30% EtOH: 70% CO$_2$ on IC Chiral Pak 25 cm Column) from the mixture of epimers separated in Example 143. $^1$H NMR (500 MHz, CDCl$_3$) δ 8.34 (d, J 1.4 Hz, 2H), 7.55 (d, J 7.2 Hz, 1H), 7.36 (d, J 10.9 Hz, 1H), 7.29-7.24 (m, 1H), 7.21-7.16 (m, 2H), 7.15-7.11 (m, 1H), 6.65 (dd, J 74.7, 72.7 Hz, 1H), 4.87 (dd, J 8.4, 4.1 Hz, 1H), 4.57 (s, 2H), 4.13 (d, J 11.2 Hz, 4H), 3.93 (dd, J 10.9, 2.1 Hz, 4H), 3.28 (dd, J 13.7, 8.5 Hz, 1H), 2.65 (dd, J 13.8, 4.1 Hz, 1H), 1.81 (s, 3H). LCMS (ES$^+$) RT 1.36 min 554.0 (M+H)$^+$.

Example 145

(1R,3R)-1-[2-(difluoromethoxy)phenyl]-7-[2-(1,1-dioxidothiomorpholin-4-yl)pyrimidin-5-yl]-6-fluoro-3-methyl-2,3-dihydro-1H-cyclopenta[4,5]imidazo[1,2-a]pyridin-3-ol

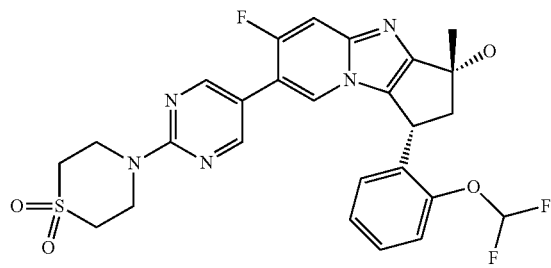 [SMILES: C[C@@]1(O)C[C@H](c2ccccc2OC(F)F)c2c1nc1cc(F)c(-c3cnc(N4CCS(=O)(=O)CC4)nc3)cn21]

Example 20 (130 mg, 0.29 mmol, 1.0 eq), and Intermediate 62 (98 mg, 0.29 mmol, 1.0 eq) and sodium carbonate (92 mg, 0.620 mmol) were stirred in 1,4-dioxane (2 mL), the mixture was degassed with nitrogen for 10 minutes before Pd(dppf)Cl$_2$ DCM adduct (24 mg, 10 mol %) was added as well as water (0.6 mL). The reaction mixture was heated at 120° C. for 1 h in a microwave reactor. The reaction mixture was filtered through celite, washed with EtOAc (3×5 mL) and concentrated in vacuo. The crude product was purified by flash column chromatography (SiO$_2$, 0-10% MeOH in DCM followed by preparative HPLC to afford 62 mg of the racemic compound. Separation of epimers by chiral SFC (30% MeOH: 70% CO$_2$ on IC Chiral Pak 25 cm Column) afforded 93 mg (64%) of the title compound as a yellow solid. $^1$H NMR (500 MHz, CDCl$_3$) δ ppm 8.37 (s, 2H), 7.56 (d, J 6.6 Hz, 1H), 7.35 (d, J 10.6 Hz, 1H), 7.28-7.22 (m, 2H), 7.19-7.10 (m, 2H), 6.66 (t, J 73.7 Hz, 1H), 5.00-4.77 (m, 1H), 4.39 (s, 4H), 3.28 (dd, J 13.3, 8.6 Hz, 1H), 3.05 (s, 4H), 2.67 (d, J 11.7 Hz, 1H), 1.83 (s, 3H). LCMS (ES+) RT 1.34 min 560.0 (M+H)$^+$.

Example 146

(1R,3S)-1-[2-(difluoromethoxy)phenyl]-7-[2-(1,1-dioxidothiomorpholin-4-yl)pyrimidin-5-yl]-6-fluoro-3-methyl-2,3-dihydro-1H-cyclopenta[4,5]imidazo[1,2-a]pyridin-3-ol

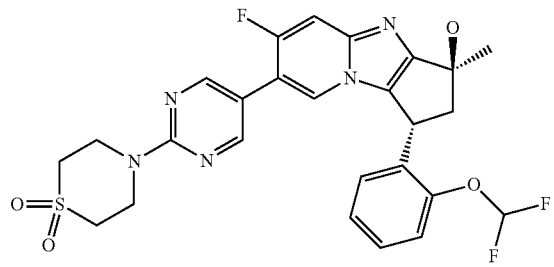 [SMILES: C[C@]1(O)C[C@H](c2ccccc2OC(F)F)c2c1nc1cc(F)c(-c3cnc(N4CCS(=O)(=O)CC4)nc3)cn21]

The title compound, 17 mg (12%), was isolated as a yellow solid by chiral SFC (30% MeOH: 70% CO$_2$ on IC Chiral Pak 25 cm Column) from the mixture of epimers separated in Example 145. $^1$H NMR (500 MHz, CDCl$_3$) δ ppm 8.37 (d, J 1.2 Hz, 2H), 7.42 (dd, J 14.5, 9.0 Hz, 2H), 7.33-7.28 (m, 1H), 7.22 (d, J 8.1 Hz, 1H), 7.13 (t, J 7.5 Hz, 1H), 6.86 (dd, J 7.7, 1.3 Hz, 1H), 6.63 (t, J 73.4 Hz, 1H), 5.13 (dd, J 7.7, 5.8 Hz, 1H), 4.40 (s, 4H), 3.33 (dd, J 13.8, 7.9 Hz, 1H), 3.12-2.92 (m, 4H), 2.50 (dd, J 13.8, 5.6 Hz, 1H), 1.83 (s, 3H). LCMS (ES+) RT 1.34 min, 560.0 (M+H) 1.

Example 147

(1R,3R)-1-[2-(difluoromethoxy)phenyl]-6-fluoro-7-{2-[(3S or R)-3-hydroxytetrahydro furan-3-yl]pyrimidin-5-yl}-2,3-dihydro-1H-cyclopenta[4,5]imidazo[1,2-a]pyridin-3-ol

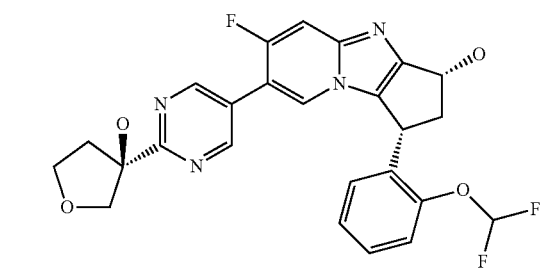 [SMILES: O[C@@H]1C[C@H](c2ccccc2OC(F)F)c2c1nc1cc(F)c(-c3cnc([C@@]4(O)CCOC4)nc3)cn21]

Example 16 (235 mg, 0.42 mmol), Intermediate 53 (372 mg, 0.67 mmol) and a 2 M aq. sodium carbonate solution (0.63 mL) were stirred in 1,4-dioxane (4 mL) and de-gassed with nitrogen. Pd(dppf)Cl$_2$ DCM adduct (34 mg, 0.04 mmol) was added and the reaction mixture heated to 100° C. for 1.5 h. The reaction mixture was cooled to r.t. and a 1M TBAF (2.52 mL) added. The mixture was stirred at r.t. for 3 h. The reaction mixture was diluted with EtOAc (20 mL) and washed with water (20 mL) and brine (30 mL). The organic phase was dried over sodium sulfate and concentrated in vacuo to afford a black gum. The crude product was purified by flash column chromatography (SiO₂, 50-100% EtOAc in heptane then 0-15% MeOH in EtOAc) to afford an off-white solid. This was further purified using chiral preparative HPLC (MeCN+0.1% DEA with Chiralcel OD-H 25 cm column) followed by trituration using DCM to afford 8 mg (4%) of the title compound as a white solid. ¹H NMR (500 MHz, CDCl₃) δ ppm 8.79 (d, J 1.4 Hz, 2H), 7.70 (d, J 7.1 Hz, 1H), 7.45 (d, J 10.9 Hz, 1H), 7.32-7.26 (m, 1H), 7.24 (d, J 1.7 Hz, 1H), 7.18 (q, J 7.8 Hz, 2H), 6.67 (dd, J 74.8, 72.6 Hz, 1H), 5.45 (dd, J 7.2, 3.0 Hz, 1H), 4.96-4.82 (m, 2H), 4.27-4.17 (m, 3H), 3.99 (d, J 9.0 Hz, 1H), 3.67-3.56 (m, 1H), 2.64 (dt, J 12.6, 8.8 Hz, 1H), 2.44 (dt, J 14.1, 3.5 Hz, 1H), 2.26 (dt, J 12.4, 5.2 Hz, 1H). LCMS (ES+) RT 1.23 min 499.0 (M+H)⁺.

Example 148

(1R,3R)-1-[2-(difluoromethoxy)phenyl]-6-fluoro-7-{2-[(3R or S)-3-hydroxytetrahydrofuran-3-yl]pyrimidin-5-yl}-2,3-dihydro-1H-cyclopenta[4,5]imidazo[1,2-a]pyridin-3-ol

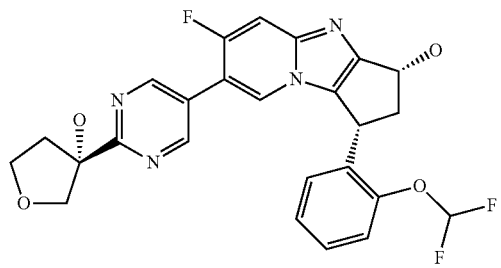 [SMILES: O[C@@H]1C[C@H](c2ccccc2OC(F)F)c2c1nc1cc(F)c(-c3cnc([C@]4(O)CCOC4)nc3)cn21]

The title compound, 31 mg (14%), was isolated as an off white solid by chiral preparative HPLC (MeCN+0.1% DEA with Chiralcel OD-H 25 cm column) from the mixture of epimers separated in Example 146. ¹H NMR (500 MHz, CDCl₃) δ ppm 8.79 (d, J 1.3 Hz, 2H), 7.71 (d, J 6.9 Hz, 1H), 7.46 (d, J 10.7 Hz, 1H), 7.32-7.27 (m, 2H), 7.22-7.14 (m, 2H), 6.68 (dd, J 74.8, 72.6 Hz, 1H), 5.47 (d, J 4.4 Hz, 1H), 4.90 (dd, J 8.4, 3.8 Hz, 1H), 4.28-4.16 (m, 3H), 3.99 (d, J 9.0 Hz, 1H), 3.68-3.55 (m, 1H), 2.64 (dt, J 12.6, 8.8 Hz, 1H), 2.45 (dt, J 14.1, 3.3 Hz, 1H), 2.26 (dt, J 12.5, 5.1 Hz, 1H). LCMS (ES+) RT 1.23 min 499.0 (M+H)⁺.

Example 149

(R)-1-[2-(difluoromethoxy)phenyl]-7-[4-(methylsulfonyl)phenyl]-3-deuterio-2,3-dihydro-1H-cyclopenta[4,5]imidazo[1,2-a]pyridin-3-ol

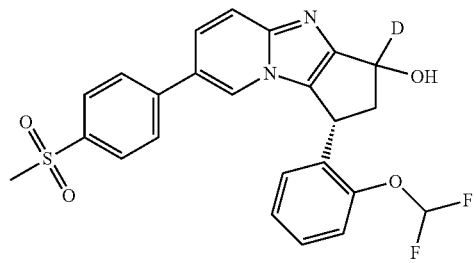 [SMILES: [2H]C1(O)C[C@H](c2ccccc2OC(F)F)c2c1nc1ccc(-c3ccc(S(C)(=O)=O)cc3)cn21]

To a solution of Example 41 (0.11 g, 0.23 mmol) in MeOH (1 mL) was added sodium borodeuteride (0.012 g, 0.25 mmol) and the mixture stirred at r.t. for 1 h. The reaction mixture was partitioned between EtOAc (10 mL) and ammonium chloride (10 mL) sat.aq. The organics were separated, washed with water (5 mL), brine (5 mL), dried over sodium sulfate, and concentrated in vacuo. The crude residue was purified by chromatography (SiO₂, 0-10% MeOH in EtOAc) and the title compound was isolated as a white solid (0.048 g 43%). ¹H NMR (DMSO-d₆) δ: 8.20 (s, 1 H), 7.98 (m, 3 H), 7.86 (m, 2 H), 7.74 (m, 1 H), 7.64 (m, 1 H), 7.39 (s, 1 H), 7.30 (m, 3 H), 7.12 (m, 1 H), 6.94 (dd, J 7.7 Hz, J 1.4 Hz, 1 H), 5.48 (s, 1 H), 4.82 (dd, J 8.6 Hz, J 3.8 Hz, 1 H), 3.47 (dd, J 13.7 Hz, J 8.6 Hz, 1 H), 3.32 (s, 1 H), 2.10 (dd, J 13.7 Hz, J 3.9 Hz, 1 H). LCMS (ES⁺) RT 1.81 min, 472.0 (M+H)⁺.

Example 150

(1R,3R)-1-[2-(difluoromethoxy)phenyl]-6-fluoro-7-[4-(S-methylsulfonimidoyl)phenyl]-2,3-dihydro-1H-cyclopenta[4,5]imidazo[1,2-a]pyridin-3-ol

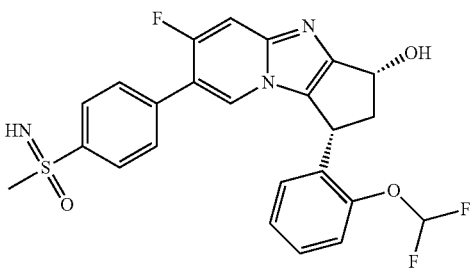 [SMILES: CS(=N)(=O)c1ccc(-c2cn3c4c(nc3cc2F)[C@H](O)C[C@@H]4c2ccccc2OC(F)F)cc1]

The title compound was prepared from Example 16 (210 mg, 0.43 mmol), Intermediate 75 (171 mg, 0.52 mmol, 85% purity), by the Method A (128 mg, 60%). ¹H NMR (500 MHz, CDCl₃) δ ppm 8.06 (d, J 8.3 Hz, 2H), 7.71 (d, J 7.1 Hz, 1H), 7.57 (d, J 7.3 Hz, 2H), 7.44 (d, J 10.8 Hz, 1H), 7.30 (t, J 7.8 Hz, 2H), 7.17 (d, J 7.6 Hz, 2H), 6.67 (dd, J 74.9, 72.5 Hz, 1H), 5.48 (d, J 4.9 Hz, 1H), 4.89 (dd, J 8.4, 3.6 Hz, 1H), 3.62 (dt, J 14.9, 7.9 Hz, 1H), 3.14 (s, 3H), 2.46 (d, J 14.1 Hz, 1H).). LCMS (ES⁺) RT 1.73 min, 488.0 (M+H)⁺.

Example 151

(1R)-1-[2-(difluoromethoxy)phenyl]-6-fluoro-3-methyl-7-[4-(S-methylsulfonimidoyl)phenyl]-2,3-dihydro-1H-cyclopenta[4,5]imidazo[1,2-a]pyridin-3-ol

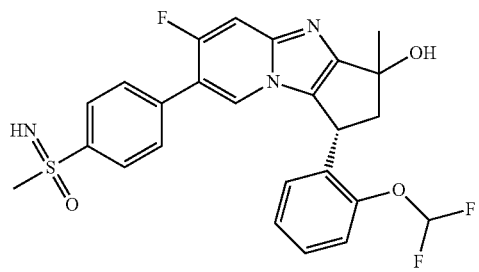 [SMILES: CC1(O)C[C@H](c2ccccc2OC(F)F)c2c1nc1cc(F)c(-c3ccc(S(C)(=N)=O)cc3)cn21]

The title compound was prepared from Example 20 (420 mg, 0.98 mmol) and Intermediate 75 (390 mg, 1.18 mmol) by the Method A (457 mg, 92%). ¹H NMR (500 MHz, CDCl₃) δ ppm 8.06 (d, J 8.3 Hz, 2H), 7.69 (d, J 7.1 Hz, 1H), 7.55 (dd, J 13.2, 7.1 Hz, 2H), 7.42 (d, J 10.1 Hz, 1H), 7.32-7.27 (m, 1H), 7.17-7.13 (m, 1H), 6.84-6.42 (m, 1H), 4.89 (dd, J 8.4, 3.8 Hz, 1H), 3.29 (dd, J 13.8, 8.5 Hz, 1H), 3.13 (s, 3H), 2.68 (dd, J 13.8, 3.8 Hz, 1H), 1.81 (s, 3H). LCMS (ES⁺) RT 1.88 min, 502.0 (M+H)⁺.

Example 152

(1R,3R)-1-[2-(difluoromethoxy)phenyl]-6-fluoro-7-[2-(1-imino-1-oxido-1lambda~4~-,4-thiazinan-4-yl)pyrimidin-5-yl]-2,3-dihydro-1H-cyclopenta[4,5]imidazo[1,2-a]pyridin-3-ol

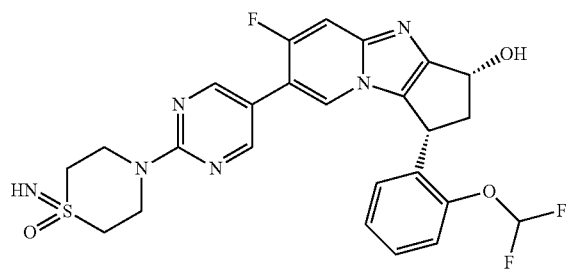 [SMILES: N=S1(=O)CCN(c2ncc(-c3cn4c5c(nc4cc3F)[C@H](O)C[C@@H]5c3ccccc3OC(F)F)cn2)CC1]

The title compound was prepared from Example 16 (100 mg, 0.22 mmol), Intermediate 79 (97 mg, 0.25 mmol), by the Method A (28 mg, 25%). $^1$H NMR (500 MHz, MeOD) δ ppm 8.46 (d, J 1.3 Hz, 2H), 7.84 (d, J 7.3 Hz, 1H), 7.44 (d, J 11.0 Hz, 1H), 7.36-7.29 (m, 1H), 7.25 (d, J 8.0 Hz, 1H), 7.19-6.82 (m, 3H), 5.29 (dd, J 7.2, 3.6 Hz, 1H), 4.56 (d, J 14.8 Hz, 2H), 4.22-4.06 (m, 2H), 3.66-3.55 (m, 1H), 3.17 (d, J 3.9 Hz, 4H), 2.24 (dt, J 13.8, 4.0 Hz, 1H). LCMS (ES$^+$) RT 1.77 min, 545.0 (M+H)$^+$.

Examples 153 to 154

The following Examples were prepared by the Method A from the given starting material using the appropriate boronate ester or boronic acid.

| Example No. | Precursor | Compound Name | LCMS |
|---|---|---|---|
| 153 | Ex 14 | (1R,3R)-1-[2-(difluoromethoxy)phenyl]-3-methoxy-7-[2-(morpholin-4-yl)pyrimidin-5-yl]-2,3-dihydro-1H-cyclopenta[4,5]imidazo[1,2-a]pyridine | LCMS (ES$^+$) RT 1.47 min 494.0 (M + H)$^+$. |
| 154 | Ex 15 | (1R,3R or S)-1-[2-(difluoromethoxy)phenyl]-3-methyl-7-[2-(morpholin-4-yl)pyrimidin-5-yl]-2,3-dihydro-1H-cyclopenta[4,5]imidazo[1,2-a]pyridin-3-ol | LCMS (ES$^+$) RT 1.32 min 494.0 (M + H)$^+$. |

Examples 155 to 169

The following Examples were prepared by the Method A from the given starting material using the appropriate commercial or synthesised boronate ester or boronic acid.

| Example No. | Precursor | Compound Name | LCMS |
|---|---|---|---|
| 155 | Int 85 | 6-fluoro-7-[2-(2-hydroxypropan-2-yl)pyrimidin-5-yl]-1-(2-methoxyphenyl)-2,3-dihydro-1H-cyclopenta[4,5]imidazo[1,2-a]pyridin-3-ol | LCMS (ES$^+$) RT 1.28 min 435.0 (M + H)$^+$. |
| 156 | Ex 16 | (1R,3R)-7-[2-(3,3-difluorocyclobutyl)pyrimidin-5-yl]-1-[2-(difluoromethoxy)phenyl]-6-fluoro-2,3-dihydro-1H-cyclopenta[4,5]imidazo[1,2-a]pyridin-3-ol | RT 1.48 min 503.0 (M + H)$^+$. |
| 157 | Ex 16 | (1R,3R)-7-[2-(1,1-difluoroethyl)pyrimidin-5-yl]-1-[2-(difluoromethoxy)phenyl]-6-fluoro-2,3-dihydro-1H-cyclopenta[4,5]imidazo[1,2-a]pyridin-3-ol | RT 1.42 min 477.0 (M + H)$^+$. |
| 158 | Ex 16 | (1R,3R)-1-[2-(difluoromethoxy)phenyl]-6-fluoro-7-[2-(2-fluoropropan-2-yl)pyrimidin-5-yl]-2,3-dihydro-1H-cyclopenta[4,5]imidazo[1,2-a]pyridin-3-ol | RT 1.45 min 473.0 (M + H)$^+$. |

-continued

| Example No. | Precursor | Compound Name | LCMS |
|---|---|---|---|
| 159 | Int 136 | 1-[5-chloro-2-(difluoromethoxy)phenyl]-6-fluoro-7-[2-(2-hydroxypropan-2-yl)pyrimidin-5-yl]-2,3-dihydro-1H-cyclopenta[4,5]imidazo[1,2-a]pyridin-3-ol | RT 1.36 min 505.0 (M + H)+. |
| 160 | Int 131 | 1-(3-chlorophenyl)-6-fluoro-7-[2-(2-hydroxypropan-2-yl)pyrimidin-5-yl]-2,3-dihydro-1H-cyclopenta[4,5]imidazo[1,2-a]pyridin-3-ol | RT 1.32 min 439.0 (M + H)+. |
| 161 | Int 126 | 1-[2-(difluoromethoxy)-6-fluorophenyl]-6-fluoro-7-[2-(2-hydroxypropan-2-yl)pyrimidin-5-yl]-2,3-dihydro-1H-cyclopenta[4,5]imidazo[1,2-a]pyridin-3-ol | RT 1.29 min 489.0 (M + H)+. |
| 162 | Int 121 | 1-[2-(difluoromethoxy)-4,5-difluorophenyl]-6-fluoro-7-[2-(3-hydroxy-3-methylazetidin-1-yl)pyrimidin-5-yl]-2,3-dihydro-1H-cyclopenta[4,5]imidazo[1,2-a]pyridin-3-ol | LCMS (ES+) RT 1.47 min, 534.0 (M + H)+. |

-continued

| Example No. | Precursor | Compound Name | LCMS |
|---|---|---|---|
| 163 | Int 115 | 1-[2-(difluoromethoxy)-5-fluorophenyl]-6-fluoro-7-[2-(3-hydroxy-3-methylazetidin-1-yl)pyrimidin-5-yl]-2,3-dihydro-1H-cyclopenta[4,5]imidazo[1,2-a]pyridin-3-ol | LCMS (ES+) RT 1.26 min, 516.0 (M + H)+. |
| 164 | Int 109 | 1-[2-(difluoromethoxy)-4-fluorophenyl]-6-fluoro-7-[2-(3-hydroxy-3-methylazetidin-1-yl)pyrimidin-5-yl]-2,3-dihydro-1H-cyclopenta[4,5]imidazo[1,2-a]pyridin-3-ol | LCMS (ES+) RT 1.26 min, 516.0 (M + H)+. |
| 165 | Ex 16 | (1R,3R)-7-(2-cyclopropylpyrimidin-5-yl)-1-[2-(difluoromethoxy)phenyl]-6-fluoro-2,3-dihydro-1H-cyclopenta[4,5]imidazo[1,2-a]pyridin-3-ol | LCMS (ES+) RT 1.43 min, 453.0 (M + H)+. |
| 166 | Ex 20 | (1R)-1-[2-(difluoromethoxy)phenyl]-6-fluoro-7-[2-(3-hydroxy-3-methylazetidin-1-yl)pyrimidin-5-yl]-3-methyl-2,3-dihydro-1H-cyclopenta[4,5]imidazo[1,2-a]pyridin-3-ol | LCMS (ES+) RT 1.27 min, 512.0 (M + H)+. |

-continued

| Example No. | Precursor | Compound Name | LCMS |
|---|---|---|---|
| 167 | Ex 186 | 2-{5-[(1R,3R)-1-[2-(difluoromethoxy)phenyl]-6-fluoro-3-(pyridin-3-ylmethoxy)-2,3-dihydro-1H-cyclopenta[4,5]imidazo[1,2-a]pyridin-7-yl]pyrimidin-2-yl}propan-2-ol | LCMS (ES+) RT 1.43 min, 562.0 (M + H)+. |

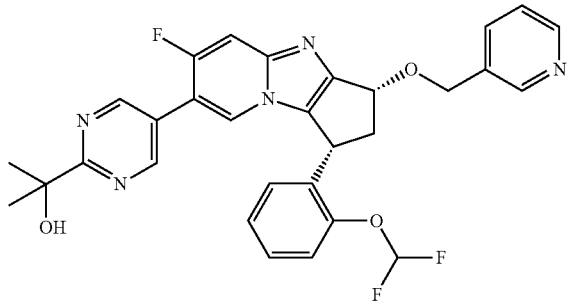

| 168 | Ex 190 | (1R,3R)-1-[5-chloro-2-(difluoromethoxy)phenyl]-7-[2-(2-hydroxypropan-2-yl)pyrimidin-5-yl]-2,3-dihydro-1H-cyclopenta[4,5]imidazo[1,2-a]pyridin-3-ol | LCMS (ES+) RT 1.32 min, 487.0 (M + H)+. |

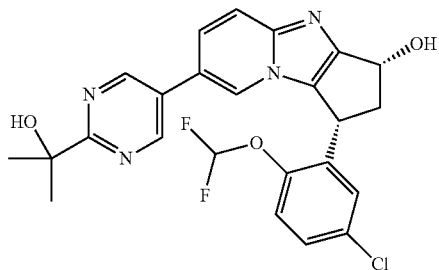 [SMILES: CC(C)(O)c1ncc(-c2ccc3nc4c(n3c2)[C@@H](c2cc(Cl)ccc2OC(F)F)C[C@H]4O)cn1]

| 169 | Ex 16 | methyl (8-anti)-3-(5-{(1R,3R)-1-[2-(difluoromethoxy)phenyl]-6-fluoro-3-hydroxy-2,3-dihydro-1H-cyclopenta[4,5]imidazo[1,2-a]pyridin-7-yl}pyrimidin-2-yl)-3-azabicyclo[3.2.1]octane-8-carboxylate | LCMS (ES+) RT 1.56 min, 580.0 (M + H)+. |

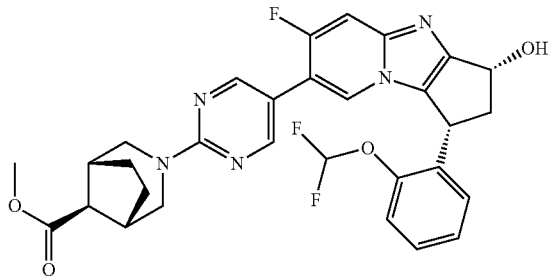 [SMILES: COC(=O)[C@@H]1[C@@H]2CC[C@H]1CN(c1ncc(-c3cn4c5c(nc4cc3F)[C@H](O)C[C@@H]5c3ccccc3OC(F)F)cn1)C2]

Example 170

(1R,3R)-7-[2-(2-aminopropan-2-yl)pyrimidin-5-yl]-1-[2-(difluoromethoxy)phenyl]-6-fluoro-2,3-dihydro-1H-cyclopenta[4,5]imidazo[1,2-a]pyridin-3-ol

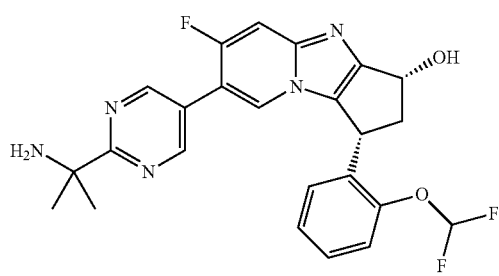 [SMILES: CC(C)(N)c1ncc(-c2cn3c4c(nc3cc2F)[C@H](O)C[C@@H]4c2ccccc2OC(F)F)cn1]

The title compound was prepared from Intermediate 137 (75 mg, 0.13 mmol) in dioxane (1.5 mL), and 4 M Hydrogen chloride in 1,4-dioxane (0.33 mL) by the Method J (59 mg, 95%).

$^1$H NMR (500 MHz, CDCl$_3$) δ 8.72 (d, J 1.4 Hz, 2H), 7.65 (d, J 7.1 Hz, 1H), 7.43 (d, J 10.9 Hz, 1H), 7.31-7.27 (m, 1H), 7.23 (dd, J 7.7, 1.7 Hz, 1H), 7.21-7.14 (m, 2H), 6.66 (dd, J 74.6, 72.8 Hz, 1H), 5.45 (dd, J 7.3, 3.2 Hz, 1H), 4.89 (dd, J 8.5, 4.0 Hz, 1H), 3.65-3.55 (m, 1H), 2.42 (dt, J 14.1, 3.6 Hz, 1H), 1.57 (s, 6H). LCMS (ES$^+$) RT 1.25 min, 470.0 (M+H)$^+$.

Example 171

(1R,5S,6r)-3-(5-{(1R)-1-[2-(difluoromethoxy)phenyl]-6-fluoro-2,3-dihydro-1H-cyclopenta[4,5]imidazo[1,2-a]pyridin-7-yl}pyrimidin-2-yl)bicyclo[3.1.0]hexane-6-carboxylic acid

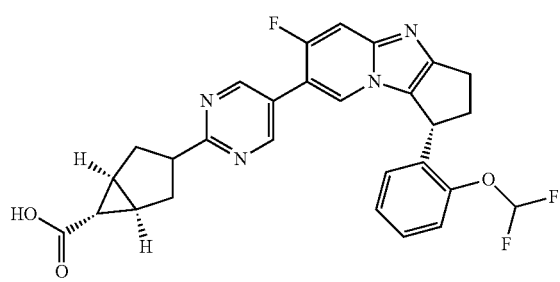 [SMILES: O=C(O)[C@H]1[C@@H]2CC(c3ncc(-c4cn5c6c(nc5cc4F)CC[C@@H]6c4ccccc4OC(F)F)cn3)C[C@@H]21]

The title compound was prepared from Intermediate 98 (100 mg, 0.18 mmol) in dioxane (2 mL), and 1M potassium hydroxide in water (0.187 mL) by the Method I (97 mg, 95%). $^1$H NMR (500 MHz, DMSO-d$_6$) δ 8.80 (d, J 1.2 Hz, 2H), 8.22 (d, J 7.5 Hz, 1H), 7.64 (d, J 11.7 Hz, 1H), 7.46-7.13 (m, 3H), 7.10 (t, J 7.2 Hz, 1H), 6.65 (d, J 6.4 Hz, 1H), 4.88 (dd, J 8.8, 3.5 Hz, 1H), 3.14 (dq, J 14.2, 8.8, 7.2 Hz, 1H), 3.02-2.77 (m, 3H), 2.28 (tt, J 8.3, 4.1 Hz, 1H), 2.11-1.97 (m, 4H), 1.46 (s, 2H), 1.13 (s, 1H). LCMS (ES$^+$) RT 1.23 min, 521.0 (M+H)$^+$.

Example 172

(1R,3R)-1-[2-(difluoromethoxy)phenyl]-6-fluoro-7-[2-(1-hydroxycyclopropyl)pyrimidin-5-yl]-2,3-dihydro-1H-cyclopenta[4,5]imidazo[1,2-a]pyridin-3-ol

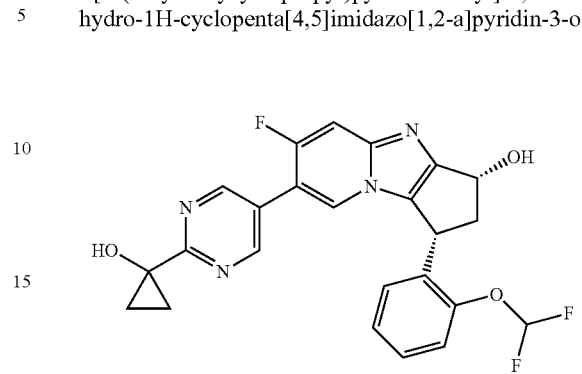

The title compound was prepared from Example 16 (100 mg, 0.21 mmol) in dioxane (4 mL), Intermediate 103 (147 mg, 0.33 mmol), 2M sodium carbonate (310 μL), and bis[3-(diphenylphosphanyl)cyclopenta-2,4-dien-1-yl]iron; dichloromethane; dichloropalladium (17 mg, 0.02 mmol), followed by 1M N,N,N-tributylbutan-1-aminium fluoride (3 mL) according to the Method K (7.6 mg, 7%). $^1$H NMR (500 MHz, CDCl$_3$) δ ppm 8.68 (d, J 1.4 Hz, 2H), 7.66 (d, J 7.1 Hz, 1H), 7.42 (d, J 10.9 Hz, 1H), 7.29 (d, J 6.9 Hz, 1H), 7.23 (dd, J 7.7, 1.6 Hz, 1H), 7.20-7.13 (m, 2H), 6.67 (dd, J 74.7, 72.7 Hz, 1H), 5.43 (dd, J 7.2, 2.9 Hz, 1H), 4.89 (dd, J 8.4, 3.8 Hz, 1H), 4.27 (s, 1H), 3.66-3.55 (m, 1H), 3.33 (s, 1H), 2.43 (dt, J 14.2, 3.4 Hz, 1H), 1.50-1.40 (m, 4H). LCMS (ES$^+$) RT 1.30 min, 469.0 (M+H)$^+$.

Example 173

(1S,3S)-1-[2-(difluoromethoxy)-4,5-difluorophenyl]-6-fluoro-7-[2-(3-hydroxy-3-methylazetidin-1-yl)pyrimidin-5-yl]-2,3-dihydro-1H-cyclopenta[4,5]imidazo[1,2-a]pyridin-3-ol

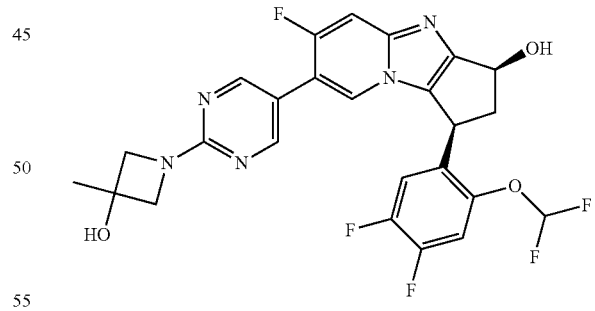

The title compound was prepared from Intermediate 121 (200 mg, 0.45 mmol) in dioxane (4 mL), Intermediate 138 (142.6 mg, 0.49 mmol), 2M sodium carbonate (668 μL), and bis[3-(diphenylphosphanyl)cyclopenta-2,4-dien-1-yl]iron; dichloromethane; dichloropalladium (18.18 mg, 0.02 mmol) by the Method A. The racemic mixture was separated by Chiral SFC (90% Heptane: 10% Ethanol on a ChiralPak AD Column) to afford the title compound as a beige solid (65 mg, 27%). $^1$H NMR (500 MHz, Methanol-d4) δ 8.40 (d, J 1.3 Hz, 2H), 7.92 (d, J 7.2 Hz, 1H), 7.42 (d, J 11.0 Hz, 1H), 7.27 (dd, J 10.9, 6.8 Hz, 1H), 7.08 (dd, J 11.2, 8.8 Hz, 1H), 7.00 (t, J 73.3 Hz, 1H), 5.25 (dd, J 7.1, 2.8 Hz, 1H), 4.88-4.85 (m, 1H), 4.09-3.97 (m, 4H), 3.66-3.50 (m, 1H), 2.23 (dt, J 14.0, 3.2 Hz, 1H), 1.54 (s, 3H), 1.29 (s, 1H). LCMS (ES$^+$) RT 1.47 min, 534.0 (M+H)$^+$.

Example 174

(1R,3R)-1-[2-(difluoromethoxy)-4,5-difluorophenyl]-6-fluoro-7-[2-(3-hydroxy-3-methylazetidin-1-yl)pyrimidin-5-yl]-2,3-dihydro-1H-cyclopenta[4,5]imidazo[1,2-a]pyridin-3-ol

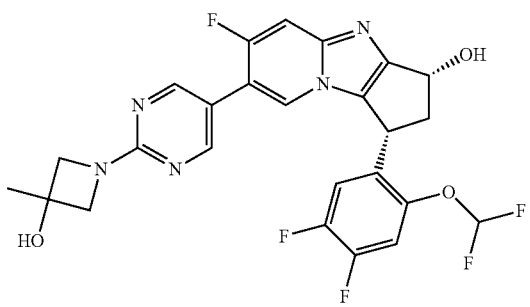 [SMILES: CC1(O)CN(c2ncc(-c3cn4c5c(nc4cc3F)[C@H](O)C[C@@H]5c3cc(F)c(F)cc3OC(F)F)cn2)C1]

The title compound was prepared from Intermediate 121 (200 mg, 0.45 mmol) in dioxane (4 mL), Intermediate 138 (142.6 mg, 0.49 mmol), 2M sodium carbonate (668 µL), and bis[3-(diphenylphosphanyl)cyclopenta-2,4-dien-1-yl]iron; dichloromethane; dichloropalladium (18.18 mg, 0.02 mmol) by the Method A. The racemic mixture was separated by Chiral SFC (90% Heptane: 10% Ethanol on a ChiralPak AD Column) to afford the title compound as a beige solid (67 mg, 28%). $^1$H NMR (500 MHz, Methanol-d4) δ 8.41 (d, J 1.3 Hz, 2H), 7.92 (d, J 7.2 Hz, 1H), 7.43 (d, J 11.0 Hz, 1H), 7.28 (dd, J 10.9, 6.8 Hz, 1H), 7.08 (dd, J 11.2, 8.8 Hz, 1H), 7.01 (t, J 73.3 Hz, 1H), 5.25 (dd, J 7.1, 2.8 Hz, 1H), 4.89-4.86 (m, 1H), 4.09-3.99 (m, 4H), 3.63-3.53 (m, 1H), 2.24 (dt, J 14.0, 3.2 Hz, 1H), 1.54 (s, 3H), 1.30 (s, 1H). LCMS (ES$^+$) RT 1.46 min, 534.0 (M+H)$^+$.

Example 175

(1R,3R)-1-[2-(difluoromethoxy)-5-fluorophenyl]-6-fluoro-7-[2-(3-hydroxy-3-methylazetidin-1-yl)pyrimidin-5-yl]-2,3-dihydro-1H-cyclopenta[4,5]imidazo[1,2-a]pyridin-3-ol

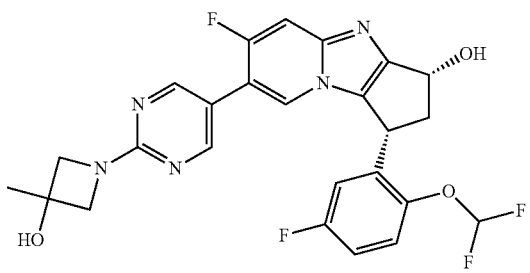 [SMILES: CC1(O)CN(c2ncc(-c3cn4c5c(nc4cc3F)[C@H](O)C[C@@H]5c3cc(F)ccc3OC(F)F)cn2)C1]

The title compound was prepared from Intermediate 115 (180 mg, 0.42 mmol) in dioxane (4 mL), Intermediate 138 (133.7 mg, 0.46 mmol), 2M sodium carbonate (626 µl), and bis[3-(diphenylphosphanyl)cyclopenta-2,4-dien-1-yl]iron; dichloromethane; dichloropalladium (17.05 mg, 0.02 mmol) by the Method A. The racemic mixture was separated by Chiral SFC (65% CO$_2$: 35% Methanol on a Chiralpak IC Column) yielding the title compound as a light brown solid (25 mg, 12%). $^1$H NMR (500 MHz, Methanol-d4) δ 8.38 (d, J 1.2 Hz, 2H), 7.89 (d, J 7.2 Hz, 1H), 7.42 (d, J 11.0 Hz, 1H), 7.28 (dd, J 9.0, 4.6 Hz, 1H), 7.04 (td, J 8.9, 8.4, 3.1 Hz, 1H), 6.95 (t, J 73.8 Hz, 1H), 6.89 (dd, J 9.2, 3.1 Hz, 1H), 5.26 (dd, J 7.2, 3.0 Hz, 1H), 4.91-4.87 (m, 1H), 4.58 (s, 1H), 4.09-3.97 (m, 4H), 3.64-3.52 (m, 1H), 2.25 (dt, J 14.0, 3.4 Hz, 1H), 1.53 (s, 3H). LCMS (ES$^+$) RT 1.25 min, 516.0 (M+H)$^+$.

Example 176

(1R,3R)-1-[2-(difluoromethoxy)-4-fluorophenyl]-6-fluoro-7-[2-(3-hydroxy-3-methylazetidin-1-yl)pyrimidin-5-yl]-2,3-dihydro-1H-cyclopenta[4,5]imidazo[1,2-a]pyridin-3-ol

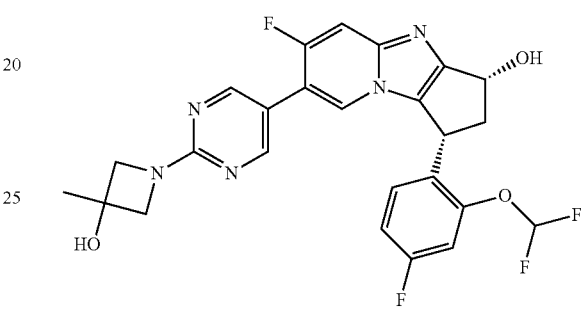

The title compound was prepared from Intermediate 109 (165 mg, 0.38 mmol) in dioxane (4 mL), Intermediate 138 (122.56 mg, 0.42 mmol), 2M sodium carbonate (574.01 µl), and bis[3-(diphenylphosphanyl)cyclopenta-2,4-dien-1-yl]iron; dichloromethane; dichloropalladium (15.63 mg, 0.02 mmol) by the Method A. The racemic mixture was separated by Chiral SFC (65% CO$_2$: 35% Methanol on a Chiralpak IC Column) yielding the title compound as a light brown solid (60 mg, 30%). $^1$H NMR (500 MHz, Methanol-d4) δ 8.38 (d, J 1.1 Hz, 2H), 7.87 (d, J 7.2 Hz, 1H), 7.42 (d, J 11.0 Hz, 1H), 7.21-6.86 (m, 4H), 5.26 (dd, J 7.2, 3.3 Hz, 1H), 4.85-4.83 (m, 2H), 4.59 (s, 1H), 4.10-3.94 (m, 4H), 3.66-3.51 (m, 1H), 2.21 (dt, J 13.9, 3.7 Hz, 1H), 1.53 (s, 3H). LCMS (ES$^+$) RT 1.26 min, 516.0 (M+H)$^+$.

Example 177

(1S,3S)-1-[2-(difluoromethoxy)-4-fluorophenyl]-6-fluoro-7-[2-(3-hydroxy-3-methylazetidin-1-yl)pyrimidin-5-yl]-2,3-dihydro-1H-cyclopenta[4,5]imidazo[1,2-a]pyridin-3-ol

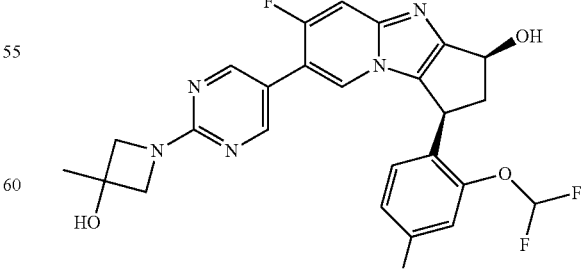

The title compound was prepared from Intermediate 109 (165 mg, 0.38 mmol) in dioxane (4 mL), Intermediate 138 (122.56 mg, 0.42 mmol), 2M sodium carbonate (574.01 µl), and bis[3-(diphenylphosphanyl)cyclopenta-2,4-dien-1-yl]iron; dichloromethane; dichloropalladium (15.63 mg, 0.02 mmol) by the Method A. The racemic mixture was separated by Chiral SFC (65% CO$_2$: 35% Methanol on a Chiralpak IC Column) yielding the title compound as a light brown solid (63 mg, 31%). $^1$H NMR (500 MHz, Methanol-d4) δ 8.40 (d, J 1.0 Hz, 2H), 7.89 (d, J 7.2 Hz, 1H), 7.46 (d, J 11.0 Hz, 1H), 7.24-6.86 (m, 4H), 5.28 (dd, J 7.2, 3.3 Hz, 1H), 4.86-4.84 (m, 2H), 4.60 (s, 1H), 4.10-3.97 (m, 4H), 3.68-3.53 (m, 1H), 2.23 (dt, J 13.9, 3.7 Hz, 1H), 1.55 (s, 3H). LCMS (ES$^+$) RT 1.26 min, 516.0 (M+H)$^+$.

Example 178

(1S,3S)-1-[2-(difluoromethoxy)-5-fluorophenyl]-6-fluoro-7-[2-(3-hydroxy-3-methylazetidin-1-yl)pyrimidin-5-yl]-2,3-dihydro-1H-cyclopenta[4,5]imidazo[1,2-a]pyridin-3-ol

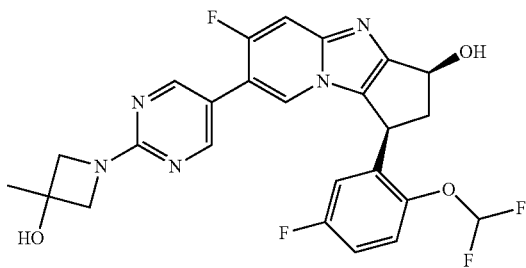 [SMILES: CC1(O)CN(c2ncc(-c3cn4c5c(nc4cc3F)[C@@H](O)C[C@H]5c3cc(F)ccc3OC(F)F)cn2)C1]

The title compound was prepared from Intermediate 115 (180 mg, 0.42 mmol) in dioxane (4 mL), Intermediate 138 (133.7 mg, 0.46 mmol), 2M sodium carbonate (626 µl), and bis[3-(diphenylphosphanyl)cyclopenta-2,4-dien-1-yl]iron; dichloromethane; dichloropalladium (17.05 mg, 0.02 mmol) by the Method A. The racemic mixture was separated by Chiral SFC (65% CO$_2$: 35% Methanol on a Chiralpak IC Column) yielding the title compound as a light brown solid (21 mg, 10%). $^1$H NMR (500 MHz, Methanol-d4) δ 8.44-8.33 (m, 2H), 7.89 (d, J 7.2 Hz, 1H), 7.43 (d, J 11.0 Hz, 1H), 7.28 (dd, J 9.0, 4.6 Hz, 1H), 7.04 (td, J 8.9, 8.4, 3.1 Hz, 1H), 6.95 (t, J 73.8 Hz, 1H), 6.89 (dd, J 9.2, 3.1 Hz, 1H), 5.26 (dd, J 7.2, 3.0 Hz, 1H), 4.90-4.87 (m, 1H), 4.58 (s, 1H), 4.08-3.96 (m, 4H), 3.59 (dt, J 14.2, 8.1 Hz, 1H), 2.25 (dt, J 14.0, 3.4 Hz, 1H), 1.53 (s, 3H). LCMS (ES$^+$) RT 1.25 min, 516.0 (M+H)$^+$.

Example 179

(1R,3S)-1-[2-(difluoromethoxy)phenyl]-6-fluoro-7-{2-[3-hydroxy-3-(trifluoromethyl)azetidin-1-yl]pyrimidin-5-yl}-3-methyl-2,3-dihydro-1H-cyclopenta[4,5]imidazo[1,2-a]pyridin-3-ol

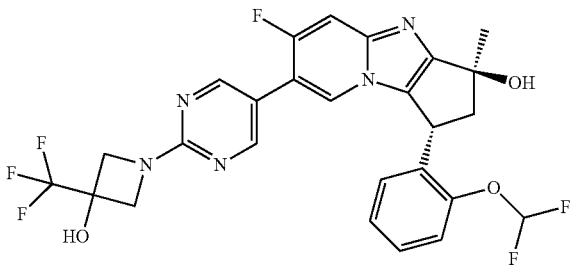 [SMILES: C[C@]1(O)C[C@H](c2ccccc2OC(F)F)c2c1nc1cc(F)c(-c3cnc(N4CC(O)(C(F)(F)F)C4)nc3)cn21]

The title compound was prepared from Example 20 (200 mg, 0.47 mmol), Intermediate 140 (178 mg, 0.52 mmol), 2M sodium carbonate (0.70 mL), dioxane (4 mL), dichloro[1,1'-bis(diphenylphosphinoferrocene)-palladium dichloromethane adduct (38 mg, 0.05 mmol) by the Method A. Followed by chiral preparative HPLC (85% CO$_2$: 15% Methanol on a Chiralpak IC column) yielding the title compound as a pale brown solid (28.0 mg, 21%). $^1$H NMR (500 MHz, CDCl$_3$) δ 8.19 (s, 2H), 7.36-7.27 (m, 2H), 7.25-7.16 (m, 2H), 7.12 (t, J 7.4 Hz, 1H), 6.86 (d, J 7.4 Hz, 1H), 6.63 (t, J 73.4 Hz, 1H), 5.38 (s, 1H), 5.11 (t, J 6.6 Hz, 1H), 4.40 (t, J 9.3 Hz, 2H), 4.08 (dd, J 18.2, 10.1 Hz, 2H), 3.32 (dd, J 13.7, 7.9 Hz, 1H), 3.03 (s, 1H), 2.50 (dd, J 13.7, 5.5 Hz, 1H), 1.81 (s, 3H). LCMS (ES$^+$) RT 1.40 min, 566.0 (M+H)$^+$.

Example 180

(1R,3R)-1-[2-(difluoromethoxy)phenyl]-6-fluoro-7-[2-(3-hydroxy-3-methylazetidin-1-yl)pyrimidin-5-yl]-3-methyl-2,3-dihydro-1H-cyclopenta[4,5]imidazo[1,2-a]pyridin-3-ol

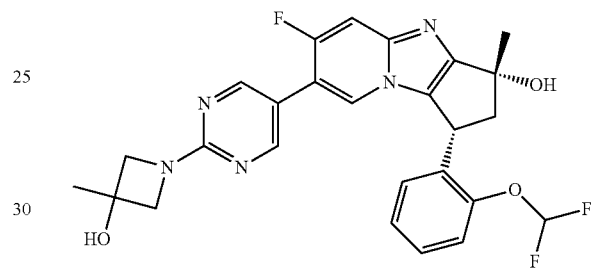

The title compound was prepared from Example 20 (200 mg, 0.47 mmol), Intermediate 138 (158 mg, 0.53 mmol), 2M sodium carbonate (0.70 mL), dioxane (4 mL), dichloro[1,1'-bis(diphenylphosphinoferrocene)-palladium dichloromethane adduct (38 mg, 0.05 mmol) by the Method A. Followed by chiral preparative HPLC (85% CO$_2$: 15% Methanol on a Chiralpak IC column) yielding the title compound as a pale brown solid (20.0 mg, 13%). $^1$H NMR (500 MHz, CDCl$_3$) δ 8.24 (s, 2H), 7.47 (d, J 7.2 Hz, 1H), 7.28 (dd, J 5.6, 2.8 Hz, 2H), 7.21-7.16 (m, 2H), 7.13 (t, J 7.4 Hz, 1H), 6.65 (dd, J 74.5, 72.8 Hz, 1H), 4.86 (dd, J 8.4, 4.0 Hz, 1H), 4.12-4.05 (m, 2H), 4.05-3.94 (m, 2H), 3.31-3.24 (m, 1H), 3.09 (d, J 23.8 Hz, 2H), 2.64 (dd, J 13.8, 4.0 Hz, 1H), 1.78 (s, 3H), 1.61 (s, 3H). LCMS (ES$^+$) RT 1.27 min, 512.0 (M+H)$^+$.

Example 181

(1R,3R)-1-[2-(difluoromethoxy)phenyl]-7-{2-[1-(methylsulfonyl)piperidin-4-yl]pyrimidin-5-yl}-2,3-dihydro-1H-cyclopenta[4,5]imidazo[1,2-a]pyridin-3-ol

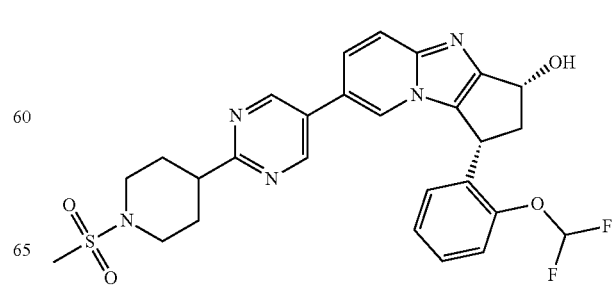

233

To a solution of Example 134 (87 mg, 0.16 mmol) in DMF (2 mL) was added N,N-diethylethanamine (105 μL, 0.75 mmol) and stirred for 5 minutes, methanesulfonyl methanesulfonate (142 mg, 0.82 mmol) was added and heated at 60° C. for 18 hours. The reaction mixture was cooled to r.t, with further cooling in an ice bath, diluted with water (20 mL) and extracted with EtOAc (25 mL), DCM (25 mL) and 1:1 IPA/chloroform (2×25 mL). The organic extracts were dried over sodium sulfate and concentratedin vacuo. The crude residue was purified by preparative HPLC yielding the title compound as an off-white solid (3 mg, 3%). $^1$H NMR (500 MHz, DMSO-d6) δ ppm 8.99 (s, 2H), 8.26 (s, 1H), 7.79-7.71 (m, 1H), 7.66 (dd, J 9.5, 1.8 Hz, 1H), 7.55-7.20 (m, 3H), 7.17-7.09 (m, 1H), 6.91 (dd, J 7.7, 1.5 Hz, 1H), 5.51 (d, J 5.0 Hz, 1H), 5.19-5.09 (m, 1H), 4.78 (dd, J 8.5, 3.8 Hz, 1H), 3.70-3.59 (m, 2H), 3.53-3.41 (m, 1H), 3.00 (ddt, J 11.3, 7.1, 3.6 Hz, 1H), 2.94-2.84 (m, 5H), 2.15-2.03 (m, 3H), 1.81 (qd, J 12.7, 4.2 Hz, 2H). LCMS (ES$^+$) RT 1.30 min, 556.0 (M+H)$^+$.

Example 182

(1R,3R)-1-[2-(difluoromethoxy)phenyl]-6-fluoro-7-{2-[3-hydroxy-3-(trifluoromethyl)azetidin-1-yl]pyrimidin-5-yl}-3-methyl-2,3-dihydro-1H-cyclopenta[4,5]imidazo[1,2-a]pyridin-3-ol

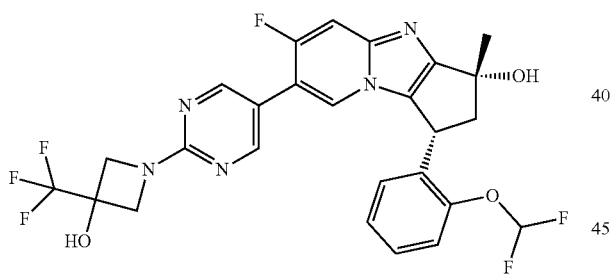

The title compound was prepared from Example 20 (200 mg, 0.47 mmol), Intermediate 140 (178 mg, 0.52 mmol), 2M sodium carbonate (0.70 mL), dioxane (4 mL), dichloro[1,1'-bis(diphenylphosphinoferrocene]-palladium dichloromethane adduct (38 mg, 0.05 mmol) by the Method A. Followed by chiral preparative HPLC (85% CO$_2$: 15% Methanol on a Chiralpak IC column) yielding the title compound as a pale brown solid (28.0 mg, 21%). $^1$H NMR (500 MHz, CDCl$_3$) δ 8.20 (s, 2H), 7.47 (d, J 7.1 Hz, 1H), 7.30-7.26 (m, 1H), 7.23-7.17 (m, 3H), 7.13 (t, J 7.5 Hz, 1H), 6.66 (dd, J 74.5, 72.7 Hz, 1H), 5.58 (s, 1H), 4.87 (dd, J 8.4, 4.1 Hz, 1H), 4.44 (d, J 10.2 Hz, 1H), 4.38 (d, J 10.0 Hz, 1H), 4.13-4.09 (m, 1H), 4.04 (d, J 10.4 Hz, 1H), 3.29 (dd, J 13.8, 8.5 Hz, 1H), 3.05 (s, 1H), 2.65 (dd, J 13.8, 4.1 Hz, 1H), 1.79 (s, 3H). LCMS (ES$^+$) RT 1.41 min, 566.0 (M+H)$^+$.

234

Example 183

(1R,3R)-7-[2-(3,3-difluoro-1-hydroxycyclobutyl)pyrimidin-5-yl]-1-[2-(difluoromethoxy)phenyl]-6-fluoro-2,3-dihydro-1H-cyclopenta[4,5]imidazo[1,2-a]pyridin-3-ol

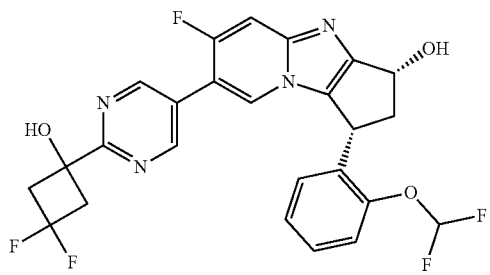 [SMILES: O[C@@H]1C[C@H](c2ccccc2OC(F)F)c2c1nc1cc(F)c(-c3cnc(C4(O)CC(F)(F)C4)nc3)cn21]

The title compound was prepared from Example 16 (120 mg, 0.25 mmol), Intermediate 143 (104 mg, 0.27 mmol),2M sodium carbonate (0.37 mL, 0.741 mmol), dioxane (6 mL), Pd(dppf)Cl$_2$ complex with dichloromethane (20.0 mg, 0.025 mmol) and subsequently 1 M solution of tetrabutyl ammonium fluoride in THF (0.741 mL, 0.741 mmol) by the Method K, yielding the title compound as a white solid (8 mg, 6%). $^1$H NMR (500 MHz, CDCl$_3$) δ 8.81 (d, J 1.4 Hz, 2H), 7.70 (d, J 7.1 Hz, 1H), 7.45 (d, J 11.0 Hz, 1H), 7.33-7.27 (m, 1H), 7.24 (dd, J 7.9, 1.8 Hz, 1H), 7.21-7.14 (m, 2H), 6.67 (dd, J 74.8, 72.6 Hz, 1H), 5.43 (dd, J 6.9, 3.5 Hz, 1H), 4.95 (s, 1H), 4.89 (dd, J 8.5, 3.8 Hz, 1H), 3.69-3.53 (m, 1H), 3.40 (td, J 14.4, 11.3 Hz, 2H), 3.13-2.92 (m, 3H), 2.43 (dt, J 14.2, 3.4 Hz, 1H). LCMS (ES$^+$) RT 1.41 min, 519.0 (M+H)$^+$.

Example 184

1-(5-{(1R,3R)-1-[2-(difluoromethoxy)phenyl]-6-fluoro-3-hydroxy-2,3-dihydro-1H-cyclopenta[4,5]imidazo[1,2-a]pyridin-7-yl}pyrimidin-2-yl)-3-methylcyclobutane-1,3-diol

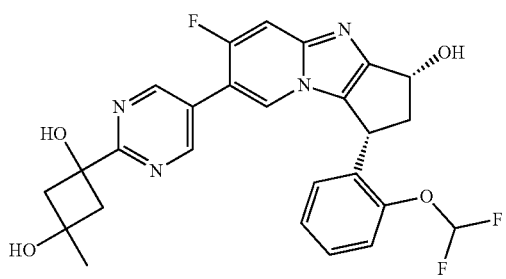 [SMILES: CC1(O)CC(O)(c2ncc(-c3cn4c5c(nc4cc3F)[C@H](O)C[C@@H]5c3ccccc3OC(F)F)cn2)C1]

The title compound was prepared from Example 16 (263 mg, 0.64 mmol), 1,4-dioxane (8 mL), Intermediate 165 (368 mg, 0.7 mmol), 2M K$_2$CO$_3$ in water (950 μL) and PdCl$_2$.dppf (53 mg, 0.06 mmol) followed by 1M TBAF in THF (5.09 mL). by the Method K (7.1 mg, 2.1%).). LCMS (ES$^+$) RT 1.21 min, 513.0 (M+H)$^+$.

Example 185

1-(5-{(1R)-1-[2-(difluoromethoxy)phenyl]-6-fluoro-3-hydroxy-3-methyl-2,3-dihydro-1H-cyclopenta[4,5]imidazo[1,2-a]pyridin-7-yl}pyrimidin-2-yl)-3-methylcyclobutane-1,3-diol

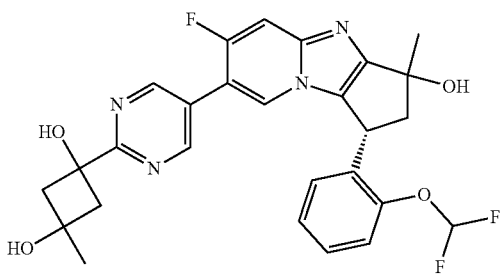 [SMILES: CC1(O)CC(O)(c2ncc(-c3cn4c5c(nc4cc3F)C(C)(O)C[C@@H]5c3ccccc3OC(F)F)cn2)C1]

Intermediate 144 (0.48 g, 0.76 mmol) was dissolved in anhydrous THF (10 mL) under an atmosphere of N₂(g) and treated with 1M TBAF in THF (1.51 mL). The reaction mixture was stirred at r.t. for 18 h and diluted with EtOAc (30 mL), washed with water (3×25 mL), brine (25 mL) and passed over a 50 mL Biotage hydrophobic phase separator. The filtrate was concentrated in vacuo and the residue was purified by chromatography (C18,0-25% MeCN in H₂O with 0.1% formic acid) yielding the title compound as a yellow crystalline solid (0.315 g, 80%). LCMS (ES⁺) RT 1.30 min, 527.0 (M+H)⁺.

Example 186 Method Q (1R,3R)-7-bromo-1-[2-(difluoromethoxy)phenyl]-6-fluoro-3-(pyridin-3-ylmethoxy)-2,3-dihydro-1H-cyclopenta[4,5]imidazo[1,2-a]pyridine

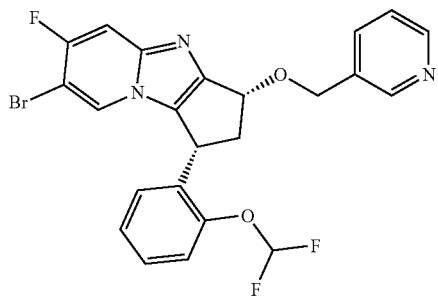 [SMILES: Fc1cc2nc3c(n2cc1Br)[C@@H](c1ccccc1OC(F)F)C[C@H]3OCc1cccnc1]

Sodium hydride, 60% dispersion in mineral oil (77.44 mg, 1.936 mmol) was added to a solution of Example 16 (A, 400 mg, 0.9681 mmol) in THF (10 mL) at −78° C. 3-(bromomethyl)pyridine hydrobromide (302.9 mg, 1.162 mmol) was added and the reaction was allowed to warm to r.t. for 18 h. The reaction mixture was treated with treated with water (10 mL) and partitioned with DCM (20 mL), the organics were extracted and dried over MgSO₄, and concentrated in vacuo. The residue was purified by chromatography (SiO₂, 0-100% EtOAc in Hexane) yielding the title compound as a yellow solid (171 mg, 35%). ¹H NMR (400 MHz, DMSO-d₆) δ: 8.49 (m, 2 H), 8.39 (d, J 6.9 Hz, 1 H), 7.78 (d, J 10.0 Hz, 1 H), 7.69 (dt, J 7.8, 1.8 Hz, 1 H), 7.33 (m, 3 H), 7.25 (m, 1 H), 7.11 (m, 1 H), 6.80 (dd, J 7.7 Hz, 1.6 Hz, 1 H), 5.02 (m, 1 H), 4.79 (m, 3 H), 4.79 (dd, J 8.7 Hz, 3.1 Hz, 1 H), 3.47 (m, 1 H). LCMS (ES⁺) RT 1.55 min, 504.0/506.0 (M+H)⁺.

Example 187

7-bromo-1-[5-chloro-2-(difluoromethoxy)phenyl]-1,2-dihydro-3H-cyclopenta[4,5]imidazo[1,2-a]pyridin-3-one

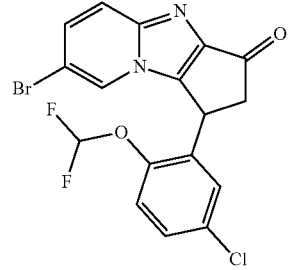 [SMILES: O=C1CC(c2cc(Cl)ccc2OC(F)F)c2c1nc1ccc(Br)cn21]

The title compound was prepared from Intermediate 148 (31.1 g, 62.2 mmol), dioxane (200 mL) and water (200 mL) by the Method M (28.3 g, 91%). ¹H NMR (DMSO-d₆) δ 8.38 (s, 1 H), 7.73 (m, 1 H), 7.56 (dd, J 9.8, 1.8 Hz, 1 H), 7.44 (m, 1 H), 7.28 (d, J 8.7 Hz, 1 H), 7.20 (t, J 73.7, Hz, 1 H), 7.09 (s, 1 H), 5.11 (dd, J 7.0, 1.9 Hz, 1 H), 3.57 (m, 1 H), 2.81 (dd, J 18.2, 2.1 Hz, 1 H). LCMS (ES⁺) RT 1.49 min, 427.0/429.0 (M+H)⁺.

Examples 188 and 189

(1S)-7-bromo-1-[5-chloro-2-(difluoromethoxy)phenyl]-1,2-dihydro-3H-cyclopenta[4,5]imidazo[1,2-a]pyridin-3-one and (1R)-7-bromo-1-[5-chloro-2-(difluoromethoxy)phenyl]-1,2-dihydro-3H-cyclopenta[4,5]imidazo[1,2-a]pyridin-3-one

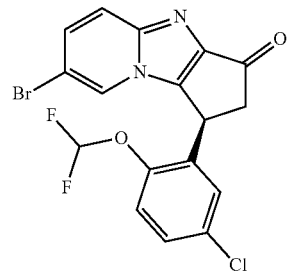

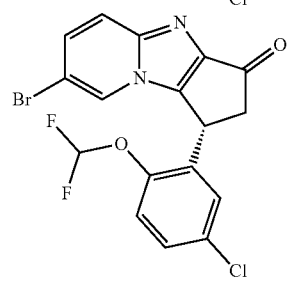

The title compounds were isolated by purification of Example 187 under LC conditions on Lux-Cell-4 (76*265 mm*mm, flow 200 mL/min, 30° C., MeOH 100%, injection of 27 mL solution at a concentration of 10 g/L).

The first eluting enantiomer (RT 10 min) was collected and the fractions were evaporated to yield (enantiomer 1) (Example 188). $^1$H NMR (DMSO-d$_6$) δ: 8.38 (d, J 0.9 Hz, 1 H), 7.73 (dd, J 9.8 Hz, 0.6 Hz, 1 H), 7.56 (dd, J 9.8 Hz, 1.9 Hz, 1 H), 7.47 (dd, J 8.8 Hz, 2.6 Hz, 1 H), 7.28 (d, J 8.7 Hz, 1 H), 7.20 (t, J 73.5 Hz), 5.10 (dd, J 7.1 Hz, 2.1 Hz, 1 H), 4.33 (d, J 4.2 Hz, 0 H), 3.57 (dd, J 18.2 Hz, 7.2 Hz, 1 H), 2.81 (dd, J 18.2 Hz, 2.2 Hz, 1H), 1.04 (d, J 6.1 Hz, 2 H). LCMS (ES+) RT 1.49 min, 427.0/429.0 (M+H)$^+$.

The second eluting enantiomer (RT 14 min) was collected and the fractions were evaporated to yield (enantiomer 2) (Example 189). $^1$H NMR (DMSO-d$_6$) δ: 8.38 (d, J 0.9 Hz, 1 H), 7.73 (dd, J 9.8 Hz, 0.6 Hz, 1 H), 7.56 (dd, J 9.8 Hz, 1.9 Hz, 1 H), 7.47 (dd, J 8.8 Hz, 2.6 Hz, 1 H), 7.28 (d, J 8.7 Hz, 1 H), 7.20 (t, J 73.5 Hz), 5.10 (dd, J 7.1 Hz, 2.1 Hz, 1 H), 4.33 (d, J 4.2 Hz, 0 H), 3.57 (dd, J 18.2 Hz, 7.2 Hz, 1 H), 2.81 (dd, J 18.2 Hz, 2.2 Hz, 1 H), 1.04 (d, J 6.1 Hz, 2 H)LCMS (ES+) RT 1.49 min, 427.0/429.0 (M+H)$^+$.

Example 190

(1R,3R)-7-bromo-1-[5-chloro-2-(difluoromethoxy)phenyl]-2,3-dihydro-1H-cyclopenta[4,5]imidazo[1,2-a]pyridin-3-ol

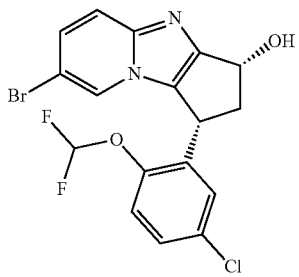 [SMILES: O[C@@H]1C[C@H](c2cc(Cl)ccc2OC(F)F)c2c1nc1ccc(Br)cn21]

The title compound was prepared from Example 189 (200 mg, 0.47 mmol), 1M lithium tri-sec-butylborohydride in THF (0.51 mL) and THF (10 mL) by the Method B (118 mg, 59%). LCMS (ES$^+$) RT 1.46 min, 429.0/431.0 (M+H)$^+$.

Example 191

(1S,3S)-7-bromo-1-[5-chloro-2-(difluoromethoxy)phenyl]-2,3-dihydro-1H-cyclopenta[4,5]imidazo[1,2-a]pyridin-3-ol

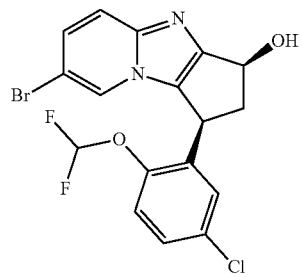 [SMILES: O[C@H]1C[C@@H](c2cc(Cl)ccc2OC(F)F)c2c1nc1ccc(Br)cn21]

The title compound was prepared from Example 188 (250 mg, 0.58 mmol), 1M lithium tri-sec-butylborohydride in THF (0.51 mL) and THF (10 mL) by the Method B (142 mg, 56.54%). LCMS (ES$^+$) RT 1.46 min, 429.0/431.0 (M+H)$^+$.

Examples 192 to 196

The following Examples were synthesised according to Method Q from the given starting material and using the appropriate commercial alkyl bromide.

| Example No. | Precursor | Compound Name | LCMS |
|---|---|---|---|
| 192 | Ex 19 | (1R)-3-(benzyloxy)-7-bromo-1-[2-(difluoromethoxy)phenyl]-6-fluoro-2,3-dihydro-1H-cyclopenta[4,5]imidazo[1,2-a]pyridine | LCMS (ES$^+$) RT 1.74 min, 503.0/505.0 (M + H)$^+$. |

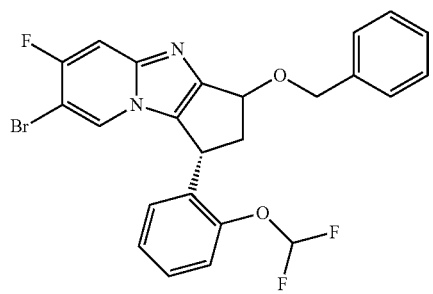

-continued

| Example No. | Precursor | Compound Name | LCMS |
|---|---|---|---|
| 193 | Ex 19 | ({(1R)-7-bromo-1-[2-(difluoromethoxy)phenyl]-6-fluoro-2,3-dihydro-1H-cyclopenta[4,5]imidazo[1,2-a]pyridin-3-yl}oxy)acetonitrile | LCMS (ES+) RT 1.56 min, 413.0/415.0 (M + H)+. |
| 194 | Ex 19 | (1R)-7-bromo-1-[2-(difluoromethoxy)phenyl]-6-fluoro-3-(pyridin-4-ylmethoxy)-2,3-dihydro-1H-cyclopenta[4,5]imidazo[1,2-a]pyridine | LCMS (ES+) RT 1.57 min, 504.0/506.0 (M + H)+. |
| 195 | Ex 19 | (1R)-7-bromo-1-[2-(difluoromethoxy)phenyl]-6-fluoro-3-(pyridin-3-ylmethoxy)-2,3-dihydro-1H-cyclopenta[4,5]imidazo[1,2-a]pyridine | LCMS (ES+) RT 1.57 min, 504.0/506.0 (M + H)+. |
| 196 | Ex 19 | methyl ({(1R,3R)-7-bromo-1-[2-(difluoromethoxy)phenyl]-6-fluoro-2,3-dihydro-1H-cyclopenta[4,5]imidazo[1,2-a]pyridin-3-yl}oxy)acetate | LCMS (ES+) RT 1.56 min, 485.0/487.0 (M + H)+. |

Example 197

({(1R,3R)-7-bromo-1-[2-(difluoromethoxy)phenyl]-6-fluoro-2,3-dihydro-1H-cyclopenta[4,5]imidazo[1,2-a]pyridin-3-yl}oxy)acetic acid

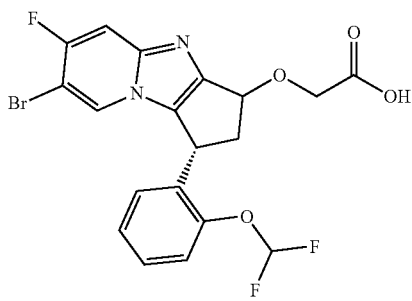 [SMILES: O=C(O)COC1C[C@H](c2ccccc2OC(F)F)c2c1nc1cc(F)c(Br)cn21]

To a solution of Example 196 (30 mg, 0.06 mmol) in THF (1 mL) was added 2M aq. sodium hydroxide (120 μL, 0.24 mmol) and the resultant mixture stirred at r.t for 18 h. The reaction was concentrated in vacuo. The resultant residue was diluted with water (5 mL), acidified by the addition of 2M aq. hydrochloric acid solution and extracted with DCM (2×5 mL). The combined organic layers were dried over sodium sulphate and concentrated in vacuo yielding the title compound as an off-white powder (26 mg, 90%). $^1$H NMR (CDCl$_3$, 500 MHz) δ 7.86 (d, J 6.5 Hz, 1H), 7.71 (d, J 8.5 Hz, 1H), 7.32 (ddd, J 8.5, 7.0, 2.0 Hz, 1H), 7.24-7.17 (m, 3H), 6.70 (dd, J 74.5, 73.0 Hz, 1H), 5.37 (dd, J 7.0, 2.0 Hz, 1H), 4.85 (dd, J 8.5, 3.0 Hz, 1H), 4.53 (d, J 17.0 Hz, 1H), 4.36 (d, J 17.0 Hz, 1H), 3.62-3.52 (m, 1H), 2.53 (dt, J 14.5, 2.5 Hz, 1H). LCMS (ES$^+$) RT 1.27 min, 471.0/473.0 (M+H)+.

Examples 198 to 200

The following Examples were prepared from the given starting material using the appropriate commercial or synthesised boronate ester or boronic acid by the Method A.

| Example No. | Precursor | Compound Name | LCMS |
|---|---|---|---|
| 198 | Ex 17 | methyl (8-anti)-3-(5-{(1R)-1-[2-(difluoromethoxy)phenyl]-6-fluoro-2,3-dihydro-1H-cyclopenta[4,5]imidazo[1,2-a]pyridin-7-yl}pyrimidin-2-yl)-3-azabicyclo[3.2.1]octane-8-carboxylate | LCMS (ES$^+$) RT 1.75 min 564.0 (M + H)$^+$. |
| | | 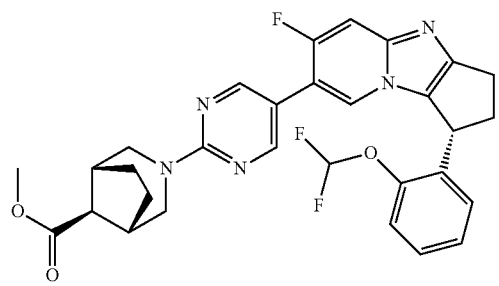 [SMILES: COC(=O)[C@@H]1[C@@H]2CC[C@H]1CN(c1ncc(-c3cn4c5c(nc4cc3F)CC[C@@H]5c3ccccc3OC(F)F)cn1)C2] | |
| 199 | Int 121 | (1R,3R)-1-[2-(difluoromethoxy)-4,5-difluorophenyl]-6-fluoro-7-[2-(2-hydroxypropan-2-yl)pyrimidin-5-yl]-2,3-dihydro-1H-cyclopenta[4,5]imidazo[1,2-a]pyridin-3-ol | LCMS (ES$^+$) RT 1.37 min 507.0 (M + H)$^+$. |
| | | 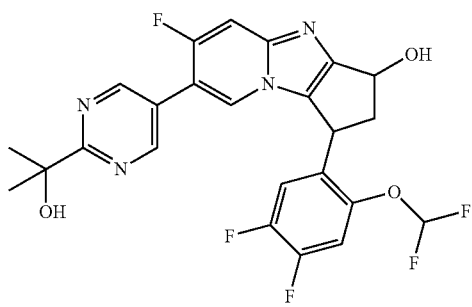 [SMILES: CC(C)(O)c1ncc(-c2cn3c4c(nc3cc2F)C(O)CC4c2cc(F)c(F)cc2OC(F)F)cn1] | |

| Example No. | Precursor | Compound Name | LCMS |
|---|---|---|---|
| 200 | Ex 16 | (1R,3R)-7-(2-cyclobutylpyrimidin-5-yl)-1-[2-(difluoromethoxy)phenyl]-6-fluoro-2,3-dihydro-1H-cyclopenta[4,5]imidazo[1,2-a]pyridin-3-ol | LCMS (ES+) RT 1.50 min 467.0 (M + H)+. |

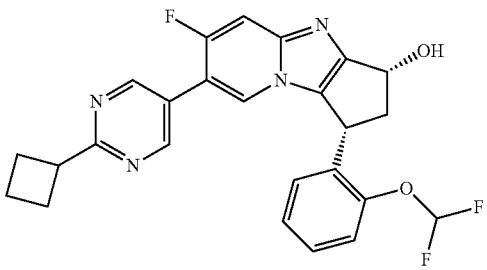 [SMILES: O[C@@H]1C[C@H](c2ccccc2OC(F)F)c2c1nc1cc(F)c(-c3cnc(C4CCC4)nc3)cn21]

Example 201

(8-anti)-3-(5-{(1R,3R)-1-[2-(difluoromethoxy)phenyl]-6-fluoro-3-hydroxy-2,3-dihydro-1H-cyclopenta[4,5]imidazo[1,2-a]pyridin-7-yl}pyrimidin-2-yl)-3-azabicyclo[3.2.1]octane-8-carboxylic acid

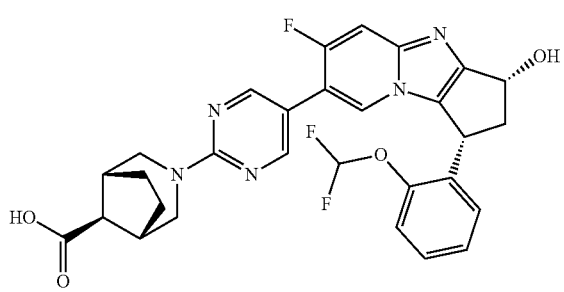 [SMILES: O=C(O)[C@@H]1[C@@H]2CC[C@H]1CN(c1ncc(-c3cn4c5c(nc4cc3F)[C@H](O)C[C@@H]5c3ccccc3OC(F)F)cn1)C2]

The title compound was prepared from Example 169 (102 mg, 0.18 mmol), 1,4-Dioxane (1 mL) and 1M potassium hydroxide in water (0.26 ml) by the Method I (82 mg, 78%). LCMS (ES+) RT 1.13 min 566.0 (M+H)+.

Example 202

Potassium (8-anti)-3-(5-{(1R)-1-[2-(difluoromethoxy)phenyl]-6-fluoro-2,3-dihydro-1H-cyclopenta[4,5]imidazo[1,2-a]pyridin-7-yl}pyrimidin-2-yl)-3-azabicyclo[3.2.1]octane-8-carboxylate

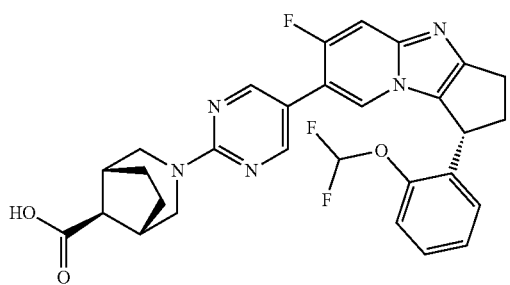 [SMILES: O=C(O)[C@@H]1[C@@H]2CC[C@H]1CN(c1ncc(-c3cn4c5c(nc4cc3F)CC[C@@H]5c3ccccc3OC(F)F)cn1)C2]

The title compound was prepared from Example 198 (42 mg, 0.08 mmol), 1,4-Dioxane (2 mL), 1M potassium hydroxide (0.08 mL) by the Method I (38 mg, 78%). LCMS (ES+) RT 1.25 min 550.0 (M+H)+.

Example 203

Methyl (8-anti)-3-(5-{(1R,3R)-1-[2-(difluoromethoxy)phenyl]-6-fluoro-3-methoxy-2,3-dihydro-1H-cyclopenta[4,5]imidazo[1,2-a]pyridin-7-yl}pyrimidin-2-yl)-3-azabicyclo[3.2.1]octane-8-carboxylate

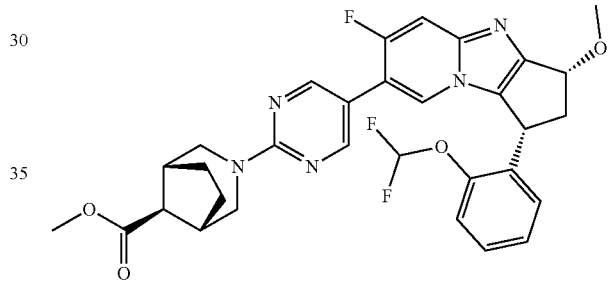

The title compound was prepared from Intermediate 166 (341 mg, 0.78 mmol), 1,4-Dioxane (3 mL), 2-{2-[(1R,5S,8R)-8-(methoxycarbonyl)-3-azabicyclo[3.2.1]octan-3-yl]pyrimidin-5-yl}boronic acid (341 mg, 1.17 mmol), 2M sodium carbonate in water (1.17 mL), bis [3-(diphenylphosphanyl)cyclopenta-2,4-dien-1-yl]iron; dichloromethane; dichloropalladium (128 mg, 0.16 mmol) by the Method A (70 mg, 17%). LCMS (ES+) RT 1.71 min 580.0 (M+H)+.

Example 204

Potassium (8-anti)-3-(5-{(1R,3R)-1-[2-(difluoromethoxy)phenyl]-6-fluoro-3-methoxy-2,3-dihydro-1H-cyclopenta[4,5]imidazo[1,2-a]pyridin-7-yl}pyrimidin-2-yl)-3-azabicyclo[3.2.1]octane-8-carboxylic acid

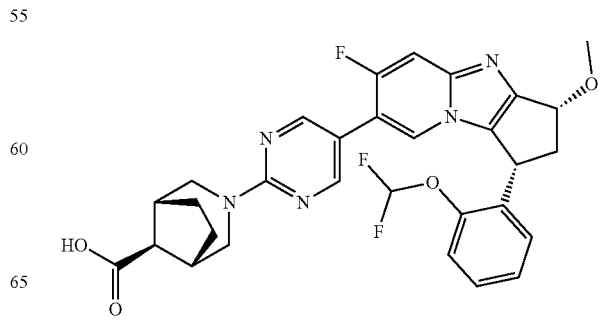

The title compound was prepared from Example 203 (85 mg, 0.14 mmol), THF (1 mL) 1M potassium hydroxide in water (0.18 mL) by the Method I (66 mg, 74%). LCMS (ES⁺) RT 1.25 min, 580.0 (M+H)⁺.

Examples 205 and 206

(1R,3R)-1-[2-(difluoromethoxy)-4,5-difluorophenyl]-6-fluoro-7-[2-(2-hydroxypropan-2-yl)pyrimidin-5-yl]-2,3-dihydro-1H-cyclopenta[4,5]imidazo[1,2-a]pyridin-3-ol and (1S,3 S)-1-[2-(difluoromethoxy)-4,5-difluorophenyl]-6-fluoro-7-[2-(2-hydroxypropan-2-yl)pyrimidin-5-yl]-2,3-dihydro-1H-cyclopenta[4,5]imidazo[1,2-a]pyridin-3-ol

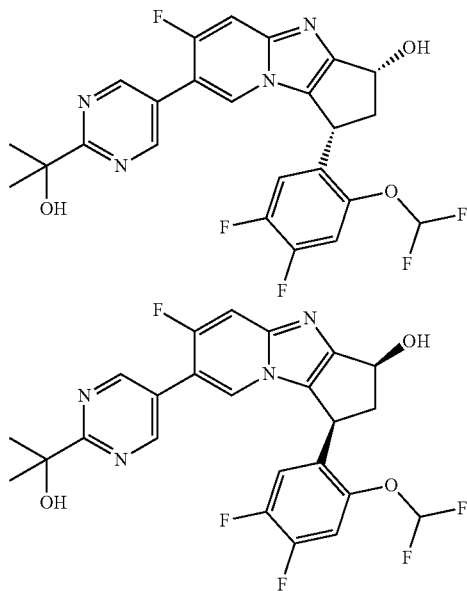

Example 199 (123 mg, 0.24 mmol) was further purified by Chiral SFC (25% Methanol: 75% CO₂ with Chiralpak IC 25 cm) to afford Example 205 as an off white solid (42 mg, 27%). ¹H NMR (500 MHz, DMSO-d₆) δ 8.92 (d, J 1.4 Hz, 2H), 8.29 (d, J 7.4 Hz, 1H), 7.71 (d, J 11.6 Hz, 1H), 7.49 (dd, J 11.2, 6.8 Hz, 1H), 7.26 (t, J 73.5 Hz, 1H), 6.97 (dd, J 11.3, 9.0 Hz, 1H), 5.60 (d, J 5.4 Hz, 1H), 5.15 (s, 1H), 5.12-5.04 (m, 1H), 4.71 (dd, J 8.5, 3.1 Hz, 1H), 3.47-3.38 (m, 1H), 2.05 (dt, J 13.7, 3.1 Hz, 1H), 1.51 (s, 6H). Method SFC (25% Methanol: 75% CO₂ with Chiralpak IC 25 cm) LCMS (ES⁺) RT 4.33 min, 507.0 (M+H)⁺. Chiral SFC also yielded Example 206 as a light brown solid (34 mg, 22%). ¹H NMR (500 MHz, DMSO-d₆) δ 8.92 (d, J 1.3 Hz, 2H), 8.29 (d, J 7.4 Hz, 1H), 7.71 (d, J 11.6 Hz, 1H), 7.53-7.45 (m, 1H), 7.26 (t, J 73.5 Hz, 1H), 6.97 (dd, J 11.3, 9.0 Hz, 1H), 5.60 (s, 1H), 5.15 (s, 1H), 5.08 (dd, J 6.8, 2.2 Hz, 1H), 4.71 (dd, J 8.5, 2.9 Hz, 1H), 3.46-3.40 (m, 1H), 2.05 (dt, J 13.7, 3.0 Hz, 1H), 1.51 (s, 6H). Method SFC (25% Methanol: 75% CO₂ with Chiralpak IC 25 cm). LCMS (ES⁺) RT 8.28 min, 507.0 (M+H)⁺.

Examples 207 and 208

(1R,3R)-1-[2-(difluoromethoxy)-6-fluorophenyl]-6-fluoro-7-[2-(2-hydroxypropan-2-yl)pyrimidin-5-yl]-2,3-dihydro-1H-cyclopenta[4,5]imidazo [1,2-a]pyridin-3-01 and (1S,3 S)-1-[2-(difluoromethoxy)-6-fluorophenyl]-6-fluoro-7-[2-(2-hydroxypropan-2-yl)pyrimidin-5-yl]-2,3-dihydro-1H-cyclopenta[4,5]imidazo[1,2-a]pyridin-3-ol

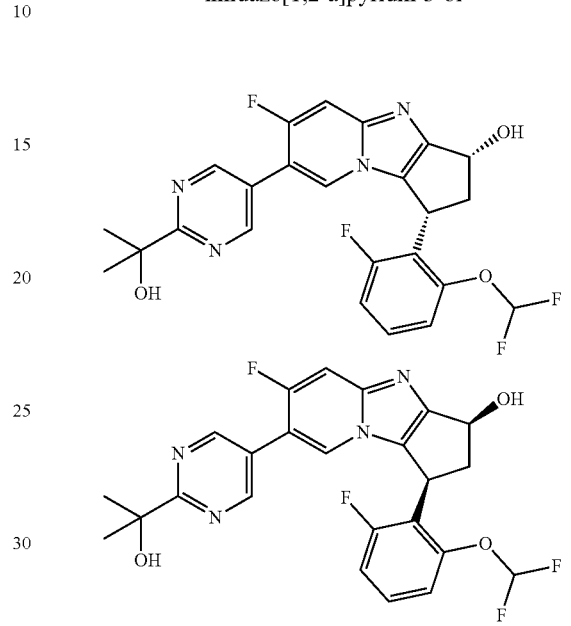

Example 161 (119 mg, 0.24 mmol) was further purified by Chiral SFC (85% CO₂: 15% Methanol+0.1% DEA on Chiralpak IC column) yielding Example 207 as an off white solid (35 mg, 21%) and Example 208 as an off white solid (30 mg, 18%). Method SFC (85% CO₂: 15% Methanol+ 0.1% DEA on Chiralpak IC column) LCMS (ES⁺) RT 21.00 min, 489.0 (M+H)' and LCMS (ES⁺) RT 27.09 min, 489.0 (M+H)' respectively.

Examples 209 and 210

Isomer A (1R,3R)-1-[2-(difluoromethoxy)phenyl]-6-fluoro-7-[2-(trans-4-hydroxy-4-methylcyclohexyl)pyrimidin-5-yl]-2,3-dihydro-1H-cyclopenta[4,5]imidazo[1,2-a]pyridin-3-ol, Isomer B (1R,3R)-1-[2-(difluoromethoxy)phenyl]-6-fluoro-7-[2-(cis-4-hydroxy-4-methylcyclohexyl)pyrimidin-5-yl]-2,3-dihydro-1H-cyclopenta[4,5]imidazo[1,2-a]pyridin-3-ol

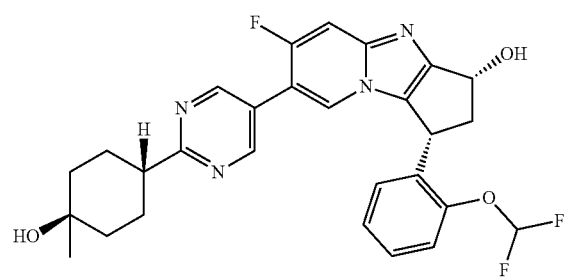

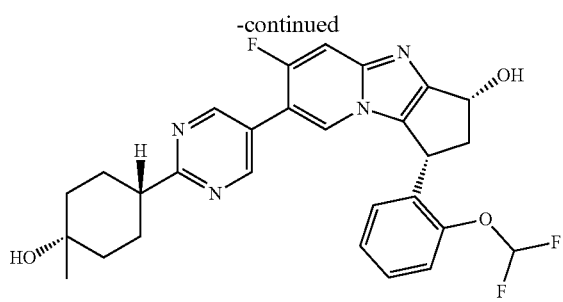

To a stirred solution of Intermediate 157 (43 mg, 0.09 mmol) in anhydrous tetrahydrofuran (2 mL) was added 1.4 M methylmagnesium bromide in toluene/THF (0.21 mL, 0.30 mmol) at r.t. The mixture was stirred at r.t. for 18 h. Further 1.4 M methylmagnesium bromide in toluene/THF (0.21 mL, 0.30 mmol) was added to the mixture at r.t. and stirred for 2 h. The mixture was quenched with saturated ammonium chloride (0.5 mL) and partitioned between EtOAc (10 mL) and water (5 mL). The aqueous layer was re-extracted into EtOAc (10 mL). The combined organic layer was washed with water (10 mL), brine (10 mL), dried (Na$_2$SO$_4$) and concentrated in vacuo.

The residue was purified by preparative HPLC to afford the Example 209 as an off-white solid (9 mg, 20%), and Example 210 s an off-white solid (41 mg, 30%). LCMS (ES$^+$) RT 1.28 min, 525.0 (M+H) ' and LCMS (ES$^+$) RT 1.37 min, 525.0 (M+H)' respectively.

Example 211

Isomer B: trans-1-(S-{(1R,3R)-1-[2-(difluoromethoxy)phenyl]-6-fluoro-3-hydroxy-2,3-dihydro-1H-cyclopenta[4,5]imidazo[1,2-a]pyridin-7-yl}pyrimidin-2-yl)-4-methylcyclohexane-1,4-diol

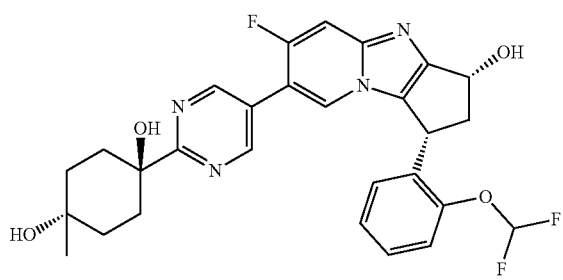 [SMILES: C[C@]1(O)CC[C@@](O)(c2ncc(-c3cn4c5c(nc4cc3F)[C@H](O)C[C@@H]5c3ccccc3OC(F)F)cn2)CC1]

The title compound was prepared from Example 16 120 mg, 0.25 mmol), Intermediate 175 (132 mg, 0.30 mmol), 2 M solution of sodium carbonate in water (0.37 mL, 0.74 mmol), 1,4-dioxane (2 mL), dichloro[1,1'-bis(diphenylphosphino)ferrocene]-palladium dichloromethane adduct (20 mg, 0.025 mmol) by the Method A. LCMS (ES$^+$) RT 1.29 min, 541.0 (M+H)$^+$.

Example 212

Isomer A: cis-1-(S-{(1R,3R)-1-[2-(difluoromethoxy)phenyl]-6-fluoro-3-hydroxy-2,3-dihydro-1H-cyclopenta[4,5]imidazo[1,2-a]pyridin-7-yl}pyrimidin-2-yl)-4-methylcyclohexane-1,4-diol

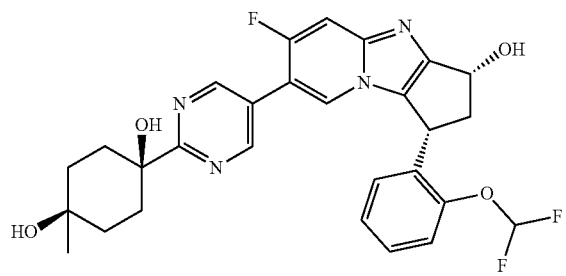 [SMILES: C[C@]1(O)CC[C@](O)(c2ncc(-c3cn4c5c(nc4cc3F)[C@H](O)C[C@@H]5c3ccccc3OC(F)F)cn2)CC1]

The title compound was prepared from Example 16 120 mg, 0.25 mmol), Intermediate 174 (132 mg, 0.30 mmol), 2 M solution of sodium carbonate in water (0.37 mL, 0.74 mmol), 1,4-dioxane (2 mL), dichloro[1,1'-bis(diphenylphosphino)ferrocene]-palladium dichloromethane adduct (20 mg, 0.025 mmol) by the Method A (41 mg, 30%). LCMS (ES$^+$) RT 1.24 min, 541.0 (M+H)$^+$.

Examples 213 and 214

(1R)-7-bromo-1-[5-chloro-2-(difluoromethoxy)phenyl]-6-fluoro-1,2-dihydro-3H-cyclopenta[4,5]imidazo[1,2-a]pyridin-3-one and (1S)-7-bromo-1-[5-chloro-2-(difluoromethoxy)phenyl]-6-fluoro-1,2-dihydro-3H-cyclopenta[4,5]imidazo[1,2-a]pyridin-3-one

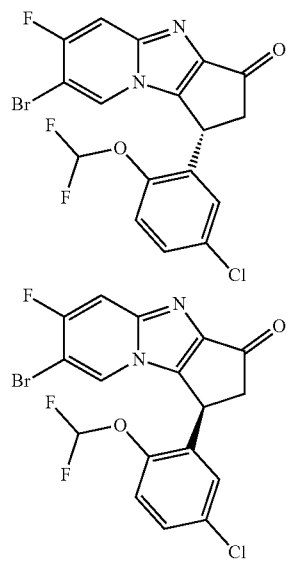

The title compounds were isolated by purification of Intermediate 135 under SFC conditions on Chiralpak AD (50*216 mm*mm, flow 360 mL/min, 40° C., CO2/2-PrOH 75/25, injection of 15 mL solution at a concentration of 11.22 g/L).

The first eluting enantiomer (RT 2.43 min) was collected and the fractions were evaporated to yield (enantiomer 1) (16.26 g, 48.3%, Example 213). $^1$H NMR (400 MHz, DMSO-d$_6$) δ 8.63 (d, J 6.8 Hz, 1 H), 7.88 (dd, J 9.8, 0.3 Hz, 1 H), 7.46 (dd, J 8.8, 2.6 Hz, 1 H), 7.28 (d, J 8.8 Hz, 1 H), 7.20 (t, J 73.7 Hz, 1 H), 7.08-7.12 (m, 1 H), 5.08 (dd, J 7.1, 2.1 Hz, 1 H), 3.57 (dd, J 18.2, 7.2 Hz, 1 H), 2.78 (dd, J 18.2, 2.2 Hz, 1 H).

The second eluting enantiomer (RT 4.23 min) was collected and the fractions were evaporated to yield (enantiomer 2) (15.61 g, 46.4%, Example 214). $^1$H NMR (400 MHz, DMSO-$d_6$) δ 8.63 (d, 1 H, J 6.8 Hz), 7.88 (d, 1 H, J 9.9 Hz), 7.46 (dd, 1 H, J 8.8, 2.6 Hz), 7.28 (d, 1 H, J 8.8 Hz), 7.20 (t, 1 H, J 73.5 Hz), 7.08-7.13 (m, 1 H), 5.08 (dd, 1 H, J 7.0, 2.1 Hz), 3.57 (dd, 1 H, J 18.2, 7.2 Hz), 2.78 (dd, 1 H, J 18.1, 2.2 Hz).

Example 215

Cis-1-(5-{(1R,3R)-1-[5-chloro-2-(difluoromethoxy)phenyl]-3-hydroxy-2,3-dihydro-1H-cyclopenta[4,5]imidazo[1,2-a]pyridin-7-yl}pyrimidin-2-yl)-3-methylcyclobutane-1,3-diol

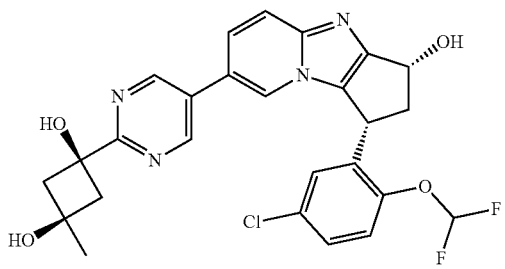 [SMILES: C[C@]1(O)C[C@](O)(c2ncc(-c3ccc4nc5c(n4c3)[C@@H](c3cc(Cl)ccc3OC(F)F)C[C@H]5O)cn2)C1]

The title compound was prepared from Example 190 and Intermediate 165 by the Method K. LCMS (ES$^+$) RT 1.19 min, 529.1 (M+H)$^+$ Example 216

Cis-1-(5-{(1R,3R)-1-[5-chloro-2-(difluoromethoxy)phenyl]-6-fluoro-3-hydroxy-2,3-dihydro-1H-cyclopenta[4,5]imidazo[1,2-a]pyridin-7-yl}pyrimidin-2-yl)-3-methylcyclobutane-1,3-diol

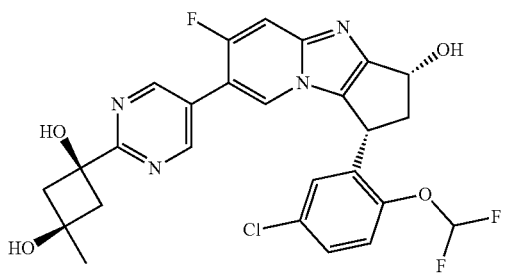 [SMILES: C[C@]1(O)C[C@](O)(c2ncc(-c3cn4c5c(nc4cc3F)[C@H](O)C[C@@H]5c3cc(Cl)ccc3OC(F)F)cn2)C1]

The title compound was prepared from Intermediate 167 and Intermediate 165 by the Method K. LCMS (ES$^+$) RT 1.23 min, 547.2 (M+H)$^+$ Example 217 Method R (1R,3R)-1-[5-chloro-2-(difluoromethoxy)phenyl]-7-[4-(methylsulfonyl)phenyl]-2,3-dihydro-1H-cyclopenta[4,5]imidazo[1,2-a]pyridin-3-ol

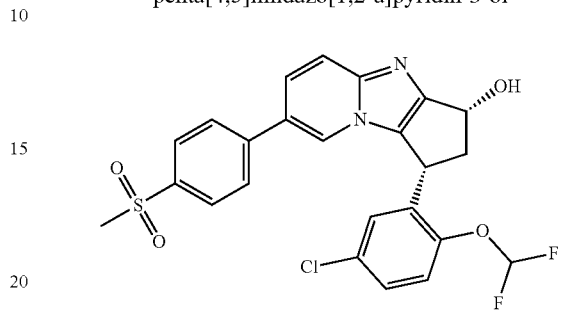

In a microwave vessel (20 ml) Example 190 (150 mg, 0.349 mmol), sodium carbonate (151 mg, 1.40 mmol), 4-(methylsulphonyl)phenylboronic acid (143 mg, 0.698 mmol), and 1,1'-bis(diphenylphosphino)ferrocene-palladium(II)dichloride dichloromethane complex (57 mg, 70 μmol) were mixed with DME (12 ml) and water (3 ml). After heating for 10 min at 100° C. and cooling to r.t., water was added and the aqueous phase was extracted with DCM (3×). The combined organic phases were dried over sodium sulphate, filtered and concentrated in vacuo. The residue was purified by chromatography (SiO$_2$, 0-90% EtOH in DCM) and further purified by preparative RP-HPLC (M2b). yielding the title compound (93 mg, 53%). $^1$H NMR (400 MHz, DMSO-$d_6$) δ ppm 8.30 (dd, J 1.6 Hz, 0.9 Hz, 1 H), 7.99 (m, 2 H), 7.88 (m, 2 H), 7.74 (m, 1 H), 7.66 (dd, J 9.5 Hz, 1.8 Hz, 1 H), 7.40 (t, J 74 Hz, 1 H), 7.38 (m, 1 H), 7.30 (m, 1 H), 6.97 (d, J 2.6 Hz, 1 H), 5.57 (d, J 5.3 Hz, 1 H), 5.12 (m, 1 H), 4.80 (dd, J 8.6 Hz, 3.1 Hz, 1 H), 3.45 (m, 1 H), 3.24 (3 H), 2.11 (dt, J 13.9 Hz, 2.9 Hz, 1 H). LCMS [M 1b] (ES$^+$) RT 1.40 min, 505.1 (M+H)$^+$.

Examples 218 to 227

The following Examples were synthesised following Method R from the given starting material and using the appropriate boronate ester or boronic acid.

| Example No. | Precursor | Compound Name | LCMS |
|---|---|---|---|
| 218 | Ex 190 | (1R,3R)-1-[5-chloro-2-(difluoromethoxy)phenyl]-7-[6-(S-methylsulfonimidoyl)pyridin-3-yl]-2,3-dihydro-1H-cyclopenta[4,5]imidazo[1,2-a]pyridin-3-ol 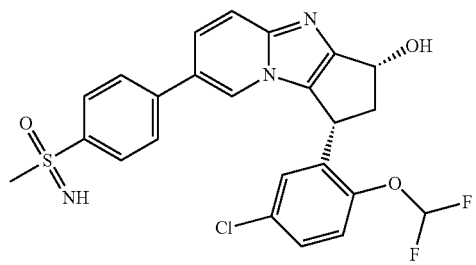 | LCMS [M 1b] (ES$^+$) RT 1.25 min 548.2 [M − H + formic acid]$^-$. |

-continued

| Example No. | Precursor | Compound Name | LCMS |
|---|---|---|---|
| 219 | Ex 190 | (1R,3R)-1-[5-chloro-2-(difluoromethoxy)phenyl]-7-(6-methoxypyridin-3-yl)-2,3-dihydro-1H-cyclopenta[4,5]imidazo[1,2-a]pyridin-3-ol | LCMS [M 1b] (ES+) RT 1.49 min 458.1 (M + H)+. |
| 220 | Ex 190 | (1R,3R)-1-[5-chloro-2-(difluoromethoxy)phenyl]-7-(2-chloro-6-methoxypyridin-3-yl)-2,3-dihydro-1H-cyclopenta[4,5]imidazo[1,2-a]pyridin-3-ol | LCMS [M 1b] (ES+) RT 1.58 min 492.1 (M + H)+. |
| 221 | Ex 190 | (1R,3R)-7-(2-aminopyrimidin-5-yl)-1-[5-chloro-2-(difluoromethoxy)phenyl]-2,3-dihydro-1H-cyclopenta[4,5]imidazo[1,2-a]pyridin-3-ol | LCMS [M 1b] (ES+) RT 1.19 min 444.1 (M + H)+. |
| 222 | Ex 190 | (1R,3R)-1-[5-chloro-2-(difluoromethoxy)phenyl]-7-[4-(methylsulfinyl)phenyl]-2,3-dihydro-1H-cyclopenta[4,5]imidazo[1,2-a]pyridin-3-ol | LCMS [M 1b] (ES+) RT 1.30 min 489.1 (M + H)+. |

-continued

| Example No. | Precursor | Compound Name | LCMS |
|---|---|---|---|
| 223 | Ex. 190 | (1R,3R)-1-(5-chloro-2-(difluoromethoxy)phenyl)-6-fluoro-7-(4-(methylsulfonyl)phenyl)-2,3-dihydro-1H-cyclopenta[4,5]imidazo[1,2-a]pyridin-3-ol | LCMS [M 1b] (ES$^+$) RT 1.48 min 523.1 (M + H)$^+$. |
| 224 | Int 176 | tert-butyl 2-(((1R,3R)-1-(5-chloro-2-(difluoromethoxy)phenyl)-7-(4-(methylsulfonyl)phenyl)-2,3-dihydro-1H-cyclopenta[4,5]imidazo[1,2-a]pyridin-3-yl)oxy)acetate | LCMS [M 1b] (ES$^+$) RT 1.79 min 619.2 (M + H)$^+$. |
| 225 | Ex 190 | (1R,3R)-1-(5-chloro-2-(difluoromethoxy)phenyl)-7-(4-(cyclopropylsulfonyl)phenyl)-2,3-dihydro-1H-cyclopenta[4,5]imidazo[1,2-a]pyridin-3-ol | LCMS [M 1b] (ES$^+$) RT 1.49 min 531.1 (M + H)$^+$. |
| 226 | Ex 190 | 4-((1R,3R)-1-(5-chloro-2-(difluoromethoxy)phenyl)-3-hydroxy-2,3-dihydro-1H-cyclopenta[4,5]imidazo[1,2-a]pyridin-7-yl)benzenesulfonamide | LCMS [M 1b] (ES+) RT 1.31 min 506.1 (M + H)+. |

| Example No. | Precursor | Compound Name | LCMS |
|---|---|---|---|
| 227 | Ex 190 | (1R,3R)-1-(5-chloro-2-(difluoromethoxy)phenyl)-7-(5-fluoro-6-methoxypyridin-3-yl)-2,3-dihydro-1H-cyclopenta[4,5]imidazo[1,2-a]pyridin-3-ol 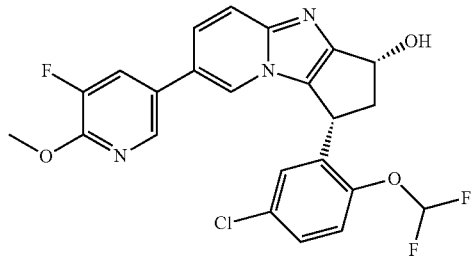 | LCMS [M 1b] (ES+) RT 1.56 min 476.1 (M + H)+. |

Example 228 Method S (1R,3R)-1-[5-chloro-2-(difluoromethoxy)phenyl]-7-(6-methoxy-4-methylpyridin-3-yl)-2,3-dihydro-1H-cyclopenta[4,5]imidazo[1,2-a]pyridin-3-ol

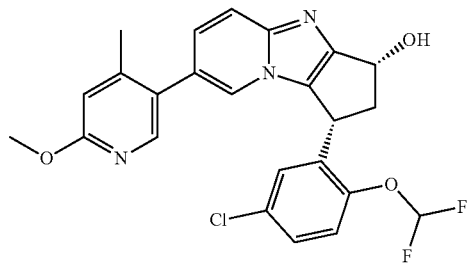 [SMILES: COc1cc(C)c(-c2ccc3nc4c(n3c2)[C@@H](c2cc(Cl)ccc2OC(F)F)C[C@H]4O)cn1]

In a microwave vessel (20 ml) Example 190 (50 mg, 116 µmol) was dissolved in 1,4-dioxane and the solution purged with argon. Then sodium carbonate (25 mg, 233 µmol), 2-methoxy-4-methyl-5-(4,4,5,5-tetramethyl-1,3,2-dioxaborolan-2-yl)pyridine (36 mg, 140 µmol) and water (1 ml) were added. This mixture was again purged with argon before tris(dibenzylideneacetone)dipalladium(0) complex (11 mg, 12 µmol) and tri-tert-butylphosphonium tetrafluoroborate (1 mg, 3.5 µmol) were added. After heating for 15 minutes at 100° C. in a microwave oven and then cooling to r.t. the same amount of sodium carbonate, boronic acid, catalyst and borate was added to complete the reaction by heating at 100° C. for 15 min in a microwave oven. After cooling to r.t. brine and EtOAc were added and after phase separation the aqueous phase was extracted twice with EtOAc. The combined organic phases were dried over sodium sulphate, filtered and concentrated in vacuo. The residue was purified by preparative RP-HPLC (M2d). yielding the title compound (20 mg, 36%). LCMS [M 1b] (ES$^+$) RT 1.51 min, 472.2 (M+H)$^+$.

Examples 229 to 233

The following Example were synthesised by the Method S from the given starting material and using the appropriate boronate ester or boronic acid.

| Example No. | Precursor | Compound Name | LCMS |
|---|---|---|---|
| 229 | Ex 190 | (1R,3R)-1-[5-chloro-2-(difluoromethoxy)phenyl]-7-(6-methoxy-5-methylpyridin-3-yl)-2,3-dihydro-1H-cyclopenta[4,5]imidazo[1,2-a]pyridin-3-ol 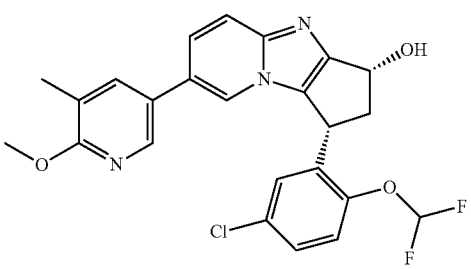 [SMILES: COc1ncc(-c2ccc3nc4c(n3c2)[C@@H](c2cc(Cl)ccc2OC(F)F)C[C@H]4O)cc1C] | LCMS [M 1b] (ES$^+$) RT 1.58 min 472.11 (M + H)$^+$. |

-continued

| Example No. | Precursor | Compound Name | LCMS |
|---|---|---|---|
| 230 | Ex 190 | 5-((1R,3R)-1-(5-chloro-2-(difluoromethoxy)phenyl)-3-hydroxy-2,3-dihydro-1H-cyclopenta[4,5]imidazo[1,2-a]pyridin-7-yl)-1-methylpyridin-2(1H)-one | LCMS [M 1b] (ES+) RT 1.22 min; 458.2 (M + H)+. |
| 231 | Ex 190 | 5-{(1R,3R)-1-[5-chloro-2-(difluoromethoxy)phenyl]-3-hydroxy-2,3-dihydro-1H-cyclopenta[4,5]imidazo[1,2-a]pyridin-7-yl}-6-methylpyridin-2(1H)-one | LCMS [M 1b] (ES+) RT 1.22 min; 458.2 (M + H)+. |
| 232 | Ex 190 | 5-((1R,3R)-1-(5-chloro-2-(difluoromethoxy)phenyl)-3-hydroxy-2,3-dihydro-1H-cyclopenta[4,5]imidazo[1,2-a]pyridin-7-yl)-1,4-dimethylpyridin-2(1H)-one | LCMS [M 1b] (ES+) RT 1.24 min; 472.1 (M + H)+. |
| 233 | Ex 190 | 5-((1R,3R)-1-(5-chloro-2-(difluoromethoxy)phenyl)-3-hydroxy-2,3-dihydro-1H-cyclopenta[4,5]imidazo[1,2-a]pyridin-7-yl)-1,3-dimethylpyridin-2(1H)-one | LCMS [M 1b] (ES+) RT 1.30 min 472.1 (M + H)+. |

Example 234

(1R,3R)-1-[5-chloro-2-(difluoromethoxy)phenyl]-6-fluoro-7-[4-(S-methylsulfonimidoyl)phenyl]-2,3-dihydro-1H-cyclopenta[4,5]imidazo[1,2-a]pyridin-3-ol

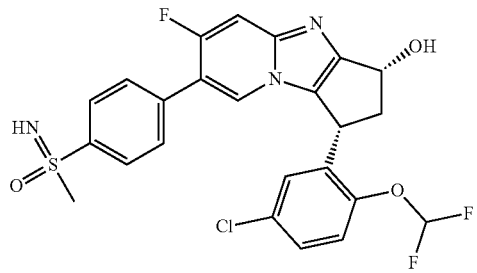

The title compound was prepared from Intermediate 167 (665 mg, 1.49 mmol) and Intermediate 75, following the Method R (274 mg, 35%). LCMS [M 1b] (ES$^+$) RT 1.32 min, 522.1 (M+H)$^+$.

Example 235

5-{(1R,3R)-1-[5-chloro-2-(difluoromethoxy)phenyl]-6-fluoro-3-hydroxy-2,3-dihydro-1H-cyclopenta[4,5]imidazo[1,2-a]pyridin-7-yl}pyridin-2(1H)-one hydrochloride salt

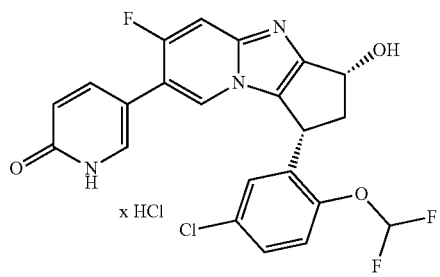 [SMILES: O=c1ccc(-c2cn3c4c(nc3cc2F)[C@H](O)C[C@@H]4c2cc(Cl)ccc2OC(F)F)c[nH]1]

The title compound was prepared from 5-(4,4,5,5-tetramethyl-1,3,2-dioxaborolan-2-yl)pyridin-2-ol (252 mg, 1.14 mmol) and Intermediate 167 (255 mg, 0.57 mmol) following Method R, but without the silica gel purification step and in the HPLC purification step HCl instead of TFA was used to obtain the hydrochloride salt of the title compound. LCMS [M 1b] (ES$^+$) RT 1.20 min, 462.0 (M+H)$^+$.

Example 236

5-((1R,3R)-1-(5-chloro-2-(difluoromethoxy)phenyl)-3-hydroxy-2,3-dihydro-1H-cyclopenta[4,5]imidazo[1,2-a]pyridin-7-yl)pyridin-2(1H)-one hydrochloride salt

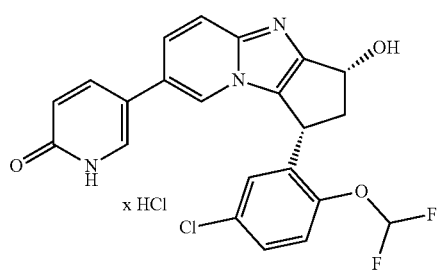 [SMILES: O=c1ccc(-c2ccc3nc4c(n3c2)[C@@H](c2cc(Cl)ccc2OC(F)F)C[C@H]4O)c[nH]1]

The title compound was prepared according to a method analogous to the one described for the synthesis of Example 235 from Example 190.

LCMS [M 1b] (ES$^+$) RT 1.16 min, 444.1 (M+H)$^+$.

Example 237

(1R,3R)-7-(6-(tert-butoxy)pyridin-3-yl)-1-(5-chloro-2-(difluoromethoxy)phenyl)-2,3-dihydro-1H-cyclopenta[4,5]imidazo[1,2-a]pyridin-3-ol

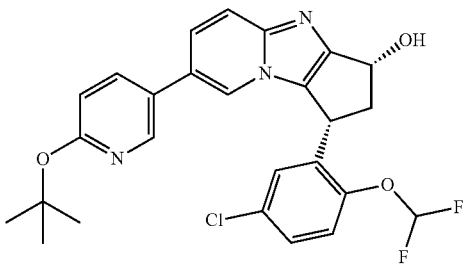 [SMILES: CC(C)(C)Oc1ccc(-c2ccc3nc4c(n3c2)[C@@H](c2cc(Cl)ccc2OC(F)F)C[C@H]4O)cn1]

The title compound was prepared from 2-(tert-butoxy)-5-(4,4,5,5-tetramethyl-1,3,2-dioxaborolan-2-yl)pyridine (194 mg, 0.698 mmol) and Example 190 (150 mg, 0.349 mmol) following Method R, but without the silica gel purification step and in the HPLC purification step no TFA was used to obtain the hydrochloride salt of the title compound. LCMS [M 1b] (ES$^+$) RT 1.72 min, 500.1 (M+H)$^+$.

Example 238

(1R,3R)-1-(5-chloro-2-(difluoromethoxy)phenyl)-6-fluoro-7-(6-(S-methylsulfonimidoyl)pyridin-3-yl)-2,3-dihydro-1H-cyclopenta[4,5]imidazo[1,2-a]pyridin-3-ol

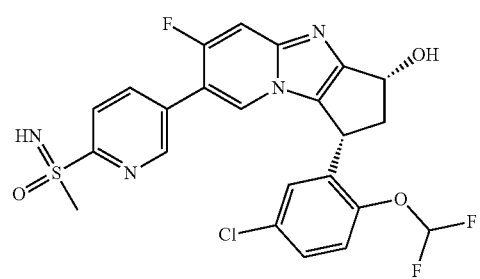 [SMILES: CS(=N)(=O)c1ccc(-c2cn3c4c(nc3cc2F)[C@H](O)C[C@@H]4c2cc(Cl)ccc2OC(F)F)cn1]

Under argon 5-bromo-2-(S-methyl-N-(2,2,2-trifluoroacetyl)sulfonylimidoyl)-pyridine (200 mg, 0.604 mmol), 4,4,4',4',5,5,5',5'-octamethyl-2,2'-bi(1,3,2-dioxaborolane) (184 mg, 0.725 mmol) and potassium acetate were mixed with dry dioxane. Then 1,1'-bis(diphenylphosphino)ferrocene-palladium(II)dichloride dichloromethane complex (13 mg, 18 µmol) was added and the mixture was stirred for 100 minutes at 100° C. To complete the reaction the same amount of catalyst and potassium carbonate as described above was added and stirring was continued at 100° C. for further 60 min.

After cooling Intermediate 167 (200 mg, 0.446 mmol), sodium carbonate (95 mg, 0.894 mmol), water (2.5 ml), Pd$_2$(dba)$_3$ (12 mg, 13 μM) and tri-tert-butylphosphinium tetrafluoroborate (13 mg, 45 μM) were added. After stirring for 30 minutes at 90° C. the heating was stopped brine and EtOAc were added. After phase separation the aqueous layer was extracted twice with EtOAc and the combined organic layers were washed with brine, dried over sodium sulphate, filtered and concentrated in vacuo. After purification by chromatography (SiO$_2$, 0-10% MeOH in DCM) followed by a second purification by RP-HPLC (M2c) yielded the title compound after lyophilisation (72 mg, 31%). LCMS [M 1b] (ES$^+$) RT 1.28 min, 523.1 (M+H)$^+$.

Example 239

(1R,3R)-1-(5-chloro-2-(difluoromethoxy)phenyl)-7-(6-(S-methylsulfonimidoyl)pyridin-3-yl)-2,3-dihydro-1H-cyclopenta[4,5]imidazo[1,2-a]pyridin-3-ol

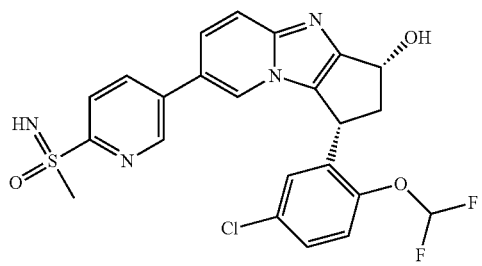 [SMILES: CS(=N)(=O)c1ccc(-c2ccc3nc4c(n3c2)[C@@H](c2cc(Cl)ccc2OC(F)F)C[C@H]4O)cn1]

The title compound was analogously prepared to Example 238 starting from Example 190 (205 mg, 477 μmol) (85 mg, 35%). LCMS [M 1b] (ES+) RT 1.21 min, 505.2 (M+H)$^+$.

Examples 240 and 241

(1R,3R)-1-(5-chloro-2-(difluoromethoxy)phenyl)-7-(4-((S)-S-methylsulfonimidoyl)phenyl)-2,3-dihydro-1H-cyclopenta[4,5]imidazo[1,2-a]pyridin-3-ol and (1R,3R)-1-(5-chloro-2-(difluoromethoxy)phenyl)-7-(4-((R)-S-methylsulfonimidoyl)phenyl)-2,3-dihydro-1H-cyclopenta[4,5]imidazo[1,2-a]pyridin-3-ol

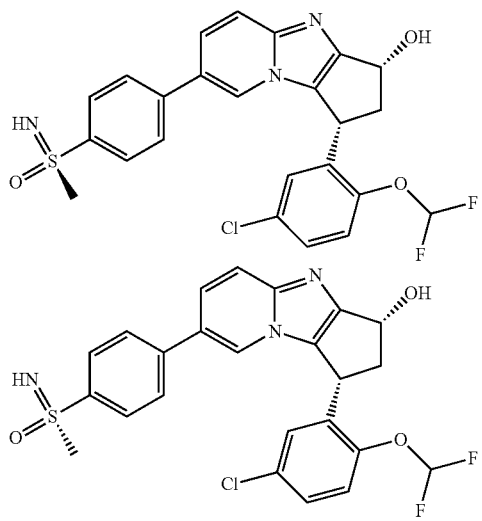

The title compounds were isolated by chiral separation of Example 218 (312 mg) under HPLC conditions on Chiralcell OJ-H (30*250 mm*mm, 5μ, flow 30 ml/min, ambient temperature, Heptane:EtOH:MeOH 5:1:1 preconditioned with diethylamine. The first eluting enantiomer (RT 14.9 min) was collected, the fractions were evaporated and the residue lyophilised from MeCN/water to yield 158 mg of Example 240.

LCMS [M 1b] (ES+) RT 1.26 min, 504.1 (M+H)$^+$. Chiral chromatography (Chiralcell OJ-H 4.6*250 mm*mm, flow 1 ml/min, 30° C., Heptane:EtOH:MeOH 5:1:1+0.1% diethylamine) RT 9.24 min The second eluting enantiomer (RT 18.2 min) was collected, the fractions were evaporated and lyophilised from MeCN/water to yield 145 mg of Example 241. LCMS [M 1b] (ES+) RT 1.25 min, 504.1 (M+H)$^+$. Chiral chromatography (Chiralcell OJ-H 4.6*250 mm*mm, flow 1 ml/min, 30° C., Hep:EtOH:MeOH 5:1:1+0.1% diethylamine) RT 11.03 min Examples 242 and 243

(1R,3R)-1-(5-chloro-2-(difluoromethoxy)phenyl)-6-fluoro-7-(4-((S)-S-methylsulfonimidoyl)phenyl)-2,3-dihydro-1H-cyclopenta[4,5]imidazo[1,2-a]pyridin-3-ol and (1R,3R)-1-(5-chloro-2-(difluoromethoxy)phenyl)-6-fluoro-7-(4-((R)-S-methylsulfonimidoyl)phenyl)-2,3-dihydro-1H-cyclopenta[1,2-a]pyridin-3-ol

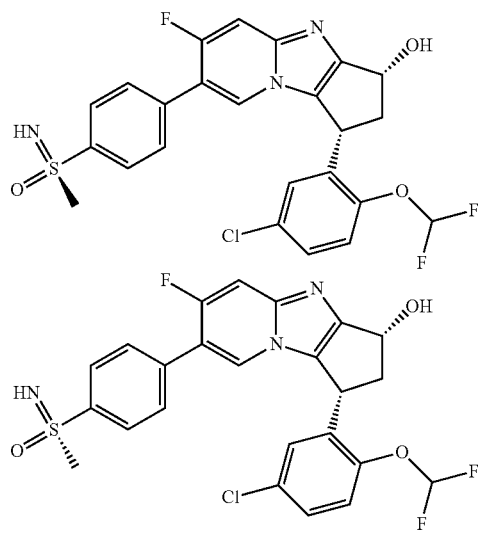

The title compounds were isolated by chiral separation of Example 234 (260 mg) under HPLC conditions on Chiralpak IC (30*250 mm*mm, 5μ, flow 30 ml/min, ambient temperature, Heptane:EtOH:MeOH 1:1:1+0.05% diethylamine. The first eluting enantiomer (RT 13.3 min) was collected, the fractions were evaporated and the residue lyophilised from MeCN/water to yield 90 mg of Example 242.

LCMS [M 1b] (ES⁺) RT 1.31 min, 522.1 (M+H)⁺. Chiral chromatography (Chiralpak IC (4.6*250 mm*mm, flow 1 ml/min, 30° C., EtOH:MeOH 1:1+0.1% diethylamine) RT 7.27 min.

The second eluting enantiomer (RT 17.3 min) was collected, the fractions were evaporated and lyophilised from MeCN/water to yield 98 mg of Example 243. LCMS [M 1b] (ES⁺) RT 1.31 min, 522.1 (M+H)⁺. Chiral chromatography (Chiralpak IC (4.6*250 mm*mm, flow 1 ml/min, 30° C., EtOH:MeOH 1:1+0.1% diethylamine) RT 8.09 min.

Example 244

Ethyl ({(1R,3R)-1-[5-chloro-2-(difluoromethoxy)phenyl]-7-[2-(2-hydroxypropan-2-yl)pyrimidin-5-yl]-2,3-dihydro-1H-cyclopenta[4,5]imidazo[1,2-a]pyridin-3-yl}oxy)acetate

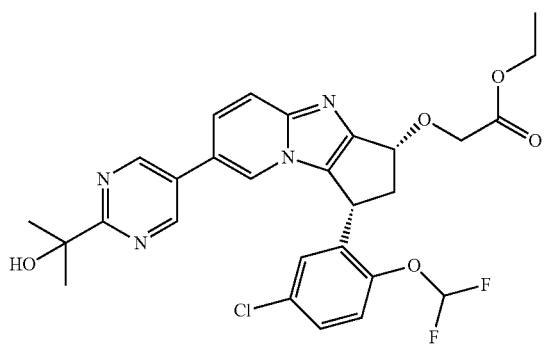 [SMILES: CCOC(=O)CO[C@@H]1C[C@H](c2cc(Cl)ccc2OC(F)F)c2c1nc1ccc(-c3cnc(C(C)(C)O)nc3)cn21]

Step 1: Synthesis of ethyl 2-(((1R,3R)-7-bromo-1-(5-chloro-2-(difluoromethoxy)phenyl)-2,3-dihydro-1H-cyclopenta[4,5]imidazo[1,2-a]pyridin-3-yl)oxy)acetate Example 190 (100 mg, 0,233 mmol) was dissolved in THF (7 ml). The solution was cooled to 0° C. and sodium hydride (21 mg, 0.51 mmol; 60% in oil) was added with stirring. After stirring for 15 minutes ethyl bromoacetate (159 mg, 0.93 mmol) dissolved in THF (0.2 ml) was added. The ice bath was removed and stirring was continued for 1 h at r.t. To complete the reaction the mixture was cooled again to 0° C. and further sodium hydride (21 mg, 0.51 mmol; 60% in oil) and ethyl bromoacetate (159 mg, 0.93 mmol) were added. This procedure was repeated for another two times until almost all starting material was gone. Water was added and the aqueous phase was extracted three times with EtOAc. The combined organic layers were dried over sodium sulphate, filtered and concentrated in vacuo. The residue was diluted with MeCN and purified by preparative HPLC yielding of the title compound (70 mg,58%). LCMS [M 1b] (ES⁺) RT 1.84 min, 515.1 (M+H)⁺.

Step 2: Synthesis of ethyl 2-(((1R,3R)-1-(5-chloro-2-(difluoromethoxy)phenyl)-7-(2-(2-hydroxypropan-2-yl)pyrimidin-5-yl)-2,3-dihydro-1H-cyclopenta[4,5]imidazo[1,2-a]pyridin-3-yl)oxy)acetate The title compound was prepared from the product obtained in step 1 (68 mg) following Method R. (41 mg, 54%). ¹H NMR (400 MHz, DMSO-d₆) δ ppm 9.04 (s, 2 H), 8.44 (m, 1 H), 7.80 (m, 1 H), 7.73 (m, 1 H), 7.40 (m, 1 H), 7.39 (t, 74 Hz, 1 H) 7.31 (m, 1 H), 6.95 (d, J 2.6 Hz, 1 H), 5.09 (s, 1 H), 5.05 (dd, J 7.1 Hz, 1.8 Hz, 1 H), 4.83 (dd, J 8.6 Hz, 2.4 Hz, 1 H), 4.47 (d, J 16.3 Hz, 1 H), 4.39 (d, J 16.3 Hz, 1 H), 4.10 (q, J 7.1 Hz, 2 H), 3.49 (m, 1 H), 2.30 (m, 1 H), 1.51 (s, 6 H), 1.16 (t, J 7.1 Hz, 3 H); LCMS [M 1b] (ES⁺) RT 1.68 min, 573.2 (M+H)⁺.

Examples 245 and 246

(1R,3R)-1-[2-(difluoromethoxy)phenyl]-3-methyl-7-[2-(morpholin-4-yl)pyrimidin-5-yl]-2,3-dihydro-1H-cyclopenta[4,5]imidazo[1,2-a]pyridin-3-ol and (1R,3S)-1-[2-(difluoromethoxy)phenyl]-3-methyl-7-[2-(morpholin-4-yl)pyrimidin-5-yl]-2,3-dihydro-1H-cyclopenta[4,5]imidazo[1,2-a]pyridin-3-ol

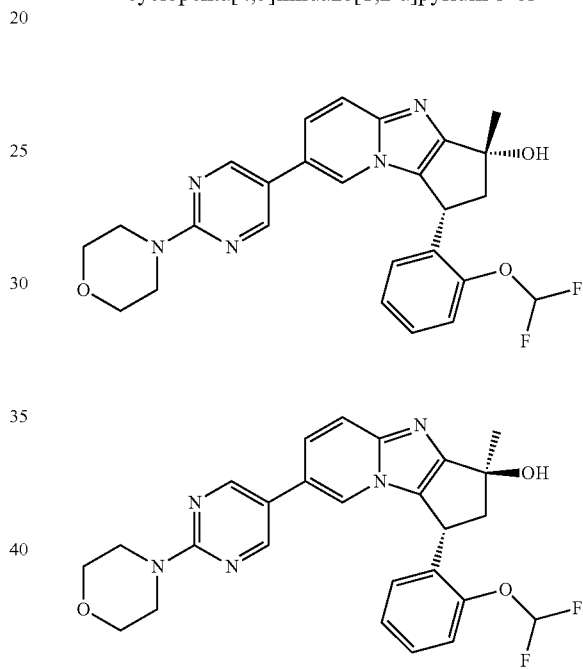

The title compounds were prepared from the preparative HPLC of Example 154. Example 245: ¹H NMR (400 MHz, DMSO-d₆) δ 8.63 (d, J 6.8 Hz, 1 H), 7.88 (d, J 9.9 Hz, 1 H), 7.46 (dd, J 8.8, 2.6 Hz, 1 H), 7.28 (d, J 8.8 Hz, 1 H), 7.20 (t, J 73.5 Hz, 1 H), 7.08-7.13 (m, 1 H), 5.08 (dd, J 7.0, 2.1 Hz, 1 H), 3.57 (dd, J 18.2, 7.2 Hz, 1 H), 2.78 (dd, J 18.1, 2.2 Hz, 1 H). LCMS (ES⁺) RT 1.32 min 494.0 (M+H)⁺. Example 246: ¹H NMR (400 MHz, DMSO-d₆) δ 8.63 (d, J 6.8 Hz, 1 H), 7.88 (d, J 9.9 Hz, 1 H), 7.46 (dd, J 8.8, 2.6 Hz, 1 H), 7.28 (d, J 8.8 Hz, 1 H), 7.20 (t, J 73.5 Hz, 1 H), 7.08-7.13 (m, 1 H), 5.08 (dd, J 7.0, 2.1 Hz, 1 H), 3.57 (dd, J 18.2, 7.2 Hz, 1 H), 2.78 (dd, J 18.1, 2.2 Hz, 1 H). LCMS (ES⁺) RT 1.35 min 494.0 (M+H)⁺.

Examples 247-254

The following Examples were prepared by the Method A from the given starting material using the appropriate boronate ester or boronic acid

| Example No. | Precursor | Compound Name | LCMS |
|---|---|---|---|
| 247 | Ex 15 | (1R)-1-[2-(difluoromethoxy)phenyl]-7-[2-(2-hydroxypropan-2-yl)pyrimidin-5-yl]-3-methyl-2,3-dihydro-1H-cyclopenta[4,5]imidazo[1,2-a]pyridin-3-ol | LCMS (ES+) RT 1.30 min 467.0 (M + H)+. |
| 248 | Ex 15 | 4-(5-{(1R)-1-[2-(difluoromethoxy)phenyl]-3-hydroxy-3-methyl-2,3-dihydro-1H-cyclopenta[4,5]imidazo[1,2-a]pyridin-7-yl}pyrimidin-2-yl)piperazin-2-one | LCMS (ES+) RT 1.22 min 507.0 (M + H)+. |
| 249 | Ex 15 | (1R)-1-[2-(difluoromethoxy)phenyl]-3-methyl-7-{2-[(1R,5S)-3-oxa-8-azabicyclo[3.2.1]oct-8-yl]pyrimidin-5-yl}-2,3-dihydro-1H-cyclopenta[4,5]imidazo[1,2-a]pyridin-3-ol | RT 1.42 min 520.0 (M + H)+. |
| 250 | Ex 16 | (1R,3R)-1-[2-(difluoromethoxy)phenyl]-6-fluoro-7-[6-(2-hydroxypropan-2-yl)pyridin-3-yl]-2,3-dihydro-1H-cyclopenta[4,5]imidazo[1,2-a]pyridin-3-ol | RT 1.33 min 470.0 (M + H)+. |

-continued

| Example No. | Precursor | Compound Name | LCMS |
|---|---|---|---|
| 251 | Int 167 | (1R,3R)-1-[5-chloro-2-(difluoromethoxy)phenyl]-6-fluoro-7-[2-(2-hydroxypropan-2-yl)pyrimidin-5-yl]-2,3-dihydro-1H-cyclopenta[4,5]imidazo[1,2-a]pyridin-3-ol | RT 1.38 min 506.0 (M + H)+. |

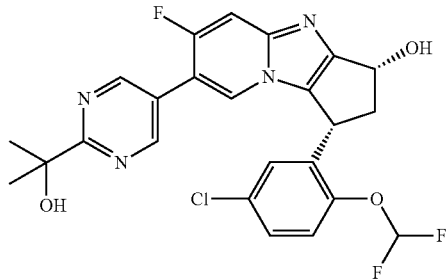 [SMILES: CC(C)(O)c1ncc(-c2cn3c4c(nc3cc2F)[C@H](O)C[C@@H]4c2cc(Cl)ccc2OC(F)F)cn1]

| 252 | Int 168 | (1S,3S)-1-[5-chloro-2-(difluoromethoxy)phenyl]-6-fluoro-7-[2-(2-hydroxypropan-2-yl)pyrimidin-5-yl]-2,3-dihydro-1H-cyclopenta[4,5]imidazo[1,2-a]pyridin-3-ol | RT 1.38 min 506.0 (M + H)+. |

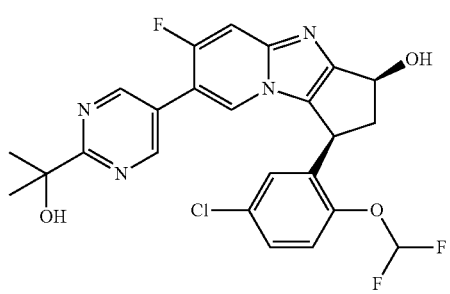 [SMILES: CC(C)(O)c1ncc(-c2cn3c4c(nc3cc2F)[C@@H](O)C[C@H]4c2cc(Cl)ccc2OC(F)F)cn1]

| 253 | Ex 190 | (1R,3R)-1-[5-chloro-2-(difluoromethoxy)phenyl]-7-[2-(2-hydroxypropan-2-yl)pyrimidin-5-yl]-2,3-dihydro-1H-cyclopenta[4,5]imidazo[1,2-a]pyridin-3-ol | RT 1.32 min 487.0 (M + H)+. |

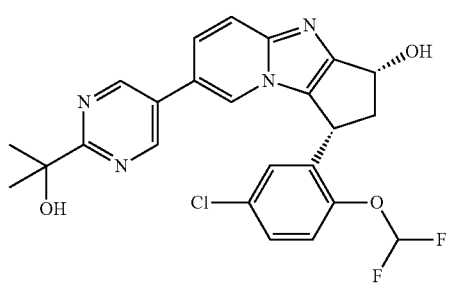 [SMILES: CC(C)(O)c1ncc(-c2ccc3nc4c(n3c2)[C@@H](c2cc(Cl)ccc2OC(F)F)C[C@H]4O)cn1]

| Example No. | Precursor | Compound Name | LCMS |
|---|---|---|---|
| 254 | Ex 191 | (1S,3S)-1-[5-chloro-2-(difluoromethoxy)phenyl]-7-[2-(2-hydroxypropan-2-yl)pyrimidin-5-yl]-2,3-dihydro-1H-cyclopenta[4,5]imidazo[1,2-a]pyridin-3-ol | RT 1.32 min 487.0 (M + H)+. |

Examples 255 and 256

(1R,3R)-1-(3-chlorophenyl)-6-fluoro-7-[2-(2-hydroxypropan-2-yl)pyrimidin-5-yl]-2,3-dihydro-1H-cyclopenta[4,5]imidazo[1,2-a]pyridin-3-ol and (1S,3S)-1-(3-chlorophenyl)-6-fluoro-7-[2-(2-hydroxypropan-2-yl)pyrimidin-5-yl]-2,3-dihydro-1H-cyclopenta[4,5]imidazo[1,2-a]pyridin-3-ol

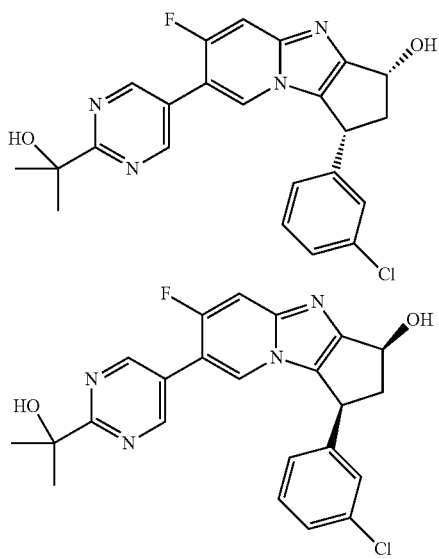

The title compounds were obtained from Example 160 by chiral SFC (92% CO$_2$: 8% Methanol+1% DEA on ChiralCel OJ-H column) yielding Example 255 as an off white solid. $^1$H NMR (500 MHz, DMSO-d$_6$) δ 8.90 (d, J 1.3 Hz, 2H), 8.30 (d, J 7.5 Hz, 1H), 7.66 (d, J 11.6 Hz, 1H), 7.44 (s, 1H), 7.34-7.29 (m, 2H), 7.26 (dt, J 7.1, 2.1 Hz, 1H), 5.64 (d, J 4.9 Hz, 1H), 5.15-5.06 (m, 2H), 4.49 (dd, J 8.5, 3.1 Hz, 1H), 3.49-3.41 (m, 1H), 2.14 (dt, J 13.8, 2.9 Hz, 1H), 1.52 (s, 6H). Method (92% CO$_2$: 8% Methanol+1% DEA on ChiralCel OJ-H column) LCMS (ES+) RT 5.75 min, 439.0 (M+H)+. Example 256 was obtained as an off white solid via the same SFC method. $^1$H NMR (500 MHz, DMSO-d$_6$) δ 8.90 (d, J 1.3 Hz, 2H), 8.30 (d, J 7.5 Hz, 1H), 7.66 (d, J 11.6 Hz, 1H), 7.44 (s, 1H), 7.36-7.29 (m, 2H), 7.26 (dt, J 7.1, 2.0 Hz, 1H), 5.64 (d, J 5.1 Hz, 1H), 5.15-5.08 (m, 2H), 4.49 (dd, J 8.5, 3.1 Hz, 1H), 3.50-3.39 (m, 1H), 2.14 (dt, J 13.8, 2.9 Hz, 1H), 1.52 (s, 6H). Method (92% CO$_2$:8% Methanol+01.% DEA on ChiralCel OJ-H column) LCMS (ES+) RT 12.76 min, 439.0 (M+H)+.

Example 257

Tert-butyl 2-(((1R,3R)-1-(5-chloro-2-(difluoromethoxy)phenyl)-7-(2-(2-hydroxypropan-2-yl)pyrimidin-5-yl)-2,3-dihydro-1H-cyclopenta[4,5]imidazo[1,2-a]pyridin-3-yl)oxy)acetate

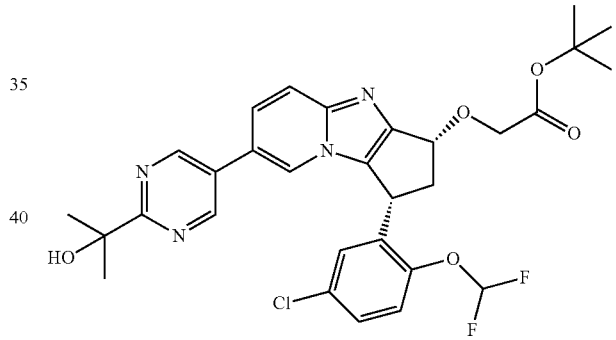

The title compound (23 mg, 52%) was prepared from Intermediate 176 following Method R without the silica gel purification step. LCMS [M 1b] (ES+) RT 1.80 min, 601.2 (M+H)+.

Example 258

2-(((1R,3R)-1-(5-chloro-2-(difluoromethoxy)phenyl)-7-(4-(methylsulfonyl)phenyl)-2,3-dihydro-1H-cyclopenta[4,5]imidazo[1,2-a]pyridin-3-yl)oxy)acetic acid

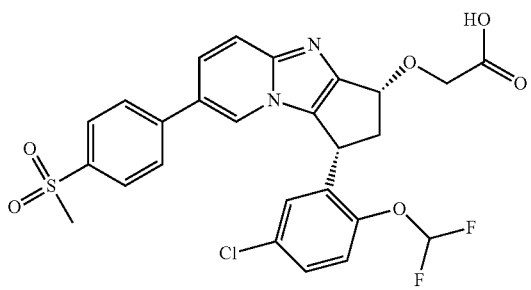 [SMILES: CS(=O)(=O)c1ccc(-c2ccc3nc4c(n3c2)[C@@H](c2cc(Cl)ccc2OC(F)F)C[C@H]4OCC(=O)O)cc1]

Example 224 (25 mg, 40 µM) was dissolved in DCM (2.5 ml). Then 80% TFA in water (0.4 ml) was slowly added with stirring. 1 h and 2 h later additional 80% TFA in water (0.2 ml) was added and the reaction mixture was heated to 40° C. for 6 h. The reaction mixture was concentrated in vacuo and after neutralising with saturated sodium hydrogencarbonate solution concentrated to dryness. The residue was purified by RP-HPLC (M2f). The pure fractions were combined and lyophilised to yield 19 mg (83%) of the title compound. LCMS [M 1b] (ES+) RT 1.47 min, 563.1 (M+H)+.

Example 259
2-(((1R,3R)-1-(5-chloro-2-(difluoromethoxy)phenyl)-7-(2-(2-hydroxypropan-2-yl)pyrimidin-5-yl)-2,3-dihydro-1H-cyclopenta[4,5]imidazo[1,2-a]pyridin-3-yl)oxy)acetic acid

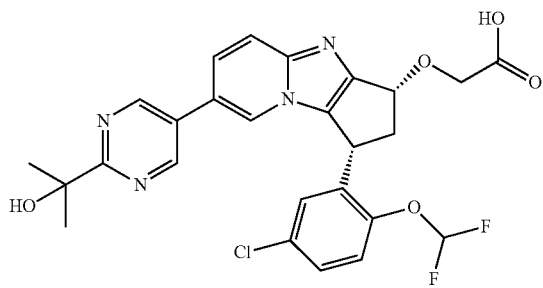 [SMILES: CC(C)(O)c1ncc(-c2ccc3nc4c(n3c2)[C@@H](c2cc(Cl)ccc2OC(F)F)C[C@H]4OCC(=O)O)cn1]

Starting from Example 257 (10 mg, 17 µmol) the title compound (8.4 mg; 93%) was obtained analogously to Example 254. LCMS [M 1b] (ES+) RT 1.46 min, 545.2 (M+H)+.

Example 260 Method T
5-((1R,3R)-1-(5-chloro-2-(difluoromethoxy)phenyl)-3-hydroxy-2,3-dihydro-1H-cyclopenta[4,5]imidazo[1,2-a]pyridin-7-yl)-3-methylpyridin-2(1H)-one

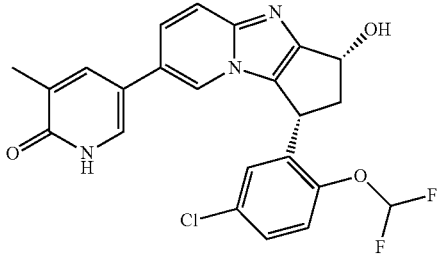 [SMILES: Cc1cc(-c2ccc3nc4c(n3c2)[C@@H](c2cc(Cl)ccc2OC(F)F)C[C@H]4O)c[nH]c1=O]

Sodium iodide (18 mg, 117 µmol) and boron trifluoride ethyl etherate (17 mg, 117 µmol) were added to a stirred solution of Example 229 (27 mg, 58 µM) in MeCN (1 mL) at r.t. The reaction was stirred for 2 h. A further amount of sodium iodide (18 mg, 117 µmol) and boron trifluoride ethyl etherate (17 mg, 117 µmol) were added and the mixture was stirred for another 2 h. EtOAc and saturated sodium hydrogencarbonate solution were added and after phase separation the aqueous phase was extracted twice with EtOAc. The combined organic layers were washed with brine, dried over sodium sulphate, filtered and concentrated in vacuo. The residue was purified by chromatography (SiO$_2$, 0-20% MeOH/DCM), followed by a second purification by RP-HPLC (M2f) to yield the title compound after lyophilisation (11 mg, 40%). LCMS [M 1b] (ES+) RT 1.24 min, 458.2 (M+H)+.

Examples 261-262

The following Examples were prepared by applying the Method T from the given starting material and using the appropriate methoxypyridine.

| Example No. | Precursor | Compound Name | LCMS |
|---|---|---|---|
| 261 | Ex 227 | 5-((1R,3R)-1-(5-chloro-2-(difluoromethoxy)phenyl)-3-hydroxy-2,3-dihydro-1H-cyclopenta[4,5]imidazo[1,2-a]pyridin-7-yl)-3-fluoropyridin-2(1H)-one | LCMS [M 1b] (ES+) RT 1.21 min, 462.1 (M + H)+. |
| 262 | Ex 220 | 6-chloro-5-((1R,3R)-1-(5-chloro-2-(difluoromethoxy)phenyl)-3-hydroxy-2,3-dihydro-1H-cyclopenta[4,5]imidazo[1,2-a]pyridin-7-yl)pyridin-2(1H)-one | LCMS [M 1b] (ES+) RT 1.29 min, 478.1 (M + H)+. |

Examples 263-265

The following Example were prepared by applying Method R from the given starting material and using the appropriate boronate ester or boronic acid.

| Example No. | Precursor | Compound Name | LCMS |
|---|---|---|---|
| 263 | Ex 16 | (1R,3R)-7-(4-(cyclopropylsulfonyl)phenyl)-1-(2-(difluoromethoxy)phenyl)-6-fluoro-2,3-dihydro-1H-cyclopenta[4,5]imidazo[1,2-a]pyridin-3-ol | LCMS [M 1b] (ES+) RT 1.50 min 515.2 (M + H)+. |
| 264 | Int 182 | 1-[2-(difluoromethoxy)-3-fluorophenyl]-6-fluoro-7-[2-(2-hydroxypropan-2-yl)pyrimidin-5-yl]-2,3-dihydro-1H-cyclopenta[4,5]imidazo[1,2-a]pyridin-3-ol | LCMS (ES+) RT 1.34 min 489.0 (M + H)+. |

Examples 265 and 266

(1R,3R)-1-[2-(difluoromethoxy)phenyl]-7-{2-[(1s,5s)-3,7-dioxa-9-azabicyclo[3.3.1]non-9-yl]pyrimidin-5-yl}-3-methyl-2,3-dihydro-1H-cyclopenta[4,5]imidazo[1,2-a]pyridin-3-ol and (1R,3S)-1-[2-(difluoromethoxy)phenyl]-7-{2-[(1s,5s)-3,7-dioxa-9-azabicyclo[3.3.1]non-9-yl]pyrimidin-5-yl}-3-methyl-2,3-dihydro-1H-cyclopenta[4,5]imidazo[1,2-a]pyridin-3-ol

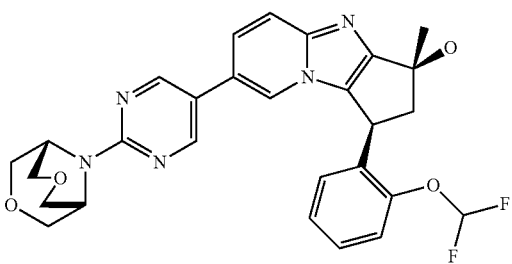

-continued

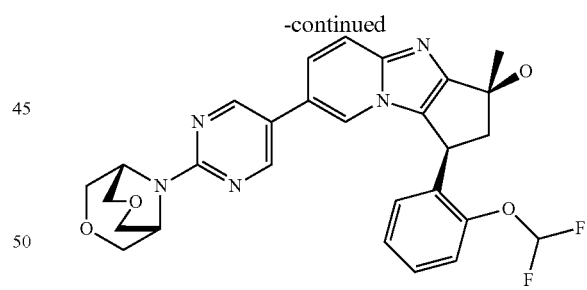

Examples 265 and 266 were prepared from Example 15 (257 mg, 0.63 mmol), Intermediate 71 (211 mg, 0.63 mmol), 1,4-dioxane (10 mL), 2 M sodium carbonate (2 mL) and 1,1'-bis(diphenlphosphino)ferrocene-palladium(II)dichloride dichloromethane complex (26 mg, 0.032 mmol) by Method A. Crude material was purified by column chromatography (SiO$_2$, 0-40% MeOH in EtOAc) and lyophilised from acetonitrile/water to give a mixture of Example 265 and 266. Example 265 and 266 were separated by chiral SFC purification (25% Methanol: 75% CO$_2$ with Chiralpak IA).

Example 265 was then further purified by column chromatography (SiO$_2$, 0-50% MeOH in EtOAc) to give the title compound as a white solid (46 mg, 14%). $\delta_H$ (300 MHz, DMSO-d$_6$) 8.61 (s, 2 H), 8.01 (dd, 1 H, J 1.7, 1.0 Hz), 7.66

(dd, 1 H, J 9.5, 0.9 Hz), 7.53 (dd, 1 H, J 9.5, 1.8 Hz), 7.36 (t, 1 H, J 74.1 Hz), 7.28-7.34 (m, 1 H), 7.23-7.28 (m, 1 H), 7.10-7.17 (m, 1 H), 6.97 (dd, 1 H, J 7.8, 1.6 Hz), 5.26 (s, 1 H), 4.79 (dd, 1 H, J 8.4, 4.4 Hz), 4.46 (br s, 2 H), 4.02 (br s, 2 H), 3.98 (br s, 2 H), 3.74 (d, 2 H, J 2.4 Hz), 3.70 (d, 2 H, J 2.4 Hz), 3.14 (dd, 1 H, J 13.3, 8.5 Hz), 2.36 (dd, 1 H, J 13.4, 4.3 Hz), 1.55 (s, 3 H). LCMS (ES+) 536 (M+H)+, RT 1.84 minutes.

Example 266 was then further purified by column chromatography (SiO$_2$, 0-50% MeOH in EtOAc) to give the title compound as a white solid (9 mg, 3%). $\delta_H$ (300 MHz, DMSO-d$_6$) 8.62 (s, 2 H), 8.01 (dd, 1 H, J 1.6, 1.0 Hz), 7.68 (dd, 1 H, J 9.5, 0.9 Hz), 7.52-7.57 (m, 1 H), 7.29-7.34 (m, 1 H), 7.32 (t, 1 H, J 74.3 Hz), 7.23-7.28 (m, 1 H), 7.11 (td, 1 H, J 7.6, 1.3 Hz), 6.63 (dd, 1 H, J 7.6, 1.4 Hz), 5.21 (s, 1 H), 4.97-5.03 (m, 1 H), 4.45 (br s, 2 H), 4.02 (br s, 2 H), 3.98 (br s, 2 H), 3.73 (d, 2 H, J 2.0 Hz), 3.70 (d, 2 H, J 2.2 Hz), 3.10 (dd, 1 H, J 13.5, 8.3 Hz), 2.27-2.34 (m, 1 H), 1.51 (s, 3 H). LCMS (ES+) 536 (M+H)+, RT 1.85 minutes.

Example 267

7-bromo-1-[2-(difluoromethoxy)phenyl]-3-methyl-2,3-dihydro-1H-cyclopenta[4,5]imidazo[1,2-a]pyridin-3-yl}acetamide

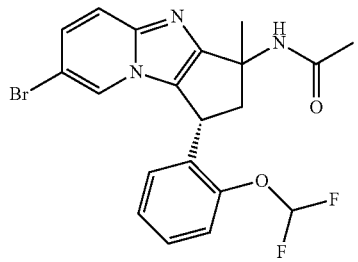 [SMILES: CC(=O)NC1(C)C[C@H](c2ccccc2OC(F)F)c2c1nc1ccc(Br)cn21]

To a stirred solution of Example 15 (99.5 mg, 0.24 mmol) in acetonitrile (4 mL) was added sulfuric acid (68.5 µL, 1.22 mmol) and reaction mixture heated to 60° C. for 50 minutes, after which time the reaction mixture cooled to room temperature and the diluted with water (25 mL), basified with 10% NaOH and extracted with DCM (4×25 mL), combined organics were passed down a phase separator and concentrated in vacuo. The residue was purified by column chromatography (SiO$_2$, 20-100% EtOAc in hexane followed by 0-100% MeOH in EtOAc) and material freeze dried from acetonitrile/water to give title compound (52.4 mg, 48%) as a beige solid. $\delta_H$ (300 MHz, DMSO-d$_6$) 8.11 (s, 1 H), 8.04 (dd, 1 H, J 1.8, 0.7 Hz), 7.52-7.58 (m, 1 H), 7.23-7.36 (m, 2 H), 7.31 (t, 1 H, J 74.1 Hz), 7.11-7.19 (m, 1 H), 6.66 (dd, 1 H, J 7.6, 1.5 Hz), 4.97 (dd, 1 H, J 8.8, 4.4 Hz), 3.45 (dd, 1 H, J 13.4, 9.0 Hz), 2.23 (dd, 1 H, J 13.6, 4.8 Hz), 1.78 (s, 3 H), 1.51 (s, 3 H). NMR assignment for the major diastereoisomer. Material is a mixture (11:9) of the two diastereoisomers. LCMS (ES+) 450/452 (M+H)+, RT 2.10 minutes.

Example 268

1-[2-(difluoromethoxy)phenyl]-3-methyl-7-[4-(methylsulfonyl)phenyl]-2,3-dihydro-1H-cyclopenta[4,5]imidazo[1,2-a]pyridin-3-yl}acetamide

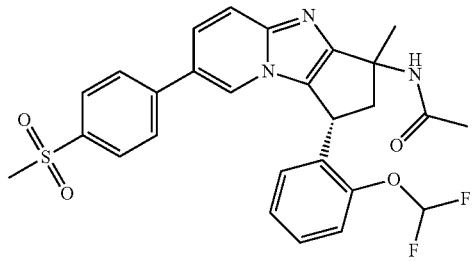 [SMILES: CC(=O)NC1(C)C[C@H](c2ccccc2OC(F)F)c2c1nc1ccc(-c3ccc(S(C)(=O)=O)cc3)cn21]

The title compound was prepared from Example 267 (48 mg, 0.11 mmol), 4-(methylsulfonyl)phenylboronic acid (30 mg, 0.15 mmol), 1,4-dioxane (5 mL), 2 M aq sodium carbonate (1 mL) and 1,1'-bis(diphenylphosphino)ferrocene-palladium(II)dichloride (4 mg, 0.006 mmol) by the Method A (19.6 mg, 35%). Example 267 contains a 73:27 mixture of diastereoisomers. $\delta_H$ (300 MHz, DMSO-d$_6$) 8.20 (s, 1 H), 8.06 (s, 1 H), 7.96-7.99 (m, 2 H), 7.83 (d, 1 H, J 8.5 Hz), 7.69-7.74 (m, 1 H), 7.64 (dd, 1 H, J 9.4, 1.7 Hz), 7.36 (t, 1 H, J 74.0 Hz), 7.30-7.35 (m, 1 H), 7.27 (s, 1 H), 7.11-7.14 (m, 1 H), 7.03 (dd, 1 H, J 7.7, 1.5 Hz), 4.92 (dd, 1 H, J 8.3, 5.8 Hz), 3.23 (s, 3 H), 3.10 (dd, 1 H, J 13.1, 8.5 Hz), 2.82 (dd, 1 H, J 13.1, 5.8 Hz), 1.75 (s, 3 H), 1.59 (s, 3 H). NMR assignment for the major diastereoisomer. LCMS (ES+) 526 (M+H)+, RT 1.91 and 1.95 minutes Example 269

(1R,3S or R)-7-bromo-1-[2-(difluoromethoxy)phenyl]-3-ethynyl-6-fluoro-2,3-dihydro-1H-cyclopenta[4,5]imidazo[1,2-a]pyridin-3-ol

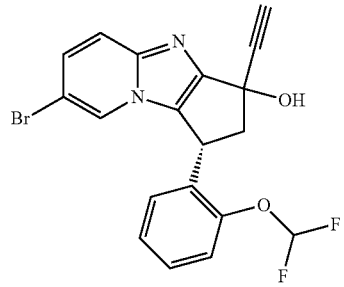 [SMILES: C#CC1(O)C[C@H](c2ccccc2OC(F)F)c2c1nc1ccc(Br)cn21]

To a stirred solution of Example 2 (1 g, 2.43 mmol) and LiCl (210 mg, 4.954 mmol) in 2-methyl tetrahydrofuran (5 mL) was added ethynylmagnesium bromide (0.5 M in THF) (10.5 mL, 5 mmol) and reaction mixture stirred at r.t. for 18 h. The reaction mixture was treated with saturated. NaHCO$_3$ solution (100 mL) and partitioned with EtOAc (100 mL), the layers were separated and the aqueous extracted with EtOAc (2×100 mL), combined organics were dried over MgSO$_4$ and filtered and concentrated in vacuo. The residue was purified by column chromatography (SiO$_2$, 50-100% EtOAc/hexane)

yielding the title compound (686 mg, 64%). LCMS (ES+) 437.0/439.0 (M+H)⁺, RT 1.46 minutes Examples 270 and 271

(1R)-7-{2-[(1S,4S)-2,5-diazabicyclo[2.2.1]hept-2-yl]pyrimidin-5-yl}-1-[2-(difluoromethoxy)phenyl]-3-methyl-2,3-dihydro-1H-cyclopenta[4,5]imidazo[1,2-a]pyridin-3-ol and (1R)-7-{2-[(1S,4S)-2,5-diazabicyclo[2.2.1]hept-2-yl]pyrimidin-5-yl}-1-[2-(difluoromethoxy)phenyl]-3-methoxy-3-methyl-2,3-dihydro-1H-cyclopenta[4,5]imidazo[1,2-a]pyridine

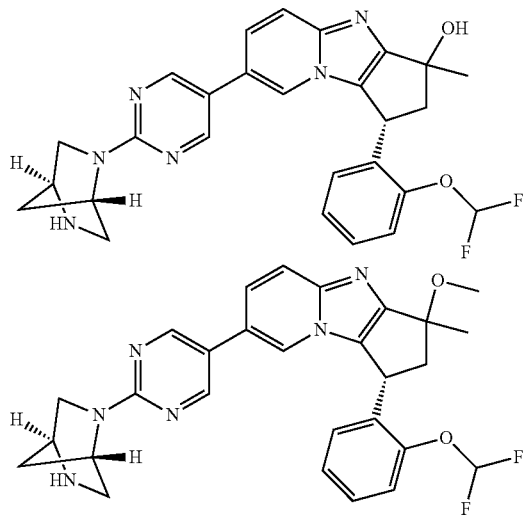

Intermediate 184 (465 mg, 0.77 mmol) was dissolved in 4 M hydrochloric acid in 1,4-dioxane (11 mL) and methanol (3 mL) and reaction stirred at r.t. for 1.5 hours. After which time the reaction mixture was concentrated in vacuo, the residue was dissolved in water (10 mL) and basified with 10% NaOH (5 mL), and this was extracted with EtOAc (4×25 mL), combined organics were washed with brine (50 mL), dried (MgSO₄), filtered and concentrated in vacuo. The residue was purified by column chromatography (SiO₂, 0% NH3/0% MeOH/100% DCM—2.5% NH3/22.5% MeOH/75% DCM) and material freeze dried from acetonitrile/water to give a mixture of both Example 270 and Example 271. This material was further purified by preparative HPLC to give the both title compounds Example 270 (54 mg, 14%) as an off-white solid and Example 271 (19 mg, 5%) as a pale yellow solid.

Example 270 contains a 14:11 mixture of diastereoisomers.

$\delta_H$ (300 MHz, DMSO-$d_6$) 8.51 (s, 2 H), 7.95 (s, 1 H), 7.64 (dd, 1 H, J 3.6, 0.8 Hz), 7.52 (dd, 1 H, J 4.3, 1.8 Hz), 7.37 (t, 1 H, J 74.1 Hz), 7.24-7.34 (m, 2 H), 7.12 (dd, 1 H, J 7.1, 1.3 Hz), 6.98 (dd, 1 H, J 7.7, 1.5 Hz), 5.29 (s, 1 H), 4.78 (dd, J 8.4, 4.3 Hz), 4.75 (s, 1 H), 3.62-3.67 (m, 1 H), 3.42-3.44 (m, 1 H), 3.05-3.18 (m, 2 H), 2.86-2.93 (m, 1 H), 2.71-2.79 (m, 1H), 2.26-2.40 (m, 1H), 1.72-1.79 (m, 1H), 1.62-1.68 (m, 1H), 1.54 (s, 3H). NMR assignment for the major diastereoisomer. Material is a mixture (14:11) of the two diastereoisomers. LCMS (ES⁺) 505 (M+H)⁺, RT 1.54 and 1.59 minutes Example 271

$\delta_H$ (300 MHz, DMSO-$d_6$) 8.53 and 8.51 (s, 2 H, diastereoisomeric), 8.06 and 7.95 (s, 1H, diastereoisomeric), 7.69 (d, 1 H, J 9.5 Hz), 7.51-7.58 (m, 1 H), 7.24-7.36 (2 H, m), 7.34 (t, 1 H, J 74.1 Hz), 7.09-7.16 (m, 1 H), 6.80 (dd, J 7.8, 1.5 Hz) and 6.66 (dd, J 8.1, 1.5 Hz) (dd, 1 H, diastereoisomeric), 4.99 (dd, J 8.4, 5.0 Hz) and 4.81 (dd, 1 H, J 8.7, 3.9 Hz) (dd, 1 H, diastereoisomeric), 4.74 (s, 1 H), 3.64 (s, 1 H), 3.45-3.48 and 3.42-3.44 (m, 1 H, diastereoisomeric), 3.22 (dd, 1 H, J 14.1, 8.4 Hz), 3.11 and 3.09 (s, 3 H, diastereoisomeric), 2.86-2.92 and 2.71-2.78 (m, 2 H, diastereoisomeric), 2.71-2.78 (m, 1 H), 2.40 (dd, J 14.0, 4.0 Hz) and 2.26 (dd, J 14.0, 5.4 Hz) (dd, 1 H, diastereoisomeric), 1.72-1.78 (m, 1 H), 1.62-4.68 (m, 1 H), 1.57 and 1.54 (s, 3 H, diastereoisomeric). LCMS (ES+) 519 (M+H)⁺, RT 1.19 and 1.89 minutes.

The invention claimed is:

1. A compound represented by formula (IIA), or a pharmaceutically acceptable salt thereof,

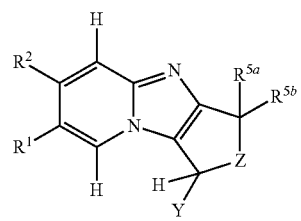

(IIA)

$R^1$ represents aryl, $C_{3-7}$ heterocycloalkenyl, heteroaryl, $(C_{3-7})$heterocycloalkyl-heteroaryl-, $(C_{4-9})$heterobicycloalkyl-heteroaryl-, $(C_{3-7})$cycloalkyl-heteroaryl-, or $(C_{4-9})$bicycloalkyl-heteroaryl-, any of which groups may be optionally substituted by one, two or three substituents selected from halogen, halo($C_{1-6}$)alkyl, cyano, cyano($C_{1-6}$)alkyl, nitro($C_{1-6}$)alkyl, $C_{1-6}$ alkyl, trifluoromethyl, trifluoroethyl, $C_{2-6}$ alkenyl, hydroxy, hydroxy($C_{1-6}$)alkyl, $C_{1-6}$ alkoxy, trifluoroethoxy, carboxy($C_{3-7}$)cycloalkyloxy, $C_{1-6}$ alkylthio, $C_{1-6}$ alkylsulphonyl, ($C_{1-6}$)alkylsulphonyl($C_{1-6}$)alkyl, oxo, amino, amino-($C_{1-6}$)alkyl, $C_{1-6}$ alkylamino, di($C_{1-6}$)alkylamino, ($C_{1-6}$)alkoxy($C_{1-6}$)alkylamino, N—[$C_{1-6}$)alkyl]-N-[hydroxy($C_{1-6}$)alkyl]amino, ($C_{2-6}$)alkylcarbonylamino($C_{1-6}$)alkyl, $C_{1-6}$alkylsulphonylamino, N—[$C_{1-6}$)alkylsulphonyl]amino, bis[($C_{1-6}$)alkyl-sulphonyl]amino, N-[($C_{1-6}$)alkyl]-N-[carboxy($C_{1-6}$)alkyl]amino, carboxy($C_{3-7}$)cycloalkyl-amino, carboxy($C_{3-7}$)cycloalkyl($C_{1-6}$)alkylamino, formyl, $C_{2-6}$ alkylcarbonyl, ($C_{2-6}$)alkyl-carbonyloxy($C_{1-6}$)alkyl, carboxy, carboxy($C_{1-6}$)alkyl, $C_{2-6}$ alkoxycarbonyl, $C_{2-6}$alkoxycarbonyl($C_{1-6}$)alkyl, morpholinyl($C_{1-6}$) alkoxycarbonyl, $C_{2-6}$ alkoxycarbonyl-methylidenyl, aminocarbonyl, di($C_{1-6}$)alkylaminocarbonyl, aminosulphonyl, ($C_{1-6}$)alkylsulphoximinyl, [($C_{1-6}$)alkyl][N—($C_{1-6}$)alkyl]sulphoximinyl, heteroaryl, difluoromethyl, $C_{1-6}$ alkylsulphinyl, and ($C_{3-7}$)cycloalkyl sulphonyl;

$R^2$ represents hydrogen, halogen, trifluoromethyl or cyano; or $C_{1-6}$ alkyl which group may be optionally substituted by $C_{2-6}$ alkoxycarbonyl;

Z represents methylene;

$R^{5a}$ represents hydrogen, hydroxy, halogen, trifluoromethyl; —NR$^b$R$^c$, S(O)$_2$R$^a$, —OR$^a$, O—(CO)—R$^d$, —NR$^c$C(O)R$^d$, or $C_{1-6}$ alkyl;

and $R^{5b}$ represents hydrogen, or $C_{1-6}$ alkyl;

Y represents phenyl optionally substituted by one or more substituents selected from chloro, fluoro, cyano, methoxy, methylsulphonyl, trifluoromethoxy and difluoromethoxy;

R$^a$ represents C$_{1-6}$ alkyl, aryl(C$_{1-6}$)alkyl or heteroaryl (C$_{1-6}$)alkyl, any of which groups may be optionally substituted by one or more substituents selected from C$_{1-6}$ alkoxy, oxo, cyano and C$_{2-6}$ alkoxycarbonyl;

R$^b$ represents hydrogen or C$_{1-6}$ alkyl;

R$^c$ represents hydrogen, C$_{1-6}$ alkyl or C$_{3-7}$ cycloalkyl; and

R$^d$ represents hydrogen; or C$_{1-6}$ alkyl, aryl or heteroaryl, any of which groups may be optionally substituted by one or more substituents selected from halogen, C$_{1-6}$ alkyl, C$_{1-6}$ alkoxy, oxo, C$_{2-6}$ alkylcarbonyloxy and di(C$_{1-6}$)alkylamino.

2. The compound as claimed in claim 1, represented by formula (IIB), or a pharmaceutically acceptable salt,

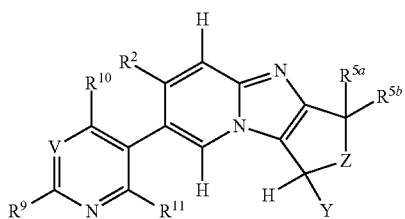

(IIB)

wherein

V represents C—R$^{12}$ or N;

R$^9$ represents halogen, hydroxy(C$_{1-6}$)alkyl, C$_{1-6}$ alkylsulphonyl, (C$_{1-6}$)alkylsulphonyl(C$_{1-6}$)alkyl, di(C$_{1-6}$)alkylaminocarbonyl, C$_{1-6}$ alkoxy, aminosulphonyl, C$_{1-6}$ alkylsulphinyl, (C$_{3-7}$)cycloalkylsulphonyl or difluoromethyl; or (C$_{3-7}$)cycloalkyl, (C$_{4-7}$)cycloalkenyl, (C$_{4-9}$)bicycloalkyl, (C$_{3-7}$)heterocycloalkyl, (C$_{4-9}$)heterobicycloalkyl, (C$_{4-9}$)bicycloalkylene, any of which groups may be optionally substituted by one or more substituents selected from halogen, halo(C$_{1-6}$)alkyl, cyano, cyano-(C$_{1-6}$)alkyl, nitro, nitro(C$_{1-6}$)alkyl, C$_{1-6}$ alkyl, C$_{3-7}$ cycloalkyl, trifluoromethyl, trifluoroethyl, C$_{2-6}$ alkenyl, hydroxy, hydroxy(C$_{1-6}$)alkyl, C$_{1-6}$ alkoxy, difluoromethoxy, trifluoromethoxy, trifluoro-ethoxy, C$_{1-6}$ alkylthio, C$_{1-6}$ alkylsulphonyl, (C$_{1-6}$)alkylsulphonyl(C$_{1-6}$)alkyl, oxo, amino, C$_{1-6}$ alkylamino, di(C$_{1-6}$) alkylamino, C$_{2-6}$alkylcarbonylamino, (C$_{2-6}$)alkylcarbonylamino-(C$_{1-6}$)alkyl, C$_{2-6}$ alkoxycarbonylamino, C$_{1-6}$ alkyl sulphonylamino, formyl, C$_{1-6}$ alkylcarbonyl, carboxy, carboxy(C$_{1-6}$)alkyl, C$_{2-6}$ alkoxycarbonyl, morpholinyl-(C$_{1-6}$)alkoxycarbonyl, C$_{2-6}$ alkoxycarbonyl(C$_{1-6}$)alkyl, C$_{2-6}$ alkoxycarbonylmethylidenyl, amino-carbonyl, C$_{1-6}$ alkylaminocarbonyl, di(C$_{1-6}$) alkylaminocarbonyl, aminosulphonyl, di(C$_{1-6}$)alkylaminosulphonyl, (C$_{1-6}$)alkylsulphoximinyl and [(C$_{1-6}$) alkyl][N—(C$_{1-6}$)alkyl]-sulphoximinyl;

R$^{10}$ and R$^{11}$ independently represents hydrogen, halogen, cyano, trifluoromethyl, or hydroxy; or —NR$^b$R$^c$, —OR$^a$; C$_{1-6}$ alkyl, or C$_{1-6}$ alkylsulphonyl;

R$^{12}$ represents hydrogen, halogen or C$_{1-6}$ alkyl;

R$^{5a}$ represents hydrogen, hydroxy, halogen, trifluoromethyl, —NR$^b$R$^c$, S(O)$_2$R$^a$, —OR$^a$, O—(CO)—R$^d$, —NR$^c$C(O)R$^d$, or C$_{1-6}$alkyl; and R$^{5b}$ represents hydrogen, or C$_{1-6}$alkyl;

R$^a$ represents C$_{1-6}$ alkyl, aryl(C$_{1-6}$)alkyl or heteroaryl (C$_{1-6}$)alkyl, any of which groups may be optionally substituted by one or more substituents selected from C$_{1-6}$ alkoxy, oxo, cyano and C$_{2-6}$ alkoxycarbonyl;

R$^b$ represents hydrogen or C$_{1-6}$ alkyl;

R$^c$ represents hydrogen, C$_{1-6}$ alkyl or C$_{3-7}$ cycloalkyl; and

R$^d$ represents hydrogen; or C$_{1-6}$ alkyl, aryl or heteroaryl, any of which groups may be optionally substituted by one or more substituents selected from halogen, C$_{1-6}$ alkyl, C$_{1-6}$ alkoxy, oxo, C$_{2-6}$ alkylcarbonyloxy and di(C$_{1-6}$)alkylamino.

3. The compound as claimed in claim 2 represented by formula (IIC), (IID), (IIE), (IIF), (IIG), (IIH), (IIJ), (IIK), (IIL), or (IIM), or a pharmaceutically acceptable salt thereof,

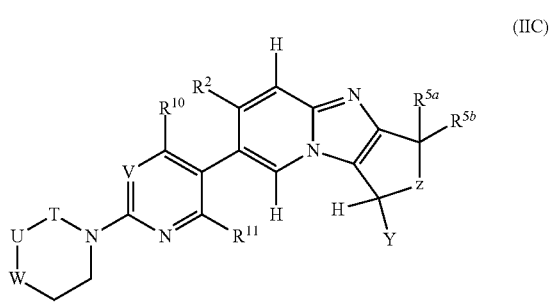

(IIC)

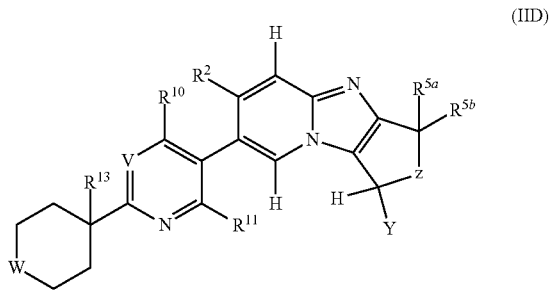

(IID)

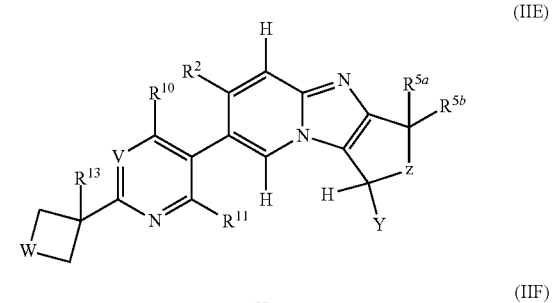

(IIE)

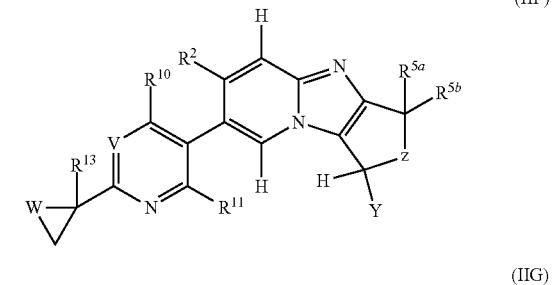

(IIF)

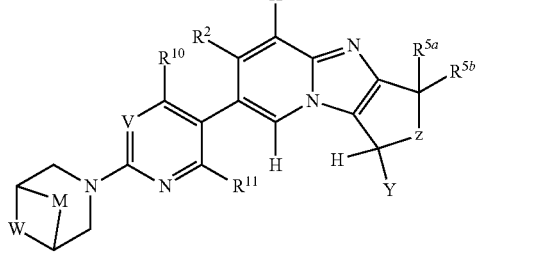

(IIG)

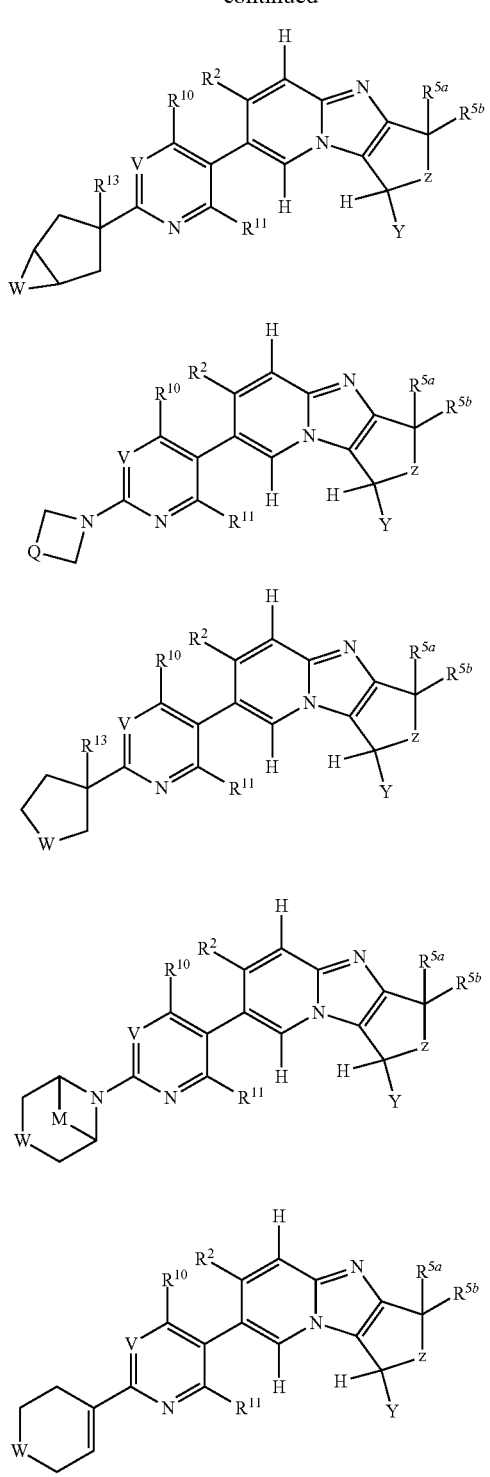

T represents —CH₂— or —CH₂CH₂,
U represents C(O) or S(O)₂;
W represents O, S, S(O), S(O)₂, N(R¹⁴), S(O)(N—Rᵈ) or C(R¹⁵)(R¹⁶);
-M- represents —CH₂—, —CH₂CH₂— or —CH₂—W—CH₂—;
Q represents C(R¹⁵)(R¹⁶);
R¹³ represents hydrogen, halogen, halo(C₁₋₆)alkyl, hydroxy or (C₂₋₆)alkylcarbonylamino(C₁₋₆)alkyl;

R¹⁴ represents hydrogen, C₁₋₆ alkyl or C₂₋₆ alkylcarbonyl;
R¹⁵ represents hydrogen, halogen, cyano, hydroxy, hydroxy(C₁₋₆)alkyl, C₁₋₆ alkylsulphonyl, formyl, carboxy, carboxy(C₁₋₆)alkyl, C₂₋₆ alkoxycarbonyl, C₂₋₆ alkoxycarbonyl(C₁₋₆)alkyl, aminosulphonyl, (C₁₋₆)alkylsulphoximinyl, [(C₁₋₆)alkyl][N—(C₁₋₆)alkyl]sulphoximinyl, (C₁₋₆)alkylsulphonylaminocarbonyl, (C₂₋₆)alkylcarbonylamino-sulphonyl, (C₁₋₆)alkoxyaminocarbonyl, tetrazolyl or hydroxyoxadiazolyl;
R¹⁶ represents hydrogen, halogen, C₃₋₇ cyloalkyl or C₁₋₆ alkyl;
R² represents hydrogen, halogen, trifluoromethyl or cyano; or C₁₋₆ alkyl which group may be optionally substituted;
R⁵ᵃ represents hydrogen, hydroxyl, halogen trifluoromethyl; —NRᵇRᶜ, S(O)₂Rᵃ, —ORᵃ, O—(CO)—Rᵈ, —NRᶜC(O)Rᵈ, or C₁₋₆ alkyl; and
R⁵ᵇ represents hydrogen, or C₁₋₆alkyl;
Rᵃ represents C₁₋₆ alkyl, aryl(C₁₋₆)alkyl or heteroaryl (C₁₋₆)alkyl, any of which groups may be optionally substituted by one or more substituents selected from C₁₋₆ alkoxy, oxo, cyano and C₂₋₆ alkoxycarbonyl;
Rᵇ represents hydrogen or C₁₋₆ alkyl;
Rᶜ represents hydrogen, C₁₋₆ alkyl or C₃₋₇ cycloalkyl;
Rᵈ represents hydrogen; or C₁₋₆ alkyl, aryl or heteroaryl, any of which groups may be optionally substituted by one or more substituents selected from halogen, C₁₋₆ alkyl, C₁₋₆ alkoxy, oxo, C₂₋₆ alkylcarbonyloxy and di(C₁₋₆)alkylamino;
V represents C—R¹² or N;
R¹⁰ and R¹¹ independently represents hydrogen, halogen, cyano, trifluoromethyl, or hydroxy; or —NRᵇRᶜ, —ORᵃ; C₁₋₆ alkyl, or C₁₋₆ alkylsulphonyl; and
R¹² represents hydrogen, halogen or C₁₋₆ alkyl.

4. The compound as claimed in claim 1 represented by formula (IIN), or a pharmaceutically acceptable salt thereof,

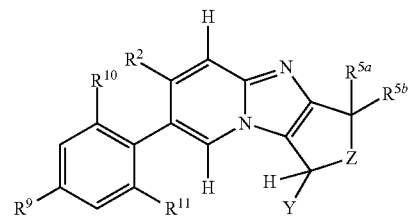

(IIN)

wherein
R⁵ᵃ represents hydrogen, hydroxy, halogen, trifluoromethyl; —NRᵇRᶜ, S(O)₂Rᵃ —ORᵃ, O—(CO)—Rᵈ, —NRᶜC(O)Rᵈ, or C₁₋₆ alkyl; and
R⁵ᵇ represents hydrogen, or C₁₋₆ alkyl;
—Rᵃ represents C₁₋₆ alkyl, aryl(C₁₋₆)alkyl or heteroaryl (C₁₋₆)alkyl, any of which groups may be optionally substituted by one or more substituents selected from C₁₋₆ alkoxy, oxo, cyano and C₂₋₆ alkoxycarbonyl;
Rᵇ represents hydrogen or C₁₋₆ alkyl;
Rᶜ represents hydrogen, C₁₋₆ alkyl or C₃₋₇ cycloalkyl;
Rᵈ represents hydrogen; or C₁₋₆ alkyl, aryl or heteroaryl, any of which groups may be optionally substituted by one or more substituents selected from halogen, C₁₋₆ alkyl, C₁₋₆ alkoxy, oxo, C₂₋₆ alkylcarbonyloxy and di(C₁₋₆)alkylamino;

$R^9$ represents halogen, hydroxy($C_{1-6}$)alkyl, $C_{1-6}$ alkylsulphonyl, ($C_{1-6}$)alkylsulphonyl($C_{1-6}$)alkyl, di($C_{1-6}$)alkylaminocarbonyl, $C_{1-6}$ alkoxy, aminosulphonyl, $C_{1-6}$ alkylsulphinyl, ($C_{3-7}$)cycloalkylsulphonyl or difluoromethyl; or ($C_{3-7}$)cycloalkyl, ($C_{4-7}$)cycloalkenyl, ($C_{4-9}$)bicycloalkyl, ($C_{3-7}$)heterocycloalkyl, ($C_{4-9}$)heterobicycloalkyl, ($C_{4-9}$)bicycloalkylene, any of which groups may be optionally substituted by one or more substituents selected from halogen, halo($C_{1-6}$)alkyl, cyano, cyano-($C_{1-6}$)alkyl, nitro, nitro($C_{1-6}$)alkyl, $C_{1-6}$ alkyl, $C_{3-7}$ cycloalkyl, trifluoromethyl, trifluoroethyl, $C_{2-6}$ alkenyl, hydroxy, hydroxy($C_{1-6}$)alkyl, $C_{1-6}$ alkoxy, difluoromethoxy, trifluoromethoxy, trifluoro-ethoxy, $C_{1-6}$ alkylthio, $C_{1-6}$ alkylsulphonyl, ($C_{1-6}$)alkylsulphonyl($C_{1-6}$)alkyl, oxo, amino, $C_{1-6}$ alkylamino, di($C_{1-6}$)alkylamino, $C_{2-6}$alkylcarbonylamino, ($C_{2-6}$)alkylcarbonylamino-($C_{1-6}$)alkyl, $C_{2-6}$ alkoxycarbonylamino, $C_{1-6}$ alkyl sulphonylamino, formyl, $C_{1-6}$ alkylcarbonyl, carboxy, carboxy($C_{1-6}$)alkyl, $C_{2-6}$ alkoxycarbonyl, morpholinyl-($C_{1-6}$)alkoxycarbonyl, $C_{2-6}$ alkoxycarbonyl($C_{1-6}$)alkyl, $C_{2-6}$ alkoxycarbonylmethylidenyl, amino-carbonyl, $C_{1-6}$ alkylaminocarbonyl, di($C_{1-6}$)alkylaminocarbonyl, aminosulphonyl, di($C_{1-6}$)alkylaminosulphonyl, ($C^{1-6}$)alkylsulphoximinyl and [($C_{1-6}$)alkyl][N—($C_{1-6}$)alkyl]-sulphoximinyl; and $R^{10}$ and $R^{11}$ independently represents hydrogen, halogen, cyano, trifluoromethyl, or hydroxy; or —NR$^b$R$^c$, —OR$^a$; $C_{1-6}$ alkyl, or $C_{1-6}$ alkylsulphonyl.

5. The compound as claimed in claim 1 represented by formula (IIN), or a pharmaceutically acceptable salt thereof,

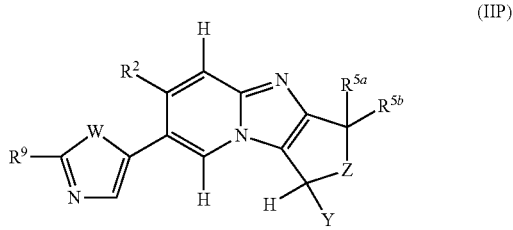

(IIP)

$R^2$ represents hydrogen, halogen, trifluoromethyl or cyano; or $C_{1-6}$ alkyl which group may be optionally substituted;

$R^{5a}$ represents hydrogen, hydroxy, halogen, trifluoromethyl, —NR$^b$ R$^c$, S(O)$_2$R$^a$, —OR$^a$, O—(CO)—R$^d$, —NR$^c$C(O)R$^d$, or $C_{1-6}$ alkyl; and $R^{5b}$ represents hydrogen, or $C_{1-6}$ alkyl; and $R^a$ represents $C_{1-6}$ alkyl, aryl($C_{1-6}$)alkyl or heteroaryl ($C_{1-6}$)alkyl, any of which groups may be optionally substituted by one or more substituents selected from $C_{1-6}$ alkoxy, oxo, cyano and $C_{2-6}$ alkoxycarbonyl;

$R^b$ represents hydrogen or $C_{1-6}$ alkyl;

$R^c$ represents hydrogen, $C_{1-6}$ alkyl or $C_{3-7}$ cycloalkyl; and $R^d$ represents hydrogen; or $C_{1-6}$ alkyl, aryl or heteroaryl, any of which groups may be optionally substituted by one or more substituents selected from halogen, $C_{1-6}$ alkyl, $C_{1-6}$ alkoxy, oxo, $C_{2-6}$ alkylcarbonyloxy and di($C_{1-6}$)alkylamino;

$R^9$ represents halogen, hydroxy($C_{1-6}$)alkyl, $C_{1-6}$ alkylsulphonyl, ($C_{1-6}$)alkylsulphonyl($C_{1-6}$)alkyl, di($C_{1-6}$)alkylaminocarbonyl, $C_{1-6}$ alkoxy, aminosulphonyl, $C_{1-6}$ alkylsulphinyl, ($C_{3-7}$)cycloalkylsulphonyl or difluoromethyl; or ($C_{3-7}$)cycloalkyl, ($C_{4-7}$)cycloalkenyl, ($C_{4-9}$)bicycloalkyl, ($C_{3-7}$)heterocycloalkyl, ($C_{4-9}$)heterobicycloalkyl, ($C_{4-9}$)bicycloalkylene, any of which groups may be optionally substituted by one or more substituents selected from halogen, halo($C_{1-6}$)alkyl, cyano, cyano-($C_{1-6}$)alkyl, nitro, nitro($C_{1-6}$)alkyl, $C_{1-6}$ alkyl, $C_{3-7}$ cycloalkyl, trifluoromethyl, trifluoroethyl, $C_{2-6}$ alkenyl, hydroxy, hydroxy($C_{1-6}$)alkyl, $C_{1-6}$ alkoxy, difluoromethoxy, trifluoromethoxy, trifluoro-ethoxy, $C_{1-6}$ alkylthio, $C_{1-6}$ alkylsulphonyl, ($C_{1-6}$)alkylsulphonyl($C_{1-6}$)alkyl, oxo, amino, $C_{1-6}$ alkylamino, di($C_{1-6}$)alkylamino, $C_{2-6}$ alkylcarbonylamino, ($C_{2-6}$)alkylcarbonylamino-($C_{1-6}$)alkyl, $C_{2-6}$ alkoxycarbonylamino, $C_{1-6}$ alkyl sulphonylamino, formyl, $C_{1-6}$ alkylcarbonyl, carboxy, carboxy($C_{1-6}$)alkyl, $C_{2-6}$alkoxycarbonyl, morpholinyl-($C_{1-6}$)alkoxycarbonyl, $C_{2-6}$ alkoxycarbonyl($C_{1-6}$)alkyl, $C_{2-6}$alkoxycarbonylmethylidenyl, aminocarbonyl, $C_{1-6}$ alkylaminocarbonyl, di($C_{1-6}$)alkylaminocarbonyl, aminosulphonyl, di($C_{1-6}$)alkylaminosulphonyl, ($C_{1-6}$)alkylsulphoximinyl and [($C_{1-6}$)alkyl][N—($C_{1-6}$)alkyl]-sulphoximinyl;

W represents O, S, S(O), S(O)$_2$, N(R$^{14}$), S(O)(N—R$^d$) or C(R$^{15}$)(R$^{16}$);

$R^{14}$ represents hydrogen, $C_{1-6}$ alkyl or $C_{2-6}$ alkylcarbonyl;

$R^{15}$ represents hydrogen, halogen, cyano, hydroxy, hydroxy($C_{1-6}$)alkyl, $C_{1-6}$ alkylsulphonyl, formyl, carboxy, carboxy($C_{1-6}$)alkyl, $C_{2-6}$ alkoxycarbonyl, $C_{2-6}$ alkoxycarbonyl($C_{1-6}$)alkyl, aminosulphonyl, ($C_{1-6}$) alkylsulphoximinyl, [($C_{1-6}$)alkyl][N—($C_{1-6}$)alkyl]sulphoximinyl, ($C_{1-6}$)alkylsulphonylaminocarbonyl, ($C_{2-6}$)alkylcarbonylamino-sulphonyl, ($C_{1-6}$) alkoxyaminocarbonyl, tetrazolyl or hydroxyoxadiazolyl; and $R^{16}$ represents hydrogen, halogen, $C_{3-7}$ cyloalkyl or $C_{1-6}$ alkyl.

6. The compound as claimed in claim 1 wherein Y represents (difluoromethoxy)phenyl, (difluoromethoxy)(fluoro)phenyl, (chloro)(difluoromethoxy)phenyl or (difluoromethoxy)(cyano)phenyl.

7. The compound as claimed in claim 1 wherein $R^2$ represents hydrogen or halogen.

8. The compound as claimed in claim 1 wherein $R^{5a}$ represents hydrogen, hydroxy, fluoro, trifluoromethyl, —N(CH$_3$)$_2$, —NH(CO)CH$_3$, —SO$_2$—CH$_3$, —CO$_2$—CH$_3$, methyl or methoxy.

9. The compound as claimed in claim 1, wherein $R^{5b}$ represents hydrogen or methyl.

10. A pharmaceutical composition comprising a compound of formula (I) as defined in claim 1, or a pharmaceutically acceptable salt thereof, in association with a pharmaceutically acceptable carrier.

11. A method for inhibiting TNFα in a patient, the method comprising administering to a patient in need of such inhibition an effective amount of a compound of formula (I) as defined in claim 1 or a pharmaceutically acceptable salt thereof.

* * * * *